United States Patent [19]

Moedritzer et al.

[11] Patent Number: 4,964,895
[45] Date of Patent: Oct. 23, 1990

[54] SUBSTITUTED 4-(4-NITROPHENOXY) PYRAZOLES AND THEIR USE AS HERBICIDES

[75] Inventors: Kurt Moedritzer, Webster Groves; Michael D. Rogers, Maryland Heights, both of Mo.

[73] Assignee: Monsanto Company, St. Louis, Mo.

[21] Appl. No.: 471,686

[22] Filed: Jan. 30, 1990

Related U.S. Application Data

[63] Continuation of Ser. No. 175,460, Apr. 13, 1988, abandoned, which is a continuation-in-part of Ser. No. 59,712, Jun. 8, 1981, abandoned.

[51] Int. Cl.$^5$ ............... C07D 231/14; C07D 231/16; C07D 231/20; A01N 43/56
[52] U.S. Cl. ..................... 71/92; 544/140; 544/60; 544/315; 546/279; 548/110; 548/266.2; 548/327; 548/376; 548/377
[58] Field of Search ............... 548/376, 377; 71/92

[56] References Cited

U.S. PATENT DOCUMENTS

| | | | |
|---|---|---|---|
| 3,303,200 | 2/1967 | Wolf et al. | 260/310 |
| 3,326,933 | 6/1967 | Wright | 260/310 |
| 3,450,694 | 6/1969 | Swett et al. | 540/488 |
| 3,590,048 | 6/1971 | Swett et al. | 260/310 |
| 3,869,274 | 3/1975 | Crovetti et al. | 71/92 |
| 3,882,142 | 5/1975 | Walworth et al. | 260/311 |
| 3,963,742 | 6/1976 | Cross et al. | 260/311 |
| 4,000,301 | 12/1976 | Walworth | 514/407 |
| 4,002,641 | 1/1977 | Möller et al. | 260/310 |
| 4,008,249 | 2/1977 | Fischer et al. | 260/310 |
| 4,009,227 | 12/1977 | Walworth | 525/71 |
| 4,063,929 | 12/1977 | Bayer et al. | 71/115 |
| 4,099,011 | 7/1978 | Möller et al. | 548/376 |
| 4,198,235 | 4/1980 | Vetter et al. | 430/222 |
| 4,209,526 | 6/1980 | Diana et al. | 514/406 |
| 4,230,481 | 10/1980 | Nishiyama et al. | 71/92 |
| 4,275,073 | 6/1981 | Moberg | 514/406 |
| 4,298,749 | 11/1981 | Plath et al. | 548/377 |
| 4,322,241 | 3/1982 | Pissiotas et al. | 71/94 |
| 4,337,263 | 6/1982 | Techer et al. | 514/376 |
| 4,406,688 | 9/1983 | Konno et al. | 71/92 |
| 4,420,328 | 12/1983 | Rempfler | 71/94 |
| 4,433,046 | 2/1984 | Vemura et al. | 430/385 |
| 4,460,597 | 7/1984 | Yanai et al. | 514/407 |
| 4,477,462 | 10/1984 | Aoyagi | 514/407 |
| 4,500,341 | 2/1985 | Förster et al. | 71/92 |
| 4,529,735 | 7/1985 | Kühle et al. | 514/407 |
| 4,673,429 | 6/1987 | Rieber et al. | 71/27 |

FOREIGN PATENT DOCUMENTS

| | | |
|---|---|---|
| 4628585 | 2/1986 | Australia . |
| 0052333 | 5/1982 | European Pat. Off. . |
| 0203428 | 12/1986 | European Pat. Off. . |
| 0257296 | 3/1987 | European Pat. Off. . |
| 0234045 | 9/1987 | European Pat. Off. . |
| 2513750 | 10/1975 | Fed. Rep. of Germany . |
| 2644588 | 4/1978 | Fed. Rep. of Germany . |
| 0629482 | 8/1949 | United Kingdom . |

OTHER PUBLICATIONS

Elguero et al., *Bull. Soc. Chim. Fr.* 12, 5019–5029 (1968).
Derwent Abstract of Fed. Rep. of Germany Patent Appl. 3602379, published 7-30-87.
Derwent Abstract Japanese Patent 73660/55, published 6/3/80.
Derwent Abstract of Japanese Patent 61358/60 published 5/26/81.
Derwent Abs. of Japanese Patent 212162/57 pub. 12/27/82.
Derwent Abs. of Japanese patent 35036/55 pub. 3/11/80.
Derwent Abs. of Japanese patent 53969/62 pub. 3/9/87.
Derwent Abs. of Japanese Patent 53970/62 pub. 3/9/87.
Freche et al., *Tetrahedron*, 33, 2069–2077 (1977).
Chem. Abstracts selects of Fed. Rep. of Germany Patent 3,602,379 published 7/30/87.
Derwent Abstrast of Japanese Patent 53969/62 pub. 3/9/87.
Kobayashi et al., *Chem. Abstracts*, 83, 394 (1975).
Sandstrom, *Arkiv. Kemi*, 8, 523–544 (1955).
Elguero et al., *Bull. Soc. Chim. Fr.*, 775–776 (1966).

*Primary Examiner*—Mary C. Lee
*Assistant Examiner*—Joseph K. McKane
*Attorney, Agent, or Firm*—Stanley M. Tarter; George R. Beck; Howard C. Stanley

[57] ABSTRACT

The present invention relates to certain novel substituted 3-(4-nitrophenoxy)pyrazoles and their use as herbicides.

38 Claims, No Drawings

SUBSTITUTED 4-(4-NITROPHENOXY) PYRAZOLES AND THEIR USE AS HERBICIDES

RELATED APPLICATIONS

This is a continuation of application Ser. No. 07/175,460, filed on Apr. 13, 1988, now abandoned, which is a continuation-in-part of Ser. No. 59,712 filed June 8, 1987 now abandoned 6-17-88.

FIELD OF THE INVENTION

The present invention relates to certain novel substituted 3-(4-nitrophenoxy)pyrazoles and their use as herbicides.

BACKGROUND OF THE INVENTION

Uncontrolled weed growth continues to be a problem in our environment. In growing crops, uncontrolled weed growth normally results in lower crop yield and reduced crop quality inasmuch as weeds compete with crops for light, water and soil nutrients. Herbicides have been developed to control weed growth. However, many herbicides injure adjacent useful plants at herbicide application rates necessary to control weed growth. Further, many non-selective herbicides have environmental problems.

Plath et al U.S. Pat. No. 4,298,749 discloses certain substituted pyrazole ether derivatives including pyrazole phenyl ethers as having herbicidal activity. However, there still is a need in the art for a class of active, broad-spectrum herbicides.

SUMMARY OF THE INVENTION

The present invention relates to a novel class of substituted 3-phenoxypyrazoles, herbicidal compositions thereof, and their use as herbicides. Applicants have discovered that certain 3-phenoxypyrazole herbicides having a substitution pattern have herbicidal activity and that many of them have exceptionally high herbicidal activity. The unique substitution pattern includes importantly a para-nitro substituent on the phenyl ring. The unique substitution pattern also provides for specific substituents in the 1-, 4- and 5-positions of the pyrazole ring. The phenyl ring also has in one meta position a substituent which is (i) a hydrido radical or, preferably (ii) a substituent other than hydrido having a molecular weight up to about 300. It has been found that it is the unique combination of the para-nitro substituent on the phenyl ring and substituents in the 1-, 4- and 5-positions of the pyrazole ring which provide the class of compounds with herbicidal activity and that the nature of the meta substituent (if any) on the phenyl ring is not critical for the presence of herbicidal activity.

The class of unique compounds is defined as 3-phenoxypyrazoles and agronomically acceptable salts thereof wherein (a) the pyrazole ring has a methyl, ethyl, halomethyl or haloethyl substituent in the 1-position; a hydrido, halo or nitro substituent in the 4-position and a chloro, cyano, halomethyl, haloethyl, methylthio, ethylthio, methylsulfinyl, ethylsulfinyl, methylsulfonyl ethylsulfonyl or methoxymethyl substituent in the 5-position and (b) the phenyl ring has a para nitro substituent and a meta substituent having a molecular weight of up to about 300 and consisting of one or more atoms selected from the group consisting of H, C, Cl, F, Br, I, N, S, O, Si and P. The meta substituent is preferably an organic radical having up to about about 10 and preferably up to about 8 carbon atoms; preferably having a molecular weight of up to about 300, preferably up to about 250, more preferably up to about 200 and having one or more atoms selected from the group consisting of H, C, Cl, F, Br, I, N, S, O, Si and P. More preferably the organic radical has one or more atoms selected from the group consisting of H, C, Cl, F, Br, N, S and O. Preferably the pyrazole ring has a halo substituent in the 4-position, preferably Cl or Br. Preferably the pyrazole ring has a halomethyl, haloethyl, methylsulfinyl, ethylsulfinyl, methylsulfonyl, ethylsulfonyl substituent in the 5-position, more preferably a halomethyl or methylsulfonyl substituent in the 5-position.

The meta organic radical normally will comprise a saturated or unsaturated carbon chain having up to about 10 (preferably up to about 8) carbon atoms which may be linear, branched or cyclic and optionally substituted by a variety of substituents such as halo, nitro, cyano, hydroxy, and the like. The radical has a molecular weight of up to about 300 and preferably up to about 250 (most preferably up to about 200). The carbon chain may be bonded directly to the phenyl ring or through one or more difunctional substituents selected from (i) substituents comprising (or consisting of) one or more heteroatoms selected from the group consisting of N, S, O and P (preferably O and N) and (ii) substituents comprising one or more atoms selected from C and S which are bonded to one or more of said heteroatoms (preferably carbonyl). The carbon chain is optionally interrupted or terminated with one or more substituents selected from (i) substituents comprising one or more heteroatoms selected from the group consisting of N, S, O and P (preferably O, N and S) and (ii) substituents comprising one or more atoms selected from C and S which are bonded to one or more of said heteroatoms (preferably carbonyl or sulfonyl). The heteroatom may optionally be substituted with substituents such as alkyl, alkoxy or the like. The carbon chain may also be optionally substituted with (i) aryl, preferably phenyl or phenylalkyl optionally substituted with substituents such as halo, nitro, cyano, alkoxy, haloalkyl, amino, hydroxy or the like or (ii) a 3 to 7 membered, saturated or unsaturated heterocyclic radical having 1 to 3 heteroatoms selected from the group consisting of N, O and S.

A preferred embodiment of the unique class of the 3-phenoxypyrazoles of the present invention are compounds represented by the Formula I and agronomically acceptable salts thereof:

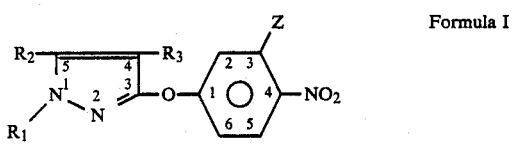

Formula I wherein:

R₁ is methyl, ethyl, halomethyl or haloethyl;
R₂ is chloro, cyano, halomethyl, haloethyl, methylthio, ethylthio, methylsulfinyl, ethylsulfinyl, methylsulfonyl, ethylsulfonyl or methoxymethyl
R₃ is hydrido, halo or nitro; and

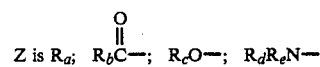

-continued $$R_gO-\underset{\underset{R_f}{|}}{N}=C-, \quad R_hS \quad R_i-\underset{\underset{R_j}{|}}{N}=C- \quad \text{or} \quad R_k- \quad \text{wherein:}$$

$R_a$ is selected from hydrido, hydroxy, halo, cyano, alkyl, alkenyl, alkynyl, unsubstituted or substituted with one or more hydroxy, halo, cyano, alkoxy, amino, alkylamino, alkylthio, phenyl, hydroxycarbonyl, alkylcarbonyl, alkoxycarbonyl, aminocarbonyl, alkylaminocarbonyl, alkylcarbonyloxy, di(alkoxy)carbonyl, di(alkoxycarbonyl), alkoxyalkylaminocarbonyl, alkylsulfinyl, alkylsulfonyl, alkoxycarbonylalkylsulfonyl, phosphonyl and alkylphosphinyl.

$R_b$ is selected from hydroxy, hydrido, halo, alkyl, alkoxy, alkenyloxy, alkynyloxy, phenoxy, benzyloxy, hydrazino, alkylhydrazino, oximino, phenylamino, phenylthio, alkylthio, amino, alkylamino, alkenylamino, alkynylamino, di-, tri- or tetra(alkoxy), di(alkylamino), alkylaminoalkoxy, alkoxyalkylamino, hydroxycarbonyl, alkylaminooxy, alkoxyamino, alkylthioalkoxy, alkylthioalkyl, alkoxyalkyl, alkylsufonylalkoxy, alkylsufinylalkyloxy, alkylsulfonylamino, alkylsulfonylalkylamino, hydroxycarbonylalkylamino, alkoxycarbonylalkyl, alkylcarbonylalkoxy, alkoxycarbonylalkenyloxy, alkoxycarbonylalkoxy, alkoxycarbonylalkylthio, alkylcarbonylamino, aminocarbonylalkylamino, di(alkoxycarbonyl)alkoxy, alkylaminocarbonylalkoxy, hydroxycarbonylalkylamino, alkoxycarbonylalkylamino, alkylcarbonyloxyalkoxy; alkylcarbonyloxydi(alkoxy); alkylcarbonyloxyalkylamino, alkoxycarbonyloxyalkoxy; alkoxyalylcarbonyloxyalkoxy; alkoxycarbonylaminoalkoxy, alkoxycarbonylalkoxyamino, alkoxycarbonylalkylcarbonyloxyalkoxy alkenylaminothiocarbonylamino, alkoxycarbonyloximino, alkoxyoximino, alkylcarbonyloximino, and alkylphosphonylalkoxy;

$R_c$ is hydrido, alkyl, benzyl, alkenyl, alkynyl, alkoxycarbonyl, alkylcarbonyl, alkylsulfonyl, alkylimino, alkoxyimino, alkoxycarbonylimino, Rx-alkyl or Rx-alkenyl wherein Rx is halo, hydroxy, cyano, mono, di-, tri- or tetra(alkoxy), alkynyloxy, alkylamino, alkylthio, alkylsulfinyl, alkylsulfonyl, alkylphosphonyl, alkylphosphinyl, halocarbonyl, alkylcarbonyl, hydroxycarbonyl, alkoxycarbonyl, alkenyloxycarbonyl, benzyloxycarbonyl, phenoxycarbonyl, phenylaminocarbonyl, alkylhydrazinocarbonyl, aminocarbonyl, alkenylaminocarbonyl, alkylaminocarbonyl, benzylaminocarbonyl, thiocarbonyl, phenylthiocarbonyl, alkylthiocarbonyl, alkoxyalkylthiocarbonyl, di(alkoxycarbonyl), alkylcarbonylalkoxycarbonyl, alkylsulfinylalkoxycarbonyl, alkoxycarbonylalkylcarbonyl, alkoxycarbonylalkylaminocarbonyl, hydroxycarbonylalkylaminocarbonyl, di, tri, tetra(alkoxy) carbonyl, alkoxyalkyl, alkenyloxycarbonyl, alkylthioalkoxycarbonyl, alkylaminoalkoxycarbonyl, di(alkylamino)carbonyl, alkoxyalkylaminocarbonyl, alkoxyaminocarbonyl, alkylsulfonylaminocarbonyl, phenylsulfonylaminocarbonyl, alkoxycarbonylcarbonyloxy, alkoxycarbonylalkylcarbonyloxy, alkoxycarbonylamino, alkoxycarbonylalkylthio, alkoxycarbonylalkylaminocarbonyl, alkylcarbonylaminocarbonyl, alkylcarbonyloxydi(alkoxy)carbonyl, alkoxyalkylcarbonyloxydi(alkoxy)carbonyl, alkoxycarbonylcarbonyloxydi(alkoxy)carbonyl, alkoxycarbonylalkylcarbonyloxy-bis(alkoxy)carbonyl, alkoxycarbonylaminoalkoxycarbonyl, alkylsulfonylalkoxy carbonyl, alkylsulfonylaminocarbonyl, alkylphosphonylalkoxycarbonyl, alkoxycarbonyloximinocarbonyl, alkoxyoximinocarbonyl, or alkyloximinocarbonyl.

$R_d$, and $R_e$ are independently selected from hydrido, alkyl, alkenyl, alkynyl, benzyl, phenyl, alkoxy, alkenyloxy, benzyloxy, hydridocarbonyl, alkylcarbonyl, phenylcarbonyl, alkylsulfonyl, aminocarbonyl, alkoxycarbonyl, alkoxyalkyl, alkylthioalkyl, alkylaminoalkyl, alkylsulfonylalkyl, halocarbonylalkyl, hydroxycarbonylalkyl, alkoxycarbonylalkyl, di-, tri-(alkoxy), phenylthioalkyl, di(alkylamino)alkyl, alkylphosphonyl alkyl or alkylsilylalkyl; or $R_d$ is hydrido or alkyl and $R_e$ is amino, alkylamino, phenylamino or alkoxycarbonylalkylamino; or $R_d$ and $R_e$ together are a cycloalkyl chain having 2 to 6 carbon atoms.

$R_g$ is selected from hydrido, alkyl, hydroxycarbonylalkyl, alkoxycarbonylalkyl, alkylaminocarbonylalkyl, alkylthiocarbonylalkyl, di(alkoxy)carbonylalkyl, and di(alkoxycarbonyl)alkyl;

$R_f$ is selected from hydrido, alkyl, and alkoxyalkyl;

$R_h$ is hydrido, halo, alkyl, alkenyl, alkoxy, alkylamino, phenoxy, alkylaminocarbonyl, alkoxycarbonyl, hydroxycarbonylalkyl, alkoxycarbonylalkyl, alkylthio, alkoxycarbonylalkylthio and alkylsilylalkoxycarbonylalkyl or alkylsulfinylamino;

$R_i$ and $R_j$ are independently selected from hydrido, alkyl, alkoxy and alkylamino;

$R_k$ is alkylphosphonyl, alkylaminoimino, alkylsulfinyl, alkylsulfonyl, alkylaminosulfonyl or halosulfonyl.

$R_a$ through $R_j$ can also comprise a heterocyclic substituent selected from triazolyl, morpholinyl, piperidyl, indolyl, piperazinyl, pyrrolidinyl, pyrazolyl, pyrrolinyl, azetidinyl, thienyl, imidazolyl, pyrimidinyl, furyl, pyridyl, tetrahydro2H-pyranyl, pyridinyl, pyrrolidinonyl, indazolyl, furanyl, dioxolanyl, 5,6-dihydro-1,4,2-dioxazinyl, tetrahydrofuranyl, tetrahydro-2-oxofuranyl, 4,5dihydro-4-oxofuranyl, benzimidazolyl, 4,5-dihydrooxazolyl, benzoxazolyl, piperidinyl, aziridinyl, 1H-2,5-dihydropyrrolyl, 1H-isoindole-1,3(2H)-dionyl, furanonyl, thiomorpholinyl, azepinyl or oxocyloalkyl, oxocycloalkenyl.

Preferred compounds of the present invention include compounds wherein $R_1$ is methyl; compounds wherein $R_2$ is halomethyl, methylsulfinyl or methylsulfonyl and most preferably where $R_2$ is halomethyl, especially difluromethyl or trifluoromethyl; compounds wherein $R_3$ is halo especially chloro and bromo.

Preferred compounds of the present invention have a Z which is

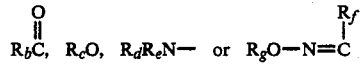

and most preferably $R_cO$ wherein $R_b$, $R_c$, $R_d$, $R_e$, $R_f$ and $R_g$ are as defined hereinabove. Z is preferably selected from alkoxy, haloalkoxy, bis(alkoxy), alkoxycarbonyl, alkoxycarbonylalkoxy, aminocarbonylalkoxy, alkylaminocarbonylalkoxy, alkylsulfonylaminocarbonylalkoxy, alkylamino, hydroxyalkylamino, alkoxyamino, alkoxyalkylamino, hydroxycarbonylalkylamino, and alkoxycarbonylalkyloxyimino.

The nature of the Z substituent is not critical to the presence of herbicidal activity for the unique class of compounds of the present invention. Compounds with other types of Z substituents are as follows:

(a) compounds according the Formula I with a Z substituent as defined above wherein substituents for $R_a$ through $R_k$ are selected from the collective group of substitutents recited above for $R_a$ through $R_k$; and (b) compounds according to Formula I with a Z substituent as defined above wherein $R_a$ through $R_k$ are substituents which comprise one or more radicals selected from carbonyl, oxy, amino, thio, carbonyloxy, carbonylamino, imino, oximino, sulfonyl, sulfinyl, thiocarbonyl, phosphinyl, phosphonyl, hydrazino, and the like and optionally also comprising bridging radicals selected from alkylene, phenyl and the like.

The phenyl ring can be optionally substituted in the other ring positions by one or more noninterferring substituents such as halo (e.g. as an ortho substituent, especially ortho halo) which do not unacceptably diminish the herbicidal activity. Compounds having such substituents are contemplated as equivalents of the compounds claimed herein.

The pyrazole ring can also be substituted in the 1-, 4- and 5-position by other substituents which do not unacceptably interfere with the herbicidal activity of the molecule. These compounds should also be contemplated as equivalents of those claimed herein.

The terms "di-, tri- and tetra-" mean that the referenced groups are polymeric such as di(methoxy) means $CH_3-O-CH_2-O-$.

The term "alkyl" means herein a straight, branched and cyclic radical having 1 to 12 carbon atoms, preferably 1 to 5 carbon atoms and includes, but is not limited to, ethyl, methyl, 2-propyl, 1-ethylpropyl, 1-methylpropyl, n-butyl, 1,1-dimethylethyl, 2,2-dimethylpropyl, pentyl, 2-methylpropyl, 1-methylethyl and dodecyl. The cyclic alkyl radicals include cycloalkylalkyl radicals and alkylcycloalkyl radicals wherein the cyclic group of the radical has from 3 to 6 carbon atoms. Examples of cycloalkyl radicals are cyclopropyl, cyclopropylmethyl, methylcyclopropyl, cyclobutyl and cyclohexyl.

The terms "alkenyl" and "alkynyl" herein mean a straight, branched or cyclic group having 2 to 6 carbon atoms. Examples of such alkenyl groups include ethenyl, 1-propenyl, 2-propenyl, 1-butenyl, 2-butenyl, 3-butenyl, 2-methyll-propenyl, 2-methyl-2-propenyl, 1-methyl-ethenyl, and the like. Examples of such alkynyl groups include ethynyl, 1-propynyl, 2-propynyl, and so forth. The term "halo" is intended to mean fluoro, chloro, bromo or iodo.

The term "haloalkyl" is intended to mean an alkyl radical substituted with one or more halogen atoms preferably selected from bromo, chloro or fluoro. The term "alkoxycarbonyl" is intended to mean

wherein $R_1$ is alkyl which may be substituted by a variety of substituents such as halo, hydroxy, nitro, cyano or the like. The term "alkylamino" is intended to mean $R_1R_mN-$ wherein $R_m$ is hydrido or lower alkyl wherein alkyl may also be substituted with a variety of substituents. The term "alkoxycarbonyl alkyl" is intended to mean

The term "alkylthio" is intended to mean $R_1S-$ and the term "alkylthiocarbonyl" is intended to mean

The term "oximino" is intended to mean

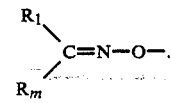

The term "alkylphosphonyl" and "alkylphosphinyl" are intended to mean, respectively

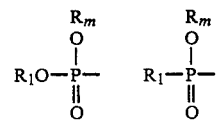

The term "alkylsulfonyl" is intended to mean

The term "alkylsulfinyl" means

The term "imino" is intended to mean $-C=N-$.

Agriculturally acceptable salts of the present invention include alkali, alkaline earth, acid addition, base addition and alkylation salts. Generally, the salts will have suitable cations which include alkali metals such as sodium, potassium, and lithium; alkaline earth metals such as calcium, organic ammoniums and ammonium salts, sulfonium, phosphonium salts, and other salt complexes. Alkylation salts are generally formed by alkylation of nitrogen or sulfur atoms in the molecule.

It has also been observed that the 5-phenoxypyrazole regioisomers of the compounds of the present invention may exhibit herbicidal activity. However, the 3-phenoxypyrazoles of the present invention are substantially more herbicidally active than their corresponding 5-phenoxypyrazole regioisomers. A 3-phenoxypyrazole regioisomer is structurally identical to its corresponding 5-phenoxypyrazole regioisomer except for the location of the substituent on the pyrazole nitrogen. It also has been discovered that the R isomer of compounds having Z as an alkoxycarbonylethylideneoxy substituent are more herbicidally active than the corresponding S isomer compounds.

The alkyl, alkenyl, alkynyl, phenyl and phenylalkyl radicals in the compounds of the present invention represented by Formula I can in turn be substituted by a variety of substituents which will not interfere with the biological activity of the compound in addition to those substituents which are specifically exemplified herein. Suitable substituents include for example substituents such as halo, cyano, nitro, amino hydroxy, haloalkyl, alkoxy, alkylthio, alkylsilyl, sulfonyl, phosphonyl and the like and such radicals in the compounds of the present invention with these substituents are intended to be within the scope of the claims of the present invention. Such substitution will normally only be mono, di or tri substitution ("mono/polysubstitution") on such radicals provided, however, in the case of halo and hydroxy, a greater degree of substitution may be suitable. Further, many of the compounds of the present invention may have more than one possible stereoisomer and structures illustrated are intended to include all such stereoisomers.

The utility of the compounds of this invention as an active ingredient in herbicidal compositions formulated therewith and the method of use thereof will be described below.

DETAILED DESCRIPTION OF THE INVENTION

The procedures described below depict suitable methods whereby the compounds of this invention may be prepared by known chemical procedures from compounds which are known in the art and/or are readily available commercially. These procedures described below are merely illustrative and those skilled in the art will know a variety of other procedures for making the compounds of the present invention.

Compounds of the present invention can generally be prepared by two procedures, Procedure A or Procedure B. Certain compounds of the present invention are prepared by Procedure A in a two-step reaction as follows: (i) reacting 2,4-dichloronitrobenzene with at least two equivalents of the appropriately substituted 3-hydroxypyrazole in a suitable solvent and (ii) reacting the product of (i) with an appropriate nucleophilic reactant selected from oxides, thiolates and amines. Suitable oxides are hydroxide, alkoxides, phenoxides, and the like. Other compounds of the present invention can be prepared from these compounds using known chemical procedures.

The compounds of the present invention can also be prepared by Procedure B by reacting a 3-hydroxypyrazole intermediate with a 4-halonitrobenzene intermediate having the following structure:

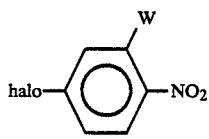

The halo atom on the nitrobenzene is preferably fluoro or chloro. W can be selected from a variety of substituents such as the desired substituent in the phenoxypyrazole product or a displaceable substituent such as fluoro which can be subsequently displaced from the phenoxypyrazole with the desired substituent.

Pyrazole Intermediate

Certain of the 3-hydroxypyrazole intermediates used to make the compounds of the present invention are novel compounds. Such novel 3-hydroxypyrazoles having the following formula:

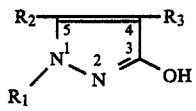

wherein:
$R_1$ is methyl or ethyl;
$R_2$ is halomethyl, haloethyl, methylsulfinyl, ethylsulfinyl or methoxymethyl;
$R_3$ is hydrido or halo.

Examples of such novel 3-hydroxypyrazoles and their melting points are:
5-Trifluoromethyl-3-hydroxy-1-methylpyrazole (130°–131° C.)
5-Difluoromethyl-3-hydroxy-1-methylpyrazole (115°–119° C.)
5-Chlorodifluoromethyl-3-hydroxy-1-methylpyrazole (122°–123° C.)
5-Pentafluoroethyl-3-hydroxy-1-methylpyrazole (119°–124° C.)
5-Trifluoromethyl-4-chloro-3 TM hydroxy-1-methylpyrazole (136°–140° C.)
5-Trifluoromethyl TM 4-bromo-3-hydroxy-1-methylpyrazole (154°–156° C.)
5-Trifluoromethyl-3-hydroxy-1-ethylpyrazole (85.5°–87.5° C.)
5-Trifluoromethyl-4-fluoro-3 hydroxy-1-methylpyrazole (101.5°–102.5° C.)
5-Trifluoromethyl-4-iodo-3-hydroxy-1-methylpyrazole (190°–192° C.)
5-Difluoromethyl-4-fluoro-3-hydroxy-1-methylpyrazole (157°–159° C.)

The 3-hydroxypyrazole intermediates can be conveniently prepared by the following processes.

The pyrazole intermediate is conveniently prepared by reacting an alkylhydrazine with an alkyl 3-haloalkylpropynoate which is in turn prepared generally in accordance with procedures set forth in Huang et al. Scientia Sinica 25, 21 (1982). The Huang phosphorane intermediate can be prepared by reacting (carbethoxymethyl)triphenylphosphonium bromide with trifluoroacetic anhydride in the presence of triethylamine and tetrahydrofuran.

The 5-trifluoromethyl-3-hydroxy-1-methyl-pyrazole intermediate may also be conveniently prepared by reacting ethyl 4,4,4-trifluoro-2-butynoate with methylhydrazine in a suitable solvent such as methylene chloride or methanol/water at a low temperature from about −78° C. to about −20° C. The reaction at higher temperatures will result in a mixture of the 3-hydroxy and 5-hydroxypyrazole isomers. It is believed that reduced temperatures and more polar solvents provide greater amounts of the desired 3-hydroxy isomer of the pyrazole. Prior to reacting the pyrazole with the nitrobenzene, it is generally preferred to purify the pyrazole to separate out the 5-hydroxypyrazole isomer. This purification can be easily accomplished by stirring the isomer mixture product in an aqueous solution of sodium bicarbonate. The 5-hydroxy isomer is dissolved into solution while the 3-hydroxy isomer remains in suspension and is readily separated.

An alternative method of forming 5-trifluoromethyl-3-hydroxy-1-methylpyrazole involves reacting ethyl 4,4,4-trifluoroacetoacetate in acetone with preferably triethylmethylammonium methylsulfate or with dimethyl sulfate in the presence of anhydrous potassium carbonate to form 3-methoxy-4,4,4-trifluoro-2-butenoic acid ethyl ester. This ester is then reacted directly with methylhydrazine to form the 3- and 5-hydroxy isomer mixture of the intermediate pyrazole. The desired isomer can be separated as described above. Alternatively, 2,4,4 trifluoroacetoacetate can be reacted in a like manner to give 1-methyl-3-hydroxy-4-fluoro-5-difluoromethylpyrazole.

Another method of making the 3-hydroxypyrazole involves reacting the ethyl 4,4,4-trifluoroacetoacetate directly with the methylhydrazine in ether to form a mixture of intermediates, 5-hydroxypyrazolidin-3-one and 3-hydroxypyrazolidin-5-one and dehydration of these intermediates by the addition of sulfuric acid in chloroform to form a mixture of the 3- and 5-hydroxypyrazoles. The desired isomer can be separated as described above.

Referring to Procedure I below, a preferred process for making 3-hydroxypyrazoles comprises reacting 3-(amino or substituted amino)-2-alkenoic acid or acid derivative with an alkyl substituted hydrazine. Suitable alkenoic acid derivatives included esters, thioesters and amides. In Procedure I, Y is hydrido or halo, preferably fluoro and R is hydrido, alkyl or phenyl, preferably hydrido. The alkenoic acid can also have a halo substituent in the 2-position.

The alkenoic acid can be substituted by noninterfering substituents known to those skilled in the art such as halo, nitro, hydroxy, and the like and the use of a reactant with such non-interfering substituents is contemplated as equivalent to the process of the present invention. Sterically hindered amines such as diethylamine and morpholine result in side reactions without product formation.

To form the 3-hydroxypyrazole, the 3-amino-2-alkenoic acid derivative can be reacted neat with the substituted hydrazines. Optionally, the reactants can be dissolved in suitable solvents. The reaction is generally run at temperatures from about 0° to about 200° C. preferably about 60° to about 100° C. for a period of about 1 to about 24 hours. The reaction will result in forming the corresponding 3-hydroxypyrazole as the product with some amount of 5-hydroxypyrazole present.

A preferred method of forming the 5-trifluoromethyl-3-hydroxy-1-methylpyrazole involves bubbling ammonia gas through ethyl 4,4,4-trifluoroacetoacetate at an elevated temperature of about 55° to 85° C. while removing water to form 3-amino-4,4,4-trifluoro-2-butenoic acid ethyl ester. This ester is then reacted directly with methylhydrazine at a temperature of about 60° to 100° C. to form the 3- and 5-hydroxy isomer mixture of the intermediate pyrazole. The desired isomer can be separated as described above.

Pyrazole intermediates having a 5-alkylthio (e.g., methylthio) and a 4-halo (e.g., chloro) substituent can be made by reacting methylhydrazine with 3-methylthio-2,3-dichloroacrylate and potassium carbonate in a suitable solvent. The corresponding phenoxypyrazole can be made by reacting the pyrazole with a 4-halonitrobenzene according to Procedure B.

The corresponding phenoxypyrazole having either a 5-alkylsulfinyl or a 5-alkylsulfonyl substituent can be made by oxidation of the corresponding 5-alkylthiophenoxypyrazole with appropriate amounts of a suitable oxidizing agent such as m-chloroperbenzoic acid in a suitable solvent such as dichloromethane.

Pyrazole intermediates having a 5-alkylthio (e.g., methylthio) and a 4-hydrido substituent can be made by a three-step process comprising (i) reacting 1-methyl-3-alkylsilyloxypyrazole in anhydrous tetrahydrofuran with n-butyl lithium at −78° C.; (ii) adding dimethyldisulfide to the solution obtained in (i); and (iii) reacting the product of (ii) with HF in acetonitrile. Corresponding sulfinyl and sulfonyl compounds are made according to the above procedures.

Except as described below, other pyrazole intermediates can be prepared generally in accordance with these procedures. The 1-ethylpyrazoles are also prepared generally in accordance with these procedures. The ethylhydrazine is conveniently liberated from its oxalate salt in situ with a suitable base (e.g., triethylamine or sodium methoxide) during the reaction. Phenoxypyrazoles having N-bromodifluoromethyl or N-difluoromethyl substituents are made by reacting dibromodifluoromethane or chlorodifluoromethane, respectively, with a phenoxypyrazole having a N-hydrido substituent which is made from the corresponding N-tetrahydropyranylpyrazole. Phenoxypyrazoles having N-trifluoromethyl substituents are made by reacting a N-bromodifluoromethylphenoxypyrazole with with AgBF$_4$.

Procedure I

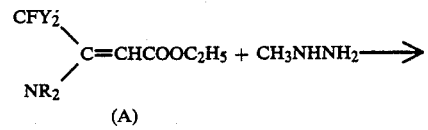

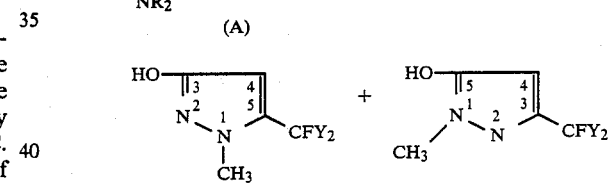

The 5-haloalkyl-3-hydroxypyrazole intermediates can be chlorinated or brominated to form the corresponding 5-haloalkyl-4-halo-3-hydroxypyrazole intermediate. Suitable chlorinating/brominating agents include bromine, chlorine, sulfuryl chloride and sulfuryl bromide. Preferred chlorinating/brominating agents are 1,3-dichloro-5,5-dimethylhydantoin and 1,3-dibromo-5, 5-dimethylhydantoin in a solvent such as diethyl ether.

The 5-haloalkylpyrazole can also be nitrated and in some cases, chlorinated or brominated after the phenoxypyrazole is formed by reaction with sulfuryl halide or 1,3-dihalo-5,5-dimethylhydantoin in a suitable solvent such as acetonitrile. Nitration is accomplished using standard nitration chemistry under controlled nitration conditions. Phenoxypyrazoles having Z as R$_c$O may experience some side reactions.

The 5-haloalkylpyrazole intermediates having a 4-fluoro, a 4-iodo, a 5-fluoromethyl or a 5-trichloromethyl substituent are made in a different manner. The pyrazole intermediate having a 4-fluoro substituent is made by reacting ethyl trifluoroacetate with ethyl fluoroacetate neat and a strong base, such as sodium hydride, to give ethyl 2,4,4,4-tetrafluoroacetoacetate which is sequentially reacted with (i) dimethylsulfate in the presence of potassium carbonate and (ii)

methylhydrazine to form the corresponding 4-fluoropyrazole. The 4-iodopyrazole is formed from the corresponding 4-bromopyrazole. In order to protect the 3-hydroxy group the 4-bromopyrazole is reacted with trialkylsilylchloride and a base. The resulting 3-trialkylsiloxy-4-bromopyrazole is then sequentially reacted with (i) n-butyl lithium at −78° C. in THF; (ii) iodine and (iii) aqueous HF in acetonitrile to form the 4-iodopyrazole intermediate. Pyrazole intermediates with a 5-fluoromethyl substituent are made from the corresponding 5-methoxycarbonylpyrazole which is in turn prepared by reacting dimethyl acetylenedicarboxylate with methylhydrazine in ether. The 5-methoxycarbonylpyrazole is sequentially reduced with lithium aluminum hydride and fluorinated with dimethylaminosulfur trifluoride (DAST) to form the 5-fluoromethylpyrazole intermediate. The 5-trichloromethylpyrazole can be made by suitable processes known to those skilled in the art such as by chlorination. The 4,5-dichloro-3-hydroxy-1-methylpyrazole intermediate is prepared from methyl 2,3,3,-trichloroacrylate and methylhydrazine. The 5-methoxymethyl-4-chloro-1-methylpyrazole intermediate is made by reacting the 5-lithio-4-chloro-3-trialkylsiloxy-1-methylpyrazole and bromomethyl ether with subsequent desilylation. The invention compounds having a 5-cyano substituent on the pyrazole ring are made from phenoxypyrazoles having a 5-hydrocarbonyl substituent. The compounds having the 5-hydrocarbonyl are made via lithiation chemistry as noted above by reaction with dimethylformamide. The 5-hydrocarbonyl phenoxypyrazole is then reacted with hydroxylamine and acetic anhydride to give the corresponding 5-cyano.

Those skilled in the art will appreciate that the 3-hydroxypyrazoles may exist in either of their tautomeric structures (the 3-hydroxypyrazole or the pyrazolidin-3-one) and the 3-hydroxy pyrazole structure used herein is intended to mean both tautomeric structures.

Nitrobenzene Intermediates

The intermediate 2-(alkoxy or alkoxycarbonylalkoxy)-4-fluoronitrobenzenes are prepared from 2-hydroxy-4-fluoronitrobenzenes which are either commercially available or are prepared by reacting 2,4-difluoronitrobenzene with sodium hydroxide in DMSO and extracting the product, from water with hexane. To form intermediate nitrobenzenes having an alkoxy or a haloalkoxy W substituent, the 2-hydroxy-4-fluoronitrobenzene is reacted with an appropriate alkylating agent (e.g., alkyl iodide, chlorodifluoromethane or alkylsulfonate) in a suitable solvent (e.g., acetone, acetonitrile, dimethylformamide (DMF) or dimethylsulfoxide (DMSO) in the presence of a base (e.g., potassium carbonate or sodium hydroxide) for an extended period (e.g., 2 to 3 days). The reaction can be run at room temperature or at higher temperatures. An alternative procedure for making a nitrobenzene intermediate having an alkoxy or alkylthio W substituent is to react 2,4-difluoronitrobenzene with sodium alkoxide or sodium alkylthiolate in a suitable solvent. The intermediate nitrobenzene is then isolated by standard laboratory techniques.

The intermediate nitrobenzenes with the alkoxycarbonylalkoxy W substituent are formed from 2-hydroxy-4-fluoronitrobenzene. 2-Hydroxy-4-fluoronitrobenzene is reacted with a haloalkylcarboxylate (e.g., ethyl 2-bromopropionate) in a suitable solvent (e.g., acetone, acetonitrile, DMF, or DMSO) in the presence of a base (e.g., potassium carbonate) for an extended period (e.g., 3 days). The intermediate nitrobenzene is then isolated by standard laboratory techniques.

A procedure for making a nitrobenzene intermediate having an alkoxycarbonyl W substituent is to esterify the corresponding commercially available 5-chloro-2-nitrobenzoic acid.

The intermediate 4-fluoro-2-alkylaminonitrobenzenes are prepared by reacting the 2,4-difluoronitrobenzene with the appropriate amine in a suitable solvent such as methanol with triethylamine. The desired isomer is separated by standard laboratory procedures. 4-Fluoronitrobenzene intermediates with an alkoxyamino substituent are made by reaction with the appropriate hydrogen chloride alkoxyamine salt in base. The 4-fluoro-2-hydrazinonitrobenzenes are made in a similar fashion.

Invention Compounds–General Procedure

Certain compounds of the present invention are prepared using Procedure A in a two-step reaction. The first step involves reacting 2,4,dichloronitrobenzene with a two molar excess of the appropriate 3-hydroxypyrazole in a suitable solvent such as DMSO or DMF with potassium carbonate under nitrogen at an elevated temperature. The product of step one, [2,4-bis(-pyrazolyloxy)nitrobenzene] is then reacted with a nucleophilic reactant in a suitable coordination solvent generally in the presence of a base. Suitable nucleophilic reactants include hydroxides, organic oxide salts, enolates, thiolates, ammonia, and primary and secondary amines, hydrazines and cyanide. Suitable nucleophilic reactants are cyano, hydroxy, alkoxy, thio, alkylthio, amino, alkylamino, hydrazino, alkylhydrazino, alkoxyamino, and alkylaminooxy which are unsubstituted or substituted with one or more substituents selected from alkoxy, alkylamino, alkylthio, alkoxyalkyl, alkylaminoalkyl, alkylthioalkyl, halo, cyano and nitro.

Generally, it is convenient to form the organic oxides and thiolates as salts in a strong base for the reaction to proceed at a suitable rate. Suitable bases include alkali metal bases, such as sodium or potassium hydroxide or carbonates. Primary and secondary amine nucleophilic reactants can be reacted with suitable bases such as potassium carbonate and in some cases, without a base.

In the process the pyrazole radical is substituted on N and/or any C by a variety of noninterfering substituents known to those skilled in the art. The nature of such non-interfering substituents is not important provided that they do not unduly interfere with the reaction. Nucleophilic reactants which are more sterically hindered or have a carboxylic ester radical may interfere with the reaction, Suitable solvents for the process of the present invention are coordination solvents which are capable of solvating alkali and alkaline cations such as $Li^+$, $Na^+$, $K^+$, $Mg^{++}$ and include ethereal solvents and hindered alcohols. Suitable coordination solvents include t-butylalcohol, isopropyl alcohol, glyme, DME, THF and dioxane.

In the process, the reactants are mixed at a temperature from about 50° to about 120° C. preferably about 70° to about 85° C. for a period of time of about 4 to about 40 hours. The 4-(pyrazolyloxy)nitrobenzene product can be separated from the reaction mixture by standard chemical procedures, e.g., by extraction.

Other compounds of the present invention are prepared using Procedure B by reacting an appropriate pyrazole intermediate with an appropriate halonitrobenzene intermediate to give the desired product generally in accordance with Procedure B below.

Procedure B

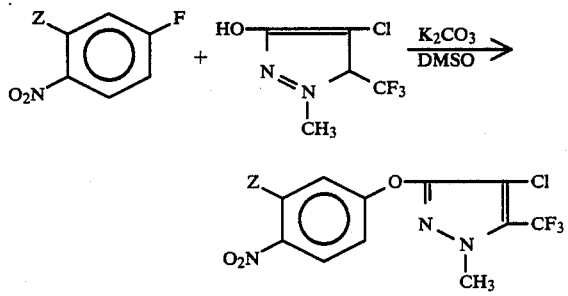

The pyrazole and halonitrobenzene are mixed together in the presence of a base such as potassium carbonate or potassium hydroxide in a suitable solvent such as DMSO, DMF or sulfolane at an elevated temperature of about 20° C. to about 150° C., conveniently at about 50° C. to about 80° C. The product is then isolated by standard laboratory procedures.

A. Invention Compounds having $R_cO$ as a Z Substituent

Compounds of the present invention having an $R_cO$ such as an alkoxy substituent can be formed by reacting an alkali alkoxide such as sodium methoxide with the corresponding 2,4-bis(pyrazolyloxy)nitrobenzene in accordance with Procedure A. Compounds of the present invention having an $R_cO$ such as alkoxy or alkoxycarbonylalkoxy as a Z substituent on the phenyl ring can be prepared by reacting the appropriate pyrazole intermediate with a halonitrobenzene intermediate having either an alkoxy or alkoxycarbonylalkoxy W substituent generally in accordance with Procedure B. Lastly, compounds having an $R_cO$ as Z generally can be prepared by reacting the appropriate $R_cOH$ with the corresponding phenoxypyrazole having a Z fluoro substituent or $R_cX$ (where X is (i) halo selected from Cl, I or Br or (ii) X is $CH_3SO_2O$—) with the corresponding phenoxypyrazole having a Z hydroxy substituent.

Compounds having a hydroxy Z substituent are made by (a) reacting 2-methoxy-4-fluoronitrobenzene in accordance with Procedure B followed with demethylation with boron tribromide or (b) sequentially reacting the appropriate pyrazole with 2-(methylcarbonyloxy)-4-chloronitrobenzene in accordance with Procedure B and then hydrolysis by standard laboratory procedures. Compounds having alkoxycarbonylalkoxy as Z can also be made by reacting a haloacetate with a phenoxypyrazole having Z as a hydroxy. Compounds having Z as alkylaminoalkoxy can be made by reacting a phenoxypyrazole having Z as fluoro with a tertiary amine having a hydroxyalkyl substituent. Compounds having Z as alkylthioalkoxy, alkylsulfonylalkoxy and alkylphosphinylalkoxy are made in a like manner. A great variety of compounds of the present invention can be made by standard esterification of the corresponding acid chloride where Z is $-O-CH(R)(CH_2)_n-COCl$. Compounds of the present invention having an alkylcarbonylalkoxy as a Z substituent are formed by reacting an appropriate pyrazole intermediate with a nitrobenzene which has a corresponding ketal radical as a W substituent to protect the alkylcarbonylalkoxy group during the reaction. After forming the phenoxypyrazole product, acid is added to the reaction mixture to hydrolyze the ketal to give the corresponding alkylcarbonylalkoxy radical as a Z substituent. Compounds having Z as alkenyloxy can be made by dehydrobromination of the corresponding haloalkoxy compound which can be prepared by Procedure A. Compounds having Z as an alkylimino are made by reacting an invention compound with a Z fluoro with ketoxime. Example 877 is made by reacting an invention compound with Z cyanoalkoxy with hydroxylamine. Example 874 is made by protection of two hydroxy groups of a triol as a ketal with subsequent hydrolysis. Compounds of the present invention having a phosphinyl Z substituent are made by the sequential reactions of (i) reacting a phosphonite with an aldehyde, (ii) reacting the product of (i) with trifluoromethanesulfonic anhydride (iii) reacting the the product of (ii) with 2-hydroxy-4-fluoronitrobenzene and (iv) reacting the product of (iii) according to Procedure B.

B. Invention Compounds having

as a Z Substituent

Compounds of the present invention having an alkoxycarbonyl as a Z substituent on the phenyl ring are made by reacting the appropriate pyrazole with a 4-halonitrobenzene having an alkoxycarbonyl W substituent generally in accordance with Procedure B.

Compounds of the present invention having the alkoxycarbonyl as a Z substituent are then converted into other compounds of the present invention which have derivative substituents of the alkoxycarbonyl substituent by transesterification or by hydrolysis of the alkoxycarbonyl substituent to form the corresponding carboxylic acid which can be (i) converted to other esters by esterification by standard laboratory procedures by forming the acid chloride and reacting it with the appropriate alcohol provided that hindered alcohols may require reaction with the sodium salt of the alcohol (e.g., alkenyloxycarbonyl substituents) or (ii) converted into aminocarbonyl compounds by sequential formation of the acid chloride and amination by standard laboratory procedures (e.g., alkylaminocarbonyl Z substituents); or (iii) converted into the thioesters by esterification of the acid chloride by standard laboratory procedures (e.g., alkylthiocarbonyl Z substituents); or (iv) converted into sulfonylaminocarbonyl compounds by sequential formation of the acid chloride and amination with a sulfonamide, neat, by standard laboratory procedures (e.g., alkylsulfonylaminocarbonyl as Z substituent) which can be N-alkylated by reaction with methyliodide and potassium carbonate in acetone; or (v) converted into oximinocarbonyl compounds by sequential formation of the acid chloride and reaction with a ketoxime (e.g., oximinocarbonyl as the Z substituent).

Compounds wherein $R_b$ is alkyl are made by reacting a 4-fluoronitrobenzene intermediate having a 2-alkylcarbonyl substituent in accordance with Procedure B. Compounds where $R_b$ is an alkoxyalkyl are made in the same manner wherein the nitrobenzene intermediate is made by reacting alkoxyalkylnitrile with 3-fluorophenyl magnesium bromide with subsequent nitration. Compounds wherein $R_b$ is an oximino are prepared by reacting the corresponding acid chloride with N-hydroxyethyl acetimidate. Compounds wherein $R_b$ is hydroxycarbonyl can be made by oxidizing the corresponding phenoxypyrazole having a Z methylcarbonyl substituent with selenium dioxide. Compounds wherein $R_b$ is poly(alkoxy) are made by reacting the corresponding phenoxypyrazole with a bromoether or bromopolyether compound. Example 903 was made by reacting the acid chloride with 2-aminoxypropionic acid hydrochloride. Example 367 was made by reacting the acid chloride with the sodium salt of dimethyl methylmalonate. Example 437 is made by reacting the acid chloride sequentially with (i) potassium thiocyanate and (ii) dipropargylamine.

C. Invention Compounds with $R_a$ as Z Substituent

A variety of compounds having a $R_a$ alkyl substituent can be made by reducing the invention compound with Z as chlorocarbonyl with sodium borohydride to the corresponding benzyl alcohol which, in turn, can be reacted with appropriate reactants to form compounds of the present invention having various types of substituted methyl radicals as Z. For example, the benzyl alcohol can be oxidized to the benzaldehyde. The Z iodomethyl compound is formed by sequentially reacting the benzyl alcohol with (i) methanesulfonyl chloride and (ii) sodium iodide. The compounds where Z is alkylaminoalkyl are made by reacting Z as iodomethyl with the appropriate amine. The Z-bromomethyl and chloromethyl compound can be made by reacting the corresponding alcohol with either phosphorus tribromide or thionyl chloride, respectively, in a suitable solvent. Compounds having a —CX$_2$H as a Z substituent are conveniently made by halogenating the benzaldehyde with a suitable agent such as diethylaminosulfur trifluoride (DAST) or thionyl chloride. The procedure for making other substituted methyl radicals as Z will be known to those skilled in the art.

Compounds having a methyl or trifluoromethyl substituent as a Z substituent on the phenyl ring are made by reacting the appropriate pyrazole intermediate with either 2-methyl-4-halonitrobenzene or 2-trifluoromethyl-4-halonitrobenzene, respectively, in accordance with the Procedure B.

Other invention compounds having an $R_a$ substituent can be made by sequentially reacting the corresponding benzyl alcohol with methanesulfonyl chloride and then with appropriate nucleophiles such as alkoxides, amines or mercaptans in a base. Invention compounds having alkylcarbonyloxymethyl as a Z substituent can be made by reacting the corresponding benzyl alcohol with the appropriate acid chloride. Compounds of the present invention having an alkoxycarbonylmethyl Z substituent are prepared by reacting the appropriate pyrazole with 2-alkoxycarbonylmethyl-4-fluoronitrobenzene generally in accordance with Procedure B. The corresponding acid, ester and amide derivatives can then be made by standard laboratory procedures. Compounds having Z as alkoxycarbonylethyl can be made by reacting the compound with Z amino sequentially with (i) t-butylnitrite and alkenyl substituents can be made from the corresponding Z aldehyde compound generally in accordance with the Wittig reaction. Compounds having an alkynyl Z substituent can be made by reacting the corresponding Z hydroxy compound with trimethylsilylacetylene and bis(triphenylphosphine)palladium chloride. Compounds having Z cyanoalkyl or cyanoalkenyl substituents are made by reacting the corresponding aldehyde with cyanoacetic acid. Compounds having a Z cyano substituent are made from the corresponding 2-nitro-5-halo benzonitrile according to Procedure B. Examples 317 and 319 can be made by reacting the corresponding aldehyde with trichloroacetoacetate and malonic acid, respectively. Compounds having a Z methylthiomethyl substituent can be made by reacting the methanesulfonate of the benzyl alcohol with sodium methyl mercaptan. Example 720 can be made by reacting the corresponding Z fluoro compound with sodium diethylmalonate. Example 825 can be made by reacting the corresponding Z methyliodide with triethylphosphite. Example 322 is made by reacting the benzyl alcohol with dihydro-2H-pyran. Example 520 is made by reacting a compound with Z fluoro with the sodium salt of diethyl methylmalonate. Example 380 can be made by reacting the acid chloride with o-phenylenediamine. Example 896 can be made by reacting the compound with Z as chloromethyl with a reactant prepared from carbon disulfide and potassium ethoxide.

D. Invention Compounds Having an $R_dR_cN$ as a Z Substituent

Compounds of the present invention having an amino or hydrazino Z substituent are prepared by reacting the appropriate amino or hydrazino nucleophilic reactant with (a) 2,4 bis(pyrazolyloxy)nitrobenzene generally in accordance with Procedure A or (b) with 2,4-difluoronitrobenzene to prepare the corresponding 2-amino or 2-hydrazino-4-fluoronitrobenzene or with the corresponding phenoxypyrazole having a Z fluoro substituent generally in accordance with the above displacement procedures. Compound having an aminocarbonylamino Z substituent can be made by reacting an invention compound having Z amino with chlorosulfonylisocyanate. Compounds having an alkylphosphonylalkylamino Z substituent can be made by reacting the corresponding phenoxypyrazole with Z fluoro with diethyl 2-aminoalkylphosphonate.

E. Invention Compounds Having an

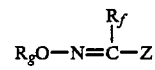

Substituent

Compound of the present invention having an

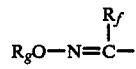

Z substituent can be prepared by two methods. The first method involves reacting a phenoxypyrazole having a methylcarbonyl Z substituent with 2-aminoxyacetic acid. The resulting carboxylic acid can be esterified by refluxing in a suitable alcohol in the presence of an acid catalyst such as toluenesulfonic acid. The acid may also be converted to amides and thioesters through the acid chloride.

These compounds can also be prepared by reacting the phenoxypyrazole having a loweralkylcarbonyl Z substituent with hydroxylamine hydrochloride and alkylation of the resulting oxime. Suitable methods for alkylation include treating the intermediate oxime with an alkyl halide (e.g., methyl iodide or methyl bromoacetate) and potassium carbonate in acetonitrile. The oxime can also be alkylated under standard phase transfer conditions.

F. Invention Compounds having $R_hS$ as a Z Substituent

Compounds of the present invention having $R_hS$ as a Z substituent are made generally following the same procedures used for making compounds having amino Z substituents. Compounds having $R_h$ as alkyl are made by reacting the Z fluorophenoxypyrazole with a mercaptan and the resulting 2 alkylthio-4-fluoronitrobenzene according to Procedure B. Compounds having Z as alkylaminothio, alkoxythio or the like are made by sequentially reacting the corresponding phenoxypyrazole having a Z-fluoro substituent with (i) $Na_2S_2$ to form the disulfide of Example 587 (which can be reduced to Z as HS—), (ii) $Cl_2$ in $CH_2Cl_2$ (to form Z as SCl) and (iii) appropriate thiolate nucleophile such as mercaptans or the like with a base. Compounds having Z as alkylaminosulfonyl are formed in a similar manner except they are chlorinated in aqueous acetic acid. Compounds having Z as alkylaminocarbonylthio are made by reacting the phenoxypyrazole having a Z as HS— substituent with an isocyanate.

G. Invention Compounds having an

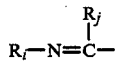

as a Z Substituent

Invention compounds having an imino Z substituent are prepared by reacting the phenoxypyrazole having a Z aldehyde group with an appropriate amine. Example 340 is made by reacting a compound having Z as methylaminocarbonyl sequentially with (i) phosphorous pentachloride and (ii) sodium methoxide. Example 341 is made by reacting the precursor of Example 340 with dimethylamine.

H. Invention Compounds having an $R_k$ as a Z Substituent

Invention compounds having an $R_k$ as a Z substituent can be made by a variety of methods known to those skilled in the art. Suitable methods are as follows. Thiocarbonyl compounds such as amino(thiocarbonyl) as Z can be made by reacting the corresponding carbonyl compound with phosphorus pentasulfide. Compounds having Z as an alkylsulfinyl and alkylsulfonyl can be made by oxidizing the corresponding alkylthio compound with m-chloroperbenzoic acid. Z imino compounds can be made by reacting compounds with Z amino with corresponding carbonyl such that for Example 416 it is reacted with N,N-dimethylformamide dimethyl acetal. Example 522 is made by reacting a compound with Z fluoro with triethylphosphite.

I. Invention Compounds having an Ortho Substituent or as Dimers

Compounds having an ortho halo substituent (ortho to pyrazolyloxy) can be formed by reacting the appropriate pyrazole with 3,4-difluoronitrobenzene or 3,4,6-trifluoronitrobenzene according to Procedure B. The meta fluoro substituent (meta to the pyrazole) can then be displaced with hydroxide or alkoxide to form the corresponding phenol or alkoxide. Invention compounds comprising dimers such as Examples 531 and 681 can be made by reacting invention compounds with a reactive Z substituent such as fluoro or chlorocarbonyl with a bridging reactant such as a diamine or a diol.

The following Examples 1–14 are detailed descriptions of methods of preparation of certain compounds of the present invention. These detailed preparations fall within the scope of, and serve to exemplify, the more generally described methods of preparation set forth above. These Examples are presented for illustrative purposes only and are not intended as a restriction on the scope of the invention. All parts are by weight unless otherwise indicated.

Intermediate Prep.

1-methyl-3-hydroxy-5-trifluoromethylpyrazole

1. A mixture of 33.82 g (0.20 mole) of methyl 4,4,4-trifluoro-3-amino-2-butenoate and 10.1 g (0.22 mole) of methylhydrazine was heated at 50° C. for 22.25 hr. The mixture was then cooled, and 15 ml. of water and about 12 ml. of conc. hydrochloric acid were added to bring the pH of the mixture to 6.5–7.0. The precipitated product was filtered off and dried to obtain 25.26 g (76% yield) of the product m.p. 130.5°–131° C.

2. 30.82 g (0.2 mol) of 4,4,4-trifluoro-3-amino-2-butenamide (prepared by addition of 2 equivalents of ammonia to the corresponding alkenoic ester) was added to 10.1 g (0.22 mol) of methylhydrazine at room temperature. A slight exotherm raised the temperature to 30° C. The mixture was stirred for 1 hr. at which time the mixture became semi-solid; 10 ml. of ethanol was added to improve stirring. After another 1.5 hr., 7 ml. of ethanol was added, again to aid in stirring the mixture. After a total of 24 hr., the mixture was taken up in 25 ml. of water, the pH was adjusted to 6.5–7.0 with conc. hydrochloric acid (17 ml.), and the precipitated product was collected by filtration and dried to obtain 21.37 g (65.3%) of product m.p. 129°–131° C.

3. A 50 ml. flask equipped with mechanical stirrer and reflux condenser was charged with 19.7 g of ethyl 3-methylamino-4,4,4-trifluoro-2-butenoate and 4.8 g of methylhydrazine and heated to 50°–65° C. for 2.75 hr., then to 40°–45° C. for 2 hr., and then allowed to cool to room temperature and stand overnight. The clear reaction mixture was taken up in 15 ml. of water and conc. hydrochloric acid added dropwise to pH 6.0–6.5 which required 5.2 ml. of acid. The precipitated product was collected by filtration and dried to obtain 7.06 g (42.5%) of product m.p. 127°–128.5° C.

PROCEDURE A EXAMPLES

1.

4-(5'-Trifluoromethyl-4'-chloro-1'-methylpyrazolyl-3'-oxy)-2-hydroxynitrobenzene A suspension of 2,4-bis(5'-trifluoromethyl-4'-chloro-1'-methylpyrazolyl-3'-oxy)nitrobenzene (260 g) in 200 ml of t-butylalcohol was heated to reflux, treated with a mixture of 50% sodium hydroxide in water (80 g) and stirred at reflux for 26 hours. An additional 3 g of the 50% sodium hydroxide was added and mixture refluxed for 3 more hours. A portion (⅓) of the alcohol was distilled off and the mixture diluted with water (1500 ml) and 10% HCl to a pH of 9. The precipitate was filtered and dried to give 158 g (94%) of a yellow solid product m.p. 67°–69° C.

2. 4-(5'-Trifluoromethyl-4'-chloro-1'-methylpyrazolyl-3'-oxy)-2-diethylaminonitrobenzene A mixture of 5.2 g (10 mmol) 2,4-bis(5'-trifluoromethyl-4'-chloro-1'-methylpyrazolyl-3'-oxy) nitrobenzene, 0.8 g (11 mmol) of diethylamine, and 1.66 g (12 mmol) of potassium carbonate in 20 ml of t-butanol was heated to reflux and stirred for 90 hours with sequential additions of 0.2 g of amine at the 44 and 66 hour points. The mixture was added to 80 ml of water. The organic layer was diluted with ether and the ether dried and concentrated under vacuum to give 3.89 g of orange oil with refractive index 1.5024.

EXAMPLE 1

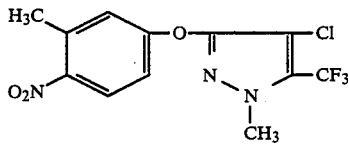

5-Trifluoromethyl-4-chloro-3-(3'-methyl-4'-nitrophenoxy)1-methylpyrazole (a) 3.94g (0.0237 mol) of 5-trifluoromethyl-3-hydroxy-1-methylpyrazole and 3.68g (0.0237 mol) of 4-fluoro-2-methylnitrobenzene were stirred overnight with 3.27 g (0.0237 mol) of potassium carbonate in 20 ml of DMSO (dimethylsulfoxide) at 115° C. The reaction mixture was poured into 400 ml of water, filtered, washed and dried. The solid was recrystalized from methylcyclohexane to give as an intermediate a yellow solid of Example 15 in Table I.

(b) 3.24 g (0.0108 mol) of the product of step (a) was then dissolved in 30 ml of acetonitrile and 1.62 g (0.012 mol) sulfuryl chloride was added to the solution. After about 10 minutes, the reaction solution was poured into a solution of 4 g of sodium bicarbonate in 150 ml of water and extracted twice with ether. The ether extracts were combined, washed twice with brine, dried with magnesium sulfate, decolorized with charcoal and solvent removed by evaporation (rotovaped) to yield 3.0 g (83% yield) of a light yellow solid product of Example 1, m.p. 72°–73.5° C.

| Elemental Analysis for $C_{12}H_9ClF_3N_3O_3$ | | | |
|---|---|---|---|
| | C | H | N |
| Calculated | 42.94 | 2.70 | 12.52 |
| Found | 42.96 | 2.70 | 12.51 |

EXAMPLE 2

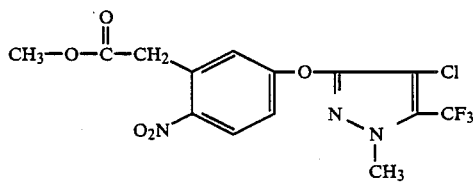

5-Trifluoromethyl-4-chloro-3-(3'-methoxycarbonylmethyl-4'nitrophenoxy)-1-methylpyrazole (a) 8.3 g (0.05 mol) of 5-trifluoromethyl-3-hydroxy-1-methylpyrazole and 11.36 g (0.05 mol) of 4-fluoro-2-ethoxycarbonylmethyl nitrobenzene was stirred and heated at about 50° C. for 40 hours and 75° C. for 17 hours with 7.6 g of potassium carbonate in 40 ml of DMSO. The product was isolated following the procedures of Example 1(a) and purified by high pressure liquid chromatography (HPLC) to give 17.4 g of the yellow solid of Example 29 of Table I.

(b) 12.1 g of the product of step (a) was dissolved in 50 ml of acetonitrile and 3.0 ml of sulfuryl chloride was added to the solution. After 1½ hours, the reaction mixture was poured into a solution of 11 g of sodium bicarbonate in 600 ml of ice water with vigorous stirring. The resulting slurry was filtered, washed twice with water and recrystallized from ethanol to give the yellow solid product of Example 28.

(c) 20.4 g (0.05 mol) of the product of step (b), were dissolved in a solution of 100 ml of ether and 100 ml of THF (tetrahydrofuran) and 22 ml of 2.5N sodium hydroxide was added to the solution. After 20 minutes, the reaction mixture was poured into a solution of 5 ml of conc, HCl in 1 liter of ice water. The product was isolated from the mixture by extracting twice with ether and the ether extracts were combined, washed 2X with brine, dried with $MgSO_4$ and decolorized with charcoal, filtered, and rotovaped. The product was then recrystallized from toluene/methylcyclohexane to give 13 g of the yellow solid of Example 25.

(d) 2.8 g (0.0074 mol) of the product of step (c) was added to 5 ml of oxalyl chloride and 1 drop of DMF (dimethylformamide) was added to the mixture. After stirring overnight, the solution was rotovaped to give a solid. The solid was added to a solution of 1 ml of methanol in 30 ml of pyridine. The product was isolated according to procedures of step (a) and recrystallized from 15% ethyl acetate in hexane to give 1.2 g of a yellow solid, m.p. 112°–115°.

| Elemental Analysis for $C_{14}H_{11}ClF_3N_3O_5$ | | | |
|---|---|---|---|
| | C | H | N |
| Calculated | 42.71 | 2.82 | 10.67 |
| Found | 42.80 | 2.84 | 10.67 |

EXAMPLE 3

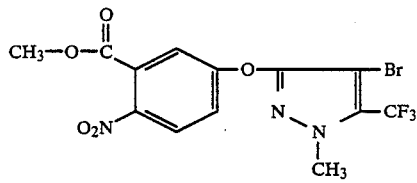

5-Trifluoromethyl-4-bromo-3-(3'-methoxycarbonyl-4'-nitrophenoxy)-1-methylpyrazole (a) 24.9 g (0.15 mol) of 5-trifluoromethyl-3-hydroxy-1-methylpyrazole and 32.4 g (0.15 mol) of 4-chloro-2-methoxycarbonylnitrobenzene were stirred with 20.7 g (0.15 mol) of potassium carbonate in 200 ml of DMSO at 80° C. for 16 hours. The mixture was then added to 3½ liters of ice water, filtered, stirred in a blender with water, filtered and dried to give 42.5 g (82% yield) of an off-white solid of Example 42 of Table I.

(b) 35.4 g (0.10 mol) of the product of step (a) was dissolved in 100 ml of acetic acid and 5.63 ml (0.11 mol) of bromine was added to the solution. The mixture was stirred overnight at 70°–80° C. Then 0.6 ml of bromine was added and the mixture stirred for another 3 hours at 85° C. The product was isolated in accordance with Example 1(b) procedure to give a yellow oil. The product consisted of a mixture of the ester and the acid. To purify the product, the oil was added to 250 ml of ethanol and 85 ml of 10% sodium hydroxide. After 1 hour, the mixture was poured into a solution of 34 ml of conc HCl in 2 liters of ice water. The mixture was extracted with ether and dried, filtered and rotovaped to give a viscous oil. The oil was then recrystallized from hot methylcyclohexane/5–10% toluene with stirring and quick cooling in dry ice to give a white solid of Example 35.

(c) 4.1 g (0.01 mol) of the product of step (b) was mixed overnight with 2 ml (0.023 mol) of oxalyl chloride in 6 ml of methylene chloride and 1 drop of DMF. The mixture was then rotovaped to provide the solid acid chloride product which was then mixed with 0.8 ml (0.02 mol) of methanol in 30 ml of pyridine. After 3 hours, the mixture was rotovaped and the residue stirred with 100 ml of 2N HCl. The product was isolated by ether extraction and rotovaped to give an oil which was stirred with petroleum ether to give 3.7 g (87%) of a white solid, m.p. 72°–73.5° C.

| Elemental Analysis for $C_{13}H_9BrF_3N_3O_5$ | | | |
|---|---|---|---|
| | C | H | N |
| Calculated | 36.81 | 2.14 | 9.91 |
| Found | 36.85 | 2.14 | 9.86 |

EXAMPLE 4

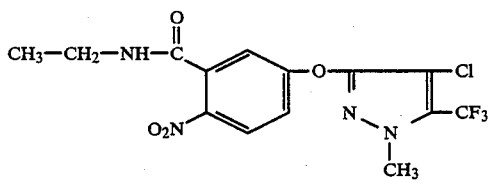

5-Trifluoromethyl-4-chloro-3-(3'-ethylaminocarbonyl-4'-nitrophenoxy)-1-methylpyrazole (a) 24.07 g (0.12 mol) of 5-trifluoromethyl-4-chloro-3-hydroxy-1-methylpyrazole and 27.55 g (0.12 mol) of 4-chloro-2-ethoxycarbonylnitrobenzene were stirred with 18 g of potassium carbonate in 150 ml of DMSO for 1 hour at 110° C. and then overnight at 87° C. The product was isolated in accordance with Example 2 (c) procedure to give the product of Example 46 of Table I.

(b) 59.1 g (0.15 mol) of the product of step (a) was dissolved in 350 ml of ethanol with 80 ml of 2.5N sodium hydroxide. The product was isolated according to Example 2 (c) procedures and recrystalized from toluene/methylcyclohexane to give the product of Example 38 of Table I.

(c) 3.65 g (0.01 mol) of the product of step (b) was mixed overnight with 2 ml (0.023 mol) of oxalyl chloride in 6 ml of methylene chloride and 1 drop of DMF.

The mixture was then rotovaped to give the acid chloride in Example 37 of Table I.

The acid chloride product was then dissolved in 50ml of ether and 40 ml of 50% aqueous ethylamine was added to the solution with stirring. The mixture was rotovaped to give a yellow slurry which was filtered. The solid was triturated with water in a blender, filtered and dried to give 3.5 g (89%) of a white solid, m.p. 129.5°–130.5° C.

| Elemental Analysis for $C_{14}H_{12}ClF_3N_4O_4$ | | | |
|---|---|---|---|
| | C | H | N |
| Calculated | 42.82 | 3.08 | 14.27 |
| Found | 42.76 | 3.14 | 14.06 |

EXAMPLE 5

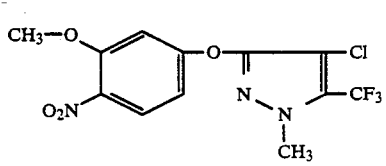

5-Trifluoromethyl-4-chloro-3-(3'-methoxy-4'-nitrophenoxy)-1-methylpyrazole 8.02 g (0.04 mol) of 5-trifluoromethyl-4-chloro-3-hydroxy-1-methylpyrazole and 6.85 g (0.04 mol) of 4-fluoro-2-methoxynitrobenzene were mixed together with 6.22 g (0.045 mol) of potassium carbonate in 50 ml of DMSO for 4 hours at a temperature of 72° C. and overnight at a temperature of 85° C. The product was isolated in accordance with Example 2(c) to give 13.1 g (93% yield) of a yellow solid, m.p. 71°–73.5° C.

Alternative Prep.

1.1 g (2.1 mmol) of 2,4-bis(5'-trifluoromethyl-4'-chloro-1'-methylpyrazolyl-3'-oxy)nitrobenzene and 0.12 g (2.3 mmol) of sodium methoxide were stirred in 8 ml of anhydrous glyme under nitrogen for 5 hours at room temperature and then 1 hour at 70° C. Then 0.05 g and 0.03 g of sodium methoxide were added sequentially and the mixture was stirred overnight at room temperature. The mixture was diluted with 100 mls of ether and the ether was washed with water and brine, dried over magnesium sulfate and concentrated under vacuum to yield 0.72 g of a yellow solid (93% yield) m.p. 74°–76° C.

EXAMPLE 6

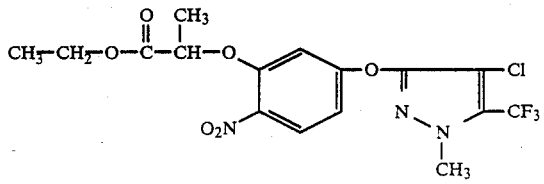

5-Trifluoromethyl-4-chloro-3-(3'-[1-ethoxycarbonyl]-ethoxy-4'-nitrophenoxy)-1-methylpyrazole 961 g (4.80 mol) of 5-trifluoromethyl-4-chloro-3-hydroxy-1-methylpyrazol, 1317 g (5.12 mol) of ethyl 2-(5-fluoro-2-nitrophenoxy)propanoate, and 380 g (2.75 mol) of potassium carbonate were stirred with 6000 ml of DMSO at 70° C. for 20 hours. Another 100 g (0.72 mol) of potassium carbonate was added. After another 16 hours at 70° C. another 163 g (1.18 mol) of potassium carbonate was added. After stirring another 6 hours at 70° C., the product was isolated in accordance with Example 2(c) procedure to give a black oil. Purification by silica gel chromatography gave 1733 g of a dark oil. Further, purification by vacuum distillation (molecular still) gave a reddish oil, which on prolonged standing gave a reddish orange solid, m.p. 40°–44° C.

| Elemental Analysis for $C_{16}H_{15}F_3Cl_1N_3O_6$ | | | |
|---|---|---|---|
| | C | H | N |
| Calculated | 43.90 | 3.45 | 9.60 |
| Found | 43.96 | 3.50 | 9.58 |

EXAMPLE 7

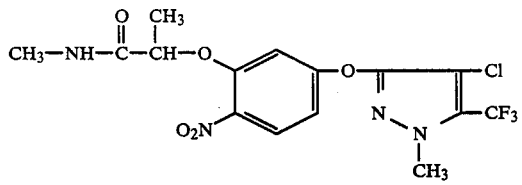

5-Trifluoromethyl-4-chloro-3-(3'-[1-methylaminocarbonylethoxy]-4'-nitrophenoxy)-1-methylpyrazole (a) 49.2 g (0.12 mol) of the product of Example 6 was dissolved in 160 ml of ethanol and 55 ml of 10% NaOH was added with stirring. The solution was rotovaped with the addition of water, washed with ether and then added to a solution of 14 ml of 12N HCl in ice water to give a sticky semi-solid. After standing overnight, the solid was stirred with water, filtered and dried to give 42.9 g of a white solid of Example 115 of Table I.

(b) 2.46 g (0.006 mol) of the product of step (a) was stirred with 6 ml of oxalyl chloride and 1 drop of DMF. After stirring overnight, the solution was decanted from insoluble material and rotovaped to provide the acid chloride of Example 121.

(c) The product of step (b) was dissolved in 20 ml of hexane and 2 ml of ether and 13 ml of 40% aqueous methylamine added to the solution with stirring. After 10 minutes, the solution was filtered, and the solid was washed with water and hexane and dried. The solid was recrystallized from aqueous hot ethanol to give a white solid. The white solid was dissolved in CHCl3, filtered and rotovaped and recrystallied again from aqueous ethanol to give 2.1 g (83%) of a white solid, m.p. 140°–142° C.

| Elemental Analysis for $C_{15}H_{14}ClF_3N_4O_5$ | | | |
|---|---|---|---|
| | C | H | N |
| Calculated | 42.62 | 3.34 | 13.25 |
| Found | 42.76 | 3.36 | 13.44 |

EXAMPLE 8

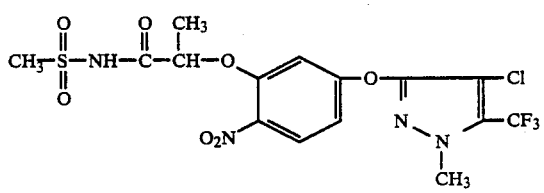

5-Trifluoromethyl-4-chloro-3-(3'-methylsulfamoylcarbonylethoxy-4'-nitrophenoxy)-1-methylpyrazole (a) 10.24 g (0.025 mol) of the product of Example 7(a) was stirred for 3 days in 25 ml of toluene with 10 ml of oxalyl chloride and 1 drop of DMF. The mixture was rotovaped to give the acid chloride intermediate.

(b) 2.61 g (0.0275 mol) of methanesulfonamide was mixed neat with the acid chloride of step (a) at 150° C. for 2 hours. The mixture was crystallized from ethanol to give 8.7 g (71% yield) of a tan solid, m.p. 170.5°–171.5° C.

EXAMPLE 9

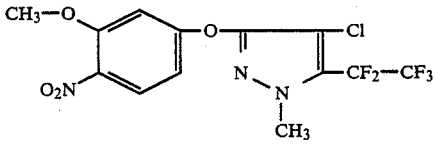

5-Pentafluoroethyl-4-chloro-3'-(3'-methoxy-4'-nitrophenoxy)-1-methylpyrazole 1.88 g (0.0075 mol) of 5-pentafluoroethyl-4-chloro-3-hydroxy-1-methylpyrazole and 1.28 g (0.0075 mol) of 4-fluoro-2-methoxynitrobenzene were stirred in 7.5 ml of DMSO with 1.10 g (0.008 mol) of potassium carbonate at about 85°–90° C. for 18 hours. The reaction mixture was poured into 150 ml of water and washed three times with 50 ml of ether. The ether extracts were combined and extracted twice with 50 ml of brine. The ether mixture was then treated with magnesium sulfate and charcoal, filtered and evaporated. The white solid formed was recrystallized from hexane to give 2.15 g (71% yield) of a white solid product, m.p. 71°–72° C.

| Elemental Analysis for $C_{13}H_9ClF_5N_3O_4$ | | | |
|---|---|---|---|
| | C | H | N |
| Calculated | 38.87 | 2.26 | 10.46 |
| Found | 38.55 | 2.32 | 10.38 |

EXAMPLE 10

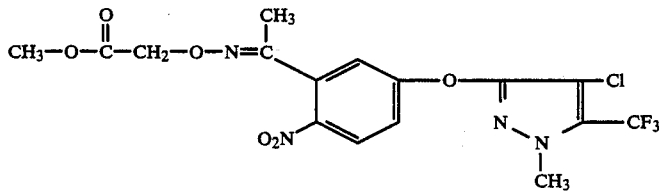

5-Trifluoromethyl-4-chloro-3-(3'-methoxycarbonylmethyloxime-4'-nitrophenoxy)-1-methylpyrazole (a) 350 ml of fuming nitric acid was cooled to −10° C. and added dropwise to 65 g (0.47 mol) of commercially available 3-fluoroacetophenone and stirred for ½ hour at −5° C. The mixture was poured into ice water, filtered, washed with water and recrystallized from aqueous ethanol to give 61 g of a white solid. m.p. 49°-52° C.

(b) 2.75 g (0.015 mol) of the product of step (a) was stirred with 3.01 g (0.015 mol) of 5-trifluoromethyl-4-chloro-3-hydroxy-1-methylpyrazole for 45 minutes at 90° C. The mixture was poured into 400 ml of ice water, filtered, and the solid was washed with water and dried. The solid was then dissolved in ether, washed with brine and MgSO₄ and carbon added. The solution was filtered and rotovaped to give 4.8 g of a yellow solid of Example 44.

(c) 10.91 g (0.03 mol) of the product of step (b) was stirred into 50 ml of cyclohexane and 50 ml of absolute ethanol. To this mixture was added a slurry of 4.17 g of hydroxylamine hydrochloride and 5.7 ml of triethylamine in 75 ml of ethanol. 75 ml of the solvent was distilled off, 75 ml of cyclohexane was added and the solution was refluxed overnight. The mixture was rotovaped, dissolved in CHCl₃, washed with water and brine, stirred with MgSO₄, and charcoal, filtered and rotovaped to give 11.0 g (97% yield) of the product of Example 178.

(d) 19.39 g (0.05 mol) of the product of step (c) was stirred at reflux for 28 hours with 12.24 g (0.08 mol) of methyl bromoacetate, 8.3 g (0.06 mol) of potassium carbonate, 0.5 g (0.003 mol) of potassium iodide in 100 ml of acetonitrile. The mixture was rotovaped and the residues stirred with ether; washed with water and brine; mixed with MgSO₄ and carbon; filtered and rotovaped to give 22.3 g of amber oil. The oil was purified by HPLC (20% ethylacetate in hexane) to give 7.4 g of a yellow oil.

| Elemental Analysis for $C_{16}H_{14}ClF_3N_4O_6$ | | | |
|---|---|---|---|
| | C | H | N |
| Calculated | 42.63 | 3.13 | 12.43 |
| Found | 42.68 | 3.16 | 12.43 |

EXAMPLE 11

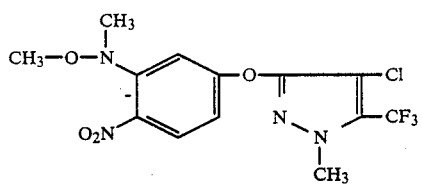

5-Trifluoromethyl-4-chloro-3-(3'-methyl[methoxy]amino4'-nitrophenoxy)-1-methylpyrazole (a) 15.9 g (0.1 mol) of 2,4-difluoronitrobenzene was mixed for 18 days in 50 ml of methanol with 16 ml of triethylamine and 9.75 g (0.1 mol) of N,O-dimethylhydroxyamine hydrochloride. The mixture was concentrated, taken in 400 ml of ether, washed with water and brine, dried over MgSO₄ and solvent removed to give 16 g of compound. The compound was flash chromatographed with hexane/ethylacetate (99:1) to qive 11.8 g of yellow oil.

(b) 2.09 g (0.01 mol) of the product of step (a) was mixed at 90° C. for 19 hours under nitrogen with 2.2 g (0.011 mol) of 5-trifluoromethyl-4-chloro-3-hydroxy-1-methylpyrazole and 1.51 g of potassium carbonate in 15 ml of DMSO. The mixture was poured into water and extracted with ether. The ether was washed with water and brine, dried with MgSO₄ and solvent removed. The product was then flash chromatographed with hexane to give 2.7 g (71%) of orange oil.

| Elemental Analysis for $C_{13}H_{12}ClF_3N_4O_4$ | | | |
|---|---|---|---|
| | C | H | N |
| Calculated | 41.01 | 3.18 | 14.72 |
| Found | 41.09 | 3.19 | 14.71 |

EXAMPLE 12

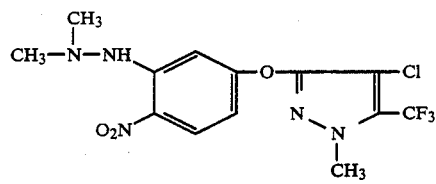

5-Trifluoromethyl-4-chloro-3-(3'-dimethylhydrazino-4'-nitrophenoxy)-1-methylpyrazole (a) 10 g (0.0628 mol) of 2,4-difluoronitrobenzene was stirred for 4 days with 4.36 g (0.0728 mol) of N,N-dimethylhydrazine in 7.08 g of triethylamine and 100 ml methanol. The mixture was concentrated and the resulting solid dissolved in methylene chloride, washed with water and brine, dried with MgSO₄ and concentrated to yield an orange solid. The solid was triturated in 95% ethanol/water, filtered and dried to give 6.1 g 4-fluoro-2-(2,2-dimethylhydrazino) nitrobenzene, m.p. 67°-71° C.

(b) 1.98 g (0.01 mol) of the product of step (a) was mixed with 2.2 g (0.011 mol) of 5-trifluoromethyl-4-chloro-3-hydroxy-1-methylpyrazole and 1.65 g of potassium carbonate in 15 ml of DMSO and heated for 24 hours at 90° C. The mixture was poured into 400 ml of H₂O and extracted with ether. The organic layer was separated, washed with H₂O, brine, dried over MgSO₄ and solvent removed to give 3.7 g of solid, m.p. 72°–76° C.

| Elemental Analysis for $C_{13}H_{13}ClF_3N_5O_3$ | | | |
|---|---|---|---|
| | C | H | N |
| Calculated | 41.12 | 3.45 | 18.44 |
| Found | 41.11 | 3.45 | 18.38 |

EXAMPLE 13

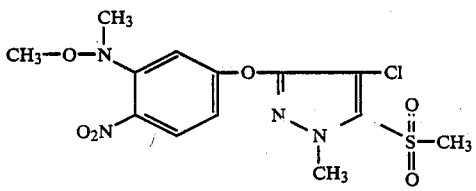

5-Methylsulfonyl-4-chloro-3-[3'-(N-methoxy-N-methylamino)-4-nitrophenoxy]-1-methylpyrazole (1) 3.96 ml of methylhydrazine was added dropwise while stirring to a mixture of 15 g methyl 2,3- dichloro-3-methylthioacrylate and 10.3 g of potassium carbonate in toluene. The mixture was stirred for 18 hours at room temperature and 18 hours at reflux. The mixture was filtered and filtrate was washed with water, dried, evaporated and recystallized from acetone to give 1.8 g of product. The water wash from the filtration was extracted with ethyl acetate and the water layer acidified with 1N HCl, cooled and filtered to give an additional 8.5 gm of product m.p. 164°–166° C.

(2) 8 g of Step 1 product, 9 g of 2-(N-methoxy-N-methylamino)4-fluoronitrobenzene, 6.5 g of potassium carbonate in 15 ml of dimethylsulfoxides was stirred at 80° C. for 15 hours. The mixture was poured into 300 ml of water and the precipitate collected and recystallized from methylcyclohexane to give 9.83 g of an off-white solid (61% yield) m.p. 63°–64° C.

(3) To a solution of 4.26 g of the product of Step 2 (11.88 mmol) in 50 ml of dichloromethane at ice temperature was added 4.51 g (80% technical) m-chloroperbenzoic acid (26.14 mmol) in 50 ml of dichloromethane and the mixture stirred for 15 hours. The mixture was then washed with aqueous sodium carbonate, aqueous sodium thiosulfate and water. The organic layer was dried and recrystallized from ethylacetate petroleum ether to give 4.18 g (90% yield) of product of Example 13 m.p. 133°–135° C.

EXAMPLE 14

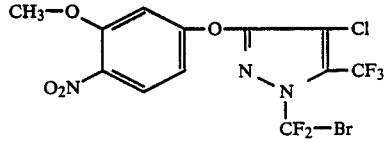

5-Trifluoromethyl-4-chloro-3-(3'-methoxy-4-nitrophenoxy)-1-bromodifluoromethylpyrazole (1) 5.29 g of 5-trifluoromethyl-4-chloro-3-(3'-methoxy-4'-nitrophenoxy)-1-hydridopyrazole (15.7 mmol) was dissolved in 25 ml of anhydrous THF and added to a stirred suspension of 0.45 g of 97% sodium hydride (18.2 mmol) in 25 ml of THF. After hydrogen evolution ceased, 36.3 g of dibromodifluoromethane (170 mmol) was bubbled through the solution over a 20 minute period. A precipitate formed and the reaction was stirred over the weekend. An additional 7.3 g of dibromodifluoromethane (34.8 mmol) was added and the mixture was then diluted with 75 ml of water and 100 ml of ethylacetate. The layers were evaporated and the aqueous layer washed 2 times with 100 ml of ether. The organic layers were combined, dried over magnesium sulfate, filtered and concentrated to give 5.79 g of light brown oil. The oil was combined with oil from previous reaction runs and purified on HPLC with 10% ethylacetate-hexane to give 1.5 g of off-white solid m.p. 61.5°–62.5° C.

| Elemental Analysis for $C_{12}H_6N_3O_4BrClF_5$ | | | |
|---|---|---|---|
| | C | H | N |
| Calculated | 30.89 | 1.30 | 9.01 |
| Found | 31.24 | 1.33 | 9.06 |

Using procedures similar to those set out in detail above, further compounds of the present invention were prepared and are shown in the following Table I. Compounds without melting points are oils. Elemental analysis is given for compounds without other physical properties.

| Ex CP # | Name | Structure |
|---|---|---|
| 15 | 1H-pyrazole 1-methyl-3-(4-nitrophenoxy)-5-(trifluoromethyl)- MP: 36.5–37.0 nD: | 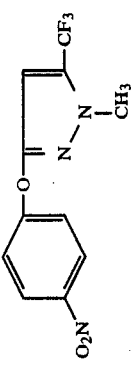 |
| 16 | 1H-pyrazole, 4-chloro-1-methyl-3-(4-nitrophenoxy)-5-(trifluoromethyl)- MP: 79.0–80.0 nD: | 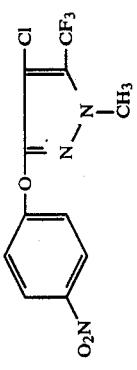 |
| 17 | 1H-pyrazole, 1-methyl-3-(3-methyl-4-nitrophenoxy)-5-(trifluoromethyl)- MP: 70.0–72.0 nD: | 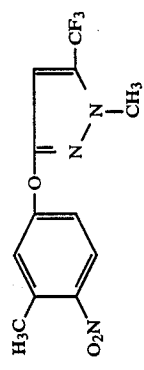 |
| 18 | phenol, 5-[[4-chloro-1-methyl-5-(trifluoromethyl)-1H-pyrazol-3-yl]oxy]-2-nitro- MP: 68.0–70.0 nD: | 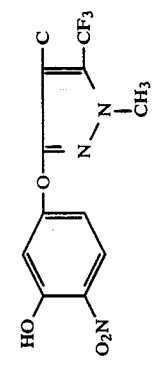 |
| 19 | benzenemethanol, 5-[[4-chloro-1-methyl-5-(trifluoromethyl)-1H-pyrazol-3-yl]oxy]-2-nitro- MP: 118.5–120.0 nD: | 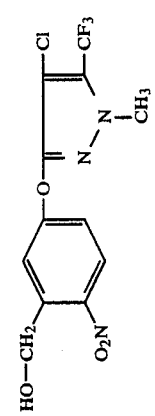 |

-continued

| Ex CP # | Name | Structure |
|---|---|---|
| 20 | 1H-pyrazole, 4-chloro-3-[3-(iodomethyl)-4-nitrophenoxy]-1-methyl-5-(trifluoromethyl)-<br>MP: 102.5–103.0<br>nD: | (structure: 4-nitrophenyl with I-CH$_2$ substituent, O-linked to pyrazole bearing Cl, CF$_3$, N-CH$_3$) |
| 21 | 1H-pyrazole, 4-chloro-3-[3-(difluoromethyl)-4-nitrophenoxy]-1-methyl-5-(trifluoromethyl)<br>MP: 61.0–63.0<br>nD: | (structure: 4-nitrophenyl with H-CF$_2$ substituent, O-linked to pyrazole bearing Cl, CF$_3$, N-CH$_3$) |
| 22 | 1H-pyrazole, 4-bromo-1-methyl-3-[4-nitro-3-(trifluoromethyl)phenoxy]-5-(trifluoromethyl)-<br>MP: 63.0–63.5<br>nD: | (structure: 4-nitro-3-CF$_3$-phenoxy linked to pyrazole bearing Br, CF$_3$, N-CH$_3$) |
| 23 | 1H-pyrazole, 1-methyl-3-[4-nitro-3-(trifluoromethyl)phenoxy]-5-(trifluoromethyl)-<br>MP: 37.0–41.0<br>nD: | (structure: 4-nitro-3-CF$_3$-phenoxy linked to pyrazole bearing CF$_3$, N-CH$_3$) |
| 24 | benzenemethanol 5-[[4-chloro-1-methyl-5-(trifluoromethyl)-1H-pyrazol-3-yl]oxy]-2-nitro-, acetate (ester)<br>MP: 77.5–79.0<br>nD: | (structure: 2-nitrophenyl with CH$_3$-C(=O)-O-CH$_2$ substituent, O-linked to pyrazole bearing Cl, CF$_3$, N-CH$_3$) |

-continued

| Ex CP # | Name | Structure |
|---|---|---|
| 25 | benzeneacetic acid, 5-[[4-chloro-1-methyl-5-(trifluoromethyl)-1H-pyrazol-3-yl]oxy]-2-nitro-<br>MP: 152.0–153.0<br>nD: | 4-chloro-5-(trifluoromethyl)-1-methylpyrazol-3-yl ether of 2-nitro-5-hydroxyphenylacetic acid |
| 26 | benzeneacetic acid, 5-[[1-methyl-5-(trifluoromethyl)-1H-pyrazol-3-yl]oxy]-2-nitro-]methyl ester<br>MP: 59.0–60.2<br>nD: | methyl ester analog |
| 27 | 1H-pyrazole, 4-chloro-3-[3-(methyoxymethyl)-4-nitrophenoxy]-1-methyl-5-(trifluoromethyl)-<br>MP: 68.0–71.0<br>nD: | methoxymethyl aryl ether |
| 28 | benzeneacetic acid, 5-[[4-chloro-1-methyl-5-(trifluoromethyl)-1H-pyrazol-3-yl]oxy]-2-nitro-, ethyl ester<br>MP: 88.0–89.0<br>nD: | ethyl ester with 4-chloro pyrazole |
| 29 | benzeneacetic acid, 5-[[1-methyl-5-(trifluoromethyl)-1H-pyrazol-3-yl]oxy]-2-nitro-, ethyl ester<br>MP: 64.5–65.5<br>nD: | ethyl ester without 4-chloro |

-continued

| Ex CP # | Name | Structure |
|---|---|---|
| 30 | benzeneacetic acid, 5-[[1-methyl-5-(trifluoromethyl)-1H-pyrazol-3-yl]oxy]-2-nitro-, 1-methylethyl ester MP: 55.0–56.0 nD: | 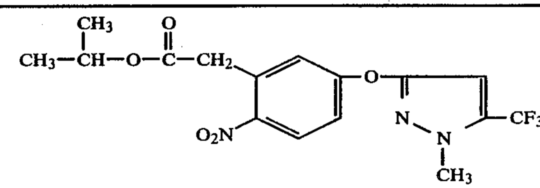 |
| 31 | benzeneacetic acid, 5-[[4-chloro-1-methyl-5-(trifluoromethyl)-1H-pyrazol-3-yl]oxy]-2-nitro-, 2-ethoxyethyl ester MP: nD: 1.5207 | 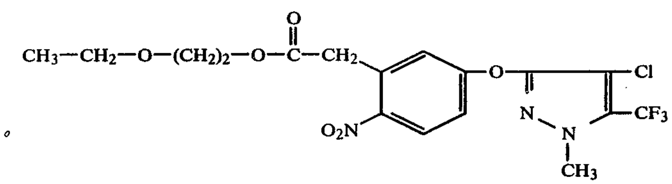 |
| 32 | benzeneacetamide, 5-[[4-chloro-1-methyl-5-(trifluoromethyl)-1H-pyrazol-3-yl]oxy]-N-ethyl-2-nitro- MP: 159.5–161.0 nD: | 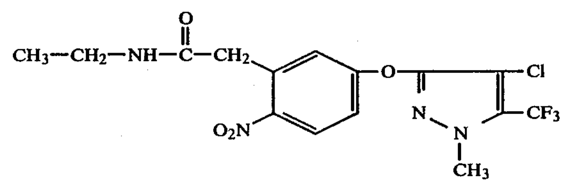 |
| 33 | benzeneacetamide, 5-[[4-chloro-1-methyl-5-(trifluoromethyl)-1H-pyrazol-3-yl]oxy]-N-(2-methoxyethyl)-2-nitro- MP: 112.5–113.5 nD: | 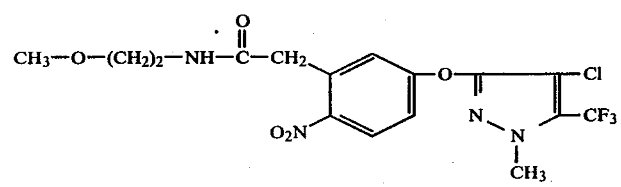 |
| 34 | benzeneacetamide, 5-[[4-chloro-1-methyl-5-(trifluoromethyl)-1H-pyrazol-3-yl]oxy]-N-(3-ethoxypropyl)-2-nitro- MP: 119.0–120.0 nD: | 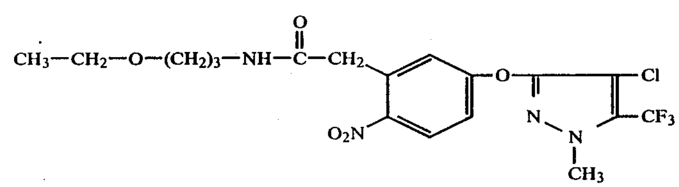 |

-continued

| Ex CP # | Name | Structure |
|---|---|---|
| 35 | benzoic acid, 5-[[4-bromo-1-methyl-5-(trifluoromethyl)-1H-pyrazol-3-yl]oxy]-2-nitro- MP: 127.0–129.0 nD: | 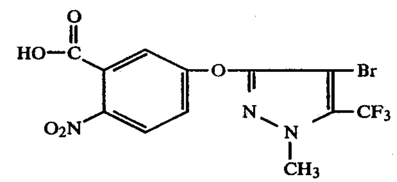 |
| 36 | benzaldehyde, 5-[[4-chloro-1-methyl-5-(trifluoromethyl)-1H-pyrazol-1-yl]oxy]-2-nitro- MP: 86.5–88.5 nD: | 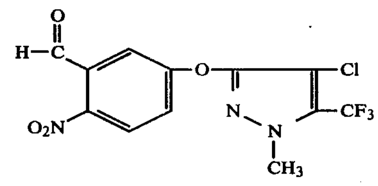 |
| 37 | benzoyl chloride, 5-[[4-chloro-1-methyl-5-(trifluoromethyl)-1H-pyrazol-3-yl]oxy]-2-nitro- MP: 75.0–78.0 nD: | 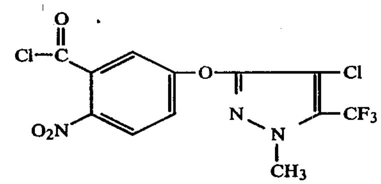 |
| 38 | benzoic acid 5-[[4-chloro-1-methyl-5-(trifluoromethyl)-1H-pyrazol-3-yl]oxy]-2-nitro- MP: 112.5–114.5 nD: | 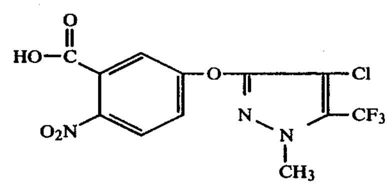 |
| 39 | benzoic acid, 5-[[4-bromo-1-methyl-5-(trifluoromethyl)-1H-pyrazol-3-yl]oxy]-2-nitro-, sodium salt, monohydrate MP: 193.0–195.5 nD: | 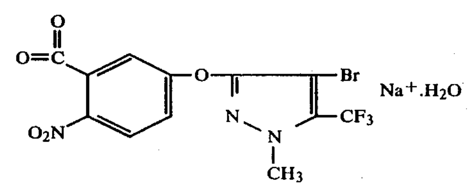 |

-continued

| Ex CP # | Name | Structure |
|---|---|---|
| 40 | benzoic acid, 5-[[4-chloro-1-methyl-5-(trifluoromethyl)-1H-pyrazol-3-yl]oxy]-2-nitro-, sodium salt<br>MP: 185.0–186.0<br>nD: | 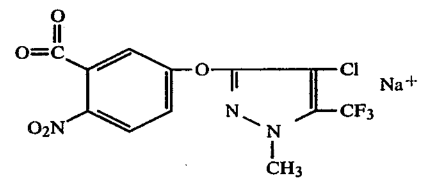 |
| 41 | benzoic acid, 5-[[4-chloro-1-methyl-5-(trifluoromethyl)-1H-pyrazol-3-yl]oxy]-2-nitro-, compound with ethanamine (1:1)<br>MP: 151.0–152.0<br>nD: | 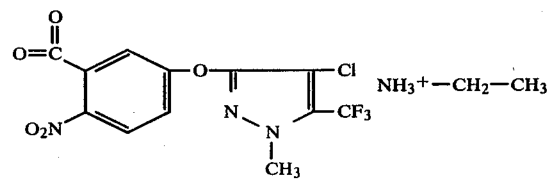 |
| 42 | benzoic acid, 5-[[1-methyl-5-(trifluoromethyl)-1H-pyrazol-3-yl]oxy]-2-nitro-, methyl ester<br>MP: 48.5–50.5<br>nD: | 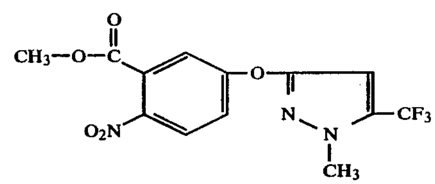 |
| 43 | benzoic acid, 5-[[3-chloro-1-methyl-5-(trifluoromethyl)-1H-pyrazol-3-yl]oxy]-2-nitro-, methyl ester<br>MP: 74.5–76.0<br>nD: | 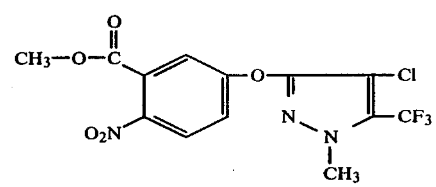 |

-continued

| Ex CP # | Name | Structure |
|---|---|---|
| 44 | ethanone, 1-[5-[[(4-chloro-1-methyl-5-(trifluoromethyl)-1H-pyrazol-3-yl]oxy]-2-nitrophenyl]-<br>MP: 94.0–95.0<br>nD: | Structure with CH₃-C(=O)- and -O₂N on phenyl ether linked to 4-chloro-5-CF₃-1-methylpyrazole |
| 45 | benzoic acid, 5-[[1-methyl-5-(trifluoromethyl)-1H-pyrazol-3-yl]oxy]-2-nitro-, ethyl ester<br>MP: 49.0–50.5<br>nD: | CH₃-CH₂-O-C(=O)- phenyl (2-NO₂) -O- 5-CF₃-1-methylpyrazole |
| 46 | benzoic acid, 5-[[(4-chloro-1-methyl-5-(trifluoromethyl)-1H-pyrazol-3-yl]oxy]-2-nitro-, ethyl ester<br>MP:<br>nD: | CH₃-CH₂-O-C(=O)- phenyl (2-NO₂) -O- 4-Cl-5-CF₃-1-methylpyrazole |
| 47 | benzoic acid, 5-[[(4-bromo-1-methyl-5-(trifluoromethyl)-1H-pyrazol-3-yl]oxy]-2-nitro-, ethyl ester<br>MP: 47.0–48.5<br>nD: | CH₃-CH₂-O-C(=O)- phenyl (2-NO₂) -O- 4-Br-5-CF₃-1-methylpyrazole |
| 48 | benzoic acid, 5-[[(4-chloro-1-methyl-5-(trifluoromethyl)-1H-pyrazol-3-yl]oxy]-2-nitro-, propyl ester<br>MP:<br>nD: 1.5203 | CH₃-(CH₂)₂-O-C(=O)- phenyl (2-NO₂) -O- 4-Cl-5-CF₃-1-methylpyrazole |

-continued

| Ex CP # | Name | Structure |
|---|---|---|
| 49 | benzoic acid, 5-[[1-methyl-5-(trifluoromethyl)-1H-pyrazol-3-yl]oxy]-2-nitro-, 1-methylethyl ester<br>MP: 68.0–69.0<br>nD: | 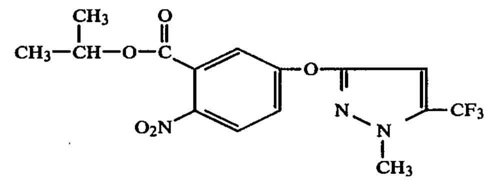 |
| 50 | benzoic acid, 5-[[4-chloro-1-methyl-5-(trifluoromethyl)-1H-pyrazol-3-yl]oxy]-2-nitro-, 1-methylethyl ester<br>MP: 38.0–43.0<br>nD: | 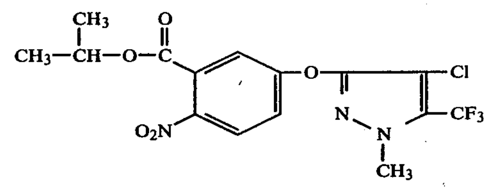 |
| 51 | benzoic acid, 5-[[1-methyl-5-(trifluoromethyl)-1H-pyrazol-3-yl]oxy]-2-nitro-, butyl ester<br>MP: 32.5–34.0<br>nD: | 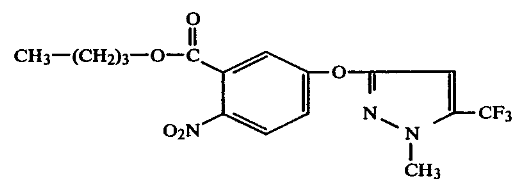 |
| 52 | benzoic acid, 5-[[1-methyl-5-(trifluoromethyl)-1H-pyrazol-3-yl]oxy]-2-nitro-, 1,1-dimethylethyl ester<br>MP: 74.5–78.0<br>nD: | 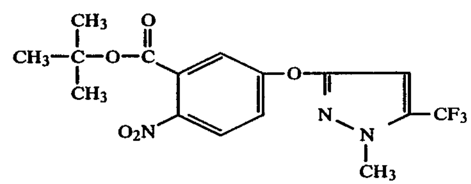 |
| 53 | benzoic acid, 5-[[4-chloro-1-methyl-5-(trifluoromethyl)-1H-pyrazol-3-yl]oxy]-2-nitro-, 1,1-dimethylethyl ester<br>MP: 56.0<br>nD: | 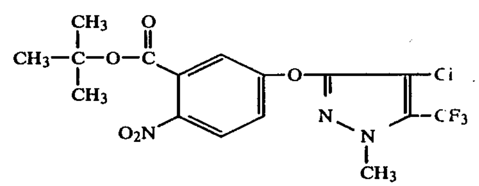 |

-continued

| Ex CP # | Name | Structure |
|---|---|---|
| 54 | benzoic acid, 5-[[4-chloro-1-methyl-5-(trifluoromethyl)-1H-pyrazol-3-yl]oxy]-2-nitro-, 2-methylpropyl ester<br>MP:<br>nD: 1.5158 | CH₃—CH(CH₃)—CH₂—O—C(=O)—[2-nitro-4-(pyrazolyloxy)phenyl] with pyrazole bearing Cl, CF₃, N-CH₃ |
| 55 | benzoic acid, 5-[[4-chloro-1-methyl-5-(trifluoromethyl)-1H-pyrazol-3-yl]oxy]-2-nitro-, pentyl ester<br>MP:<br>nD: 1.5136 | CH₃—(CH₂)₄—O—C(=O)—[2-nitro-4-(pyrazolyloxy)phenyl] with pyrazole bearing Cl, CF₃, N-CH₃ |
| 56 | benzoic acid, 5-[[4-chloro-1-methyl-5-(trifluoromethyl)-1H-pyrazol-3-yl]oxy]-2-nitro-, 3,3,3-trifluoroethyl ester<br>MP:<br>nD: 1.4983 | F₃C—CH₂—O—C(=O)—[2-nitro-4-(pyrazolyloxy)phenyl] with pyrazole bearing Cl, CF₃, N-CH₃ |
| 57 | benzoic acid, 5-[[4-chloro-1-methyl-5-(trifluoromethyl)-1H-pyrazol-3-yl]oxy]-2-nitro-, 2,2,2-trichloroethyl ester<br>MP:<br>nD: 1.5401 | Cl₃C—CH₂—O—C(=O)—[2-nitro-4-(pyrazolyloxy)phenyl] with pyrazole bearing Cl, CF₃, N-CH₃ |

-continued

| Ex CP # | Name | Structure |
|---|---|---|
| 58 | benzoic acid, 5-[[4-chloro-1-methyl-5-(trifluoromethyl)-1H-pyrazol-3-yl]oxy]-2-nitro-, 2,2-dichloroethyl ester MP: 58.0 nD: | 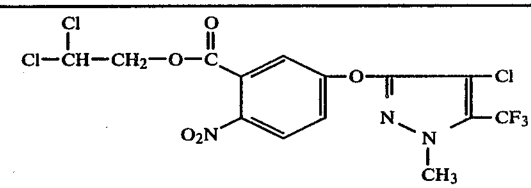 |
| 59 | benzoic acid, 5-[[4-chloro-1-methyl-5-(trifluoromethyl)-1H-pyrazol-3-yl]oxy]-2-nitro-, 2-propynyl ester MP: 58.0–60.0 nD: | 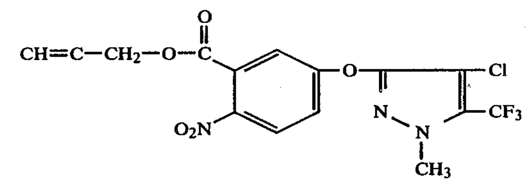 |
| 60 | benzoic acid, 5-[[4-chloro-1-methyl-5-(trifluoromethyl)-1H-pyrazol-3-yl]oxy]-2-nitro-, 2-propenyl ester MP: nD: 1.5304 | 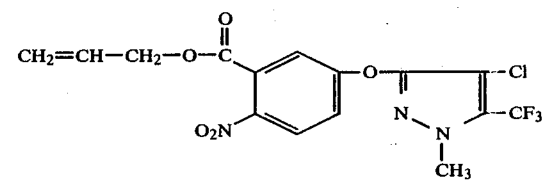 |
| 61 | benzoic acid, 5-[[4-chloro-1-methyl-5-(trifluoromethyl)-1H-pyrazol-3-yl]oxy]-2-nitro-, 3-methyl-3-butenyl ester MP: nD: 1.5245 | 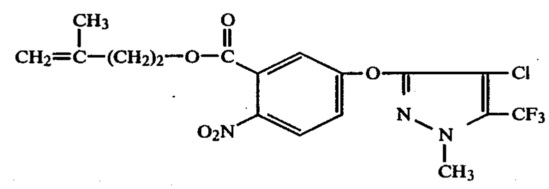 |
| 63 | benzoic acid, 5-[[4-chloro-1-methyl-5-(trifluoromethyl)-1H-pyrazol-3-yl]oxy]-2-nitro-, phenylmethyl ester MP: 66.0 nD: | 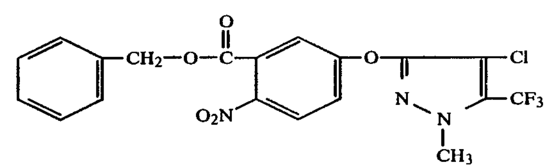 |

-continued

| Ex CP # | Name | Structure |
|---|---|---|
| 64 | benzoic acid, 5-[[4-chloro-1-methyl-5-(trifluoromethyl)-1H-pyrazol-3-yl]oxy]-2-nitro-, 2-methyloxyethyl ester<br>MP: 67.0–70.0<br>nD: | 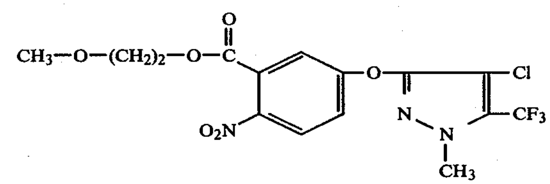 |
| 65 | benzoic acid, 5-[[4-chloro-1-methyl-5-(trifluoromethyl)-1H-pyrazol-3-yl]oxy]-2-nitro-, 2-ethoxy-1-methyl-2-oxoethylester, (S)-<br>MP:<br>nD: 1.5126 | L - ISOMER |
| 66 | benzoic acid, 5-[[1-methyl-5-(trifluoromethyl)-1H-imidazol-3-yl]oxy]-2-nitro-, 2-ethoxy-1-methyl-2-oxoethyl ester<br>MP:<br>nD: 1.5052 | I - ISOMER |
| 67 | benzoic acid, 5-[[4-chloro-1-methyl-5-(trifluoromethyl)-1H-pyrazol-3-yl]oxy]-2-nitro-, 2-butoxy-1-methyl-2-oxoethyl ester<br>MP:<br>nD: 1.5065 | 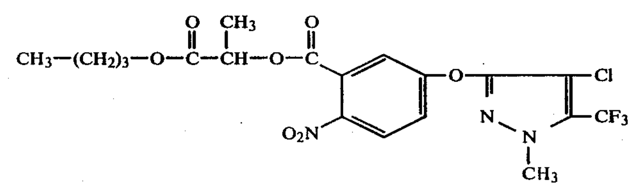 |

-continued

| Ex CP # | Name | Structure |
|---|---|---|
| 68 | benzamide, 5-[[1-methyl-5-(trifluoromethyl)-1H-pyrazol-3-yl]oxy]-2-nitro-<br>MP: 177.0–178.5<br>nD: | 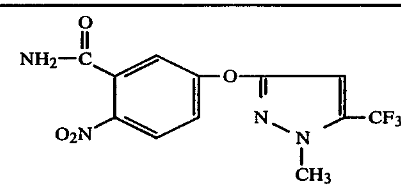 |
| 69 | benzamide, 5-[[4-chloro-1-methyl-5-(trifluoromethyl)-1H-pyrazol-3-yl]oxy]-2-nitro-<br>MP: 188.0<br>nD: | 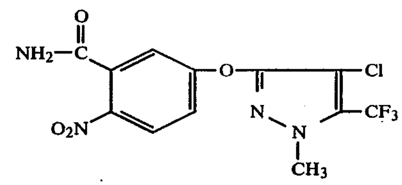 |
| 70 | benzamide, N-methyl-5-[[1-methyl-5-(trifluoromethyl)-1H-pyrazol-3-yl]oxy]-2-nitro-<br>MP: 127.0–128.0<br>nD: | 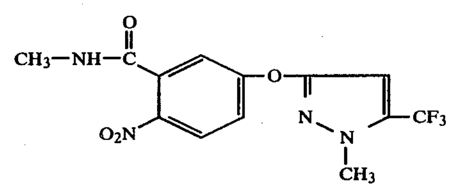 |
| 71 | benzamide, 5-[[4-chloro-1-methyl-5-(trifluoromethyl)-1H-pyrazol-3-yl]oxy]-N,N-dimethyl-2-nitro-<br>MP:<br>nD: | 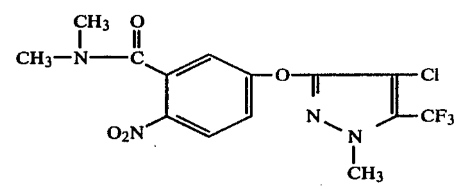 |
| 72 | benzamide, 5-[[4-bromo-1-methyl-5-(trifluoromethyl)-1H-pyrazol-3-yl]oxy]-N-methyl-2-nitro-<br>MP: 161.0–162.5<br>nD: | 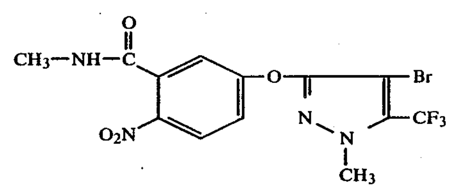 |

-continued

| Ex CP # | Name | Structure |
|---|---|---|
| 73 | benzamide, N-butyl-5-[[4-chloro-1-methyl-5-(trifluoromethyl)-1H-pyrazol-3-yl]oxy]-2-nitro-<br>MP: 140.0–141.0<br>nD: | CH₃—(CH₂)₃—NH—C(=O)—[2-nitro-4-(pyrazolyloxy)phenyl] |
| 74 | benzamide, N,N-diethyl-5-[[1-methyl-5-(trifluoromethyl)-1H-pyrazol-3-yl]oxy]-2-nitro-<br>MP: 84.0–87.0<br>nD: | (CH₃—CH₂)₂N—C(=O)—[2-nitro-4-(pyrazolyloxy)phenyl] |
| 75 | benzamide, 5-[[4-chloro-1-methyl-5-(trifluoromethyl)-1H-pyrazol-3-yl]oxy]-2-nitro-N-2-propenyl-<br>MP: 116.0–116.5<br>nD: | CH₂=CH—CH₂—NH—C(=O)—[2-nitro-4-(pyrazolyloxy)phenyl] |
| 76 | benzamide, 5-[[4-chloro-1-methyl-5-(trifluoromethyl)-1H-pyrazol-3-yl]oxy]-2-nitro-N-2-propynyl-<br>MP: 160.0–161.0<br>nD: | CH≡C—CH₂—NH—C(=O)—[2-nitro-4-(pyrazolyloxy)phenyl] |
| 77 | benzamide, 5-[[4-chloro-1-methyl-5-(trifluoromethyl)-1H-pyrazol-3-yl]oxy]-N-(3-ethoxypropyl)-2-nitro-<br>MP: 110.5–112.5<br>nD: | CH₃—CH₂—O—(CH₂)₃—NH—C(=O)—[2-nitro-4-(pyrazolyloxy)phenyl] |

-continued

| Ex CP # | Name | Structure |
|---|---|---|
| 78 | benzamide, 5-[[4-chloro-1-methyl-5-(trifluoromethyl)-1H-pyrazol-3-yl]oxy-N-methoxy-2-nitro- MP: 146.5-147.5 nD: | 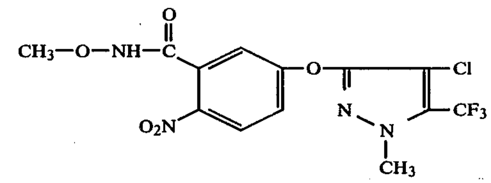 |
| 79 | benzenecarbothioic acid, 5-[[4-chloro-1-methyl-5-(trifluoromethyl)-1H-pyrazol-3-yl]oxy]-2-nitro-, S-methyl ester MP: nD: 1.5600 | 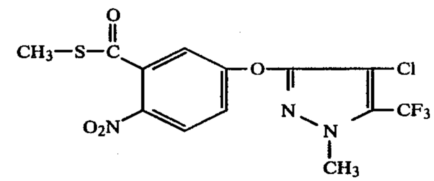 |
| 80 | benzenecarbothioic acid, 5-[[4-chloro-1-methyl-5-(trifluoromethyl)-1H-pyrazol-3-yl]oxy]-2-nitro-, S-ethyl ester MP: nD: 1.5556 | 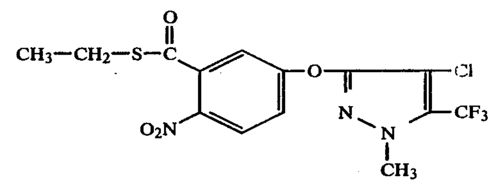 |
| 81 | benzoic acid, 5-[[4-chloro-1-methyl-5-(trifluoromethyl)-1H-pyrazol-3-yl]oxy]-2-nitro-, 2-(methylthio)ethyl ester MP: nD: 1.5438 | 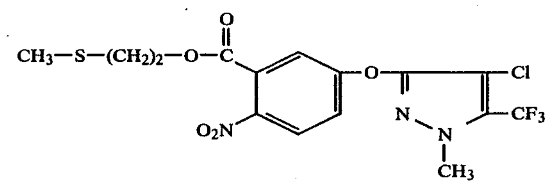 |
| 82 | 2-propanone, O-5-[[4-chloro-1-methyl-5-(trifluoromethyl)-1H-pyrazol-3-yl]oxy]-2-nitrobenzoyl]oxime MP: 109.0-111.0 nD: | 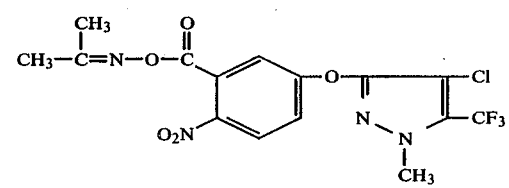 |

-continued

| Ex CP # | Name | Structure |
|---|---|---|
| 83 | benzoic acid, 5-[4-chloro-1-methyl-5-(trifluoromethyl)-1H-pyrazol-3-yl]oxy]-2-nitro-1-cyanoethyl ester<br>MP: 78.0–79.0<br>nD: | 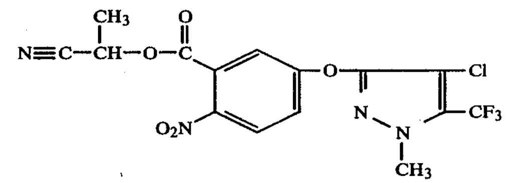 |
| 84 | 2-propanimine, N-[[5-[[4-bromo-1-methyl-5-(trifluoromethyl)-1H-pyrazol-3-yl oxy 2-nitrobenzoyl]oxy]-<br>MP: 124.5–125.5<br>nD: | 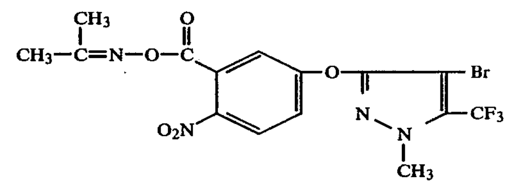 |
| 85 | benzamide, 5-[4-chloro-1-methyl-5-(trifluoromethyl)-1H-pyrazol-3-yl]oxy-N-methyl-N-(methylsulfonyl)-3-nitro-<br>MP: 115.0–118.0<br>nD: | 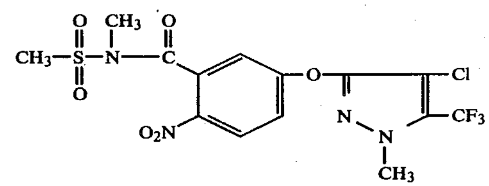 |
| 86 | benzamide, 5-[[4-chloro-1-methyl-5-(trifluoromethyl)-1H-pyrazol-3-yl]oxy]-N-(methylsulfonyl)-2-nitro-<br>MP: 173.0–175.0<br>nD: | 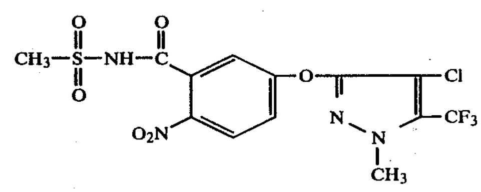 |
| 87 | 1H-pyrazole, 3-(3-methoxy-4-nitrophenoxy)-1-methyl-5-(trifluoromethyl)-<br>MP: 62.0–63.0<br>nD: | 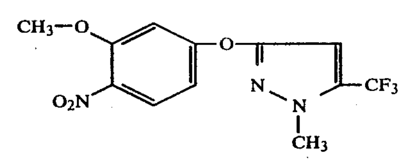 |

-continued

| Ex CP # | Name | Structure |
|---|---|---|
| 88 | 1H-pyrazole, 4-fluoro-3-(3-methoxy-4-nitrophenoxy)-1-methyl-5-(trifluoromethyl)- MP: 78.0–79.0 nD: | 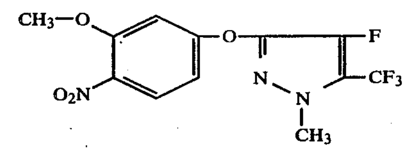 |
| 89 | 1H-pyrazole, 4-chloro-1-ethyl-3-[3-methoxy-4-(nitrophenoxy)-5-(trifluoromethyl)- MP: 47.5–50.0 nD: | 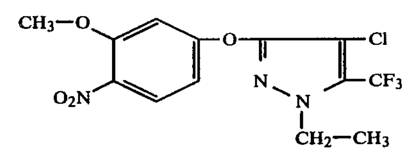 |
| 90 | 1H-pyrazole, 4-bromo-3-(3-methoxy-4-nitrophenoxy)-1-methyl-5-(trifluoromethyl)- MP: 72.0–73.0 nD: | 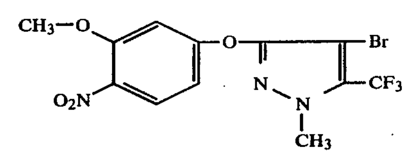 |
| 91 | 1H-pyrazole, 3-(3-ethoxy-4-nitrophenoxy)-1-methyl-5-(trifluoromethyl)- MP: nD: | 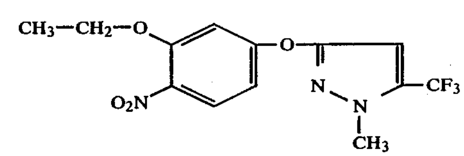 |
| 92 | 1H-pyrazole, 4-chloro-3-(3-ethoxy-4-nitrophenoxy)-1-methyl-5-(trifluoromethyl)- MP: 53.0–56.0 nD: | 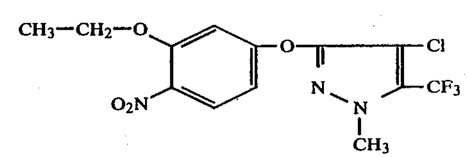 |

-continued

| Ex CP # | Name | Structure |
|---|---|---|
| 93 | 1H-pyrazole, 4-bromo-3-[3-(ethoxymethyl)-4-nitrophenoxy]-1-methyl-5-(trifluoromethyl)- MP: 70.0–70.2 nD: | CH₃—CH₂—O— attached to phenyl(NO₂)—O—pyrazole(Br, CF₃, N—N—CH₃) |
| 94 | 1H-pyrazole, 1-methyl-3-(4-nitro-3-propoxyphenoxy)-5-(trifluoromethyl)- MP: nD: 1.5229 | CH₃—(CH₂)₂—O— attached to phenyl(NO₂)—O—pyrazole(CF₃, N—N—CH₃) |
| 95 | 1H-pyrazole, 4-chloro-1-methyl-3-(4-nitro-3-propoxyphenoxy)-5-(trifluoromethyl)- MP: 40.0–43.0 nD: | CH₃—(CH₂)₂—O— attached to phenyl(NO₂)—O—pyrazole(Cl, CF₃, N—N—CH₃) |
| 96 | 1H-pyrazole, 4-chloro-3-3-(1-methylethoxy)-4-nitrophenoxy]-1-methyl-5-(trifluoromethyl)- MP: 52.0–53.0 nD: | (CH₃)₂CH—O— attached to phenyl(NO₂)—O—pyrazole(Cl, CF₃, N—N—CH₃) |
| 97 | 1H-pyrazole, 4-chloro-1-methyl-3-[4-nitro-3-(pentyloxy)]-5-(trifluoromethyl)- MP: nD: 1.5232 | CH₃—(CH₂)₄—O— attached to phenyl(NO₂)—O—pyrazole(Cl, CF₃, N—N—CH₃) |

-continued

| Ex CP # | Name | Structure |
|---|---|---|
| 98 | 1H-pyrazole, 4-chloro-3-[3-(dodecyloxy)-4-nitrophenoxy]-1-methyl-5-(trifluoromethyl)-<br>MP: 37.5–38.5<br>nD: | $CH_3-(CH_2)_{11}-O$ — phenyl(NO$_2$) — O — pyrazole(Cl, CF$_3$, N-CH$_3$) |
| 99 | 1H-pyrazole, 3-(3-butoxy-4-nitrophenoxy)-4-chloro-1-methyl-5-(trifluoromethyl)-<br>MP:<br>nD: 1.5261 | $CH_3-(CH_2)_3-O$ — phenyl(NO$_2$) — O — pyrazole(Cl, CF$_3$, N-CH$_3$) |
| 100 | 1H-pyrazole, 1-methyl-3-[3-[3-(1-methylethoxy)-4-nitrophenoxy]-5-(trifluoromethyl)-<br>MP:<br>nD: 1.5182 | $CH_3-CH(CH_3)-O$ — phenyl(NO$_2$) — O — pyrazole(CF$_3$, N-CH$_3$) |
| 101 | 1H-pyrazole, 4-chloro-3-[3-(cyclopropylmethoxy)-4-nitrophenoxy]-1-methyl-5-(trifluoromethyl)-<br>MP: 53.5–55.5<br>nD: | cyclopropyl-CH$_2$-O — phenyl(NO$_2$) — O — pyrazole(Cl, CF$_3$, N-CH$_3$) |
| 102 | ethanol 2-[5-[[4-chloro-1-methyl-5-(trifluoromethyl)-1H-pyrazol-3-yl]oxy]-2-nitrophenoxy]-<br>MP: 87.0–88.0<br>nD: | $HO-(CH_2)_2-O$ — phenyl(NO$_2$) — O — pyrazole(Cl, CF$_3$, N-CH$_3$) |

-continued

| Ex CP # | Name | Structure |
|---|---|---|
| 103 | 1H-pyrazole, 3-[3-(difluoromethoxy)-4-nitrophenoxy]-1-methyl-5-(trifluoromethyl)- MP: 39.5-41.0 nD: | H—CF₂—O—(phenyl, O₂N)—O—CH=C(CF₃)—N—N(CH₃) |
| 104 | 1H-pyrazole, 4-chloro-3-[3-(difluoromethoxy)-4-nitrophenoxy]-1-methyl-5-(trifluoromethyl)- MP: 55.0-57.0 nD: | H—CF₂—O—(phenyl, O₂N)—O—C(Cl)=C(CF₃)—N—N(CH₃) |
| 105 | 1H-pyrazole, 4-chloro-3-[3-(2-fluoroethoxy)-4-nitrophenoxy]-1-methyl-5-(trifluoromethyl)- MP: 75.0-76.5 nD: | F—(CH₂)₂—O—(phenyl, O₂N)—O—C(Cl)=C(CF₃)—N—N(CH₃) |
| 106 | 1H-pyrazole, 4-fluoro-3-[3-(2-fluoroethoxy)-4-nitrophenoxy]-1-methyl-5-(trifluoromethyl)- MP: 62.0-63.0 nD: | F—(CH₂)₂—O—(phenyl, O₂N)—O—C(F)=C(CF₃)—N—N(CH₃) |
| 107 | 1H-pyrazole, 4-chloro-1-ethyl-3-[3-(2-fluoroethoxy)-4-nitrophenoxy]-5-(trifluoromethyl)- MP: 73.0-75.0 nD: | F—(CH₂)₂—O—(phenyl, O₂N)—O—C(Cl)=C(CF₃)—N—N(CH₂—CH₃) |

-continued

| Ex CP # | Name | Structure |
|---|---|---|
| 108 | 1H-pyrazole, 4-chloro-1-methyl-3-[4-nitro-3-(2-propenyloxy)phenoxy]-5-(trifluoromethyl)-<br>MP: 71.0–73.0<br>nD: | CH₂=CH—CH₂—O— (4-O₂N, 3-O-linked phenyl)—O—pyrazole(Cl, CF₃, N-CH₃) |
| 109 | 1H-pyrazole, 4-fluoro-1-methyl-3-[4-nitro-3-(2-propynyloxy)phenoxy]-5-(trifluoromethyl)-<br>MP: 70.0–71.0<br>nD: | CH≡C—CH₂—O— (4-O₂N-phenyl)—O—pyrazole(F, CF₃, N-CH₃) |
| 110 | 1H-pyrazole, 4-chloro-1-methyl-3-[4-nitro-3-(3-butenyloxy)phenoxy]-5-(trifluoromethyl)-<br>MP:<br>nD: 1.5257 | CH₂=CH—(CH₂)₂—O— (4-O₂N-phenyl)—O—pyrazole(Cl, CF₃, N-CH₃) |
| 111 | 1H-pyrazole, 4-chloro-1-methyl-3-[3-(2-propynyloxy)-4-nitrophenoxy]-5-(trifluoromethyl)-<br>MP: 86.5–88.5<br>nD: | CH≡C—CH₂—O— (4-O₂N-phenyl)—O—pyrazole(Cl, CF₃, N-CH₃) |
| 112 | 1H-pyrazole, 4-chloro-3-[3-(2-methoxyethoxy)-4-nitrophenoxy]-1-methyl-5-(trifluoromethyl)-<br>MP: 44.0–46.0<br>nD: | CH₃—O—(CH₂)₂—O— (4-O₂N-phenyl)—O—pyrazole(Cl, CF₃, N-CH₃) |

-continued

| Ex CP # | Name | Structure |
|---|---|---|
| 113 | 2-butanone, 1-[5-[4-chloro-1-methyl-5-(trifluoromethyl)-1H-pyrazol-3-yl]oxy]-2-nitrophenoxy]- MP: 98.5–99.0 nD: | 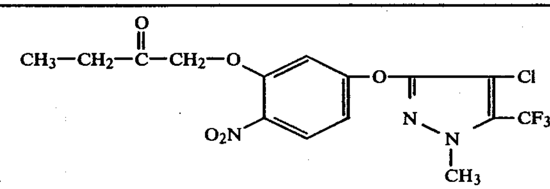 |
| 114 | acetonitrile, 5-[4-chloro-1-methyl-5-(trifluoromethyl)-1H-pyrazol-3-yl]oxy]-2-nitrophenoxy]- MP: 76.5–78.5 nD: | 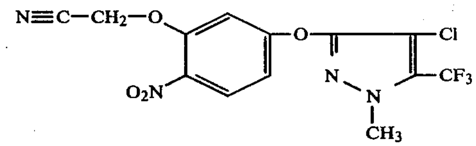 |
| 115 | propanoic acid, 2-[5-[[4-chloro-1-methyl-5-(trifluoromethyl)-1H-pyrazol-3-yl]]oxy]-2-nitrophenoxy]- MP: 117.5–120.5 nD: | 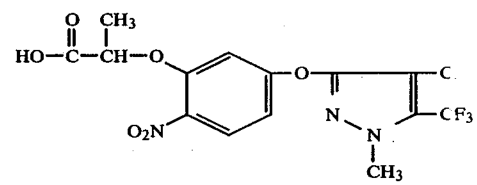 |
| 116 | propanoic acid, 2-[5-[[4-bromo-1-methyl-5-(trifluoromethyl)-1H-pyrazol-3-yl]oxy]-2-nitrophenoxy]- MP: 132.0–133.2 nD: | 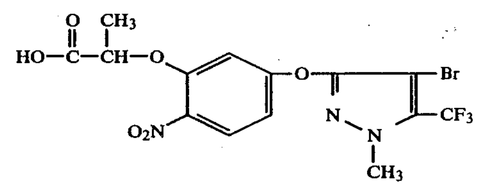 |
| 117 | propanoic acid, 2-[[5-[4-chloro-1-methyl-5-(trifluoromethyl)-1H-pyrazol-3-yl]oxy]-2-nitrophenoxy]-, compd. with morpholine (1:1) MP: 125.0–128.0 nD: | 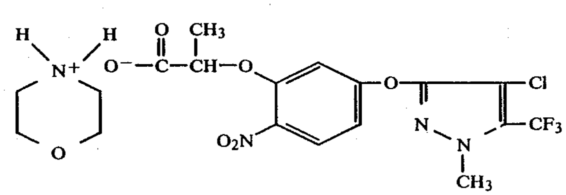 |

| Ex CP # | Name | Structure |
|---|---|---|
| 118 | propanoic acid, 2-[5-[[4-chloro-1-methyl-5-(trifluoromethyl)-1H-pyrazol-3-yl]oxy]-2-nitrophenoxy]-potassium salt MP: 236.0–240.0 nD: | 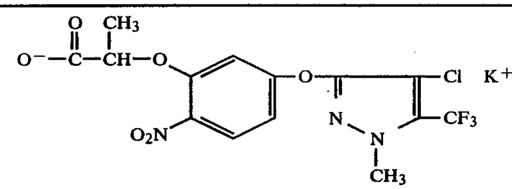 |
| 119 | propanoic acid, 2-[[5-4-chloro-1-methyl-5-(trifluoromethyl)-1H-pyrazol-3-yl]oxy]-2-nitrophenoxy]-, compd. with 2-propanamine (1:1) MP: 138.0–141.0 nD: | 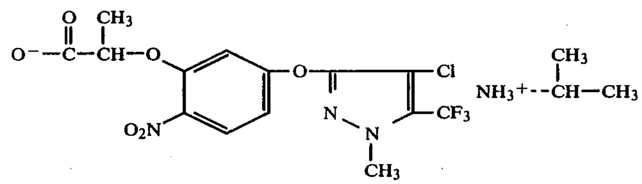 |
| 120 | propanoic acid, 2-[5-[4-chloro-1-methyl-5-(trifluoromethyl)-1H-pyrazol-3-yl] oxy ]-2-nitrophenoxy]-sodium salt MP: 189.0–192.0 nD: | 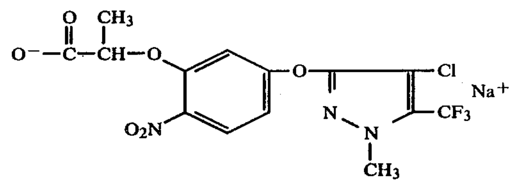 |
| 121 | propanoyl chloride, 2-[5-[4-chloro-1-methyl-5-(trifluoromethyl)-1H-pyrazol-3-yl oxy]-2-nitrophenoxy]- MP: nD: 1.5366 | 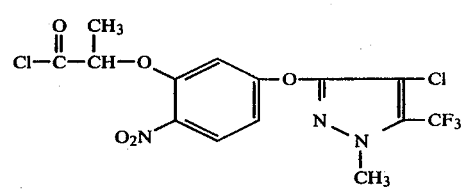 |
| 122 | propanoic acid, 2-[5-[[chloro-1-methyl-5-(trifluoromethyl)-1H-pyrazol-3-yl]oxy]-2-nitrophenoxy]-, methyl ester MP: 44.0–46.0 nD: | 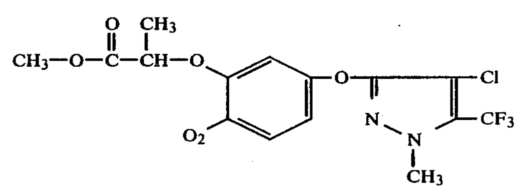 |

| Ex CP # | Name | Structure |
|---|---|---|
| 123 | propanoic acid, 2-[5-[[4-chloro-1-methyl-5-(trifluoromethyl)-1H-pyrazol-3-yl]oxy]-2-nitrophenoxy]-,methyl ester MP: 39.0-41.0 nD: | 85% R ISOMER 15% S ISOMER |
| 124 | propanoic acid, 2-[5-[4-bromo-1-methyl-5-(trifluoromethyl)-1H-pyrazol-3-yl]oxy]-2-nitrophenoxy],methyl ester MP: 43.0-45.5 nD: | 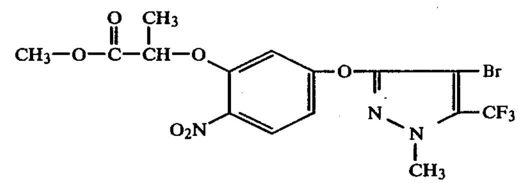 |
| 125 | propanoic acid, 2-[5-[[1-methyl-5-(trifluoromethyl)-1H-pyrazol-3-yl]oxy]-2-nitrophenoxy],ethyl ester MP: 68.5-70.0 nD: | 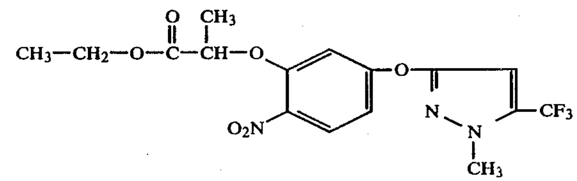 |
| 126 | propanoic acid, 2- 5-[[4-chloro-1-ethyl-5-(trifluoromethyl)-1H-pyrazol-3-yl oxy]-2-nitrophenoxy],ethyl ester MP: 84.0-85.5 nD: | 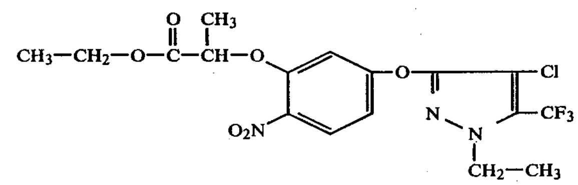 |
| 127 | propanoic acid, 2-[5-[4-bromo-1-methyl-5-(trifluoromethyl)-1H-pyrazol-3-yl]oxy]-2-nitrophenoxy], ethyl ester MP: nD: 1.5275 | 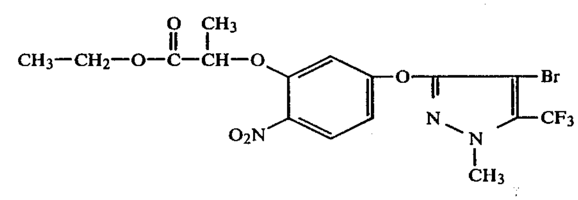 |

-continued

| Ex CP # | Name | Structure |
|---|---|---|
| 128 | propanoic acid, 2-[5-[[4-chloro-1-methyl-5-(trifluoromethyl)-1H-pyrazol-3-yl]oxy]-2-nitrophenoxy]-, 2,2,2-trifluoroethyl ester<br>MP: 68.5–69.0<br>nD: | F₃C—CH₂—O—C(=O)—CH(CH₃)—O—[4-nitro-phenyl-O—pyrazole(Cl,CF₃,N-CH₃)] |
| 129 | propanoic acid, 2-[5-[[4-chloro-1-methyl-5-(trifluoromethyl)-1H-pyrazol-3-yl]oxy]-2-nitrophenoxy]-, 2-nitropropyl ester<br>MP: 66.0–69.0<br>nD: | CH₃—CH(NO₂)—CH₂—O—C(=O)—CH(CH₃)—O—[4-nitro-phenyl-O—pyrazole(Cl,CF₃,N-CH₃)] |
| 130 | butanoic acid, 2-[5-[[4-chloro-1-methyl-5-(trifluoromethyl)-1H-pyrazol-3-yl]oxy]-2-nitrophenoxy]-, ethyl ester<br>MP:<br>nD: 1.5149 | CH₃—CH₂—O—C(=O)—CH(CH₂—CH₃)—O—[4-nitro-phenyl-O—pyrazole(Cl,CF₃,N-CH₃)] |
| 131 | propanoic acid, 2-[5-[[4-chloro-1-methyl-5-(trifluoromethyl)-1H-pyrazol-3-yl]oxy]-2-nitrophenoxy]-, propyl ester<br>MP:<br>nD: | CH₃—(CH₂)₂—O—C(=O)—CH(CH₃)—O—[4-nitro-phenyl-O—pyrazole(Cl,CF₃,N-CH₃)] |

-continued

| Ex CP # | Name | Structure |
|---|---|---|
| 132 | acetic acid, [5-[[4-chloro-1-methyl-5-(trifluoromethyl)-1H-pyrazol-3-yl]oxy]-2-nitrophenoxy]-1,1-dimethylethyl ester MP: 76.5–78.5 nD: | 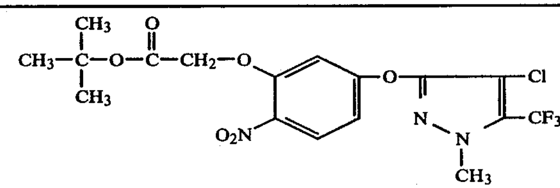 |
| 133 | propanoic acid, 2-[5-[[4-chloro-1-methyl-5-(trifluoromethyl)-1H-pyrazol-3-yl]oxy]-2-nitrophenoxy]-, butyl ester MP: nD: 1.5102 | 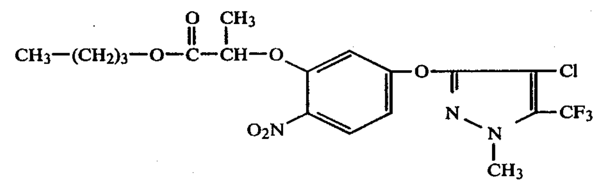 |
| 134 | propanoic acid, 2-[5-[[4-chloro-1-methyl-5-(trifluoromethyl)-1H-pyrazol-3-yl]oxy]-2-nitrophenoxy]-, 2-methylpropyl ester MP: 38.0–41.0 nD: | 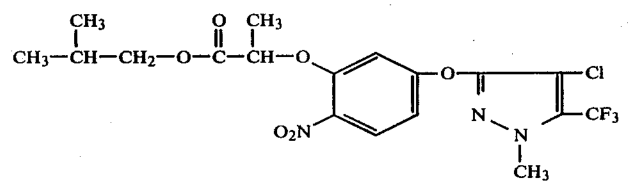 |
| 135 | propanoic acid, 2-[5-[[4-chloro-1-methyl-5-(trifluoromethyl)-1H-pyrazol-3-yl]oxy]-2-nitrophenoxy]-, pentyl ester MP: nD: 1.5093 | 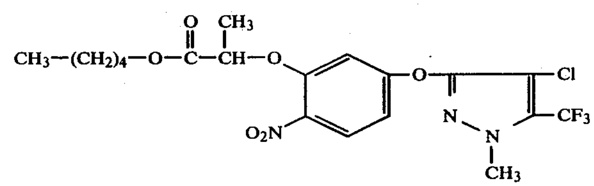 |
| 136 | propanoic acid, 2-[5-[[4-chloro-1-methyl-5-(trifluoromethyl)-1H-pyrazol-3-yl]oxy]-2-nitrophenoxy]-, dodecyl ester MP: nD: 1.5979 | 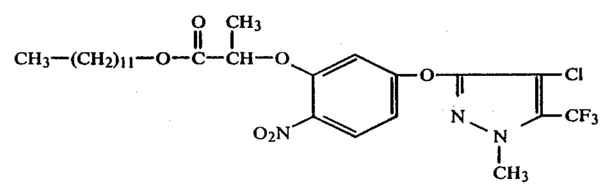 |

-continued

| Ex CP # | Name | Structure |
|---|---|---|
| 137 | propanoic acid, 2-[5-[[4-chloro-1-methyl-5-(trifluoromethyl)-1H-pyrazol-3-yl]oxy]-2-nitrophenoxy]-,1-methylpropyl ester MP: 40.0–44.0 nD: | 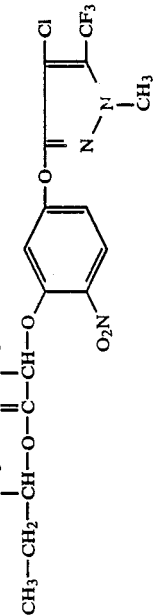 |
| 138 | propanoic acid, 2-[5-[[4-chloro-1-methyl-5-(trifluoromethyl)-1H-pyrazol-3-yl]oxy]-2-nitrophenoxy]-,1-methylethyl ester MP: 45.0–47.0 nD: | 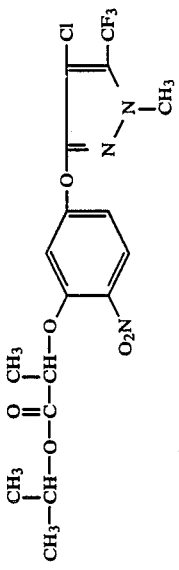 |
| 139 | propanoic acid, 2-[5-[[4-chloro-1-methyl-5-(trifluoromethyl)-1H-pyrazol-3-yl]oxy]-2-nitrophenoxy]-,1,1-dimethylethyl ester MP: 119.0–120.0 nD: | 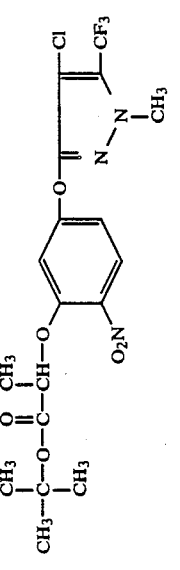 |
| 140 | propanoic acid 2-[5-[[4-chloro-1-methyl-5-(trifluoromethyl)-1H-pyrazol-3-yl]oxy]-2-nitrophenoxy]-,2-propenyl ester MP: nD: 1.5234 | 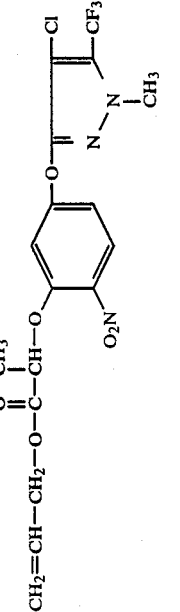 |
| 141 | propanoic acid, 2-[5-[[4-chloro-1-methyl-5-(trifluoromethyl)-1H-pyrazol-3-yl]oxy]-2-nitrophenoxy]-, 2-ethoxyethyl ester MP: nD: 1.5145 | 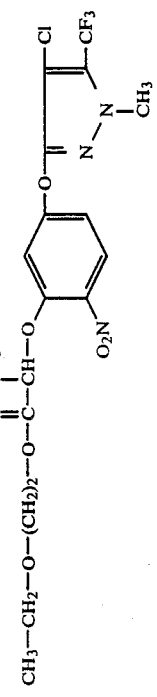 |

-continued

| Ex CP # | Name | Structure |
|---|---|---|
| 142 | propanoic acid, 2-[5-[[4-chloro-1-methyl-5-(trifluoromethyl)-1H-pyrazol-3-yl]oxy]-2-nitrophenoxy]-, 2-methoxyethyl ester<br>MP:<br>nD: 1.5173 | 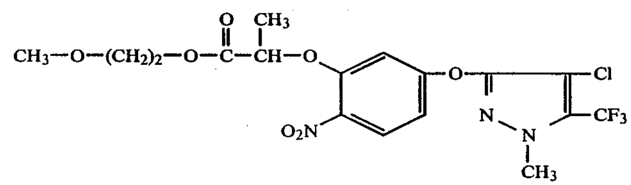 |
| 143 | propanoic acid, 2-[5-[[4-chloro-1-methyl-5-(trifluoromethyl)-1H-pyrazol-3-yl]oxy]-2-nitrophenoxy]-, 2-ethoxy-1-methyl-2-oxoethyl ester, (1S)-(+-)-<br>MP:<br>nD: 1.5089 | 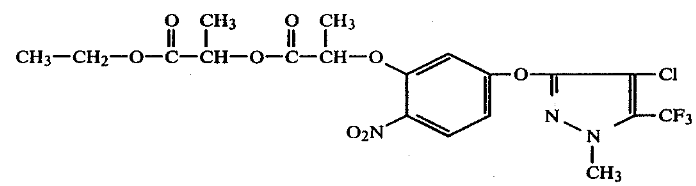 |
| 144 | propanethioic acid, 2-[5-[[4-chloro-1-methyl-5-(trifluoromethyl)-1H-pyrazol-3-yl]oxy]-2-nitrophenoxy]-, S-methyl ester<br>MP:<br>nD: 1.5490 | 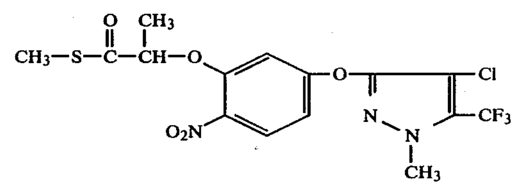 |
| 145 | propanethioic acid, 2-[5-[[4-chloro-1-methyl-5-(trifluoromethyl)-1H-pyrazol-3-yl]oxy]-2-nitrophenoxy]-, S-ethyl ester<br>MP: 40.0–43.0<br>nD: | 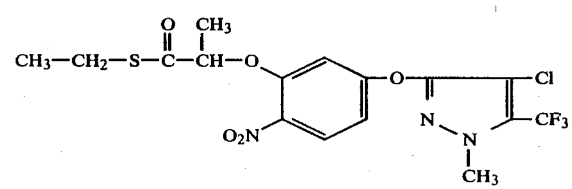 |

-continued

| Ex CP # | Name | Structure |
|---|---|---|
| 146 | phosphinic acid, [1-[5-[[4-chloro-1-methyl-5-(trifluoromethyl)-1H-pyrazol-3-yl]oxy]-2-nitrophenoxy]ethyl]methyl-, ethyl ester<br>MP:<br>nD: 1.5255 | 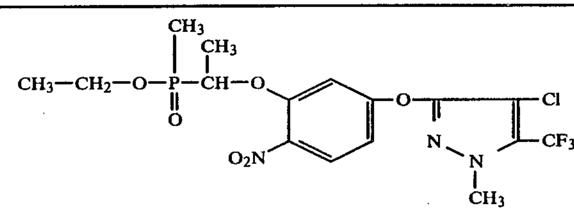 |
| 147 | 1H-pyrazole, 5-(fluoromethyl)-3-(3-methoxy-4-nitrophenoxy)-1-methyl-<br>MP: 64.0–65.0<br>nD: | 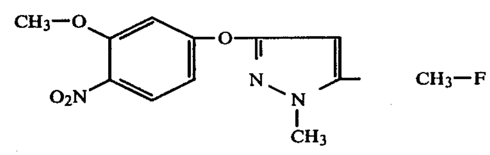 |
| 148 | 1H-pyrazole, 4-chloro-5-(fluoromethyl)-3-(3-methoxy-4-nitrophenoxy)-1-methyl-<br>MP: 121.0–122.0<br>nD: | 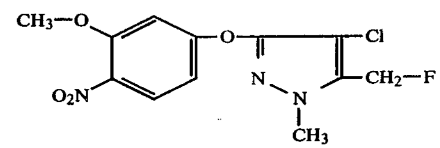 |
| 149 | 1H-pyrazole, 4-chloro-3-(3-ethoxy-4-nitrophenoxy)-5-(fluoromethyl)-1-methyl-<br>MP: 77.0–78.0<br>nD: | 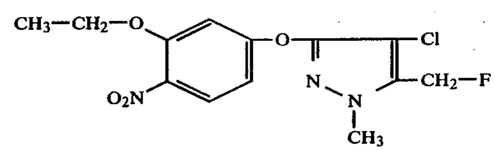 |
| 150 | propanoic acid, 2-[5-[[4-chloro-1-methyl-5-(trifluoromethyl)-1H-pyrazol-3-yl]oxy]-2-nitrophenoxy]-, 2-(dimethylamino)ethyl ester<br>MP: 85.0–88.0<br>nD: | 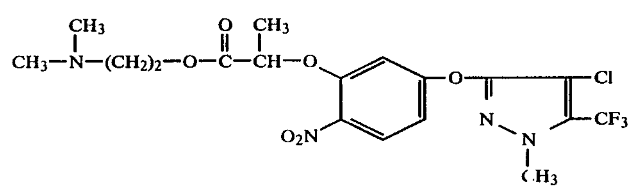 |

| Ex CP # | Name | Structure |
|---|---|---|
| 151 | propanamide, 2-[[5-[4-chloro-1-methyl-5-(trifluoromethyl)-1H-pyrazol-3-yl]oxy]-2-nitrophenoxy]- MP: 128.0–130.0 nD: | 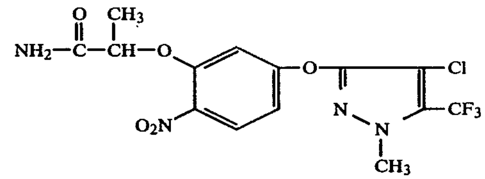 |
| 152 | propanamide, 2-[5-[[4-chloro-1-methyl-5-(trifluoromethyl)-1H-pyrazol-3-yl]oxy]-2-nitrophenoxy]-N-ethyl- MP: 109.5–110.0 nD: | 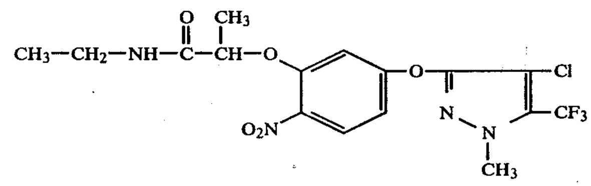 |
| 153 | propanamide, N-butyl-2-[5-[[4-chloro-1-methyl-5-(trifluoromethyl)-1H-pyrazol-3-yl]oxy]-2-nitrophenoxy]- MP: 89.0–90.2 nD: | 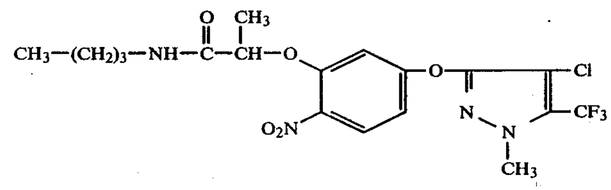 |
| 154 | propanamide, 2-[5-[[4-chloro-1-methyl-5-(trifluoromethyl)-1H-pyrazol-3-yl]oxy]-2-nitrophenoxy]-N-(3-ethoxypropyl)- MP: nD: 1.5226 | 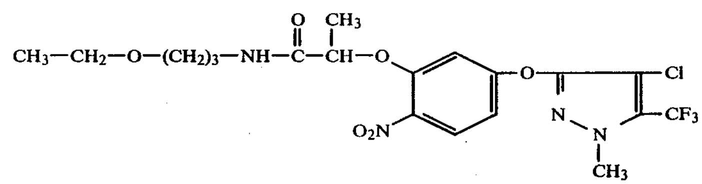 |
| 155 | propanamide, 2-[5-[[4-chloro-1-methyl-5-(trifluoromethyl)-1H-pyrazol-3-yl]oxy]-2-nitrophenoxy]-N,N-dimethyl- MP: 87.0–90.0 nD: | 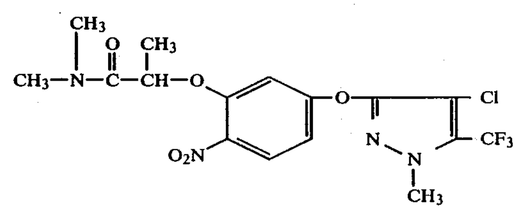 |

-continued

| Ex CP # | Name | Structure |
|---|---|---|
| 156 | propanamide, 2-[5-[[4-chloro-1-methyl-5-(trifluoromethyl)-1H-pyrazol-3-yl]oxy]-2-nitrophenoxy]-N-ethyl-N-methyl-<br>MP: 58.0–61.0<br>nD: | (structure: 4-chloro-1-methyl-5-(trifluoromethyl)pyrazole linked via O to 4-nitrophenyl ether bearing OCH(CH₃)C(O)N(CH₃)(CH₂CH₃)) |
| 157 | propanamide, 2-[5-[[4-chloro-1-methyl-5-(trifluoromethyl)-1H-pyrazol-3-yl]oxy]-2-nitrophenoxy]-N,N-diethyl-<br>MP: 71.5–74.0<br>nD: | (structure: analogous with N,N-diethyl amide) |
| 158 | 2-propanone, O-[2-[5-[[4-chloro-1-methyl-5-(trifluoromethyl)-1H-pyrazol-3-yl]oxy]-2-nitrophenoxy]-1-oxopropyl]oxime<br>MP: 69.5–71.5<br>nD: | (structure: acetone oxime ester derivative) |
| 159 | 1H-pyrazole, 5-(difluoromethyl)-3-(3-methoxy-4-nitrophenoxy)-1-methyl-<br>MP: 53.0–54.0<br>nD: | (structure: 5-(difluoromethyl)-1-methylpyrazole, 3-O-aryl with 3-methoxy-4-nitrophenyl) |
| 160 | 1H-pyrazole, 4-chloro-5-(difluoromethyl)-3-(3-methoxy-4-nitrophenoxy)-1-methyl-<br>MP: 102.0–103.0<br>nD: | (structure: 4-chloro-5-(difluoromethyl)-1-methylpyrazole, 3-O-aryl with 3-methoxy-4-nitrophenyl) |

| Ex CP # | Name | Structure |
|---|---|---|
| 161 | 1H-pyrazole, 4-chloro-5-(difluoromethyl)-3-(3-ethoxy-4-nitrophenoxy)-1-methyl-<br>MP: 67.0–68.0<br>nD: | CH$_3$—CH$_2$—O— (3-ethoxy-4-nitrophenoxy) linked to pyrazole with Cl, CF$_2$—H, N—N—CH$_3$ |
| 162 | 1H-pyrazole, 4-chloro-5-(chlorodifluoromethyl)-3-(3-methoxy-4-nitrophenoxy)-1-methyl-, mixt. with 4-chloro-5-(chlorodifluoromethyl)-3-[2-chloro-3-methoxy-4-nitrophenoxy]-1-methyl-1H-pyrazole, 4-chloro-3-(chlorodifluoromethyl)-5-(3-methoxy-4-nitrophenoxy)-1-methyl-1H-pyrazole, and 5-(chlorodifluoromethyl)-3-(3-methoxy-4-nitrophenoxy)-1-methyl-1H-pyrazole<br>MP: 39.0–41.0<br>nD: | CH$_3$—O— (3-methoxy-4-nitrophenoxy) linked to pyrazole with Cl, CF$_2$—Cl, N—N—CH$_3$<br>MAIN COMPONENT, 81% |
| 163 | 1H-pyrazole, 4-chloro-5-(chlorodifluoromethyl)-3-(3-ethoxy-4-nitrophenoxy)-1-methyl-, mixt. with 4-chloro-5-ethoxy-4-nitrophenoxy-1-methyl-1H-pyrazole and 4-chloro-3-(chlorodifluoromethyl)-5-(3-ethoxy-4-nitrophenoxy)-1-methyl-1H-pyrazole and 5-(chlorodifluoromethyl)-3-(3-ethoxy-4-nitrophenoxy)-1-methyl-1H-pyrazole<br>MP:<br>nD: 1.5534 | CH$_3$—CH$_2$—O— (3-ethoxy-4-nitrophenoxy) linked to pyrazole with Cl, CF$_2$—Cl, N—N—CH$_3$<br>78.6%<br>SEE DATA SHEET FOR MINOR COMPONENTS |
| 164 | 1H-pyrazole, 4-chloro-5-(difluoromethyl)-3-[3-(2-fluoroethoxy)-4-nitrophenoxy]-1-methyl-<br>MP: 72.0–73.0<br>nD: | F—(CH$_2$)$_2$—O— (3-(2-fluoroethoxy)-4-nitrophenoxy) linked to pyrazole with Cl, CF$_2$—H, N—N—CH$_3$ |
| 165 | benzoic acid, 5-[[4-chloro-5-(difluoromethyl)-1-methyl-1H-pyrazol-3-yl]oxy]-2-nitro-<br>MP: 120.0–121.0<br>nD: | HOOC— on nitrobenzene linked via O to pyrazole with Cl, CF$_2$—H, N—N—CH$_3$ |

-continued

| Ex CP # | Name | Structure |
|---|---|---|
| 166 | benzoic acid, 5-[[4-chloro-5-(difluoromethyl)-1-methyl-1H-pyrazol-3-yl]oxy]-2-nitro- methyl ester<br>MP: 73.0–74.0<br>nD: | 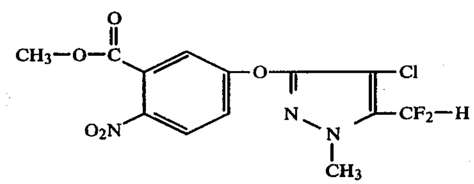 |
| 167 | propanoic acid, 2-[5-[[4-chloro-5-(difluoromethyl)-1-methyl-1H-pyrazol-3-yl]oxy]-2-nitrophenoxy]-, ethyl ester<br>MP:<br>nD: | 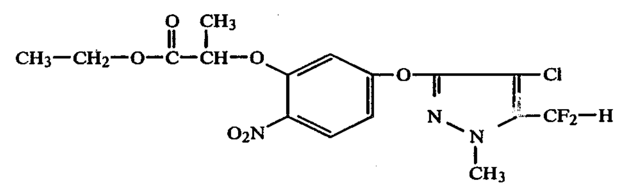 |
| 168 | benzamide, 5-[[4-chloro-2-(difluoromethyl)-1-methyl-1H-pyrazol-3-yl]oxy]-N-(methylsulfonyl)-2-nitro-<br>MP: 116.0–119.0<br>nD: | 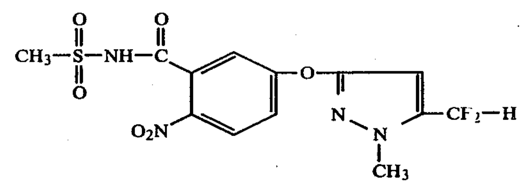 |
| 169 | 1H-pyrazole, 5-(chlorodifluoromethyl)-3-(3-methoxy-4-nitrophenoxy)-1-methyl-<br>MP: 50.0–53.0<br>nD: | 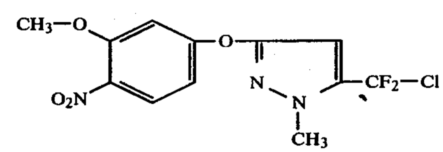 |
| 170 | propanoic acid, 2-[5-[[5-(chlorodifluoromethyl)-1-methyl-1H-pyrazol-3-yl]oxy]-2-nitrophenoxy]-, ethyl ester<br>MP: 42.0–45.0<br>nD: | 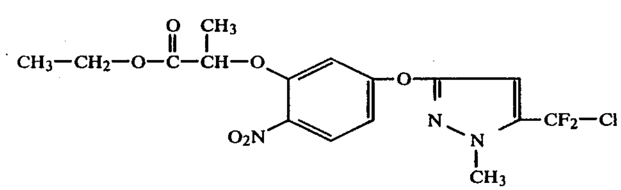 |

-continued

| Ex CP # | Name | Structure |
|---|---|---|
| 171 | 1H-pyrazole, 5-(chlorodifluoromethyl)-3-(3-ethoxy-4-nitrophenoxy)-1-methyl-<br>MP:<br>nD: 1.5472 | *Structure: 3-ethoxy-4-nitrophenoxy group attached to pyrazole with CF₂—Cl and N—CH₃* |
| 172 | 1H-pyrazole, 3-(3-methoxy-4-nitrophenoxy)-1-methyl-5-(pentafluoroethyl)-<br>MP: 76.5<br>nD: | *Structure: 3-methoxy-4-nitrophenoxy group attached to pyrazole with CF₂—CF₃ and N—CH₃* |
| 173 | benzoic acid, 5-[1-methyl-5-(pentafluoroethyl)-1H-pyrazol-3-yl]oxy]-2-nitro-, ethyl ester<br>MP: 43.0<br>nD: | *Structure: ethyl benzoate with 2-nitro and pyrazolyloxy substituents, pyrazole bearing CF₂—CF₃ and N—CH₃* |
| 174 | benzoic acid, 5-[[1-methyl-5-(pentafluoroethyl)-1H-pyrazol-3-yl]oxy]-4-chloro-1H-pyrazol-3-yl]oxy]-2-nitro-, ethyl ester<br>MP:<br>nD: 1.5045 | *Structure: ethyl benzoate with Cl, 2-nitro and pyrazolyloxy substituents, pyrazole bearing CF₂—CF₃ and N—CH₃* |
| 175 | propanoic acid, 2-[5-[[5-(pentafluoroethyl)-1-methyl-1H-pyrazol-3-yl]oxy]-2-nitrophenoxy]-, ethyl ester<br>MP: 59.0–59.5<br>nD: | *Structure: ethyl 2-(aryloxy)propanoate with 2-nitrophenoxy linked to pyrazole bearing CF₂—CF₃ and N—CH₃* |

| Ex CP # | Name | Structure |
|---|---|---|
| 176 | propanoic acid, 2- 5-[[(4-chloro-1-methyl-5-(pentafluoroethyl)-1H-pyrazol-3-yl]oxy]-2-nitrophenoxy]-,ethyl ester<br>MP: 47.0–48.0<br>nD: | (structure) |
| 177 | benzaldehyde, 5-[4-chloro-1-methyl-5-(trifluoromethyl)-1H-pryazol-3-yl]oxy]-2-nitro-, oxime<br>MP: 143.5–145.5<br>nD: | (structure) |
| 178 | ethanone, 2-[5-[[(4-chloro-1-methyl-5-(trifluoromethyl)-1H-pyrazol-3-yl]oxy]-2-nitrophenyl - oxime<br>MP: 103.5–114.0<br>nD: | (structure) |
| 179 | ethanone, 1-[5-[[(4-chloro-1-methyl-5-(trifluoromethyl)-1H-pyrazol-3-yl]oxy]-2-nitrophenyl - oxime, (E)-<br>MP: 126.0–127.0<br>nD: | (structure) |
| 180 | ethanone,1-[5-[4-chloro-1-methyl-5-(trifluoromethyl)-1H-pyrazol-3-yl]-2-nitrophenyl]-, O-ethyloxime<br>MP: 45.5–47.0<br>nD: | (structure) |

-continued

| Ex CP # | Name | Structure |
|---|---|---|
| 181 | benzenamine, 5-[[4-chloro-1-methyl-5-(trifluoromethyl)-1H-pyrazol-3-yl]oxy]-2-nitro-<br>MP: 97.0–98.0<br>nD: | 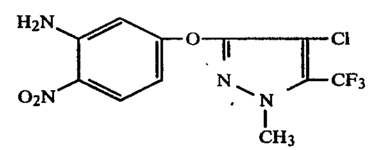 |
| 182 | benzenamine, 5-[[4-bromo-1-methyl-5-(trifluoromethyl)-1H-pyrazol-3-yl]oxy]-2-nitro-<br>MP: 106.0–108.0<br>nD: | 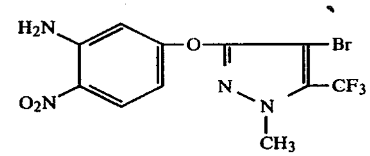 |
| 183 | benzenamine, 5-[[4-chloro-1-methyl-5-(trifluoromethyl)-1H-pyrazol-3-yl]oxy]-2-nitro-N-methyl-<br>MP: 105.0–107.0<br>nD: | 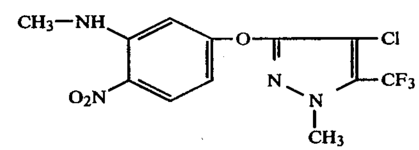 |
| 184 | benzenamine, N-ethyl-5-[[1-methyl-5-(trifluoromethyl)-1H-pyrazol-3-yl]oxy]-2-nitro-<br>MP: 84.0–86.0<br>nD: | 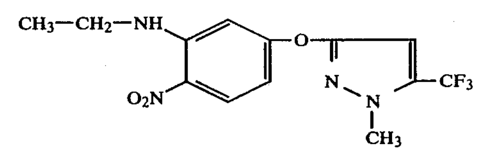 |
| 185 | benzenamine, 5-[[4-chloro-1-methyl-5-(trifluoromethyl)-1H-pyrazol-3-yl]oxy]-N-ethyl-2-nitro-<br>MP: 76.0–79.0<br>nD: | 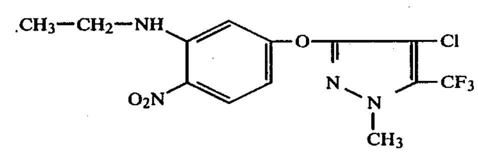 |

-continued

| Ex CP # | Name | Structure |
|---|---|---|
| 186 | benzenamine, 5-[[4-chloro-1-methyl-5-(trifluoromethyl)-1H-pyrazol-3-yl]oxy]-N-(1,1-dimethylethyl)-2-nitro- MP: nD: 1.5700 | 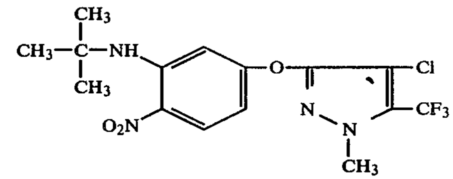 |
| 187 | benzenamine, 5-[[4-chloro-1-methyl-5-(trifluoromethyl)-1H-pyrazol-3-yl]oxy]-N-(1-methylethyl)-2-nitro- MP: 69.0-72.0 nD: | 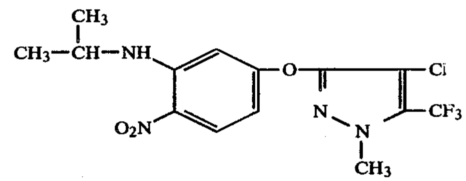 |
| 188 | benzenamine, 5-[[4-chloro-1-methyl-5-(trifluoromethyl)-1H-pyrazol-3-yl]oxy]-2-nitro-N-propyl- MP: 98.0-100.0 nD: | 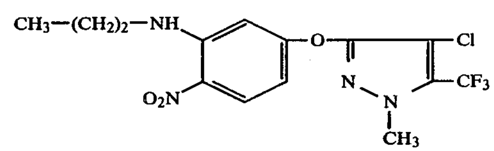 |
| 189 | benzenamine, N-butyl-5-[[4-chloro-1-methyl-5-(trifluoromethyl)-1H-pyrazol-3-yl]oxy]-2-nitro- MP: nD: 1.5720 | 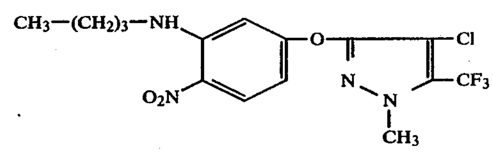 |
| 190 | benzenamine, 5-[4-chloro-1-methyl-5-(trifluoromethyl)-1H-pyrazol-3-yl]oxy]-N,N-dimethyl-2-nitro- MP: 66.0-68.0 nD: | 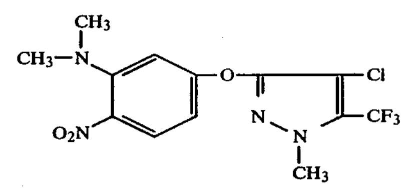 |

| Ex CP # | Name | Structure |
|---|---|---|
| 191 | benzenamine, 5-[4-chloro-1-methyl-5-(trifluoromethyl)-1H-pyrazol-3-yl]oxy]-N-methyl-2-nitro-N-propyl- MP: 75.0-76.5 nD: | 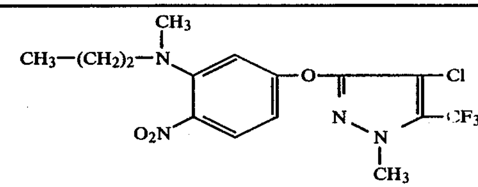 |
| 192 | benzenamine, 5-[[4-chloro-1-methyl-5-(trifluoromethyl)-1H-pyrazol-3-yl]oxy]-N,N-diethyl-2-nitro- MP: nD: 1.5466 | 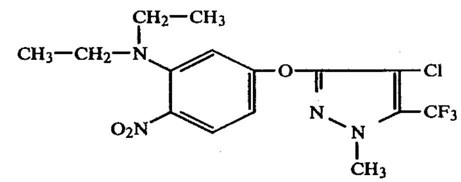 |
| 193 | benzenamine, 5-[[4-chloro-1-methyl-5-(trifluoromethyl)-1H-pyrazol-3-yl]oxy]-2-nitro-N,N-dipropyl- MP: nD: 1.5394 | 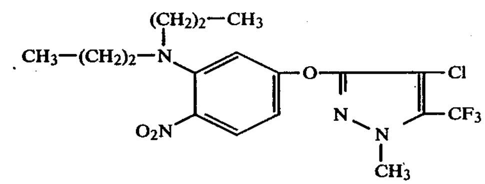 |
| 194 | benzenamine, 5-[[4-chloro-1-methyl-5-(trifluoromethyl)-1H-pyrazol-3-yl]oxy]-2-nitro-N-2-propenyl- MP: 68.0-71.0 nD: | 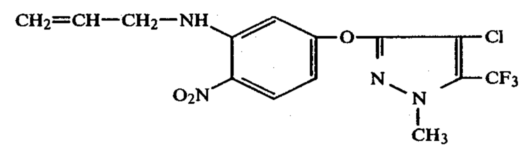 |

| Ex CP # | Name | Structure |
|---|---|---|
| 195 | benzenamine, 5-[[4-chloro-1-methyl-5-(trifluoromethyl)-1H-pyrazol-3-yl]oxy]-N-methyl-2-nitro-N-2-propynyl- MP: 81.0–83.0 nD: | 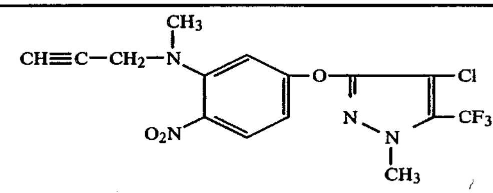 |
| 196 | benzenamine, 5-[[4-chloro-1-methyl-5-(trifluoromethyl)-1H-pyrazol-3-yl]oxy]-N-methoxy-2-nitro-N-2-propenyl- MP: nD: | 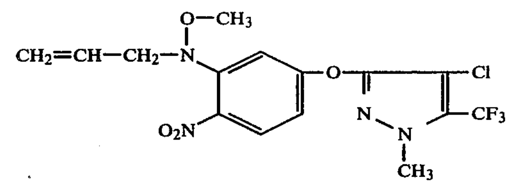 |
| 197 | benzenamine, 5-[[4-chloro-1-methyl-5-(trifluoromethyl)-1H-pyrazol-3-yl]oxy]-2-nitro-N,N-di-2-propenyl- MP: nD: | 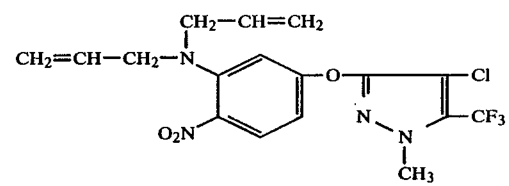 |
| 198 | benzenamine, 5-[[4-chloro-1-methyl-5-(trifluoromethyl)-1H-pyrazol-3-yl]oxy]-2-nitro-N-2-propynyl- MP: 104.0 nD: | 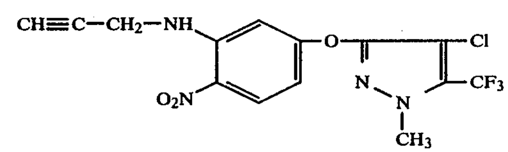 |
| 199 | benzenamine, 5-[[4-chloro-1-methyl-5-(trifluoromethyl)-1H-pyrazol-3-yl]oxy]-N-(2,2-dimethyoxyethyl)-2-nitro- MP: 52.0–55.0 nD: | 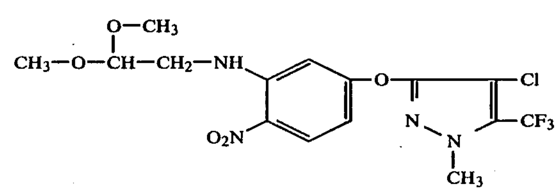 |

| Ex CP # | Name | Structure |
|---|---|---|
| 200 | benzenamine, 5-[[4-chloro-1-methyl-5-(trifluoromethyl)-1H-pyrazol-3-yl]oxy]-N-(3-methoxyphenyl)-2-nitro- MP: 111.0–112.5 nD: | 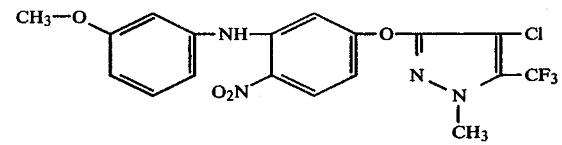 |
| 201 | benzenamine, 5-[[4-chloro-1-methyl-5-(trifluoromethyl)-1H-pyrazol-3-yl]oxy]N-cyclobutyl-2-nitro- MP: 87.0–89.0 nD: | 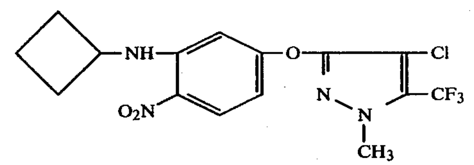 |
| 202 | benzenamine, 5-[[4-chloro-1-methyl-5-(trifluoromethyl)-1H-pyrazol-3-yl]oxy]N-cyclopropyl-2-nitro- MP: 109.0–112.0 nD: | 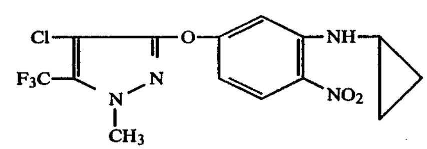 |
| 203 | 1H-pyrazole, 3-(3-ethoxy-4-nitrophenoxy)-4-iodo-1-methyl-5-(trifluoromethyl)- MP: 82.0–83.0 nD: | 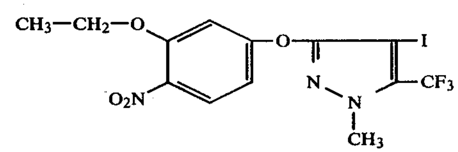 |
| 204 | acetamide, 2-chloro-N-[5-[[4-chloro-1-methyl-5-(trifluoromethyl)-1H-pyrazol-3-yl]oxy]-2-nitrophenyl]- MP: 118.0–121.0 nD: | 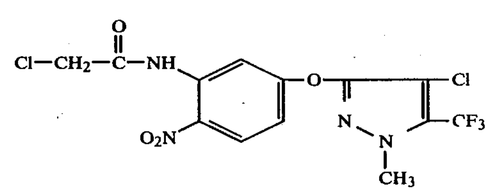 |

-continued

| Ex CP # | Name | Structure |
|---|---|---|
| 205 | propanoic acid, 2-[5-[[4-chloro-1-methyl-5-(trifluoromethyl)-1H-pyrazol-3-yl]oxy]-2-nitrophenyl]amino]-, ethyl ester<br>MP:<br>nD: 1.5577 | (structure) |
| 206 | 1H-pyrazole, 4-chloro-3-(2-fluoro-5-methoxy-4-nitrophenoxy)-1-methyl-5-(trifluoromethyl)-<br>MP: 64.0–66.0<br>nD: | (structure) |
| 207 | benzoic acid, 2-nitro-5-[[1-methyl-5-(trifluoromethyl)-1H-pyrazol-3-yl]oxy]-<br>MP: 131.0–133.0<br>nD: | (structure) |
| 208 | benzoic acid, 5-[[1-methyl-5-(trifluoromethyl)-1H-pyrazol-3-yl]oxy]-2-nitro-, compound with 2-propanamine-(1:1)<br>MP: 123.0–125.0<br>nD: | (structure) |
| 209 | benzoic acid, 5-[[1-methyl-5-(trifluoromethyl)-1H-pyrazol-3-yl]oxy]-2-nitro-sodium salt<br>MP: 71.0–72.0<br>nD: | (structure) |

-continued

| Ex CP # | Name | Structure |
|---|---|---|
| 210 | benzenamide, N-(methylsulfonyl)-5-[[1-methyl-5-(trifluoromethyl)-1H-pyrazol-3-yl]oxy]-2-nitro-<br>MP: 160.0-161.0<br>nD: | 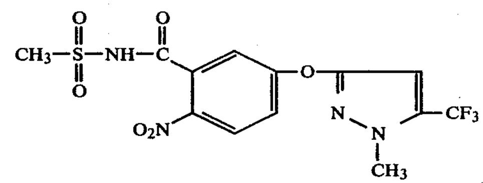 |
| 211 | benzenecarbothioic acid, 5-[[1-methyl-5-(trifluoromethyl)-1H-pyrazol-3-yl]oxy]-2-nitro-, S-methyl ester<br>MP:<br>nD: 1.5595 | 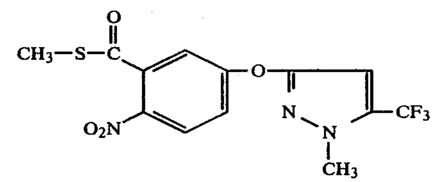 |
| 212 | benzonitrile 5-[[1-methyl-5-(trifluoromethyl)-1H-pyrazol-3-yl]oxy]-2-nitro-<br>MP: 85.0-86.0<br>nD: | 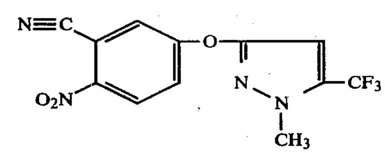 |
| 213 | phenol, 5-[[1-methyl-5-(trifluoromethyl)-1H-pyrazol-3-yl]oxy]-2-nitro-<br>MP: 73.0-75.0<br>nD: | 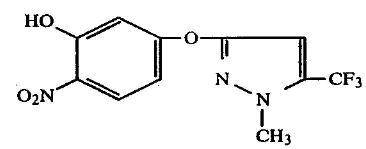 |
| 214 | phenol, 5-[[1-methyl-5-(trifluoromethyl)-1H-pyrazol-3-yl]oxy]-2-nitro-, sodium salt<br>MP: 278.0-280.0<br>nD: | 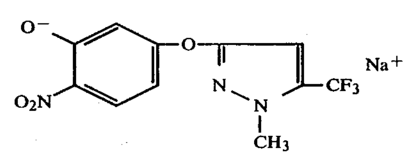 |

-continued

| Ex CP # | Name | Structure |
|---|---|---|
| 215 | benzoic acid 5-[[4-chloro-1-methyl-5-(trifluoromethyl)-1H-pyrazol-3-yl]oxy]-2-nitro, 2-chloro-4-nitrophenyl ester<br>MP: 132.0–135.0<br>nD: | 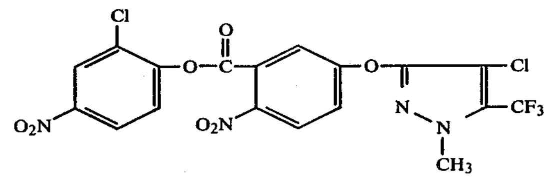 |
| 216 | acetic acid, chloro-5-[[1-methyl-5-(trifluoromethyl)-1H-pyrazol-3-yl]oxy]-2-nitrophenyl ester<br>MP: 61.0–62.5<br>nD: | 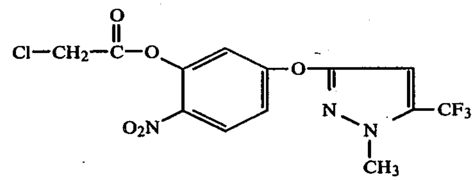 |
| 217 | benzoic acid, 5-[(4,5-dichloro-1-methyl-1H-pyrazol-3-yl)oxy]-2-nitro, methyl ester<br>MP: 74.0–75.0<br>nD: | 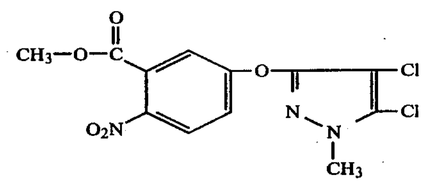 |
| 218 | 1H-pyrazole, 4,5-dichloro-3-(3-ethoxy-4-nitrophenoxy)-1-methyl-<br>MP: 80.0–81.0<br>nD: | 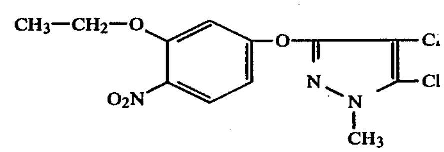 |
| 219 | 1H-pyrazole, 3-(3-chloro-4-nitrophenoxy)-1-methyl-5-(trifluoromethyl)-<br>MP: 52.5–54.0<br>nD: | 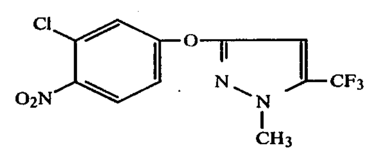 |

| Ex CP # | Name | Structure |
|---|---|---|
| 220 | 1H-pyrazole, 4-chloro-3-(3-chloro-4-nitrophenoxy)-1-methyl-5-(trifluoromethyl)-<br>MP: 69.0-72.0<br>nD: | 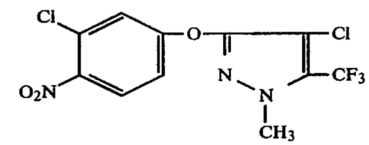 |
| 221 | benzoic acid, 5-[[4-chloro-1-methyl-5-(trifluoromethyl)-1H-pyrazol-3-yl]oxy]-2-nitro-, hydrazide<br>MP: 130.0-131.0<br>nD: | 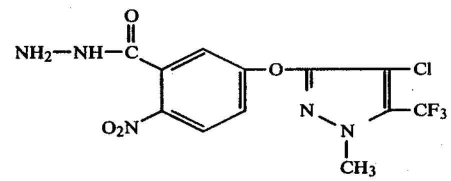 |
| 222 | benzoic acid, 5-[[4-chloro-1-methyl-5-(trifluoromethyl)-1H-pyrazol-3-yl]oxy]-2-nitro-, 2-(trimethylsilyl)ethyl ester<br>MP:<br>nD: 1.5136 | 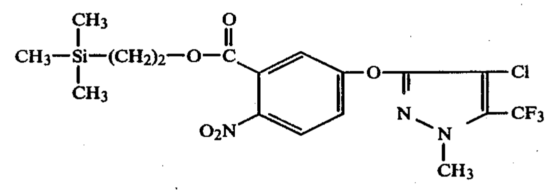 |
| 223 | benzoic acid, 5-[[4-chloro-1-methyl-5-(trifluoromethyl)-1H-pyrazol-3-yl]oxy]-2-nitro-, tetrahydro-3-furanyl ester<br>MP:<br>nD: | 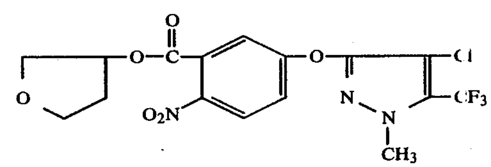 |
| 224 | benzoic acid, 5-[[4-chloro-1-methyl-5-(trifluoromethyl)-1H-pyrazol-3-yl]oxy]-2-nitro-, 1-methyl-3-(trifluoromethyl)-1H-pyrazol-5-yl ester<br>MP: 150.5-152.0<br>nD: | 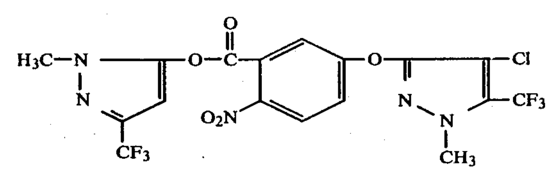 |

-continued

| Ex CP # | Name | Structure |
|---|---|---|
| 225 | ethanone, 1-[5-[[4,5-dichloro-1-methyl-1H-pyrazol-3-yl]oxy]-2-nitrophenyl-]<br>MP: 84.0–85.0<br>nD: | 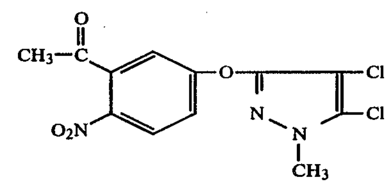 |
| 226 | 1H-pyrazole, 3-(3-chloro-4-nitrophenoxy)-4,5-dichloro-1-methyl-<br>MP: 73.0–74.0<br>nD: | 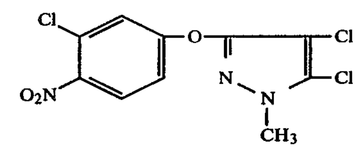 |
| 227 | 1H-pyrazole, 4,5-dichloro-1-methyl-3-(4-nitro-3-propoxyphenoxy)-<br>MP: 55.0–56.0<br>nD: | 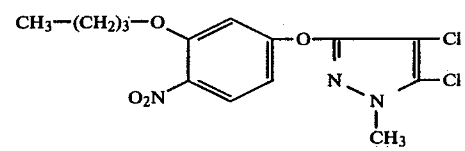 |
| 228 | benzoic acid, 5-[[(4,5-dichloro-1-methyl-1H-pyrazol-3-yl)oxy]-2-nitro-, 1-methylethyl ester<br>MP: 85.0–86.0<br>nD: | 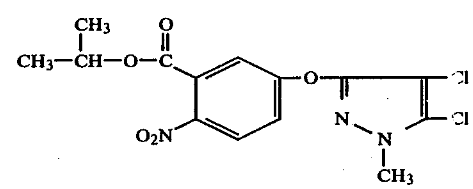 |
| 229 | 1H-pyrazole-4,5-dichloro-1-methyl-3-(4-nitrophenoxy)-, hydrate (1:0.2)<br>MP: 93.0–94.0<br>nD: | 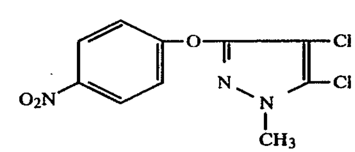 |

-continued

| Ex CP # | Name | Structure |
|---|---|---|
| 230 | 1H-pyrazole, 4,5-dichloro-3-(3-methoxy-4-nitrophenoxy)-1-methyl-<br>MP: 114.0-115.0<br>nD: | 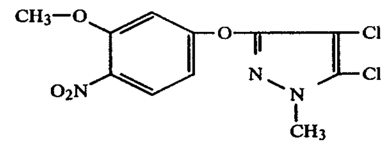 |
| 231 | 1H-pyrazole, 4-chloro-1-methyl-5-(methylthio)-3-(4-nitrophenoxy)-<br>MP: 93.0-94.0<br>nD: | 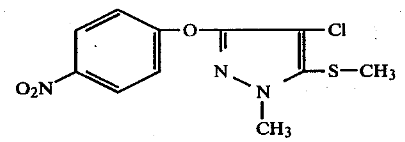 |
| 232 | 1H-pyrazole, 4-chloro-3-(3-methoxy-4-nitrophenoxy)-1-methyl-5-(methylthio)-<br>MP: 92.0-93.0<br>nD: | 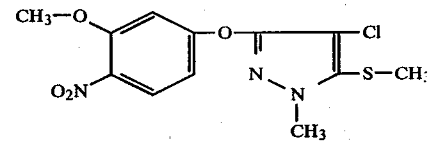 |
| 233 | 1H-pyrazole, 4,5-dichloro-1-methyl-3-[3-(1-methylethoxy)-4-nitrophenoxy]-<br>MP: 47.0-48.0<br>nD: | 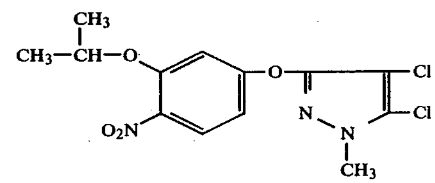 |
| 234 | benzoic acid, 5-[[4-chloro-1-methyl-5-(methylthio)-1H-pyrazol-3-yl]oxy]-2-nitro-, methyl ester<br>MP:<br>nD: | 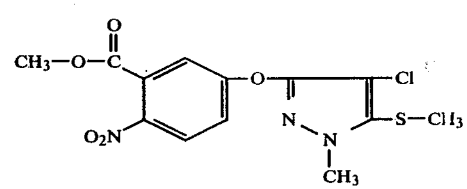 |

-continued

| Ex CP # | Name | Structure |
|---|---|---|
| 235 | 1H-pyrazole, 4-chloro-3-(3-ethoxy-4-nitrophenoxy)-1-methyl-5-(methylthio)- MP: 89.0–90.0 nD: | 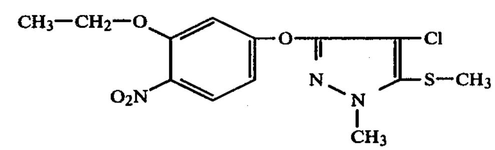 |
| 236 | 1H-pyrazole, 4-chloro-3-(3-methoxy-4-nitrophenoxy)-1-methyl-5-(methylsulfinyl)- MP: 71.0–73.0 nD: | 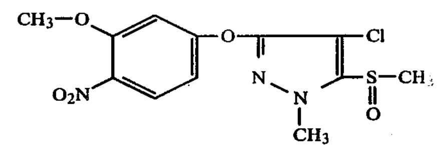 |
| 237 | 1H-pyrazole, 4-chloro-3-(4-nitro-3-propoxyphenoxy)-1-methyl-5-(methylthio)- MP: nD: | 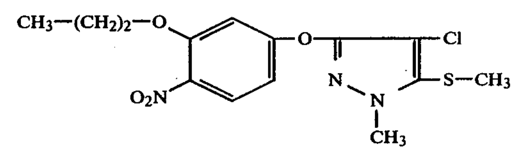 |
| 238 | 1H-pyrazole, 4-chloro-1-methyl-3-[3-(1-methylethoxy)-4-nitrophenoxy]-5-(methylthio)- MP: nD: 1.5399 | 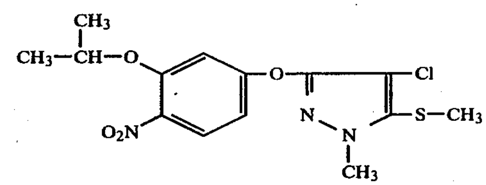 |
| 239 | 1H-pyrazole, 4-chloro-1-methyl-5-(methylsulfonyl)-3-(3-methoxy-4-nitrophenoxy)- MP: 119.0–120.0 nD: | 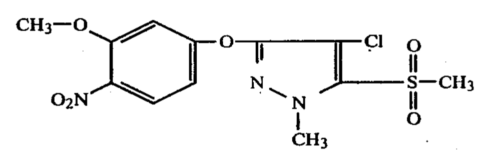 |

-continued

| Ex CP # | Name | Structure |
|---|---|---|
| 240 | 1H-pyrazole, 4-chloro-3-(3-ethoxy-4-nitrophenoxy)-1-methyl-5-(methylsulfonyl)-<br>MP: 139.0-140.0<br>nD: | 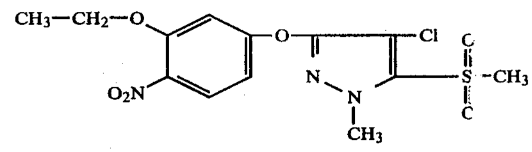 |
| 241 | benzoic acid, 5-[[4-chloro-5-(ethylthio)-1-methyl-1H-pyrazol-3-yl]oxy]-2-nitro-, methyl ester<br>MP: 52.0-54.0<br>nD: | 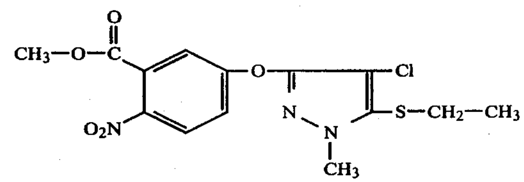 |
| 242 | 1H-pyrazole, 4-chloro-5-(ethylthio)-1-methyl-3-(4-nitrophenoxy)-<br>MP: 47.0-48.0<br>nD: | 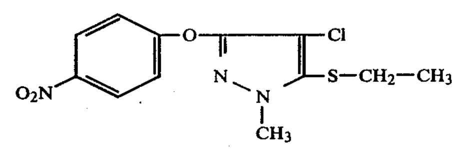 |
| 243 | propanoic acid, 2-[5-[[4-chloro-1-methyl-5-(methylthio)-1H-pyrazol-3-yl]oxy]-2-nitrophenoxy]-, ethyl ester<br>MP:<br>nD: 1.5644 | 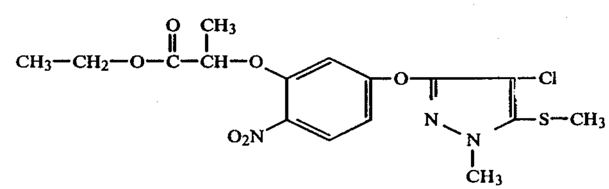 |
| 244 | 1H-pyrazole, 4-chloro-5-(ethylthio)-3-(3-methoxy-4-nitrophenoxy)-1-methyl-<br>MP:<br>nD: | 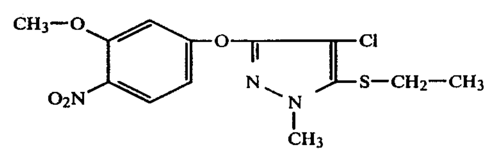 |

| Ex CP # | Name | Structure |
|---|---|---|
| 245 | benzoic acid, 5-[[4-chloro-1-methyl-5-(trifluoromethyl)-1H-pyrazol-3-yl]oxy]-2-nitro-, 2-thienylmethyl ester<br>MD: 82.5–84.5<br>nD: | 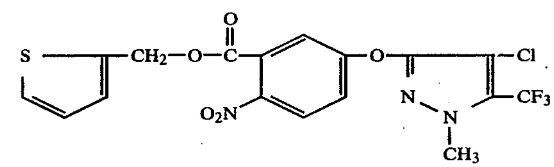 |
| 246 | 1H-pyrazole, 3-chloro-1-methyl-3-[4-nitro-3-[(tetrahydro-3-furanyl)oxy]phenoxy]-5-(trifluoromethyl)-<br>MP: 64.5–66.5<br>nD: | 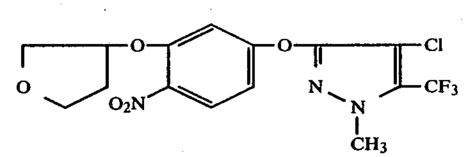 |
| 247 | 1H-pyrazole, 3,3'-[(4-nitro-1,3-phenylene)bis(oxy)]-bis 4-chloro-1-methyl-5-(trifluoromethyl)<br>MP: 95.2–97.0<br>nD: | 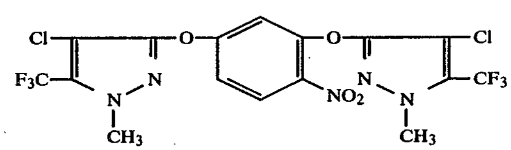 |
| 248 | 1H-pyrazole, 4-chloro-3-[3-(2-ethyl-1,3-dioxolan-2-yl)methoxy]-4-nitrophenoxy]-1-methyl-5-(trifluoromethyl)<br>MP: 87.5–89.5<br>nD: | 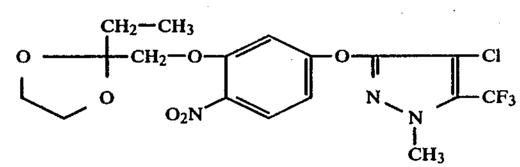 |
| 249 | benzonitrile, 5-[[4-chloro-1-methyl-5-(trifluoromethyl)-1H-pyrazol-3-yl]oxy]-2-nitro-<br>MP: 128.0–130.0<br>nD: | 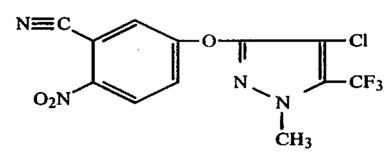 |

-continued

| Ex CP # | Name | Structure |
|---|---|---|
| 250 | morpholine, 4-[2-5-[[4-chloro-1-methyl-5-(trifluoromethyl)-1H-pyrazol-3-yl]oxy]-2-nitrophenoxy]-1-oxopropyl]-<br>MP: 76.0–78.5<br>nD: | *(structure)* |
| 251 | 1H-pyrazole, 4-chloro-3-(3-ethoxy-4-nitrophenoxy)-1-methyl-5-(methylsulfinyl)-<br>MP: 72.0–73.0<br>nD: | *(structure)* |
| 252 | butanoic acid, 2-[5-[[4-chloro-5-(ethylthio)-1-methyl-1H-pyrazol-3-yl]oxy]-2-nitrophenoxy]-, ethyl ester<br>MP:<br>nD: 1.5388 | *(structure)* |
| 253 | propanoic acid, 2-[5-[[4-chloro-5-(ethylthio)-1-methyl-1H-pyrazol-3-yl]oxy]-2-nitrophenoxy]-, ethyl ester<br>MP:<br>nD: 1.5637 | *(structure)* |
| 254 | propanoic acid, 2-[5-[[4-chloro-1-methyl-5-(methylthio)-1H-pyrazol-3-yl]oxy]-2-nitrophenoxy]-<br>MP: 135.0–136.0<br>nD: | *(structure)* |

-continued

| Ex CP # | Name |
|---|---|
| 255 | 1H-pyrazole, 4-chloro-5-(ethylsulfinyl)-3-(3-methoxy-4-nitrophenoxy)-1-methyl-<br>MP: 126.0–127.0<br>nD: |
| 256 | 1H-pyrazole, 4-chloro-5-(ethylsulfonyl)-3-(3-methoxy-4-nitrophenoxy)-1-methyl<br>MP: 126.0–127.0<br>nD: |
| 257 | 1H-pyrazole, 4-chloro-3-(3-ethoxy-4-nitrophenoxy)-5-(ethylthio)-1-methyl-<br>MP: 47.0–48.0<br>nD: |
| 258 | 1H-pyrazole, 4-chloro-3-(3-ethoxy-4-nitrophenoxy)-5-(ethylsulfinyl)-1-methyl-<br>MP: 112.0–113.0<br>nD: |
| 259 | 1H-pyrazole, 4-chloro-3-(3-ethoxy-4-nitrophenoxy)-5-(ethylsulfinyl)-1-methyl-<br>MP: 89.0–90.0<br>nD: |

-continued

| Ex CP # | Name | Structure |
|---|---|---|
| 260 | 1H-pyrazole, 4-chloro-3-(2-fluoro-4-nitrophenoxy)-1-methyl-5-(trifluoromethyl)- MP: 48.0–50.0 nD: | 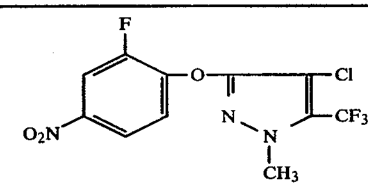 |
| 261 | benzenemethanol, 5-[[4-chloro-1-methyl-5-(trifluoromethyl)-1H-pyrazol-3-yl]oxy]-2-nitro-, methanesulfonate (ester) MP: 85.0–86.0 nD: | 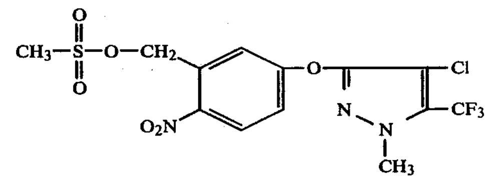 |
| 262 | 1H-pyrazole, 4-chloro-1-methyl-3-[3-(methylthio)-4-nitrophenoxy]-5-(trifluoromethyl)- MP: 95.5–97.5 nD: | 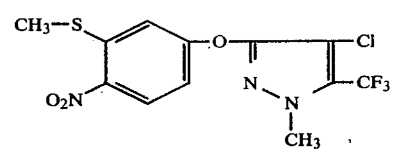 |
| 263 | 1H-pyrazole, 4-chloro-1-methyl-3-[3-(methylsulfinyl)-4-nitrophenoxy]-5-(trifluoromethyl)- MP: 89.5–91.5 nD: | 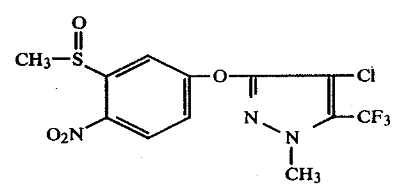 |
| 264 | 1H-pyrazole, 4-chloro-1-methyl-3-[3-(methylsulfonyl)-4-nitrophenoxy]-5-(trifluoromethyl)- MP: 111.5–112.5 nD: | 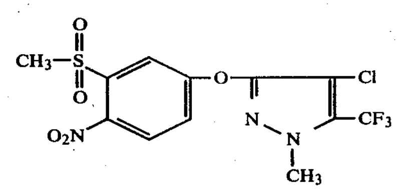 |

| Ex CP # | Name | Structure |
|---|---|---|
| 265 | 1H-pyrazole, 4-chloro-3-[3-[3-(1,3-dioxolan-2-yl)-4-nitrophenoxy]-1-methyl-5-(trifluoromethyl)- <br> MP: <br> nD: 1.5401 | 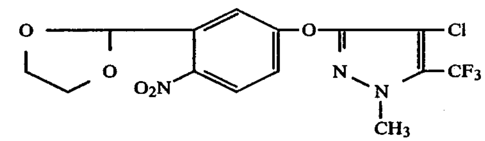 |
| 266 | 1H-pyrazole, 3,3'-[methylenebis[oxy(4-nitro-3,1-phenylene)oxy]]-bis[4-chloro-1-methyl-5-(trifluoromethyl)]- <br> MP: 123.5–124.5 <br> nD: | 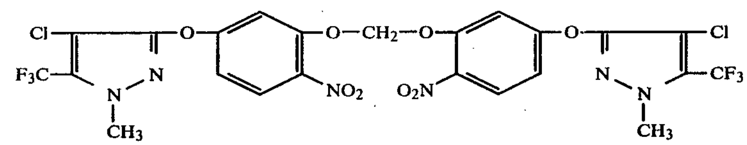 |
| 267 | propanoic acid, 2-[[[1-[5-[[4-chloro-1-methyl-5-(trifluoromethyl)-1H-pyrazol-3-yl]oxy]-2-nitrophenyl]ethylidene]imino]oxy]-, methyl ester <br> MP: <br> nD: | 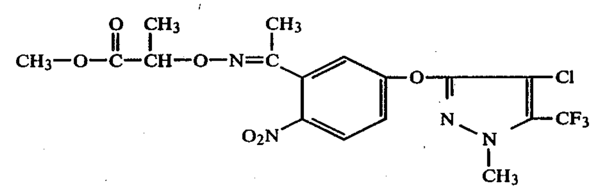 |
| 268 | 1H-pyrazole, 4-chloro-1-methyl-3-[4-nitro-3-(2-propenylthio)phenoxy]-5-(trifluoromethyl)- <br> MP: 72.0–73.0 <br> nD: | 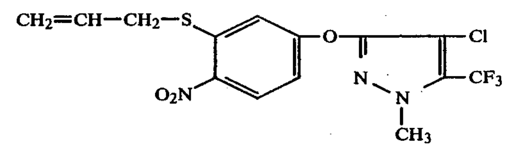 |
| 269 | 1H-pyrazole, 3-[3-(bromoethyl)-4-nitrophenoxy]-4-chloro-1-methyl-5-(trifluoromethyl)- <br> MP: 78.5–80.5 <br> nD: | 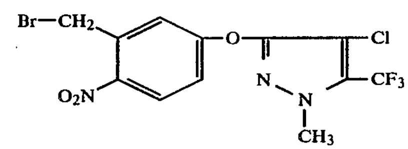 |

-continued

| Ex CP # | Name | Structure |
|---|---|---|
| 270 | propanoic acid, 2-[5-[[4-chloro-1-methyl-5-(trifluoromethyl)-1H-pyrazol-3-yl]oxy]-2-nitrophenoxy]-, 1H-pyrazol-1-ylmethyl ester<br>MP: 75.0–78.0<br>nD: | 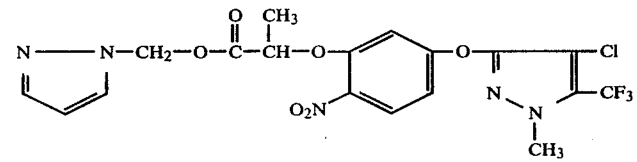 |
| 271 | benzoic acid, 5-[[4-chloro-1-ethyl-5-(trifluoromethyl)-1H-pyrazol-3-yl]oxy]-2-nitro-, methyl ester<br>MP:<br>nD: | 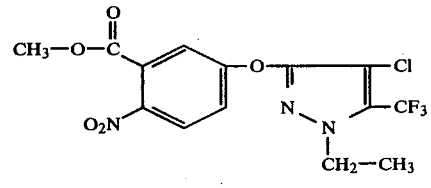 |
| 272 | propanoic acid, 2-[5-[[4-chloro-1-methyl-5-(methylsulfinyl)-1H-pyrazol-3-yl]oxy]-2-nitrophenoxy]-, ethyl ester<br>MP:<br>nD: | 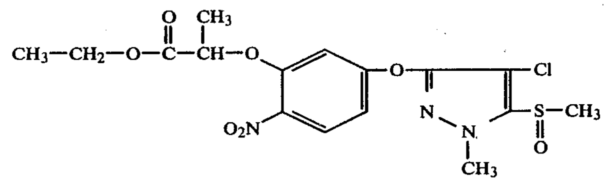 |
| 273 | benzoic acid, 5-[[4-chloro-1-methyl-5-[(1-methylethyl)thio]-1H-pyrazol-3-yl]oxy]-2-nitro-, methyl ester<br>MP: 51.0–52.0<br>nD: | 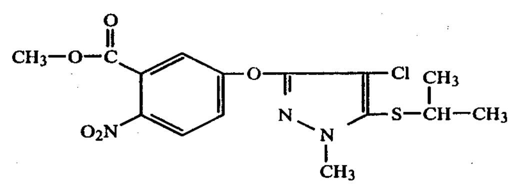 |
| 274 | morpholine 4-[5-[[4-chloro-1-methyl-5-(trifluoromethyl)-1H-pyrazol-3-yl]oxy]-2-nitrophenyl]-<br>MP: 93.0–95.0<br>nD: | 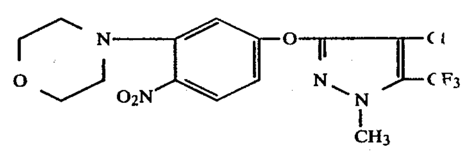 |

-continued

| Ex CP # | Name | Structure |
|---|---|---|
| 275 | 1H-pyrazole, 4-chloro-3-(3-fluoro-4-nitrophenoxy)-1-methyl-5-(trifluoromethyl)- MP: 86.0–88.0 nD: | 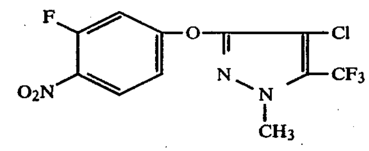 |
| 276 | benzamide, 5-[[4-chloro-1-methyl-5-(trifluoromethyl)-1H-pyrazol-3-yl]oxy]-N-methyl-2-nitro- MP: 157.0–159.0 nD: | 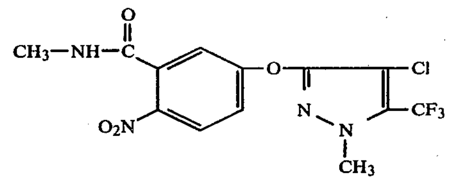 |
| 277 | propanoic acid, 2-5-[[4-chloro-5-(1-methylethyl)thio]-1H-pyrazol-3-yl]oxy]-2-nitrophenoxy]-, ethyl ester MP: nD: 1.5603 | 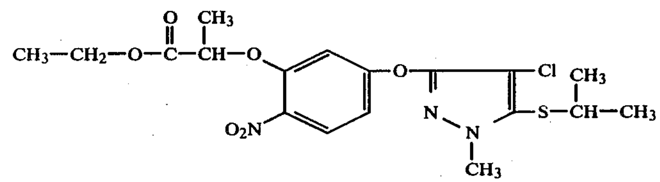 |
| 278 | 1H-pyrazole, 4-chloro-3-(3-ethoxy-2-nitrophenoxy)-1-methyl-5-[(1-methylethyl)thio]- MP: nD: 1.5705 | 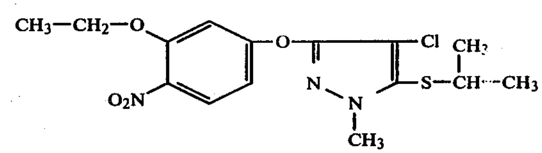 |
| 279 | 1H-pyrazole-5-carbonitrile, 4-chloro-3-(3-ethoxy-4-nitrophenoxy)-1-methyl- MP: 109.0–110.0 nD: | 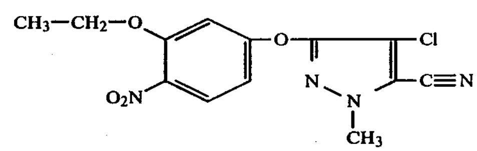 |

-continued

| Ex CP # | Name | Structure |
|---|---|---|
| 280 | 1H-1,2,4-triazole, 1-[5-[[4-chloro-1-methyl-5-(trifluoromethyl)-1H-pyrazol-3-yl]oxy]-2-nitrophenyl]- MP: 113.0–114.0 nD: | 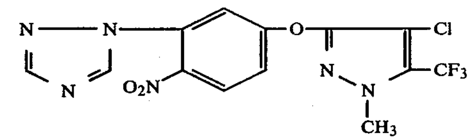 |
| 281 | benzamine, 5-[[4-chloro-1-methyl-5-(trifluoromethyl)-1H-pyrazol-3-yl]oxy]-2-nitro-N-[3-(trifluoromethyl)phenyl]- MP: 114.0–115.0 nD: | 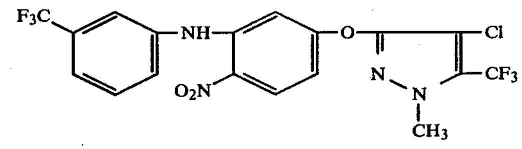 |
| 282 | morpholine, 4-[5-[[4-chloro-1-methyl-5-(trifluoromethyl)-1H-pyrazol-3-yl]oxy]-2-nitrophenyl]-2,6-dimethyl- MP: 121.0–123.0 nD: | 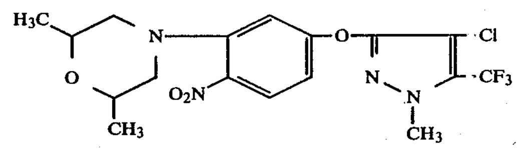 |
| 283 | 1H-pyrazole-5-carbonitrile, 4-chloro-3-[3-(2-fluoroethoxy)-4-nitrophenoxy]-1-methyl- MP: 104.0–105.0 nD: | 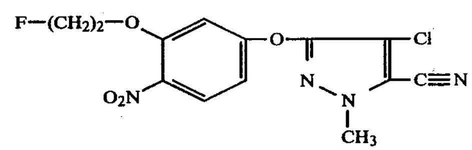 |
| 284 | benzenamine, 5-[[4-chloro-1-methyl-5-(trifluoromethyl)-1H-pyrazol-3-yl]oxy]-N-ethyl-N-methyl-2-nitro- MP: nD: 1.5631 | 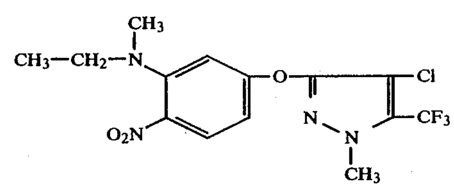 |

-continued

| Ex CP # | Name | Structure |
|---|---|---|
| 285 | 1H-pyrazolium, 4-chloro-3-(3-methoxy-4-nitrophenoxy)-1,2-dimethyl-5-(trifluoromethyl)-methyl sulfate<br>MP: 184.0–185.0<br>nD: | 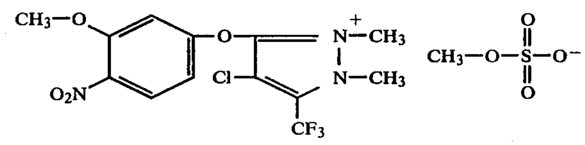 |
| 286 | 1H-pyrazolium, 4-chloro-3-[3-(2-ethoxy-1-methyl-2-oxoethoxy)-4-nitrophenoxy]-1,2-dimethyl-5-(trifluoromethyl)-, methyl sulfate<br>MP:<br>nD: 1.4802 | 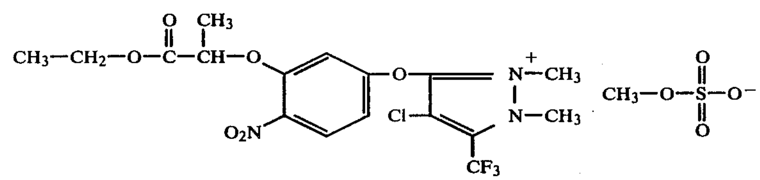 |
| 287 | 1H-pyrazole, 4-chloro-1-methyl-3-[4-nitro-3-(1-pyrrolidinyl)phenoxy]-5-(trifluoromethyl)-<br>MP: 86.0–88.0<br>nD: | 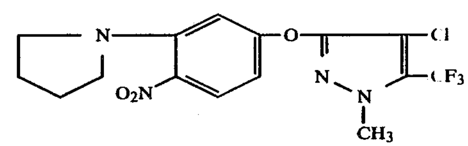 |
| 288 | 1H-pyrazole, 3-[3-(1-azetidinyl)-4-nitrophenoxy]-4-chloro-1-methyl-5-(trifluoromethyl)-<br>MP: 84.0–85.0<br>nD: | 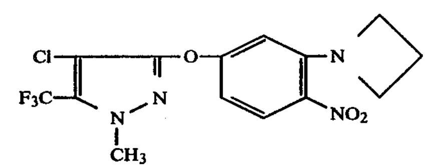 |
| 289 | 1H-pyrazole, 4-chloro-1-methyl-3-[4-nitro-3-(4-thiomorpholinyl)phenoxy]-5-(trifluoromethyl)-<br>MP: 78.0–81.0<br>nD: | 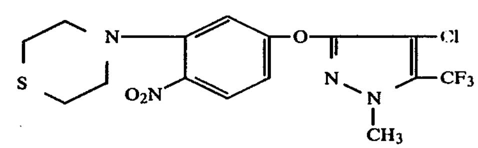 |

-continued

| Ex CP # | Name | Structure |
|---|---|---|
| 290 | 1-piperidinamine, N-[5-[[4-chloro-1-methyl-5-(trifluoromethyl)-1H-pyrazol-3-yl]oxy]-2-nitrophenyl]- MP: 101.0–104.0 nD: | 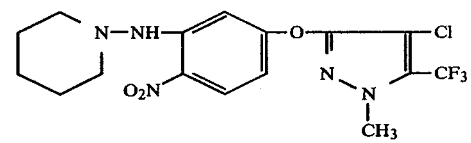 |
| 291 | 1H-pyrazole, 1-[5-[[4-chloro-1-methyl-5-(trifluoromethyl)-1H-pyrazol-3-yl]oxy]-2-nitrobenzoyl]- MP: 117.0–118.0 nD: | 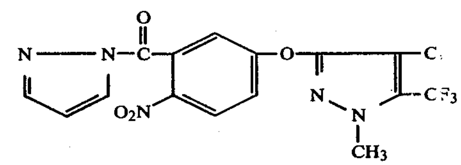 |
| 292 | benzoic acid, 5-[[4-chloro-1-methyl-5-(trifluoromethyl)-1H-pyrazol-3-yl]oxy]-2-nitro-, 4-chlorophenyl ester MP: 110.0–111.0 nD: | 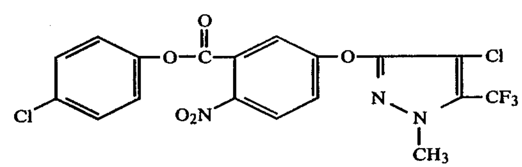 |
| 293 | propanoic acid, 2-[5-[[4-chloro-1-methyl-5-(trifluoromethyl)-1H-pyrazol-3-yl]oxy]-2-nitrophenoxy]-2-furanylmethyl-ester MP: 70.0–71.0 nD: | 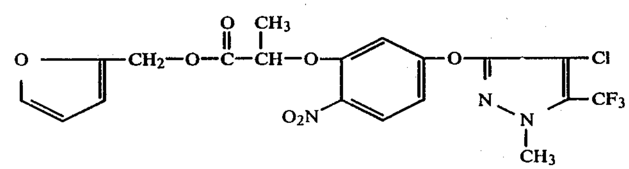 |
| 294 | 1-butanamine, N-[[5-[[4-chloro-1-methyl-5-(trifluoromethyl)-1H-pyrazol-3-yl]oxy]-2-nitrophenyl]methylene]- MP: nD: | 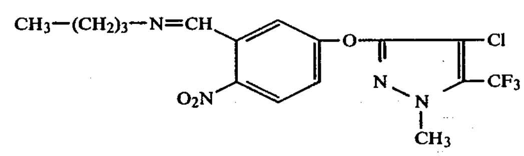 |

| Ex CP # | Name | Structure |
|---|---|---|
| 295 | propanoic acid, 2-[5-[[(4-chloro-1-methyl-5-(trifluormethyl)-1H-pyrazol-3-yl]oxy]-2-nitrophenoxy]-phenylmethyl ester<br>MP: 63.0–66.0<br>nD: | 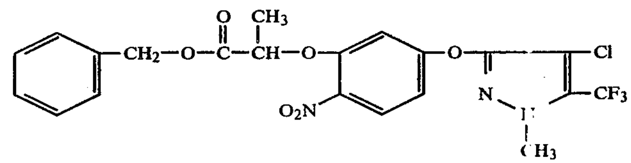 |
| 296 | propanamide, 2-[5-[[(4-chloro-1-methyl-5-(trifluoromethyl)-1H-pyrazol-3-yl]oxy]-2-nitrophenoxy]-N-(ethylsulfonyl)-<br>MP: 115.0–117.0<br>nD: | 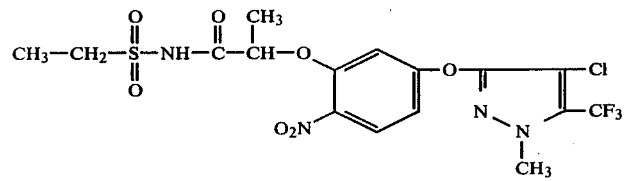 |
| 297 | propanamide, 2-[5-[[(4-chloro-1-methyl-5-(trifluoromethyl)-1H-pyrazol-3-yl]oxy]-2-nitrophenoxy]-N-[(4-methylphenyl)sulfonyl]-<br>MP: 130.0–132.0<br>nD: | 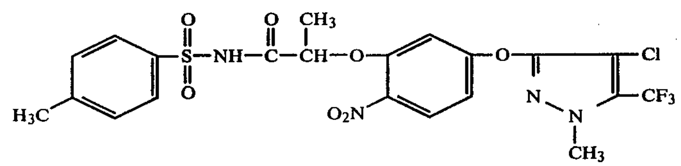 |
| 298 | 1H-pyrazole, 4-chloro-1-methyl-3-[[(methylthio)-methyl-4-nitrophenoxy]-5-(trifluoromethyl)-<br>MP:<br>nD: 1.5620 | 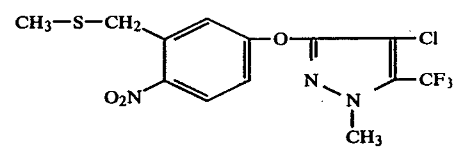 |
| 299 | propanamide, 2-[5-[[(4-chloro-1-methyl-5-(trifluoromethyl)-1H-pyrazol-3-yl]oxy]-2-nitrophenoxy]-N-(methylsulfonyl)-, sodium salt<br>MP: 110.0–120.0<br>nD: | 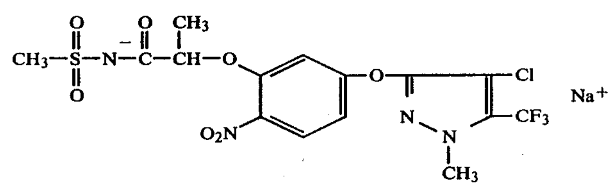 |

-continued

| Ex CP # | Name | Structure |
|---|---|---|
| 300 | benzaldehyde, 5-[[4-chloro-1-methyl-5-(trifluoromethyl)-1H-pyrazol-3-yl]oxy]-2-nitro-, (2-2,2-trifluoromethyl)hydrazone MP: 125.5-126.5 nD: | F₃C—CH₂—NH—N=CH—(aryl with Cl, NO₂, O-pyrazole bearing Cl, CF₃, N-N-CH₃) |
| 301 | propanoic acid, 2-[5-[[4-chloro-1-methyl-5-(trifluoromethyl)-1H-pyrazol-3-yl]oxy]-2-nitrophenoxy]-, 2-(diethylamino) ester MP: nD: 1.5235 | CH₃—CH₂—N(—CH₂—CH₃)—(CH₂)₂—O—C(=O)—CH(CH₃)—O—(aryl-NO₂-O-pyrazole) |
| 302 | propanoic acid, 2-[5-[[4-chloro-1-methyl-5-(trifluoromethyl)-1H-pyrazol-3-yl]oxy]-2-nitrophenoxy]-, 4-bromophenyl ester MP: 93.0-95.0 nD: | (4-bromophenyl)—O—C(=O)—CH(CH₃)—O—(aryl-NO₂-O-pyrazole) |
| 303 | propanoic acid, 2-[5-[[4-chloro-1-methyl-5-(trifluoromethyl)-1H-pyrazol-3-yl]oxy]-2-nitrophenoxy]-, 2-chloroethyl ester MP: 35.0-38.0 nD: | Cl—(CH₂)₂—O—C(=O)—CH(CH₃)—O—(aryl-NO₂-O-pyrazole) |
| 304 | propanethioic acid, 2-[5-[[4-chloro-1-methyl-5-(trifluoromethyl)-1H-pyrazol-3-yl]oxy]-2-nitrophenoxy]-, S-propyl ester MP: 39.0-40.0 nD: | CH₃—(CH₂)₂—S—C(=O)—CH(CH₃)—O—(aryl-NO₂-O-pyrazole) |

-continued

| Ex CP # | Name | Structure |
|---|---|---|
| 305 | butanamide, 2-[5-[[4-chloro-1-methyl-5-(trifluoromethyl)-1H-pyrazol-3-yl]oxy]-2-nitrophenoxy]-N-(methylsulfonyl)- MP: 138.5–139.5 nD: | 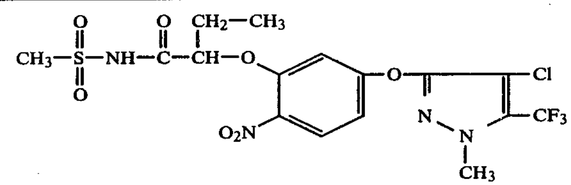 |
| 306 | benzamide, 5-[[4-chloro-1-methyl-5-(trifluoromethyl)-1H-pyrazol-3-yl]oxy]-N-(ethylsulfonyl)-2-nitro- MP: 151.5–153.5 nD: | 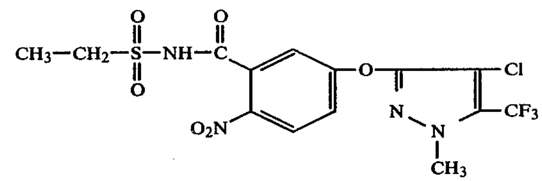 |
| 307 | butanoic acid, 2-[5-[[4-chloro-1-methyl-5-(trifluoromethyl)-1H-pyrazol-3-yl]oxy]-2-nitrophenoxy]- MP: 122.0–124.0 nD: | 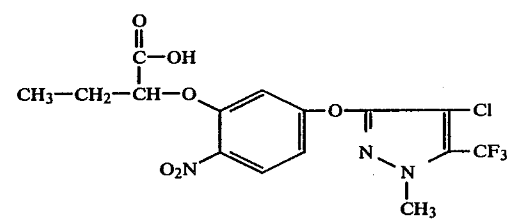 |
| 308 | propanoic acid, 2-[5-[[4-chloro-1-methyl-5-(trifluoromethyl)-1H-pyrazol-3-yl]oxy]-2-nitrophenoxy]-, cyclopropylmethyl ester MP: 43.0–44.0 nD: | 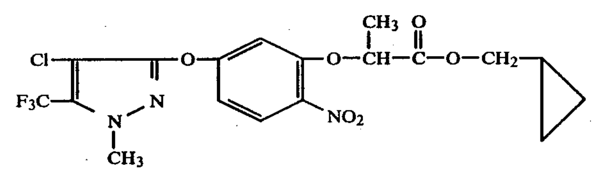 |
| 309 | propanoic acid, 2-[5-[[4-chloro-1-methyl-5-(trifluoromethyl)-1H-pyrazol-3-yl]oxy]-2-nitrophenoxy]-, 2-methylbutyl ester MP: 28.5–31.5 nD: | 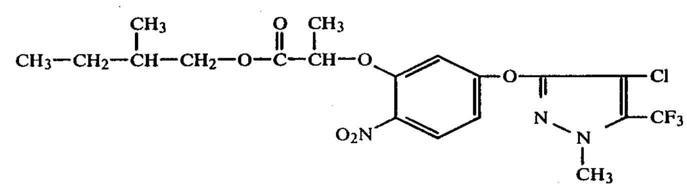 |

-continued

| Ex CP # | Name | Structure |
|---|---|---|
| 310 | propanoic acid, 2-[5-[[4-chloro-1-methyl-5-(trifluoromethyl)-1H-pyrazol-3-yl]oxy]-2-nitrophenoxy]-, 3-methylbutyl ester  MP:  nD: 1.5091 | 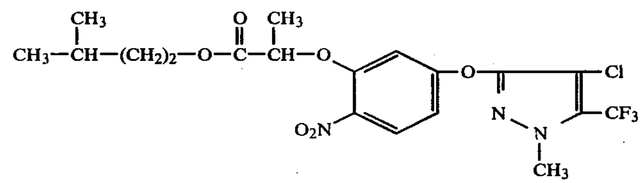 |
| 311 | propanoic acid, 2-[5-[[4-chloro-1-methyl-5-(trifluoromethyl)-1H-pyrazol-3-yl]oxy]-2-nitrophenoxy]-, 2,2-dimethylpropyl ester  MP: 46.0–47.0  nD: | 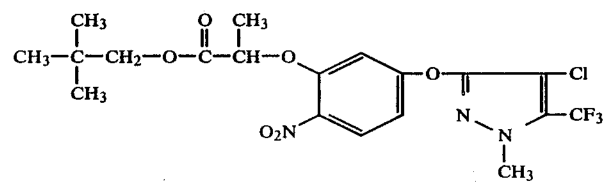 |
| 312 | propanoic acid, 2-[5-[[4-chloro-1-methyl-5-(trifluoromethyl)-1H-pyrazol-3-yl]oxy]-2-nitrophenoxy]-, cyclobutyl ester  MP: 62.0–63.5  nD: | 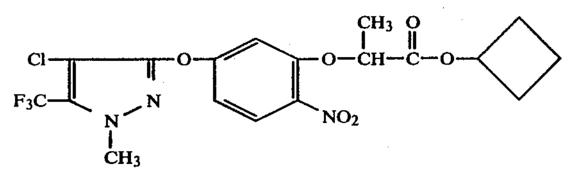 |
| 313 | acetic acid, [5-[[4-chloro-1-methyl-5-(trifluoromethyl)-1H-pyrazol-3-yl]oxy]-2-nitrophenyl]thio]-, ethyl ester  MP: 87.5–89.0  nD: | 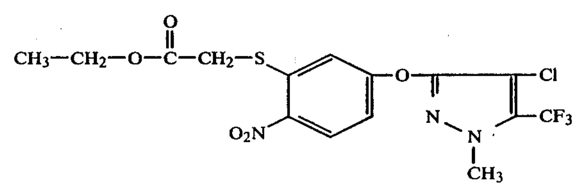 |
| 314 | propanamide, 2-[5-[[4-chloro-1-methyl-5-(trifluoromethyl)-1H-pyrazol-3-yl]oxy]-2-nitrophenoxy]-N-(propylsulfonyl)-  MP: 105.5–107.0  nD: | 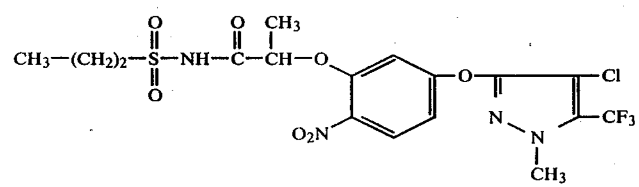 |

-continued

| Ex CP # | Name | Structure |
|---|---|---|
| 315 | butanoic acid, 4-[5-[[4-chloro-1-methyl-5-(trifluoromethyl)-1H-pyrazol-3-yl]oxy]-2-nitrophenoxy]-, ethyl ester<br>MP:<br>nD: 1.5229 | CH₃—CH₂—O—C(=O)—(CH₂)₃—O-phenyl(O₂N)-O-pyrazole[Cl, CF₃, N-N-CH₃] |
| 316 | butanoic acid 4-[5-[[4-chloro-1-methyl-5-(trifluoromethyl)-1H-pyrazol-3-yl]oxy]-2-nitrophenoxy]-<br>MP: 100.0–101.0<br>nD: | HO—C(=O)—(CH₂)₃—O-phenyl(O₂N)-O-pyrazole[Cl, CF₃, N-N-CH₃] |
| 317 | butanoic acid, 4,4,4-trichloro-3-[5-[[4-chloro-1-methyl-5-(trifluoromethyl)-1H-pyrazol-3-yl]oxy-2-nitrophenyl]methylene-3-oxo-, methyl ester<br>MP: 125.0–126.5<br>nD: | Cl₃C—C(=O)—CH=CH—(O₂N-phenyl)-O-pyrazole[Cl, CF₃, N-N-CH₃], with C(=O)—O—CH₃ |
| 318 | benzenemethanamine, 5-[[4-chloro-1-methyl-5-(trifluoromethyl)-1H-pyrazol-3-yl]oxy]-N,N-diethyl-2-nitro-<br>MP:<br>nD: 1.5246 | CH₃—CH₂—N(CH₂CH₃)—CH₂-phenyl(O₂N)-O-pyrazole[Cl, CF₃, N-N-CH₃] |

-continued

| Ex CP # | Name | Structure |
|---|---|---|
| 319 | 2-propenoic acid, 3-[5-[[4-chloro-1-methyl-5-(trifluoromethyl)-1H-pyrazol-3-yl]oxy]-2-nitrophenyl]- MP: 124.5-128.5 nD: | 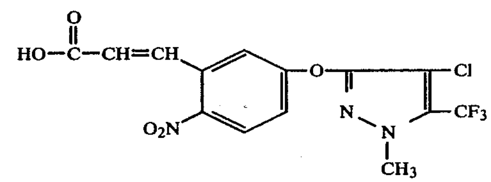 |
| 320 | benzamide, 5-[[4-chloro-1-methyl-5-(trifluoromethyl)-1H-pyrazol-3-yl]oxy]-2-nitro-N-(propylsulfonyl)- MP: 144.5-146.5 nD: | 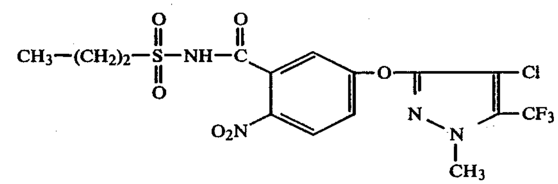 |
| 321 | 1H-pyrazole, 4-chloro-1-methyl-3-[4-nitro-3-(trifluoromethyl)phenoxy]-5-(trifluoromethyl)- MP: 58.0-60.0 nD: | 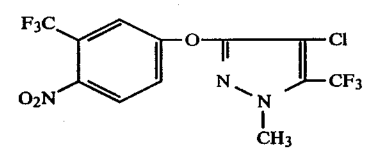 |
| 322 | 1H-pyrazole, 4-chloro-1-methyl-3-[4-nitro-3-[[-(tetrahydro-2H-pyran-2-yl)oxy]methyl]phenoxy]-5-(trifluoromethyl)- MP: nD: 1.5317 | 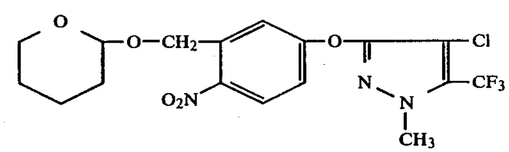 |
| 323 | 1H-pyrazole, 4-chloro-3-[3-(dichloromethyl)-4-nitrophenoxy]-1-methyl-5-(trifluoromethyl)- MP: nD: | 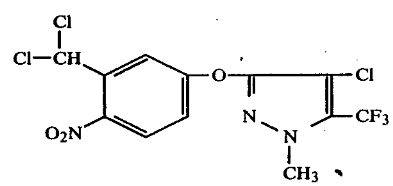 |

-continued

| Ex CP # | Name | Structure |
|---|---|---|
| 324 | 1H-pyrazole, 4-chloro-1-(difluoromethyl)-3-(3-methoxy-4-nitrophenoxy)-5-(trifluoromethyl)-<br>MP: 54.5–57.0<br>nD: | 98% <br> 2% CP 124780 |
| 325 | 2(3H)-furanone, 3-[5-[[4-chloro-1-methyl-5-(trifluoromethyl)-1H-pyrazol-3-yl]oxy]-2-nitrophenoxy]dihydro-<br>MP: 75.5–76.5<br>nD: | 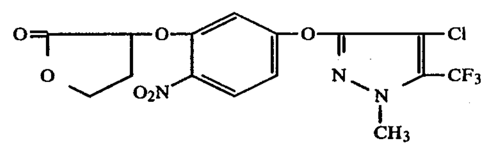 |
| 326 | propanoic acid, 2-[5-[[4-chloro-1-methyl-5-(trifluoromethyl)-1H-pyrazol-3-yl]oxy]-nitrophenoxy]-, 4-methoxyphenyl ester<br>MP: 82.0–82.5<br>nD: | 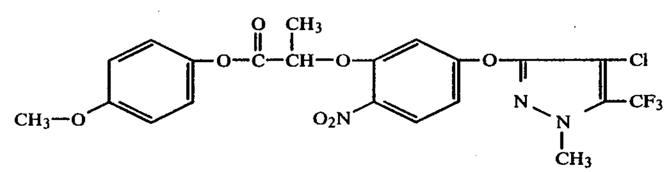 |
| 327 | acetic acid, [[[1-[5-[[4-chloro-1-methyl-5-(trifluoromethyl)-1H-pyrazol-3-yl]oxy]-2-nitrophenyl]ethylidene]amino]oxy]-, propyl ester<br>MP:<br>nD: | 75%<br>Z ISOMER = 75% |

-continued

| Ex CP # | Name | Structure |
|---|---|---|
| 328 | butanoic acid, 2-[5-[[4-chloro-1-methyl-5-(trifluoromethyl)-1H-pyrazol-3-yl]oxy]-2-nitrophenoxy]-3-methyl-, ethyl ester<br>MP:<br>nD: 1.5139 | 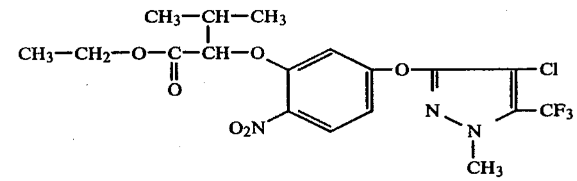 |
| 329 | butanamide, 2-[5-[[4-chloro-1-methyl-5-(trifluoromethyl))-1H-pyrazol-3-yl]oxy]-2-nitrophenoxy]-N,3-dimethyl-<br>MP: 148.5–149.5<br>nD: | 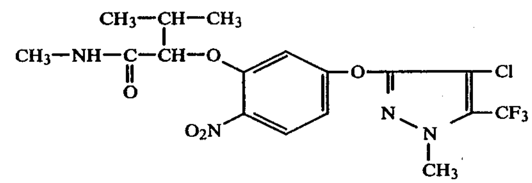 |
| 330 | butanamide, 4-[5-[[4-chloro-1-methyl-5-(trifluoromethyl))-1H-pyrazol-3-yl]oxy]-2-nitrophenoxy]-N-methyl-<br>MP: 116.0–116.5<br>nD: | 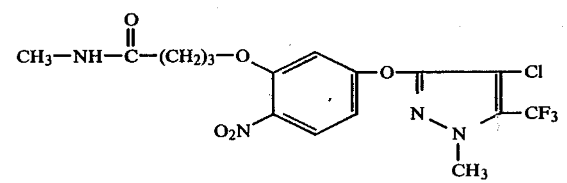 |
| 331 | butanamide, 2-[5-[[4-chloro-1-methyl-5-(trifluoromethyl))-1H-pyrazol-3-yl]oxy]-2-nitrophenoxy]-N-methyl-<br>MP: 133.0–134.0<br>nD: | 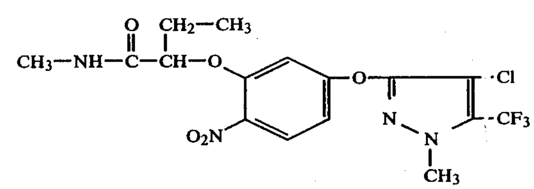 |
| 332 | butanamide, 4-[5-[[4-chloro-1-methyl-5-(trifluoromethyl))-1H-pyrazol-3-yl]oxy]-2-nitrophenoxy]-N-(methylsulfonyl)-<br>MP: 135.0–136.0<br>nD: | 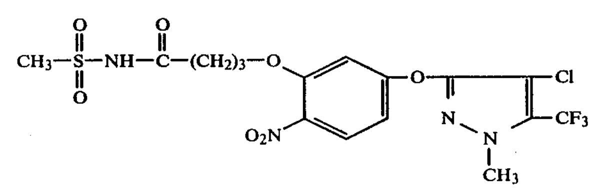 |

| Ex CP # | Name |
|---|---|
| 333 | butanamide, 2-[5-[[4-chloro-1-methyl-5-(trifluoromethyl)-1H-pyrazol-3-yl]oxy]-2-nitrophenoxy]-3-methyl-N-(methylsulfonyl)-<br>MP: 150.0–151.0<br>nD: |
| 334 | propanoic acid, 2-[5-[[4-chloro-1-methyl-5-(trifluoromethyl)-1H-pyrazol-3-yl]oxy]-2-nitrophenoxy]-, ethyl ester, (S)-<br>MP:<br>nD: 1.5186 |
| 335 | propanoic acid, 2-[5-[[4-chloro-1-methyl-5-(trifluoromethyl)-1H-pyrazol-3-yl]oxy]-2-nitrophenoxy]-, ethyl ester, (R)-<br>MP:<br>nD: 1.5187 |
| 336 | 1H-pyrazole, 4-chloro-3-(3-ethenyl-4-nitrophenoxy)-1-methyl-5-(trifluoromethyl)-<br>MP: 60.5–62.0<br>nD: |

-continued

| Ex CP # | Name | Structure |
|---|---|---|
| 337 | propanoic acid, 2-[5-[[fluoro-1-methyl-5-(trifluoromethyl)-1H-pyrazol-3-yl]oxy]-2-nitrophenoxy]-, ethyl ester MP: nD: 1.5037 | 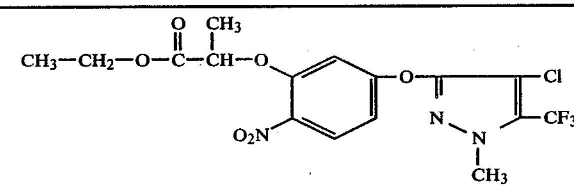 |
| 338 | 1H-pyrazole, 4-iodo-3-(3-methoxy-2-nitrophenoxy)-1-methyl-5-(trifluoromethyl)- MP: 82.0–83.0 nD: | 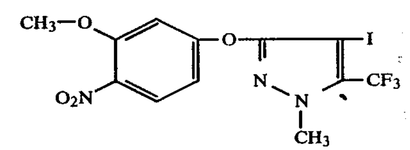 |
| 339 | benzoic acid, 5-[[4-iodo-1-methyl-5-(trifluoromethyl)-1H-pyrazol-3-yl]oxy]-2-nitro-, methyl ester MP: 106.0–107.0 nD: | 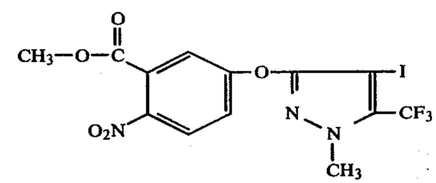 |
| 340 | benzenecarboximidic acid, 5-[[4-chloro-1-methyl-5-(trifluoromethyl)-1H-pyrazol-3-yl oxy]-N-methyl-2-nitro-, methyl ester MP: 64.0–65.0 nD: | 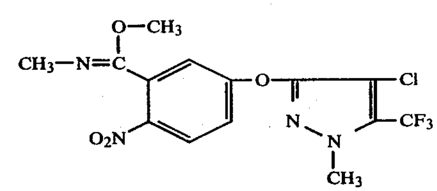 |
| 341 | benzenecarboximidamide, 5-[[4-chloro-1-methyl-5-(trifluoromethyl)-1H-pyrazol-3-yl]oxy]-N,N,n'-trimethyl-2-nitro- MP: 110.0–111.5 nD: | 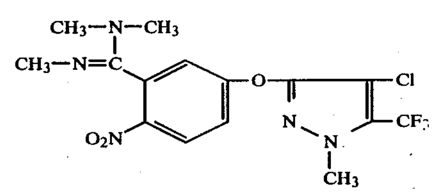 |

-continued

| Ex CP # | Name | Structure |
|---|---|---|
| 342 | benzenecarboximidamide, 5-[[4-chloro-1-methyl-5-(trifluoromethyl)-1H-pyrazol-3-yl oxy]-N,N-diethyl-n'-methyl-2-nitro- MP: 83.5-85.5 nD: | 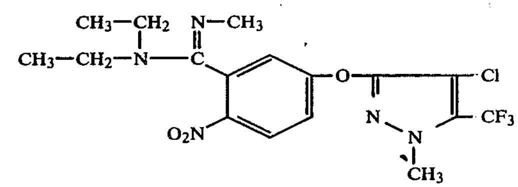 |
| 343 | benzenamine, 5-[[4-chloro-1-methyl-5-(trifluoromethyl)-1H-pyrazol-3-yl]oxy]-N-(1-ethylpropyl)-2-nitro- MP: nD: 1.5791 | 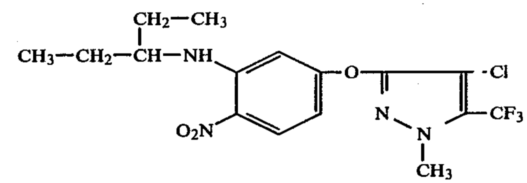 |
| 344 | benzenamine, 5-[[4-chloro-1-methyl-5-(trifluoromethyl)-1H-pyrazol-3-yl]oxy]-2-nitro-N-(2,2,2-trifluoroethyl)- MP: 134.0-137.0 nD: | 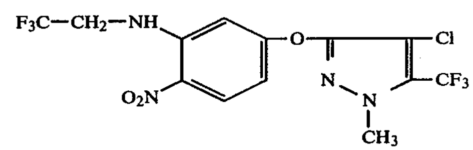 |
| 345 | benzoic acid, 5-[[4-chloro-1-methyl-5-(trifluoromethyl)-1H-pyrazol-3-yl]oxy]-2-nitro-, 3-nitrophenyl ester MP: 151.0 nD: | 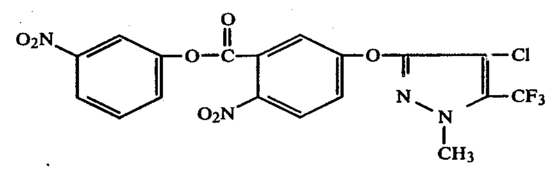 |
| 346 | benzoic acid, 4-[[4-chloro-1-methyl-5-(trifluoromethyl)-1H-pyrazol-3-yl]oxy]-2-nitrobenzoyl]amino]-, methyl ester MP: 160.5-161.0 nD: | 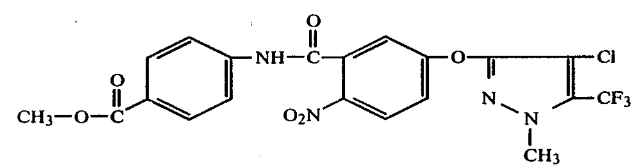 |

-continued

| Ex CP # | Name | Structure |
|---|---|---|
| 347 | benzoic acid, 5-[[4-chloro-1-methyl-5-(trifluoromethyl)-1H-pyrazol-3-yl]oxy]-2-nitro-, 3,4-dichlorophenyl ester<br>MP: 145.0<br>nD: | 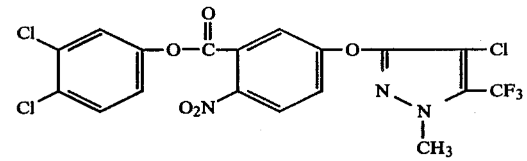 |
| 348 | benzoic acid, 5-[[4-chloro-1-methyl-5-(trifluoromethyl)-1H-pyrazol-3-yl]oxy]-2-nitro-, 4-(methoxycarbonyl)phenyl ester<br>MP: 106.0<br>nD: | 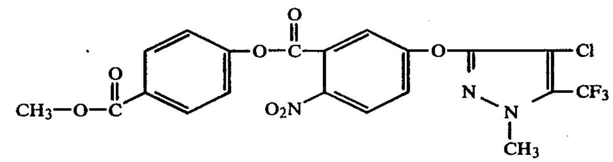 |
| 349 | benzoic acid, 5-[[4-chloro-1-methyl-5-(trifluoromethyl)-1H-pyrazol-3-yl]oxy]-2-nitro-, 4-cyanophenyl ester<br>MP: 147.0<br>nD: | 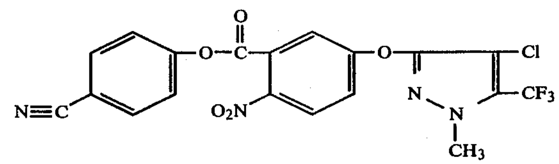 |
| 350 | benzenecarbothioic acid, 5-[[4-chloro-1-methyl-5-(trifluoromethyl)-1H-pyrazol-3-yl]oxy]-2-nitro-, S-(4-methylphenyl)ester<br>MP: 115.0<br>nD: | 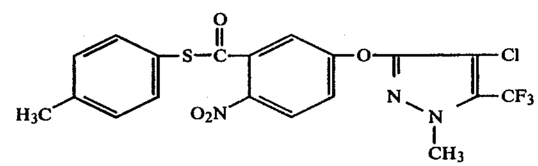 |
| 351 | benzamide, 5-[[4-chloro-1-methyl-5-(trifluoromethyl)-1H-pyrazol-3-yl]oxy]-N-(2,4-dichlorophenyl)-2-nitro-<br>MP: 187.0<br>nD: | 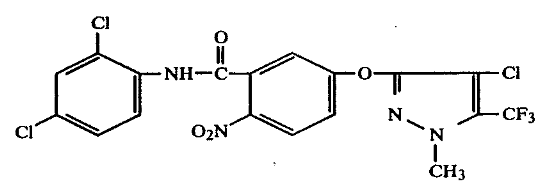 |

-continued

| Ex CP # | Name | Structure |
|---|---|---|
| 352 | benzoic acid, 5-[[4-chloro-1-methyl-5-(trifluoromethyl)-1H-pyrazol-3-yl]oxy]-2-nitro-1H-pyrazol-1-ylmethyl ester<br>MP: 95.0<br>nD: | (structure) |
| 353 | benzamide, 5-[[4-chloro-1-methyl-5-(trifluoromethyl)-1H-pyrazol-3-yl]oxy]-2-nitro-, 4-cyanophenyl ester<br>MP: 158.5-160.0<br>nD: | (structure) |
| 354 | benzamide, 5-[[4-chloro-1-methyl-5-(trifluoromethyl)-1H-pyrazol-3-yl]oxy]-2-nitro-N-[4-(trifluoromethyl)phenyl]-<br>MP: 192.0<br>nD: | (structure) |
| 355 | benzamide, 5-[[4-chloro-1-methyl-5-(trifluoromethyl)-1H-pyrazol-3-yl]oxy]-N-4-morpholinyl-2-nitro-<br>MP: 192.0<br>nD: | (structure) |
| 356 | morpholine, 4-[5-[[4-chloro-1-methyl-5-(trifluoromethyl)-1H-pyrazol-3-yl]oxy]-2-nitrobenzoyl]-<br>MP: 135.0<br>nD: | (structure) |

-continued

| Ex CP # | Name | Structure |
|---|---|---|
| 357 | benzamide, 5-[[4-chloro-1-methyl-5-(trifluoromethyl)-1H-pyrazol-3-yl]oxy]-2-nitro-N-2-pyridinyl-<br>MP: 158.0<br>nD: | 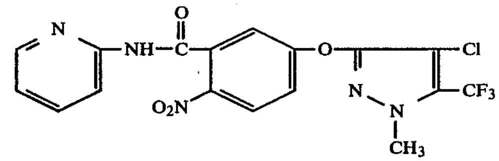 |
| 358 | benzoic acid, 4-[[5-[[4-chloro-1-methyl-5-(trifluoromethyl)-1H-pyrazol-3-yl]oxy]-2-nitrobenzoyl]amino]-<br>MP: 250.0<br>nD: | 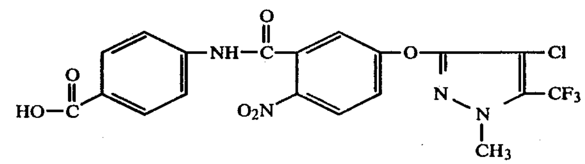 |
| 359 | benzamide, 5-[[4-chloro-1-methyl-5-(trifluoromethyl)-1H-pyrazol-3-yl]oxy]-N-(4-hydroxyphenyl)-2-nitro-<br>MP: 178.0<br>nD: | 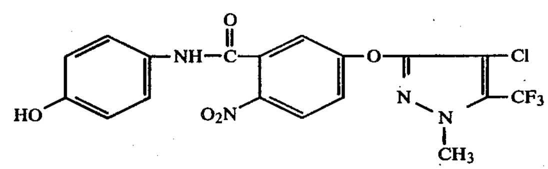 |
| 360 | benzenecarbothioic acid, 5-[[4-chloro-1-methyl-5-(trifluoromethyl)-1H-pyrazol-3-yl]oxy]-2-nitro-, S-(4-chlorophenyl) ester<br>MP: 118.0–120.0<br>nD: | 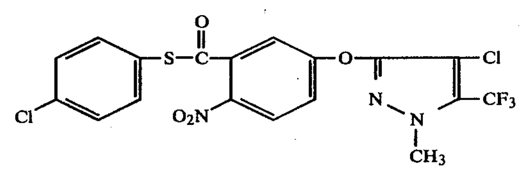 |
| 361 | benzamide, 5-[4-chloro-1-methyl-5-(trifluoromethyl)-1H-pyrazol-3-yl]oxy]-2-nitro-N-phenyl-<br>MP: 85.0–86.0<br>nD: | 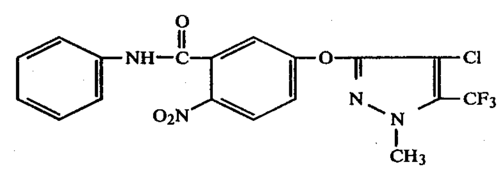 |

| Ex CP # | Name | Structure |
|---|---|---|
| 362 | benzoic acid, 3-[[5-[[4-chloro-1-methyl-5-(trifluoromethyl)-1H-pyrazol-3-yl]oxy]-2-nitrobenzoyl]amino]-, methyl ester<br>MP: 140.0–142.0<br>nD: | 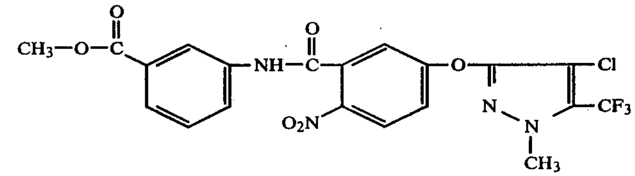 |
| 363 | benzoic acid, 3-[[5-[[4-chloro-1-methyl-5-(trifluoromethyl)-1H-pyrazol-3-yl]oxy]-2-nitrobenzoyl]amino]-<br>MP: 225.0–226.0<br>nD: | 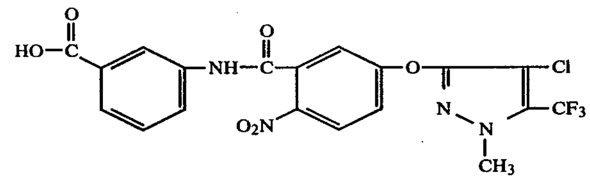 |
| 364 | benzoic acid, 5-[[4-chloro-1-methyl-5-(trifluoromethyl)-1H-pyrazol-3-yl]oxy]-2-nitro-, 4-methoxyphenyl ester<br>MP: 119.0<br>nD: | 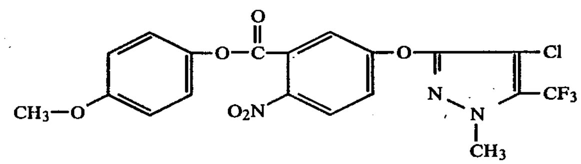 |
| 365 | benzenecarbothioic acid, 5-[[4-chloro-1-methyl-5-(trifluoromethyl)-1H-pyrazol-3-yl]oxy]-2-nitro-, S-(4,6-dimethyl-2-pyrimidinyl)ester<br>MP: 125.0–126.0<br>nD: | 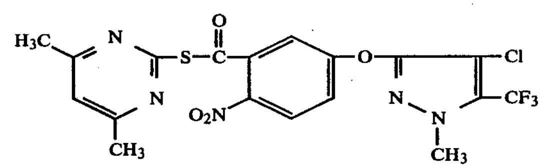 |
| 366 | benzamide, N-acetyl-5-[[4-chloro-1-methyl-5-(trifluoromethyl)-1H-pyrazol-3-yl]oxy]-2-nitro-<br>MP: 158.0<br>nD: | 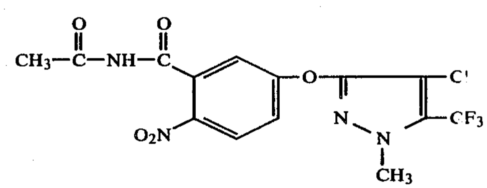 |

| Ex CP # | Name | Structure |
|---|---|---|
| 367 | propanedioic acid, 2-[5-[[4-chloro-1-methyl-5-(trifluoromethyl)-1H-pyrazol-3-yl]oxy]-2-nitrobenzoyl]-2-methyl-, diethyl ester<br>MP:<br>nD: 1.5134 | 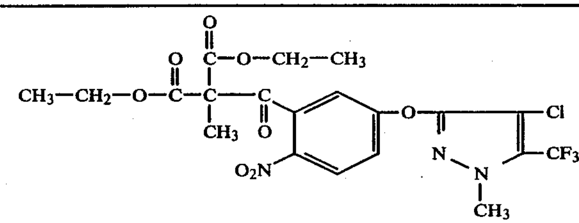 |
| 368 | benzamide, 5-[[4-chloro-1-methyl-5-(trifluoromethyl)-1H-pyrazol-3-yl]oxy]-2-nitro-N,N-di-2-propenyl-<br>MP: 86.0<br>nD: | 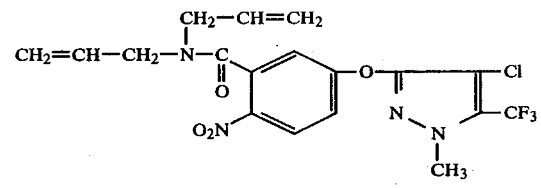 |
| 369 | 1H-indazole, 1-[5-[[4-chloro-1-methyl-5-(trifluoromethyl)-1H-pyrazol-3-yl]oxy]-2-nitrobenzoyl]-<br>MP: 134.0–144.0<br>nD: | 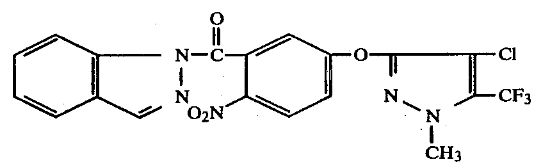 |
| 370 | benzamide, 5-[[4-chloro-1-methyl-5-(trifluoromethyl)-1H-pyrazol-3-yl]oxy]-N-(3-methoxypropyl)-2-nitro-<br>MP: 115.0<br>nD: | 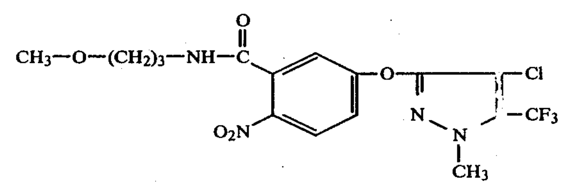 |
| 371 | benzamide, 5-[[4-chloro-1-methyl-5-(trifluoromethyl)-1H-pyrazol-3-yl]oxy]-N-(4,6-dimethyl-2-pyridinyl)-2-nitro-<br>MP: 174.0–175.0<br>nD: | 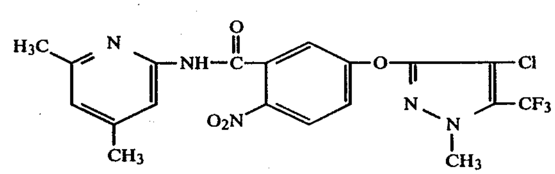 |

| Ex CP # | Name | Structure |
|---|---|---|
| 372 | benzoic acid, 5-[[4-chloro-1-methyl-5-(trifluoromethyl)-1H-pyrazol-3-yl]oxy]-2-nitro-, 2-oxopropyl ester<br>MP: 76.0–77.0<br>nD: | 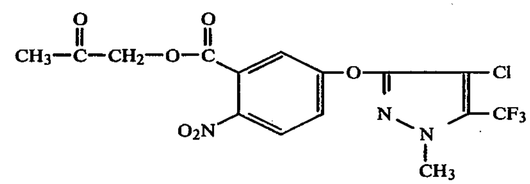 |
| 373 | benzamide, 5-[4-chloro-1-methyl-5-(trifluoromethyl)-1H-pyrazol-3-yl]oxy]-N-(3,5-dimethoxyphenyl)-2-nitro-<br>MP: 160.0<br>nD: | 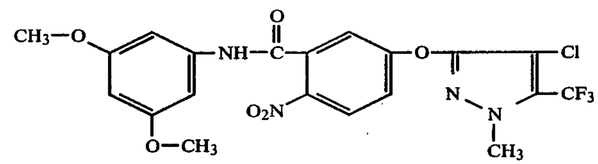 |
| 374 | benzamide, N-[bis(methoxymethyl)]-5-[[4-chloro-1-methyl-5-(trifluoromethyl)-1H-pyrazol-3-yl]oxy]-2-nitro-<br>MP: 84.0<br>nD: | 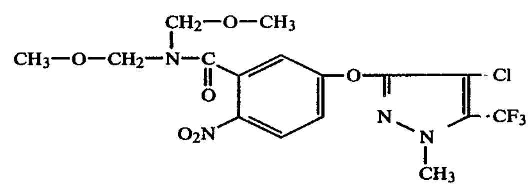 |
| 375 | propanoic acid, 2-[4-[[5-[[4-chloro-1-methyl-5-(trifluoromethyl)-1H-pyrazol-3-yl]oxy]-2-nitrobenzoyl]amino]phenoxy]-, methyl ester<br>MP: 72.0–77.0<br>nD: | 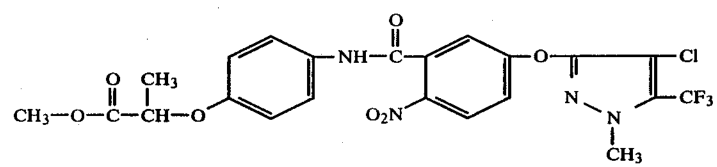 |

| Ex CP # | Name | Structure |
|---|---|---|
| 376 | benzamide, N-(2-aminophenyl)-5-[[4-chloro-1-methyl-5-(trifluoromethyl)-1H-pyrazol-3-yl]oxy]-2-nitro-<br>MP: 162.0-164.0<br>nD: | 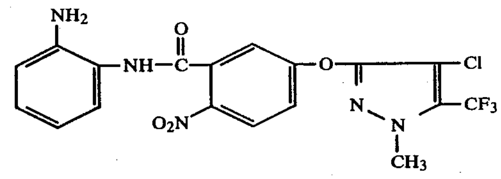 |
| 377 | benzenecarbothioic acid, 5-[[4-chloro-1-methyl-5-(trifluoromethyl)-1H-pyrazol-3-yl]oxy]-2-nitro-, S-(2-ethylhexyl)ester<br>MP:<br>nD: 1.5349 | 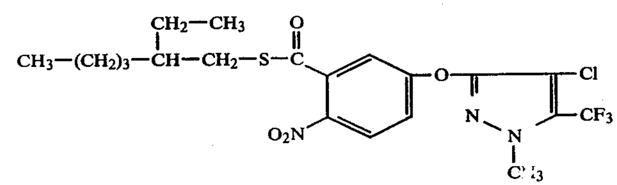 |
| 378 | benzamide, 5-[[4-chloro-1-methyl-5-(trifluoromethyl)-1H-pyrazol-3-yl]oxy]-N-(4,6-dimethyl-2-pyrimidinyl)-<br>MP: 182.0-184.0<br>nD: | 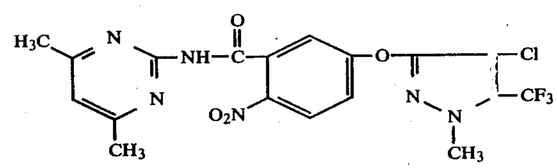 |
| 379 | benzamide, 5-[[4-chloro-1-methyl-5-(trifluoromethyl)-1H-pyrazol-3-yl]oxy]-N-(2-hydroxyphenyl)-2-nitro-<br>MP: 184.5-185.0<br>nD: | 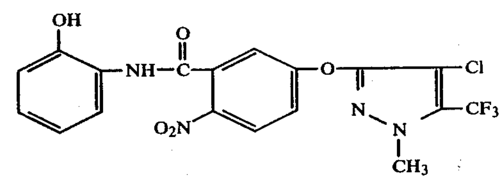 |
| 380 | 1H-pyrazole, 3-[3-(1H-benzimidazol-2-yl)-4-nitrophenoxy]-4-chloro-1-methyl-5-(trifluoromethyl)-<br>MP: 85.0-87.0<br>nD: | 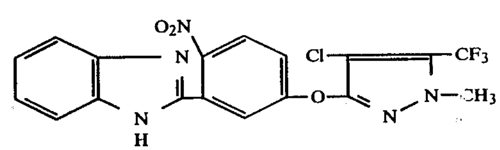 |

| Ex CP # | Name | Structure |
|---|---|---|
| 381 | benzoic acid, 5-[[4-chloro-1-methyl-5-(trifluoromethyl)-1H-pyrazol-3-yl]oxy]-2-nitro-, 2-ethoxy-1-methylethyl ester MP: nD: 1.5115 | 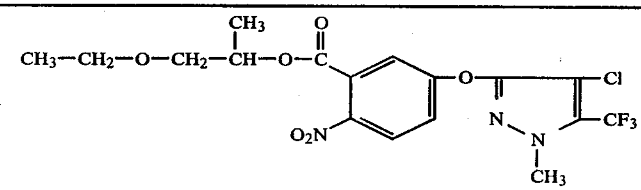 |
| 382 | benzoic acid, 5-[[4-chloro-1-methyl-5-(trifluoromethyl)-1H-pyrazol-3-yl]oxy]-2-nitro-, 2-ethoxy-2-oxoethyl ester MP: nD: 1.5191 | 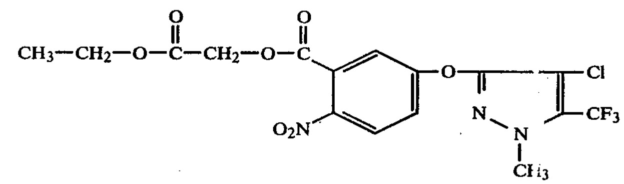 |
| 383 | benzoic acid, 5-[[4-chloro-1-methyl-5-(trifluoromethyl)-1H-pyrazol-3-yl]oxy]-2-nitro-, 2-methylpentyl ester MP: nD: 1.5117 | 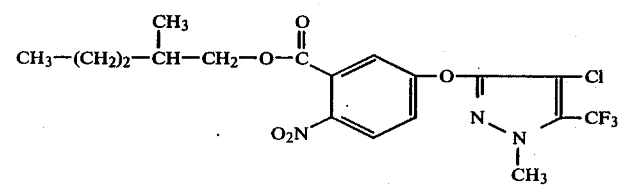 |
| 384 | benzoic acid, 5-[[4-chloro-1-methyl-5-(trifluoromethyl)-1H-pyrazol-3-yl]oxy]-2-nitro-, 2-(2-methoxyethoxy)ethyl ester MP: nD: 1.5165 | 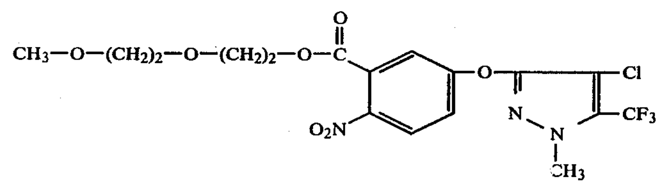 |
| 385 | benzoic acid, 5-[[4-chloro-1-methyl-5-(trifluoromethyl)-1H-pyrazol-3-yl]oxy]-2-nitro-, 2-furanylmethyl ester MP: nD: 1.5426 | 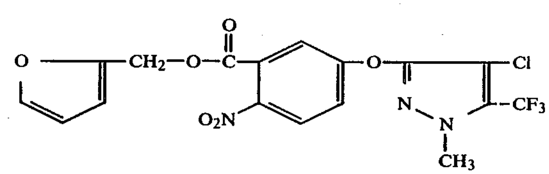 |

-continued

| Ex CP # | Name |
|---|---|
| 386 | benzoic acid, 5-[[4-chloro-1-methyl-5-(trifluoromethyl)-1H-pyrazol-3-yl]oxy]-2-nitro-, 4-carboxyphenyl ester<br>MP: 113.0<br>nD: |
| 387 | benzoic acid, 5-[[4-chloro-1-methyl-5-(trifluoromethyl)-1H-pyrazol-3-yl]oxy]-2-nitro-, methoxymethyl ester<br>MP:<br>nD: 1.5251 |
| 388 | benzoic acid, 5-[[4-chloro-1-methyl-5-(trifluoromethyl)-1H-pyrazol-3-yl]oxy]-2-nitro-, (methylthio)methyl ester<br>MP:<br>nD: 1.5468 |
| 389 | benzoxazole, 2-[5-[[4-chloro-1-methyl-5-(trifluoromethyl)-1H-pyrazol-3-yl]oxy]-2-nitrophenyl]-<br>MP: 74.0–76.0<br>nD: |
| 390 | benzoic acid, 5-[[4-chloro-1-methyl-5-(trifluoromethyl)-1H-pyrazol-3-yl]oxy]-2-nitro-, 5-ethoxy-5-oxopentyl ester<br>MP:<br>nD: 1.5116 |

| Ex CP # | Name | Structure |
|---|---|---|
| 391 | benzamide, 5-[[4-chloro-1-methyl-5-(trifluoromethyl)-1H-pyrazol-3-yl]oxy]-N-(1,1-dimethylethyl)-2-nitro- MP: 59.0–60.0 nD: | (structure) |
| 392 | pyrrolidine, 1-[5-[[4-chloro-1-methyl-5-(trifluoromethyl)-1H-pyrazol-3-yl]oxy]-2-nitrobenzoyl]- MP: 85.0 nD: | (structure) |
| 393 | benzoic acid, 5-[[4-chloro-1-methyl-5-(trifluoromethyl)-1H-pyrazol-3-yl]oxy]-2-nitro, 2-butoxyethyl ester MP: nD: 1.5100 | $CH_3-(CH_2)_3-O-(CH_2)_2-O-$ (structure) |
| 394 | benzoic acid, 5-[[4-chloro-1-methyl-5-(trifluoromethyl)-1H-pyrazol-3-yl]oxy]-2-nitro, 2-(2-butoxyethoxy)ethyl ester MP: nD: 1.5063 | $CH_3-(CH_2)_3-O-(CH_2)_2-O-(CH_2)_2-O-$ (structure) |
| 395 | benzoic acid, 5-[[4-chloro-1-methyl-5-(trifluoromethyl)-1H-pyrazol-3-yl]oxy]-2-nitro, 2-nitropropyl ester MP: nD: 1.5258 | $CH_3-CH-CH_2-O-$ with $NO_2$ (structure) |

| Ex CP # | Name | Structure |
|---|---|---|
| 396 | benzamide, N-[1-(aminocarbonyl)-1,2-dimethylpropyl]-5-[[4-chloro-1-methyl-5-(trifluoromethyl)-1H-pyrazol-3-yl]oxy]-2-nitro-<br>MP: 188.0–189.0<br>nD: | 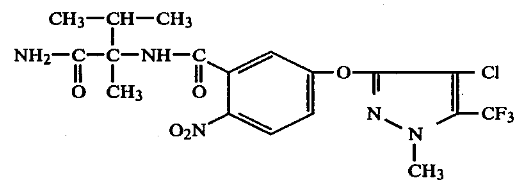 |
| 397 | benzamide, 5-[[4-chloro-1-methyl-5-(trifluoromethyl)-1H-pyrazol-3-yl]oxy]-N-(1-cyano-1,2-dimethylpropyl)-2-nitro-<br>MP: 68.0–72.0<br>nD: | 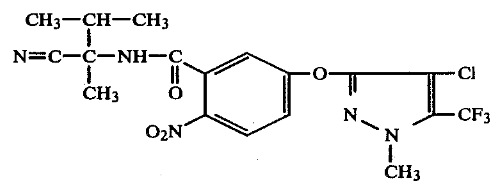 |
| 398 | 2-pyrrolidinone, 1-[5-[[4-chloro-1-methyl-5-(trifluoromethyl)-1H-pyrazol-3-yl]oxy]-2-nitrobenzoyl]-<br>MP: 144.0<br>nD: | 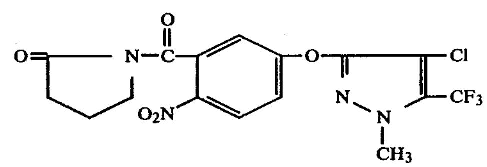 |
| 399 | benzenamine, 5-[[4-chloro-1-methyl-5-(trifluoromethyl)-1H-pyrazol-3-yl]oxy]-N-(2-fluoroethyl)-2-nitro-<br>MP: 65.0–67.0<br>nD: | 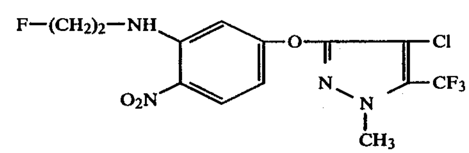 |
| 400 | benzenamine, 5-[[4-chloro-1-methyl-5-(trifluoromethyl)-1H-pyrazol-3-yl]oxy]-N-(2-methoxyethyl)-2-nitro-<br>MP: 58.0–62.0<br>nD: | 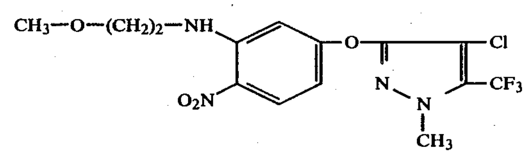 |

-continued

| Ex CP # | Name | Structure |
|---|---|---|
| 401 | benzenamine, 5-[[4-chloro-1-methyl-5-(trifluoromethyl)-1H-pyrazol-3-yl]oxy]-N-(2-ethylbutyl)-2-nitro- MP: 47.0–50.0 nD: | 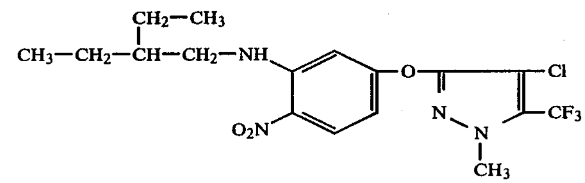 |
| 402 | benzenamine, 5-[[4-bromo-1-methyl-5-(trifluoromethyl)-1H-pyrazol-3-yl]oxy]-N-ethyl-2-nitro- MP: 94.0–97.0 nD: | 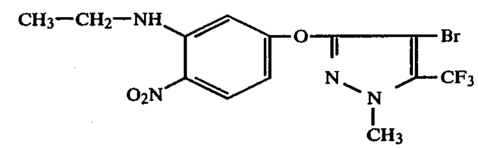 |
| 403 | benzenamine, 5-[[4-chloro-1-methyl-5-(trifluoromethyl)-1H-pyrazol-3-yl]oxy]-N-ethyl-2-nitro-N-2-propenyl- MP: nD: 1.5532 | 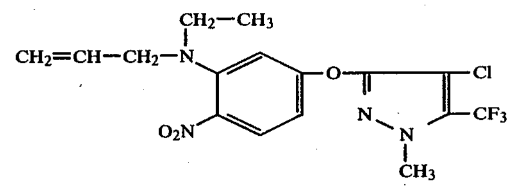 |
| 404 | benzenamine, 5-[[5-chloro-1-methyl-5-(trifluoromethyl)-1H-pyrazol-3-yl]oxy]-N-ethoxy-2-nitro-N-2-propenyl- MP: nD: 1.5305 | 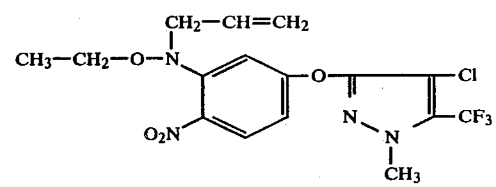 |
| 405 | benzenamine, 5-[[4-chloro-1-methyl-5-(trifluoromethyl)-1H-pyrazol-3-yl]oxy]-N-ethoxy-N-methyl-2-nitro- MP: nD: 1.5306 | 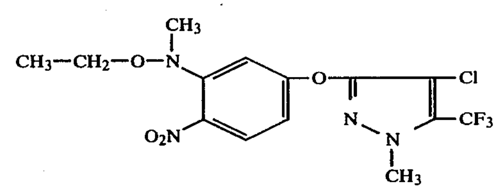 |

-continued

| Ex CP # | Name | Structure |
|---|---|---|
| 406 | benzenamine, 5-[[4-chloro-1-methyl-5-(trifluoromethyl)-1H-pyrazol-3-yl]oxy]-N-(2-methylpropyl)-2-nitro-<br>MP: 76.0–80.0<br>nD: | 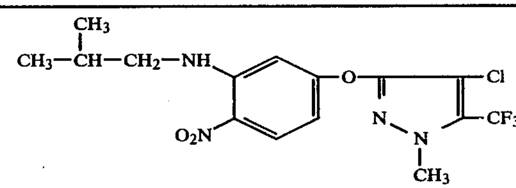 |
| 407 | benzenamine, 5-[[4-chloro-1-methyl-5-(trifluoromethyl)-1H-pyrazol-3-yl]oxy]-N-methyl-2-nitro-N-2-propenyl-<br>MP:<br>nD: 1.5622 | 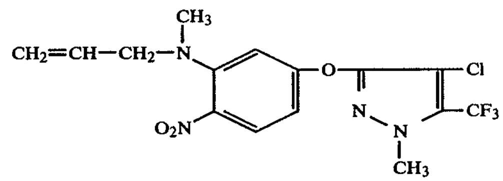 |
| 408 | benzenamine, 5-[[4-chloro-1-methyl-5-(trifluoromethyl)-1H-pyrazol-3-yl]oxy]-N-ethyl-N-methoxy-2-nitro-<br>MP:<br>nD: 1.5297 | 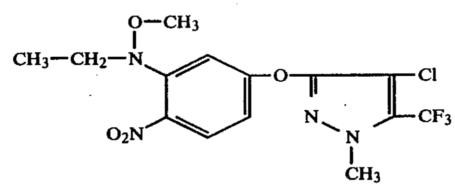 |
| 409 | 1H-pyrazole, 4-chloro-1-methyl-3-[4-nitro-3-(trimethylhydrazino)phenoxy]-5-(trifluoromethyl)-<br>MP:<br>nD: | 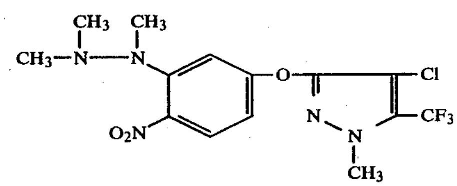 |
| 410 | 1-pyrrolidinamine, N-[5-[[4-chloro-1-methyl-5-(trifluoromethyl)-1H-pyrazol-3-yl]oxy]-2-nitrophenyl-<br>MP: 82.0–84.0<br>nD: | 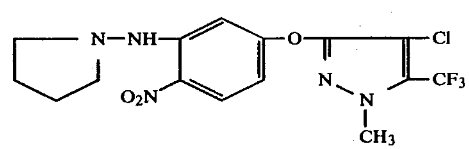 |

| Ex CP # | Name | Structure |
|---|---|---|
| 411 | 4-morpholinamine, N-[5-[[4-chloro-1-methyl-5-(trifluoromethyl)-1H-pyrazol-3-yl]oxy]-2-nitrophenyl]- MP: 113.0–114.0 nD: | 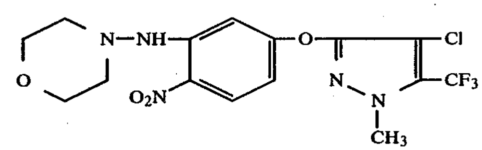 |
| 412 | 1H-pyrazole, 4-chloro-1-methyl-3-[3-(1-methylhydrazino)-4-nitrophenoxy]-5-(trifluoromethyl)- MP: 78.0–81.0 nD: | 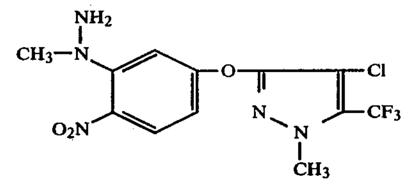 |
| 413 | piperazine, 1-[5-[[4-chloro-1-methyl-5-(trifluoromethyl)-1H-pyrazol-3-yl]oxy]-2-nitrophenyl]-4-methyl- MP: nD: 1.5626 | 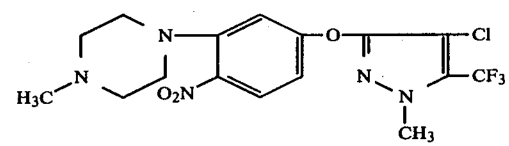 |
| 414 | benzenamine, 5-[4-chloro-1-methyl-5-(trifluoromethyl)-1H-pyrazol-3-yl]oxy]-N-methoxy-2-nitro- MP: 62.0–64.0 nD: | 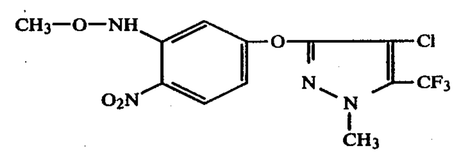 |
| 415 | formamide, N-[[4-chloro-1-methyl-5-(trifluoromethyl)-1H-pyrazol-3-yl]oxy]-2-nitrophenyl]- MP: 97.0–99.0 nD: | 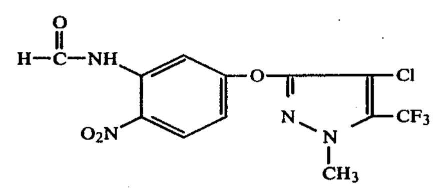 |

-continued

| Ex CP # | Name | Structure |
|---|---|---|
| 416 | methanimidamide, n'-[5-[[4-chloro-1-methyl-5-(trifluoromethyl)-1H-pyrazol-3-yl]oxy]-2-nitrophenyl]-N,N-dimethyl- MP: 75.0–77.0 nD: | 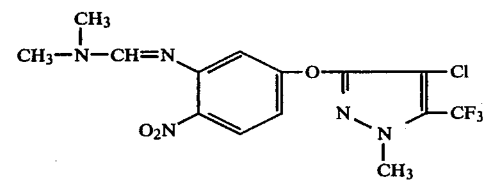 |
| 417 | 1H-pyrazole, 3-[3-(butylthio)-4-nitrophenoxy]-4-chloro-1-methyl-5-(trifluoromethyl)- MP: 50.0–51.0 nD: | 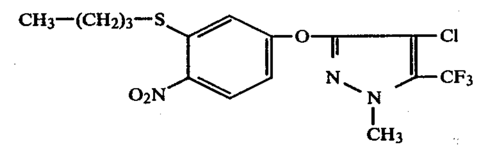 |
| 418 | 1H-azepine, 1-[5-[[4-chloro-1-methyl-5-(trifluoromethyl)-1H-pyrazol-3-yl]oxy]-2-nitrophenyl] hexahydro- MP: 57.0–59.0 nD: | 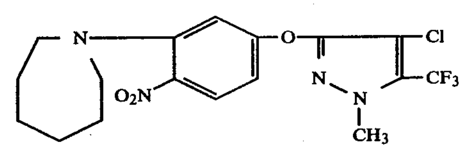 |
| 419 | 1H-isoindole-1,3(2H)-dione, 2-[5-[[4-chloro-1-methyl-5-(trifluoromethyl)-1H-pyrazol-3-yl]oxy]-2-nitrophenyl]- MP: 127.0–128.0 nD: | 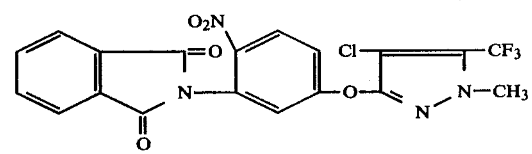 |
| 420 | 1H-pyrazole, 4-chloro-5-(methoxymethyl)-3-(3-methoxy-4-nitrophenoxy)-1-methyl- MP: 92.0–93.0 nD: | 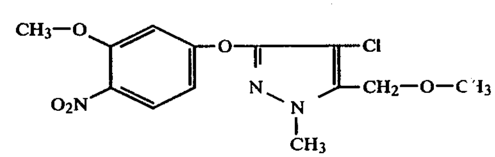 |

-continued

| Ex CP # | Name | Structure |
|---|---|---|
| 421 | benzoic acid, 5-[[4-chloro-5-(methoxymethyl)-1-methyl-1H-pyrazol-3-yl]oxy]-2-nitro-, methyl ester<br>MP: 108.0–109.0<br>nD: | 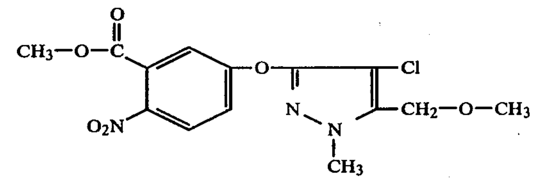 |
| 422 | 1H-imidazole, 1-[5-[[4-chloro-1-methyl-5-(trifluoromethyl)-1H-pyrazol-3-yl]oxy]-2-nitrobenzoyl]-<br>MP: 71.0–73.0<br>nD: | 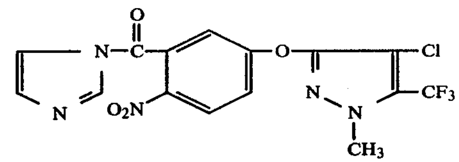 |
| 423 | benzoic acid, 5-[[4-chloro-1-methyl-5-(trifluoromethyl)-1H-pyrazol-3-yl]oxy]-2-nitro-, 1-(ethoxycarbonyl)propyl ester<br>MP:<br>nD: 1.5053 | 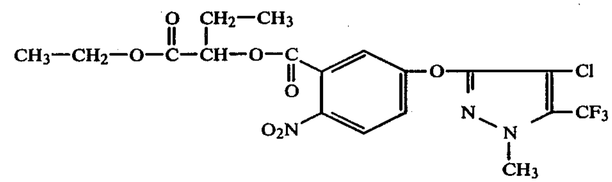 |
| 424 | benzoic acid, 5-[[4-chloro-1-methyl-5-(trifluoromethyl)-1H-pyrazol-3-yl]oxy]-2-nitro-, 1-(ethoxycarbonyl)butyl ester<br>MP:<br>nD: 1.5060 | 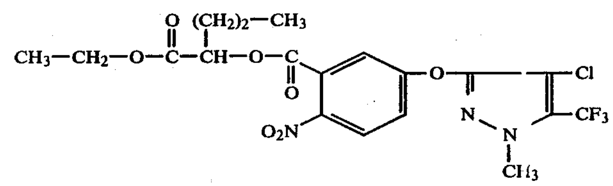 |
| 425 | 1H-pyrazole, 4-bromo-1-[5-[[4-chloro-1-methyl-5-(trifluoromethyl)-1H-pyrazol-3-yl]oxy]-2-nitrobenzoyl]-3-methyl-<br>MP: 91.0<br>nD: | 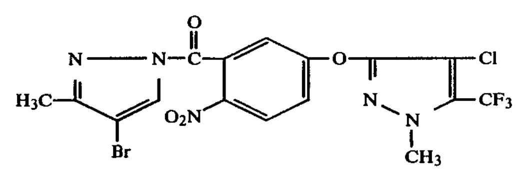 |

-continued

| Ex CP # | Name | Structure |
|---|---|---|
| 426 | benzoic acid, 5-[[4-chloro-1-methyl-5-(trifluoromethyl)-1H-pyrazol-3-yl]oxy]-2-nitro-, 2-(2-methoxyethoxy)ethoxy ethyl ester<br>MP:<br>nD: 1.5106 | $CH_3-O-(CH_2)_2-O-(CH_2)_2-O-(CH_2)_2-O-\overset{O}{\underset{\|}{C}}$ ... |
| 427 | benzoic acid, 5-[[4-chloro-1-methyl-5-(trifluoromethyl)-1H-pyrazol-3-yl]oxy]-2-nitro-, 2-(methylsulfonyl)ethyl ester<br>MP: 90.0<br>nD: | 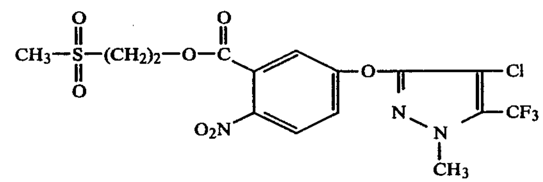 |
| 428 | ethanimidic acid, N-[[5-[[4-chloro-1-methyl-5-(trifluoromethyl)-1H-pyrazol-3-yl]oxy]-2-nitrobenzoyl]oxy]-, ethyl ester<br>MP: 41.0<br>nD: | 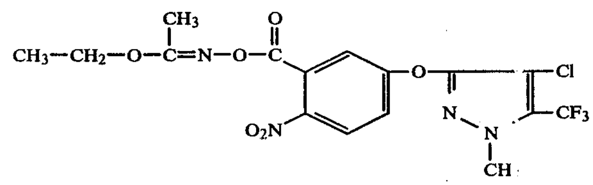 |
| 429 | benzoic acid, 5-[[4-chloro-1-methyl-5-(trifluoromethyl)-1H-pyrazol-3-yl]oxy]-2-nitro-, 2-hydroxyethyl ester<br>MP:<br>nD: 1.5348 | 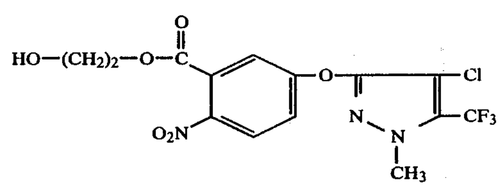 |
| 430 | 1H-pyrazole, 1-[5-[[4-chloro-1-methyl-5-(trifluoromethyl)-1H-pyrazol-3-yl]oxy]-2-nitrobenzoyl]-4-iodo-<br>MP: 37.0<br>nD: | 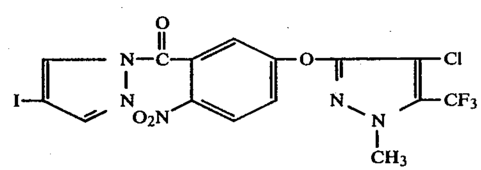 |

-continued

| Ex CP # | Name | Structure |
|---|---|---|
| 431 | 1H-pyrazole, 1-[5-[[4-chloro-1-methyl-5-(trifluoromethyl)-1H-pyrazol-3-yl]oxy]-2-nitrobenzoyl]-3-methyl- MP: 113.0–117.0 nD: | 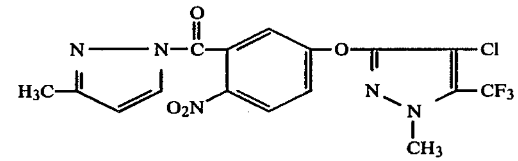 |
| 432 | benzoic acid, 5-[[4-chloro-1-methyl-5-(trifluoromethyl)-1H-pyrazol-3-yl]oxy]-2-nitro-,2-(methylsulfinyl)ethyl ester MP: nD: 1.5434 | 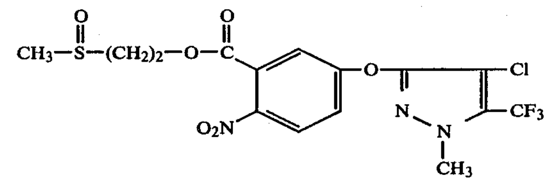 |
| 433 | methanamine, N-[[5-[[4-chloro-1-methyl-5-(trifluoromethyl)-1H-pyrazol-3-yl]oxy]-2-nitrobenzoyl]oxy]-N-methyl- MP: nD: 1.5345 | 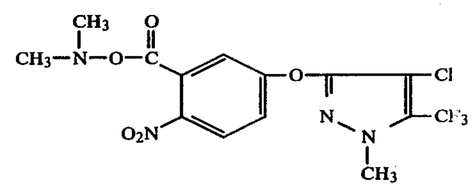 |
| 434 | benzoic acid, 5-[[4-chloro-1-methyl-5-(trifluoromethyl)-1H-pyrazol-3-yl]oxy]-2-nitro, 2-(dimethylamino)ethyl ester MP: nD: 1.5217 | 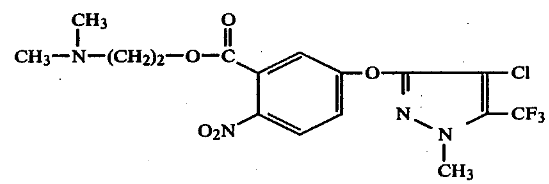 |
| 435 | benzoic acid, 5-[[4-chloro-1-methyl-5-(trifluoromethyl)-1H-pyrazol-3-yl]oxy]-2-nitro-, 2-(chloroacetyl)oxy]ethyl ester MP: nD: 1.5298 | 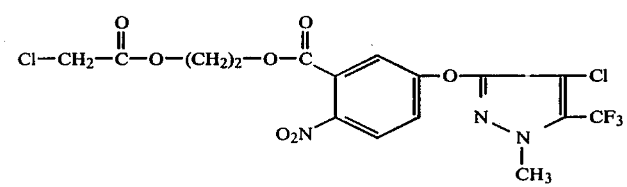 |

-continued

| Ex CP # | Name | Structure |
|---|---|---|
| 436 | benzoic acid, 5-[[4-chloro-1-methyl-5-(trifluoromethyl)-1H-pyrazol-3-yl]oxy]-2-nitro-, 2,2,-dimethylpropyl ester<br>MP:<br>nD: 1.5106 | 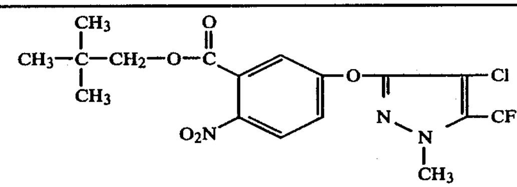 |
| 437 | benzamide, 5-[[4-chloro-1-methyl-5-(trifluoromethyl)-1H-pyrazol-3-yl]oxy]-N-[(di-2-propynylamino)thioxomethyl]-2-nitro-<br>MP: 149.0<br>nD: | 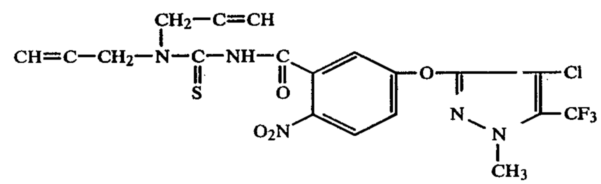 |
| 438 | benzoic acid, 5-[[4-chloro-1-methyl-5-(trifluoromethyl)-1H-pyrazol-3-yl]oxy]-2-nitro-, 2-(trifluoroacetyl)oxy]ethyl ester<br>MP:<br>nD: 1.4943 | 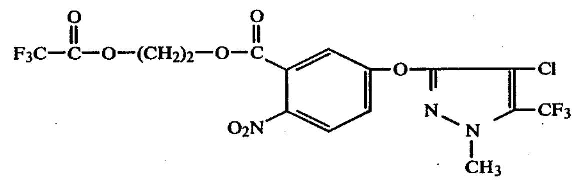 |
| 439 | benzamide, 5-[[4-chloro-1-methyl-5-(trifluoromethyl)-1H-pyrazol-3-yl]oxy]-2-nitro-N,N-di-2-propynyl-<br>MP: 135.0–135.5<br>nD: | 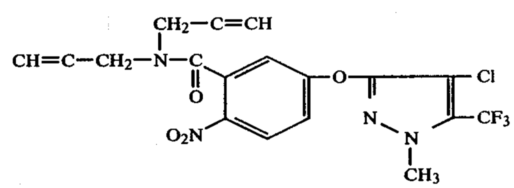 |
| 440 | benzoic acid, 5-[[4-chloro-1-methyl-5-(trifluoromethyl)-1H-pyrazol-3-yl]oxy]-2-nitro-, 2-(1-oxopropoxy)ethyl ester<br>MP:<br>nD: 1.5168 | 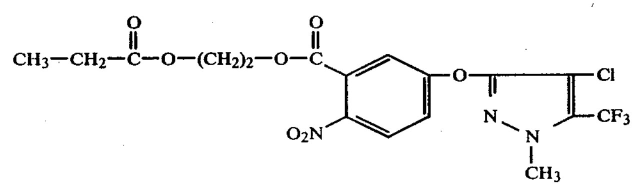 |

| Ex CP # | Name | Structure |
|---|---|---|
| 441 | 2-furancarboxylic acid, 2-[[5-[[4-chloro-1-methyl-5-(trifluoromethyl)-1H-pyrazol-3-yl]oxy]-2-nitrobenzoyl]oxy]ethyl ester<br>MP: 71.0<br>nD: | 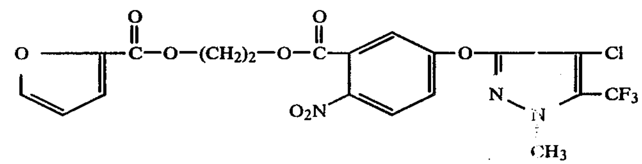 |
| 442 | benzamide, 5-[[4-chloro-1-methyl-5-(trifluoromethyl)-1H-pyrazol-3-yl]oxy]-N-methyl-2-nitro-N-2-propynyl-<br>MP: 90.0–92.0<br>nD: | 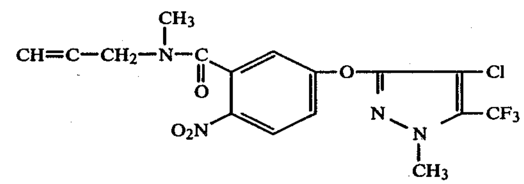 |
| 443 | benzamide, 5-[[4-chloro-1-methyl-5-(trifluoromethyl)-1H-pyrazol-3-yl]oxy]-N-(2-hydroxyethyl)-2-nitro-<br>MP: 154.0<br>nD: | 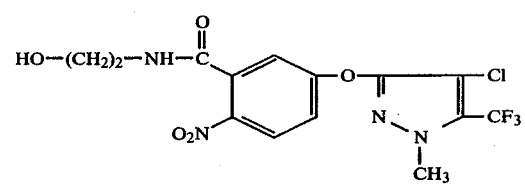 |
| 444 | benzoic acid, 5-[[4-chloro-1-methyl-5-(trifluoromethyl)-1H-pyrazol-3-yl]oxy]-2-nitro, 2-(methoxyacetyl)oxy ethyl ester<br>MP:<br>nD: 1.5158 | 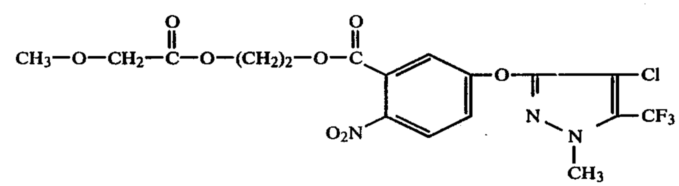 |
| 445 | butanedioic acid, 2-[[5-[[4-chloro-1-methyl-5-(trifluoromethyl)-1H-pyrazol-3-yl]oxy]-2-nitrobenzoyl]oxy]ethyl ethyl ester<br>MP:<br>nD: 1.5096 | 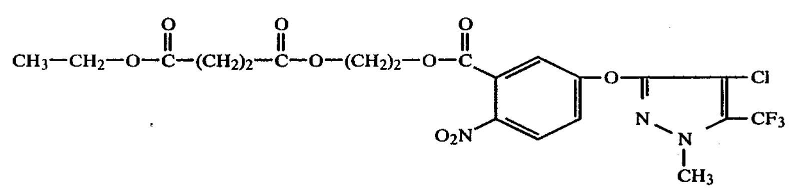 |

| Ex CP # | Name | Structure |
|---|---|---|
| 446 | 1H-pyrazole, 4-chloro-3-[3-(methoxymethoxy)-4-nitrophenoxy]-1-methyl-5-(trifluoromethyl)-<br>MP:<br>nD: 1.5303 | CH₃—O—CH₂—O—[aryl]—O—[pyrazole with Cl, CF₃, N-CH₃]; NO₂ on ring |
| 447 | benzoic acid, 5-[[4-chloro-1-methyl-5-(trifluoromethyl)-1H-pyrazol-3-yl]oxy]-2-nitro-, 2-(2-hydroxyethoxy)ethyl ester<br>MP:<br>nD: 1.5281 | HO—(CH₂)₂—O—(CH₂)₂—O—C(=O)—[aryl-NO₂]—O—[pyrazole] |
| 448 | benzoic acid, 5-[[4-chloro-1-methyl-5-(trifluoromethyl)-1H-pyrazol-3-yl]oxy]-2-nitro-, 2-(iodoacetyl)oxy]ethyl ester<br>MP:<br>nD: 1.5224 | I—CH₂—C(=O)—O—(CH₂)₂—O—C(=O)—[aryl-NO₂]—O—[pyrazole] |
| 449 | cyclohexanone, O-[5-[[4-chloro-1-methyl-5-(trifluoromethyl)-1H-pyrazol-3-yl]oxy]-2-nitrobenzoyl]oxime<br>MP: 115.0<br>nD: | cyclohexyl=N—O—C(=O)—[aryl-NO₂]—O—[pyrazole] |
| 450 | benzoic acid, 5-[[4-chloro-1-methyl-5-(trifluoromethyl)-1H-pyrazol-3-yl]oxy]-2-nitro-, 2-2-(chloroacetyl)oxy]ethoxy ethyl ester<br>MP:<br>nD: 1.5238 | Cl—CH₂—C(=O)—O—(CH₂)₂—O—(CH₂)₂—O—C(=O)—[aryl-NO₂]—O—[pyrazole] |

-continued

| Ex CP # | Name | Structure |
|---|---|---|
| 451 | benzamide, 5-[[4-chloro-1-methyl-5-(trifluoromethyl)-1H-pyrazol-3-yl]oxy]-N-(2-methylpropyl)-2-nitro- MP: 97.5–98.0 nD: | 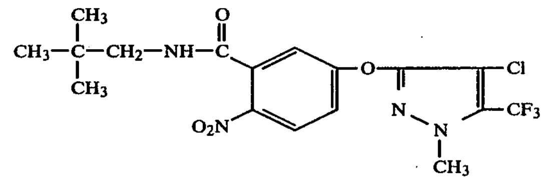 |
| 452 | benzoic acid, 5-[[4-chloro-1-methyl-5-(trifluormethyl)-1H-pyrazol-3-yl]oxy]-2-nitro-, 2-chloro-4-(trifluoromethyl)phenyl ester MP: 111.0 nD: | 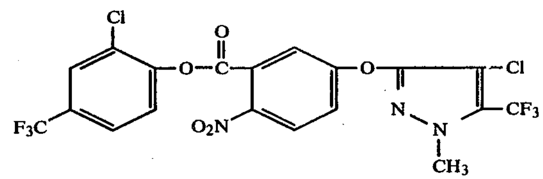 |
| 453 | acetic acid, chloro-, 5-[[4-chloro-1-methyl-5-(trifluoromethyl)-1H-pyrazol-3-yl]oxy]-2-nitrophenyl ester MP: 70.0 nD: | 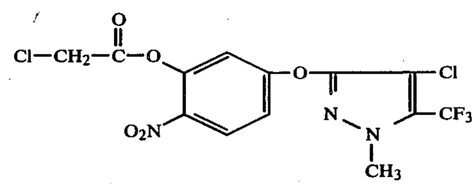 |
| 454 | benzoic acid, 5-[[4-chloro-1-methyl-5-(trifluoromethyl)-1H-pyrazol-3-yl]oxy]-2-nitro-, 4-chloro-1-methyl-5-(trifluoromethyl)-1H-pyrazol-3-yl ester MP: 155.0 nD: | 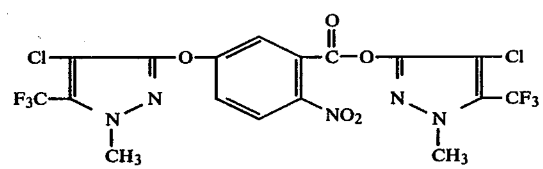 |
| 455 | 1H-pyrazole, 4-chloro-3-[3-(4,5-dihydro-2-oxazolyl)-4-nitrophenoxy]-1-methyl-5-(trifluoromethyl)- MP: 73.0–74.0 nD: | 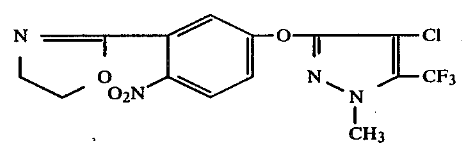 |

| Ex CP # | Name | Structure |
|---|---|---|
| 456 | benzoic acid, 5-[[4-chloro-1-methyl-5-(trifluoromethyl)-1H-pyrazol-3-yl]oxy]-2-nitro-, 2-(1-methylethyl)amino-2-oxoethyl ester<br>MP: 134.0<br>nD: | 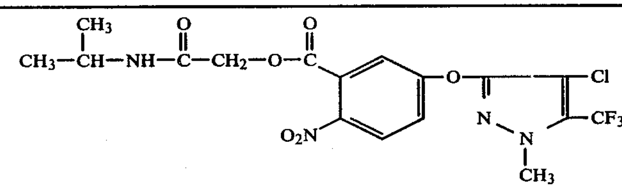 |
| 457 | benzoic acid, 5-[[4-chloro-5-(difluoromethyl)-1-methyl-1H-pyrazol-3-yl]oxy]-2-nitro-, ethyl ester<br>MP:<br>nD: 1.5418 | 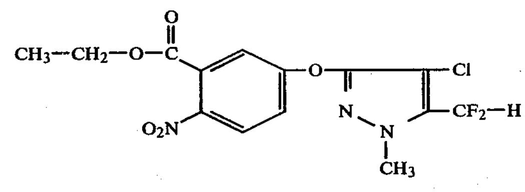 |
| 458 | acetic acid, chloro-, 2-[[5-[[4-chloro-1-methyl-5-(trifluoromethyl)-1H-pyrazol-3-yl]oxy]-2-nitrobenzoyl]amino]ethyl ester<br>MP: 90.0<br>nD: | 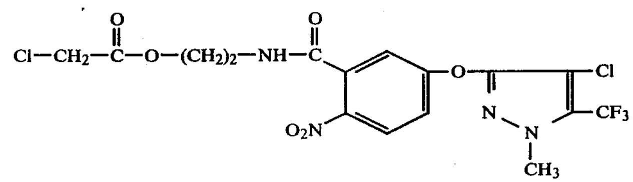 |
| 459 | benzoic acid, 5-[[4-chloro-1-methyl-5-(trifluoromethyl)-1H-pyrazol-3-yl]oxy]-2-nitro-, (1-methylethoxy)methyl ester<br>MP: 102.0–107.0<br>nD: | 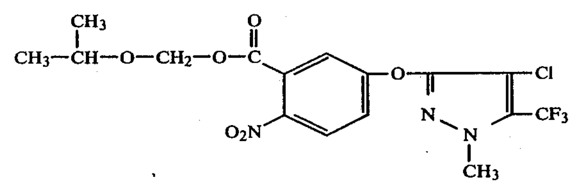 |
| 460 | propanoic acid, 2-[5-[[4-chloro-1-methyl-5-(trifluoromethyl)-1H-pyrazol-3-yl]oxy]-2-nitrophenoxy]-, methoxymethyl ester<br>MP:<br>nD: 1.5181 | 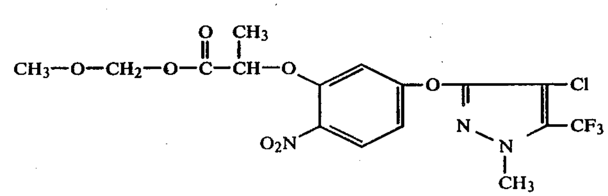 |

-continued

| Ex CP # | Name | Structure |
|---|---|---|
| 461 | 2,3-butanedione,- mono[O-[5-[[4-chloro-1-methyl-5-(trifluoromethyl)- 1H-pyrazol-3-yl]oxy]-2-nitrobenzoyl]oxime] MP: nD: 1.5284 | 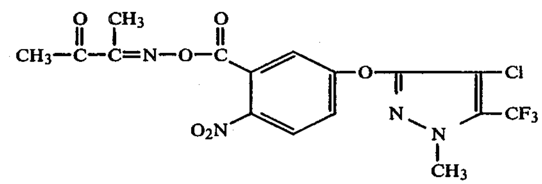 |
| 462 | propanoic acid, 2-[5-[[4-chloro-5-(methoxymethyl)- 1-methyl-1H-pyrazol-3-yl]oxy]-2-nitrophenoxy]-, ethyl ester MP: 46.0-47.0 nD: | 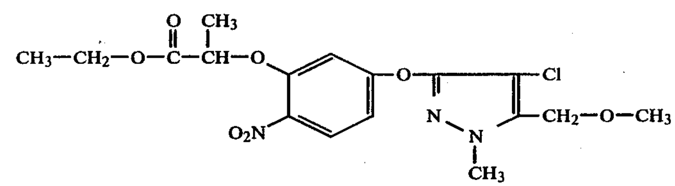 |
| 463 | benzenamine, 5-[[4-iodo-1-methyl-5-(trifluoromethyl)-1H-pyrazol- 3-yl]oxy]-N-methyl-2-nitro- MP: 107.0-108.0 nD: | 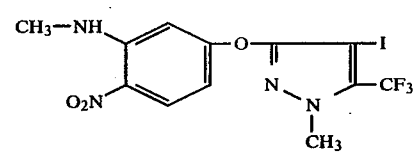 |
| 464 | 1H-pyrazole, 4-bromo-5-(difluoromethyl)-3-[3-(2- fluoroethoxy)-4-nitrophenoxy]-1-methyl- MP: 78.0-79.0 nD: | 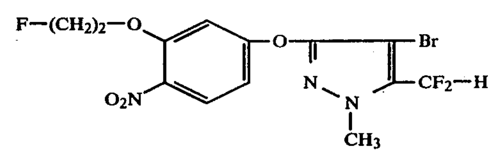 |
| 465 | 1H-pyrazole, 4-bromo-5-(difluoromethyl)-3-(3- methoxy-4-nitrophenoxy)-1-methyl- MP: 98.0-99.0 nD: | 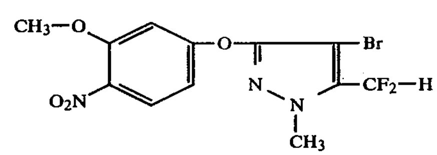 |

| Ex CP # | Name | Structure |
|---|---|---|
| 466 | 1H-pyrazole, 5-(difluoromethyl)-4-fluoro-3-[3-(2-fluoroethoxy)-4-nitrophenoxy]-1-methyl-<br>MP: 51.0–52.0<br>nD: | 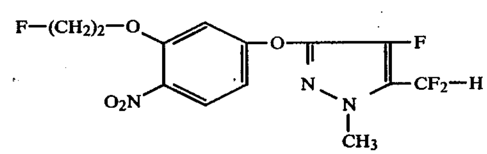 |
| 467 | benzenamine, 5-[[5-(difluoromethyl)-4-fluoro-1-methyl-1H-pyrazol-3-yl]oxy]-N-methyl-2-nitro-<br>MP: 134.0–135.0<br>nD: | 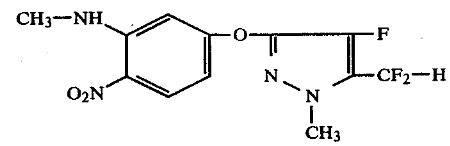 |
| 468 | 1H-pyrazole, 5-(difluoromethyl)-4-fluoro-3-(3-methoxy-4-nitrophenoxy)-1-methyl-<br>MP: 69.0–70.0<br>nD: | 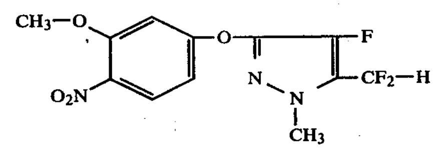 |
| 469 | benzenamine, 5-[[4-bromo-5-(difluoromethyl)-1-methyl-1H-pyrazol-3-yl]oxy]-N-methyl-2-nitro-<br>MP: 149.0–151.0<br>nD: | 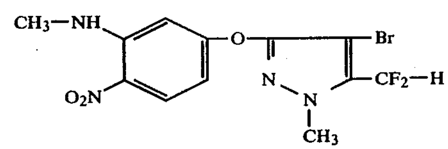 |
| 470 | benzoic acid, 5-[[4-bromo-5-(difluoromethyl)-1-methyl-1H-pyrazol-3-yl]oxy]-2-nitro-, methyl ester<br>MP: 75.0–76.0<br>nD: | 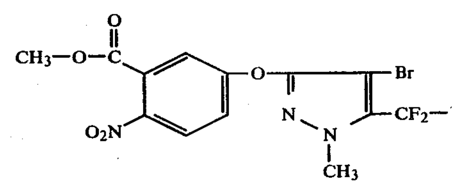 |

| Ex CP # | Name | Structure |
|---|---|---|
| 471 | benzenamine, 5-[[4-chloro-1-methyl-5-(trifluoromethyl)-1H-pyrazol-3-yl]oxy]-2-nitro-N-2-propenyl-N-(2-propenyloxy)-<br>MP:<br>nD: 1.5295 | 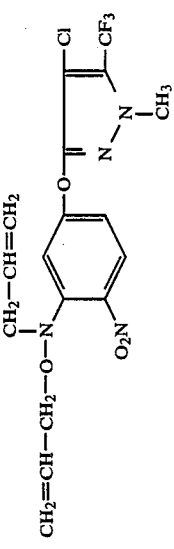 |
| 472 | benzenamine, 5-[[4-chloro-1-methyl-5-(trifluoromethyl)-1H-pyrazol-3-yl]oxy]-N-methyl-2-nitro-N-(2-propenyloxy)-<br>MP:<br>nD: 1.5357 | 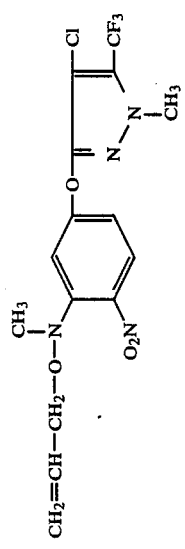 |
| 473 | 1H-pyrazole, 4-chloro-1-methyl-3-[3-(2-methyl-1-aziridinyl)-4-nitrophenoxy]-5-(trifluoromethyl)-<br>MP:<br>nD: 1.5489 | 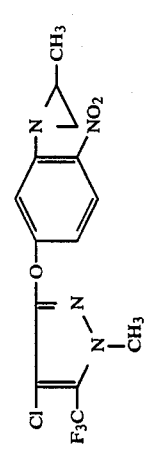 |
| 474 | benzenamine, 5-[[4-chloro-1-methyl-5-(trifluoromethyl)-1H-pyrazol-3-yl]oxy]-N-(1,2-dimethylpropyl)-2-nitro-<br>MP:<br>nD: 1.5698 | 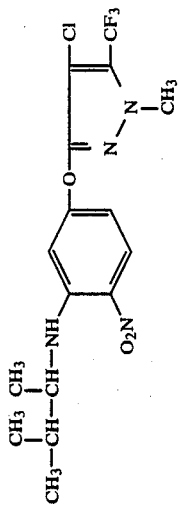 |
| 475 | benzenamine, 5-[[4-chloro-1-methyl-5-(trifluoromethyl)-1H-pyrazol-3-yl]oxy]-N-(3-methylbutyl)-2-nitro-<br>MP: 65.0–66.0<br>nD: | 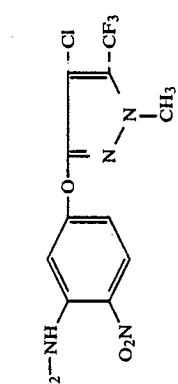 |

-continued

| Ex CP # | Name | Structure |
|---|---|---|
| 476 | benzenamine, 5-[[(4-chloro-1-methyl-5-(trifluoromethyl))-1H-pyrazol-3-yl]oxy]-N-(2,2-dimethylpropyl)-2-nitro- MP: 47.0–49.0 nD: | 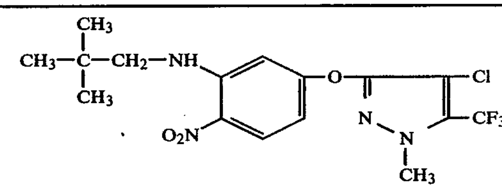 |
| 477 | propanamide, N-[5-[[4-chloro-1-methyl-5-(trifluoromethyl)-1H-pyrazol-3-yl]oxy]-2-nitrophenyl]-N-methyl- MP: 98.0–100.0 nD: | 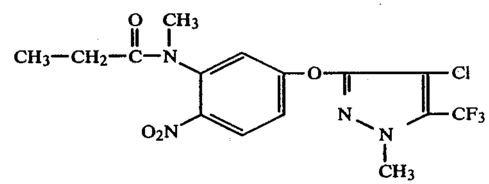 |
| 478 | piperidine, 1-[5-[[4-chloro-1-methyl-5-(trifluoromethyl)-1H-pyrazol-3-yl]oxy]-2-nitrophenyl]- MP: nD: 1.5324 | 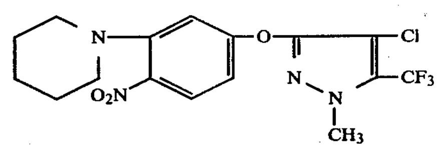 |
| 479 | 1H-pyrazole, 4-chloro-3-[3-(1,2-dimethylhydrazino)-4-nitrophenoxy]-1-methyl-5-(trifluoromethyl)- MP: 71.0–73.0 nD: | 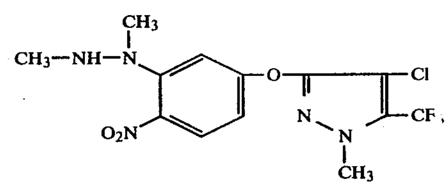 |
| 480 | benzenamine, 5-[[(4-bromo-1-methyl-5-(trifluoromethyl))-1H-pyrazol-3-yl]oxy]-N-methoxy-N-methyl-2-nitro- MP: nD: 1.5502 | 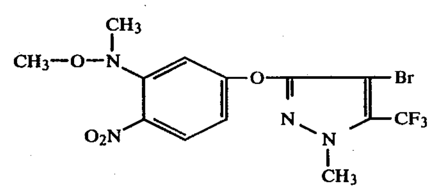 |

| Ex CP # | Name | Structure |
|---|---|---|
| 481 | 1,2-ethanediamine, n[-5-[[4-chloro-1-methyl-5-(trifluoromethyl)-1H-pyrazol-3-yl]oxy]-2-nitrophenyl]-N,N-dimethyl- MP: 102.0–103.0 nD: | 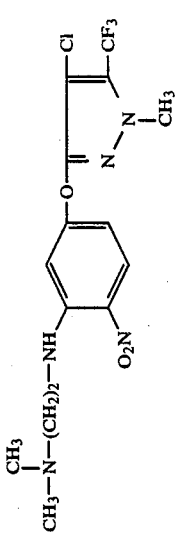 |
| 482 | benzenamine, N-methoxy-N-methyl-5-[[1-methyl-5-(trifluoromethyl)-1H-pyrazol-3-yl]oxy]-2-nitro- MP: nD: 1.5324 | 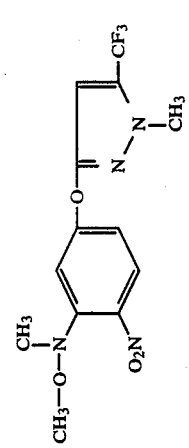 |
| 483 | propanamide, N-[5-[[4-chloro-1-methyl-5-(trifluoromethyl)-1H-pyrazol-3-yl]oxy]-2-nitrophenyl]- MP: 98.0–103.0 nD: | 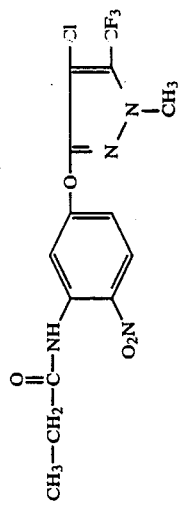 |
| 484 | benzenamine, N-butyl-N-[5-[[4-chloro-1-methyl-5-(trifluoromethyl)-1H-pyrazol-3-yl]oxy]-2-nitrophenyl]-N-methyl- MP: nD: 1.5265 | 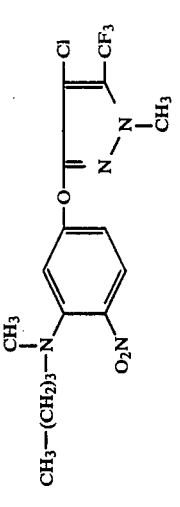 |
| 485 | 1H-pyrazole, 4-chloro-3-[3-(2,5-dihydro-1H-pyrrol-1-yl)-4-nitrophenoxy]-1-methyl-5-(trifluoromethyl)- MP: 76.0–78.0 nD: | 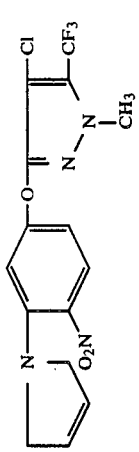 |

-continued

| Ex CP # | Name | Structure |
|---|---|---|
| 486 | benzoic acid, 5-[[1-methyl-4-nitro-5-(trifluoromethyl)-1H-pyrazol-3-yl]oxy]-2-nitro-, ethyl ester<br>MP: 78.0-79.0<br>nD: | structure with CH₃—CH₂—O—C(=O)— attached to benzene ring with O₂N, O-linked to pyrazole with NO₂, CF₃, N—N—CH₃ |
| 487 | 2-piperidinone, 1-[5-[[4-chloro-1-methyl)-1H-pyrazol-3-yl]oxy]-2-nitrobenzoyl]-<br>MP: 77.0<br>nD: | structure with 2-piperidinone N—C(=O)— attached to benzene ring with O₂N, O-linked to pyrazole with Cl, CF₃, N—N—CH₃ |
| 488 | benzoic acid, 5-[[4-chloro-1-methyl-5-(trifluoromethyl)-1H-pyrazol-3-yl]oxy]-2-nitro-, 3-butynyl ester<br>MP: 86.0-87.0<br>nD: | structure with CH≡C—(CH₂)₂—O—C(=O)— attached to benzene ring with O₂N, O-linked to pyrazole with Cl, CF₃, N—N—CH₃ |
| 489 | benzoic acid, 5-[[4-chloro-1-methyl-5-(trifluoromethyl)-1H-pyrazol-3-yl]oxy]-2-nitro-, 1-methyl-2-propynyl ester<br>MP:<br>nD: 1.5290 | structure with CH≡C—CH(CH₃)—O—C(=O)— attached to benzene ring with O₂N, O-linked to pyrazole with Cl, CF₃, N—N—CH₃ |
| 490 | benzoic acid, 5-[[4-chloro-1-methyl-5-(trifluoromethyl)-1H-pyrazol-3-yl]oxy]-2-nitro-, 2-butynyl ester<br>MP:<br>nD: 1.5358 | structure with CH₃—C≡C—CH₂—O—C(=O)— attached to benzene ring with O₂N, O-linked to pyrazole with Cl, CF₃, N—N—CH₃ |

| Ex CP # | Name | Structure |
|---|---|---|
| 491 | morpholine, 4-[5-[[4-chloro-5-(difluoromethyl)-1-methyl-1H-pyrazol-3-yl]oxy]-2-nitrobenzoyl]- MP: 43.0–47.0 nD: | 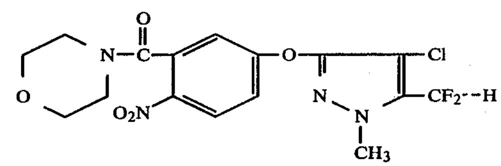 |
| 492 | benzamide, 5-[[4-chloro-1-methyl-5-(trifluoromethyl)-1H-pyrazol-3-yl]oxy]-N-methoxy-N-methyl-2-nitro- MP: nD: 1.5358 | 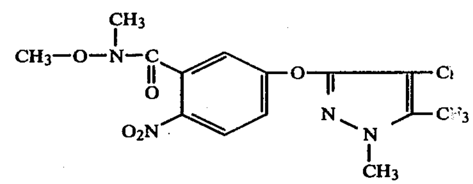 |
| 493 | benzoic acid, 5-[[4-chloro-5-(difluoromethyl)-1-methyl-1H-pyrazol-3-yl]oxy]-2-nitro-, 2-ethoxy-2-oxoethyl ester MP: nD: 1.5326 | 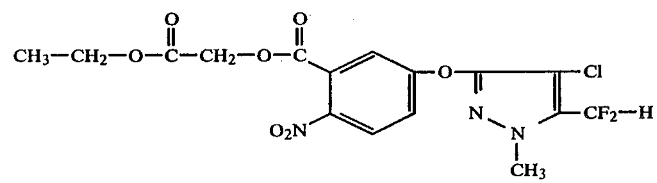 |
| 494 | benzoic acid, 5-[[4-chloro-1-methyl-5-(trifluoromethyl)-1H-pyrazol-3-yl]oxy]-2-nitro-, (2-methylpropoxy)methyl ester MP: nD: 1.5095 | 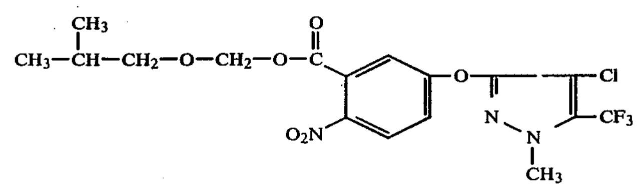 |
| 495 | acetic acid, [[5-[[4-chloro-1-methyl-5-(trifluoromethyl)-1H-pyrazol-3-yl]oxy]-2-nitrobenzoyl]thio]-, ethyl ester MP: nD: 1.5476 | 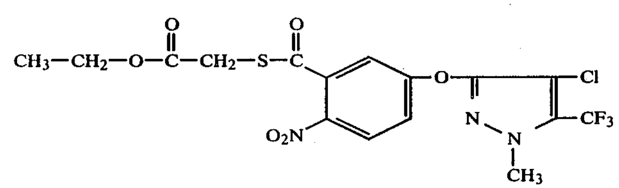 |

-continued

| Ex CP # | Name |
|---|---|
| 496 | 1H-pyrazole, 1-[5-[[4-chloro-1-methyl-5-(trifluoromethyl)-1H-pyrazol-3-yl]oxy]-2-nitrobenzoyl]-3,5-bis(trifluoromethyl)-<br>MP: 93.0<br>nD: |
| 497 | benzeneacetic acid, 5-[[4-chloro-1-methyl-5-(trifluoromethyl)-1H-pyrazol-3-yl]oxy]-2-nitro-, 1-methylethyl ester<br>MP: 105.0<br>nD: |
| 498 | 1H-pyrazole, 4-chloro-1-methyl-3-[3-[(1-methylethoxy)methoxy]-4-nitrophenoxy]-5-(trifluoromethyl)-<br>MP:<br>nD: 1.5217 |
| 499 | benzoic acid, 5-[[4-chloro-1-methyl-5-(trifluoromethyl)-1H-pyrazol-3-yl]oxy]-2-nitro-, 2-methoxy-1-methyl-2-oxoethyl ester, (+-)-<br>MP:<br>nD: 1.5144 |
| 500 | benzoic acid, 5-[[4-chloro-1-methyl-5-(trifluoromethyl)-1H-pyrazol-3-yl]oxy]-2-nitro-, 2-ethoxy-1-oxopropyl ester<br>MP:<br>nD: 1.5169 |

-continued

| Ex CP # | Name | Structure |
|---|---|---|
| 501 | benzoic acid, 5-[[4-chloro-1-methyl-5-(trifluoromethyl)-1H-pyrazol-3-yl]oxy]-2-nitro-, (2-methoxyethoxy)methyl ester<br>MP:<br>nD: 1.5196 | 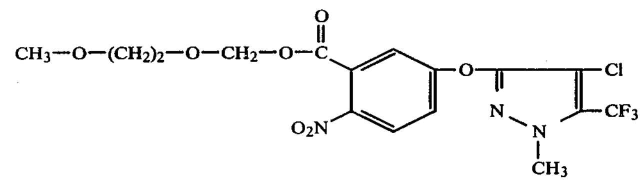 |
| 502 | 1H-pyrazole 4-chloro-3-[3-[(2-methoxyethoxy)methoxy]-4-nitrophenoxy]-1-methyl-5-(trifluoromethyl)-<br>MP:<br>nD: 1.5224 | 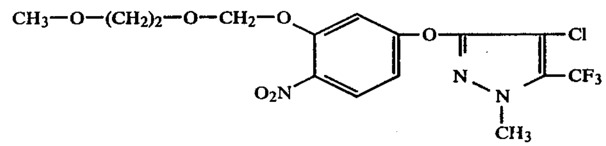 |
| 503 | acetic acid, [5-[[4-chloro-1-methyl-5-(trifluoromethyl)-1H-pyrazol-3-yl]oxy]-2-nitrophenoxy]-, ethyl ester<br>MP:<br>nD: 1.5287 | 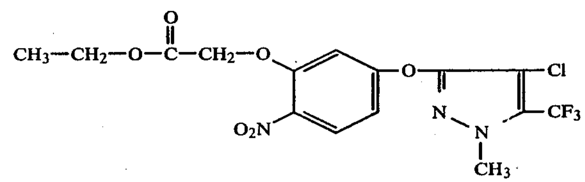 |
| 504 | benzoic acid, 5-[[4-chloro-1-methyl-5-(trifluoromethyl)-1H-pyrazol-3-yl]oxy]-2-nitro-, 2-isocyano-2-methylpropyl ester<br>MP: 51.0–53.0<br>nD: | 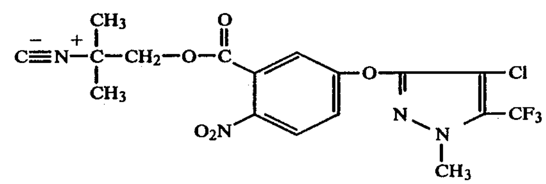 |
| 505 | 1H-pyrazole, 4-chloro-1-methyl-3-[3-[(2-methylpropoxy)methoxy]-4-nitrophenoxy]-5-(trifluoromethyl)-<br>MP:<br>nD: 1.5157 | 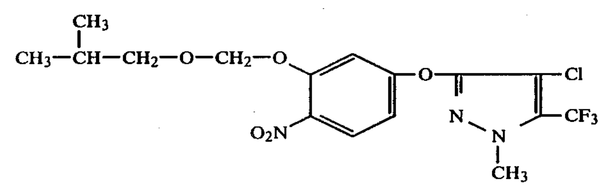 |

| Ex CP # | Name | Structure |
|---|---|---|
| 506 | benzeneacetic acid, 5-[[4-chloro-1-methyl-5-(trifluoromethyl)-1H-pyrazol-3-yl]oxy]-2-nitro,2-ethoxy-2-oxoethyl ester<br>MP: 49.0–50.0<br>nD: | 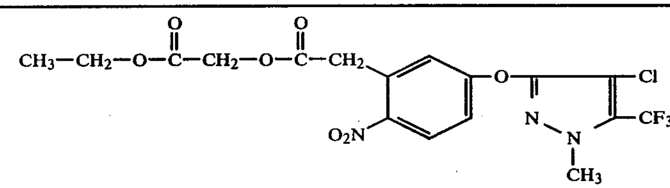 |
| 507 | benzeneacetic acid, 5-[[4-chloro-1-methyl-5-(trifluoromethyl)-1H-pyrazol-3-yl]oxy]-2-nitro,2-methoxy-1-methyl-2-oxoethyl ester, (+-)-<br>MP: 86.0–87.0<br>nD: | 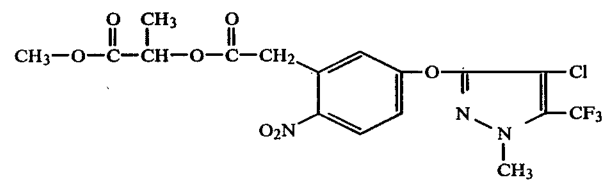 |
| 508 | benzeneacetamide, 5-[[4-chloro-1-methyl-5-(trifluoromethyl)-1H-pyrazol-3-yl]oxy]-2-nitro-<br>MP: 193.0<br>nD: | 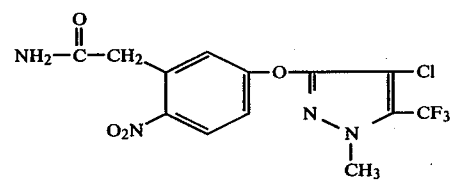 |
| 509 | glycine, N-[5-[[4-chloro-1-methyl-5-(trifluoromethyl)-1H-pyrazol-3-yl]oxy]-2-nitrobenzoyl]-, methyl ester<br>MP: 129.0<br>nD: | 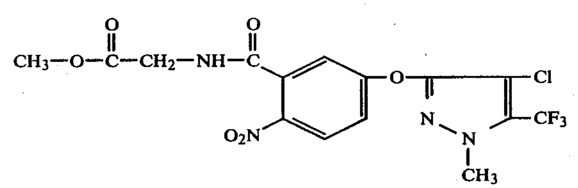 |
| 510 | propanoic acid, 2-[5-[[4-chloro-1-methyl-5-(trifluoromethyl)-1H-pyrazol-3-yl]oxy]-2-nitrophenoxy]-, 2-ethoxy-2-oxoethyl ester<br>MP:<br>nD: 1.5143 | 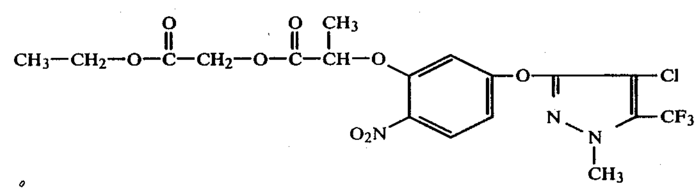 |

| Ex CP # | Name | Structure |
|---|---|---|
| 511 | benzoic acid, 5-[[4-chloro-1-methyl-5-(trifluoromethyl)-1H-pyrazol-3-yl]oxy]-2-nitro-, tetrahydro-2-oxo-3-furanyl ester MP: 107.0 nD: | 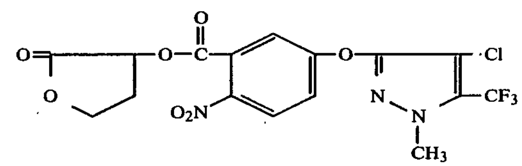 |
| 512 | benzoic acid, 5-[[4-chloro-1-methyl-5-(trifluoromethyl)-1H-pyrazol-3-yl]oxy]-2-nitro-,6-hydroxyhexyl ester MP: nD: 1.5103 | HO—(CH$_2$)$_6$—O— |
| 513 | benzoic acid, 5-[[4-chloro-1-methyl-5-(trifluoromethyl)-1H-pyrazol-3-yl]oxy]-2-nitro, 4-ethoxy-4-oxobutyl ester MP: nD: 1.5157 | CH$_3$—CH$_2$—O—C(=O)—(CH$_2$)$_2$—O— |
| 514 | benzoic acid, 5-[[4-chloro-1-methyl-5-(trifluoromethyl)-1H-pyrazol-3-yl]oxy]-2-nitro, 2,2-dimethoxyethyl ester MP: nD: 1.5164 | CH$_3$—O—CH(O—CH$_3$)—CH$_2$—O— |
| 515 | glycine, N-[5-[[4-chloro-1-methyl-5-(trifluoromethyl)-1H-pyrazol-3-yl]oxy]-2-nitrobenzoyl]- MP: 164.0 nD: | HO—C(=O)—CH$_2$—NH— |

-continued

| Ex CP # | Name | Structure |
|---|---|---|
| 516 | benzoic acid, 5-[[4-chloro-1-methyl-5-(trifluoromethyl)-1H-pyrazol-3-yl]oxy]-2-nitro,2,2-dimethylhydrazide<br>MP: 137.0<br>nD: | 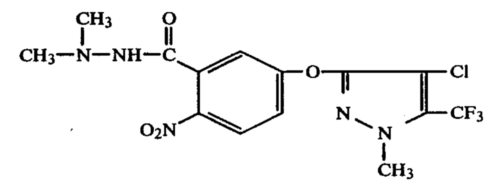 |
| 517 | 1H-pyrazole, 3-(3-bromo-4-nitrophenoxy)-4-chloro-1-methyl-5-(trifluoromethyl)-<br>MP: 56.0–57.0<br>nD: | 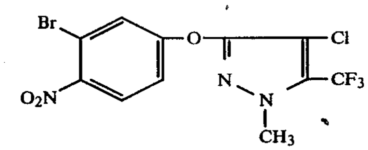 |
| 518 | 2-pyrrolidinone, 1-[5-[[4-chloro-1-methyl-5-(trifluoromethyl)-1H-pyrazol-3-yl]oxy]-2-nitrophenyl]-<br>MP: 91.0–94.0<br>nD: | 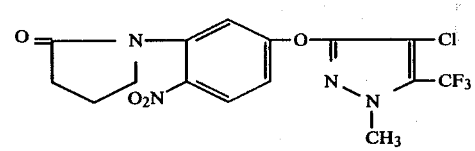 |
| 519 | 1H-pyrazole, 4-chloro-3-[3-[2-chloro-4-(trifluoromethyl)phenoxy]-4-nitrophenoxy]-1-methyl-5-(trifluoromethyl)-<br>MP: 72.0–75.0<br>nD: | 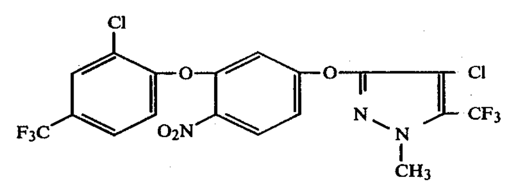 |
| 520 | propanedioic acid, [5-[[4-chloro-1-methyl-5-(trifluoromethyl)-1H-pyrazol-3-yl]oxy]-2-nitrophenyl]-methyl-,diethyl ester<br>MP:<br>nD: 1.5112 | 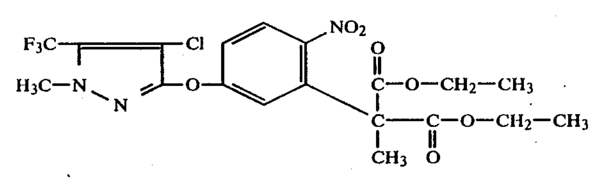 |

-continued

| Ex CP # | Name | Structure |
|---|---|---|
| 521 | benzenamine, 5-[[4-chloro-1-methyl-5-(trifluoromethyl)-1H-pyrazol-3-yl]oxy]-2-nitro-N-[2-[(1,1-dimethylethyl)thio]ethyl]-<br>MP: 61.0–62.0<br>nD: | F₃C, Cl pyrazole linked via O to nitrophenyl with NH–(CH₂)₂–S–C(CH₃)₂–CH₃ substituent |
| 522 | phosphonic acid, [5-[[4-chloro-1-methyl-4-(trifluoromethyl)-1H-pyrazol-3-yl]oxy]-2-nitrophenyl]-, diethyl ester<br>MP: 92.0–94.0<br>nD: | F₃C, Cl pyrazole linked via O to nitrophenyl bearing P(=O)(O–CH₂–CH₃)(O–CH₂–CH₃) |
| 523 | benzenamine, 5-[[4-chloro-1-methyl-5-(trifluoromethyl)-1H-pyrazol-3-yl]oxy]-N-[2-(methylthio)ethyl]-2-nitro-<br>MP: 98.0–101.0<br>nD: | CH₃–S–(CH₂)₂–NH on nitrophenyl linked via O to Cl,CF₃-pyrazole |
| 524 | ethanol, 2-[[5-[[4-chloro-1-methyl-5-(trifluoromethyl)-1H-pyrazol-3-yl]oxy]-2-nitrophenyl]amino]-<br>MP: 98.0–101.0<br>nD: | HO–(CH₂)₂–NH on nitrophenyl linked via O to Cl,CF₃-pyrazole |
| 525 | 1H-pyrazole, 4-chloro-3-[3-hydrazino-4-nitrophenoxy]-1-methyl-5-(trifluoromethyl)-<br>MP: 78.0–81.0<br>nD: | NH₂–NH on nitrophenyl linked via O to Cl,CF₃-pyrazole |

-continued

| Ex CP # | Name | Structure |
|---|---|---|
| 526 | benzenamine, 5-[[4-chloro-1-methyl-5-(trifluoromethyl)-1H-pyrazol-3-yl]oxy]-N-(1-methylpropyl)-2-nitro- MP: nD: 1.5726 | CH₃−CH₂−CH(CH₃)−NH−[phenyl(O₂N)]−O−[pyrazole: Cl, CF₃, N−N−CH₃] |
| 527 | benzenamine, 5-[[4-chloro-1-methyl-5-(trifluoromethyl)-1H-pyrazol-3-yl]oxy]-N-ethoxy-2-nitro- MP: 76.0-79.0 nD: | CH₃−CH₂−O−NH−[phenyl(O₂N)]−O−[pyrazole: Cl, CF₃, N−N−CH₃] |
| 528 | benzenamine, 5-[[4-chloro-1-methyl-5-(trifluoromethyl)-1H-pyrazol-3-yl]oxy]-2-nitro-N-(2-propenyloxy)- MP: 44.0-46.0 nD: | CH₂=CH−CH₂−O−NH−[phenyl(O₂N)]−O−[pyrazole: Cl, CF₃, N−N−CH₃] |
| 529 | benzenamine, 5-[[4-chloro-1-methyl-5-(trifluoromethyl)-1H-pyrazol-3-yl]oxy]-N-(cyclopropylmethyl)-2-nitro- MP: 96.0-98.0 nD: | cyclopropyl-CH₂−NH−[phenyl(NO₂)]−O−[C(Cl)=C(CF₃)−N(CH₃)−N] |
| 530 | benzenamine, 5-[[4-chloro-1-methyl-5-(trifluoromethyl)-1H-pyrazol-3-yl]oxy]-2-nitro-N-(phenylmethyl)- MP: 86.0-88.0 nD: | phenyl−CH₂−NH−[phenyl(O₂N)]−O−[pyrazole: Cl, CF₃, N−N−CH₃] |

| Ex CP # | Name | Structure |
|---|---|---|
| 531 | 1,2-ethanediamine, N,n'-bis[5-[[4-chloro-1-methyl-5-(trifluoromethyl)-1H-pyrazol-3-yl]oxy]-2-nitrophenyl]-N,n'-dimethyl-<br>MP: 130.0–132.0<br>nD: | 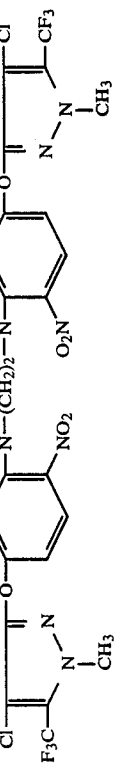 |
| 532 | benzenamine, 5-[[4-bromo-1-methyl-5-(trifluoromethyl)-1H-pyrazol-3-yl]oxy]-N-methyl-2-nitro-<br>MP: 96.0–99.0<br>nD: | 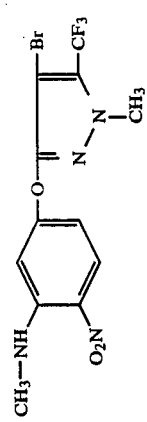 |
| 533 | benzenamine, 5-[[4-bromo-1-methyl-5-(trifluoromethyl)-1H-pyrazol-3-yl]oxy]-N,N-dimethyl-2-nitro-<br>MP:<br>nD: 1.5808 | 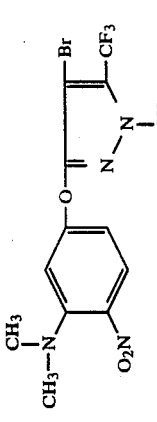 |
| 534 | benzenamine, 5-[[4-bromo-1-methyl-5-(trifluoromethyl)-1H-pyrazol-3-yl]oxy]-N-ethyl-N-methyl-2-nitro-<br>MP:<br>nD: 1.5750 | 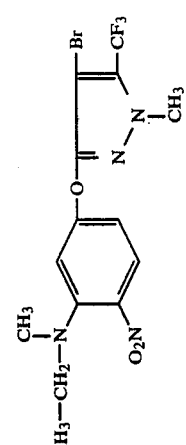 |
| 535 | benzenamine, 5-[[4-bromo-1-methyl-5-(trifluoromethyl)-1H-pyrazol-3-yl]oxy]-N,N-diethyl-2-nitro-<br>MP:<br>nD: 1.5492 | 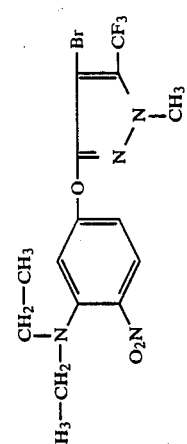 |

| Ex CP # | Name | Structure |
|---|---|---|
| 536 | methanesulfonamide, N-[5-[[4-chloro-1-methyl-5-(trifluoromethyl)-1H-pyrazol-3-yl]oxy]-2-nitrophenyl]- MP: 142.0–145.0 nD: | CH₃-S(O)(O)-NH-C₆H₃(NO₂)-O-pyrazole(Cl,CF₃,N-CH₃) |
| 537 | benzenamine, 5-[[4-bromo-1-methyl-5-(trifluoromethyl)-1H-pyrazol-3-yl]oxy]-N-[(3,4-dichlorophenyl)methyl]-2-nitro- MP: 118.0–119.0 nD: | (3,4-Cl₂C₆H₃)-CH₂-NH-C₆H₃(NO₂)-O-pyrazole(Cl,CF₃,N-CH₃) |
| 538 | benzenamine, 5-[[4-chloro-1-methyl-5-(trifluoromethyl)-1H-pyrazol-3-yl]oxy]-N-(phenylmethoxy)-2-nitro- MP: 53.0–55.0 nD: | C₆H₅-CH₂-O-NH-C₆H₃(NO₂)-O-pyrazole(Cl,CF₃,N-CH₃) |
| 539 | 2-propanol, 1-[[5-[[4-chloro-1-methyl-5-(trifluoromethyl)-1H-pyrazol-3-yl]oxy]-2-nitrophenyl]amino]- MP: 93.0–96.0 nD: | CH₃-CH(OH)-CH₂-NH-C₆H₃(NO₂)-O-pyrazole(Cl,CF₃,N-CH₃) |
| 540 | 1,2-propanediol, 3-[[5-[[4-chloro-1-methyl-5-(trifluoromethyl)-1H-pyrazol-3-yl]oxy]-2-nitrophenyl]amino]- MP: 90.0–96.0 nD: | HO-CH₂-CH(OH)-CH₂-NH-C₆H₃(NO₂)-O-pyrazole(Cl,CF₃,N-CH₃) |

| Ex CP # | Name | Structure |
|---|---|---|
| 541 | 1H-pyrazole, 4-chloro-3,3-(chloromethyl)-4-nitrophenoxy]-1-methyl-5-(trifluoromethyl)- MP: 64.0–66.0 nD: | 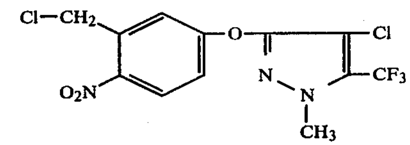 |
| 542 | propanoic acid, 2-[5-[[4-chloro-1-methyl-5-(trifluoromethyl)-1H-pyrazol-3-yl]oxy]-2-nitrophenoxy]-, 1-methylpropyl ester, (S)- MP: 36.0–37.0 nD: | 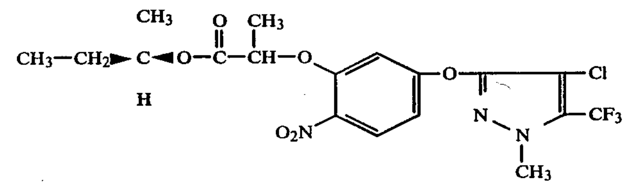 |
| 543 | propanoic acid, 2-[5-[[4-chloro-1-methyl-5-(trifluoromethyl)-1H-pyrazol-3-yl]oxy]-2-nitrophenoxy]-cyclohexyl ester MP: 59.5–61.0 nD: | 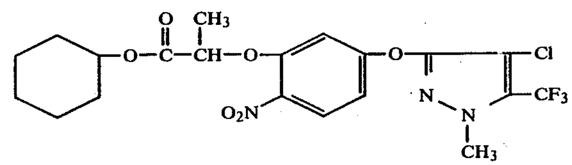 |
| 544 | propanoic acid, 2-[5-[[4-chloro-1-methyl-5-(trifluoromethyl)-1H-pyrazol-3-yl]oxy]-2-nitrophenoxy]-, 1-methylpropyl ester, (R)- MP: 37.0–39.0 nD: | 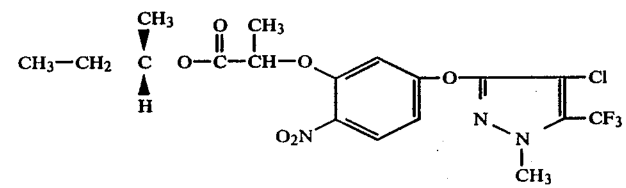 |
| 545 | propanoic acid, 2-[5-[[4-chloro-1-methyl-5-(trifluoromethyl)-1H-pyrazol-3-yl]oxy]-2-nitrophenoxy]-, 5-chloro-2-pyridinyl ester MP: 104.0 nD: | 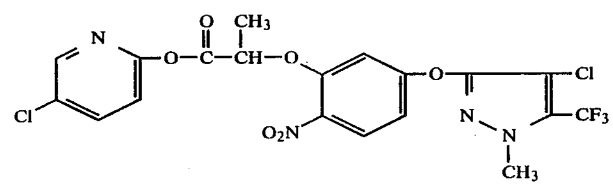 |

-continued

| Ex CP # | Name | Structure |
|---|---|---|
| 546 | propanoic acid, 2-[5-[[(4-chloro-1-methyl-5-(trifluoromethyl)-1H-pyrazol-3-yl]oxy]-2-nitrophenoxy]-, 2-butynyl ester MP: 60.0–61.0 nD: | 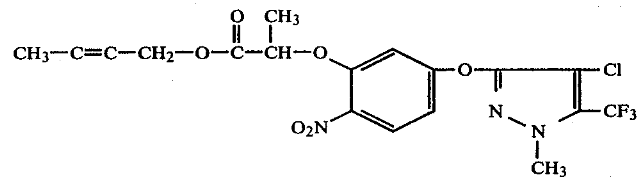 |
| 547 | propanethioic acid, 2-[5-[[(4-chloro-1-methyl-5-(trifluoromethyl)-1H-pyrazol-3-yl]oxy]-2-nitrophenoxy]-, S-(4-chlorophenyl) ester MP: nD: 1.5850 | 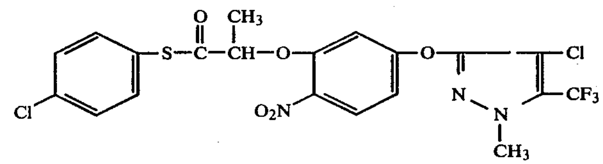 |
| 548 | propanoic acid, 2-[5-[[(4-chloro-1-methyl-5-(trifluoromethyl)-1H-pyrazol-3-yl]oxy]-2-nitrophenoxy]-, 2,2,3,3,4,4,4-heptafluorobutyl ester MP: 39.0–40.0 nD: | 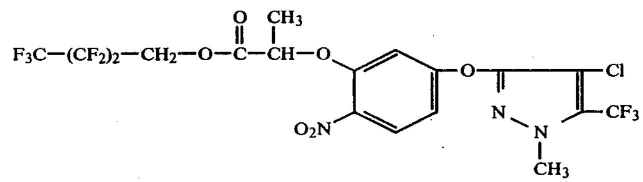 |
| 549 | propanamide, 2-[5-[[(4-chloro-1-methyl-5-(trifluoromethyl)-1H-pyrazol-3-yl]oxy]-2-nitrophenoxy]-N-[(tetrahydro-2-furanyl)methyl]- MP: 64.0–70.0 nD: | 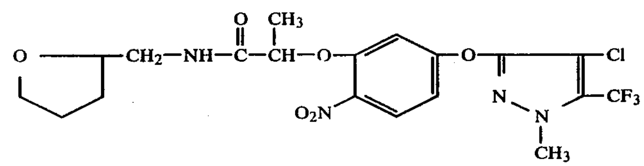 |
| 550 | propanoic acid, 2-[5-[[(4-chloro-1-methyl-5-(trifluoromethyl)-1H-pyrazol-3-yl]oxy]-2-nitrophenoxy]-, 2-naphthalenyl ester MP: 101.0–102.0 nD: | 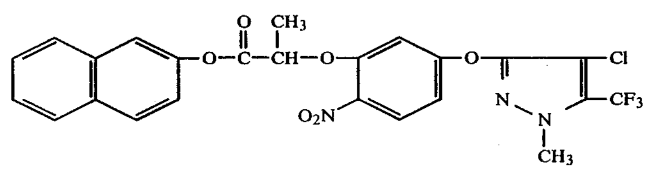 |

-continued

| Ex CP # | Name | Structure |
|---|---|---|
| 551 | alanine, N-[2-[5-[[4-chloro-1-methyl-5-(trifluoromethyl)-1H-pyrazol-3-yl]oxy]-2-nitrophenoxy]-1-oxopropyl]-, ethyl ester MP: 63.0–64.0 nD: | 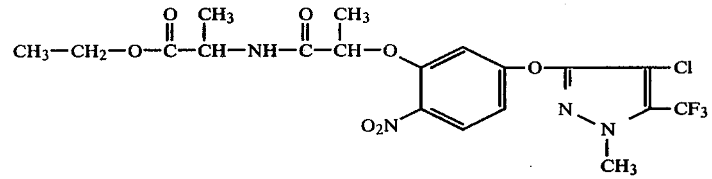 |
| 552 | acetic acid, [[2-[5-[[4-chloro-1-methyl-5-(trifluoromethyl)-1H-pyrazol-3-yl]oxy]-2-nitrophenoxy]-1-oxopropyl]amino]-, methyl ester MP: 94.0–95.0 nD: | 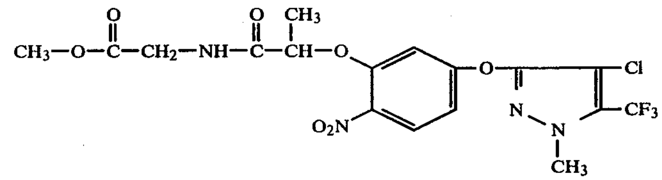 |
| 553 | 1H-pyrazole, 4-chloro-3-(3-(methoxy-4-nitrophenoxy)-1,5-bis(trifluoromethyl)- MP: 54.5–56.5 nD: | 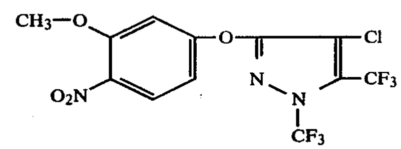 |
| 554 | 1H-pyrazole, 1-(difluoromethyl)-3-(3-methoxy-4-nitrophenoxy)-5-(trifluoromethyl)-, mixt. with 1-(difluoromethyl)-5-(3-methoxy-4-nitrophenoxy)-3-(trifluoromethyl)-1H-pyrazole MP: nD: | 1  1.09 ISOMERS |

| Ex CP # | Name | Structure |
|---|---|---|
| 555 | pentanoic acid, 2-[5-[[(4-chloro-1-methyl-5-(trifluoromethyl)-1H-pyrazol-3-yl]oxy]-2-nitrophenoxy]-, ethyl ester<br>MP:<br>nD: 1.5132 | ![structure] CH$_3$—CH$_2$—O—C(=O)—CH(—(CH$_2$)$_2$—CH$_3$)—O—[phenyl(2-NO$_2$)]—O—[pyrazole: 4-Cl, 5-CF$_3$, N—N—CH$_3$] |

| Ex CP # | Name | Structure |
|---|---|---|
| 556 | pentanoic acid 2-[5-[[4-chloro-1-methyl-5-(trifluoromethyl)-1H-pyrazol-3-yl]oxy]-2-nitrophenoxy]- MP: 101.0-102.0 nD: | 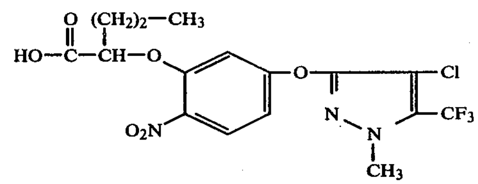 |
| 557 | propanoic acid, 2-[5-[[4-chloro-1-methyl-5-(trifluoromethyl)-1H-pyrazol-3-yl]oxy]-2-nitrophenoxy]-, 3,4-dichlorophenyl ester MP: 95.0-96.0 nD: | 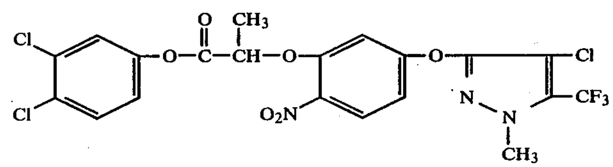 |
| 558 | octanoic acid, 2-[5-[[4-chloro-1-methyl-5-(trifluoromethyl)-1H-pyrazol-3-yl]oxy]-2-nitrophenoxy]-, ethyl ester MP: 35.0 nD: | 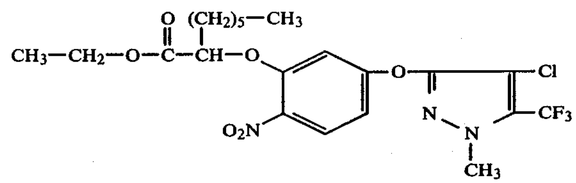 |
| 559 | 1H-pyrazole, 3,3'-[oxybis[(4-nitro-3,1-phenylene)oxy]]bis[4-chloro-1-methyl-5-(trifluoromethyl)- MP: 129.0-130.0 nD: | 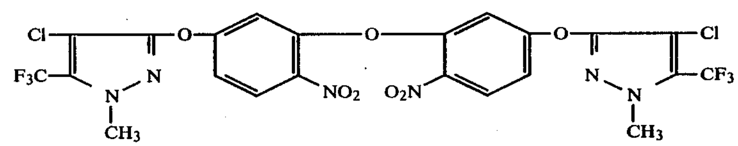 |
| 560 | 1H-pyrazole,-1-[2-[5-[[4-chloro-1-methyl-5-(trifluoromethyl)-1H-pyrazol-3-yl]oxy]-2-nitrophenoxy]-1-oxopropyl]- MP: 90.0-91.0 nD: | 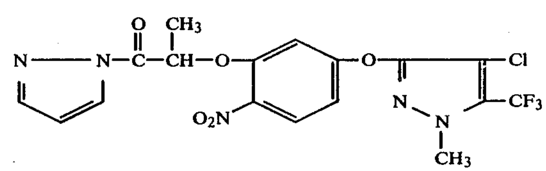 |

| Ex CP # | Name | Structure |
|---|---|---|
| 561 | propanamide, 2-[5-[[4-chloro-1-methyl-5-(trifluoromethyl))-1H-pyrazol-3-yl]oxy]-2-nitrophenoxy]-N-phenyl- MP: 115.0–116.0 nD: | 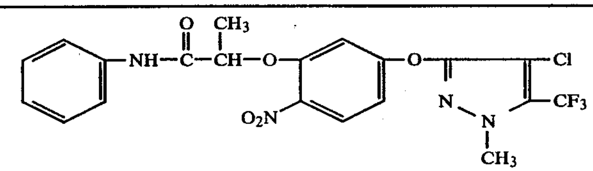 |
| 562 | alanine,- N-[2-[5-[[4-chloro-1-methyl-5-(trifluoromethyl))-1H-pyrazol-3-yl]oxy]-2-nitrophenoxy]-1-oxopropyl]- MP: 71.0–72.0 nD: | 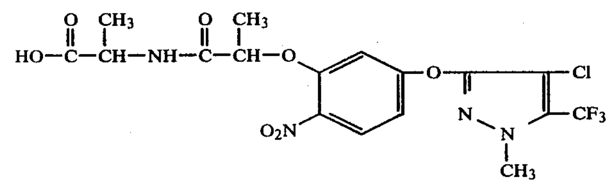 |
| 563 | propanamide, 2-[5-[[4-chloro-1-methyl-5-(trifluoromethyl))-1H-pyrazol-3-yl]oxy]-2-nitrophenoxy]-N-methoxy- MP: 164.0 nD: | 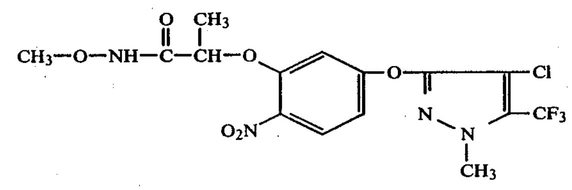 |
| 564 | propanoic acid, 2-[5-[[4-chloro-1-methyl-5-(trifluoromethyl))-1H-pyrazol-3-yl]oxy]-2-nitrophenoxy]-, 2,4,6-trichlorophenyl ester MP: 90.0–91.0 nD: | 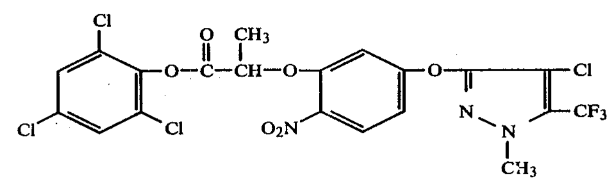 |
| 565 | propanamide, 2-[5-[[4-chloro-1-methyl-5-(trifluoromethyl))-1H-pyrazol-3-yl]oxy]-2-nitrophenoxy]-N-methoxy-N-methyl- MP: 80.0–82.0 nD: | 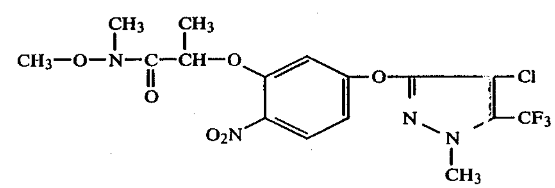 |

-continued

| Ex CP # | Name | Structure |
|---|---|---|
| 566 | propanoic acid, 2-[5-[[4-chloro-1-methyl-5-(trifluoromethyl)-1H-pyrazol-3-yl]oxy]-2-nitrophenoxy]-, butyl ester, (R)- MP: nD: | 97% R ISOMER |
| 567 | pentanoic acid, 2-[5-[[4-chloro-1-methyl-5-(trifluoromethyl)-1H-pyrazol-3-yl]oxy]-2-nitrophenoxy]-, butyl ester MP: nD: 1.5081 | 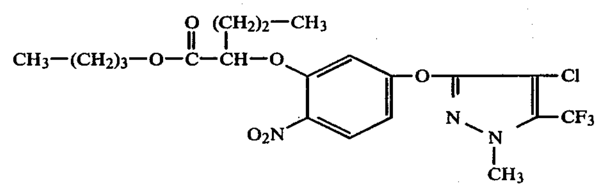 |
| 568 | acetic acid, [[[1-[5-[[4-chloro-1-methyl-5-(trifluoromethyl)-1H-pyrazol-3-yl]oxy]-2-nitrophenyl]ethylidene]amino]oxy]- MP: nD: | 70% 30% Z ISOMER |
| 569 | propanoic acid, 2-[5-[[4-chloro-1-methyl-5-(trifluoromethyl)-1H-pyrazol-3-yl]oxy]-2-nitrophenoxy]-, butyl ester, (S)- MP: 34.0–35.0 nD: | S ISOMER |

| Ex CP # | Name | Structure |
|---|---|---|
| 570 | propanoic acid, 2-[5-[[4-chloro-1-methyl-5-(trifluoromethyl)-1H-pyrazol-3-yl]oxy]-2-nitrophenoxy]-, methyl ester, (R)-<br>MP: 45.0<br>nD: | 96% R ISOMER |
| 571 | acetic acid, [[[1-[5-[[4-chloro-1-methyl-5-(trifluoromethyl)-1H-pyrazol-3-yl]oxy]-2-nitrophenyl]-2-methoxyethylidene]amino]oxy]-, methyl ester<br>MP:<br>nD: 1.5297 | 75% Z<br>25% E ISOMER |
| 572 | propanamide, 2-[5-[[4-chloro-1-methyl-5-(trifluoromethyl)-1H-pyrazol-3-yl]oxy]-2-nitrophenoxy]-N-(methylsulfonyl)-, (R)-<br>MP: 165.0–166.0<br>nD: | R ISOMER |
| 573 | octanoic acid, 2-[5-[[4-chloro-1-methyl-5-(trifluoromethyl)-1H-pyrazol-3-yl]oxy]-2-nitrophenoxy]-, butyl ester<br>MP:<br>nD: 1.5040 | 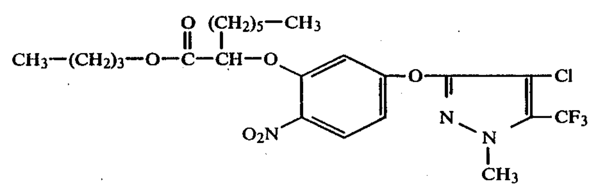 |

-continued

| Ex CP # | Name | Structure |
|---|---|---|
| 574 | octanamide, 2-[5-[[4-chloro-1-methyl-5-(trifluoromethyl)-1H-pyrazol-3-yl]oxy]-2-nitrophenoxy]-N-(methsulfonyl)-<br>MP: 94.0–95.0<br>nD: | *structure* |
| 575 | pentanamide, 2-[5-[[4-chloro-1-methyl-5-(trifluoromethyl)-1H-pyrazol-3-yl]oxy]-2-nitrophenoxy]-N-(methylsulfonyl)-<br>MP: 160.0–161.0<br>nD: | *structure* |
| 576 | propanoic acid, 2-[5-[[4-chloro-1-methyl-5-(trifluoromethyl)-1H-pyrazol-3-yl]oxy]-2-nitrophenoxy]-, octyl ester<br>MP:<br>nD: 1.5047 | *structure* |
| 577 | propanoic acid, 2-[5-[[4-chloro-1-methyl-5-(trifluoromethyl)-1H-pyrazol-3-yl]oxy]-2-nitrophenoxy]-, tetrahydro-3-furanyl ester<br>MP: 59.0–60.0<br>nD: | *structure* |
| 578 | propanoic acid, 2-[5-[[4-chloro-1-methyl-5-(trifluoromethyl)-1H-pyrazol-3-yl]oxy]-2-nitrophenoxy]-, 2-(trimethylsilyl)ethyl ester<br>MP: 62.0–63.0<br>nD: | *structure* |

-continued

| Ex CP # | Name | Structure |
|---|---|---|
| 579 | propanoic acid, 2-[5-[[4-chloro-1-methyl-5-(trifluoromethyl)-1H-pyrazol-3-yl]oxy]-2-nitrophenoxy]-, hexyl ester MP: nD: 1.5076 | CH$_3$—(CH$_2$)$_5$—O—C(=O)—CH(CH$_3$)—O—(phenyl, 2-NO$_2$, 4-O—pyrazole[4-Cl, 5-CF$_3$, 1-N-N-CH$_3$]) |
| 580 | propanethioic acid, 2-[5-[[4-chloro-1-methyl-5-(trifluoromethyl)-1H-pyrazol-3-yl]oxy]-2-nitrophenoxy]-, S-butyl ester MP: nD: 1.5349 | CH$_3$—(CH$_2$)$_3$—S—C(=O)—CH(CH$_3$)—O—(phenyl, 2-NO$_2$, 4-O—pyrazole[4-Cl, 5-CF$_3$, 1-N-N-CH$_3$]) |
| 581 | ethanone, 1-[5-[[4-chloro-1-methyl-5-(trifluoromethyl)-1H-pyrazol-3-yl]oxy]-2-nitrophenyl]-2-methoxy- MP: 70.0–70.5 nD: | CH$_3$—O—CH$_2$—C(=O)—(phenyl, 2-NO$_2$, 4-O—pyrazole[4-Cl, 5-CF$_3$, 1-N-N-CH$_3$]) |
| 582 | acetamide, 2-[[[1-[5-[[4-chloro-1-methyl-5-(trifluoromethyl)-1H-pyrazol-3-yl]oxy]-2-nitrophenyl]ethylidene]amino]oxy]-N-methyl- MP: 75–85 nD: | CH$_3$—NH—C(=O)—CH$_2$—O—N=C(CH$_3$)—(phenyl, 2-NO$_2$, 4-O—pyrazole[4-Cl, 5-CF$_3$, 1-N-N-CH$_3$]) 75% E 25% Z ISOMER |
| 583 | 1H-pyrazole, 3,3'-[thiobis[(4-nitro-3,1-phenylene)oxy]]bis[4-chloro-1-methyl-5-(trifluoromethyl)- MP: 159.5–160.0 nD: | Symmetric bis-pyrazolyloxy-nitrophenyl thioether: pyrazole[4-Cl, 5-CF$_3$, 1-N-N-CH$_3$]—O—(phenyl, NO$_2$)—S—(phenyl, NO$_2$)—O—pyrazole[4-Cl, 5-CF$_3$, 1-N-N-CH$_3$] |

| Ex CP # | Name | Structure |
|---|---|---|
| 584 | propanethioic acid, 2-[5-[[4-chloro-1-methyl-5-(trifluoromethyl)-1H-pyrazol-3-yl]oxy]-2-nitrophenoxy]- <br> MP: <br> nD: 1.5174 | 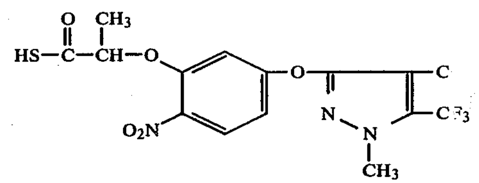 |
| 585 | propanoic acid, 2-[5-[[4-chloro-1-methyl-5-(trifluoromethyl)-1H-pyrazol-3-yl]oxy]-2-nitrophenoxy], 2-methoxy-1-methylethyl ester <br> MP: <br> nD: 1.5123 | 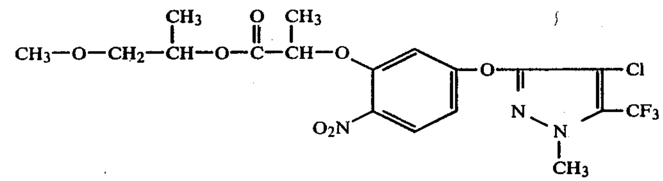 |
| 586 | pentanamide, 2-[5-[[4-chloro-1-methyl-5-(trifluoromethyl)-1H-pyrazol-3-yl]oxy]-2-nitrophenoxy-N-methyl- <br> MP: 109.0–110.0 <br> nD: | 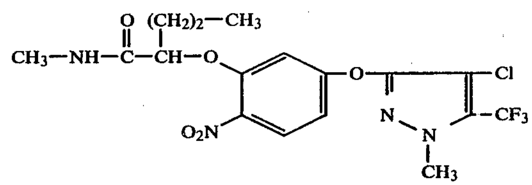 |
| 587 | 1H-pyrazole, 3,3'-[dithiobis[(4-nitro-3,1-phenylene)oxy]]bis[4-chloro-1-methyl-5-((trifluoromethyl))- <br> MP: 163.0–164.0 <br> nD: | 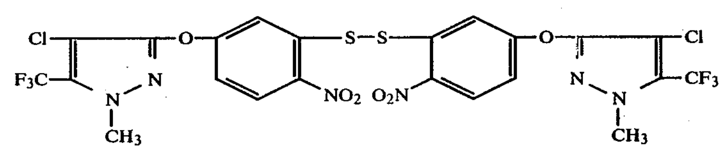 |
| 588 | propanoic acid, 2-[5-[[4-chloro-1-methyl-5-(trifluoromethyl)-1H-pyrazol-3-yl]oxy]-2-nitrophenoxy], methyl ester, (S)- <br> MP: 44.0–45.0 <br> nD: | S ISOMER |

-continued

| Ex CP # | Name | Structure |
|---|---|---|
| 589 | propanoic acid, 3-[5-[[4-chloro-1-methyl-5-(trifluoromethyl)-1H-pyrazol-3-yl]oxy]-2-nitrophenoxy]-2,2-dimethyl-, methyl ester<br>MP:<br>nD: 1.5220 | 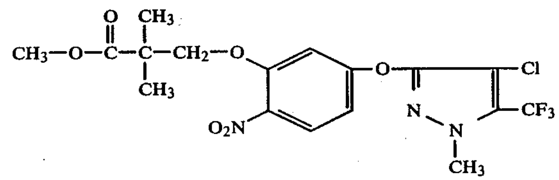 |
| 590 | propanamide, 2-[5-[[4-chloro-1-methyl-5-(trifluoromethyl)-1H-pyrazol-3-yl]oxy]-2-nitrophenoxy]-N-(methylsulfonyl)-, (S)<br>MP: 167.0–168.0<br>nD:<br>S ISOMER | 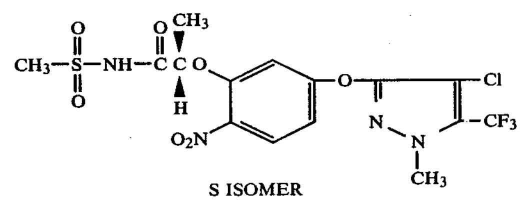 |
| 591 | ethanethioic acid, [[[1-[5-[[4-chloro-1-methyl-5-(trifluoromethyl)-1H-pyrazol-3-yl]oxy]-2-nitrophenyl]ethylidene]amino]oxy]-, S-butyl ester<br>MP:<br>nD: 1.5415<br>75% E<br>25% Z ISOMER | 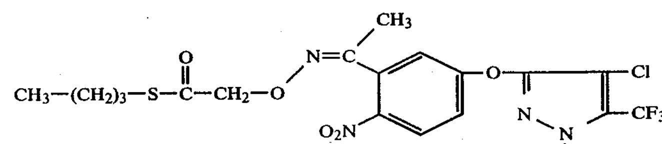 |
| 592 | octanoic acid, 2-[5-[[4-chloro-1-methyl-5-(trifluoromethyl)-1H-pyrazol-3-yl]oxy]-2-nitrophenoxy]-<br>MP: 65.0<br>nD: | 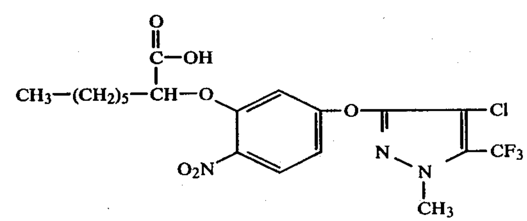 |

| Ex CP # | Name | Structure |
|---|---|---|
| 593 | propanoic acid, 3-[5-[[4-chloro-1-methyl-5-(trifluoromethyl)-1H-pyrazol-3-yl]oxy]-2-nitrophenoxy]-2,2-dimethyl-<br>MP: 149.0–150.0<br>nD: | 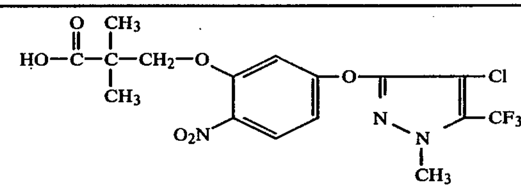 |
| 594 | propanoic acid, 2-[5-[[4-chloro-1-methyl-5-(trifluoromethyl)-1H-pyrazol-3-yl]oxy]-2-nitrophenoxy]-, 4-oxopentyl ester<br>MP:<br>nD: 1.5214 | 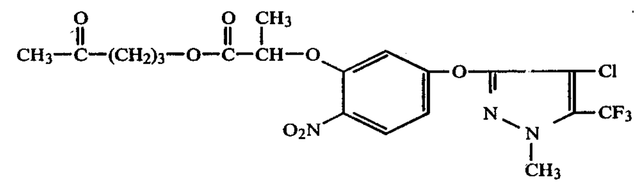 |
| 595 | pyrrolidine-, 1-[2-[5-[[4-chloro-1-methyl-5-(trifluoromethyl)-1H-pyrazol-3-yl]oxy]-2-nitrophenoxy]-1-oxopropyl]-<br>MP:<br>nD: | 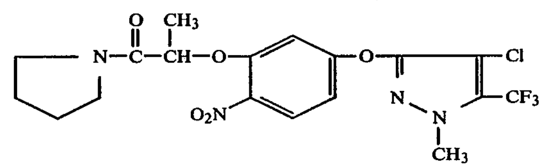 |
| 596 | propanamide, 3-[5-[[4-chloro-1-methyl-5-(trifluoromethyl)-1H-pyrazol-3-yl]oxy]-2-nitrophenoxy]-N,N,2,2-tetramethyl-<br>MP:<br>nD: | 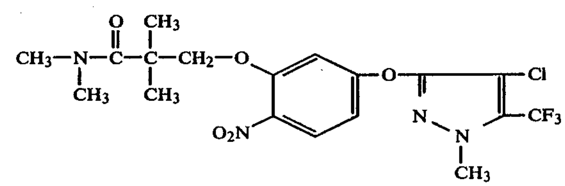 |
| 597 | propanoic acid, 3-[5-[[4-chloro-1-methyl-5-(trifluoromethyl)-1H-pyrazol-3-yl]oxy]-2-nitrophenoxy]-2,2-dimethyl-, ethyl ester<br>MP:<br>nD: 1.5170 | 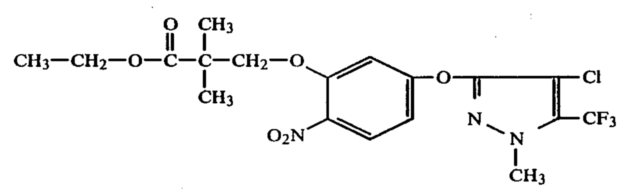 |

-continued

| Ex CP # | Name | Structure |
|---|---|---|
| 598 | acetic acid, [[1-[5-[[4-chloro-1-methyl-5-(trifluoromethyl)]ethylidene]amino]oxy]-, ethyl ester<br>MP:<br>nD: 1.5274 | (96% E, 4% Z ISOMER) |
| 599 | acetic acid, [[1-[5-[[4-chloro-1-methyl-5-(trifluoromethyl)-1H-pyrazol-3-yl]oxy]-2-nitrophenyl]ethylidene]amino]oxy]-, ethyl ester<br>MP:<br>nD: 1.5261 | (95% Z, 5% E ISOMER) |
| 600 | propanoic acid, 2-[5-[[4-chloro-1-methyl-5-(trifluoromethyl)-1H-pyrazol-3-yl]oxy]-2-nitrophenoxy]-, 4-nitrophenyl ester<br>MP: 71.0–73.0<br>nD: | 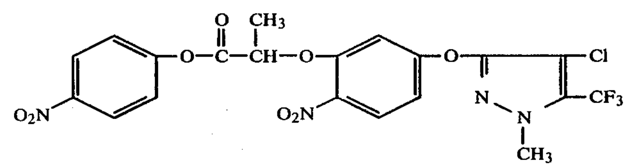 |
| 601 | propanoic acid, 2-[5-[[4-chloro-1-methyl-5-(trifluoromethyl)-1H-pyrazol-3-yl]oxy]-2-nitrophenoxy]-, (trimethylsilyl)methyl ester<br>MP:<br>nD: 1.5105 | 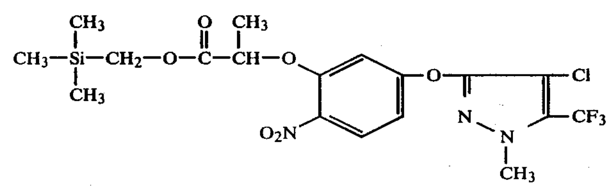 |

| Ex CP # | Name | Structure |
|---|---|---|
| 602 | octanamide, 2-[5-[[4-chloro-1-methyl-5-(trifluoromethyl)-1H-pyrazol-3-yl]oxy]-2-nitrophenoxy]-N-methyl- MP: 142.0–143.0 nD: | ![structure] CH₃—NH—C(=O)—CH((CH₂)₅—CH₃)—O—C₆H₃(NO₂)—O—pyrazole(Cl, CF₃, N-CH₃) |
| 603 | propanoic acid, 3-[5-[[4-chloro-1-methyl-5-(trifluoromethyl)-1H-pyrazol-3-yl]oxy]-2-nitrophenoxy]-2,2-dimethyl, butyl ester MP: nD: 1.5110 | CH₃—(CH₂)₅—O—C(=O)—C(CH₃)₂—CH₂—O—C₆H₃(NO₂)—O—pyrazole(Cl, CF₃, N-CH₃) |
| 604 | glycine, N-[2-[5-[[4-chloro-1-methyl-5-(trifluoromethyl)-1H-pyrazol-3-yl]oxy]-2-nitrophenoxy]-1-oxopropyl]- MP: 51.0 nD: | HO—C(=O)—CH₂—NH—C(=O)—CH(CH₃)—O—C₆H₃(NO₂)—O—pyrazole(Cl, CF₃, N-CH₃) |
| 605 | propanethioic acid, 2-[5-[[4-chloro-1-methyl-5-(trifluoromethyl)-1H-pyrazol-3-yl]oxy]-2-nitrophenoxy]-, S-(methoxymethyl)ester MP: 52.0–53.0 nD: | CH₃—O—CH₂—S—C(=O)—CH(CH₃)—O—C₆H₃(NO₂)—O—pyrazole(Cl, CF₃, N-CH₃) |
| 606 | propanamide, 2-[5-[[4-chloro-1-methyl-5-(trifluoromethyl)-1H-pyrazol-3-yl]oxy]-2-nitrophenoxy]-N-[4-(trifluoromethoxy)phenyl]- MP: 118.0 nD: | F₃C—O—C₆H₄—NH—C(=O)—CH(CH₃)—O—C₆H₃(NO₂)—O—pyrazole(Cl, CF₃, N-CH₃) |

| Ex CP # | Name | Structure |
|---|---|---|
| 607 | propanoic acid, 2-[5-[[4-chloro-1-methyl-5-(trifluoromethyl)-1H-pyrazol-3-yl]oxy]-2-nitrophenoxy]-, 2,2-dimethylhydrazide<br>MP: 99.0<br>nD: | 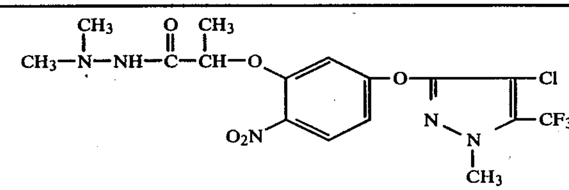 |
| 608 | 1H-pyrazole, 4-chloro-1-methyl-3-[3-(2-methyl-1,3-dioxolan-2-yl)-4-nitrophenoxy]-5-(trifluoromethyl)-<br>MP: 91.5–93.0<br>nD: | 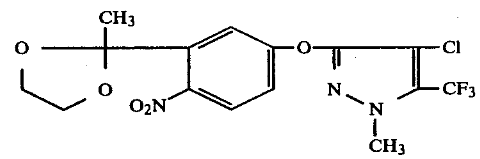 |
| 609 | acetic acid, [[5-[[4-chloro-1-methyl-5-(trifluoromethyl)-1H-pyrazol-3-yl]oxy]-2-nitrophenyl]thio]-<br>MP: 139.0–140.0<br>nD: | 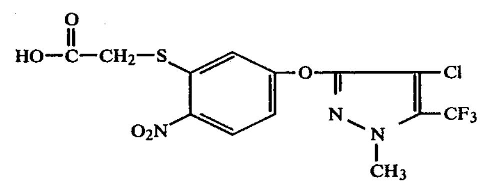 |
| 610 | propanoic acid, 2-[[5-[[4-chloro-1-methyl-5-(trifluoromethyl)-1H-pyrazol-3-yl]oxy]-2-nitrophenyl]thio]-, ethyl ester<br>MP:<br>nD: 1.5548 | 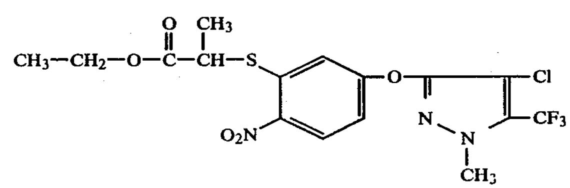 |
| 611 | benzenethiol, 5-[[4-chloro-1-methyl-5-(trifluoromethyl)-1H-pyrazol-3-yl]oxy]-2-nitro-<br>MP: 103.5–104.5<br>nD: | 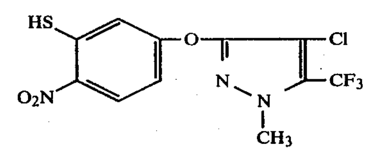 |

| Ex CP # | Name |
|---|---|
| 612 | benzenesulfenamide, 5-[[4-chloro-1-methyl-5-(trifluoromethyl)-1H-pyrazol-3-yl]oxy]-N-methyl-2-nitro-<br>MP: 69.0–71.5<br>nD: |
| 613 | benzenesulfonamide, 5-[[4-chloro-1-methyl-5-(trifluoromethyl)-1H-pyrazol-3-yl]oxy]-N,N-dimethyl-2-nitro-<br>MP: 75.5–78.5<br>nD: |
| 614 | propanamide, 3-[5-[[4-chloro-1-methyl-5-(trifluoromethyl)-1H-pyrazol-3-yl]oxy]-2-nitrophenoxy]-N,2,2-trimethyl-<br>MP: 100.0–101.0<br>nD: |
| 615 | propanoic acid, 2-[5-[[4-chloro-1-methyl-5-(trifluoromethyl)-1H-pyrazol-3-yl]oxy]-2-nitrophenoxy]-2-phenylethyl ester<br>MP:<br>nD: 1.5445 |
| 616 | propanamide, 2-[5-[[4-chloro-1-methyl-5-(trifluoromethyl)-1H-pyrazol-3-yl]oxy]-2-nitrophenoxy]-, 2-(2-methoxyphenyl)ethyl ester<br>MP: 99.0–100.0<br>nD: |

-continued

| Ex CP # | Name | Structure |
|---|---|---|
| 617 | benzenesulfenyl chloride, 5-[[4-chloro-1-methyl-5-(trifluoromethyl)-1H-pyrazol-3-yl]oxy]-2-nitro-<br>MP: 95.0–98.0<br>nD: | 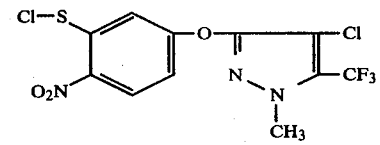 |
| 618 | benzenesulfenic acid, 5-[[4-chloro-1-methyl-5-(trifluoromethyl)-1H-pyrazol-3-yl]oxy]-2-nitro-, methyl ester<br>MP: 66.0–68.0<br>nD: | 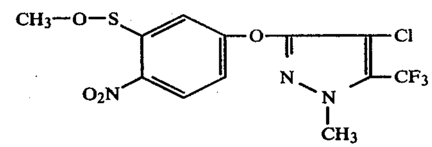 |
| 619 | propanoic acid, 2-[[5-[[4-chloro-1-methyl-5-(trifluoromethyl)-1H-pyrazol-3-yl]oxy]-2-nitrophenyl]dithio]-, ethyl ester<br>MP:<br>nD: 1.5721 | 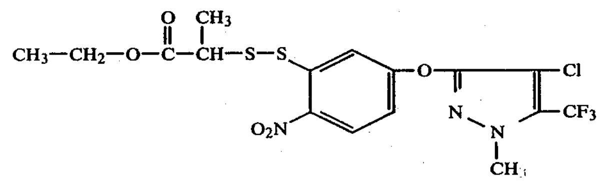 |
| 620. | benzenesulfenic acid, 5-[[4-chloro-1-methyl-5-(trifluoromethyl)-1H-pyrazol-3-yl]oxy]-2-nitro-,2,4-dichlorophenyl ester<br>MP: 107.0–114.0<br>nD: | 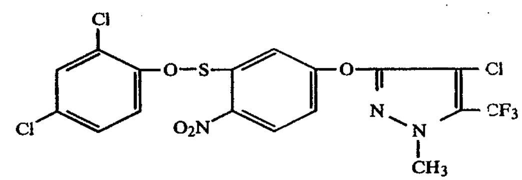 |
| 621 | benzenesulfenothioic acid, 5-[[4-chloro-1-methyl-5-(trifluoromethyl)-1H-pyrazol-3-yl]oxy]-2-nitro-, methyl ester<br>MP: 82.5–84.5<br>nD: | 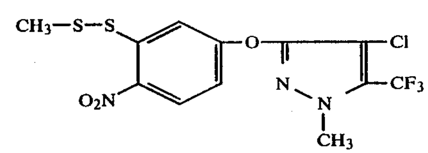 |

| Ex CP # | Name | Structure |
|---|---|---|
| 622 | acetic acid, [[[1-5-[[4-chloro-1-methyl-5-(trifluoromethyl)]-1H-pyrazol-3-yl]oxy]-2-nitrophenyl]-2-methoxyethylidene]aminoJoxy]-<br>MP: 95.0-120.0<br>nD: | 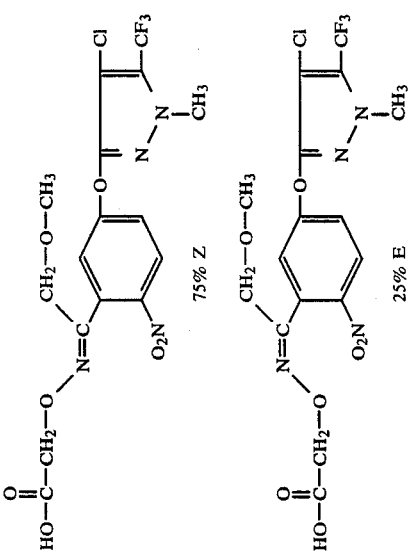 75% Z  25% E  ISOMERS |
| 623 | carbamothioic acid, methyl-, S-[5-[[4-chloro-1-methyl-5-(trifluoromethyl)-1H-pyrazol-3-yl]oxy]-2-nitrophenyl]ester<br>MP: 132.0-134.0<br>nD: | 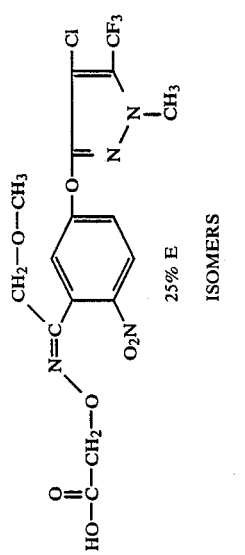 |
| 624 | acetic acid, [[[1-[5-[[4-chloro-1-methyl-5-(trifluoromethyl)-1H-pyrazol-3-yl]oxy]-2-nitrophenyl]ethylidene]-amino]oxy]-, 1-methylethyl ester<br>MP: 55.0-58.0<br>nD: | 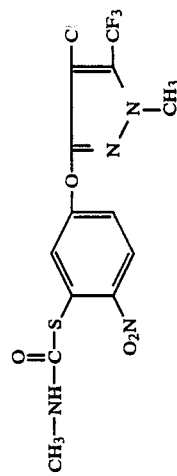 75% E |

| Ex CP # | Name | Structure |
|---|---|---|
| 625 | acetic acid, [[[1-[5-[[4-chloro-1-methyl-5-(trifluoromethyl)-1H-pyrazol-3-yl]oxy]-2-nitrophenyl]ethylidene]amino]oxy], butyl ester<br>MP:<br>nD: 1.5192 | 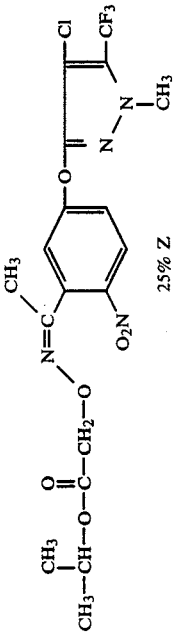<br>25% Z ISOMERS<br>75% E |
| 626 | acetic acid, [[[1-[5-[[4-chloro-1-methyl-5-(trifluoromethyl)-1H-pyrazol-3-yl]oxy]-2-nitrophenyl]ethylidene]amino]oxy], 2-methylpropyl ester<br>MP:<br>nD: 1.5174 | 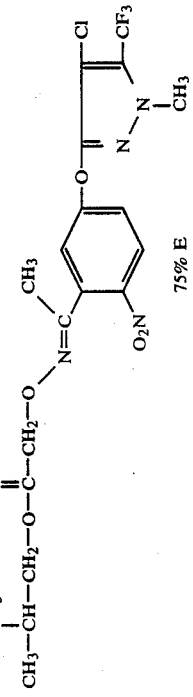<br>25% Z ISOMERS<br>75% E |

| Ex CP # | Name | Structure |
|---|---|---|
| 627 | benzenamine, 5-[[4-chloro-5-(difluoromethyl)-1-methyl-1H-pyrazol-3-yl]oxy]-N-methyl-2-nitro-<br>MP: 144.0–145.0<br>nD: | (structure shown; 25% Z ISOMERS) |
| 629 | propanoic acid, 2-[5-[[5-(difluoromethyl)-4-fluoro-1-methyl-1H-pyrazol-3-yl]oxy]-2-nitrophenoxy]-ethyl ester<br>MP:<br>nD: 1.5216 | (structure shown) |
| 630 | benzenamine, 5-[[4-chloro-1-methyl-5-(methylthio)-1H-pyrazol-3-yl]oxy]-N-methoxy-N-methyl-2-nitro-<br>MP: 63.0–64.0<br>nD: | (structure shown) |
| 631 | benzoic acid, 5-[[4-chloro-1-methyl-5-(methylsulfonyl)-1H-pyrazol-3-yl]oxy]-2-nitro-, methyl ester<br>MP: 140.0.0–142.0<br>nD: | (structure shown) |

-continued

| Ex CP # | Name | Structure |
|---|---|---|
| 632 | 1H-pyrazole, 4-chloro-3-[3-(2-fluoroethoxy)-4-nitrophenoxy]-1-methyl-5-(methylthio)-<br>MP: 56.0–57.0<br>nD: | F—(CH₂)₂—O— (aryl, O₂N) —O— pyrazole (Cl, S—CH₃, N—N—CH₃) |
| 633 | benzoic acid, 5-[[4-chloro-1-methyl-5-(methylsulfinyl)-1H-pyrazol-3-yl]oxy]-2-nitro- methyl ester<br>MP: 130.0–133.0<br>nD: | CH₃—O—C(=O)— (aryl, O₂N) —O— pyrazole (Cl, S(=O)—CH₃, N—N—CH₃) |
| 634 | 1H-pyrazole, 4-chloro-3-[3-(2-fluoroethoxy)-4-nitrophenoxy]-1-methyl-5-(methylsulfonyl)-<br>MP: 137.0–139.0<br>nD: | F—(CH₂)₂—O— (aryl, O₂N) —O— pyrazole (Cl, SO₂—CH₃, N—N—CH₃) |
| 635 | 1H-pyrazole, 4-chloro-3-[3-(2-fluoroethoxy)-4-nitrophenoxy]-1-methyl-5-(methylsulfinyl)-<br>MP: 94.0–96.0<br>nD: | F—(CH₂)₂—O— (aryl, O₂N) —O— pyrazole (Cl, S(=O)—CH₃, N—N—CH₃) |
| 636 | benzenamine, 5-[[4-chloro-1-methyl-5-(methylthio)-1H-pyrazol-3-yl]oxy]-N-methyl-2-nitro-<br>MP: 123.0–125.0<br>nD: | CH₃—NH— (aryl, O₂N) —O— pyrazole (Cl, S—CH₃, N—N—CH₃) |

-continued

| Ex CP # | Name | Structure |
|---|---|---|
| 637 | benzoic acid, 5-[[5-(difluoromethyl)-4-fluoro-1-methyl-1H-pyrazol-3-yl]oxy]-2-nitro-, methyl ester<br>MP:<br>nD: | 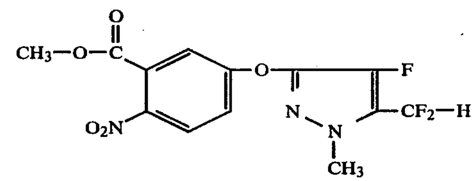 |
| 638 | benzoic acid, 5-[[5-(difluoromethyl)-4-fluoro-1-methyl-1H-pyrazol-3-yl]oxy]-2-<br>MP: 162.0–163.0<br>nD: | 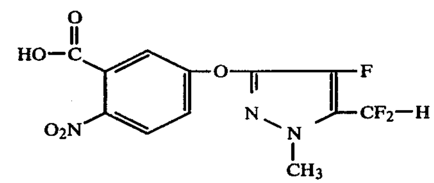 |
| 639 | benzenamine, 5-[[4-chloro-1-methyl-5-(methylsulfonyl)-1H-pyrazol-3-yl]oxy]-N-methyl-2-nitro-<br>MP: 183.0–185.0<br>nD: | 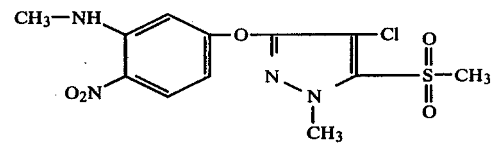 |
| 640 | benzenamine, 5-[[4-chloro-1-methyl-5-(methylsulfinyl)-1H-pyrazol-3-yl]oxy]-N-methyl-2-nitro-<br>MP: 150.0–152.0<br>nD: | 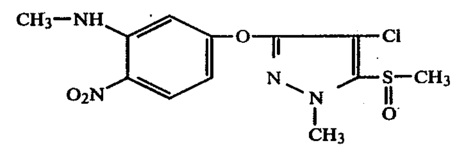 |
| 641 | benzenamine, 5-[[5-(difluoromethyl)-4-fluoro-1-methyl-1H-pyrazol-3-yl]oxy]-N-methoxy-N-methyl-2-nitro-<br>MP:<br>nD: | 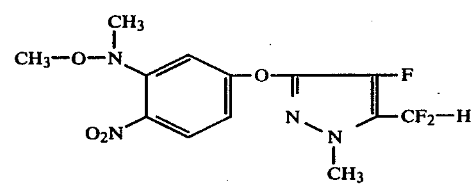 |

-continued

| Ex CP # | Name | Structure |
|---|---|---|
| 642 | benzenamine, 5-[[4-chloro-1-methyl-5-(methylsulfinyl)-1H-pyrazol-3-yl]oxy]-N-methoxy-N-methyl-2-nitro- MP: 75.0–78.0 nD: | 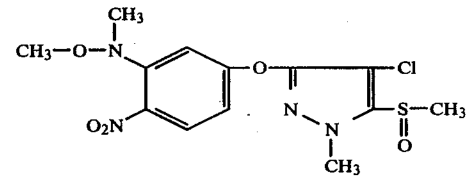 |
| 643 | 1H-pyrazole, 5-(difluoromethyl)-3-(3-ethoxy-4-nitrophenoxy)-4-fluoro-1-methyl- MP: 57.0–58.0 nD: | 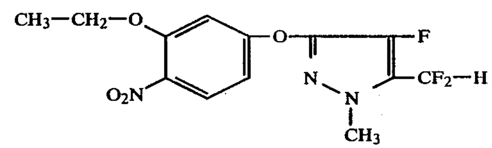 |
| 644 | benzenamine, 5-[[4-(bromo)-5-(difluoromethyl)-1-methyl-1H-pyrazol-3-yl]oxy]-N-methoxy-N-methyl-2-nitro- MP: nD: | 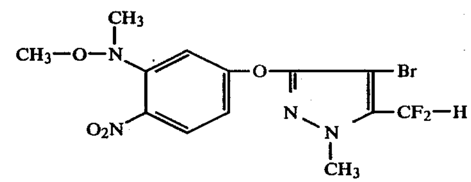 |
| 645 | benzamide, 5-[[5-(difluoromethyl)-4-fluoro-1-methyl-1H-pyrazol-3-yl]oxy]-N-(methylsulfonyl)-2-nitro- MP: 152.0–154.0 nD: | 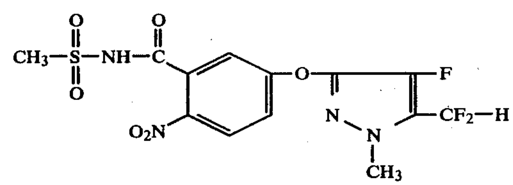 |
| 646 | benzoic acid, 5-[[4-chloro-1-methyl-5-(trifluoromethyl)-1H-pyrazol-3-yl]oxy]-2-nitro-, (2-propynyloxy)methyl ester MP: nD: 1.5293 | 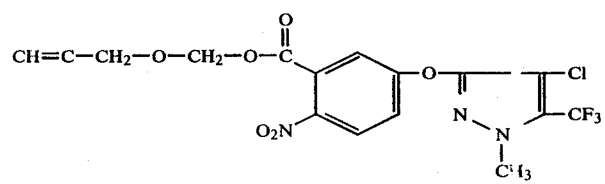 |

| Ex CP # | Name | Structure |
|---|---|---|
| 647 | oxazolidine, 3-[5-[[4-chloro-1-methyl-5-(trifluoromethyl)-1H-pyrazol-3-yl]oxy]-2-nitrobenzoyl]-2,2-dimethyl<br>MP: 109.0<br>nD: | 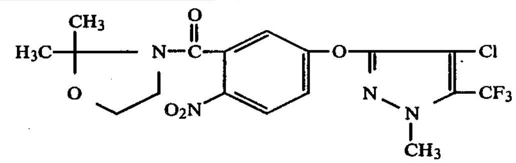 |
| 648 | benzoic acid, 5-[[4-chloro-1-methyl-5-(trifluoromethyl)-1H-pyrazol-3-yl]oxy]-2-nitro-, 6-(chloroacetyl)oxy]hexyl ester<br>MP:<br>nD: 1.5165 | 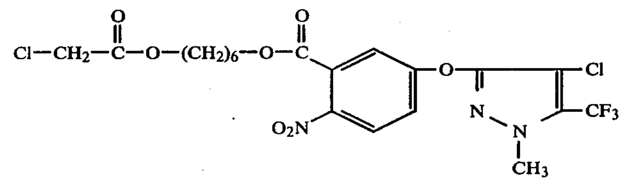 |
| 649 | glycine, N-[5-[[4-chloro-1-methyl-5-(trifluoromethyl)-1H-pyrazol-3-yl]oxy]-2-nitrobenzoyl]-, compd. with n-(1-methylethyl)-2-propanamine (1:1)<br>MP: 129.0–134.0<br>nD: | 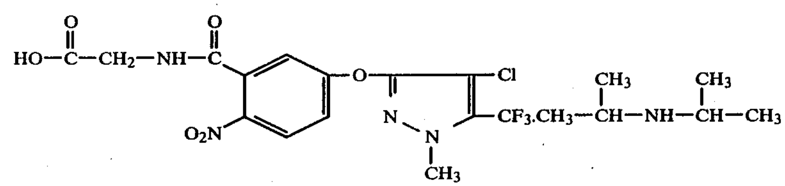 |
| 650 | benzoic acid, 5-[[4-chloro-1-methyl-5-(trifluoromethyl)-1H-pyrazol-3-yl]oxy]-2-nitro-, 2,2-dimethylhydrazide, compd. with iodomethane (1:1)<br>MP: 155.0–157.0<br>nD: | 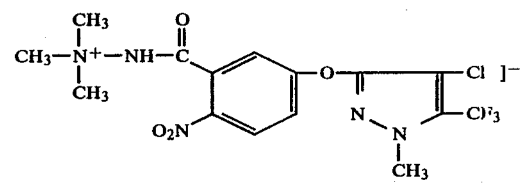 |
| 651 | benzoic acid, 5-[[4-chloro-1-methyl-5-(trifluoromethyl)-1H-pyrazol-3-yl]oxy]-2-nitro-, 6-[(iodoacetyl)oxy]hexyl ester<br>MP:<br>nD: 1.5365 | 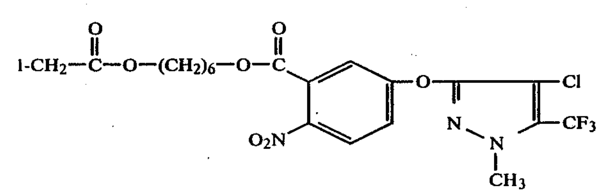 |

| Ex CP # | Name | Structure |
|---|---|---|
| 652 | acetic acid, chloro-, 2-[5-[[4-chloro-1-methyl-5-(trifluoromethyl)-1H-pyrazol-3-yl]oxy]-2-nitrophenoxy]ethyl ester<br>MP: 85.0–86.0<br>nD: | 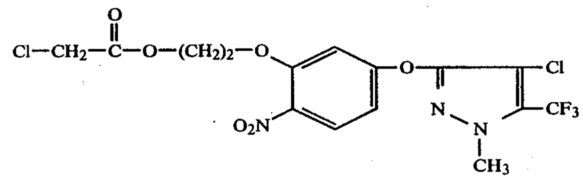 |
| 653 | acetic acid, methoxy-, 2-[5-[[4-chloro-1-methyl-5-(trifluoromethyl)-1H-pyrazol-3-yl]oxy]-2-nitrophenoxy]ethyl ester<br>MP: 89.0<br>nD: | 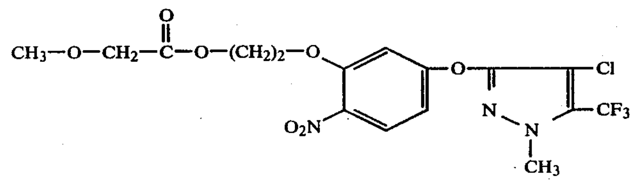 |
| 654 | acetic acid, [5-[[4-chloro-1-methyl-5-(trifluoromethyl)-1H-pyrazol-3-yl]oxy]-2-nitrophenoxy]-<br>MP: 87.0–90.0<br>nD: | 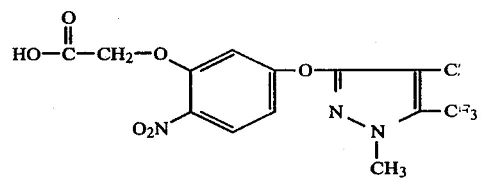 |
| 655 | 1H-pyrazole, 4-chloro-3-[3-(2,2-dimethyoxyethoxy)-4-nitrophenoxy]-1-methyl-5-(trifluoromethyl)-<br>MP:<br>nD: 1.5250 | 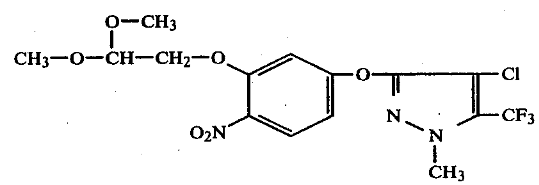 |
| 656 | 2-butenoic acid, 4-[5-[[4-chloro-1-methyl-5-(trifluoromethyl)-1H-pyrazol-3-yl]oxy]-2-nitrophenoxy]-, methyl ester<br>MP: 118.0<br>nD: | 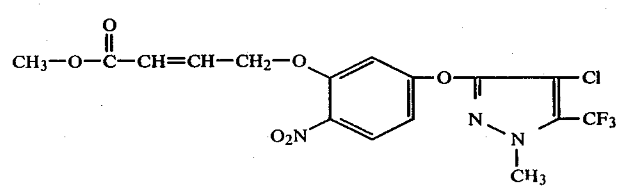 |

-continued

| Ex CP # | Name | Structure |
|---|---|---|
| 657 | benzoic acid, 5-[[4-chloro-1-methyl-5-(trifluoromethyl)-1H-pyrazol-3-yl]oxy]-2-nitro-, 4-methoxy-4-oxo-2-butenyl ester<br>MP: 73.0<br>nD: | 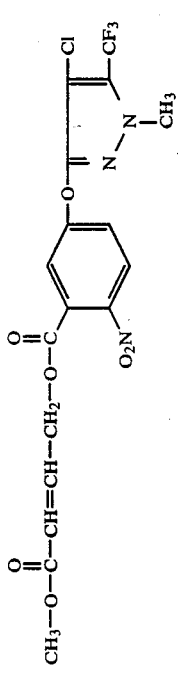 |
| 658 | benzoic acid, 5-[[5-(difluoromethyl)-4-fluoro-1-methyl-1H-pyrazol-3-yl]oxy]-2-nitro-, 2-ethoxy-2-oxoethyl ester<br>MP:<br>nD: 1.5188 | 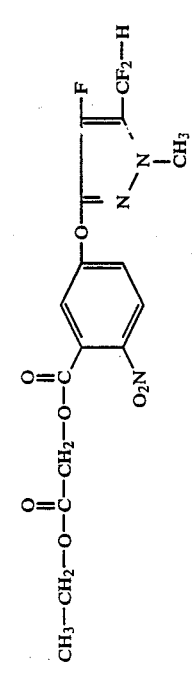 |
| 659 | propanedioic acid, [[5-[[4-chloro-1-methyl-5-(trifluoromethyl)-1H-pyrazol-3-yl]oxy]-2-nitrobenzoyl]oxy]-, diethyl ester<br>MP:<br>nD: 1.5084 | 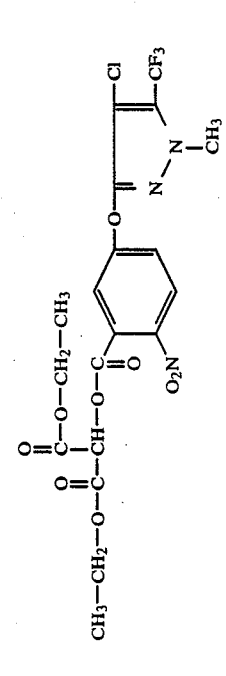 |
| 660 | propanedioic acid, [5-[[4-chloro-1-methyl-5-(trifluoromethyl)-1H-pyrazol-3-yl]oxy]-2-nitrophenoxy]-, diethyl ester<br>MP:<br>nD: 1.5152 | 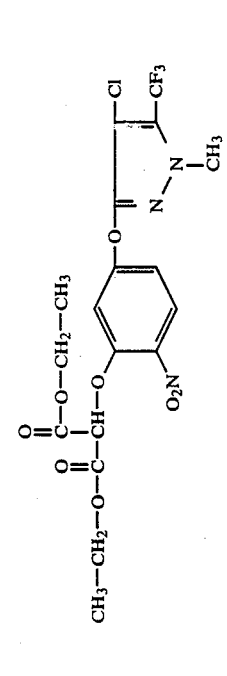 |

-continued

| Ex CP # | Name |
|---|---|
| 661 | benzoic acid, 5-[[4-chloro-1-methyl-5-(trifluoromethyl)-1H-pyrazol-3-yl]oxy]-2-nitro-, 2-chloroethyl ester<br>MP:<br>nD: 1.5350 |
| 662 | 1H-pyrazole, 4-chloro-3-[3-(2-chloroethoxy)-4-nitrophenoxy]-1-methyl-5-(trifluoromethyl)-<br>MP:<br>nD: 1.5467 |
| 663 | benzoic acid, 5-[[4-chloro-1-methyl-5-(trifluoromethyl)-1H-pyrazol-3-yl]oxy]-2-nitro-, 2-nitrophenyl ester<br>MP: 100.0<br>nD: |
| 664 | morpholine, 4-[5-[[5-(difluoromethyl)-4-fluoro-1-methyl-1H-pyrazol-3-yl]oxy]-2-nitrobenzoyl]-<br>MP: 146.0<br>nD: |
| 665 | benzoic acid, 5-[[5-(difluoromethyl)-4-fluoro-1-methyl-1H-pyrazol-3-yl]oxy]-2-nitro-, 2-(2-methoxyethoxy)ethyl ester<br>MP:<br>nD: 1.5110 |

| Ex CP # | Name | Structure |
|---|---|---|
| 666 | 1H-pyrazole, 4-chloro-3-[3-[2-(2-methoxyethoxy)ethoxy]-4-nitrophenoxy]-1-methyl-5-(trifluoromethyl)- <br> MP: <br> nD: 1.5234 | CH$_3$—O—(CH$_2$)$_2$—O—(CH$_2$)$_2$—O— phenyl(O$_2$N)—O—pyrazole(Cl, CF$_3$, N—N—CH$_3$) |
| 667 | 1H-pyrazole, 4-chloro-3-[3-[2-(2-ethoxyethoxy)ethoxy]-4-nitrophenoxy]-1-methyl-5-(trifluoromethyl)- <br> MP: <br> nD: 1.5196 | CH$_3$—CH$_2$—O—(CH$_2$)$_2$—O—(CH$_2$)$_2$—O— phenyl(O$_2$N)—O—pyrazole(Cl, CF$_3$, N—N—CH$_3$) |
| 668 | benzoic acid, 5-[[4-chloro-1-methyl-5-(methylthio)-1H-pyrazol-3-yl]oxy]-2-nitro-, ethyl ester <br> MP: <br> nD: 1.5805 | CH$_3$—CH$_2$—O—C(=O)— phenyl(O$_2$N)—O—pyrazole(Cl, S—CH$_3$, N—N—CH$_3$) |
| 669 | acetic acid, 5-[[4-chloro-1-methyl-5-(methylthio)-1H-pyrazol-3-yl]oxy]-2-nitrophenoxy], ethyl ester <br> MP: <br> nD: 1.5770 | CH$_3$—CH$_2$—O—C(=O)—CH$_2$—O— phenyl(O$_2$N)—O—pyrazole(Cl, S—CH$_3$, N—N—CH$_3$) |
| 670 | 1H-pyrazole, 4-chloro-1-methyl-3-[3-(5-hexenyloxy)-4-nitrophenoxy]-5-(trifluoromethyl)- <br> MP: <br> nD: 1.5274 | CH$_2$=CH—(CH$_2$)$_4$—O— phenyl(O$_2$N)—O—pyrazole(Cl, CF$_3$, N—N—CH$_3$) |

| Ex CP # | Name | Structure |
|---|---|---|
| 671 | benzoic acid, 5-[[5-(difluoromethyl)-4-fluoro-1-methyl-1H-pyrazol-3-yl]oxy]-2-nitro-, 2-hydroxyethyl ester<br>MP: 61.0<br>nD: | HO—(CH$_2$)$_2$—O—C(=O)—[benzene ring with O$_2$N]—O—[pyrazole with F, CF$_2$—H, N—N—CH$_3$] |
| 672 | acetic acid, 5-[[4-chloro-1-methyl-5-(methylthio)-1H-pyrazol-3-yl]oxy]-2-nitrophenoxy]-<br>MP: 142.0<br>nD: | HO—C(=O)—CH$_2$—O—[benzene with O$_2$N]—O—[pyrazole with Cl, S—CH$_3$, N—N—CH$_3$] |
| 673 | benzoic acid, 5-[[4-chloro-1-methyl-5-(methylthio)-1H-pyrazol-3-yl]oxy]-2-nitro-<br>MP: 131.5–132.0<br>nD: | HO—C(=O)—[benzene with O$_2$N]—O—[pyrazole with Cl, S—CH$_3$, N—N—CH$_3$] |
| 674 | 1H-pyrazole, 4-chloro-3-[3-[2-[2-(2-methoxyethoxy)ethoxy]ethoxy]-4-nitrophenoxy]-1-methyl-5-(trifluoromethyl)-<br>MP:<br>nD: 1.5183 | CH$_3$—O—(CH$_2$)$_2$—O—(CH$_2$)$_2$—O—(CH$_2$)$_2$—O—[benzene with O$_2$N]—O—[pyrazole with Cl, CF$_3$, N—N—CH$_3$] |
| 675 | 1H-pyrazole, 4-chloro-1-methyl-3-[3-[(2-propynyloxy)methoxy]-4-nitrophenoxy]-5-(trifluoromethyl)-<br>MP:<br>nD: 1.5345 | CH≡C—CH$_2$—O—CH$_2$—O—[benzene with O$_2$N]—O—[pyrazole with Cl, CF$_3$, N—N—CH$_3$] |

-continued

| Ex CP # | Name | Structure |
|---|---|---|
| 676 | acetic acid, [5-[[4-chloro-1-methyl-5-(trifluoromethyl)-1H-pyrazol-3-yl]oxy]-2-nitrophenoxy], methoxymethyl ester<br>MP: 75.0<br>nD: | 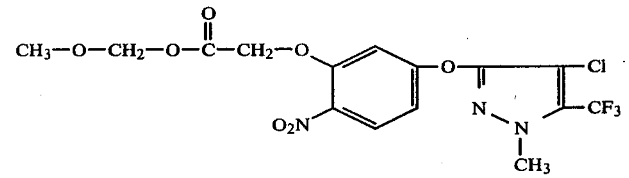 |
| 677 | benzoic acid, 5-[[4-chloro-1-methyl-5-(trifluoromethyl)-1H-pyrazol-3-yl]oxy]-2-nitro-,5-hexenyl ester<br>MP:<br>nD: 1.5196 | 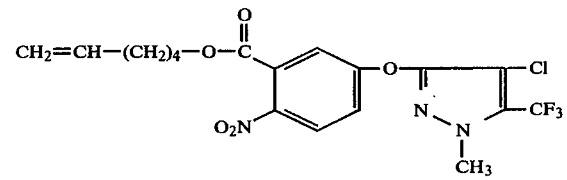 |
| 678 | 2-propanone, O-[5-[[4-chloro-1-methyl-5-(trifluoromethyl)-1H-pyrazol-3-yl]oxy]-2-nitrophenyl]oxime<br>MP:<br>nD: 1.5436 | 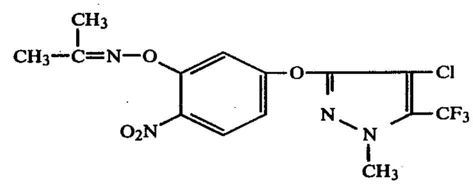 |
| 679 | 1H-pyrazole, 4-chloro-1-methyl-3-[4-nitro-3-(1H-pyrazol-1-ylmethoxy)phenoxy]-5-(trifluoromethyl)-<br>MP: 104.0<br>nD: | 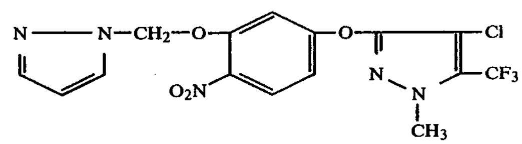 |
| 680 | benzoic acid, 5-[[4-chloro-1-methyl-5-(trifluoromethyl)-1H-pyrazol-3-yl]oxy]-2-nitro-, (trimethylsilyl)methyl ester<br>MP:<br>nD: 1.5131 | 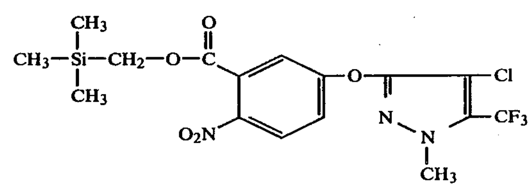 |

| Ex CP # | Name | Structure |
|---|---|---|
| 681 | 1H-pyrazole, 3,3'-[[1,2-ethanediylbis[oxy(4-nitro-3,1-phenylene)oxy]]bis[4-chloro-1-methyl-5-(trifluoromethyl)]-<br>MP: 158.0<br>nD: | 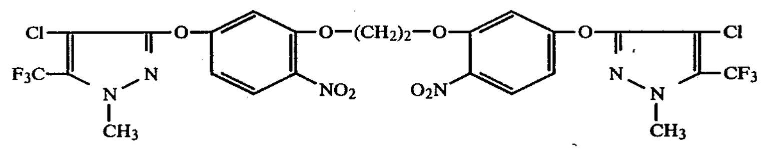 |
| 682 | propanamide, N-[5-[[4-chloro-1-methyl-5-(trifluoromethyl)-1H-pyrazol-3-yl]oxy]-2-nitrophenyl]-2,2,3,3,3-pentafluoro-<br>MP: 68.0<br>nD: | 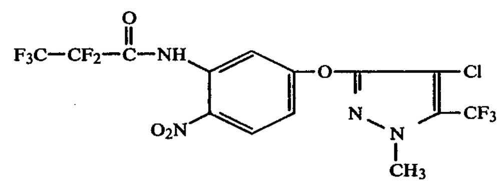 |
| 683 | acetamide, N-[5-[[4-chloro-1-methyl-5-(trifluoromethyl)-1H-pyrazol-3-yl]oxy]-2-nitrophenyl]-2,2,2-trifluoro-<br>MP: 78.0<br>nD: | 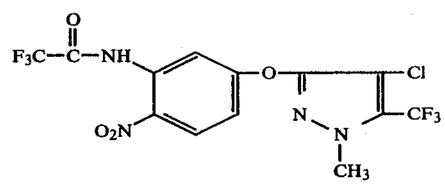 |
| 684 | urea, [5-[[4-chloro-1-methyl-5-(trifluoromethyl)-1H-pyrazol-3-yl]oxy]-2-nitrophenyl]-<br>MP: 193.0<br>nD: | 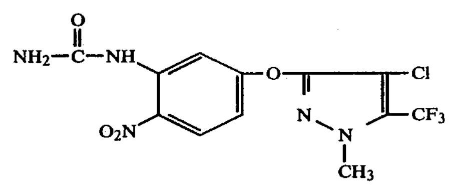 |
| 685 | acetamide, N-[5-[[4-chloro-1-methyl-5-(trifluoromethyl)-1H-pyrazol-3-yl]oxy]-2-nitrophenyl]-<br>MP: 85.0-87.0<br>nD: | 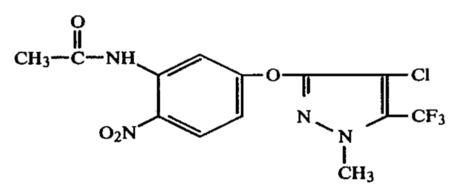 |

| Ex CP # | Name | Structure |
|---|---|---|
| 686 | carbamic acid, [5-[[4-chloro-1-methyl-5-(trifluoromethyl)-1H-pyrazol-3-yl]oxy]-2-nitrophenyl]-, ethyl ester MP: 59.0-61.0 nD: | 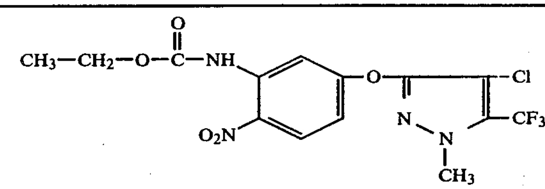 |
| 687 | propanamide, N-[5-[[4-chloro-1-methyl-5-(trifluoromethyl)-1H-pyrazol-3-yl]oxy]-2-nitrophenyl]-2,2-dimethyl- MP: nD: 1.5501 | 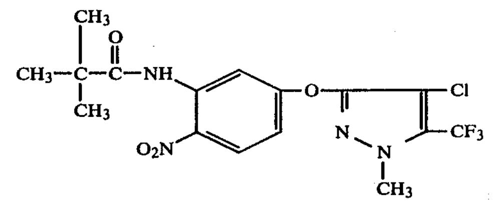 |
| 688 | benzamide, N-[5-[[4-chloro-1-methyl-5-(trifluoromethyl)-1H-pyrazol-3-yl]oxy]-2-nitrophenyl]-2,3,4,5,6-pentafluoro- MP: 98.0-100.0 nD: | 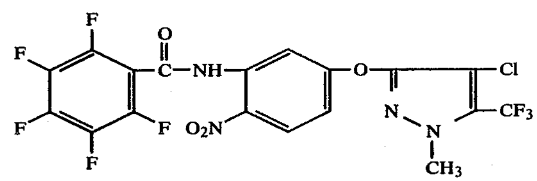 |
| 689 | urea, N-[5-[[4-chloro-1-methyl-5-(trifluoromethyl)-1H-pyrazol-3-yl]oxy]-2-nitrophenyl]-N-methyl- MP: 95.0-99.0 nD: | 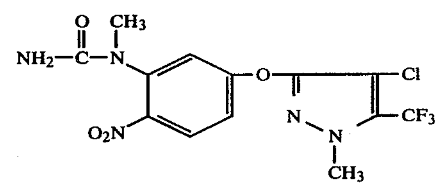 |
| 690 | carbamic acid, [5-[[4-chloro-1-methyl-5-(trifluoromethyl)-1H-pyrazol-3-yl]oxy]-2-nitrophenyl]methyl-, ethyl ester MP: 76.0-80.0 nD: | 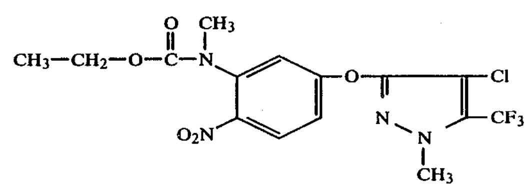 |

| Ex CP # | Name | Structure |
|---|---|---|
| 691 | cyclopropanecarboxamide, N-[5-[[4-chloro-1-methyl-5-(trifluoromethyl)-1H-pyrazol-3-yl]oxy]-2-nitrophenyl]- MP: 118.0–119.0 nD: | 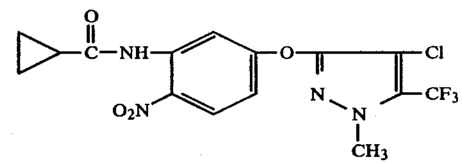 |
| 692 | propanoyl chloride, 3-[[5-[[4-chloro-1-methyl-5-(trifluoromethyl)-1H-pyrazol-3-yl]oxy]-2-nitrophenyl]amino]- MP: 111.0–112.0 nD: | 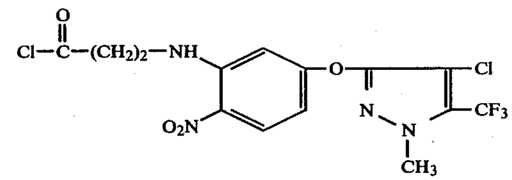 |
| 693 | 1H-pyrazole, 4-chloro-3-[3-(1,1-dimethylethoxy)-4-nitrophenoxy]-1-methyl-5-(trifluoromethyl)- MP: nD: 1.5171 | 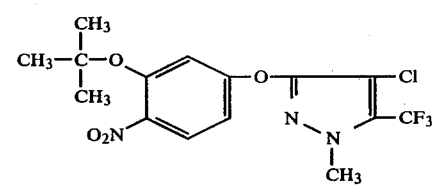 |
| 694 | 1,2-ethanediamine, N-[5-[[4-chloro-1-methyl-5-(trifluoromethyl)-1H-pyrazol-3-yl]oxy]-2-nitrophenyl]-N,n'-dimethyl- MP: nD: | 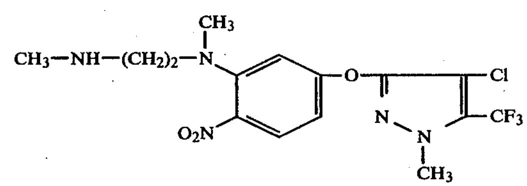 |
| 695 | benzenamine, [5-[[4-chloro-1-methyl-5-(trifluoromethyl)-1H-pyrazol-3-yl]oxy]-N-[2-(ethylthio)ethyl]-2-nitro- MP: 64.0–65.0 nD: | 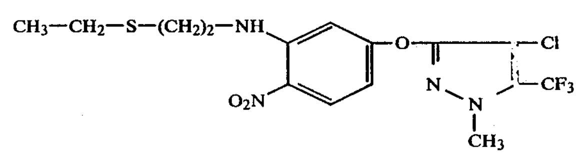 |

| Ex CP # | Name | Structure |
|---|---|---|
| 696 | 1-propanol, 2-[[5-[[4-chloro-1-methyl-5-(trifluoromethyl)-1H-pyrazol-3-yl]oxy]-2-nitrophenyl]amino]- MP: 88.0-91.0 nD: | HO—CH$_2$—CH(CH$_3$)—NH—[3-O-pyrazolyl-phenyl-NO$_2$ with Cl, CF$_3$, N—N—CH$_3$] |
| 697 | benzenamine, 5-[[4-chloro-1-methyl-5-(trifluoromethyl)-1H-pyrazol-3-yl]oxy]-N-(2-methoxypropyl)-2-nitro- MP: nD: 1.5716 | CH$_3$—O—(CH$_2$)$_3$—NH—[pyrazolyl-phenyl] |
| 698 | acetic acid, [2-[5-[[4-chloro-1-methyl-5-(trifluoromethyl)-1H-pyrazol-3-yl]oxy]-2-nitrophenyl]-1-methylhydrazino]-, ethyl ester MP: nD: 1.5533 | CH$_3$—CH$_2$—O—C(O)—CH$_2$—N(CH$_3$)—NH—[pyrazolyl-phenyl] |
| 699 | 1-butanol, 4-[[5-[[4-chloro-1-methyl-5-(trifluoromethyl)-1H-pyrazol-3-yl]oxy]-2-nitrophenyl]amino]- MP: nD: 1.5882 | HO—(CH$_2$)$_4$—NH—[pyrazolyl-phenyl] |
| 700 | benzenamine, 5-[[4-chloro-1-methyl-5-(trifluoromethyl)-1H-pyrazol-3-yl]oxy]-2-nitro-N-[(trimethylsilyl)methyl]- MP: nD: | (CH$_3$)$_3$Si—CH$_2$—NH—[pyrazolyl-phenyl] |

-continued

| Ex CP # | Name | Structure |
|---|---|---|
| 701 | undecanoic acid, 11-[[5-[[4-chloro-1-methyl-5-(trifluoromethyl)-1H-pyrazol-3-yl]oxy]-2-nitrophenyl]amino]- MP: 60.0–63.0 nD: | HO—C(=O)—(CH₂)₁₀—NH—[4-nitro-phenyl-O-pyrazole(Cl, CF₃, N-CH₃)] |
| 702 | 1,3-propanediol, 2-[[5-[[4-chloro-1-methyl-5-(trifluoromethyl)-1H-pyrazol-3-yl]oxy]-2-nitrophenyl]amino]-2-methyl- MP: 154.0–157.0 nD: | HO—CH₂—C(CH₂OH)(CH₃)—NH—[4-nitro-phenyl-O-pyrazole(Cl, CF₃, N-CH₃)] |
| 703 | undecanoic acid, 11-[[5-[[4-chloro-1-methyl-5-(trifluoromethyl)-1H-pyrazol-3-yl]oxy]-2-nitrophenyl]amino]-, methyl ester MP: 51.0–54.0 nD: | CH₃—O—C(=O)—(CH₂)₁₀—NH—[4-nitro-phenyl-O-pyrazole(Cl, CF₃, N-CH₃)] |
| 704 | propanenitrile, 3-[[5-[[4-chloro-1-methyl-5-(trifluoromethyl)-1H-pyrazol-3-yl]oxy]-2-nitrophenyl]amino]- M: 130.0–133.0 nD: | N≡C—(CH₂)₂—NH—[4-nitro-phenyl-O-pyrazole(Cl, CF₃, N-CH₃)] |
| 705 | 1-propanol, 3-[[5-[[4-chloro-1-methyl-5-(trifluoromethyl)-1H-pyrazol-3-yl]oxy]-2-nitrophenyl]amino]- MP: 93.0–97.0 nD: | HO—(CH₂)₃—NH—[4-nitro-phenyl-O-pyrazole(Cl, CF₃, N-CH₃)] |

| Ex CP # | Name | Structure |
|---|---|---|
| 706 | benzenamine, N-(2-chloroethyl)-5-[[4-chloro-1-methyl-5-(trifluoromethyl)-1H-pyrazol-3-yl]oxy]-2-nitro- MP: 72.0–74.0 nD: | Cl—(CH₂)₂—NH structure with 4-chloro-1-methyl-5-(trifluoromethyl)-1H-pyrazol-3-yloxy group on 2-nitrophenyl |
| 707 | benzenamine, 5-[[4-chloro-1-methyl-5-(trifluoromethyl)-1H-pyrazol-3-yl]oxy]-N-[3-(methylthio)propyl]-2-nitro- MP: nD: 1.5950 | CH₃—S—(CH₂)₃—NH analog |
| 708 | glycine, N-[5-[[4-chloro-1-methyl-5-(trifluoromethyl)-1H-pyrazol-3-yl]oxy]-2-nitrophenyl]-, ethyl ester MP: 112.0–116.0 nD: | CH₃—CH₂—O—C(=O)—CH₂—NH analog |
| 709 | 1H-pyrazole, 4-chloro-1-methyl-3-[3-(2-methyl-2-phenylhydrazino)-4-nitrophenoxy]-5-(trifluoromethyl)- MP: 105.0–109.0 nD: | phenyl-N(CH₃)-NH analog |
| 710 | butanoic acid, 3-[[5-[[4-chloro-1-methyl-5-(trifluoromethyl)-1H-pyrazol-3-yl]oxy]-2-nitrophenyl]amino]-, ethyl ester MP: nD: 1.5713 | CH₃—CH₂—O—C(=O)—CH₂—CH(CH₃)—NH analog |

-continued

| Ex CP # | Name | Structure |
|---|---|---|
| 711 | 1,2-ethanediamine, N-[5-[[4-chloro-1-methyl-5-(trifluoromethyl)-1H-pyrazol-3-yl]oxy]-2-nitrophenyl]-N-ethyl-n',n'-dimethyl- MP: nD: 1.5402 | 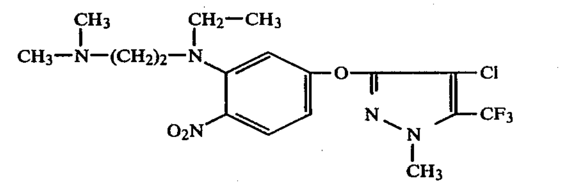 |
| 712 | propanoic acid, 3-[[5-[[4-chloro-1-methyl-5-(trifluoromethyl)-1H-pyrazol-3-yl]oxy]-2-nitrophenyl]amino]-, ethyl ester MP: 60.0–63.0 nD: | 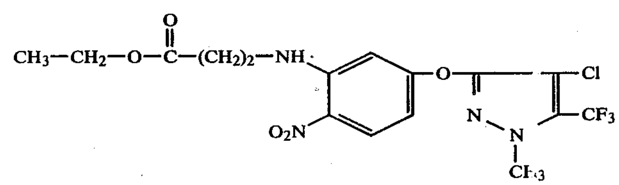 |
| 713 | propanoic acid, 2-[5-[[4-chloro-1-methyl-5-(trifluoromethyl)-1H-pyrazol-3-yl]oxy]-4-fluoro-2-nitrophenoxy]-, ethyl ester MP: 45.0–47.0 nD: | 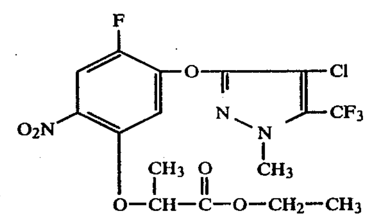 |
| 714 | benzoic acid, 5-[[4-bromo-5-(difluoromethyl)-1-methyl-1H-pyrazol-3-yl]oxy]-2-nitro-, ethyl ester MP: 55.0–58.0 nD: | 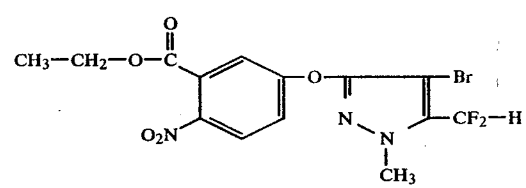 |

-continued

| Ex CP # | Name | Structure |
|---|---|---|
| 715 | benzoic acid, 5-[[4-bromo-5-(difluoromethyl)-1-methyl-1H-pyrazol-3-yl]oxy]-2-nitro-<br>MP: 95.0-97.0<br>nD: | 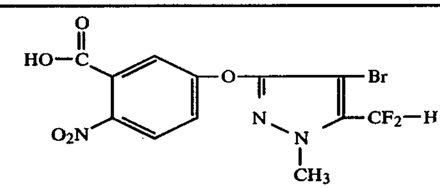 |
| 716 | propanoic acid, 2-[5-[[4-bromo-5-(difluoromethyl)-1-methyl-1H-pyrazol-3-yl]oxy]-2-nitrophenoxy]-, ethyl ester<br>MP:<br>nD: 1.5423 | 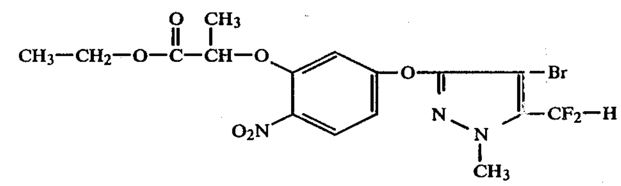 |
| 717 | benzoic acid, 5-[[5-(difluoromethyl)-1-methyl-1H-pyrazol-3-yl]oxy]-2-nitro-, ethyl ester<br>MP:<br>nD: 1.5237 | 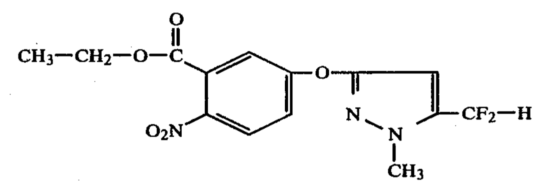 |
| 718 | propanoic acid, 2-[5-[[4-chloro-1-methyl-5-(methylsulfonyl)-1H-pyrazol-3-yl]oxy]-2-nitrophenoxy]-, ethyl ester<br>MP:<br>nD: | 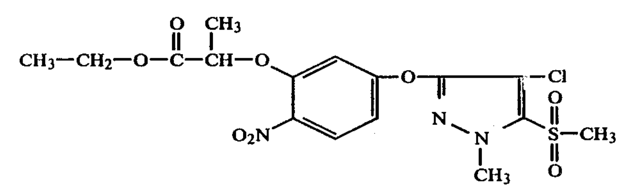 |
| 719 | methanesulfonic acid, trifluoro-, 5-[[4-chloro-1-methyl-5-(trifluoromethyl)-1H-pyrazol-3-yl]oxy]-2-nitrophenyl ester<br>MP: 77.0-78.0<br>nD: | 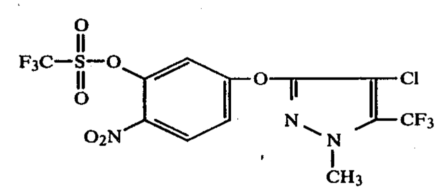 |

-continued

| Ex CP # | Name | Structure |
|---|---|---|
| 720 | propanedioic acid, [5-[[4-chloro-1-methyl-5-(trifluoromethyl)-1H-pyrazol-3-yl]oxy]-2-nitrophenyl]-, dimethyl ester<br>MP: 61.0–63.0<br>nD: | 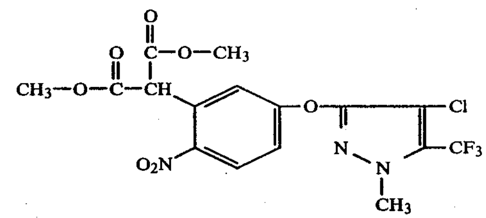 |
| 721 | 1H-pyrazole, 4-chloro-1-methyl-3-[4-nitro-3-(phenylethynyl)phenoxy]-5-(trifluoromethyl)-<br>MP: 98.0–100.0<br>nD: | 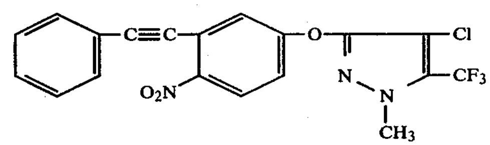 |
| 722 | 1H-pyrazole, 4-chloro-3-[3-(methoxyethenyl)-4-nitrophenoxy]-1-methyl-5-(trifluoromethyl)-<br>MP:<br>nD: | 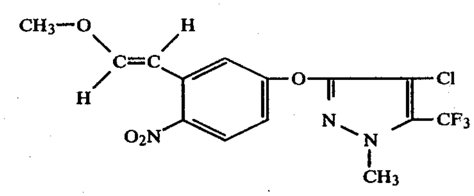 |
| 723 | 1H-pyrazole, 4-chloro-3-(3-ethynyl-4-nitrophenoxy)-1-methyl-5-(trifluoromethyl)-<br>MP: 52.0–54.0<br>nD: | 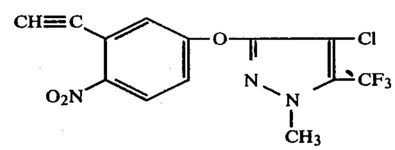 |

-continued

| Ex CP # | Name | Structure |
|---|---|---|
| 724 | 2-propenoic acid, 3-[5-[[4-chloro-1-methyl-5-(trifluoromethyl)-1H-pyrazol-3-yl]oxy]-2-nitrophenyl]-, ethyl ester<br>MP:<br>nD: 1.5522 | 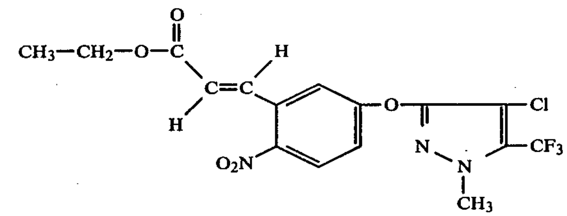 |
| 725 | 1H-pyrazole,-<br>4-chloro-1-methyl-3-[3-[2-(1-methylethoxy)ethoxy]-4-nitrophenoxy]-5-(trifluoromethyl)-<br>MP:<br>nD: 1.5200 | 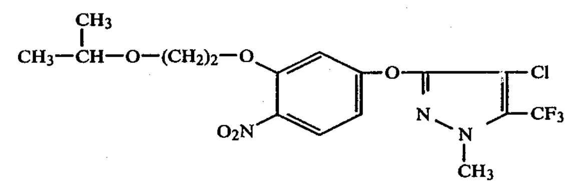 |
| 726 | 1H-pyrazole,<br>2-chloro-1-methyl-3-[3-[(2-methylpentyl)oxy]-4-nitrophenoxy]-5-(trifluoromethyl)-<br>MP:<br>nD: 1.5205 | 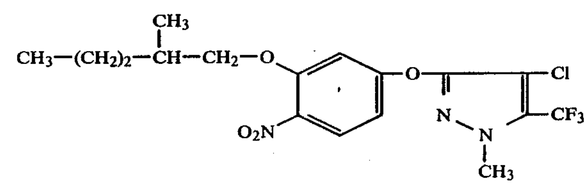 |
| 727 | 1H-pyrazole,<br>4-chloro-1-methyl-3-[4-nitro-3-[[(trimethylsilyl)methoxy]phenoxy]-5-(trifluoromethyl)-<br>MP:<br>nD: 1.5213 | 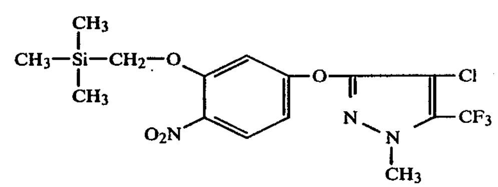 |

-continued

| Ex CP # | Name | Structure |
|---|---|---|
| 728 | butanedioic acid, [[5-[[4-chloro-1-methyl-5-(trifluoromethyl)-1H-pyrazol-3-yl]oxy]-2-nitrobenzoyl]oxy]-,diethyl ester MP: nD: 1.5070 | $CH_3-CH_2-O-\overset{O}{\underset{\|}{C}}-CH_2-CH-O-\overset{O}{\underset{\|}{C}}-O-CH_2-CH_3$ attached to phenyl ring with $O_2N$ and O-linked to pyrazole bearing Cl, $CF_3$, N-N-$CH_3$ |
| 729 | 1H-pyrazole, 4-chloro-3-[3-(2-ethoxy-1-methylethoxy)-4-nitrophenoxy]-1-methyl-5-(trifluoromethyl)- MP: nD: 1.5190 | $CH_3-CH_2-O-CH_2-\underset{CH_3}{\overset{\|}{CH}}-O-$ phenyl with $O_2N$, O-pyrazole (Cl, $CF_3$, N-N-$CH_3$) |
| 730 | 1H-pyrazole, 4-chloro-1-methyl-3-[3-[2-(methylthio)ethoxy]-4-nitrophenoxy]-5-(trifluoromethyl)- MP: nD: 1.5555 | $CH_3-S-(CH_2)_2-O-$ phenyl with $O_2N$, O-pyrazole (Cl, $CF_3$, N-N-$CH_3$) |
| 731 | acetic acid, [5-[[4-chloro-1-methyl-5-(trifluoromethyl)-1H-pyrazole-3-yl]oxy]-, -2-nitrophenoxy], 2-propynyl ester MP: nD: 1.5367 | $CH\equiv C-CH_2-O-\overset{O}{\underset{\|}{C}}-CH_2-O-$ phenyl with $O_2N$, O-pyrazole (Cl, $CF_3$, N-N-$CH_3$) |
| 732 | acetic acid, [[2-[5-[[4-chloro-1-methyl-5-(trifluoromethyl)-1H-pyrazol-3-yl]oxy]-2-nitrophenoxy]ethyl]thio]-,methyl ester MP: nD: 1.5465 | $CH_3-O-\overset{O}{\underset{\|}{C}}-CH_2-S-(CH_2)_2-O-$ phenyl with $O_2N$, O-pyrazole (Cl, $CF_3$, N-N-$CH_3$) |

-continued

| Ex CP # | Name | Structure |
|---|---|---|
| 733 | ethanamine, 2-[5-[[4-chloro-1-methyl-5-(trifluoromethyl)-1H-pyrazol-3-yl]oxy]-2-nitrophenoxy]-N,N-diethyl-<br>MP:<br>nD: 1.5255 | 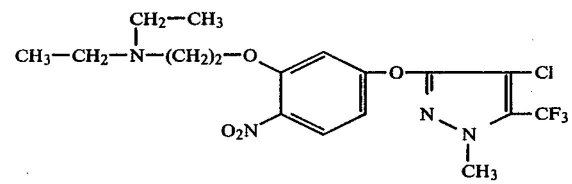 |
| 734 | benzoic acid, 5-[[4-chloro-1-methyl-5-(trifluoromethyl)-1H-pyrazol-3-yl]oxy]-2-nitro-, 3-(dimethylamino)propyl ester<br>MP:<br>nD: 1.5194 | 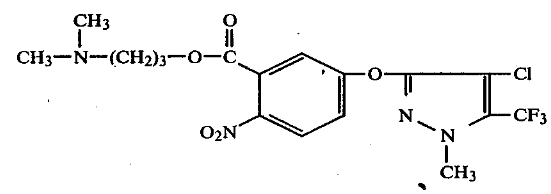 |
| 735 | butanedioic acid, 2-[5-[[4-chloro-1-methyl-5-(trifluoromethyl)-1H-pyrazol-3-yl]oxy]-2-nitrophenoxy]ethyl ethyl ester<br>MP: 70.0<br>nD: | 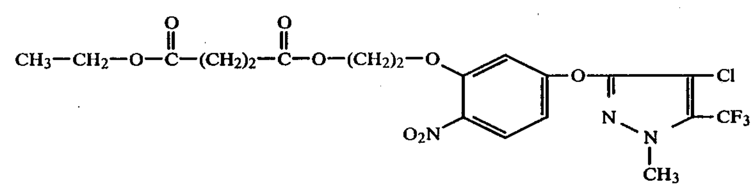 |
| 736 | 1H-pyrazole,-4-chloro-1-methyl-3-[3-[2-(methylsulfonyl)ethoxy]-4-nitrophenoxy]-5-(trifluoromethyl)-<br>MP: 137.0<br>nD: | 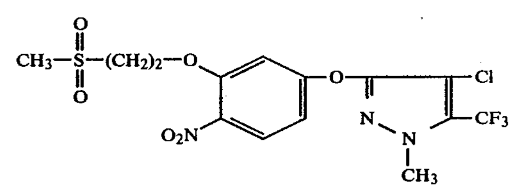 |
| 737 | benzoic acid, 5-[[4-chloro-1-methyl-5-(trifluoromethyl)-1H-pyrazol-3-yl]oxy]-2-nitro-, 2-(diethylamino)ethyl ester<br>MP:<br>nD: 1.5175 | 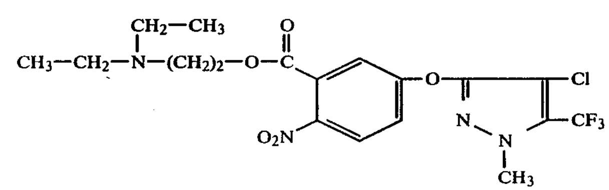 |

| Ex CP # | Name | Structure |
|---|---|---|
| 738 | ethanedioic acid, 2-[5-[[4-chloro-1-methyl-5-(trifluoromethyl)-1H-pyrazol-3-yl]oxy]-2-nitrophenoxy]ethyl ethyl ester MP: 84.0–85.0 nD: | CH$_3$—CH$_2$—O—C(=O)—C(=O)—O—(CH$_2$)$_2$—O—[aryl-pyrazole] |
| 739 | 1-propanamine, 3-[5-[[4-chloro-1-methyl-5-(trifluoromethyl)-1H-pyrazol-3-yl]oxy]-2-nitrophenoxy]-N,N-dimethyl- MP: nD: 1.5275 | (CH$_3$)$_2$N—(CH$_2$)$_3$—O—[aryl-pyrazole] |
| 740 | 1H-pyrazole, 4-chloro-1-methyl-3-[3-[2-(methylsulfinyl)ethoxy]-4-nitrophenoxy]-5-trifluoromethyl- MP: 92.0–93.0 nD: | CH$_3$—S(=O)—(CH$_2$)$_2$—O—[aryl-pyrazole] |
| 741 | acetyl chloride, [5-[[4-chloro-1-methyl-5-(trifluoromethyl)-1H-pyrazol-3-yl]oxy]-2-nitrophenoxy]- MP: 62.0–65.0 nD: | Cl—C(=O)—CH$_2$—O—[aryl-pyrazole] |
| 742 | 2-pentenoic acid, 4-[5-[[4-chloro-1-methyl-5-(trifluoromethyl)-1H-pyrazol-3-yl]oxy]-2-nitrophenoxy]-, methyl ester MP: 77.0–78.0 nD: | CH$_3$—O—C(=O)—CH=CH—CH(CH$_3$)—O—[aryl-pyrazole] |

-continued

| Ex CP # | Name | Structure |
|---|---|---|
| 743 | benzoic acid, 5-[[4-chloro-1-methyl-5-(trifluoromethyl)-1H-pyrazol-3-yl]oxy]-2-nitro-, phenyl ester<br>MP: 109.0-110.0<br>nD: | 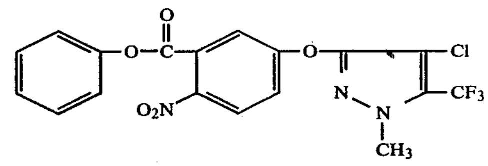 |
| 744 | phenol, 5-[[4-chloro-1-methyl-5-(trifluoromethyl)-1H-pyrazol-3-yl]oxy]-2-nitro-, acetate (ester)<br>MP: 64.0<br>nD: | 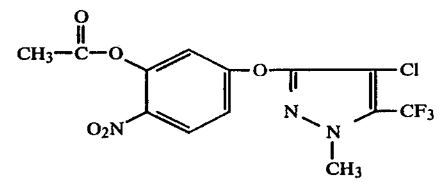 |
| 745 | butanedioic acid, 5-[[4-chloro-1-methyl-5-(trifluoromethyl)-1H-pyrazol-3-yl]oxy]-2-nitrophenyl ethyl ester<br>MP:<br>nD: 1.5168 | 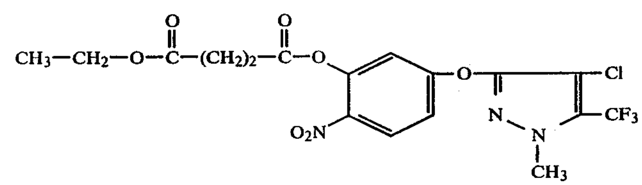 |
| 746 | benzoic acid, 5-[[4-chloro-1-methyl-5-(trifluoromethyl)-1H-pyrazol-3-yl]oxy]-2-nitro, 4-methoxy-1-methyl-4-oxo-2-butenyl ester<br>MP:<br>nD: 1.5253 | 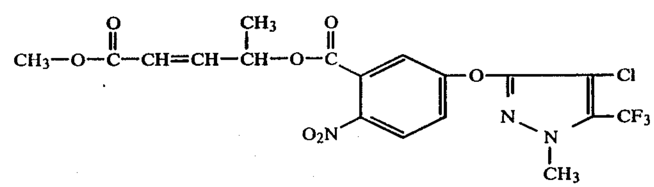 |
| 747 | 2-pentenoic acid, 4-[[[5-[[4-chloro-1-methyl-5-(trifluoromethyl)-1H-pyrazol-3-yl]oxy]-2-nitrophenoxy]acetyl]oxy]-, methyl ester<br>MP:<br>nD: 1.5267 | 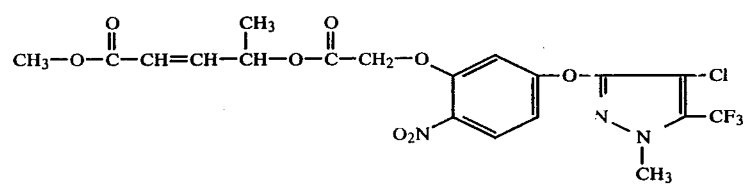 |

-continued

| Ex CP # | Name | Structure |
|---|---|---|
| 748 | acetic acid, [5-[[4-chloro-1-methyl-5-(trifluoromethyl)-1H-pyrazol-3-yl]oxy]-2-nitrophenoxy]-, butyl ester MP: nD: 1.5200 | CH₃—(CH₂)₃—O—C(=O)—CH₂—O—(4-nitro-2-[(4-chloro-5-(trifluoromethyl)-1-methylpyrazol-3-yl)oxy]phenyl) |
| 749 | acetic acid, [5-[[4-chloro-1-methyl-5-(trifluoromethyl)-1H-pyrazol-3-yl]oxy]-2-nitrophenoxy]methoxy, methyl ester MP: nD: 1.5221 | CH₃—O—C(=O)—CH(OCH₃)—O—(4-nitro-2-[(4-chloro-5-(trifluoromethyl)-1-methylpyrazol-3-yl)oxy]phenyl) |
| 750 | acetic acid, [5-[[4-chloro-1-methyl-5-(trifluoromethyl)-1H-pyrazol-3-yl]oxy]-2-nitrophenoxy]-, 2-methylpropyl ester MP: 39.0 nD: | (CH₃)₂CH—CH₂—O—C(=O)—CH₂—O—(4-nitro-2-[(4-chloro-5-(trifluoromethyl)-1-methylpyrazol-3-yl)oxy]phenyl) |
| 751 | acetic acid, [5-[[4-chloro-1-methyl-5-(trifluoromethyl)-1H-pyrazol-3-yl]oxy]-2-nitrophenoxy]-, 1-methylethyl ester MP: 84.0 nD: | (CH₃)₂CH—O—C(=O)—CH₂—O—(4-nitro-2-[(4-chloro-5-(trifluoromethyl)-1-methylpyrazol-3-yl)oxy]phenyl) |
| 752 | acetic acid, [5-[[4-chloro-1-methyl-5-(trifluoromethyl)-1H-pyrazol-3-yl]oxy]-2-nitrophenoxy]-, 2-[2-(2-methoxyethoxy)ethoxy]ethyl ester MP: nD: 1.5159 | CH₃—O—(CH₂)₃—O—(CH₂)₃—O—(CH₃)₂—O—C(=O)—CH₂—O—(4-nitro-2-[(4-chloro-5-(trifluoromethyl)-1-methylpyrazol-3-yl)oxy]phenyl) |

-continued

| Ex CP # | Name | Structure |
|---|---|---|
| 753 | benzoic acid, 5-[[4-chloro-1-methyl-5-(trifluoromethyl)-1H-pyrazol-3-yl]oxy]-2-nitro-, 1,2-dimethoxy-2-oxoethyl ester<br>MP:<br>nD: 1.5147 | 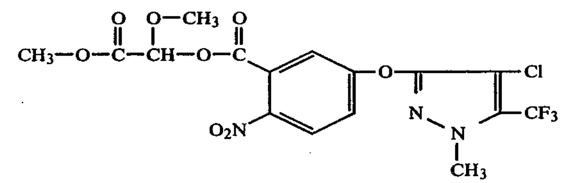 |
| 754 | acetic acid, [[[5-[[4-chloro-1-methyl-5-(trifluoromethyl)-1H-pyrazol-3-yl]oxy]-2-nitrophenoxy]acetyl]oxy]methoxy-, methyl ester<br>MP:<br>nD: 1.5182 | 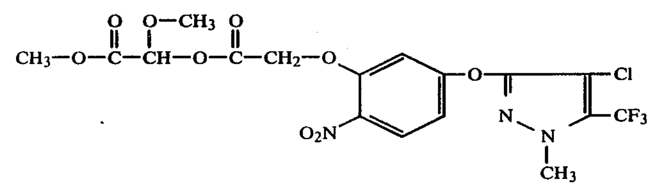 |
| 755 | 1H-pyrazole, 3-(3-(2-bromoethoxy)-4-nitrophenoxy)-4-chloro-1-methyl-5-(trifluoromethyl)-<br>MP:<br>nD: 1.5565 | 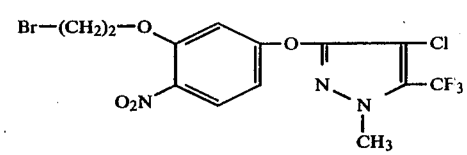 |
| 756 | acetic acid, [5-[[4-chloro-1-methyl-5-(trifluoromethyl)-1H-pyrazol-3-yl)oxy]-2-nitrophenoxy]-, (trimethylsilyl)-methyl ester<br>MP: 73.0<br>nD: | 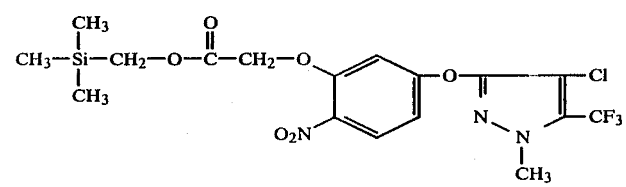 |
| 757 | acetic acid, [5-[[4-chloro-1-methyl-5-(trifluoromethyl)-1H-pyrazol-3-yl]oxy]-2-nitrophenoxy]-, methyl ester<br>MP:<br>nD: 1.5352 | 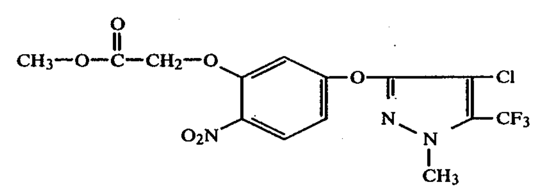 |

-continued

| Ex CP # | Name | Structure |
|---|---|---|
| 758 | propanoic acid, 2-[[[5-[[4-chloro-1-methyl-5-(trifluoromethyl)-1H-pyrazol-3-yl]oxy]-2-nitrophenoxy]imino]-, ethyl ester MP: 99.5 nD: | 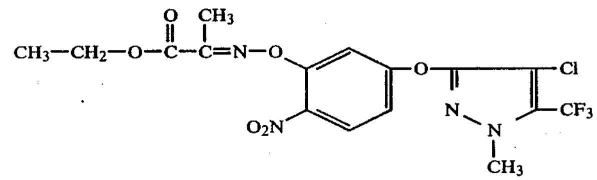 |
| 759 | propanoic acid, 2-[[[[5-[[4-chloro-1-methyl-5-(trifluoromethyl)-1H-pyrazol-3-yl]oxy]-2-nitrophenoxy]acetyl]oxy]imino]-, ethyl ester MP: 97.0 nD: | 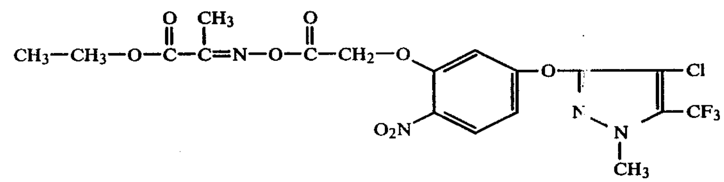 |
| 760 | acetic acid, [5-[[4-chloro-1-methyl-5-(trifluoromethyl)-1H-pyrazol-3-yl]oxy]-2-nitrophenoxy]-, 2-(methylthio)-ethyl ester MP: nD: 1.5436 | 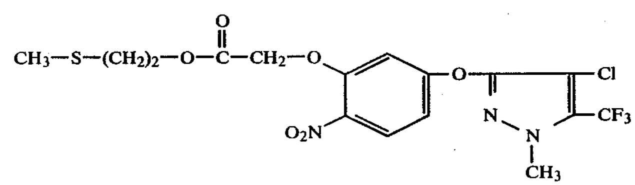 |
| 761 | ethanethioic acid, [5-[[4-chloro-1-methyl-5-(trifluoromethyl)-1H-pyrazol-3-yl]oxy]-2-nitrophenoxy]-, S-butyl ester MP: 74.0 nD: | 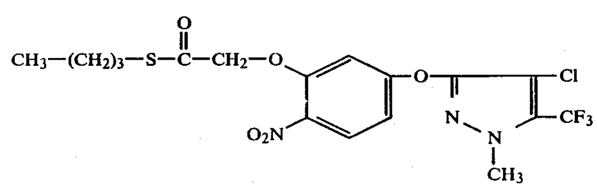 |

| Ex CP # | Name | Structure |
|---|---|---|
| 762 | benzenamine, 5-[[4-chloro-1-methyl-5-(trifluoromethyl)-1H-pyrazol-3-yl]oxy]-N-[2-(ethylsufonyl)ethyl]-2-nitro- MP: 107.0-109.0 nD: | CH$_3$—CH$_2$—S(=O)(=O)—(CH$_2$)$_2$—NH—(aryl: 2-nitro, 5-O-pyrazole with Cl, CF$_3$, N—N—CH$_3$) |
| 763 | sulfonium, [3-[[5-[[4-chloro-1-methyl-5-(trifluoromethyl)-1H-pyrazol-3-yl]oxy]-2-nitrophenyl]amino]propyl]dimethyl, iodide MP: 121.0-124.0 nD: | CH$_3$—S$^+$(CH$_3$)—(CH$_2$)$_3$—NH—(aryl: 2-nitro, 5-O-pyrazole with Cl, CF$_3$, N—N—CH$_3$), I$^-$ |
| 764 | propanamide, 2-[[5-[[4-chloro-1-methyl-5-(trifluoromethyl)-1H-pyrazol-3-yl]oxy]-2-nitrophenyl]amino]- MP: 187.0-188.0 nD: | (pyrazole with F$_3$C, Cl, H$_3$C—N—N)—O—(aryl: NO$_2$, NH—CH(CH$_3$)—C(=O)—NH$_2$) |
| 765 | benzenamine, N-(2-bromoethyl)-5-[[4-chloro-1-methyl-5-(trifluoromethyl)-1H-pyrazol-3-yl]oxy]-2-nitro- MP: 96.0-98.0 nD: | (pyrazole with F$_3$C, Cl, H$_3$C—N—N)—O—(aryl: NO$_2$, NH—(CH$_2$)$_2$—Br) |
| 766 | benzenamine, N-(3-bromopropyl)-5-[[4-chloro-1-methyl-5-(trifluoromethyl)-1H-pyrazol-3-yl]oxy]-2-nitro- MP: 91.0-93.0 nD: | (pyrazole with F$_3$C, Cl, H$_3$C—N—N)—O—(aryl: NO$_2$, NH—(CH$_2$)$_3$—Br) |
| 767 | benzenamine, 5-[[4-chloro-1-methyl-5-(trifluoromethyl)-1H-pyrazol-3-yl]oxy]-N-[3-[2-(2-ethoxyethoxy)ethoxy]propyl]-2-nitro- MP: nD: 1.5278 | (pyrazole with F$_3$C, Cl, H$_3$C—N—N)—O—(aryl: NO$_2$, NH—(CH$_2$)$_3$—O—(CH$_2$)$_3$—O—(CH$_2$)$_2$—O—(CH$_2$)$_2$—O—CH$_2$—CH$_3$) |

-continued

| Ex CP # | Name | Structure |
|---|---|---|
| 768 | phosphonic acid, [1-[[5-[[4-chloro-1-methyl-5-(trifluoromethyl)-1H-pyrazol-3-yl]oxy]-2-nitrophenyl]amino]ethyl]-, diethyl ester<br>MP:<br>nD: 1.5490 | 4-chloro-5-trifluoromethyl-pyrazolyloxy-nitrophenyl-NH-CH(CH₃)-P(=O)(O-CH₂-CH₃)(O-CH₂-CH₃) |
| 769 | benzenamine, 5-[[4-chloro-1-methyl-5-(trifluoromethyl)-1H-pyrazol-3-yl]oxy]-2-nitro-N-[2-(phenylthio)ethyl]-<br>MP: 58.0–60.0<br>nD: | NH—(CH₂)₂—S—Ph |
| 770 | benzenamine, 5-[[4-chloro-1-methyl-5-(trifluoromethyl)-1H-pyrazol-3-yl]oxy]-N-(2-ethoxyethyl)-2-nitro-<br>MP:<br>nD: 1.5692 | NH—(CH₂)₂—O—CH₂—CH₃ |
| 771 | benzenamine, 5-[[4-chloro-1-methyl-5-(trifluoromethyl)-1H-pyrazol-3-yl]oxy]-N-[3-(2-methoxyethoxy)propyl]-2-nitro-<br>MP:<br>nD: 1.5636 | NH—(CH₂)₃—O—(CH₂)₂—O—CH₃ |
| 772 | benzenamine, 5-[[4-chloro-1-methyl-5-(trifluoromethyl)-1H-pyrazol-3-yl]oxy]-N-(2-methoxy-1-methylethyl)-2-nitro-<br>MP:<br>nD: 1.5550 | NH—CH(CH₃)—CH₂—O—CH₃ |
| 773 | ethanol, 2-[[2-[5-[[4-chloro-1-methyl-5-(trifluoromethyl)-1H-pyrazol-3-yl]oxy]-2-nitrophenyl]amino]ethoxy]-<br>MP: 54.0–57.0<br>nD: | NH—(CH₂)₂—O—(CH₂)₂—OH |
| 774 | benzenamine, 5-[[4-chloro-1-methyl-5-(trifluoromethyl)-1H-pyrazol-3-yl]oxy]-N-[3-(2-ethoxyethoxy)propyl]-2-nitro-<br>MP:<br>nD: 1.5552 | NH—(CH₂)₃—O—(CH₂)₂—O—CH₂—CH₃ |

-continued

| Ex CP # | Name | Structure |
|---|---|---|
| 775 | phosphonic acid, [2-[[5-[[4-chloro-1-methyl-5-(trifluoromethyl)-1H-pyrazol-3-yl]oxy]-2-nitrophenyl]amino]ethyl]-, diethyl ester MP: 54.0-58.0 nD: | |
| 776 | 1,2-ethanediamine, N-[5-[[4-chloro-1-methyl-5-(trifluoromethyl)-1H-pyrazol-3-yl]oxy]-2-nitrophenyl]-N,n',n'-trimethyl- MP: 56.0-59.0 nD: | 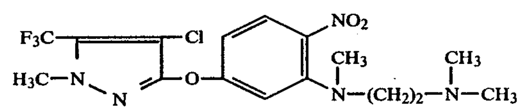 |
| 777 | benzenamine, 5-[[4-chloro-1-methyl-5-(trifluoromethyl)-1H-pyrazol-3-yl]oxy]-2-nitro-N-[-(tetrahydro-2-furanyl)methyl]- MP: nD: 1.5513 | 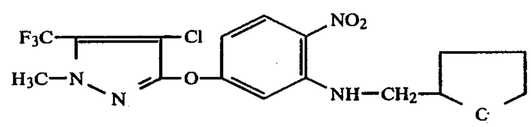 |
| 778 | 1-butanol, 2-[[5-[[4-chloro-1-methyl-5-(trifluoromethyl)-1H-pyrazol-3-yl]oxy]-2-nitrophenyl]amino]-(R)-(−)- MP: 76.0-77.0 nD: | R ISOMER |
| 779 | 1-butanol, 2[[5-[[4-chloro-1-methyl-5-(trifluoromethyl)-1H-pyrazol-3-yl]oxy]-2-nitrophenyl]amino]-(S)-(+)- MP: 72.0-74.0 nD: | S ISOMER |
| 780 | ethanaminium, 2-[[5-[[4-chloro-1-methyl-5-(trifluoromethyl)-1H-pyrazol-3-yl]oxy]-2-nitrophenyl]methylamino]-N,N,N-(trimethyl)-iodide MP: 171.0-174.0 nD: | 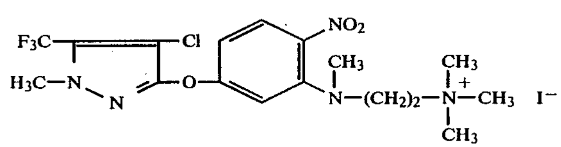 |

| Ex CP # | Name | Structure |
|---|---|---|
| 781 | sulfonium, [2-[5-[[4-chloro-1-methyl-5-(trifluoromethyl)-1H-pyrazol-3-yl]oxy]-2-nitrophenoxy]ethyl]dimethyl-, iodide<br>MP: 120.0<br>nD: | 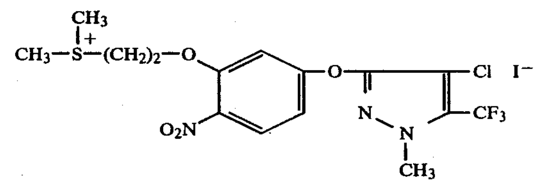 |
| 782 | propanoic acid, 2-[[[5-[[4-chloro-1-methyl-5-(trifluoromethyl)-1H-pyrazol-3-yl]oxy]-2-nitrobenzoyl]oxy]imino]-, ethyl ester<br>MP: 92.0<br>nD: | 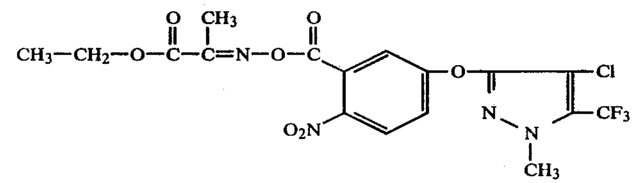 |
| 783 | acetic acid, [5-[[4-chloro-1-methyl-5-(trifluoromethyl)-1H-pyrazol-3-yl]oxy]-2-(methylsulfinyl)ethyl ester<br>MP:<br>nD:1.5400 | 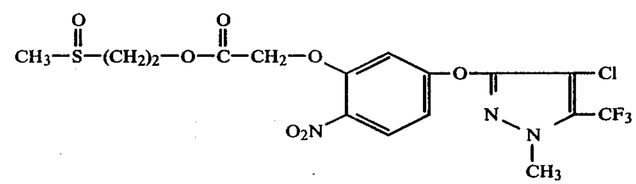 |
| 784 | acetic acid, [5-[[4-chloro-1-methyl-5-(trifluoromethyl)-1H-pyrazol-3-yl]oxy]-2-(methylsulfonyl)ethyl ester<br>MP: 104.0<br>nD: | 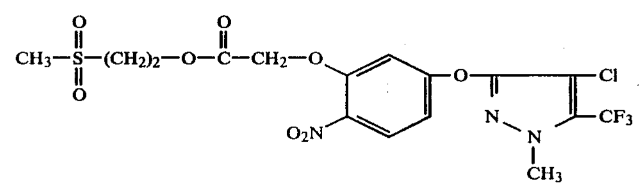 |

| Ex CP # | Name | Structure |
|---|---|---|
| 785 | acetamide, 2-[5-[[4-chloro-1-methyl-5-(trifluoromethyl)-1H-pyrazol-3-yl]oxy]-2-nitrophenoxy]-N-(methylsulfonyl)- MP: 171.0–172.0 nD: | 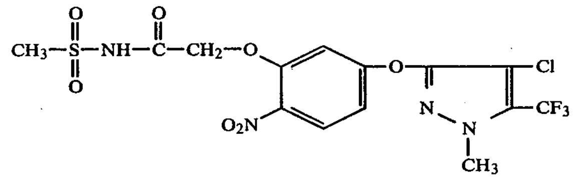 |
| 786 | acetamide, 2-[5-[[4-chloro-1-methyl-5-(trifluoromethyl)-1H-pyrazol-3-yl]oxy]-2-nitrophenoxy]-N-methyl- MP: 144.0 nD: | 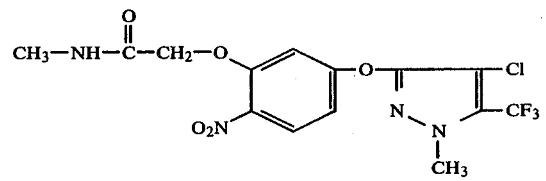 |
| 787 | glycine, N-[[5-[[4-chloro-1-methyl-5-(trifluoromethyl)-1H-pyrazol-3-yl]oxy]-2-nitrophenoxy]acetyl]-,methyl ester MP: 115.0–115.0 nD: | 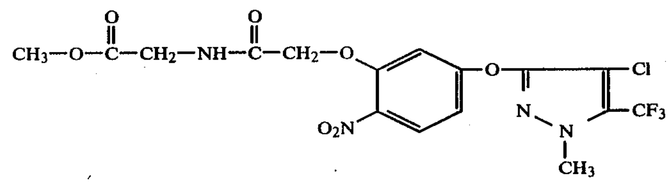 |
| 788 | alanine, N-[[5-[[4-chloro-1-methyl-5-(trifluoromethyl)-1H-pyrazol-3-yl]oxy]-2-nitrophenoxy]acetyl]-, ethyl ester MP: 93.0–94.0 nD: | 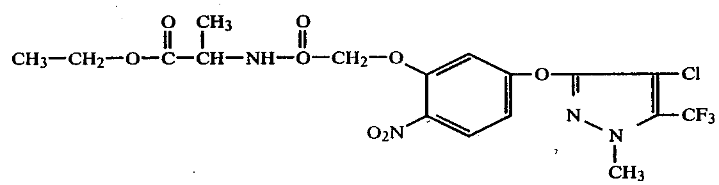 |
| 789 | ethanethioic acid, [5-[[4-chloro-1-methyl-5-(trifluoromethyl)-1H-pyrazol-3-yl]oxy]-2-nitrophenoxy]-,S-(1-methylethyl)ester MP: 94.0–95.0 nD: | 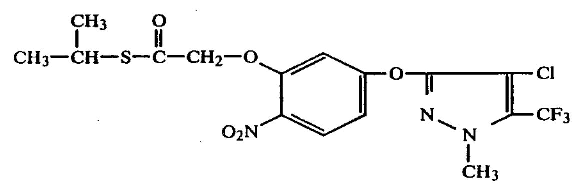 |

| Ex CP # | Name |
|---|---|
| 790 | benzoic acid, 5-[[4-chloro-1-methyl-5-(trifluoromethyl)-1H-pyrazol-3-yl]oxy]-2-nitro-2-methyl-5-oxo-1-cyclopenten-1-yl ester<br>MP: 114.0–115.0<br>nD: |
| 791 | acetic acid, [5-[[4-chloro-1-methyl-5-(trifluoromethyl)-1H-pyrazol-3-yl]oxy]-2-nitrophenoxy]-, 2-methyl-5-oxo-1-cyclopenten-1-yl ester<br>MP: 104.0<br>nD: |
| 792 | 2-cyclopenten-1-one, 2-[5-[[4-chloro-1-methyl-5-(trifluoromethyl)-1H-pyrazol-3-yl]oxy]-2-nitrophenoxy]-3-methyl-<br>MP: 115.0<br>nD: |
| 793 | ethanimidic acid-N-[[[5-[[4-chloro-1-methyl-5-(trifluoromethyl)-1H-pyrazol-3-yl]oxy]-2-nitrophenoxy]acetyl]oxy]-, ethyl ester<br>MP: 112.0–114.0<br>nD: |
| 794 | benzamide, 5-[[4-chloro-1-methyl-5-(trifluoromethyl)-1H-pyrazol-3-yl]oxy]-N-[2-(dimethylamino)ethyl]-2-nitro-<br>MP: 101.5–102.0<br>nD: |

| Ex CP # | Name | Structure |
|---|---|---|
| 795 | 1H-pyrazole, 4-chloro-1-methyl-3-[3-(1-methylpropoxy)-4-nitrophenoxy]-5-(trifluoromethyl)- MP: nD: 1.5240 | 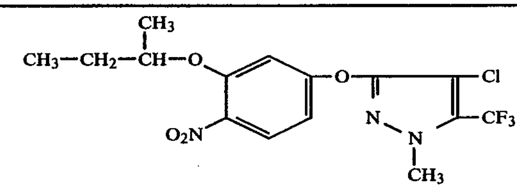 |
| 796 | 1H-pyrazole, 4-chloro-1-methyl-3-[3-(2-methylbutoxy)-4-nitrophenoxy]-5-(trifluoromethyl)- MP: nD: 1.5230 | 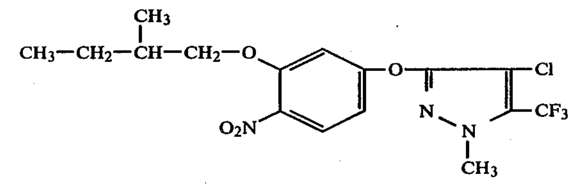 |
| 797 | ethanimidic acid, N-[5-[[4-chloro-1-methyl-5-(trifluoromethyl)-1H-pyrazol-3-yl]oxy]-2-nitrophenoxy], ethyl ester MP: 112.5–113.0 nD: | 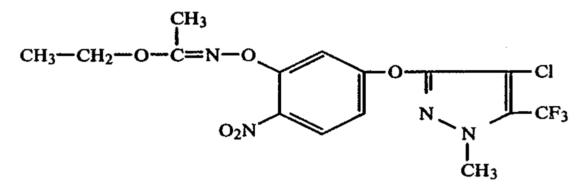 |
| 798 | propanoic acid, 2-[[2-[5-[[4-chloro-1-methyl-5-(trifluoromethyl)-1H-pyrazol-3-yl]oxy]-2-nitrophenoxy]ethyl]thio]-, ethyl ester MP: nD: 1.5360 | 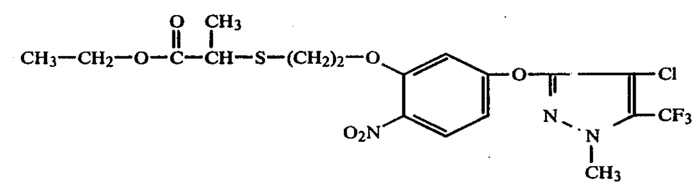 |
| 799 | acetic acid, [5-[[4-chloro-1-methyl-5-(trifluoromethyl)-1H-pyrazol-3-yl]oxy]-2-nitrophenoxy]-, 2-ethoxy-2-oxoethyl ester MP: nD: 1.5195 | 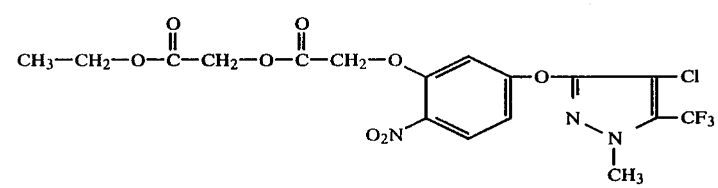 |

-continued

| Ex CP # | Name | Structure |
|---|---|---|
| 800 | propanoic acid, 2-[[[5-[[4-chloro-1-methyl-5-(trifluoromethyl)-1H-pyrazol-3-yl]oxy]-2-nitrophenoxy]acetyl]oxy]-, methyl ester MP: nD: 1.5169 | (structure) |
| 801 | carbamic acid, [2-[5-[[4-chloro-1-methyl-5-(trifluoromethyl)-1H-pyrazol-3-yl]oxy]-2-nitrophenoxy]ethyl]-, methyl ester MP: 83.0–84.0 nD: | (structure) |
| 802 | benzoic acid, 5-[[4-chloro-1-methyl-5-(trifluoromethyl)-1H-pyrazol-3-yl]oxy]-2-nitro-, 2-[(methoxycarbonyl)amino]ethyl ester MP: 74.0–75.0 nD: | (structure) |
| 803 | ethanaminium, 2-[[5-[[4-chloro-1-methyl-5-(trifluoromethyl)-1H-pyrazol-3-yl]oxy]-2-nitrobenzoyl]amino]-N,N,N-trimethyl-, iodide MP: 183.0 nD: | (structure) |
| 804 | acetamide, 2-[4-[[5-chloro-1-methyl-5-(trifluoromethyl)-1H-pyrazol-3-yl]oxy]-2-nitrophenoxy]-N-[2-(diethylamino)ethyl]- MP: 102.0 nD: | (structure) |

| Ex CP # | Name | Structure |
|---|---|---|
| 805 | acetic acid, [[[5-[[4-chloro-1-methyl-5-(trifluoromethyl)-1H-pyrazol-3-yl]oxy]-2-nitrophenoxy]acetyl]thio]-, methyl ester MP: 80.0 nD: | 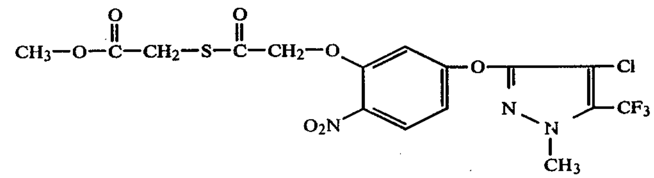 |
| 806 | acetic acid, [[[5-[[4-chloro-1-methyl-5-(trifluoromethyl)-1H-pyrazol-3-yl]oxy]-2-nitrophenoxy]-, 2-(diethylamino)ethyl ester MP: nD: 1.5180 | 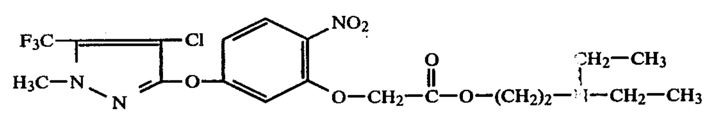 |
| 807 | ethanaminium, 2-[[5-[[4-chloro-1-methyl-5-(trifluoromethyl)-1H-pyrazol-3-yl]oxy]-2-nitrophenoxy]acetyl]amino]-N,N,N-trimethyl-, iodide MP: 200.0–202.0 nD: | 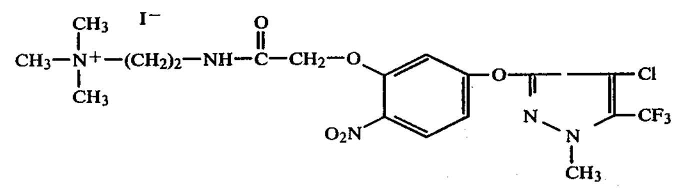 |
| 808 | acetic acid, [5-[[4-chloro-1-methyl-5-(trifluoromethyl)-1H-pyrazol-3-yl]oxy]-2-nitrophenoxy]-, 2,2-dimethylhydrazide MP: 130.0–131.0 nD: | 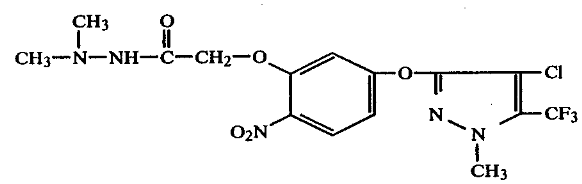 |
| 809 | hydrazinium, 2-[[5-[[4-chloro-1-methyl-5-(trifluoromethyl)-1H-pyrazol-3-yl]oxy]-2-nitrophenoxy]acetyl]-1,1,1-trimethyl-, iodide MP: 142.0 nD: | 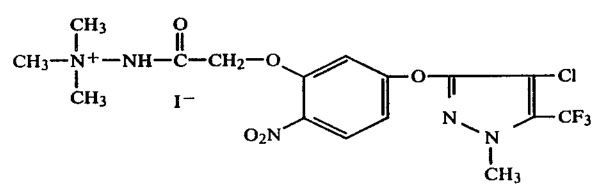 |

-continued

| Ex CP # | Name | Structure |
|---|---|---|
| 810 | 1H-pyrazole, 4-chloro-3-[3-(ethenyloxy)-4-nitrophenoxy]-1-methyl-5-(trifluoromethyl)-<br>MP: 54.0<br>nD: | 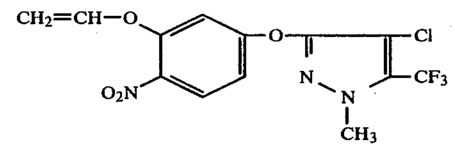 |
| 811 | 2-propanone, O-[[5-[[4-chloro-1-methyl-5-(trifluoromethyl)-1H-pyrazol-3-yl]oxy]-2-nitrophenoxy]acetyl]oxime<br>MP: 96.0<br>nD: | 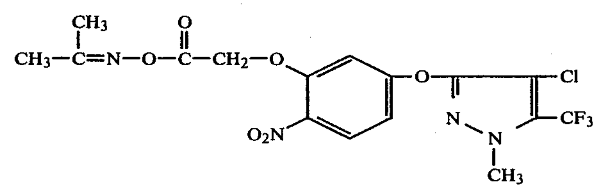 |
| 812 | acetic acid, [5-[[4-chloro-1-methyl-5-(trifluoromethyl)-1H-pyrazol-3-yl]oxy]-2-nitrophenoxy]-, 2-methoxy-1-methylethyl ester<br>MP:<br>nD: 1.5190 | 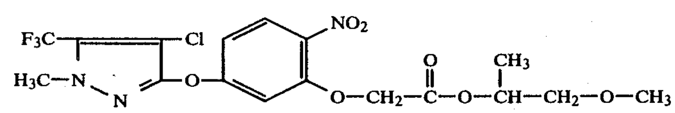 |
| 813 | acetic acid, [5-[[4-chloro-1-methyl-5-(trifluoromethyl)-1H-pyrazol-3-yl]oxy]-2-nitrophenoxy]-, 2-[(methoxycarbonyl)amino]ethyl ester<br>MP:<br>nD: 1.5294 | 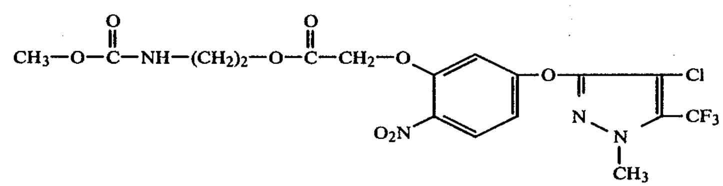 |
| 814 | ethanaminium, 2-[[[5-[[4-chloro-1-methyl-5-(trifluoromethyl)-1H-pyrazol-3-yl]oxy]-2-nitrophenoxy]acetyl]oxy]-N,N-diethyl-N-methyl-iodide<br>MP: 137.0<br>nD: | 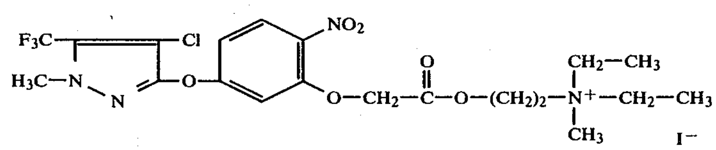 |

| Ex CP # | Name | Structure |
|---|---|---|
| 815 | acetamide, 2-[5-[[4-chloro-1-methyl-5-(trifluoromethyl)-1H-pyrazol-3-yl]oxy]-2-nitrophenoxy]-N,N-dimethyl-<br>MP: 94.0<br>nD: | 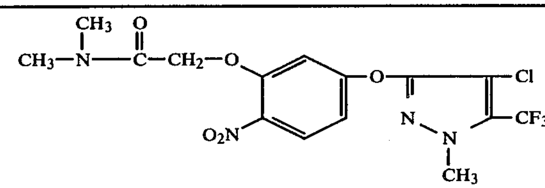 |
| 816 | acetic acid, [5-[[4-chloro-1-methyl-5-(trifluoromethyl)-1H-pyrazol-3-yl]oxy]-2-nitrophenoxy]-, 2-methoxyethyl ester<br>MP:<br>nD: 1.5271 | 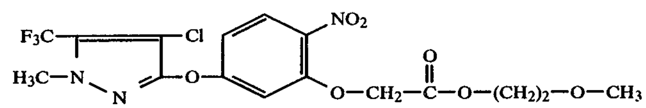 |
| 817 | benzoic acid, 5-[[4-chloro-1-methyl-5-(trifluoromethyl)-1H-pyrazol-3-yl]oxy]-2-nitro-, (diethoxyphosphinyl)methyl ester<br>MP:<br>nD: 1.5114 | 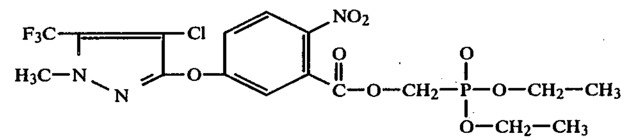 |
| 818 | phosphonic acid, [[5-[[4-chloro-1-methyl-5-(trifluoromethyl)-1H-pyrazol-3-yl]oxy]-2-nitrophenoxy]methyl]-, diethyl ester<br>MP: 86.0<br>nD: | 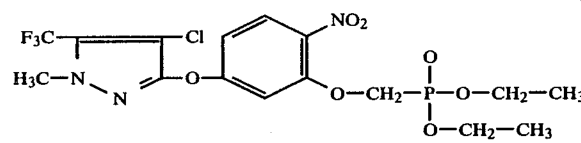 |
| 819 | 1H-pyrazole, 4-chloro-3-[3-(dimethoxymethyl)-4-nitrophenoxy]-1-methyl-5-(trifluoromethyl)-, mixt. with 5-[[4-chloro-1-methyl-5-(trifluoromethyl)-1H-pyrazol-3-yl]oxy]-2-nitrobenzaldehyde<br>MP:<br>nD: 1.5252 | |

-continued

| Ex CP # | Name | Structure |
|---|---|---|
| 820 | benzenemethanaminium, 5-[[4-chloro-1-methyl-5-(trifluoromethyl)-1H-pyrazol-3-yl]oxy]-N,N,N-trimethyl-2-nitro-, iodide MP: 182.0–184.0 nD: | 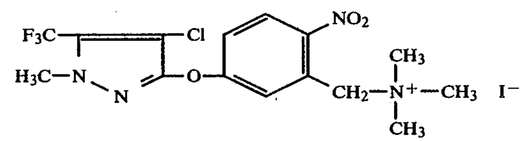 |
| 821 | methanediol, [5-[[4-chloro-1-methyl-5-(trifluoromethyl)-1H-pyrazol-3-yl]oxy]-2-nitrophenyl]-, diacetate (ester) MP: 110.0–115.0 nD: | 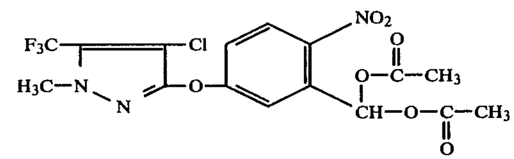 |
| 822 | 1H-pyrazole,- 4-chloro-1-methyl-3-[3-[(methylsulfinyl)methyl]-4-nitrophenoxy]-5-(trifluoromethyl)- MP: nD: | 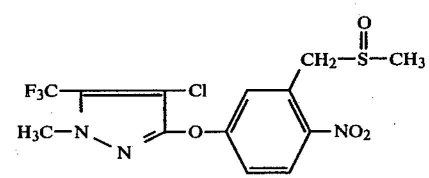 |
| 823 | 1H-pyrazole,- 4-chloro-1-methyl-3-[3-[(methylsulfonyl)methyl]-4-nitrophenoxy]-5-(trifluoromethyl)- NP: 101.5–103.5 nD: | 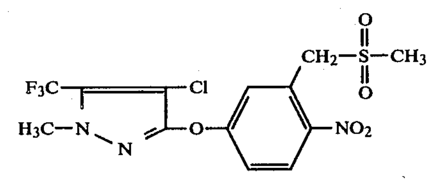 |
| 824 | acetic acid, [[[5-[[4-chloro-1-methyl-5-(trifluoromethyl)-1H-pyrazol-3-yl]oxy]-2-nitrophenyl]methyl]sulfonyl]-, ethyl ester MP: 75.0–77.0 nD: | 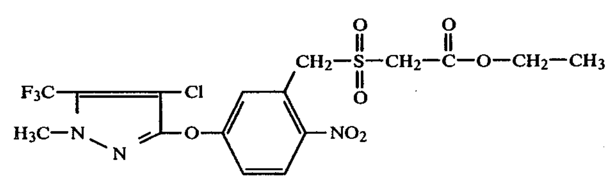 |

| Ex CP # | Name | Structure |
|---|---|---|
| 825 | phosphonic acid, [[5-[[4-chloro-1-methyl-5-(trifluoromethyl)-1H-pyrazol-3-yl]oxy]-2-nitrophenyl]methyl]-, diethyl ester MP: 60.0–62.0 nD: | 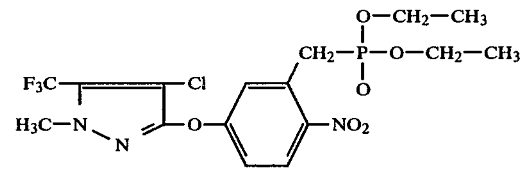 |
| 826 | phosphonic acid, [[5-[[4-chloro-1-methyl-5-(trifluoromethyl)-1H-pyrazol-3-yl]oxy]-2-nitrophenyl]methyl]- MP: 163.0–164.0 nD: | 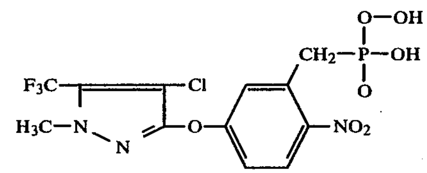 |
| 827 | phosphonic acid, [[5-[[4-chloro-1-methyl-5-(trifluoromethyl)-1H-pyrazol-3-yl]oxy]-2-nitrophenyl]methyl]-, dicalcium salt MP: 300.0 nD: | 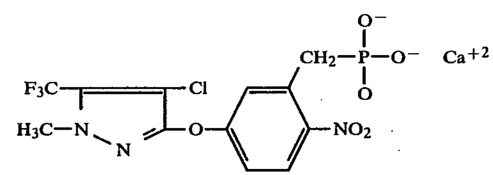 |
| 828 | propanamide, 2-[5-[[4-chloro-5-(difluoromethyl)-1-methyl-1H-pyrazol-3-yl]oxy]-2-nitrophenoxy]-N-methyl- MP: 127.0–128.0 nD: | 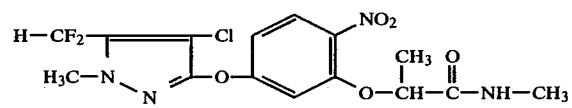 |
| 829 | propanamide, 2-[5-[[4-chloro-1-methyl-5-(methylthio)-1H-pyrazol-3-yl]oxy]-2-nitrophenoxy]-N-methyl- MP: 121.0–122.0 nD: | 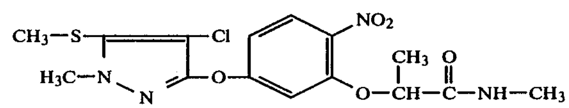 |
| 830 | propanamide, 2-[5-[[4-chloro-1-methyl-5-(methylthio)-1H-pyrazol-3-yl]oxy]-2-nitrophenoxy]-N,N-dimethyl- MP: 81.0–84.0 nD: | 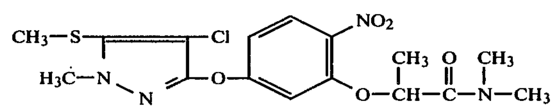 |

-continued

| Ex CP # | Name | Structure |
|---|---|---|
| 831 | propanamide, 2-[5-[[4-chloro-5-(difluoromethyl)-1-methyl-1H-pyrazol-3-yl]oxy]-2-nitrophenoxy]-N,N-dimethyl-<br>MP: 109.0–110.0<br>nD: | 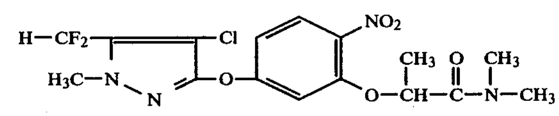 |
| 832 | benzoic acid, 5-[[5-(difluoromethyl)-1-methyl-4-nitro-1H-pyrazol-3-yl]oxy]-2-nitro-, ethyl ester<br>MP: 72.0–73.0<br>nD: | 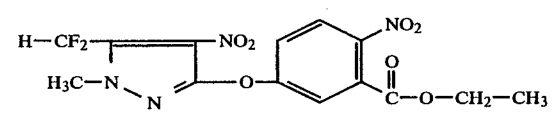 |
| 833 | benzenamine, 5-[[4-chloro-1-methyl-5-(difluoromethyl)-1H-pyrazol-3-yl]oxy]-N-methyl-N-methoxy-2-nitro<br>MP: 59.0–60.0<br>nD: | 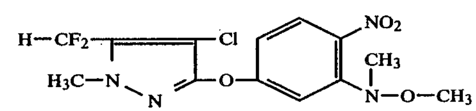 |
| 834 | 1H-pyrazole, 4-bromo-5-(difluoromethyl)-3-(3-ethoxy-4-nitrophenoxy)-1-methyl-<br>MP: 71.0–72.0<br>nD: | 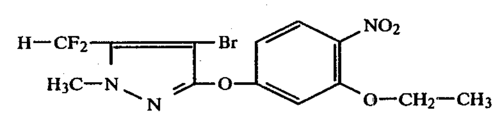 |
| 835 | propanoic acid 2-[5-[[4-chloro-1-methyl-5-(trifluoromethyl)-1H-pyrazol-3-yl]oxy]-2-nitrophenoxy]-, 5-methyl-2-(1-methylethyl)cyclohexyl ester<br>MP:<br>nD: 1.5142 | 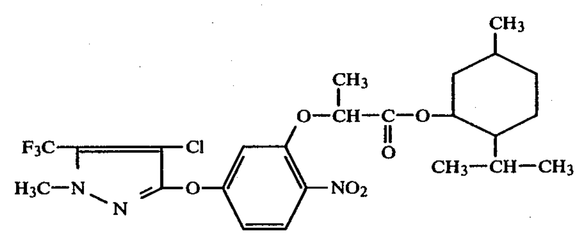 |
| 836 | propanamide, 2-[5-[[4-chloro-1-methyl-5-(trifluoromethyl)-1H-pyrazol-3-yl]oxy]-2-nitrophenoxy]-N-(cyanomethyl)-N-methyl-<br>MP:<br>nD: 1.5415 | 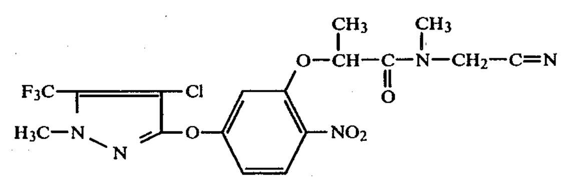 |

| Ex CP # | Name |
|---|---|
| 837 | propanoic acid, 2-[5-[[4-chloro-1-methyl-5-(trifluoromethyl)-1H-pyrazol-3-yl]oxy]-2-nitrophenoxy]-, 2-[2-[5-[[4-chloro-1-methyl-5-(trifluoromethyl)-1H-pyrazol-3-yl]oxy]-2-nitrophenoxy]-1-oxopropyl]hydrazide<br>MP: 216.0-219.0<br>nD: |
| 838 | acetic acid, [[[1-[5-[[4-chloro-1-methyl-5-(trifluoromethyl)-1H-pyrazol-3-yl]oxy]-2-nitrophenoxy]ethylideneamino]oxy]-, 2-methoxy-1-methylethyl ester<br>MP:<br>nD: 1.5204 |
| 839 | acetic acid, [[[1-[5-[[4-chloro-1-methyl-5-(trifluoromethyl)-1H-pyrazol-3-yl]oxy]-2-nitrophenoxy]ethylidene]amino]oxy]-, cyclopentyl ester<br>MP:<br>nD: 1.5309 |
| 840 | acetic acid, [[[1-[5-[[4-chloro-1-methyl-5-(trifluoromethyl)-1H-pyrazol-3-yl]oxy]-2-nitrophenoxy]ethylidene]amino]oxy]-, 2-ethoxy-2-oxoethyl ester<br>MP:<br>nD: 1.5239 |
| 841 | acetic acid, [[5-[[4-chloro-1-methyl-5-(trifluoromethyl)-1H-pyrazol-3-yl]oxy]-2-nitrophenyl]thio]-, methyl ester<br>MP: 107.5-109.0<br>nD: |

-continued

| Ex CP # | Name | Structure |
|---|---|---|
| 842 | propanoic acid, 2-[5-[[4-chloro-1-methyl-5-(trifluoromethyl)-1H-pyrazol-3-yl]oxy]-2-nitrophenoxy], 2-[(methoxycarbonyl)amino]ethyl ester<br>MP:<br>nD: 1.5261 | (structure) |
| 843 | propanamide, N-acetyl-2-[5-[[4-chloro-1-methyl-5-(trifluoromethyl)-1H-pyrazol-3-yl]oxy]-2-nitrophenoxy]-<br>MP: 151.0-152.0<br>nD: | (structure) |
| 844 | propanamide, 2-[5-[[4-chloro-1-methyl-5-(trifluoromethyl)-1H-pyrazol-3-yl]oxy]-2-nitrophenoxy]-N,N-di-2-propenyl-<br>MP:<br>nD: 1.5404 | (structure) |
| 845 | propanoic acid, 2-[5-[[4-chloro-1-methyl-5-(trifluoromethyl)-1H-pyrazol-3-yl]oxy]-2-nitrophenoxy]-, (diethoxyphosphinyl)methyl ester<br>MP:<br>nD: 1.5118 | (structure) |
| 846 | benzeneacetic acid, alpha-[5-[[4-chloro-1-methyl-5-(trifluoromethyl)-1H-pyrazol-3-yl]oxy]-2-nitrophenoxy]-, methyl ester<br>MP:<br>nD: 1.5415 | (structure) |

| Ex CP # | Name | Structure |
|---|---|---|
| 847 | hexanoic acid, 2-[5-[[4-chloro-1-methyl-5-(trifluoromethyl)-1H-pyrazol-3-yl]oxy]-2-nitrophenoxy]-, ethyl ester<br>MP:<br>nD: 1.5111 | (structure) |
| 848 | 1,4,2-dioxazine, 3-[1-[5-[[4-chloro-1-methyl-5-(trifluoromethyl)-1H-pyrazol-3-yl]oxy]-2-nitrophenoxy]ethyl]-5,6-dihydro-<br>MP: 111.0–112.0<br>nD: | (structure) |
| 849 | hexanoic acid, 2-[5-[[4-chloro-1-methyl-5-(trifluoromethyl)-1H-pyrazol-3-yl]oxy]-2-nitrophenoxy]-<br>MP: 97.0<br>nD: | (structure) |
| 850 | propanoic acid, 2-[5-[[4-chloro-1-methyl-5-(trifluoromethyl)-1H-pyrazol-3-yl]oxy]-2-nitrophenoxy]-, 1-(5,6-dihydro-1,4,2-dioxazin-3-yl)ethyl ester<br>MP:<br>nD: 1.5290 | (structure) |
| 851 | acetic acid, [[5-[[4-chloro-1-methyl-5-(trifluoromethyl)-1H-pyrazol-3-yl]oxy]-2-nitrophenyl]thio]-, 2-(trimethylsilyl)ethyl ester<br>MP: 75.0–75.5<br>nD: | (structure) |

| Ex CP # | Name | Structure |
|---|---|---|
| 852 | acetic acid, [[5-[[4-chloro-1-methyl-5-(trifluoromethyl)-1H-pyrazol-3-yl]oxy]-2-nitrophenyl]thio]-, (trimethylsilyl)methyl ester<br>MP:<br>nD: 1.5466 | 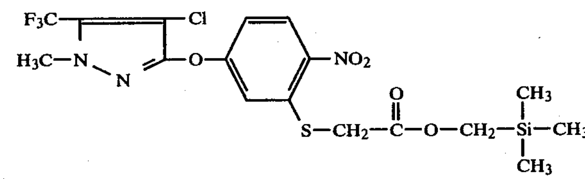 |
| 853 | benzenesulfonyl chloride, 5-[[4-chloro-1-methyl-5-(trifluoromethyl)-1H-pyrazol-3-yl]oxy]-2-nitro-<br>MP: 65.5–67.0<br>nD: | 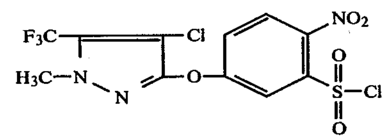 |
| 854 | propanoic acid, 3-[[[1-[5-[[4-chloro-1-methyl-5-(trifluoromethyl)-1H-pyrazol-3-yl]oxy]-2-nitrophenyl]ethylidene]amino]oxy]-, methyl ester<br>MP:<br>nD: 1.5330 | 75% E<br>25% Z ISOMER |
| 855 | methanesulfonamide, N-[[5-[[4-chloro-1-methyl-5-(trifluoromethyl)-1H-pyrazol-3-yl]oxy]-2-nitrophenyl]thio]-<br>MP: 197.0–199.0<br>nD: | 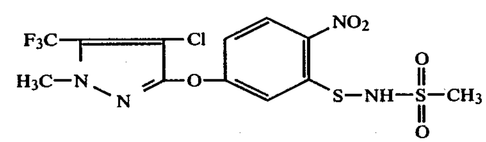 |
| 856 | 1H-pyrazole, 4-chloro-1-methyl-3-[4-nitro-3-(pentylthio)phenoxy]-5-(trifluoromethyl)-<br>MP:<br>nD:1.5614 | 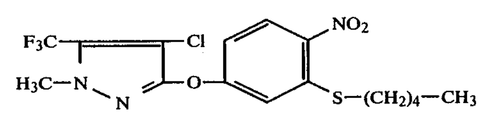 |

| Ex CP # | Name | Structure |
|---|---|---|
| 857 | 2-propenenitrile, 3-[5-[[4-chloro-1-methyl-5-(trifluoromethyl)-1H-pyrazol-3-yl]oxy]-2-nitrophenyl]-, (E)- MP:99.0-100.0 nD: | 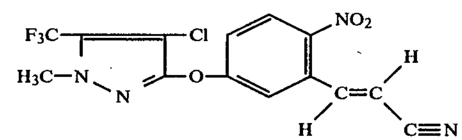 |
| 858 | pentanedinitrile, 3-[5-[[4-chloro-1-methyl-5-(trifluoromethyl)-1H-pyrazol-3-yl]oxy]-2-nitrophenyl]- MP: 106.0 nD: | 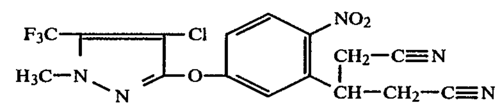 |
| 859 | 2-propenenitrile, 3-[5-[[4-chloro-1-methyl-5-(triflouromethyl)-1H-pyrazol-3-yl]oxy]-2-nitrophenyl]-, (Z)- MP: 93.0-97.0 nD: | 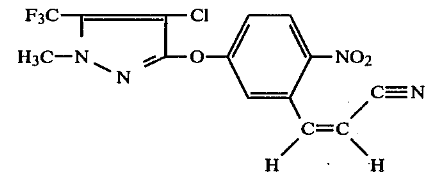 |
| 860 | 2-propenoic acid 3-[5-[[4-chloro-1-methyl-5-(trifluoromethyl)-1H-pyrazol-3-yl]oxy]-2-nitrophenyl]-,sodium salt MP:197.0-198.0 nD: | 90% ISOMER |
| 861 | 1H-pyrazole, 4-chloro-1-methyl-3-(4-nitrophenoxy)-5-(trifluoromethyl)-, compd. with beta-cyclodextrin (1:1) MP: 255.0 nD: | n = 7 1 = CYCLIC POLYMER |

| Ex CP # | Name | Structure |
|---|---|---|
| 862 | acetic acid, [5-[[4-chloro-1-methyl-5-(trifluoromethyl)-1H-pyrazol-3-yl]oxy]-2-nitrophenoxy]-, (diethoxyphosphinyl)methyl ester<br>MP:<br>nD: 1.5151 | 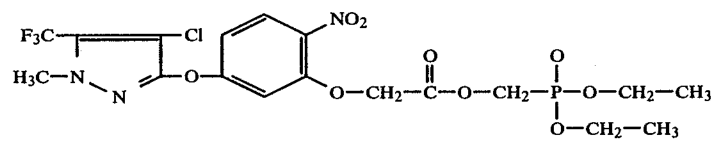 |
| 863 | acetic acid, [5-[[4-chloro-1-methyl-5-(trifluoromethyl)-1H-pyrazol-3-yl]oxy]-2-nitrophenoxy]-, 2-(2-hydroxyethoxy)ethyl ester<br>MP: 90.0<br>nD: | 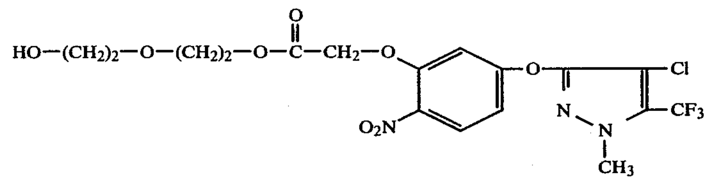 |
| 864 | acetic acid, [5-[[4-chloro-1-methyl-5-(trifluoromethyl)-1H-pyrazol-3-yl]oxy]-2-nitrophenoxy]-, 1-cyanoethyl ester<br>MP: 80.0–82.0<br>nD: | 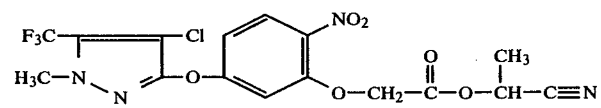 |
| 865 | acetic acid, [5-[[4-chloro-1-methyl-5-(trifluoromethyl)-1H-pyrazol-3-yl]oxy]-2-nitrophenoxy]-, 2-(2-butoxyethoxy)ethyl ester<br>MP:<br>nD: 1.5118 | 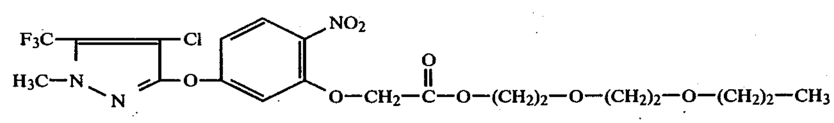 |
| 866 | acetic acid, [5-[[4-chloro-1-methyl-5-(trifluoromethyl)-1H-pyrazol-3-yl]oxy]-2-nitrophenoxy]-, 2-[2-(acetyloxy)ethoxy]ethyl ester<br>MP:<br>nD: 1.5209 | 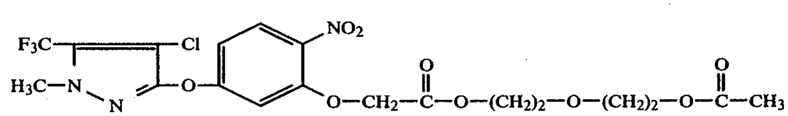 |
| 867 | acetic acid, chloro, 2-[2-[[[5-[[4-chloro-1-methyl-5-(trifluoromethyl)-1H-pyrazol-3-yl]oxy]-2-nitrophenoxy]acetyl]oxy]ethoxy]ethyl ester<br>MP:<br>nD: 1.5283 | 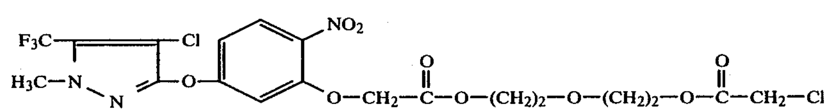 |

| Ex CP # | Name | Structure |
|---|---|---|
| 868 | 1H-pyrazole, 4-chloro-3-[3-[(2,2-dimethyl-1,3-dioxolan-4-yl)methoxy]-4-nitrophenoxy]-1-methyl-5-(trifluoromethyl)-<br>MP: 99.0<br>nD: | 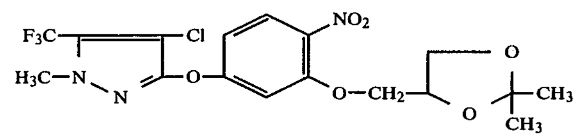 |
| 869 | acetic acid, [5-[[4-chloro-1-methyl-5-(trifluoromethyl)-1H-pyrazol-3-yl]oxy]-2-nitrophenoxy]-, 2-butoxyethyl ester<br>MP:<br>nD: 1.5164 | 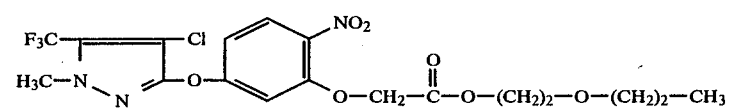 |
| 870 | acetic acid, [5-[[4-chloro-1-methyl-5-(trifluoromethyl))-1H-pyrazol-3-yl]oxy]-2-nitrophenoxy]-, 2-[2-[(methoxyacetyl)oxy]ethoxy]ethyl ester<br>MP:<br>nD: 1.5183 | 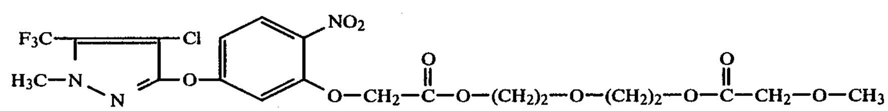 |
| 871 | butanedioic acid, 2-[2-[[5-[[4-chloro-1-methyl-5-(trifluoromethyl)-1H-pyrazol-3-yl]oxy]-2-nitrophenoxy]acetyl]oxy ethoxy ethyl ester<br>MP:<br>nD: 1.5110 | 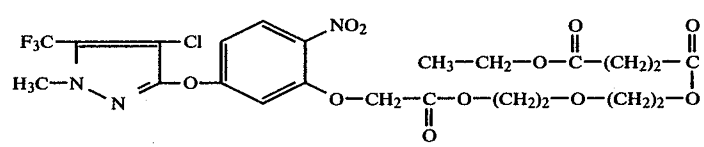 |
| 872 | 1H-pyrazole, -3-[3-[2-(2-butoxyethoxy)ethoxy]-4-nitrophenoxy]-4-chloro-1-methyl-5-(trifluoromethyl)-<br>MP:<br>nD: 1.5140 | 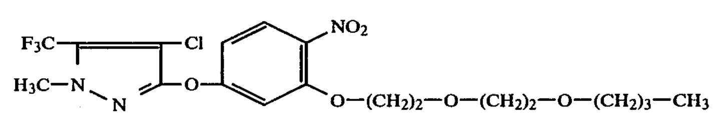 |
| 873 | 1H-pyrazole, 3-[3-(2-butoxyethoxy)-4-nitrophenoxy]-4-chloro-1-methy-5-(trifluromethyl)-<br>MP:<br>nD: 1.5198 | 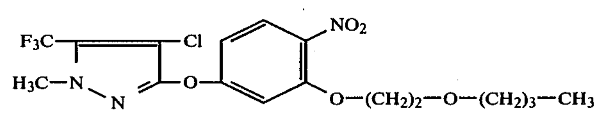 |
| 874 | 1,2-propanediol, 3-[5-[[4-chloro-1-methyl-5-(triflouromethyl)-1H-pyrazol-3-yl]oxy]-2-nitrophenoxy]-<br>MP: 75.0<br>nD: | 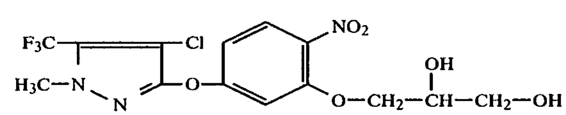 |

| Ex CP # | Name | Structure |
|---|---|---|
| 875 | ethanedioic acid, 2-[2-[[[5-[[4-chloro-1-methyl-5-(trifluoromethyl)-1H-pyrazol-3-yl]oxy]-2-nitrophenoxy]acetyl]oxy]ethoxy]ethyl ester MP: nD: 1.5164 | 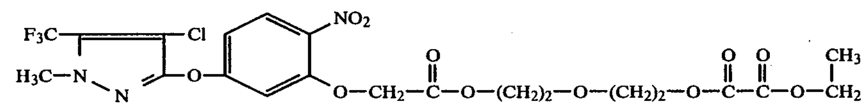 |
| 876 | propanedioic acid, 2-[2-[[[5-[[4-chloro-1-methyl-5-(trifluoromethyl)-1H-pyrazol-3-yl]oxy]-2-nitrophenoxy]acetyl]oxy]ethoxy]ethyl ester MP: nD: 1.5124 | 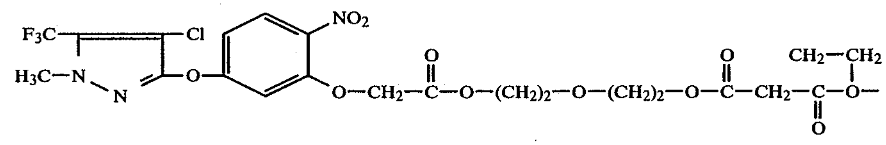 |
| 877 | ethanimidamide, 2-[5-[[4-chloro-1-methyl-5-(trifluoromethyl)-1H-pyrazol-3-yl]oxy]-2-nitrophenoxy]-n'-hydroxy- MP: 185.0 nD: | 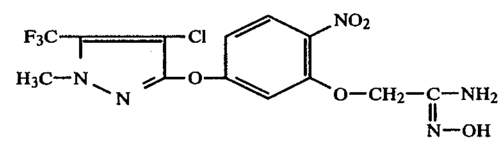 |
| 878 | acetic acid, [5-[[4-chloro-1-methyl-5-(trifluoromethyl)-1H-pyrazol-3-yl]oxy]-2-nitrophenoxy]-, (2,2-dimethyl-1,3-dioxolan-4-yl)methyl ester MP: 105.0 nD: | 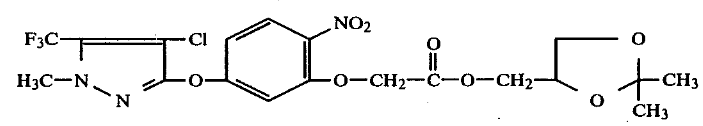 |
| 879 | benzoic acid, 5-[[4-chloro-1-methyl-5-(trifluoromethyl)-1H-pyrazol-3-yl]oxy]-2-nitro-, (2,2-dimethyl-1,3-dioxolan-4-yl)methyl ester MP: nD: 1.5174 | 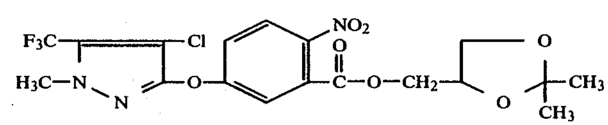 |
| 880 | 1,3-cyclohexanedione, 2-[5-[[4-chloro-1-methyl-5-(trifluoromethyl)-1H-pyrazol-3-yl]oxy]-2-nitrobenzoyl]- MP: 117.0–118.0 nD: | 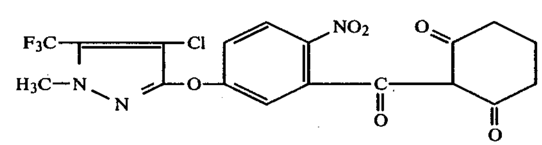 |

-continued

| Ex CP # | Name | Structure |
|---|---|---|
| 881 | benzoic acid, 5-[[4-chloro-1-methyl-5-(trifluoromethyl)-1H-pyrazol-3-yl]oxy]-2-nitro-, 3-oxo-1-cyclohexen-1-yl ester<br>MP: 94.0<br>nD: | 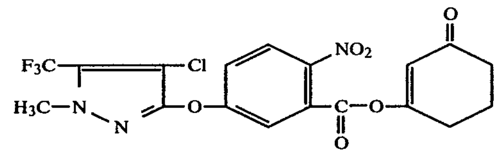 |
| 882 | acetic acid, [5-[[4-chloro-1-methyl-5-(trifluoromethyl)-1H-pyrazol-3-yl]oxy]-2-nitrophenoxy]-, propyl ester<br>MP:<br>nD: 1.5245 | 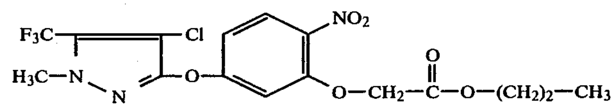 |
| 883 | benzoic acid, 5-[[4-chloro-1-methyl-5-(trifluoromethyl)-1H-pyrazol-3-yl]oxy]-2-nitro-, 4,5-dihydro-2,5-dimethyl-4-oxo-3-furanyl ester<br>MP:<br>nD: 1.5302 | 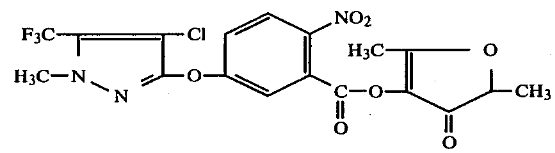 |
| 884 | acetic acid, [5-[[4-chloro-1-methyl-5-(trifluoromethyl)-1H-pyrazol-3-yl]oxy]-2-nitrophenoxy]-, 4,5-dihydro-2,5-dimethyl-4-oxo-3-furanyl ester<br>MP: 112.0<br>nD: | 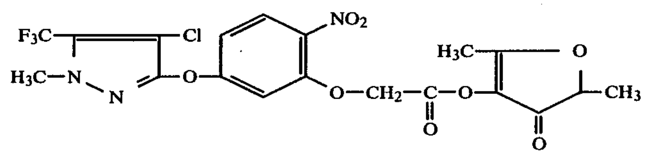 |
| 885 | 3(2H)-furanone, 4-[5-[[4-chloro-1-methyl-5-(trifluoromethyl)-1H-pyrazol-3-yl]oxy]-2-nitrophenoxy]-2,5-dimethyl-<br>MP: 130.0–131.0<br>nD: | 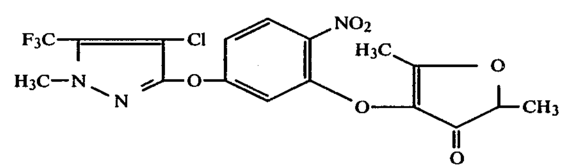 |

-continued

| Ex CP # | Name | Structure |
|---|---|---|
| 886 | benzenepropanoic acid, 5-[[4-chloro-1-methyl-5-(trifluoromethyl)-1H-pyrazol-3-yl]oxy]-2-nitro-beta-oxo-, 1,1-dimethylethyl ester MP: 108.0 nD: | 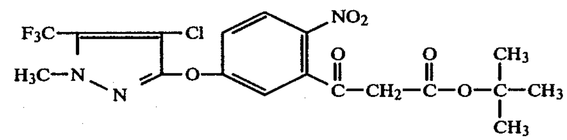 |
| 887 | benzeneacetic acid, 5-[[4-chloro-1-methyl-5-(trifluoromethyl)-1H-pyrazol-3-yl]oxy]-2-nitro-apha-oxo- MP: 146.0 nD: | 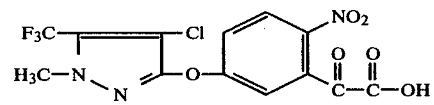 |
| 888 | benzenacarbothioamide, 5-[[4-chloro-1-methyl-5-(trifluoromethyl)-1H-pyrazol-3-yl]oxy]-2-nitro- MP: 128.0 nD: | 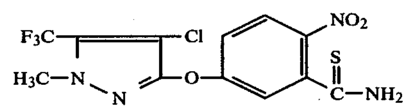 |
| 889 | benzeneacetic acid, 5-[[4-chloro-1-methyl-5-(trifluoromethyl)-1H-pyrazol-3-yl]oxy]-2-nitro-aplha-oxo-,ethyl ester MP: 72.0 nD: | 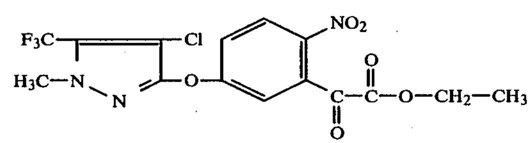 |
| 890 | benzoic acid, 5-[[4-chloro-1-methyl-5-(trifluoromethyl)-1H-pyrazol-3-yl]oxy]-2-nitro-, 1-(5,6-dihydro-1,4,2-dioxazin-3-yl)ethyl ester MP: nD: 1.5264 | 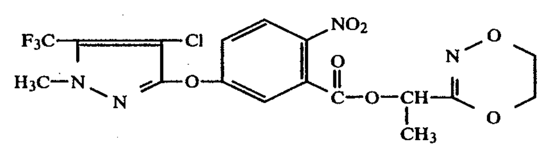 |
| 891 | acetic acid, [5-[[4-chloro-1-methyl-5-(trifluoromethyl)-1H-pyrazol-3-yl]oxy]-2-nitrophenoxy]-, 1-(5,6-dihydro-1,4,2-dimoazin-3-yl)ethyl ester MP: nD: 1.5221 | 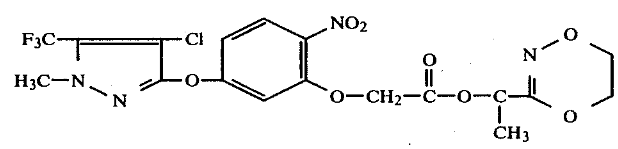 |

| Ex CP # | Name | Structure |
|---|---|---|
| 892 | 1H-pyrazole, 4-chloro-3-[3-(ethoxymethoxy)-4-nitrophenoxy]-1-methyl-5-(trifluoromethyl)- MP: nD: 1.5255 | 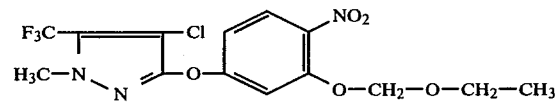 |
| 893 | acetamide, 2-[5-[[4-chloro-1-methyl-5-(trifluoromethyl)-1H-pyrazol-3-yl]oxy]-2-nitrophenoxy]- MP: 138.0 nD: | 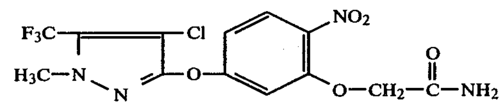 |
| 894 | benzoic acid, 5-[[4-chloro-1-methyl-5-(trifluoromethyl)-1H-pyrazol-3-yl]oxy]-2-nitro-, 2,3-dihydroxypropyl ester MP: nD: 1.5313 | 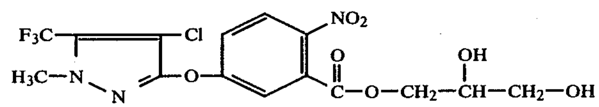 |
| 895 | benzoic acid, 5-[[4-chloro-1-methyl-5-(trifluoromethyl)-1H-pyrazol-3-yl]oxy]-2-nitro-, cyanomethyl ester MP: 111.0 nD: | 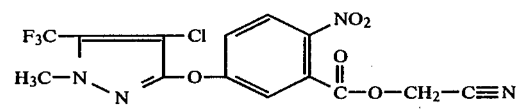 |
| 896 | carbonodithioic acid, S-[[5-[[4-chloro-1-methyl-5-(trifluoromethyl)-1H-pyrazol-3-yl]oxy]-2-nitrophenyl]methyl] O-ethyl ester MP: 66.0–67.5 nD: | 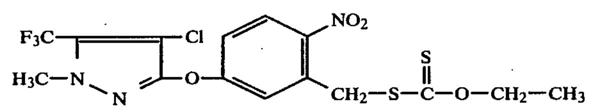 |
| 897 | 1H-pyrazole, 4-chloro-1-methyl-3-[4-nitro-3-(1H-imidazol-1-ylmethyl)phenoxy]-5-(trifluoromethyl)- MP: 85.0–87.0 nD: | 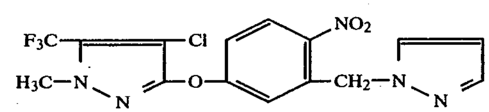 |
| 898 | benzenepropanoic acid, alpha-chloro-5-[[4-chloro-1-methyl-5-(trifluoromethyl)-1H-pyrazol-3-yl]oxy]-2-nitro-, methyl ester MP: nD: 1.5365 | 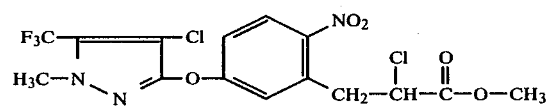 |

-continued

| Ex CP # | Name | Structure |
|---|---|---|
| 899 | 1H-pyrazole, 3,3'-[dithiobis[(methlene-4-nitro-3,1-phenylene)oxy]]bis[4-chloro-1-methyl-5-(trifluoromethyl)]-<br>MP: 115.0–116.0<br>nD: | 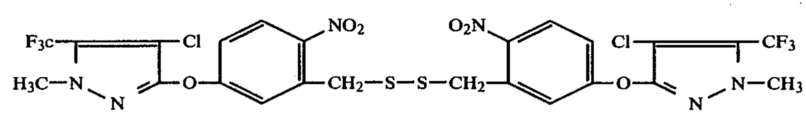 |
| 900 | benzenepropanoic acid, alpha-chloro-5-[[4-chloro-1-methyl-5-(trifluoromethyl)-1H-pyrazol-3-yl]oxy]-2-nitro-<br>MP: 104.0–106.0<br>nD: | 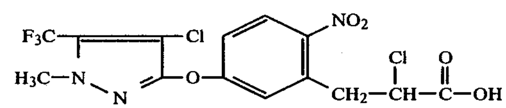 |
| 901 | benzenepropanoic acid, alpha-chloro-5-[[4-chloro-1-methyl-5-(trifluoromethyl)-1H-pyrazol-3-yl]oxy]-2-nitro-, 3-methoxy-3-oxopropyl ester<br>MP:<br>nD: 1.5267 | 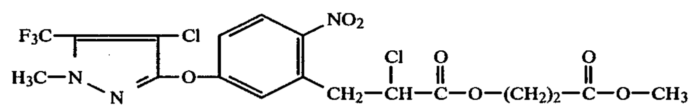 |
| 902 | acetamide, N-[5-[[4-chloro-1-methyl-5-(trifluromethyl)-1H-pyrazol-3-yl]oxy]-2-nitrophenyl]-N-methyl-<br>MP: 124.0–125.0<br>nD: | 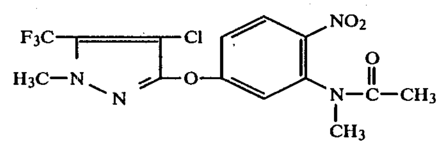 |
| 903 | propanoic acid, 2-[[[5-[[4-chloro-1-methyl-5-(trifluoromethyl)-1H-pyrasol-3-yl]oxy]-2-nitrobenzoyl]amino]oxy]-, methyl ester<br>MP:<br>nD: 1.5141 | 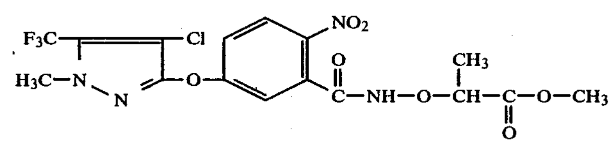 |
| 904 | 1H-pyrazole, 3-[3-(1-butenyl)-4-nitrophenoxy]-4-chloro-1-methyl-5-(trifluoromethyl)-<br>MP:<br>nD: 1.5440 | 70% Z ISOMER, 30% E ISOMER |

-continued

| Ex CP # | Name | Structure |
|---|---|---|
| 905 | propanoic acid, 2-[[[[5-[[4-chloro-1-methyl-5-(trifluormethyl)-1H-pyrasol-3-yl]oxy]-2-nitrophenyl]methylene]amino]oxy]-<br>MP: 121.0-122.0<br>nD: | ![structure: F3C-pyrazole-N(CH3)-O-phenyl(Cl)(NO2)-CH=N-O-CH(CH3)-C(=O)-OH] |

ELEMENTAL ANALYSIS OF CERTAIN EXAMPLES

| Example | Calculated (found) |
|---|---|
| 46 | C, 42.88(42.71); H, 2.81(2.83); N, 10.64(10.67) |
| 71 | C, 42.06(42.82); H, 2.98(3.08); N, 13.85(14.27) |
| 91 | C, 47.19(47.14); H, 3.54(3.65); N, 12.82(12.69) |
| 167 | C, 45.72(45.78); H, 3.86(3.84); N, 9.97(10.01) |
| 196 | C, 44.33(44.29); H, 3.52(3.47); N, 13.73(13.77) |
| 197 | C, 48.94(48.99); H, 3.87(3.87); N, 13.40(13.44) |
| 234 | C, 43.66(43.64); H, 3.40(3.38); N, 11.75(11.75) |
| 244 | C, 45.50(45.42); H, 4.10(4.10); N, 12.19(12.22) |
| 267 | C, 43.89(43.93); H, 3.53(3.47); N, 12.02(12.05) |
| 271 | C, 42.75(42.71); H, 2.84(2.82); N, 10.64(10.67) |
| 272 | C, 44.33(44.50); H, 4.18(4.20); N, 9.70(9.73) |
| 294 | C, 47.36(47.48); H, 4.00(3.98); N, 13.79(13.84) |
| 323 | C, 35.69(35.63); H, 1.55(1.74); N, 10.41(10.39) |
| 327 | C, 45.09(45.15); H, 3.81(3.79); N, 11.67(11.70) |
| 522 | C, 39.26(39.36); H, 3.54(3.52); N, 9.13(9.18) |
| 554 | C, 40.73(40.81); H, 2.31(2.28); N, 11.87(11.90) |
| 568 | C, 41.28(41.25); H, 2.82(2.77); N, 12.83(12.83) |
| 595 | C, 46.73(46.71); H, 4.09(3.92); N, 11.84(12.10) |
| 596 | C, 46.29(46.51); H, 4.31(4.33); N, 11.95(12.05) |
| 637 | C, 45.16(45.23); H, 2.94(2.92); N, 12.14(12.17) |
| 641 | C, 44.33(44.40); H, 3.77(3.90); N, 15.89(15.93) |
| 644 | C, 38.44(38.35); H, 3.22(3.22); N, 13.77(13.76) |
| 694 | C, 44.11(44.18); H, 4.33(4.20); N, 16.52(17.17) |
| 700 | C, 42.54(42.60); H, 4.30(4.29); N, 13.23(13.25) |
| 722 | C, 44.59(44.52); H, 2.92(2.94); N, 11.09(11.13) |
| 822 | C, 39.24(39.25); H, 2.83(2.79); N, 10.54(10.56) |

PRE-EMERGENT ACTIVITY ON WEEDS

One set of pre-emergent tests was conducted as follows:

Topsoil was placed in a pan and compacted to a depth of 0.95 to 1.27 cm. from the top of the pan. A predetermined number of seeds of each of several monocotyledonous and dicotyledonous annual plant species and/or vegetative propagules of various perennial plant species were placed on top of the soil. The soil required to level fill a pan after seeding or adding vegetative propagules was weighed into another pan. A known amount of the test compound dissolved or suspended in an organic solvent or water and applied in acetone or water as a carrier was thoroughly mixed with this cover soil, and the herbicide/soil mixture was used as a cover layer for the previously prepared pan. In Table A below the amount of active ingredient was equivalent to an application rate of 11.2 kg/ha. After treatment, the pans were moved to a greenhouse bench where they were watered as needed to give adequate moisture for germination and growth.

Approximately 10–14 days (usually 14 days) after planting and treating, the pans were observed and the results recorded. In some instances, a second observation was made approximately 24–28 days after seeding and treating, and these observations are indicated in the following tables by a "pound" sign (#) immediately following the Example number.

The plant species usually regarded as weeds which were utilized in one set of pre-emergent activity tests, the data for which are shown in Table A, are identified by letter headings printed diagonally above the columns according to the following legend:

CATH—Canada thistle*
RHQG—Quackgrass*
COBU—Cocklebur
  RHJG—Rhizome Johnsongrass*
VELE—Velvetleaf
DOBR—Downy Brome
MOGL—Morningglory
BYGR—Barnyardgrass
COLQ—Common Lambsquarters
ANBG—Annual Bluegrass
PESW—Pennsylvania Smartweed
SEJG—Seedling Johnsongrass
YENS—Yellow Nutsedge*
INMU—Indian Mustard
WIBW—Wild Buckwheat
*Grown from vegetative propagules In Table A, the first column is the application rate of the compound being tested in kg/ha.

PRE-EMERGENT HERBICIDE EXAMPLES

As noted above, compounds of this invention have been found to be effective as herbicides, particularly pre-emergent herbicides. Table A summarize results of tests conducted to determine the pre-emergent herbicidal activity of the compounds of this invention. The herbicidal ratings used in Table A was assigned according to a scale based on the percent inhibition of each plant species. The herbicide rating symbols in Table A is defined as follows:

| % Inhibition | Rating |
|---|---|
| 0–24 | 0 |
| 25–49 | 1 |
| 50–74 | 2 |
| 75–100 | 3 |
| Not planted | — or a blank |
| Species planted, (no data) | N |

Footnotes are shown at the end of the table.

For some compounds of this invention data were originally recorded as percent inhibition (or control) in ten percent increments. In most cases, where this system was used, the percentages have been mathematically converted to the above equivalent system using the correlation table above.

TABLE A

| Ex. No. | Rate kg/ha | Yens | Anbg | Sejg | Dobr | Bygr | Mogl | Colq | Vele | Inmu | Wibw | Cath | Colq | Pesw | Rhqg | Rhjg |
|---|---|---|---|---|---|---|---|---|---|---|---|---|---|---|---|---|
| \multicolumn{17}{l}{Herbicide Primary Pre, spectrums 25 and 90} |
| 1 | 11.2100 | 2 | | | — | 3 | 3 | 3 | 3 | | | 2 | 3 | 3 | 3 | 0 |
| 2 | 11.2100 | 0 | | | 3 | 3 | 3 | 2 | 3 | | | 2 | 3 | 3 | 3 | 0 |
| 3 | 11.2100 | 3 | | | 3 | 3 | 3 | 3 | 3 | | | 3 | 3 | 3 | 1 | 0 |
| 4 | 11.2100 | 3 | | | 0 | 3 | 1 | 2 | 3 | | | 0 | 3 | 3 | 3 | 2 |
| 5 | 11.2100 | 3 | | | 3 | 3 | 3 | 3 | 3 | | | 0 | 3 | 3 | 3 | 3 |
| 6 | 11.2100 | 3 | | | 0 | 3 | 3 | 3 | 3 | | | 2 | 3 | 3 | 1 | 0 |
| 7 | 11.2100 | 3 | | | 3 | 3 | 3 | 3 | 3 | | | 3 | 3 | 3 | 3 | 3 |
| 8 | 11.2100 | 3 | | | 2 | 3 | 3 | 3 | 3 | | | 3 | 3 | 3 | 0 | 2 |
| 9 | 11.2100 | 0 | | | 3 | 3 | 3 | 0 | 3 | | | 0 | 3 | 3 | 1 | 0 |
| 10 | 11.2100 | 2 | | | 3 | 3 | 3 | 3 | 3 | | | 3 | 3 | 3 | 3 | 0 |
| 11 | 11.2100 | 3 | | | 3 | 3 | 3 | 3 | 3 | | | 3 | 3 | 3 | 3 | 2 |
| 12 | 11.2100 | 3 | | | 3 | 3 | 3 | 3 | 3 | | | 1 | 3 | 3 | 3 | 1 |
| 13 | 11.2100 | 3 | 3 | 3 | 3 | 3 | 3 | 2 | 3 | 3 | 3 | | | | | |
| 15 | 11.2100 | 2 | | | 3 | 3 | 3 | 3 | 3 | | | 0 | 3 | 3 | 3 | 1 |
| 16 | 11.2100 | 2 | | | 3 | 3 | 3 | 3 | 3 | | | 3 | 3 | 3 | 3 | 2 |
| 60 | 11.2100 | 2 | | | 0 | 3 | 3 | 3 | 3 | | | 0 | 3 | 3 | 2 | 0 |
| 61 | 11.2100 | 0 | | | 0 | 3 | 0 | 0 | 0 | | | 0 | 3 | 3 | 0 | 0 |
| 63 | 11.2100 | 1 | | | 0 | 2 | 2 | 2 | 3 | | | 3 | 3 | N | 0 | 0 |
| 64 | 11.2100 | 3 | | | — | 3 | 3 | 3 | 3 | | | 0 | 3 | 3 | 2 | 0 |
| 65 | 11.2100 | 0 | | | 1 | 3 | 3 | 3 | 2 | | | 2 | 3 | 3 | 0 | 0 |
| 66 | 11.2100 | 2 | | | 1 | 3 | 3 | 1 | 3 | | | 2 | 3 | 3 | 0 | 0 |
| 67 | 11.2100 | 3 | | | — | 3 | 3 | 3 | 3 | | | 1 | 3 | 3 | 2 | 0 |
| 68 | 11.2100 | 0 | | | 0 | 0 | 0 | 0 | 2 | | | 1 | 3 | 3 | 0 | 0 |
| 69 | 11.2100 | 3 | | | 0 | 3 | 3 | 3 | 3 | | | 1 | 3 | N | 2 | 0 |
| 70 | 11.2100 | 1 | | | 0 | 3 | 0 | 0 | 3 | | | 0 | 3 | 3 | 0 | 0 |
|  | 11.2100 | 2 | | | 0 | 3 | 0 | 0 | 3 | | | 2 | 3 | 3 | 0 | 0 |

TABLE A-continued

Herbicide Primary Pre, spectrums 25 and 90

| Ex. No. | Rate kg/ha | Yens | Anbg | Sejg | Dobr | Bygr | Mogl | Cobu | Vele | Inmu | Wibw | Catch | Colq | Pesw | Rhqg | Rhjg |
|---|---|---|---|---|---|---|---|---|---|---|---|---|---|---|---|---|
| 71 | 11.2100 | 3 | | | 3 | 3 | 1 | 3 | 3 | | | 3 | 3 | 3 | 2 | — |
| 72 | 11.2100 | 2 | | | 1 | 3 | 1 | 2 | 3 | | | 1 | 3 | 3 | 3 | 1 |
| 73 | 11.2100 | 1 | | | 0 | 1 | 0 | 0 | 3 | | | 0 | 3 | 3 | 1 | 0 |
| 74 | 11.2100 | 0 | | | 1 | 3 | 0 | 0 | 3 | | | 1 | 3 | 3 | 0 | 0 |
| 75 | 11.2100 | 2 | | | 0 | 3 | 1 | 2 | 3 | | | 1 | 3 | N | 3 | 0 |
| 76 | 11.2100 | 2 | | | 0 | 3 | 1 | 3 | 3 | | | 1 | 3 | N | 1 | 0 |
| 77 | 11.2100 | 2 | | | 3 | 3 | 2 | 1 | 3 | | | 3 | 3 | 3 | 2 | 0 |
| 78 | 11.2100 | 1 | | | 0 | 3 | 3 | 3 | 3 | | | 1 | 3 | N | 1 | 1 |
| 79 | 11.2100 | 2 | | | 3 | 3 | 3 | 3 | 3 | | | 1 | 3 | 3 | 1 | — |
| 80 | 11.2100 | 0 | | | 3 | 3 | 3 | 3 | 3 | | | 2 | 3 | N | 0 | 0 |
| 81 | 11.2100 | 1 | | | 0 | 3 | 3 | 3 | 3 | | | 2 | 3 | N | 1 | 0 |
| 82 | 11.2100 | 1 | | | — | 3 | 3 | 3 | 2 | | | 2 | 3 | 1 | 0 | 0 |
| 83 | 11.2100 | 2 | | | 2 | 3 | 2 | 3 | 3 | | | 1 | 3 | N | 1 | 0 |
| 84 | 11.2100 | 0 | | | 0 | 3 | 0 | 1 | 0 | | | 0 | 3 | 0 | 0 | 3 |
| 85 | 11.2100 | 1 | | | 1 | 3 | 2 | 3 | 2 | | | 0 | 3 | 3 | 1 | 0 |
| 86 | 11.2100 | 3 | | | 0 | 3 | 3 | 3 | 3 | | | 3 | 3 | 3 | 0 | 0 |
| 87 | 11.2100 | 2 | | | 3 | 3 | 3 | 0 | 3 | | | 0 | 3 | 3 | 2 | 2 |
| 88 | 11.2100 | 3 | | | 3 | 3 | 3 | 3 | 3 | | | 3 | 3 | 3 | 3 | — |
| 89 | 11.2100 | 0 | | | 3 | 3 | 1 | 0 | 3 | | | 1 | 3 | 3 | 2 | — |
| 90 | 11.2100 | 1 | | | 3 | 3 | 3 | 3 | 3 | | | 2 | 3 | 3 | 3 | 0 |
| 91 | 11.2100 | 2 | | | 3 | 3 | 3 | 2 | 3 | | | 0 | 3 | 3 | 3 | 0 |
|  | 11.2100 | 0 | | | 3 | 3 | 3 | 2 | 3 | | | 2 | 3 | 3 | 3 | 0 |
| 92 | 11.2100 | 3 | | | — | 3 | 3 | 3 | 3 | | | 3 | 3 | 3 | 3 | 3 |
| 93 | 11.2100 | 2 | | | 3 | 3 | 3 | 1 | 3 | | | 0 | 3 | 3 | 3 | 0 |
| 94 | 11.2100 | 2 | 3 | 3 | 3 | 3 | 3 | 0 | 3 | 3 | 3 | | | | | |
|  | 11.2100 | 1 | 3 | 3 | 3 | 3 | 2 | 0 | 2 | 3 | 3 | | | | | |
|  | 11.2100 | 0 | | | 3 | 3 | 2 | 1 | 2 | | | 0 | 3 | 3 | 3 | 0 |
|  | 11.2100 | 1 | 3 | 3 | 3 | 3 | 1 | 0 | 3 | 3 | 3 | | | | | |
|  | 11.2100 | 0 | 3 | 3 | 3 | 3 | 3 | 0 | 3 | 2 | 3 | | | | | |
|  | 11.2100 | 1 | 3 | 3 | 3 | 3 | 3 | 0 | 3 | 3 | 3 | | | | | |
|  | 11.2100 | 0 | 3 | 3 | 3 | 3 | 3 | 1 | 3 | 3 | 3 | | | | | |
|  | 11.2100 | 2 | 3 | 3 | 3 | 3 | 2 | 1 | 3 | 3 | 3 | | | | | |
|  | 11.2100 | 1 | 3 | 3 | 3 | 3 | 1 | 0 | 3 | 3 | 3 | | | | | |
|  | 11.2100 | 1 | 3 | 3 | 3 | 3 | 0 | 0 | 3 | 3 | 3 | | | | | |
|  | 11.2100 | 2 | 3 | 3 | 3 | 3 | 2 | 2 | 3 | 3 | 3 | | | | | |
|  | 11.2100 | 1 | 3 | 3 | 3 | 3 | 2 | 2 | 3 | 3 | 3 | | | | | |
|  | 11.2100 | 1 | 3 | 3 | 3 | 3 | 2 | 0 | 3 | 2 | 3 | | | | | |
|  | 11.2100 | 0 | 3 | 3 | 3 | 3 | 2 | 0 | 3 | 3 | 3 | | | | | |
|  | 11.2100 | 2 | 3 | 3 | 3 | 3 | 3 | 3 | 3 | 3 | 3 | | | | | |
|  | 11.2100 | 1 | 3 | 3 | 3 | 3 | 1 | 0 | 3 | 2 | 3 | | | | | |
| 95 | 11.2100 | 1 | | | 3 | 3 | 3 | 3 | 3 | | | 0 | 3 | 3 | 3 | 1 |
| 96 | 11.2100 | 1 | | | 3 | 3 | 3 | 3 | 3 | | | 1 | 3 | 3 | 3 | 0 |
| 97 | 11.2100 | 0 | | | 3 | 3 | 2 | 1 | 2 | | | 0 | 3 | 3 | 2 | 0 |
| 98 | 11.2100 | 0 | | | 0 | 0 | 0 | 0 | 0 | | | 0 | 3 | 3 | 0 | N |
| 99 | 11.2100 | 2 | | | 3 | 3 | 3 | 1 | 3 | | | 0 | 3 | 3 | 3 | 0 |
| 100 | 11.2100 | 2 | | | 3 | 3 | 3 | 0 | 3 | | | 0 | 3 | 3 | 3 | 1 |
| 101 | 11.2100 | 2 | | | 3 | 3 | 3 | 3 | 3 | | | 0 | 3 | 3 | 2 | 0 |
| 102 | 11.2100 | 2 | | | 0 | 3 | 3 | 1 | 3 | | | 0 | 3 | 3 | 3 | 0 |
| 103 | 11.2100 | 1 | | | 3 | 3 | 1 | 0 | 3 | | | 0 | 3 | 3 | 2 | 0 |
| 104 | 11.2100 | 1 | | | 3 | 3 | 3 | 3 | 3 | | | 3 | 3 | 3 | 3 | 1 |
| 105 | 11.2100 | 1 | | | 3 | 3 | 3 | 3 | 3 | | | 2 | 3 | 3 | 3 | 0 |
| 106 | 11.2100 | 2 | | | 3 | 3 | 3 | 3 | 3 | | | 3 | 3 | 3 | 3 | — |
| 107 | 11.2100 | 0 | | | 3 | 3 | 1 | 0 | 3 | | | 0 | 3 | 3 | 0 | — |
| 108 | 11.2100 | 3 | | | 3 | 3 | 3 | 2 | 3 | | | 0 | 3 | 3 | 3 | 0 |
| 109 | 11.2100 | 1 | | | 3 | 3 | 3 | 3 | 3 | | | 3 | 3 | 3 | 3 | — |
| 110 | 11.2100 | 0 | | | 3 | 3 | 3 | 1 | 3 | | | 0 | 3 | 3 | 3 | 0 |
| 111 | 11.2100 | 1 | | | 3 | 3 | 3 | 3 | 3 | | | 0 | 3 | 3 | 2 | N |
| 112 | 11.2100 | 3 | | | 3 | 3 | 3 | 3 | 3 | | | 0 | 3 | 3 | 3 | 0 |
| 113 | 11.2100 | 0 | | | 2 | 3 | 2 | 3 | 3 | | | 0 | 3 | 3 | 2 | 3 |
| 114 | 11.2100 | 3 | | | 3 | 3 | 3 | 3 | 3 | | | 3 | 3 | 3 | 0 | 0 |
| 115 | 11.2100 | 0 | | | 0 | 3 | 3 | 3 | 3 | | | 0 | 3 | 3 | 0 | 0 |
| 116 | 11.2100 | 0 | | | 0 | 3 | 3 | 3 | 3 | | | 0 | 3 | 3 | 0 | 0 |
| 117 | 11.2100 | 1 | | | 0 | 3 | 3 | 3 | 3 | | | 2 | 3 | 3 | 0 | 0 |
| 118 | 11.2100 | 1 | | | 0 | 3 | 3 | 3 | 3 | | | 0 | 3 | 3 | 0 | 0 |
| 119 | 11.2100 | 1 | | | 0 | 3 | 3 | 3 | 3 | | | 3 | 3 | 3 | 0 | 0 |
| 120 | 11.2100 | 0 | | | 0 | 3 | 3 | 3 | 3 | | | 0 | 3 | 3 | 0 | 0 |
| 121 | 11.2100 | 0 | | | 2 | 2 | 3 | 3 | 3 | | | 3 | 3 | N | 0 | 0 |
| 122 | 11.2100 | 2 | | | 0 | 3 | 3 | 3 | 3 | | | 0 | 3 | 3 | 0 | 0 |
| 123 | 11.2100 | 3 | | | 1 | 3 | 3 | 3 | 3 | | | 3 | 3 | 3 | 0 | 0 |
| 124 | 11.2100 | 1 | | | 2 | 3 | 3 | 3 | 3 | | | 3 | 3 | 3 | 0 | 0 |
| 125 | 11.2100 | 3 | | | 0 | 3 | 3 | 3 | 1 | | | 0 | 3 | 2 | 0 | 0 |
| 126 | 11.2100 | 0 | | | 0 | 0 | 3 | 2 | 3 | | | 0 | 3 | 0 | 0 | — |
| 127 | 11.2100 | 3 | | | 0 | 3 | 3 | 3 | 3 | | | 2 | 3 | 2 | 0 | 0 |
| 128 | 11.2100 | 3 | | | 1 | 3 | 3 | 3 | 3 | | | 3 | 3 | N | 0 | 0 |
| 129 | 11.2100 | 2 | | | 0 | 3 | 3 | 3 | 3 | | | 2 | 3 | N | 0 | 0 |
| 130 | 11.2100 | 2 | | | 3 | 3 | 3 | 3 | 3 | | | 3 | 3 | 3 | 0 | 0 |
| 131 | 11.2100 | 2 | | | 1 | 3 | 3 | 3 | 3 | | | 3 | 3 | 3 | 0 | 3 |

TABLE A-continued

| | | Herbicide Primary Pre, spectrums 25 and 90 | | | | | | | | | | | | | | |
|---|---|---|---|---|---|---|---|---|---|---|---|---|---|---|---|---|
| Ex. No. | Rate kg/ha | Yens | Anbg | Sejg | Dobr | Bygr | Mogl | Cobu | Vble | Inmu | Wibw | Cath | Colq | Pesw | Rhqg | Rhjg |
| 132 | 11.2100 | 3 | | | 1 | 3 | 3 | 1 | 3 | | | 0 | 3 | 3 | 0 | 0 |
| 133 | 11.2100 | 3 | | | 0 | 3 | 3 | 3 | 3 | | | 1 | 3 | 3 | 1 | 0 |
| 134 | 11.2100 | 3 | | | 0 | 3 | 3 | 3 | 3 | | | 3 | 3 | 3 | 0 | 0 |
| 135 | 11.2100 | 3 | | | 0 | 3 | 3 | 3 | 3 | | | 2 | 3 | N | 0 | 0 |
| 136 | 11.2100 | 2 | | | 0 | 2 | 3 | 3 | 3 | | | 3 | 3 | N | 0 | 0 |
| 137 | 11.2100 | 3 | | | 1 | 3 | 3 | 3 | 3 | | | 1 | 3 | N | 0 | 1 |
| 138 | 11.2100 | 3 | | | 2 | 3 | 3 | 3 | 3 | | | 3 | 3 | 3 | 1 | 0 |
| 139 | 11.2100 | 0 | | | 0 | 2 | 1 | 1 | 0 | | | 1 | 3 | N | 0 | 0 |
| 140 | 11.2100 | 3 | | | 0 | 3 | 3 | 3 | 3 | | | 3 | 3 | N | 2 | 2 |
| 141 | 11.2100 | 2 | | | 0 | 3 | 3 | 3 | 3 | | | 2 | 3 | 3 | 0 | 0 |
| 142 | 11.2100 | 2 | | | 0 | 1 | 3 | 3 | 3 | | | 2 | 3 | 2 | 0 | 0 |
| 143 | 11.2100 | 1 | | | 0 | 3 | 3 | 3 | 3 | | | 2 | 3 | 3 | 0 | 0 |
| 144 | 11.2100 | 2 | | | 2 | 3 | 3 | 3 | 3 | | | 3 | 3 | 3 | 0 | 0 |
| 145 | 11.2100 | 3 | | | 1 | 3 | 3 | 3 | 3 | | | 3 | 3 | 3 | 1 | 1 |
| 146 | 11.2100 | 2 | | | 3 | 3 | 3 | 3 | 3 | | | 0 | 3 | 3 | 3 | 1 |
| 147 | 11.2100 | 0 | | | 0 | 3 | 0 | 0 | 1 | | | 0 | 3 | 3 | 0 | 0 |
| 148 | 11.2100 | 3 | | | 1 | 3 | 3 | 3 | 3 | | | 0 | 3 | 3 | 3 | 0 |
| 149 | 11.2100 | 3 | | | 3 | 3 | 3 | 2 | 3 | | | 0 | 3 | 3 | 2 | 0 |
| 150 | 11.2100 | 3 | | | 0 | 3 | 3 | 3 | 3 | | | 3 | 3 | 3 | 1 | 3 |
| 151 | 11.2100 | 3 | | | 2 | 3 | 3 | 3 | 3 | | | 3 | 3 | 3 | 3 | 0 |
| 152 | 11.2100 | 2 | | | 3 | 3 | 3 | 3 | 3 | | | 3 | 3 | 3 | 3 | 0 |
| 153 | 11.2100 | 0 | | | 1 | 3 | 2 | 2 | 3 | | | 0 | 3 | 3 | 1 | 0 |
| 154 | 11.2100 | 0 | | | 3 | 3 | 3 | 2 | 3 | | | 0 | 3 | 3 | 3 | 1 |
| 155 | 11.2100 | 3 | | | 3 | 3 | 3 | 3 | 3 | | | 3 | 3 | 3 | 3 | 2 |
| 156 | 11.2100 | 0 | | | 1 | 3 | 3 | 2 | 3 | | | 1 | 3 | N | 3 | 0 |
| 157 | 11.2100 | 1 | | | 3 | 3 | 3 | 0 | 3 | | | 0 | 3 | 3 | 3 | 0 |
| 158 | 11.2100 | 3 | | | 0 | 3 | 3 | 3 | 3 | | | 2 | 3 | 3 | 0 | 0 |
| 159 | 11.2100 | 1 | | | 1 | 3 | 3 | 0 | 3 | | | 0 | 3 | 3 | 0 | 0 |
| 160 | 11.2100 | 3 | | | 3 | 3 | 3 | 3 | 3 | | | 0 | 3 | 3 | 3 | 0 |
| 161 | 11.2100 | 3 | | | 3 | 3 | 3 | 3 | 3 | | | 3 | 3 | 3 | 3 | 2 |
| 162 | 11.2100 | 2 | | | 3 | 3 | 3 | 3 | 3 | | | 0 | 3 | 3 | 2 | — |
| 163 | 11.2100 | 0 | | | 3 | 3 | 3 | 2 | 3 | | | 1 | 3 | 3 | 2 | 0 |
| 164 | 11.2100 | 3 | | | 3 | 3 | 3 | 3 | 3 | | | 2 | 3 | 3 | 1 | 0 |
| 165 | 11.2100 | 0 | | | 0 | 3 | 2 | 2 | 2 | | | 2 | 3 | 3 | 0 | 0 |
| 166 | 11.2100 | 1 | | | 1 | 3 | 3 | 3 | 3 | | | 3 | 3 | 3 | 1 | 1 |
| 167 | 11.2100 | 3 | | | 1 | 3 | 3 | 3 | 3 | | | 3 | 3 | 3 | 1 | 1 |
| 168 | 11.2100 | 0 | | | 0 | 1 | 3 | 2 | 3 | | | 1 | 3 | 2 | 0 | 0 |
| 169 | 11.2100 | 3 | | | 2 | 3 | 3 | 2 | 3 | | | — | 3 | 3 | 1 | N |
| 170 | 11.2100 | 0 | | | 0 | 3 | 3 | 3 | 3 | | | — | 3 | 0 | 0 | N |
| 171 | 11.2100 | 1 | | | 3 | 3 | 3 | 1 | 3 | | | — | 3 | 3 | 2 | N |
| 172 | 11.2100 | 0 | | | 0 | 3 | 0 | 0 | 1 | | | 0 | 3 | 3 | 0 | 1 |
| 173 | 11.2100 | 0 | | | 0 | 3 | 0 | 0 | 0 | | | 0 | 3 | 3 | 0 | 0 |
| 174 | 11.2100 | 0 | | | 0 | 3 | 1 | 0 | 1 | | | 0 | 3 | 3 | 0 | N |
| 175 | 11.2100 | 0 | | | 0 | 0 | 0 | 0 | N | | | 1 | N | 0 | 0 | 0 |
| 176 | 11.2100 | 1 | | | 0 | 3 | 3 | 2 | 3 | | | 2 | 3 | 3 | 0 | 0 |
| 177 | 11.2100 | 0 | | | 0 | 3 | 0 | 0 | 3 | | | 0 | 3 | 3 | 0 | N |
| 178 | 11.2100 | 0 | | | 2 | 3 | 3 | 1 | 3 | | | 0 | 3 | 3 | 2 | 0 |
| 179 | 11.2100 | 0 | | | 3 | 3 | 3 | 3 | 3 | | | 2 | 3 | 3 | 1 | N |
| 180 | 11.2100 | 0 | | | 3 | 3 | 3 | 3 | 3 | | | 0 | 3 | 3 | 3 | N |
| 181 | 11.2100 | 1 | | | 3 | 3 | 3 | 3 | 3 | | | 3 | 3 | 3 | 3 | 0 |
| 182 | 11.2100 | 0 | | | 1 | 3 | 2 | 2 | 3 | | | 1 | 3 | 3 | 1 | 0 |
| 183 | 11.2100 | 2 | | | 3 | 3 | 3 | 3 | 3 | | | 3 | 3 | 3 | 1 | 1 |
| 184 | 11.2100 | 0 | | | 2 | 3 | 2 | 1 | 2 | | | 0 | 3 | 3 | 1 | 0 |
| 185 | 11.2100 | 2 | | | 3 | 3 | 3 | 3 | 3 | | | 2 | 3 | 3 | 2 | 3 |
| 186 | 11.2100 | 1 | | | 3 | 3 | 3 | 3 | 3 | | | 0 | 3 | 3 | 1 | — |
| 187 | 11.2100 | 0 | | | 3 | 3 | 3 | 2 | 3 | | | 2 | 3 | N | 2 | 1 |
| 188 | 11.2100 | 0 | | | 3 | 3 | 3 | 0 | 3 | | | 0 | 3 | N | 3 | 0 |
| 189 | 11.2100 | 0 | | | 3 | 3 | 3 | 1 | 3 | | | 0 | 3 | N | 1 | 0 |
| 190 | 11.2100 | 1 | | | 3 | 3 | 3 | 3 | 3 | | | 1 | 3 | 3 | 3 | 3 |
| 191 | 11.2100 | 0 | | | 3 | 3 | 3 | 2 | 3 | | | 0 | 3 | N | 3 | 1 |
| 192 | 11.2100 | 0 | | | 3 | 3 | 3 | 3 | 3 | | | 3 | 3 | 3 | 2 | 0 |
| 193 | 11.2100 | 3 | | | 3 | 3 | 3 | 1 | 2 | | | 0 | 3 | 3 | 1 | — |
| 194 | 11.2100 | 3 | | | 3 | 3 | 3 | 3 | 3 | | | 0 | 3 | 3 | 2 | 0 |
| 195 | 11.2100 | 0 | | | 3 | 3 | 3 | 2 | 3 | | | 0 | 3 | 3 | 1 | 3 |
| 196 | 11.2100 | 0 | | | 3 | 3 | 3 | 2 | 3 | | | 0 | 3 | N | 3 | 0 |
| 197 | 11.2100 | 1 | | | 3 | 3 | 3 | 3 | 3 | | | 0 | 3 | 3 | 0 | 0 |
| 198 | 11.2100 | 0 | | | 3 | 3 | 3 | 1 | 3 | | | 3 | 3 | N | 2 | 0 |
| 199 | 11.2100 | 0 | | | 3 | 3 | 3 | 3 | 3 | | | 0 | 3 | N | 2 | 0 |
| 200 | 11.2100 | 0 | | | 1 | 3 | 0 | 0 | 1 | | | 1 | 3 | N | 0 | 0 |
| 201 | 11.2100 | 0 | | | 2 | 3 | 3 | 2 | 2 | | | 0 | 3 | 3 | 0 | 0 |
| 202 | 11.2100 | 0 | | | 2 | 3 | 1 | 0 | 3 | | | 0 | 3 | 3 | 1 | 0 |
| 203 | 11.2100 | 0 | | | 3 | 3 | 1 | 0 | 1 | | | 0 | 3 | N | 3 | 0 |
| 204 | 11.2100 | 0 | | | 0 | 3 | 3 | 0 | 1 | | | 0 | 3 | 3 | 0 | 0 |
| 205 | 11.2100 | 1 | | | 1 | 3 | 3 | 2 | 3 | | | 1 | 3 | 3 | 1 | — |
| 206 | 11.2100 | 2 | 3 | 1 | 3 | 3 | 3 | 2 | 3 | 3 | 3 | | | | | |
| 207 | 11.2100 | 0 | | | 0 | 0 | 0 | 0 | 0 | | | 1 | 0 | 0 | 0 | 0 |
| | 11.2100 | 1 | | | 0 | 0 | 0 | 0 | 0 | | | 0 | 3 | 0 | 0 | 3 |

TABLE A-continued

| | | Herbicide Primary Pre, spectrums 25 and 90 | | | | | | | | | | | | | |
|---|---|---|---|---|---|---|---|---|---|---|---|---|---|---|---|
| Ex. No. | Rate kg/ha | Yens | Abg | Sejg | Dobr | Bygr | Mogl | Cobue | Vele | Inmu | Wibw | Catqh | Colqw | Pesw | Rhqg | Rhjg |
| 208 | 11.2100 | 2 | | | 0 | 0 | 0 | 0 | 0 | | | 1 | 3 | 2 | 0 | 0 |
| 209 | 11.2100 | 2 | | | 0 | 3 | 0 | 0 | 0 | | | 1 | 3 | 0 | 0 | 0 |
| 210 | 11.2100 | 1 | | | 0 | 0 | 0 | 0 | 0 | | | 0 | 1 | 0 | 0 | 0 |
| 211 | 11.2100 | 1 | | | 2 | 3 | 3 | 2 | 3 | | | 1 | 3 | 3 | 0 | 0 |
| 212 | 11.2100 | 0 | | | 0 | 0 | 0 | 0 | 0 | | | 0 | 3 | 1 | 0 | 0 |
| 213 | 11.2100 | 0 | | | 0 | 1 | 0 | 1 | | | 0 | 1 | 2 | 0 | 0 | |
| 214 | 11.2100 | 2 | | | 0 | 0 | 0 | 0 | 1 | | | 0 | 1 | 0 | 0 | 0 |
| 215 | 11.2100 | 3 | | | — | 1 | 0 | 0 | 1 | | | 0 | 3 | 0 | 0 | 0 |
| 216 | 11.2100 | 0 | | | — | 0 | 0 | 0 | 3 | | | 0 | 3 | 2 | 0 | 0 |
| 217 | 11.2100 | 0 | | | 0 | 3 | 0 | 1 | 1 | | | 0 | 3 | 3 | 0 | 0 |
| 218 | 11.2100 | 1 | | | 1 | 3 | 1 | 1 | 3 | | | 0 | 3 | 3 | 1 | 0 |
| 219 | 11.2100 | 2 | | | 3 | 3 | 3 | 0 | 3 | | | 3 | 3 | 3 | 2 | 0 |
| 220 | 11.2100 | | | | 3 | 3 | 3 | 3 | 3 | | | 1 | 3 | 3 | 3 | 3 |
| 221 | 11.2100 | 0 | | | 0 | 0 | 0 | 0 | 0 | | | 1 | 3 | 1 | 0 | 0 |
| 222 | 11.2100 | 0 | | | 0 | 0 | 0 | 0 | 0 | | | 0 | 3 | 3 | 1 | 0 |
| 223 | 11.2100 | 1 | | | 2 | 3 | 3 | 3 | 3 | | | 0 | 3 | 3 | 2 | 0 |
| 224 | 11.2100 | 3 | | | 0 | 2 | 0 | 0 | 0 | | | 0 | 3 | 3 | 0 | 0 |
| 225 | 11.2100 | 0 | | | 0 | 3 | 2 | 0 | 3 | | | 0 | 3 | 3 | 3 | 3 |
| 226 | 11.2100 | 0 | | | 0 | 3 | 3 | 0 | 3 | | | 0 | 3 | 3 | 0 | 0 |
| 227 | 11.2100 | 0 | | | 1 | 3 | 2 | 3 | 1 | | | 0 | 3 | 3 | 3 | 0 |
| 228 | 11.2100 | 0 | | | 2 | 3 | 2 | 0 | 2 | | | 0 | 3 | 3 | 1 | 0 |
| 229 | 11.2100 | 1 | | | 2 | 3 | 2 | 1 | 2 | | | 0 | 3 | 3 | 3 | 0 |
| 230 | 11.2100 | 0 | | | 1 | 3 | 3 | 1 | 3 | | | 0 | 3 | 3 | 0 | 0 |
| 231 | 11.2100 | 2 | | | 2 | 3 | 3 | 0 | 3 | | | 0 | 3 | 3 | 1 | 0 |
| 232 | 11.2100 | 3 | | | 3 | 3 | 3 | 1 | 3 | | | 0 | 3 | 3 | 3 | 0 |
| 233 | 11.2100 | 1 | | | 3 | 3 | 1 | 0 | 3 | | | 0 | 3 | 3 | 2 | 0 |
| 234 | 11.2100 | 1 | | | 1 | 3 | 3 | 2 | 3 | | | 0 | 3 | 3 | 1 | 0 |
| 235 | 11.2100 | 2 | | | 3 | 3 | 3 | 2 | 3 | | | 1 | 3 | 3 | 3 | 1 |
| 236 | 11.2100 | 3 | | | 2 | 3 | 3 | 3 | 3 | | | 2 | 3 | 3 | 3 | 2 |
| 237 | 11.2100 | 0 | | | 3 | 3 | 2 | 0 | 2 | | | 0 | 3 | 3 | 2 | 0 |
| 238 | 11.2100 | 1 | | | 0 | 3 | 3 | 0 | 1 | | | 1 | 3 | 3 | 2 | 0 |
| 239 | 11.2100 | 3 | | | 3 | 3 | 3 | 3 | 3 | | | 0 | 3 | 3 | 3 | 2 |
| 240 | 11.2100 | 3 | | | 0 | 3 | 2 | 3 | 3 | | | 0 | 3 | 3 | 1 | 0 |
| 241 | 11.2100 | 0 | | | 0 | 3 | 0 | 0 | 1 | | | 0 | 3 | 3 | 0 | 0 |
| 242 | 11.2100 | 0 | | | 1 | 3 | 3 | 0 | 3 | | | 0 | 3 | 3 | 0 | 0 |
| 243 | 11.2100 | 1 | | | 0 | 3 | 3 | 3 | 3 | | | 1 | 3 | 3 | 2 | 1 |
| 244 | 11.2100 | 1 | | | 0 | 3 | 1 | 1 | 2 | | | 0 | 3 | 3 | 0 | 0 |
| 245 | 11.2100 | 1 | | | 0 | 2 | 2 | 3 | 1 | | | 1 | 3 | 3 | 0 | 0 |
| 246 | 11.2100 | 1 | | | 3 | 3 | 3 | 1 | 3 | | | 0 | 3 | 3 | 2 | 0 |
| 247 | 11.2100 | 0 | | | 1 | 3 | 3 | 0 | 3 | | | 0 | 3 | 3 | 0 | 0 |
| 248 | 11.2100 | 0 | | | 0 | 3 | 3 | 2 | 3 | | | 0 | 3 | 3 | 1 | 0 |
| 249 | 11.2100 | 0 | | | 0 | 1 | 0 | 0 | 0 | | | 0 | 3 | 2 | 0 | 0 |
| 250 C | 11.2100 | 1 | | | 3 | 3 | 1 | 3 | 3 | | | 0 | 3 | 3 | 3 | 3 |
| 251 | 11.2100 | 3 | | | 3 | 3 | 3 | 3 | 3 | | | 0 | 3 | 3 | 3 | 0 |
| 252 | 11.2100 | 0 | | | 0 | 2 | 0 | 0 | 0 | | | 0 | 3 | 3 | 0 | 3 |
| 253 | 11.2100 | 0 | | | 0 | 1 | 0 | 0 | 0 | | | 0 | 3 | 3 | 0 | 0 |
| 254 | 11.2100 | 0 | | | 1 | 1 | 1 | 1 | 0 | | | 0 | 3 | 3 | 3 | 0 |
| 255 | 11.2100 | 0 | | | 0 | 2 | 0 | 0 | 2 | | | 0 | 3 | 3 | 0 | 3 |
| 256 | 11.2100 | 1 | | | 0 | 3 | 0 | 0 | 2 | | | 0 | 3 | 3 | 0 | 0 |
| 257 | 11.2100 | 0 | | | 0 | 3 | 0 | 0 | 2 | | | 0 | 3 | 3 | 0 | 3 |
| 258 | 11.2100 | 0 | | | 0 | 3 | 2 | 0 | 3 | | | 0 | 3 | 3 | 0 | 0 |
| 259 | 11.2100 | 0 | | | 0 | 3 | 0 | 0 | 3 | | | 0 | 3 | 3 | 0 | 0 |
| 260 | 11.2100 | 1 | | | 3 | 3 | 3 | 0 | 3 | | | 2 | 3 | 3 | 3 | 0 |
| 261 | 11.2100 | 0 | | | 0 | 3 | 3 | 0 | 3 | | | 1 | 3 | 3 | 0 | 0 |
| 262 | 11.2100 | 0 | | | 3 | 3 | 3 | 2 | 3 | | | 0 | 3 | 3 | 2 | 0 |
| 263 | 11.2100 | 0 | | | 2 | 3 | 3 | 1 | 3 | | | 0 | 3 | 3 | 0 | N |
| 264 | 11.2100 | 0 | | | 1 | 3 | 3 | 2 | 3 | | | 0 | 3 | 3 | 0 | 0 |
| 265 | 11.2100 | 1 | | | 3 | 3 | 3 | 1 | 3 | | | 0 | 3 | 3 | 1 | 0 |
| 266 | 11.2100 | 0 | | | 0 | 0 | 1 | 0 | 1 | | | 3 | N | 3 | 0 | 0 |
| 267 | 11.2100 | 0 | | | 3 | 3 | 3 | 3 | 3 | | | 3 | 3 | 3 | 2 | 0 |
| 268 | 11.2100 | 0 | | | 3 | 3 | 3 | 1 | 3 | | | 0 | 3 | 3 | 2 | 0 |
| 269 | 11.2100 | 1 | | | 0 | 3 | 3 | 2 | 3 | | | 0 | 3 | 3 | 0 | 0 |
| 270 | 11.2100 | 3 | | | 2 | 3 | 3 | 3 | 3 | | | 2 | 3 | 3 | 0 | 1 |
| 271 | 11.2100 | 0 | | | 0 | 3 | 2 | 0 | 3 | | | 0 | 3 | 3 | 0 | — |
| 272 | 11.2100 | 0 | | | 2 | 3 | 3 | 3 | 2 | | | 3 | 3 | 3 | 1 | 0 |
| 273 | 11.2100 | 0 | | | 1 | 3 | 1 | 0 | 2 | | | 0 | N | 3 | 0 | 0 |
| 274 | 11.2100 | 3 | | | 3 | 3 | 3 | 1 | 3 | | | 1 | 3 | 3 | 1 | 3 |
| 275 | 11.2100 | 0 | | | 3 | 3 | 3 | 3 | 3 | | | 2 | 3 | 3 | 1 | N |
| 276 | 11.2100 | 3 | | | 0 | 3 | 0 | 2 | 3 | | | 1 | 3 | 3 | 2 | — |
| 277 | 11.2100 | 0 | | | 0 | 2 | 0 | 0 | 1 | | | 0 | N | 2 | 0 | 0 |
| 278 | 11.2100 | 0 | | | 3 | 3 | 0 | 0 | 2 | | | 1 | N | 3 | 0 | N |
| 279 | 11.2100 | 1 | | | 2 | 3 | 2 | 1 | 3 | | | 1 | 3 | 3 | 0 | N |
| 280 | 11.2100 | 3 | | | 0 | 3 | 0 | 3 | 3 | | | 3 | 3 | 3 | 1 | 0 |
| 281 | 11.2100 | 0 | | | 0 | 0 | 0 | 0 | 0 | | | 0 | 0 | 0 | 0 | 0 |
| 282 | 11.2100 | 1 | | | 0 | 3 | 3 | 1 | 2 | | | 0 | 3 | 3 | 0 | 0 |
| 283 | 11.2100 | 0 | | | 1 | 3 | 3 | 1 | 3 | | | 0 | 3 | 3 | 1 | 0 |
| 284 | 11.2100 | 1 | 3 | 3 | 3 | 3 | 3 | 2 | 3 | 3 | 3 | | | | | |

TABLE A-continued

Herbicide Primary Pre, spectrums 25 and 90

| Ex. No. | | Rate kg/ha | Yens | Anbg | Sejg | Dbyr | Bggr | Mgl | Cobu | Vble | Inmu | Wibw | Cath | Colq | Pesw | Rhqg | Rhjg |
|---|---|---|---|---|---|---|---|---|---|---|---|---|---|---|---|---|---|
| 285 | | 11.2100 | 0 | | | 0 | 2 | 1 | 1 | 2 | | | 0 | 3 | 2 | 1 | 1 |
| 286 | | 11.2100 | 0 | | | 0 | 0 | 0 | 0 | 0 | | | 0 | N | 0 | 0 | — |
| 287 | | 11.2100 | 1 | | | 3 | 3 | 3 | 1 | 3 | | | 0 | 3 | 3 | 0 | 0 |
| 288 | | 11.2100 | 1 | | | 3 | 3 | 3 | 1 | 3 | | | 0 | 3 | 3 | 3 | 0 |
| 289 | = | 11.2100 | 3 | | | 3 | 3 | 3 | 2 | 3 | | | 0 | 3 | N | 2 | 1 |
| 290 | | 11.2100 | 1 | | | 2 | 3 | 2 | 1 | 2 | | | 1 | 3 | N | 3 | 1 |
| 291 | | 11.2100 | 2 | | | 0 | 2 | 3 | 2 | 3 | | | 2 | 3 | N | 0 | 0 |
| 292 | | 11.2100 | 0 | | | 0 | 0 | 0 | 0 | 0 | | | 0 | 3 | N | 0 | 0 |
| 293 | | 11.2100 | 3 | | | 0 | 3 | 3 | 3 | 3 | | | 3 | 3 | N | 0 | 0 |
| 294 | | 11.2100 | 1 | | | 0 | 3 | 3 | 1 | 3 | | | 0 | 3 | N | 2 | 0 |
| 295 | = | 11.2100 | 3 | | | 0 | 3 | 3 | 3 | 3 | | | 3 | 3 | N | 0 | 0 |
| 296 | = | 11.2100 | 1 | | | 0 | 3 | 3 | 3 | 3 | | | 0 | 3 | N | 0 | 0 |
| 297 | = | 11.2100 | 1 | | | 0 | 3 | 3 | 3 | 3 | | | 0 | 3 | N | 0 | 0 |
| 298 | ( | 11.2100 | 2 | | | 3 | 3 | 3 | 3 | 3 | | | 2 | 3 | N | 3 | 0 |
| 299 | | 11.2100 | 0 | | | 1 | 3 | 3 | 3 | 3 | | | 3 | 3 | N | 0 | 0 |
| 300 | ( | 11.2100 | 0 | | | 0 | 3 | 2 | 0 | 1 | | | 0 | 3 | N | 1 | 0 |
| 301 | ( | 11.2100 | 2 | | | 0 | 3 | 3 | 3 | 3 | | | 3 | 3 | N | 2 | 0 |
| 302 | ( | 11.2100 | 3 | | | 0 | 3 | 3 | 3 | 3 | | | 1 | 3 | N | 1 | 0 |
| 303 | ( | 11.2100 | 3 | | | 0 | 3 | 3 | 3 | 3 | | | 3 | 3 | N | 1 | 0 |
| 304 | ( | 11.2100 | 3 | | | 0 | 3 | 3 | 3 | 3 | | | 3 | 3 | N | 1 | 0 |
| 305 | ( | 11.2100 | 1 | | | 0 | 1 | 3 | 3 | 3 | | | 3 | 3 | N | 0 | 0 |
| 306 | ) | 11.2100 | 0 | | | 0 | 0 | 1 | 3 | 3 | | | 3 | 3 | N | 0 | 0 |
| 307 | | 11.2100 | 1 | | | 0 | 2 | 3 | 3 | 3 | | | 2 | 3 | N | 1 | 0 |
| 308 | | 11.2100 | 3 | | | 2 | 3 | 3 | 3 | 3 | | | 3 | 3 | N | 2 | 0 |
| 309 | | 11.2100 | 3 | | | 3 | 3 | 3 | 3 | 3 | | | 3 | 3 | N | 0 | 0 |
| 310 | | 11.2100 | 3 | | | 1 | 3 | 3 | 3 | 3 | | | 3 | 3 | N | 1 | 1 |
| 311 | | 11.2100 | 3 | | | 1 | 3 | 3 | 3 | 3 | | | 3 | 3 | N | 1 | 0 |
| 312 | | 11.2100 | 3 | | | 1 | 3 | 3 | 3 | 3 | | | 3 | 3 | N | 1 | 0 |
| 313 | | 11.2100 | 3 | 2 | 1 | 3 | 2 | 3 | 3 | 3 | 3 | 3 | | | | | |
| 314 | | 11.2100 | 3 | 1 | 1 | 3 | 3 | 3 | 3 | 3 | 3 | 3 | | | | | |
| 315 | | 11.2100 | 1 | 2 | 3 | 3 | 3 | 3 | 3 | 3 | 3 | 3 | | | | | |
| 316 | | 11.2100 | 1 | 1 | 2 | 1 | 3 | 3 | 3 | 3 | 3 | 3 | | | | | |
| 317 | | 11.2100 | 0 | 0 | 2 | 3 | 2 | 2 | 1 | 1 | 3 | 3 | | | | | |
| 318 | | 11.2100 | 0 | 0 | 2 | 0 | 2 | 0 | 0 | 0 | 1 | 0 | | | | | |
| 319 | | 11.2100 | 0 | 0 | 1 | 0 | 0 | 3 | 2 | 3 | 3 | 3 | | | | | |
| 320 | | 11.2100 | 1 | 0 | 0 | 0 | 0 | 1 | 3 | 1 | 0 | 3 | | | | | |
| 321 | | 11.2100 | 0 | 3 | 3 | 3 | 3 | 3 | 1 | 3 | 3 | 3 | | | | | |
| 322 | | 11.2100 | 0 | 3 | 3 | 3 | 3 | 1 | 0 | 3 | 1 | 3 | | | | | |
| 323 | | 11.2100 | 0 | 3 | 3 | 3 | 3 | 3 | 2 | 3 | 3 | 3 | | | | | |
| 324 | | 11.2100 | 0 | 3 | 3 | 3 | 3 | 3 | 2 | 3 | 3 | 3 | | | | | |
| 325 | | 11.2100 | 2 | 1 | 3 | 0 | 3 | 3 | 2 | 3 | 3 | 3 | | | | | |
| 326 | | 11.2100 | 3 | 1 | 3 | 0 | 3 | 3 | 3 | 3 | 3 | 3 | | | | | |
| 327 | | 11.2100 | 1 | 3 | 3 | 3 | 3 | 3 | 3 | 3 | 3 | 3 | | | | | |
| 328 | | 11.2100 | 0 | 3 | 2 | 3 | 3 | 3 | 2 | 3 | 3 | 3 | | | | | |
| 329 | | 11.2100 | 1 | 3 | 3 | 3 | 3 | 2 | 3 | 3 | 3 | 3 | | | | | |
| 330 | | 11.2100 | 2 | 3 | 3 | 3 | 3 | 3 | 2 | 3 | 3 | 3 | | | | | |
| 331 | | 11.2100 | 2 | 3 | 3 | 3 | 3 | 3 | 1 | 3 | 3 | 3 | | | | | |
| 332 | | 11.2100 | 0 | 0 | 1 | 0 | 1 | 3 | 1 | 3 | 3 | 3 | | | | | |
| 333 | | 11.2100 | 0 | 1 | 0 | 0 | 0 | 3 | 3 | 3 | 3 | 3 | | | | | |
| 334 | | 11.2100 | 0 | 0 | 0 | 0 | 1 | 3 | 0 | 3 | 3 | 1 | | | | | |
| 335 | | 11.2100 | 3 | 3 | 3 | 3 | 3 | 3 | 3 | 3 | 3 | 3 | | | | | |
| 336 | | 11.2100 | 1 | 3 | 3 | 3 | 3 | 3 | 1 | 3 | 3 | 3 | | | | | |
| 337 | | 11.2100 | 3 | | | 1 | 3 | 3 | 3 | 3 | | | 3 | 3 | N | 1 | 0 |
| 338 | | 11.2100 | 0 | | | 3 | 3 | 3 | 0 | 1 | | | 0 | 3 | N | 1 | 0 |
| 339 | | 11.2100 | 0 | | | 0 | 3 | 0 | 0 | 1 | | | 0 | 3 | N | 0 | 0 |
| 340 | | 11.2100 | 3 | | | 3 | 3 | 3 | 3 | 3 | | | 2 | 3 | 3 | 3 | — |
| 341 | | 11.2100 | 0 | | | 0 | 0 | 0 | 0 | 0 | | | 0 | 0 | N | 0 | 0 |
| 342 | | 11.2100 | 0 | | | 0 | 0 | 0 | 0 | 0 | | | 0 | 2 | N | 0 | 0 |
| 343 | | 11.2100 | 0 | 3 | 3 | 3 | 3 | 2 | 2 | 3 | 3 | 3 | | | | | |
| 344 | ( | 11.2100 | 0 | | | 3 | 3 | 1 | 1 | 1 | | | 0 | 3 | N | 2 | 0 |
| 345 | | 11.2100 | 0 | | | 0 | 0 | 0 | 0 | 0 | | | N | 0 | N | 0 | 0 |
| 346 | | 11.2100 | 0 | | | 0 | 1 | 2 | 3 | 1 | | | 0 | 3 | N | 0 | 0 |
| 347 | | 11.2100 | 0 | | | 0 | 0 | 0 | 0 | 0 | | | 0 | 0 | N | 0 | 0 |
| 348 | | 11.2100 | 2 | | | 0 | 0 | 0 | 3 | 1 | | | 3 | 3 | N | 0 | 0 |
| 349 | | 11.2100 | 1 | | | 0 | 0 | 0 | 1 | 1 | | | 0 | 3 | N | 0 | 0 |
| 350 | | 11.2100 | 0 | | | 0 | 0 | 0 | 0 | 2 | | | 0 | 3 | N | 0 | 0 |
| 351 | | 11.2100 | 0 | | | 0 | 0 | 0 | 0 | 0 | | | 0 | 1 | N | 0 | 0 |
| 352 | | 11.2100 | 3 | | | 0 | 1 | 3 | 3 | 3 | | | 3 | 3 | N | 0 | 0 |
| 353 | | 11.2100 | 0 | | | 0 | 0 | 1 | 0 | 1 | | | 0 | 3 | N | 0 | 0 |
| 354 | | 11.2100 | 0 | | | 0 | 0 | 0 | 0 | 0 | | | 0 | 0 | N | 0 | 0 |
| 355 | | 11.2100 | 1 | | | 0 | 2 | 0 | 1 | 3 | | | 3 | 3 | N | 0 | 0 |
| 356 | | 11.2100 | 2 | | | 0 | 3 | 1 | 3 | 2 | | | 3 | 3 | N | 1 | 0 |
| 357 | | 11.2100 | 1 | | | 0 | 0 | 1 | 0 | 3 | | | 0 | 3 | N | 2 | 0 |
| 358 | | 11.2100 | 3 | | | 0 | 0 | 2 | 3 | 1 | | | 3 | 3 | N | 0 | 0 |
| 359 | | 11.2100 | 2 | | | 0 | 2 | 1 | 2 | 1 | | | 1 | 3 | N | 1 | 0 |
| 360 | | 11.2100 | 0 | | | 0 | 0 | 0 | 0 | 0 | | | 0 | 2 | N | 0 | 0 |
| 361 | | 11.2100 | 0 | | | 0 | 0 | 0 | 0 | 1 | | | 0 | 3 | N | 0 | 0 |

TABLE A-continued

| | | Herbicide Primary Pre, spectrums 25 and 90 | | | | | | | | | | | | | |
|---|---|---|---|---|---|---|---|---|---|---|---|---|---|---|---|
| Ex. No. | Rate kg/ha | Yens | Abg g | Sej g | Dobr | Bygr | Mogl | Cobu | Vele | Inmu | Wibw | Cath | Clq q | Psew | Rhqg | Rhjg |
| 362 | 11.2100 | 0 | | | 1 | 2 | 1 | 2 | 1 | | | 0 | 3 | N | 2 | 0 |
| 363 | 11.2100 | 2 | | | 0 | 1 | 0 | 0 | 1 | | | 1 | 3 | N | 1 | 0 |
| 364 = | 11.2100 | 0 | | | 0 | 0 | 0 | 0 | 0 | | | 0 | 3 | N | 0 | 0 |
| 365 = | 11.2100 | 1 | | | 0 | 3 | 2 | 2 | 3 | | | 1 | 3 | N | 0 | 0 |
| 366 = | 11.2100 | 3 | | | 0 | 3 | 1 | 3 | 3 | | | 3 | 3 | N | 1 | 0 |
| 367 = | 11.2100 | 0 | | | 0 | 3 | 0 | 0 | 0 | | | 0 | 0 | N | 1 | 0 |
| 368 = | 11.2100 | 0 | | | 0 | 2 | 0 | 0 | 1 | | | 0 | 3 | N | 0 | 0 |
| 369 ( | 11.2100 | 0 | | | 0 | 1 | 1 | 2 | 2 | | | 0 | 1 | N | 0 | 0 |
| 370 ( | 11.2100 | 1 | | | 0 | 3 | 1 | 2 | 3 | | | 3 | 3 | N | 2 | 1 |
| 371 ( | 11.2100 | 0 | | | 0 | 0 | 0 | 0 | 1 | | | 0 | 3 | N | 0 | 0 |
| 372 ( | 11.2100 | 1 | | | 0 | 3 | 1 | 2 | 2 | | | 3 | 3 | N | 0 | 0 |
| 373 ( | 11.2100 | 0 | | | 0 | 0 | 0 | 0 | 0 | | | 0 | 3 | N | 0 | 0 |
| 374 ( | 11.2100 | 0 | | | 0 | 3 | 1 | 0 | 3 | | | 0 | 3 | N | 1 | 0 |
| 375 ( | 11.2100 | 0 | | | 0 | 0 | 0 | 0 | 1 | | | 0 | 3 | N | 0 | 0 |
| 376 ( | 11.2100 | 0 | | | 0 | 0 | 0 | 0 | 0 | | | 0 | 3 | N | 0 | 0 |
| 377 ) | 11.2100 | 0 | | | 0 | 0 | 0 | 0 | 0 | | | N | 2 | N | 0 | 0 |
| 378 ) | 11.2100 | 0 | | | 0 | 1 | 0 | 0 | 2 | | | 0 | 3 | N | 0 | 0 |
| 379 ) | 11.2100 | 1 | | | 0 | 2 | 0 | 0 | 1 | | | 0 | 3 | N | 0 | 0 |
| 380 ) | 11.2100 | 0 | | | 0 | 0 | 0 | 0 | 0 | | | N | 2 | N | 0 | 0 |
| 381 ) | 11.2100 | 1 | | | 3 | 3 | 3 | 2 | 3 | | | 3 | 3 | N | 1 | 0 |
| 382 ) | 11.2100 | 0 | | | 0 | 1 | 2 | 3 | 1 | | | 0 | 3 | N | 0 | 0 |
| 383 ) | 11.2100 | 2 | | | 2 | 2 | 2 | 0 | 0 | | | 3 | 3 | N | 0 | 0 |
| 384 ) | 11.2100 | 1 | | | 0 | 3 | 3 | 2 | 3 | | | 3 | 3 | N | 1 | 0 |
| 385 ) | 11.2100 | 2 | | | 0 | 2 | 1 | 1 | 1 | | | 3 | 3 | N | 0 | 0 |
| 386 | 11.2100 | 1 | | | 0 | 0 | 2 | 1 | 1 | | | 1 | 3 | N | 0 | 0 |
| 387 | 11.2100 | 0 | | | 0 | 0 | 1 | 1 | 1 | | | 3 | 3 | N | 0 | 0 |
| 388 | 11.2100 | 1 | | | 0 | 0 | 1 | 1 | 2 | | | 0 | 3 | N | 0 | 0 |
| 389 | 11.2100 | 0 | | | 1 | 0 | 1 | 0 | 0 | | | 0 | 3 | N | 0 | 0 |
| 390 | 11.2100 | 1 | | | 0 | 0 | 2 | 2 | 3 | | | 3 | 3 | N | 0 | 0 |
| 391 | 11.2100 | 1 | | | 3 | 3 | 3 | 2 | 3 | | | 1 | 3 | N | 3 | 2 |
| 392 | 11.2100 | 2 | 3 | 3 | 3 | 3 | 2 | 0 | 2 | 3 | 3 | | | | | |
| 393 | 11.2100 | 2 | 3 | 2 | 3 | 3 | 2 | 3 | 3 | 3 | 3 | | | | | |
| 394 | 11.2100 | 2 | 2 | 2 | 3 | 3 | 2 | 3 | 3 | 3 | 3 | | | | | |
| 395 | 11.2100 | 1 | 0 | 0 | 0 | 0 | 0 | 3 | 1 | 1 | 2 | | | | | |
| 396 | 11.2100 | 0 | 0 | 3 | 3 | 3 | 1 | 1 | 3 | 3 | 1 | | | | | |
| 397 | 11.2100 | 0 | 1 | 3 | 3 | 3 | 1 | 0 | 3 | 3 | 3 | | | | | |
| 398 | 11.2100 | 1 | 3 | 3 | 3 | 3 | 3 | 3 | 3 | 3 | 3 | | | | | |
| 399 ( | 11.2100 | 0 | | | 3 | 3 | 3 | 2 | 3 | | | 0 | 3 | N | 2 | 0 |
| 400 ( | 11.2100 | 0 | | | 3 | 3 | 3 | 1 | 3 | | | 0 | 3 | N | 1 | 0 |
| 401 ( | 11.2100 | 0 | | | 1 | 0 | 0 | 0 | 0 | | | 0 | 3 | N | 0 | 0 |
| 402 | 11.2100 | 0 | | | 3 | 3 | 3 | 1 | 3 | | | 3 | 3 | N | 2 | 2 |
| 403 | 11.2100 | 1 | 3 | 3 | 3 | 3 | 3 | 2 | 3 | 3 | 3 | | | | | |
| 404 | 11.2100 | 0 | 3 | 3 | 3 | 3 | 3 | 0 | 3 | 3 | 3 | | | | | |
| 405 | 11.2100 | 0 | 3 | 3 | 3 | 3 | 3 | 2 | 3 | 3 | 3 | | | | | |
| 406 | 11.2100 | 0 | 3 | 3 | 3 | 3 | 3 | 1 | 2 | 3 | 3 | | | | | |
| 407 | 11.2100 | 0 | | | 3 | 3 | 3 | 2 | 3 | | | 2 | 3 | N | 3 | 0 |
| 408 | 11.2100 | 1 | | | 3 | 3 | 3 | 3 | 3 | | | 3 | 3 | N | 3 | 3 |
| 409 | 11.2100 | 1 | 3 | 3 | 3 | 3 | 3 | 2 | 3 | 3 | 3 | | | | | |
| 410 | 11.2100 | 1 | 3 | 3 | 3 | 0 | 3 | 1 | 3 | 3 | 3 | | | | | |
| 411 | 11.2100 | 1 | 3 | 3 | 3 | 3 | 3 | 2 | 3 | 3 | 3 | | | | | |
| 412 | 11.2100 | 1 | 3 | 3 | 3 | 3 | 3 | 2 | 3 | 3 | 3 | | | | | |
| 413 | 11.2100 | 0 | 0 | 0 | 0 | 2 | 0 | 0 | 1 | 1 | 1 | | | | | |
| 414 | 11.2100 | 0 | 3 | 2 | 1 | 2 | 2 | 0 | 2 | 1 | 3 | | | | | |
| 415 | 11.2100 | 0 | 3 | 3 | 3 | 3 | 3 | 0 | 3 | 3 | 3 | | | | | |
| 417 | 11.2100 | 0 | 3 | 2 | 3 | 2 | 0 | 1 | 1 | 3 | 3 | | | | | |
| 418 | 11.2100 | 0 | 3 | 3 | 3 | 3 | 2 | 2 | 3 | 3 | 3 | | | | | |
| 419 | 11.2100 | 0 | 1 | 1 | 2 | 1 | 1 | 1 | 3 | 3 | 3 | | | | | |
| 420 | 11.2100 | 3 | | | 0 | 3 | 3 | 0 | 3 | | | 1 | 3 | N | 1 | 3 |
| 421 | 11.2100 | 1 | | | 0 | 3 | 1 | 1 | 3 | | | 0 | 3 | N | 1 | 0 |
| 422 | 11.2100 | 0 | 0 | 2 | 0 | 2 | 2 | 0 | 1 | 3 | 3 | | | | | |
| 423 | 11.2100 | 0 | 2 | 0 | 2 | 0 | 2 | 3 | 2 | 3 | 2 | | | | | |
| 424 | 11.2100 | 1 | 2 | 0 | 0 | 0 | 1 | 3 | 1 | 3 | 3 | | | | | |
| 425 | 11.2100 | 0 | 0 | 0 | 0 | 0 | 1 | 0 | 0 | 1 | 1 | | | | | |
| 426 | 11.2100 | 2 | 3 | 0 | 3 | 3 | 1 | 1 | 3 | 3 | 3 | | | | | |
| 427 | 11.2100 | 0 | 3 | 1 | 2 | 2 | 1 | 2 | 1 | 3 | 3 | | | | | |
| 428 | 11.2100 | 0 | 3 | 3 | 3 | 3 | 3 | 3 | 3 | 3 | 3 | | | | | |
| 429 | 11.2100 | 1 | 2 | 2 | 1 | 3 | 3 | 2 | 3 | 3 | 3 | | | | | |
| 430 | 11.2100 | 1 | 0 | 1 | 0 | 0 | 0 | 0 | 1 | 3 | 2 | | | | | |
| 431 | 11.2100 | 1 | 3 | 3 | 2 | 3 | 1 | 3 | 1 | 3 | 3 | | | | | |
| 432 | 11.2100 | 1 | 1 | 2 | 0 | 3 | 1 | 2 | 3 | 3 | 3 | | | | | |
| 433 | 11.2100 | 1 | 0 | 2 | 0 | 2 | 1 | 1 | 1 | 3 | 3 | | | | | |
| 434 | 11.2100 | 0 | 0 | 2 | 0 | 1 | 0 | 0 | 2 | 2 | 1 | | | | | |
| 435 | 11.2100 | 1 | 3 | 3 | 0 | 3 | 3 | 1 | 1 | 3 | 3 | | | | | |
| 436 | 11.2100 | 1 | 3 | 3 | 3 | 3 | 1 | 1 | 1 | 1 | 3 | | | | | |
| 437 | 11.2100 | 0 | 1 | 2 | 0 | 0 | 2 | 0 | 1 | 3 | 3 | | | | | |
| 438 | 11.2100 | 1 | 2 | 2 | 0 | 3 | 0 | 1 | 1 | 3 | 3 | | | | | |
| 439 | 11.2100 | 0 | 0 | 1 | 0 | 2 | 0 | 0 | 0 | 3 | 3 | | | | | |

TABLE A-continued

Herbicide Primary Pre, spectrums 25 and 90

| Ex. No. | | Rate kg/ha | Yens | Anbg | Sejg | Dobr | Bygr | Mogl | Cobu | Vele | Inmu | Wibw | Cath | Colsq | Peshw | Rhqg | Rhjg |
|---|---|---|---|---|---|---|---|---|---|---|---|---|---|---|---|---|---|
| 440 | | 11.2100 | 1 | 2 | 2 | 0 | 3 | 1 | 2 | 2 | 3 | 3 | | | | | |
| 441 | | 11.2100 | 1 | 2 | 1 | 0 | 2 | 1 | 2 | 3 | 3 | 3 | | | | | |
| 442 | | 11.2100 | 0 | 3 | 2 | 0 | 2 | 1 | 0 | 3 | 3 | 3 | | | | | |
| 443 | | 11.2100 | 1 | 1 | 3 | 0 | 3 | 1 | 3 | 2 | 3 | 3 | | | | | |
| 444 | | 11.2100 | 1 | 2 | 2 | 0 | 3 | 2 | 2 | 3 | 3 | 3 | | | | | |
| 445 | | 11.2100 | 1 | 2 | 0 | 0 | 2 | 2 | 3 | 3 | 3 | 3 | | | | | |
| 446 | | 11.2100 | 2 | 3 | 3 | 3 | 3 | 3 | 3 | 3 | 3 | 3 | | | | | |
| 447 | | 11.2100 | 1 | 2 | 2 | 1 | 3 | 3 | 3 | 3 | 3 | 3 | | | | | |
| 448 | | 11.2100 | 1 | 3 | 3 | 1 | 3 | 3 | 3 | 3 | 3 | 3 | | | | | |
| 449 | | 11.2100 | 1 | 0 | 1 | 0 | 0 | 3 | 3 | 3 | 0 | 1 | | | | | |
| 450 | | 11.2100 | 1 | 3 | 2 | 2 | 3 | 3 | 3 | 3 | 3 | 3 | | | | | |
| 451 | | 11.2100 | 0 | 3 | 3 | 0 | 2 | 1 | 1 | 3 | 3 | 3 | | | | | |
| 452 | | 11.2100 | 0 | 0 | 0 | 0 | 0 | 0 | 0 | 0 | 1 | 1 | | | | | |
| 453 | | 11.2100 | 0 | 3 | 0 | 2 | 2 | 3 | 2 | 3 | 3 | 3 | | | | | |
| 454 | | 11.2100 | 0 | 0 | 0 | 0 | 0 | 0 | 0 | 0 | 0 | 0 | | | | | |
| 455 | | 11.2100 | 0 | 1 | 3 | 0 | 3 | 0 | 0 | 3 | 3 | 3 | | | | | |
| 456 | | 11.2100 | 1 | 1 | 1 | 0 | 0 | 0 | 0 | 0 | 0 | 0 | | | | | |
| 457 | | 11.2100 | 0 | 3 | 3 | 3 | 3 | 3 | 2 | 3 | 3 | 3 | | | | | |
| 458 | | 11.2100 | 1 | 1 | 3 | 0 | 3 | 3 | 1 | 3 | 2 | 3 | | | | | |
| 459 | | 11.2100 | 1 | 0 | 0 | 0 | 0 | 0 | 1 | 0 | 0 | 0 | | | | | |
| 460 | | 11.2100 | 1 | 0 | 3 | 0 | 3 | 3 | 3 | 3 | 3 | 3 | | | | | |
| 461 | | 11.2100 | 0 | 0 | 0 | 0 | 1 | 3 | 1 | 3 | 1 | 3 | | | | | |
| 462 | | 11.2100 | 0 | 0 | 0 | 0 | 0 | 2 | 0 | 2 | 1 | 2 | | | | | |
| 463 | | 11.2100 | 0 | 3 | 3 | 3 | 3 | 0 | 0 | 2 | 1 | 3 | | | | | |
| 464 | | 11.2100 | 1 | 3 | 3 | 3 | 3 | 3 | 2 | 3 | 3 | 3 | | | | | |
| 465 | | 11.2100 | 2 | 3 | 3 | 3 | 3 | 3 | 0 | 3 | 3 | 3 | | | | | |
| 466 | | 11.2100 | 2 | 3 | 3 | 3 | 3 | 3 | 2 | 3 | 3 | 3 | | | | | |
| 467 | | 11.2100 | 0 | 3 | 3 | 2 | 3 | 3 | 2 | 3 | 3 | 3 | | | | | |
| 468 | | 11.2100 | 3 | 3 | 3 | 3 | 3 | 3 | 3 | 3 | 3 | 3 | | | | | |
| 469 | | 11.2100 | 0 | 3 | 3 | 3 | 3 | 3 | 1 | 3 | 3 | 3 | | | | | |
| 470 | | 11.2100 | 1 | 3 | 3 | 3 | 3 | 3 | 2 | 3 | 3 | 3 | | | | | |
| 471 | | 11.2100 | 0 | 3 | 3 | 3 | 3 | 1 | 0 | 3 | 3 | 3 | | | | | |
| 472 | | 11.2100 | 0 | 3 | 3 | 3 | 3 | 3 | 1 | 3 | 3 | 3 | | | | | |
| 473 | | 11.2100 | 0 | 3 | 3 | 3 | 3 | 3 | 0 | 3 | 3 | 3 | | | | | |
| 474 | | 11.2100 | 0 | 3 | 3 | 3 | 3 | 3 | 1 | 3 | 3 | 3 | | | | | |
| 475 | | 11.2100 | 0 | 3 | 3 | 3 | 2 | 1 | 0 | 2 | 2 | 3 | | | | | |
| 476 | | 11.2100 | 0 | 3 | 0 | 3 | 3 | 3 | 2 | 2 | 3 | 3 | | | | | |
| 477 | | 11.2100 | 1 | 3 | 3 | 3 | 3 | 3 | 1 | 3 | 3 | 3 | | | | | |
| 478 | — | 11.2100 | 0 | 3 | 3 | 3 | 3 | 3 | 3 | 3 | 3 | 3 | | | | | |
| 494 | — | 11.2100 | 1 | 0 | 0 | 0 | 0 | 1 | 2 | 2 | 0 | 0 | | | | | |
| 495 | — | 11.2100 | 0 | 2 | 0 | 0 | 0 | 1 | 1 | 1 | 3 | 3 | | | | | |
| 496 | — | 11.2100 | 0 | 1 | 1 | 0 | 3 | 0 | N | 1 | 2 | 3 | | | | | |
| 497 | | 11.2100 | 0 | 1 | 1 | 1 | 2 | 1 | 0 | 3 | 2 | 1 | | | | | |
| 498 | | 11.2100 | 0 | 3 | 3 | 3 | 3 | 3 | 1 | 3 | 3 | 3 | | | | | |
| 499 | | 11.2100 | 1 | 0 | 1 | 2 | 2 | 3 | 3 | 3 | 3 | 3 | | | | | |
| 500 | | 11.2100 | 1 | 0 | 0 | 0 | 0 | 1 | 1 | 3 | 3 | 0 | | | | | |
| 501 | | 11.2100 | 2 | 0 | 1 | 0 | 1 | 1 | 2 | 3 | 0 | 0 | | | | | |
| 502 | | 11.2100 | 0 | 3 | 3 | 3 | 3 | 3 | 0 | 3 | 3 | 3 | | | | | |
| 503 | | 11.2100 | 3 | 1 | 0 | 0 | 0 | 3 | 3 | 3 | 3 | 3 | | | | | |
| 504 | | 11.2100 | 0 | 1 | 0 | 0 | 3 | 1 | 0 | 3 | 3 | 3 | | | | | |
| 505 | | 11.2100 | 0 | 3 | 1 | 2 | 3 | 1 | 0 | 2 | 2 | 3 | | | | | |
| 506 | | 11.2100 | 0 | 3 | 3 | 3 | 3 | 3 | 0 | 3 | 3 | 3 | | | | | |
| 507 | | 11.2100 | 0 | 3 | 3 | 3 | 1 | 2 | 0 | 3 | 3 | 3 | | | | | |
| 508 | | 11.2100 | 2 | 3 | 3 | 2 | 3 | 0 | 0 | 3 | 3 | 3 | | | | | |
| 479 | — | 11.2100 | 1 | 3 | 3 | 3 | 3 | 3 | 3 | 3 | 3 | 3 | | | | | |
| 480 | | 11.2100 | 1 | 3 | 3 | 3 | 3 | 3 | 2 | 3 | 3 | 3 | | | | | |
| 481 | | 11.2100 | 0 | 1 | 2 | 0 | 2 | 1 | 1 | 3 | 3 | 3 | | | | | |
| 482 | | 11.2100 | 1 | 3 | 3 | 3 | 3 | 2 | 0 | 3 | 3 | 3 | | | | | |
| 483 | | 11.2100 | 0 | 3 | 2 | 3 | 3 | 2 | 0 | 3 | 3 | 3 | | | | | |
| 484 | | 11.2100 | 0 | 3 | 3 | 3 | 3 | 2 | 0 | 3 | 3 | 3 | | | | | |
| 485 | | 11.2100 | 0 | 3 | 3 | 3 | 3 | 2 | 1 | 3 | 3 | 3 | | | | | |
| 486 | > | 11.2100 | 1 | 3 | 2 | 0 | 3 | 0 | 0 | 3 | 3 | 3 | | | | | |
| 487 | | 11.2100 | 1 | 3 | 3 | 3 | 3 | 3 | 3 | 3 | 3 | 3 | | | | | |
| 488 | | 11.2100 | 2 | 3 | 3 | 3 | 3 | 1 | 2 | 3 | 3 | 3 | | | | | |
| 489 | | 11.2100 | 1 | 3 | 3 | 3 | 3 | 3 | 3 | 3 | 3 | 3 | | | | | |
| 490 | | 11.2100 | 1 | 3 | 3 | 0 | 3 | 2 | 3 | 3 | 3 | 3 | | | | | |
| 491 | — | 11.2100 | 2 | 3 | 3 | 0 | 3 | 2 | 2 | 3 | 3 | 3 | | | | | |
| 492 | — | 11.2100 | 2 | 3 | 3 | 1 | 3 | 1 | 0 | 3 | 3 | 3 | | | | | |
| 493 | | 11.2100 | 0 | 0 | 3 | 0 | 2 | 3 | 3 | 3 | 3 | 3 | | | | | |
| 509 | | 11.2100 | 2 | 0 | 3 | 0 | 3 | 3 | 1 | 3 | 2 | 3 | | | | | |
| 510 | | 11.2100 | 3 | 0 | 2 | 0 | 3 | 3 | 3 | 3 | 3 | 3 | | | | | |
| 511 | | 11.2100 | 2 | 0 | 2 | 0 | 3 | 3 | 1 | 3 | 3 | 3 | | | | | |
| 512 | | 11.2100 | 2 | 2 | 0 | 0 | 3 | 3 | 0 | 3 | 3 | 3 | | | | | |
| 513 | | 11.2100 | 2 | 2 | 1 | 1 | 3 | 3 | 1 | 3 | 3 | 3 | | | | | |
| 514 | · | 11.2100 | 2 | 1 | 0 | 1 | 2 | 2 | 2 | 3 | 3 | 3 | | | | | |
| 515 | | 11.2100 | 0 | 0 | 2 | 0 | 1 | 3 | 0 | 3 | 2 | 3 | | | | | |
| 516 | | 11.2100 | 0 | 0 | 3 | 0 | 3 | 0 | 0 | 3 | 2 | 2 | | | | | |

TABLE A-continued

| Ex. No. | | Rate kg/ha | Yens | Abg | Sejg | Dobr | Bygr | Mogl | Cogbu | Veble | Inmue | Wibuw | Cath | Colq | Pesw | Rhqg | Rhjg |
|---|---|---|---|---|---|---|---|---|---|---|---|---|---|---|---|---|---|
| 517 | | 11.2100 | 1 | 3 | 3 | 3 | 0 | 3 | 2 | 3 | 3 | 3 | | | | | |
| 518 | | 11.2100 | 3 | 3 | 3 | 3 | 3 | 2 | 2 | 3 | 3 | 3 | | | | | |
| 519 | > | 11.2100 | 0 | 3 | 1 | 1 | 1 | 0 | 0 | 0 | 1 | 1 | | | | | |
| 520 | > | 11.2100 | 0 | 3 | 1 | 3 | 3 | 2 | 0 | 3 | 3 | 3 | | | | | |
| 521 | > | 11.2100 | 0 | 3 | 0 | 0 | 3 | 2 | 0 | 3 | 3 | 3 | | | | | |
| 522 | > | 11.2100 | 0 | 3 | 2 | 3 | 3 | 0 | 1 | 3 | 3 | 3 | | | | | |
| 523 | | 11.2100 | 1 | 3 | 3 | 3 | 3 | 3 | 0 | 3 | 3 | 3 | | | | | |
| 524 | | 11.2100 | 0 | 3 | 3 | 2 | 3 | 3 | 1 | 3 | 3 | 3 | | | | | |
| 525 | | 11.2100 | 2 | 3 | 3 | 3 | 3 | 3 | 2 | 3 | 3 | 3 | | | | | |
| 526 | | 11.2100 | 0 | 3 | 3 | 3 | 3 | 3 | 2 | 3 | 3 | 3 | | | | | |
| 527 | | 11.2100 | 0 | 2 | 3 | 3 | 3 | 3 | 1 | 3 | 3 | 3 | | | | | |
| 528 | | 11.2100 | 0 | 3 | 3 | 3 | 3 | 3 | 1 | 3 | 3 | 3 | | | | | |
| 529 | | 11.2100 | 0 | 3 | 3 | 3 | 3 | 3 | 2 | 3 | 3 | 3 | | | | | |
| 530 | | 11.2100 | 0 | 3 | 3 | 2 | 2 | 2 | 0 | 2 | 3 | 3 | | | | | |
| 531 | | 11.2100 | 0 | 2 | 3 | 3 | 3 | 0 | 0 | 1 | 3 | 3 | | | | | |
| 532 | | 11.2100 | 0 | 3 | 3 | 3 | 3 | 2 | 1 | 3 | 3 | 3 | | | | | |
| 533 | | 11.2100 | 0 | 3 | 3 | 3 | 3 | 3 | 2 | 3 | 3 | 3 | | | | | |
| 534 | | 11.2100 | 0 | 3 | 3 | 3 | 3 | 2 | 1 | 3 | 3 | 3 | | | | | |
| 535 | | 11.2100 | 0 | 3 | 3 | 3 | 3 | 3 | 1 | 3 | 3 | 3 | | | | | |
| 536 | | 11.2100 | 0 | 0 | 0 | 0 | 0 | 1 | 0 | 2 | 3 | 0 | | | | | |
| 537 | | 11.2100 | 0 | 0 | 0 | 0 | 0 | 0 | 0 | 0 | 0 | 0 | | | | | |
| 538 | | 11.2100 | 0 | 0 | 0 | 0 | 0 | 1 | 0 | 3 | 1 | 2 | | | | | |
| 539 | < | 11.2100 | 2 | 2 | 3 | 3 | 3 | 3 | 3 | 3 | 3 | 3 | | | | | |
| 540 | < | 11.2100 | 0 | 3 | 3 | 3 | 3 | 3 | 3 | 3 | 3 | 3 | | | | | |
| 541 | | 11.2100 | 1 | 3 | 2 | 0 | 3 | 2 | 1 | 3 | 3 | 3 | | | | | |
| 542 | | 11.2100 | 3 | 2 | 3 | 2 | 3 | 3 | 3 | 3 | 3 | 3 | | | | | |
| 543 | | 11.2100 | 2 | 0 | 2 | 0 | 3 | 3 | 3 | 3 | 3 | 2 | | | | | |
| 544 | | 11.2100 | 3 | 3 | 3 | 3 | 3 | 3 | 3 | 3 | 3 | 3 | | | | | |
| 545 | | 11.2100 | 3 | 0 | 2 | 0 | 3 | 3 | 3 | 3 | 3 | 3 | | | | | |
| 546 | | 11.2100 | 3 | 0 | 2 | 0 | 3 | 3 | 2 | 3 | 2 | 1 | | | | | |
| 547 | | 11.2100 | 2 | 0 | 2 | 0 | 3 | 3 | 3 | 3 | 2 | 3 | | | | | |
| 548 | | 11.2100 | 2 | 0 | 1 | 3 | 3 | 3 | 3 | 3 | 2 | 2 | | | | | |
| 549 | | 11.2100 | 0 | 3 | 3 | 3 | 3 | 3 | 2 | 3 | 3 | 3 | | | | | |
| 550 | | 11.2100 | 3 | 0 | 1 | 1 | 3 | 3 | 3 | 3 | 3 | 3 | | | | | |
| 551 | | 11.2100 | 1 | 3 | 3 | 3 | 3 | 3 | 3 | 3 | 3 | 3 | | | | | |
| 552 | | 11.2100 | 1 | 3 | 3 | 3 | 3 | 3 | 3 | 3 | 3 | 3 | | | | | |
| 554 | | 11.2100 | 1 | 3 | 3 | 3 | 3 | 1 | 0 | 3 | 2 | 3 | | | | | |
| 555 | | 11.2100 | 1 | 2 | 1 | 0 | 3 | 3 | 3 | 3 | 3 | 3 | | | | | |
| 556 | | 11.2100 | 1 | 0 | 0 | 0 | 2 | 3 | 3 | 3 | 3 | 3 | | | | | |
| 557 | | 11.2100 | 3 | 0 | 2 | 0 | 3 | 3 | 3 | 3 | 3 | 2 | | | | | |
| 558 | | 11.2100 | 0 | 1 | 0 | 0 | 0 | 2 | 1 | 3 | 3 | 3 | | | | | |
| 559 | | 11.2100 | 0 | 0 | 0 | 0 | 0 | 0 | 0 | 0 | 0 | 0 | | | | | |
| 560 | | 11.2100 | 1 | 0 | 1 | 0 | 3 | 3 | 3 | 3 | 3 | 3 | | | | | |
| 561 | | 11.2100 | 0 | 3 | 1 | 1 | 3 | 2 | 2 | 3 | 3 | 3 | | | | | |
| 562 | | 11.2100 | 1 | 1 | 3 | 2 | 3 | 3 | 3 | 3 | 3 | 3 | | | | | |
| 563 | | 11.2100 | 3 | 0 | 2 | 0 | 3 | 3 | 3 | 3 | 3 | 3 | | | | | |
| 564 | < | 11.2100 | 0 | 0 | 2 | 0 | 3 | 3 | 3 | 3 | 3 | 3 | | | | | |
| 565 | < | 11.2100 | 3 | 3 | 3 | 2 | 3 | 3 | 3 | 3 | 3 | 3 | | | | | |
| 566 | > | 11.2100 | 3 | 0 | 2 | 1 | 3 | 3 | 3 | 3 | 3 | 3 | | | | | |
| 567 | < | 11.2100 | 0 | 0 | 0 | 1 | 2 | 3 | 2 | 3 | 3 | 3 | | | | | |
| 568 | < | 11.2100 | 0 | 0 | 3 | 3 | 3 | 3 | 3 | 3 | 3 | 3 | | | | | |
| 569 | > | 11.2100 | 0 | 0 | 1 | 0 | 0 | 3 | 0 | 3 | 2 | 2 | | | | | |
| 570 | > | 11.2100 | 3 | 0 | 3 | 0 | 3 | 3 | 3 | 3 | 3 | 3 | | | | | |
| 571 | $ | 11.2100 | 3 | 1 | 2 | 1 | 3 | 3 | 3 | 3 | 3 | 3 | | | | | |
| 572 | $ | 11.2100 | 3 | 1 | 2 | 1 | 3 | 3 | 3 | 3 | 3 | 2 | | | | | |
| 573 | $ | 11.2100 | 0 | 0 | 0 | 0 | 0 | 0 | 1 | 1 | 2 | 1 | | | | | |
| 574 | $ | 11.2100 | 0 | 2 | 0 | 0 | 1 | 1 | 2 | 3 | 3 | 2 | | | | | |
| 575 | $ | 11.2100 | 0 | 0 | 0 | 0 | 0 | 3 | 3 | 3 | 3 | 3 | | | | | |
| 576 | $ | 11.2100 | 3 | 0 | 2 | 0 | 3 | 3 | 3 | 3 | 3 | 3 | | | | | |
| 577 | $ | 11.2100 | 3 | 0 | 2 | 0 | 3 | 3 | 3 | 3 | 3 | 3 | | | | | |
| 578 | $ | 11.2100 | 2 | 0 | 0 | 0 | 2 | 3 | 3 | 3 | 2 | 1 | | | | | |
| 579 | $ | 11.2100 | 3 | 1 | 1 | 0 | 3 | 3 | 3 | 3 | 3 | 3 | | | | | |
| 580 | $ | 11.2100 | 2 | 2 | 1 | 0 | 3 | 3 | 3 | 3 | 2 | 3 | | | | | |
| 581 | $ | 11.2100 | 2 | 0 | 1 | 0 | 3 | 2 | 1 | 3 | 3 | 3 | | | | | |
| 582 | > | 11.2100 | 2 | 3 | 3 | 3 | 3 | 2 | 1 | 3 | 3 | 3 | | | | | |
| 583 | & | 11.2100 | 0 | 0 | 0 | 0 | 0 | 0 | 0 | 0 | 0 | 0 | | | | | |
| 584 | & | 11.2100 | 3 | 2 | 3 | 0 | 3 | 3 | 3 | 3 | 3 | 3 | | | | | |
| 585 | & | 11.2100 | 3 | 2 | 3 | 0 | 3 | 3 | 3 | 3 | 3 | 3 | | | | | |
| 586 | & | 11.2100 | 0 | 3 | 3 | 3 | 3 | 3 | 3 | 3 | 3 | 3 | | | | | |
| 587 | > | 11.2100 | 0 | 0 | 0 | 0 | 0 | 0 | 0 | 1 | N | N | | | | | |
| 588 | > | 11.2100 | 1 | 2 | 2 | 3 | 3 | 3 | 2 | 3 | 3 | 3 | | | | | |
| 589 | > | 11.2100 | 0 | 3 | 2 | 3 | 3 | 3 | 2 | 3 | 3 | 3 | | | | | |
| 590 | > | 11.2100 | 0 | 0 | 1 | 1 | 1 | 3 | 3 | 3 | 3 | 3 | | | | | |
| 591 | > | 11.2100 | 3 | 3 | 3 | 3 | 3 | 3 | 3 | 3 | 3 | 3 | | | | | |
| 592 | > | 11.2100 | 0 | 1 | 0 | 0 | 0 | 3 | 3 | 3 | 3 | 3 | | | | | |
| 593 | > | 11.2100 | 0 | 3 | 1 | 2 | 3 | 1 | 3 | 3 | 3 | 3 | | | | | |
| 594 | > | 11.2100 | 3 | 1 | 3 | 1 | 3 | 3 | 3 | 3 | 3 | 3 | | | | | |

TABLE A-continued

| | | Herbicide Primary Pre, spectrums 25 and 90 | | | | | | | | | | | | | |
|---|---|---|---|---|---|---|---|---|---|---|---|---|---|---|---|
| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
| 595 | > 11.2100 | 0 | 3 | 3 | 3 | 3 | 3 | 1 | 3 | 3 | 3 | | | | | |
| 596 | > 11.2100 | 0 | 3 | 0 | 3 | 3 | 1 | 0 | 3 | 3 | 3 | | | | | |
| 597 | > 11.2100 | 3 | 3 | 3 | 3 | 3 | 3 | 3 | 3 | 3 | 3 | | | | | |
| 598 | > 11.2100 | 1 | 3 | 3 | 3 | 3 | 3 | 3 | 3 | 3 | 3 | | | | | |
| 599 | > 11.2100 | 1 | 3 | 3 | 3 | 3 | 3 | 3 | 3 | 3 | 3 | | | | | |
| 600 | > 11.2100 | 1 | 0 | 1 | 0 | 3 | 3 | 3 | 3 | 2 | 3 | | | | | |
| 601 | : 11.2100 | 2 | 0 | 1 | 1 | 3 | 3 | 2 | 3 | 3 | 3 | | | | | |
| 602 | : 11.2100 | 0 | 0 | 0 | 0 | 0 | 0 | 0 | 1 | 2 | 0 | | | | | |
| 603 | : 11.2100 | 0 | 3 | 0 | 3 | 3 | 2 | 0 | 3 | 3 | 3 | | | | | |
| 604 | ; 11.2100 | 0 | 3 | 3 | 3 | 3 | 3 | 3 | 3 | 3 | 3 | | | | | |
| 605 | ; 11.2100 | 3 | 0 | 3 | 2 | 3 | 3 | 3 | 3 | 3 | 3 | | | | | |
| 606 | ; 11.2100 | 0 | 0 | 0 | 0 | 0 | 0 | 0 | 0 | 0 | 0 | | | | | |
| 607 | ; 11.2100 | 3 | 1 | 3 | 2 | 3 | 3 | 3 | 3 | 3 | 3 | | | | | |
| 608 | ; 11.2100 | 0 | 3 | 3 | 3 | 3 | 3 | 0 | 3 | 3 | 3 | | | | | |
| 609 | > 11.2100 | 1 | 0 | 0 | 1 | 0 | 3 | 1 | 3 | 3 | 3 | | | | | |
| 610 | > 11.2100 | 0 | 0 | 0 | 0 | 0 | 3 | 2 | 3 | 3 | 3 | | | | | |
| 611 | > 11.2100 | 0 | 1 | 0 | 0 | 0 | 0 | 0 | 0 | 0 | 0 | | | | | |
| 612 | > 11.2100 | 0 | 0 | 0 | 0 | 0 | 1 | 0 | 1 | 1 | 3 | | | | | |
| 613 | > 11.2100 | 0 | 0 | 2 | 3 | 1 | 2 | 2 | 0 | 3 | 3 | | | | | |
| 614 | > 11.2100 | 3 | 3 | 3 | 3 | 3 | 3 | 3 | 3 | 3 | 3 | | | | | |
| 615 | > 11.2100 | 3 | 0 | 1 | 0 | 3 | 3 | 3 | 3 | 3 | 3 | | | | | |
| 616 | > 11.2100 | 0 | 3 | 0 | 0 | 2 | 1 | 1 | 3 | 3 | 3 | | | | | |
| 617 | 11.2100 | 0 | 0 | 0 | 0 | 0 | 2 | 0 | 1 | 0 | 1 | | | | | |
| 618 | 11.2100 | 0 | 2 | 2 | 1 | 3 | 2 | 0 | 3 | 3 | 3 | | | | | |
| 619 | 11.2100 | 0 | 0 | 0 | 0 | 1 | 1 | 0 | 1 | 1 | 3 | | | | | |
| 620 | 11.2100 | 0 | 0 | 0 | 0 | 3 | 2 | 0 | 3 | 3 | 3 | | | | | |
| 621 | 11.2100 | 0 | 0 | 1 | 1 | 3 | 1 | 0 | 3 | 3 | 3 | | | | | |
| 622 | } 11.2100 | 2 | 0 | 3 | 2 | 3 | 3 | 3 | 3 | 3 | 3 | | | | | |
| 623 | } 11.2100 | 0 | 0 | 0 | 0 | 0 | 0 | 0 | 1 | 1 | 2 | | | | | |
| 624 | 11.2100 | 3 | 3 | 3 | 3 | 3 | 3 | 3 | 3 | 3 | 3 | | | | | |
| 625 | 11.2100 | 3 | 3 | 3 | 3 | 3 | 3 | 3 | 3 | 3 | 3 | | | | | |
| 626 | 11.2100 | 2 | 3 | 3 | 3 | 3 | 3 | 3 | 3 | 3 | 3 | | | | | |
| 627 | 11.2100 | 0 | 3 | 3 | 3 | 3 | 3 | 0 | 3 | 3 | 3 | | | | | |
| 629 | 11.2100 | 3 | 0 | 3 | 0 | 3 | 3 | 3 | 3 | 2 | 3 | | | | | |
| 630 | 11.2100 | 1 | 3 | 3 | 3 | 3 | 3 | 0 | 3 | 3 | 3 | | | | | |
| 631 | 11.2100 | 2 | 1 | 2 | 0 | 3 | 3 | 2 | 3 | 3 | 3 | | | | | |
| 632 | 11.2100 | 2 | 3 | 3 | 3 | 3 | 3 | 0 | 3 | 3 | 3 | | | | | |
| 633 | 11.2100 | 2 | 2 | 3 | 0 | 3 | 3 | 2 | 3 | 3 | 3 | | | | | |
| 634 | 11.2100 | 3 | 3 | 3 | 2 | 3 | 3 | 3 | 3 | 3 | 3 | | | | | |
| 635 | 11.2100 | 2 | 3 | 3 | 2 | 3 | 3 | 3 | 3 | 3 | 3 | | | | | |
| 636 | 11.2100 | 1 | 3 | 3 | 3 | 3 | 3 | 0 | 3 | 3 | 3 | | | | | |
| 637 | 11.2100 | 1 | 3 | 3 | 3 | 3 | 3 | 2 | 3 | 3 | 3 | | | | | |
| 638 | 11.2100 | 0 | 2 | 1 | 0 | 1 | 3 | 0 | 0 | 1 | 0 | | | | | |
| 639 | 11.2100 | 2 | 3 | 3 | 3 | 3 | 3 | 0 | 3 | 3 | 3 | | | | | |
| 640 | 11.2100 | 3 | 3 | 3 | 3 | 3 | 3 | 0 | 3 | 3 | 3 | | | | | |
| 641 | 11.2100 | 2 | 3 | 3 | 3 | 3 | 3 | 3 | 3 | 3 | 3 | | | | | |
| 642 | 11.2100 | 3 | 3 | 3 | 2 | 3 | 3 | 3 | 3 | 3 | 3 | | | | | |
| 643 | 11.2100 | 2 | 3 | 3 | 3 | 3 | 3 | 1 | 3 | 3 | 3 | | | | | |
| 644 | 11.2100 | 2 | 3 | 3 | 3 | 3 | 3 | 2 | 3 | 3 | 3 | | | | | |
| 645 | 11.2100 | 0 | 0 | 0 | 0 | 1 | 2 | 0 | 3 | 1 | 2 | | | | | |
| 646 | 11.2100 | 2 | 3 | 3 | 3 | 3 | 3 | 2 | 3 | 3 | 3 | | | | | |
| 647 | 11.2100 | 1 | 0 | 2 | 1 | 3 | 1 | 0 | 3 | 3 | 3 | | | | | |
| 648 | 11.2100 | 2 | 0 | 0 | 0 | 2 | 2 | 0 | 3 | 3 | 3 | | | | | |
| 649 | 11.2100 | 2 | 0 | 0 | 0 | 0 | 2 | 0 | 3 | 0 | 2 | | | | | |
| 650 | 11.2100 | 2 | 3 | 3 | 3 | 3 | 2 | 3 | 3 | 3 | 3 | | | | | |
| 651 | 11.2100 | 2 | 0 | 0 | 0 | 2 | 2 | 1 | 3 | 3 | 2 | | | | | |
| 652 | 11.2100 | 3 | 2 | 3 | 3 | 3 | 3 | 3 | 3 | 3 | 3 | | | | | |
| 653 | 11.2100 | 2 | 3 | 3 | 3 | 3 | 3 | 2 | 3 | 3 | 3 | | | | | |
| 654 | 11.2100 | 1 | 0 | 1 | 0 | 1 | 3 | 2 | 3 | 3 | 3 | | | | | |
| 655 | 11.2100 | 1 | 3 | 3 | 3 | 3 | 3 | 1 | 3 | 3 | 3 | | | | | |
| 656 | 11.2100 | 0 | 0 | 1 | 0 | 1 | 2 | 3 | 3 | 3 | 3 | | | | | |
| 657 | 11.2100 | 2 | 0 | 0 | 0 | 1 | 3 | 2 | 3 | 3 | 3 | | | | | |
| 658 | 11.2100 | 0 | 0 | 1 | 0 | 2 | 3 | 1 | 1 | 3 | 3 | | | | | |
| 659 | 11.2100 | 2 | 0 | 0 | 0 | 1 | 1 | 1 | 3 | 3 | 3 | | | | | |
| 660 | 11.2100 | 0 | 0 | 0 | 0 | 0 | 2 | 1 | 3 | 3 | 3 | | | | | |
| 661 | 11.2100 | 2 | 2 | 3 | 0 | 3 | 2 | 3 | 3 | 2 | 3 | | | | | |
| 662 | 11.2100 | 1 | 3 | 3 | 3 | 3 | 3 | 1 | 3 | 3 | 3 | | | | | |
| 663 | > 11.2100 | 1 | 0 | 0 | 0 | 0 | 0 | 0 | 1 | 1 | 0 | | | | | |
| 664 | > 11.2100 | 1 | 0 | 1 | 0 | 3 | 1 | 2 | 3 | 3 | 3 | | | | | |
| 665 | > 11.2100 | 0 | 0 | 1 | 0 | 1 | 2 | 0 | 3 | 3 | 3 | | | | | |
| 666 | & 11.2100 | 3 | 3 | 3 | 3 | 3 | 3 | 0 | 3 | 3 | 3 | | | | | |
| 667 | & 11.2100 | 3 | 3 | 3 | 3 | 3 | 3 | 3 | 3 | 3 | 3 | | | | | |
| 668 | > 11.2100 | 0 | 2 | 3 | 0 | 3 | 2 | 1 | 3 | 3 | 3 | | | | | |
| 669 | > 11.2100 | 0 | 0 | 0 | 0 | 1 | 1 | 0 | 2 | 3 | 3 | | | | | |
| 670 | > 11.2100 | 0 | 3 | 3 | 3 | 3 | 1 | 1 | 3 | 3 | 3 | | | | | |
| 671 | > 11.2100 | 0 | 0 | 1 | 0 | 1 | 2 | 1 | 2 | 3 | 3 | | | | | |
| 672 | > 11.2100 | 0 | 0 | 1 | 0 | 2 | 1 | 0 | 2 | 3 | 3 | | | | | |

TABLE A-continued

| | | Herbicide Primary Pre, spectrums 25 and 90 | | | | | | | | | | | | |
|---|---|---|---|---|---|---|---|---|---|---|---|---|---|---|
| Ex. No. | Rate kg/ha | Yens | Abng | Sejg | Dobr | Bygr | Mogl | Cobu | Vele | Inmu | Wibw | Cath | Colq | Pesw | Rhqg | Rhjg |
| 673 | > 11.2100 | 0 | 0 | 1 | 0 | 0 | 0 | 0 | 0 | 1 | 3 | | | | |
| 674 | & 11.2100 | 3 | 3 | 3 | 3 | 3 | 3 | 0 | 3 | 3 | 3 | | | | |
| 675 | & 11.2100 | 0 | 3 | 3 | 3 | 3 | 3 | 0 | 3 | 3 | 3 | | | | |
| 676 | $ 11.2100 | 3 | 0 | 0 | 0 | 1 | 3 | 3 | 3 | 2 | 3 | | | | |
| 677 | $ 11.2100 | 2 | 1 | 2 | 0 | 1 | 3 | 1 | 3 | 3 | 3 | | | | |
| 678 | $ 11.2100 | 0 | 3 | 3 | 3 | 3 | 3 | 2 | 3 | 3 | 3 | | | | |
| 679 | $ 11.2100 | 0 | 2 | 3 | 3 | 3 | 2 | 3 | 3 | 3 | 3 | | | | |
| 680 | > 11.2100 | 0 | 2 | 2 | 2 | 1 | 0 | 1 | 0 | N | 3 | | | | |
| 681 | $ 11.2100 | 0 | 0 | 0 | 0 | 0 | 0 | 0 | 0 | 0 | 0 | | | | |
| 682 | 11.2100 | 0 | 3 | 2 | 3 | 3 | 3 | 1 | 3 | 3 | 3 | | | | |
| 683 | 11.2100 | 0 | 3 | 3 | 3 | 3 | 3 | 1 | 3 | 3 | 3 | | | | |
| 684 | 11.2100 | 0 | 0 | 0 | 0 | 2 | 1 | 0 | 3 | 3 | 3 | | | | |
| 685 | 11.2100 | 0 | 3 | 3 | 3 | 3 | 0 | 3 | 3 | 3 | 3 | | | | |
| 686 | 11.2100 | 0 | 3 | 3 | 2 | 3 | 2 | 0 | 2 | 2 | 3 | | | | |
| 687 | 11.2100 | 0 | 3 | 3 | 3 | 3 | 1 | 1 | 3 | 3 | 3 | | | | |
| 688 | 11.2100 | 0 | 0 | 0 | 0 | 0 | 1 | 1 | 1 | 3 | 3 | | | | |
| 689 | 11.2100 | 0 | 3 | 3 | 3 | 3 | 3 | 1 | 3 | 3 | 3 | | | | |
| 690 | 11.2100 | 0 | 3 | 3 | 3 | 3 | 2 | 0 | 3 | 3 | 3 | | | | |
| 691 | 11.2100 | 0 | 2 | 1 | 0 | 1 | 1 | 0 | 2 | 2 | 3 | | | | |
| 692 | 11.2100 | 0 | 1 | 0 | 0 | 2 | 0 | 0 | 0 | 1 | 3 | | | | |
| 693 | 11.2100 | 0 | 3 | 3 | 3 | 3 | 3 | 2 | 3 | 3 | 3 | | | | |
| 694 | 11.2100 | 0 | 1 | 3 | 0 | 3 | 2 | 0 | 3 | 3 | 3 | | | | |
| 695 | 11.2100 | 2 | 3 | 3 | 2 | 3 | 3 | 1 | 3 | 3 | 3 | | | | |
| 696 | 11.2100 | 0 | 2 | 3 | 1 | 3 | 3 | 2 | 3 | 3 | 3 | | | | |
| 697 | 11.2100 | 1 | 3 | 3 | 3 | 3 | 3 | 2 | 3 | 3 | 3 | | | | |
| 698 | 11.2100 | 2 | 3 | 3 | 3 | 3 | 3 | 2 | 3 | 3 | 3 | | | | |
| 699 | 11.2100 | 0 | 3 | 2 | 2 | 2 | 3 | 3 | 3 | 3 | 3 | | | | |
| 700 | 11.2100 | 0 | 3 | 3 | 3 | 3 | 2 | 1 | 3 | 3 | 3 | | | | |
| 701 | 11.2100 | 0 | 3 | 0 | 0 | 1 | 3 | 3 | 3 | 3 | 3 | | | | |
| 702 | 11.2100 | 0 | 3 | 1 | 1 | 3 | 3 | 1 | 3 | 3 | 3 | | | | |
| 703 | 11.2100 | 0 | 0 | 0 | 0 | 0 | 3 | 3 | 3 | 3 | 3 | | | | |
| 704 | 11.2100 | 0 | 2 | 1 | 1 | 3 | 3 | 1 | 3 | 3 | 3 | | | | |
| 705 | 11.2100 | 0 | 3 | 1 | 1 | 3 | 3 | 3 | 3 | 3 | 3 | | | | |
| 706 | 11.2100 | 0 | 3 | 3 | 3 | 3 | 3 | 2 | 3 | 3 | 3 | | | | |
| 707 | 11.2100 | 1 | 3 | 3 | 3 | 3 | 3 | 1 | 3 | 3 | 3 | | | | |
| 708 | 11.2100 | 0 | 3 | 1 | 1 | 3 | 3 | 3 | 3 | 3 | 3 | | | | |
| 709 | 11.2100 | 0 | 3 | 3 | 3 | 3 | 3 | 0 | 3 | 3 | 3 | | | | |
| 710 | 11.2100 | 0 | 3 | 2 | 3 | 3 | 3 | 2 | 3 | 3 | 3 | | | | |
| 711 | 11.2100 | 0 | 2 | 1 | 0 | 2 | 0 | 0 | 1 | 0 | 0 | | | | |
| 712 | 11.2100 | 0 | 2 | 1 | 0 | 0 | 3 | 3 | 3 | 3 | 3 | | | | |
| 713 | 11.2100 | 3 | 3 | 0 | 3 | 3 | 1 | 3 | 1 | 3 | 3 | | | | |
| 714 | 11.2100 | 0 | 3 | 3 | 3 | 3 | 3 | 2 | 3 | 3 | 3 | | | | |
| 715 | 11.2100 | 0 | 0 | 1 | 0 | 1 | 2 | 3 | 1 | 2 | 1 | | | | |
| 716 | 11.2100 | 3 | 2 | 3 | 3 | 3 | 3 | 3 | 3 | 3 | 3 | | | | |
| 717 | 11.2100 | 0 | 3 | 3 | 1 | 3 | 3 | 0 | 3 | 1 | 3 | | | | |
| 718 | 11.2100 | 3 | 0 | 3 | 0 | 3 | 3 | 3 | 3 | 3 | 3 | | | | |
| 719 | 11.2100 | 0 | 2 | 3 | 2 | 0 | 3 | 1 | 3 | 2 | 3 | | | | |
| 720 | 11.2100 | 1 | 3 | 3 | 3 | 3 | 3 | 2 | 3 | 3 | 3 | | | | |
| 721 | 11.2100 | 0 | 0 | 0 | 0 | 0 | 0 | 0 | 0 | 0 | 0 | | | | |
| 722 | . 11.2100 | 0 | 3 | 3 | 3 | 3 | 3 | 0 | 3 | 3 | 3 | | | | |
| 723 | . 11.2100 | 0 | 3 | 3 | 3 | 3 | 3 | 2 | 3 | 3 | 3 | | | | |
| 724 | . 11.2100 | 0 | 1 | 1 | 0 | 1 | 2 | 0 | 3 | 3 | 2 | | | | |
| 725 | ; 11.2100 | 2 | 3 | 3 | 3 | 3 | 3 | 3 | 3 | 3 | 3 | | | | |
| 726 | ; 11.2100 | 0 | 3 | 3 | 3 | 2 | 1 | 0 | 2 | 2 | 3 | | | | |
| 727 | . 11.2100 | 0 | 3 | 3 | 3 | 3 | 1 | 1 | 2 | 2 | 3 | | | | |
| 728 | , 11.2100 | 1 | 0 | 1 | 0 | 1 | 1 | 3 | 3 | 2 | 3 | | | | |
| 729 | ; 11.2100 | 2 | 3 | 3 | 3 | 3 | 3 | 3 | 3 | 3 | 3 | | | | |
| 730 | > 11.2100 | 3 | 3 | 3 | 3 | 3 | 3 | 3 | 3 | 3 | 3 | | | | |
| 731 | > 11.2100 | 2 | 0 | 1 | 0 | 1 | 3 | 3 | 3 | 3 | 3 | | | | |
| 732 | 11.2100 | 3 | 1 | 3 | 0 | 3 | 3 | 2 | 3 | 3 | 3 | | | | |
| 733 | > 11.2100 | 0 | 0 | 2 | 0 | 2 | 0 | 0 | 0 | 0 | 1 | | | | |
| 734 | > 11.2100 | 0 | 0 | 2 | 0 | 1 | 0 | 0 | 1 | 0 | 1 | | | | |
| 735 | 11.2100 | 3 | 3 | 3 | 3 | 3 | 3 | 3 | 3 | 3 | 3 | | | | |
| 736 | 11.2100 | 2 | 3 | 3 | 0 | 3 | 3 | 3 | 3 | 3 | 3 | | | | |
| 737 | 11.2100 | 0 | 0 | 2 | 0 | 2 | 0 | 0 | 1 | 2 | 1 | | | | |
| 738 | 11.2100 | 3 | 3 | 3 | 3 | 3 | 3 | 1 | 3 | 3 | 3 | | | | |
| 739 | 11.2100 | 0 | 0 | 1 | 0 | 2 | 0 | 0 | 0 | 2 | 2 | | | | |
| 740 | 11.2100 | 3 | 3 | 3 | 0 | 3 | 2 | 3 | 3 | 3 | 3 | | | | |
| 741 | 11.2100 | 1 | 0 | 0 | 0 | 1 | 3 | 3 | 3 | 2 | 3 | | | | |
| 742 | 11.2100 | 0 | 1 | 1 | 0 | 3 | 3 | 3 | 3 | 3 | 3 | | | | |
| 743 | 11.2100 | 1 | 0 | 0 | 0 | 0 | 1 | 3 | 0 | 0 | 1 | | | | |
| 744 | 11.2100 | 1 | 3 | 0 | 3 | 3 | 0 | 0 | 0 | 3 | 3 | | | | |
| 745 | 11.2100 | 0 | 2 | 0 | 2 | 3 | 3 | 2 | 3 | 3 | 3 | | | | |
| 746 | 11.2100 | 0 | 1 | 0 | 0 | 1 | 2 | 1 | 3 | 3 | 3 | | | | |
| 747 | 11.2100 | 3 | 0 | 0 | 0 | 1 | 3 | 2 | 3 | 1 | 3 | | | | |
| 748 | 11.2100 | 3 | 0 | 0 | 0 | 3 | 3 | 3 | 3 | 2 | 3 | | | | |
| 749 | 11.2100 | 0 | 1 | 0 | 1 | 2 | 3 | 2 | 3 | 3 | 3 | | | | |

TABLE A-continued

Herbicide Primary Pre, spectrums 25 and 90

| Ex. No. | | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|---|
| 750 | | 11.2100 | 3 | 0 | 0 | 0 | 2 | 3 | 3 | 3 | 3 | 3 | | | | | |
| 751 | | 11.2100 | 3 | 0 | 1 | 0 | 1 | 3 | 2 | 3 | 3 | 3 | | | | | |
| 752 | | 11.2100 | 1 | 0 | 0 | 0 | 2 | 3 | 3 | 3 | 3 | 3 | | | | | |
| 753 | | 11.2100 | 0 | 0 | 0 | 0 | 0 | 1 | 1 | 0 | 0 | 0 | | | | | |
| 754 | | 11.2100 | 2 | 0 | 0 | 0 | 1 | 3 | 1 | 3 | 1 | 3 | | | | | |
| 755 | | 11.2100 | 1 | 3 | 3 | 3 | 3 | 3 | 3 | 3 | 3 | 3 | | | | | |
| 756 | | 11.2100 | 3 | 0 | 1 | 0 | 3 | 3 | 2 | 3 | 3 | 3 | | | | | |
| 757 | | 11.2100 | 2 | 0 | 0 | 0 | 1 | 3 | 2 | 3 | 3 | 3 | | | | | |
| 758 | | 11.2100 | 0 | 0 | 0 | 0 | 0 | 1 | 0 | 3 | 3 | 3 | | | | | |
| 759 | | 11.2100 | 2 | 0 | 0 | 0 | 2 | 3 | 3 | 3 | 2 | 3 | | | | | |
| 760 | | 11.2100 | 2 | 0 | 0 | 0 | 0 | 3 | 1 | 3 | 2 | 2 | | | | | |
| 761 | | 11.2100 | 3 | 0 | 0 | 0 | 2 | 3 | 2 | 3 | 3 | 3 | | | | | |
| 762 | | 11.2100 | 0 | 3 | 3 | 0 | 3 | 3 | 3 | 3 | 3 | 3 | | | | | |
| 763 | | 11.2100 | 1 | 3 | 3 | 3 | 3 | 3 | 2 | 3 | 3 | 3 | | | | | |
| 764 | | 11.2100 | 2 | 3 | 2 | 0 | 3 | 3 | 0 | 3 | 3 | 3 | | | | | |
| 765 | | 11.2100 | 0 | 3 | 3 | 3 | 3 | 1 | 0 | 3 | 3 | 3 | | | | | |
| 766 | | 11.2100 | 0 | 3 | 1 | 1 | 3 | 2 | 0 | 3 | 3 | 3 | | | | | |
| 767 | | 11.2100 | 0 | 3 | 3 | 3 | 3 | 3 | 2 | 3 | 3 | 3 | | | | | |
| 768 | | 11.2100 | 0 | 3 | 3 | 3 | 3 | 3 | 3 | 3 | 3 | 3 | | | | | |
| 769 | | 11.2100 | 0 | 3 | 3 | 2 | 2 | 1 | 0 | 3 | 3 | 3 | | | | | |
| 770 | | 11.2100 | 0 | 3 | 3 | 3 | 3 | 3 | 2 | 3 | 0 | 3 | | | | | |
| 771 | | 11.2100 | 0 | 3 | 3 | 3 | 3 | 3 | 3 | 3 | 3 | 3 | | | | | |
| 772 | | 11.2100 | 0 | 3 | 3 | 3 | 3 | 3 | 3 | 3 | 3 | 3 | | | | | |
| 773 | | 11.2100 | 2 | 3 | 3 | 1 | 3 | 3 | 3 | 3 | 3 | 3 | | | | | |
| 774 | . | 11.2100 | 0 | 3 | 3 | 3 | 3 | 3 | 3 | 3 | 3 | 3 | | | | | |
| 775 | | 11.2100 | 0 | 3 | 3 | 3 | 3 | 3 | 1 | 3 | 3 | 3 | | | | | |
| 776 | | 11.2100 | 0 | 1 | 0 | 0 | 2 | 0 | 0 | 0 | 0 | 3 | | | | | |
| 777 | . | 11.2100 | 0 | 3 | 3 | 3 | 3 | 3 | 1 | 3 | 3 | 3 | | | | | |
| 778 | . | 11.2100 | 0 | 3 | 3 | 3 | 3 | 3 | 3 | 3 | 3 | 3 | | | | | |
| 779 | . | 11.2100 | 0 | 3 | 3 | 3 | 3 | 3 | 1 | 3 | 3 | 3 | | | | | |
| 780 | | 11.2100 | 0 | 0 | 0 | 0 | 0 | 0 | 0 | 0 | 0 | 0 | | | | | |
| 781 | | 11.2100 | 3 | 3 | 3 | 3 | 3 | 3 | 3 | 3 | 3 | 3 | | | | | |
| 782 | | 11.2100 | 1 | 0 | 0 | 0 | 1 | 3 | 2 | 3 | 0 | 1 | | | | | |
| 783 | | 11.2100 | 1 | 0 | 0 | 0 | 0 | 3 | 3 | 3 | 2 | 2 | | | | | |
| 784 | | 11.2100 | 1 | 0 | 0 | 0 | 0 | 3 | 1 | 3 | 3 | 2 | | | | | |
| 785 | | 11.2100 | 0 | 0 | 0 | 0 | 0 | 2 | 2 | 3 | 3 | 3 | | | | | |
| 786 | | 11.2100 | 2 | 1 | 2 | 0 | 3 | 3 | 0 | 3 | 3 | 3 | | | | | |
| 787 | | 11.2100 | 2 | 0 | 1 | 0 | 1 | 3 | 1 | 3 | 2 | 3 | | | | | |
| 788 | | 11.2100 | 3 | 2 | 3 | 3 | 3 | 3 | 2 | 3 | 3 | 3 | | | | | |
| 789 | | 11.2100 | 3 | 0 | 1 | 0 | 2 | 3 | 3 | 3 | 3 | 3 | | | | | |
| 790 | | 11.2100 | 0 | 0 | 2 | 0 | 2 | 3 | 1 | 3 | 3 | 3 | | | | | |
| 791 | | 11.2100 | 2 | 0 | 1 | 0 | 2 | 3 | 2 | 3 | 3 | 3 | | | | | |
| 792 | | 11.2100 | 1 | 3 | 3 | 3 | 3 | 3 | 3 | 3 | 3 | 3 | | | | | |
| 793 | | 11.2100 | 3 | 0 | 1 | 0 | 1 | 3 | 1 | 3 | 2 | 3 | | | | | |
| 794 | { | 11.2100 | 0 | 0 | 0 | 0 | 1 | 2 | 0 | 3 | 0 | 3 | | | | | |
| 795 | | 11.2100 | 1 | 3 | 3 | 3 | 3 | 3 | 3 | 3 | 3 | 3 | | | | | |
| 796 | | 11.2100 | 0 | 3 | 3 | 3 | 3 | 3 | 1 | 2 | 3 | 3 | | | | | |
| 797 | | 11.2100 | 0 | 1 | 1 | 0 | 1 | 0 | 0 | 1 | 0 | 2 | | | | | |
| 798 | | 11.2100 | 3 | 3 | 3 | 3 | 3 | 3 | 3 | 3 | 3 | 3 | | | | | |
| 799 | | 11.2100 | 3 | 1 | 0 | 0 | 3 | 3 | 3 | 3 | 3 | 3 | | | | | |
| 800 | | 11.2100 | 3 | 0 | 0 | 0 | 3 | 3 | 3 | 3 | 3 | 3 | | | | | |
| 801 | | 11.2100 | 1 | 3 | 3 | 2 | 3 | 3 | 2 | 3 | 3 | 3 | | | | | |
| 802 | | 11.2100 | 2 | 1 | 1 | 0 | 2 | 3 | 3 | 3 | 3 | 3 | | | | | |
| 803 | | 11.2100 | 0 | 0 | 0 | 0 | 2 | 0 | 0 | 3 | 0 | 2 | | | | | |
| 804 | | 11.2100 | 0 | 0 | 0 | 0 | 0 | 0 | 0 | 0 | 0 | 0 | | | | | |
| 805 | | 11.2100 | 3 | 0 | 1 | 0 | 2 | 3 | 3 | 3 | 3 | 3 | | | | | |
| 806 | | 11.2100 | 2 | 0 | 1 | 0 | 2 | 3 | 0 | 3 | 3 | 3 | | | | | |
| 807 | | 11.2100 | 0 | 0 | 0 | 0 | 0 | 0 | 0 | 0 | 0 | 0 | | | | | |
| 808 | | 11.2100 | 3 | 0 | 0 | 0 | 3 | 3 | 3 | 3 | 3 | 3 | | | | | |
| 809 | | 11.2100 | 0 | 0 | 2 | 0 | 3 | 3 | 2 | 3 | 3 | 1 | | | | | |
| 810 | | 11.2100 | 2 | 3 | 3 | 3 | 3 | 3 | 3 | 3 | 3 | 3 | | | | | |
| 811 | | 11.2100 | 3 | 0 | 0 | 0 | 0 | 3 | 2 | 3 | 2 | 3 | | | | | |
| 812 | | 11.2100 | 3 | 0 | 0 | 0 | 0 | 3 | 0 | 3 | 3 | 3 | | | | | |
| 813 | | 11.2100 | 3 | 0 | 0 | 0 | 0 | 3 | 3 | 3 | 2 | 3 | | | | | |
| 814 | | 11.2100 | 2 | 0 | 0 | 0 | 0 | 2 | 0 | 1 | 0 | 3 | | | | | |
| 815 | | 11.2100 | 3 | 3 | 3 | 3 | 3 | 3 | 3 | 3 | 3 | 3 | | | | | |
| 816 | | 11.2100 | 3 | 0 | 0 | 0 | 1 | 3 | 3 | 3 | 1 | 3 | | | | | |
| 817 | | 11.2100 | 2 | 0 | 0 | 0 | 0 | 3 | 2 | 3 | 2 | 0 | | | | | |
| 818 | | 11.2100 | 1 | 3 | 3 | 3 | 3 | 3 | 2 | 3 | 3 | 3 | | | | | |
| 819 | , | 11.2100 | 1 | 3 | 3 | 3 | 3 | 3 | 1 | 3 | 3 | 3 | | | | | |
| 820 | > | 11.2100 | 0 | 0 | 0 | 0 | 0 | 0 | 0 | 0 | 0 | 0 | | | | | |
| 821 | . | 11.2100 | 0 | 1 | 2 | 0 | 3 | 2 | 0 | 3 | 1 | 3 | | | | | |
| 822 | > | 11.2100 | 3 | 3 | 3 | 2 | 3 | 2 | 1 | 3 | 3 | 3 | | | | | |
| 823 | . | 11.2100 | 3 | 3 | 3 | 3 | 3 | 3 | 1 | 3 | 3 | 3 | | | | | |
| 824 | . | 11.2100 | 3 | 0 | 1 | 0 | 1 | 3 | 1 | 3 | 3 | 3 | | | | | |
| 825 | | 11.2100 | 0 | 3 | 2 | 3 | 3 | 3 | 0 | 3 | 3 | 3 | | | | | |
| 826 | | 11.2100 | 0 | 3 | 3 | 0 | 0 | 0 | 0 | 0 | 1 | 3 | | | | | |

TABLE A-continued

Herbicide Primary Pre, spectrums 25 and 90

| Ex. No. | | Rate kg/ha | Yens | Anbg | Sejbg | Dobr | Bygr | Mogl | Cblu | Vloe | Inmbu | Wibw | Cathq | Clsqw | Pehqg | Rhjg |
|---|---|---|---|---|---|---|---|---|---|---|---|---|---|---|---|---|
| 827 | | 11.2100 | 0 | 3 | 1 | 3 | 0 | 0 | 0 | 0 | 3 | 3 | | | | |
| 828 | | 11.2100 | 2 | 3 | 3 | 3 | 3 | 3 | 3 | 3 | 3 | 3 | | | | |
| 829 | | 11.2100 | 1 | 3 | 3 | 3 | 3 | 2 | 1 | 3 | 3 | 3 | | | | |
| 830 | | 11.2100 | 1 | 3 | 3 | 3 | 3 | 2 | 0 | 3 | 3 | 3 | | | | |
| 831 | | 11.2100 | 3 | 3 | 3 | 3 | 3 | 3 | 3 | 3 | 3 | 3 | | | | |
| 835 | | 11.2100 | 0 | 0 | 0 | 0 | 0 | 1 | 0 | 1 | 0 | 0 | | | | |
| 836 | | 11.2100 | 3 | 3 | 3 | 3 | 3 | 3 | 3 | 3 | 3 | 3 | | | | |
| 837 | | 11.2100 | 0 | 0 | 0 | 0 | 0 | 0 | 0 | 3 | 0 | 0 | | | | |
| 838 | | 11.2100 | 2 | 0 | 3 | 3 | 3 | 3 | 3 | 3 | 3 | 3 | | | | |
| 839 | | 11.2100 | 2 | 0 | 3 | 3 | 3 | 3 | 3 | 3 | 3 | 3 | | | | |
| 840 | | 11.2100 | 2 | 0 | 3 | 3 | 3 | 3 | 3 | 3 | 3 | 3 | | | | |
| 841 | | 11.2100 | 2 | 0 | 0 | 0 | 0 | 3 | 2 | 3 | 3 | 3 | | | | |
| 842 | | 11.2100 | 3 | 0 | 3 | 0 | 3 | 3 | 3 | 3 | 3 | 3 | | | | |
| 843 | | 11.2100 | 3 | 3 | 3 | 2 | 3 | 3 | 3 | 3 | 3 | 3 | | | | |
| 844 | | 11.2100 | 0 | 3 | 3 | 2 | 3 | 3 | 0 | 3 | 3 | 3 | | | | |
| 845 | | 11.2100 | 2 | 0 | 2 | 0 | 3 | 3 | 3 | 3 | 3 | 2 | | | | |
| 846 | | 11.2100 | 0 | 0 | 0 | 0 | 0 | 3 | 1 | 3 | 3 | 3 | | | | |
| 847 | | 11.2100 | 0 | 1 | 1 | 0 | 3 | 3 | 3 | 3 | 3 | 3 | | | | |
| 848 | | 11.2100 | 0 | 0 | 0 | 0 | 2 | 3 | 0 | 3 | 3 | 3 | | | | |
| 849 | | 11.2100 | 0 | 0 | 0 | 0 | 2 | 3 | 0 | 3 | 3 | 3 | | | | |
| 850 | | 11.2100 | 3 | 0 | 2 | 0 | 3 | 3 | 3 | 3 | 3 | 3 | | | | |
| 851 | | 11.2100 | 1 | 0 | 0 | 0 | 1 | 3 | 0 | 3 | 2 | 3 | | | | |
| 852 | | 11.2100 | 1 | 0 | 1 | 0 | 1 | 3 | 2 | 3 | 3 | 3 | | | | |
| 853 | | 11.2100 | 0 | 0 | 0 | 0 | 0 | 0 | 0 | 1 | 0 | 0 | | | | |
| 854 | B | 11.2100 | 0 | 3 | 2 | 2 | 3 | 3 | 1 | 3 | 3 | 3 | | | | |
| 855 | B | 11.2100 | 0 | 0 | 0 | 0 | 0 | 0 | 0 | 2 | 0 | 3 | | | | |
| 856 | > | 11.2100 | 0 | 0 | 0 | 0 | 0 | 0 | 0 | 0 | 2 | 3 | | | | |
| 857 | > | 11.2100 | 0 | 3 | 3 | 3 | 3 | 2 | 0 | 3 | 3 | 3 | | | | |
| 858 | | 11.2100 | 1 | 3 | 3 | 1 | 3 | 3 | 0 | 3 | 3 | 3 | | | | |
| 859 | | 11.2100 | 0 | 3 | 3 | 3 | 3 | 3 | 0 | 3 | 3 | 3 | | | | |
| 860 | | 11.2100 | 0 | 0 | 2 | 2 | 1 | 3 | 2 | 3 | 3 | 3 | | | | |
| 862 | | 11.2100 | 3 | 0 | 0 | 0 | 2 | 3 | 3 | 3 | 3 | 3 | | | | |
| 863 | | 11.2100 | 3 | 0 | 0 | 0 | 2 | 3 | 3 | 3 | 3 | 3 | | | | |
| 864 | | 11.2100 | 2 | 0 | 0 | 0 | 1 | 3 | 3 | 3 | 3 | 3 | | | | |
| 865 | | 11.2100 | 3 | 0 | 0 | 0 | 0 | 3 | 2 | 3 | 2 | 3 | | | | |
| 866 | | 11.2100 | 3 | 0 | 0 | 0 | 0 | 3 | 0 | 3 | 3 | 3 | | | | |
| 867 | | 11.2100 | 2 | 0 | 1 | 0 | 2 | 3 | 1 | 3 | 3 | 3 | | | | |
| 868 | | 11.2100 | 1 | 3 | 3 | 3 | 3 | 3 | 1 | 3 | 3 | 3 | | | | |
| 869 | | 11.2100 | 3 | 0 | 0 | 0 | 1 | 3 | 2 | 3 | 2 | 3 | | | | |
| 870 | | 11.2100 | 3 | 0 | 1 | 0 | 1 | 3 | 1 | 3 | 2 | 3 | | | | |
| 871 | | 11.2100 | 3 | 0 | 0 | 0 | 1 | 3 | 1 | 3 | 3 | 3 | | | | |
| 872 | | 11.2100 | 0 | 3 | 3 | 3 | 3 | 3 | 2 | 3 | 3 | 3 | | | | |
| 873 | | 11.2100 | 0 | 3 | 3 | 3 | 3 | 3 | 1 | 3 | 3 | 3 | | | | |
| 874 | | 11.2100 | 2 | 2 | 3 | 1 | 3 | 3 | 3 | 3 | 3 | 3 | | | | |
| 875 | | 11.2100 | 2 | 0 | 2 | 0 | 3 | 3 | 1 | 3 | 3 | 3 | | | | |
| 876 | | 11.2100 | 3 | 0 | 1 | 0 | 0 | 3 | 1 | 3 | 2 | 3 | | | | |
| 877 | | 11.2100 | 3 | 1 | 2 | 0 | 3 | 3 | 0 | 3 | 3 | 3 | | | | |
| 878 | | 11.2100 | 3 | 0 | 1 | 2 | 3 | 3 | 1 | 3 | 1 | 3 | | | | |
| 879 | | 11.2100 | 3 | 2 | 0 | 1 | 3 | 3 | 0 | 3 | 2 | 3 | | | | |
| 880 | | 11.2100 | 0 | 0 | 1 | 0 | 2 | 3 | 0 | 3 | 0 | 3 | | | | |
| 881 | | 11.2100 | 3 | 0 | 0 | 0 | 2 | 2 | 0 | 3 | 2 | 0 | | | | |
| 882 | | 11.2100 | 2 | 0 | 0 | 0 | 1 | 3 | 1 | 3 | 3 | 3 | | | | |
| 883 | | 11.2100 | 3 | 0 | 0 | 0 | 3 | 3 | 1 | 3 | 2 | 3 | | | | |
| 884 | | 11.2100 | 3 | 0 | 1 | 0 | 3 | 3 | 1 | 3 | 2 | 3 | | | | |
| 885 | | 11.2100 | 0 | 3 | 3 | 2 | 3 | 3 | 1 | 3 | 3 | 3 | | | | |
| 886 | | 11.2100 | 0 | 2 | 2 | 3 | 3 | 3 | 0 | 3 | 3 | 3 | | | | |
| 887 | A | 11.2100 | 0 | 0 | 0 | 0 | 1 | 1 | 0 | 1 | 2 | 3 | | | | |
| 888 | A | 11.2100 | 1 | 0 | 2 | 0 | 3 | 0 | 0 | 2 | 2 | 3 | | | | |
| 889 | | 11.2100 | 2 | 1 | 1 | 0 | 3 | 3 | 0 | 3 | 2 | 3 | | | | |
| 890 | | 11.2100 | 1 | 3 | 2 | 1 | 3 | 3 | 0 | 3 | 3 | 3 | | | | |
| 891 | | 11.2100 | 3 | 0 | 1 | 0 | 2 | 3 | 0 | 3 | 1 | 3 | | | | |
| 892 | | 11.2100 | 0 | 3 | 3 | 3 | 3 | 3 | 3 | 3 | 3 | 3 | | | | |
| 893 | | 11.2100 | 3 | 0 | 1 | 0 | 3 | 3 | 1 | 3 | 3 | 3 | | | | |
| 896 | | 11.2100 | 0 | 0 | 2 | 0 | 1 | 0 | 0 | 1 | 2 | 3 | | | | |
| 897 | | 11.2100 | 2 | 3 | 3 | 3 | 3 | 3 | 0 | 3 | 3 | 3 | | | | |
| 898 | | 11.2100 | 0 | 0 | 3 | 3 | 3 | 3 | 1 | 3 | 3 | 3 | | | | |
| 899 | | 11.2100 | 0 | 0 | 0 | 0 | 0 | 0 | 0 | 0 | 0 | 0 | | | | |
| 900 | | 11.2100 | 0 | 0 | 0 | 0 | 0 | 3 | 1 | 3 | 3 | 3 | | | | |
| 901 | | 11.2100 | 0 | 0 | 0 | 0 | 0 | 3 | 0 | 3 | 3 | 3 | | | | |
| 902 | | 11.2100 | 3 | 3 | 3 | 3 | 3 | 3 | 1 | 3 | 3 | 3 | | | | |

TABLE A-continued

| | | Herbicide Primary Pre, spectrums 25 and 90 | | | | | | | | | | | | |
|---|---|---|---|---|---|---|---|---|---|---|---|---|---|---|
| Ex. No. | Rate kg/ha | Yens | Anbg | Sejg | Dobr | Bygr | Mogl | Cobu | Vene | Inmw | Wibw | Cath | Cosw | Pheq | Rhsg | Rhjg |
| 903 | 11.2100 | 1 | 0 | 2 | 0 | 3 | 3 | 0 | 3 | 3 | 3 | | | | |

\*DAMPING OFF-LQ.
  NO TO POOR SMARTWEED GERMINATION.
@ VEINAL CHLOROSIS-CB.
= POOR SMARTWEED GERMINATION
( POOR GERMINATION-SW
) POOR SW AND CA GERMINATION.
− POOR GERMINATION-CB,SJ.
  DAMPING OFF-IM,WB.
  FREQUENT DAMPING OFF-IM,WB.
< DAMPING OFF-IM,WB. POOR GERMINATION-CB.
> DAMPING OFF-IM,WB. POOR GERMINATION-WB.
$ DAMPING OFF-IM,WB. POOR GERMINATION-CB,WB.
& DAMPING OFF-IM,WB POOR GERMINATION-CB
> DAMPING OFFIM,WB. POOR GERMINATION-CB,WB.
: DAMPING OFF IM,WB.
; DAMPING OFF-IM. POOR GERMINATION-WB.
{ DAMPING OFF-IM.POOR GERMINATION-WB.
, DAMPING OFF - IM,WB. POOR GERMINATION - WB.
. DAMPING OFF-IM.
A DAMPING OFF- MG,CB,VL,IM,WB. POOR GERMINATION-WB.
B DAMPING OFF- IM,WB. POOR GERMINATION IM,WB.
C POOR GERMINATION-RJ, DAMPING OFF-DB.
D CHLOROSIS-CB

POST-EMERGENT HERBICIDE EXAMPLES

The post-emergence herbicidal activity of compounds of this invention was demonstrated by greenhouse testing, and the results are shown in the following Table B. The post-emergent herbicidal activity index used in Table B is as follows:

| Plant Response | Index |
|---|---|
| 0–24% inhibition | 0 |
| 25–49% inhibition | 1 |
| 50–74% inhibition | 2 |
| 75–99% inhibition | 3 |
| 100% inhibition | 4 |
| Species not planted | — or a blank |
| Species planted, no data | N |

Where appropriate, footnotes are shown at the end of the table.

As was the case with the pre-emergence data, some of the compounds initially received ratings for plant response directly as percent inhibition in ten percent increments. Where this is the case, the percentage have generally been converted according to the scale above.

POST-EMERGENCE ACTIVITY ON WEEDS

Top soil was placed in pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules were covered with soil and leveled. The pans were then placed on a bench in the greenhouse and watered as needed for germination and growth. After the plants reached the desired age (9–14 days), each pan (except the control pans) was removed to a spraying chamber and sprayed by means of an atomizer. The spray solution or suspension contained about 0.4% by volume of an emulsifying agent and a sufficient amount of the candidate chemical to give an application rate of the active ingredient of 11.2 kg/ha while applying a total amount of solution or suspension equivalent to 1870 L/Ha (200 gallons/acre). The pans were returned to the greenhouse and watered as before and the injury to the plants as compared to those in control pans was observed at approximately 10–14 days (usually 14 days) and in some instances observed again at 24–28 days (usually 25 days) after spraying. These latter observations are designated by a "pound" sign (#) following the column of example numbers in the Table. The plant species used in this set of tests were the same as those used in the first set of pre-emergence tests, and the plant identifying codes are the same as those shown for Table A.

TABLE B

| | | Herbicide Primary Post, spectrums 25 and 90 | | | | | | | | | | | | |
|---|---|---|---|---|---|---|---|---|---|---|---|---|---|---|
| Ex. No. | Rate kg/ha | Yens | Anbg | Sejg | Dobr | Bygr | Mogl | Cobu | Vene | Inmw | Wibw | Cath | Cosw | Pheq | Rhsg | Rhjg |
| 1 | 11.2100 | 2 | | — | 4 | 4 | 3 | 4 | | 2 | 4 | 3 | 1 | 1 |
| 2 | 11.2100 | 0 | 1 | 2 | 3 | 1 | 4 | | | 1 | 4 | 2 | 0 | 0 |
| 3 | 11.2100 | 1 | 0 | 4 | 3 | 2 | 3 | | | 0 | 4 | 3 | 0 | 2 |
| 4 | 11.2100 | 1 | 0 | 3 | 2 | 2 | 1 | | | 1 | 3 | 1 | 0 | 0 |
| 5 | 11.2100 | 2 | 4 | 4 | 4 | 3 | 4 | | | 4 | 4 | 4 | 4 | N |
| 6 | 11.2100 | 1 | 1 | 4 | 4 | 4 | 4 | | | 4 | 4 | 3 | 0 | 0 |
| 7 | 11.2100 | 1 | 2 | 4 | 3 | 3 | 4 | | | 2 | 4 | 4 | 2 | 1 |
| 8 | 11.2100 | 2 | 0 | 4 | 4 | 4 | 4 | | | 3 | — | 4 | 0 | 0 |
| 9 | 11.2100 | 1. | 0 | 0 | 3 | 1 | 4 | | | 0 | 4 | 2 | 0 | 0 |
| 10 | 11.2100 | 3 | 4 | 4 | 4 | 4 | 4 | | | 2 | 4 | 4 | 4 | 4 |
| 11 | 11.2100 | 2 | 4 | 4 | 4 | 4 | 4 | | | 3 | 4 | 4 | 2 | 2 |

TABLE B-continued

| | | | Herbicide Primary Post, spectrums 25 and 90 | | | | | | | | | | | | | |
|---|---|---|---|---|---|---|---|---|---|---|---|---|---|---|---|---|
| Ex. No. | | Rate kg/ha | Yens | Abng | Sejg | Dobr | Bygr | Mogl | Cobu | Vle | Imu | Wbw | Cath | Colq | Psw | Rhqg | Rhjg |
| 12 | | 11.2100 | 3 | | | 4 | 4 | 4 | 4 | 4 | | | 3 | 4 | 4 | 3 | 3 |
| 13 | | 11.2100 | 0 | 2 | 4 | 2 | 4 | 3 | 3 | 4 | 3 | 4 | | | | | |
| 15 | | 11.2100 | 0 | | | 0 | 2 | 2 | 0 | 0 | | | 0 | 1 | 1 | 0 | 0 |
| 16 | | 11.2100 | 2 | | | 3 | 4 | 3 | 3 | 3 | | | 1 | 4 | 4 | 2 | 3 |
| 17 | | 11.2100 | 0 | | | 0 | 0 | 0 | 0 | 1 | | | 0 | 0 | 0 | 0 | 0 |
| 18 | | 11.2100 | 0 | | | 0 | 0 | 2 | 1 | 3 | | | 2 | 0 | 0 | 0 | 0 |
| 19 | | 11.2100 | 0 | | | 0 | 1 | 2 | 0 | 0 | | | 0 | 1 | 0 | 0 | 0 |
| 20 | | 11.2100 | 0 | | | 0 | 4 | 4 | 3 | 4 | | | 1 | 4 | 2 | 0 | 0 |
| 21 | | 11.2100 | 1 | | | 0 | 3 | 3 | 1 | 4 | | | 1 | 4 | 3 | 0 | 2 |
| 22 | | 11.2100 | 0 | | | 0 | 3 | 2 | 1 | 3 | | | 1 | 4 | 2 | 0 | N |
| 23 | | 11.2100 | 0 | | | 0 | 0 | 0 | 0 | 1 | | | N | 0 | 0 | 0 | 0 |
| 24 | | 11.2100 | 0 | | | 0 | 1 | 4 | 2 | 3 | | | 0 | 4 | 3 | 0 | 0 |
| 25 | | 11.2100 | 0 | | | 0 | 3 | 4 | 2 | 4 | | | 1 | 4 | 3 | 0 | 1 |
| 26 | | 11.2100 | 0 | | | 0 | 0 | 3 | 2 | 3 | | | 0 | 1 | 0 | 0 | 0 |
| 27 | | 11.2100 | 0 | | | 0 | 3 | 3 | 2 | 4 | | | 2 | 4 | N | 0 | 0 |
| 28 | | 11.2100 | 0 | | | 1 | 2 | 4 | 1 | 3 | | | 4 | 4 | 2 | 0 | 0 |
| 29 | | 11.2100 | 0 | | | 0 | 1 | 1 | 0 | 3 | | | 1 | 1 | 1 | 0 | 0 |
| 30 | | 11.2100 | 0 | | | 0 | 2 | 0 | 1 | 4 | | | N | 4 | 0 | 0 | 0 |
| 31 | | 11.2100 | 0 | | | 1 | 3 | 3 | 2 | 3 | | | 0 | 4 | 3 | 1 | 0 |
| 32 | | 11.2100 | 0 | | | 1 | 1 | 1 | 1 | 1 | | | 1 | 3 | 3 | 0 | 0 |
| 33 | | 11.2100 | 0 | | | 1 | 2 | 3 | 3 | 3 | | | 1 | 4 | 4 | 1 | 0 |
| 34 | | 11.2100 | 0 | | | 0 | 3 | 3 | 1 | 4 | | | 1 | 4 | 2 | 0 | 0 |
| 35 | | 11.2100 | 0 | | | 0 | 3 | 3 | 3 | 4 | | | 3 | 3 | 1 | 0 | N |
| 36 | | 11.2100 | 0 | | | 0 | 1 | 2 | 0 | 0 | | | 0 | 1 | 0 | 0 | 0 |
| 37 | | 11.2100 | 0 | | | 0 | 0 | 3 | 4 | 4 | | | 3 | 4 | N | 0 | N |
| 38 | | 11.2100 | 1 | | | — | 1 | 3 | 4 | 3 | | | 4 | 4 | 0 | 0 | 0 |
| 39 | | 11.2100 | 0 | | | 0 | 1 | 3 | 3 | 1 | | | 0 | 2 | 0 | 0 | 1 |
| 40 | | 11.2100 | 1 | | | 1 | 2 | 3 | 2 | 2 | | | 0 | 3 | 2 | 0 | 0 |
| 41 | | 11.2100 | 1 | | | 0 | 2 | 3 | 2 | 3 | | | 2 | 3 | 2 | 0 | 0 |
| 42 | | 11.2100 | 2 | | | 1 | 3 | 3 | 1 | 4 | | | 1 | 3 | 2 | 1 | 0 |
| 43 | | 11.2100 | 3 | | | — | 4 | 4 | 3 | 4 | | | 2 | 4 | 4 | 1 | 1 |
| 44 | | 11.2100 | 0 | | | 0 | 1 | 3 | 3 | 3 | | | 1 | 3 | 2 | 0 | N |
| 45 | | 11.2100 | 2 | | | 2 | 2 | 2 | 1 | 3 | | | 1 | 3 | 3 | 0 | 0 |
| 46 | | 11.2100 | 2 | | | 0 | 3 | 3 | 3 | 3 | | | 2 | 3 | 3 | 2 | 1 |
| | | 11.2100 | 1 | | | 1 | 3 | 4 | 2 | 4 | | | 4 | 4 | 4 | 3 | 0 |
| 47 | | 11.2100 | 1 | | | 3 | 4 | 3 | 3 | 4 | | | 1 | 4 | 4 | 1 | N |
| 48 | | 11.2100 | 1 | | | — | 3 | 3 | 3 | 3 | | | 1 | 4 | 2 | 0 | 1 |
| 49 | | 11.2100 | 0 | | | 0 | 0 | 2 | 1 | 2 | | | 0 | 2 | 1 | 0 | 0 |
| 50 | | 11.2100 | 0 | | | 4 | 4 | 4 | 2 | 4 | | | 1 | 4 | 4 | 3 | 1 |
| 51 | | 11.2100 | 0 | | | 1 | 1 | 1 | 0 | 1 | | | 0 | 0 | 0 | 0 | 1 |
| 52 | | 11.2100 | 0 | | | 0 | 1 | 1 | 1 | 2 | | | 0 | 0 | 0 | 0 | 0 |
| 53 | | 11.2100 | 0 | | | 2 | 3 | 4 | 3 | 4 | | | 2 | 4 | N | 1 | 3 |
| 54 | | 11.2100 | 0 | | | — | 3 | 2 | 2 | 2 | | | 0 | 4 | 1 | 0 | 0 |
| 55 | | 11.2100 | 0 | | | 0 | 1 | 2 | 2 | 1 | | | 0 | 4 | 1 | N | 0 |
| 56 | | 11.2100 | 1 | | | 0 | 3 | 3 | 3 | 3 | | | 3 | 3 | 1 | 1 | 1 |
| 57 | | 11.2100 | 0 | | | 0 | 0 | 3 | 2 | 1 | | | 0 | 3 | 0 | 0 | 0 |
| 58 | | 11.2100 | 0 | | | 1 | 2 | 3 | 3 | 4 | | | 2 | 4 | N | 1 | 0 |
| 59 | | 11.2100 | 0 | | | 0 | 1 | 2 | 2 | 1 | | | 0 | 2 | 0 | 0 | 0 |
| 60 | | 11.2100 | 2 | | | 0 | 3 | 3 | 3 | 3 | | | 0 | 4 | 4 | 2 | 0 |
| 61 | | 11.2100 | 0 | | | 0 | 0 | 1 | 1 | 1 | | | 0 | 4 | 1 | 0 | 0 |
| 63 | + | 11.2100 | 0 | | | 0 | 1 | 3 | 3 | 3 | | | 2 | 4 | N | 1 | 0 |
| 64 | | 11.2100 | 0 | | | — | 3 | 3 | 3 | 3 | | | 0 | 4 | 1 | 0 | 0 |
| 65 | | 11.2100 | 3 | | | 1 | 4 | 3 | 3 | 4 | | | 1 | 4 | 4 | 4 | 0 |
| 66 | | 11.2100 | 2 | | | 2 | 1 | 2 | 2 | 3 | | | 1 | 2 | N | 0 | N |
| 67 | | 11.2100 | 1 | | | — | 3 | 3 | 3 | 3 | | | 3 | 4 | 1 | 0 | 0 |
| 68 | | 11.2100 | 1 | | | 0 | 0 | 1 | 0 | 1 | | | 0 | 1 | 0 | 1 | 0 |
| 69 | + | 11.2100 | 0 | | | 0 | 3 | 3 | 3 | 3 | | | 0 | 4 | N | 1 | 0 |
| 70 | | 11.2100 | 0 | | | 0 | 0 | 0 | 0 | 1 | | | 0 | 0 | 0 | 0 | 0 |
| 71 | | 11.2100 | 1 | | | 0 | 2 | 3 | 3 | 3 | | | 2 | 4 | N | 1 | 0 |
| 72 | | 11.2100 | 0 | | | 0 | 0 | 0 | 0 | 0 | | | 0 | 1 | 0 | 0 | 0 |
| 73 | | 11.2100 | 0 | | | 0 | 0 | 0 | 0 | 0 | | | 0 | 3 | 0 | 0 | 0 |
| 74 | | 11.2100 | 0 | | | 0 | 0 | 0 | 0 | 0 | | | 0 | 0 | 0 | 0 | 0 |
| 75 | + | 11.2100 | 0 | | | 0 | 1 | 2 | 1 | 1 | | | 0 | 4 | N | 0 | 0 |
| 76 | + | 11.2100 | 0 | | | 0 | 1 | 1 | 1 | 1 | | | 0 | 4 | N | 0 | 0 |
| 77 | | 11.2100 | 1 | | | 1 | 1 | 3 | 3 | 4 | | | 2 | 4 | 4 | 0 | 0 |
| 78 | | 11.2100 | 0 | | | 0 | 0 | 1 | 1 | 2 | | | 1 | 3 | 2 | 0 | 0 |
| 79 | | 11.2100 | 2 | | | 1 | 3 | 4 | 3 | 3 | | | 3 | 4 | N | 1 | 0 |
| 80 | | 11.2100 | 0 | | | 0 | 3 | 3 | 3 | 3 | | | 1 | 3 | N | 0 | 0 |
| 81 | | 11.2100 | 0 | | | 0 | 3 | 4 | 4 | 4 | | | 1 | 4 | N | 1 | 0 |
| 82 | | 11.2100 | 0 | | | — | 2 | 3 | 3 | 3 | | | 1 | 4 | 0 | 0 | 0 |
| 83 | | 11.2100 | 0 | | | 1 | 2 | 4 | 3 | 3 | | | 3 | 4 | N | 1 | 0 |
| 84 | | 11.2100 | 0 | | | 0 | 3 | 3 | 2 | 3 | | | 0 | 2 | 0 | 0 | 0 |
| 85 | | 11.2100 | 2 | | | 0 | 2 | 3 | 3 | 1 | | | 0 | 4 | 3 | 1 | 0 |
| 86 | | 11.2100 | 0 | | | 0 | 2 | 3 | 3 | 2 | | | 1 | 3 | 1 | 0 | 0 |
| 87 | | 11.2100 | 1 | | | 1 | 3 | 3 | 0 | 4 | | | 0 | 3 | 3 | 0 | 0 |
| 88 | | 11.2100 | 3 | | | 3 | 3 | 4 | 3 | 4 | | | 2 | 4 | N | 3 | 2 |
| 89 | | 11.2100 | 1 | | | 1 | 3 | 3 | 1 | 3 | | | 0 | 3 | 3 | 1 | 1 |

TABLE B-continued

Herbicide Primary Post, spectrums 25 and 90

| Ex. No. | Rate kg/ha | Yens | Abng | Sejg | Dobr | Bygr | Mogl | Cobu | Vlee | Inmu | Wibw | Cath | Colq | Pesw | Rhqg | Rhjg |
|---|---|---|---|---|---|---|---|---|---|---|---|---|---|---|---|---|
| 90 | 11.2100 | 0 | | | 1 | 3 | 3 | 1 | 3 | | | 0 | 4 | 4 | 1 | 1 |
| 91 | 11.2100 | 0 | | | 1 | 2 | 1 | 0 | 3 | | | 0 | 3 | 2 | 0 | 2 |
|  | 11.2100 | 0 | | | 2 | 3 | 3 | 1 | 2 | | | 4 | 3 | 2 | 3 | 0 |
| 92 | 11.2100 | 2 | | | 3 | 4 | 4 | 3 | 4 | | | 3 | 4 | 4 | 4 | N |
| 93 | 11.2100 | 0 | | | 2 | 4 | 3 | 2 | 3 | | | 0 | 4 | 4 | 2 | 0 |
| 94 | 11.2100 | 1 | 2 | 3 | 2 | 3 | 2 | 0 | 2 | 1 | 4 | | | | | |
|  | 11.2100 | 1 | | | 0 | 3 | 2 | 1 | 1 | | | N | 3 | 2 | 0 | 1 |
|  | 11.2100 | 0 | 0 | 2 | 1 | 3 | 2 | 0 | 3 | 2 | 4 | | | | | |
|  | 11.2100 | 0 | 2 | 3 | 2 | 3 | 2 | 0 | 2 | 1 | 2 | | | | | |
|  | 11.2100 | 2 | 2 | 4 | 2 | 3 | 3 | 0 | 2 | 2 | 3 | | | | | |
|  | 11.2100 | 1 | 2 | 3 | 2 | 3 | 2 | 0 | 2 | 2 | 4 | | | | | |
|  | 11.2100 | 2 | 3 | 3 | 2 | 4 | 2 | 1 | 4 | 0 | 4 | | | | | |
|  | 11.2100 | 0 | 4 | 4 | 4 | 4 | 4 | 1 | 4 | 3 | 4 | | | | | |
|  | 11.2100 | 2 | 2 | 4 | 1 | 3 | 2 | 0 | 3 | 0 | 3 | | | | | |
|  | < 11.2100 | 1 | 4 | 4 | 3 | 4 | 2 | 2 | 4 | 2 | 3 | | | | | |
|  | 11.2100 | 2 | 2 | 3 | 1 | 3 | 2 | 1 | 2 | 0 | 3 | | | | | |
|  | 11.2100 | 2 | 3 | 3 | 3 | 3 | 2 | 0 | 3 | 2 | 3 | | | | | |
|  | ~ 11.2100 | 2 | 4 | 4 | 4 | 4 | 3 | 2 | 4 | 2 | 4 | | | | | |
|  | 11.2100 | 2 | 4 | 4 | 4 | 4 | 3 | 2 | 4 | 1 | 4 | | | | | |
|  | 11.2100 | 0 | 3 | 4 | 4 | 4 | 3 | 2 | 4 | 1 | 4 | | | | | |
|  | 11.2100 | 2 | 4 | 4 | 4 | 4 | 2 | 1 | 4 | 3 | 4 | | | | | |
| 95 | 11.2100 | 3 | | | 4 | 4 | 4 | 4 | 4 | | | 3 | 4 | 4 | 3 | 1 |
| 96 | 11.2100 | 1 | | | 3 | 4 | 4 | 2 | 4 | | | — | 4 | 4 | 2 | 3 |
| 97 | 11.2100 | 0 | | | 1 | 3 | 4 | 1 | 3 | | | 1 | 4 | 2 | 0 | 0 |
| 98 | 11.2100 | 0 | | | 0 | 1 | 3 | 1 | 3 | | | 0 | 3 | 1 | 0 | 0 |
| 99 | 11.2100 | 1 | | | 3 | 3 | 3 | 2 | 3 | | | 1 | 4 | 4 | 2 | 1 |
| 100 | 11.2100 | 0 | | | 1 | 3 | 4 | 0 | 3 | | | N | 4 | 3 | 0 | 0 |
| 101 | 11.2100 | 0 | | | 2 | 3 | 3 | 2 | 2 | | | 0 | 4 | 3 | 3 | 1 |
| 102 | 11.2100 | 0 | | | 2 | 3 | 4 | 1 | 4 | | | 0 | 4 | 0 | 1 | 0 |
| 103 | 11.2100 | 0 | | | 0 | 1 | 2 | 0 | 2 | | | 0 | 2 | 3 | 0 | N |
| 104 | 11.2100 | 0 | | | 3 | 4 | 4 | 3 | 4 | | | 3 | — | 4 | 1 | 0 |
| 105 | 11.2100 | 1 | | | 4 | 4 | 4 | 3 | 4 | | | 2 | 4 | 4 | 3 | 2 |
| 106 | 11.2100 | 3 | | | 3 | 4 | 4 | 4 | 4 | | | 1 | 4 | N | 3 | N |
| 107 | 11.2100 | 0 | | | 0 | 3 | 3 | 1 | 2 | | | 0 | 4 | 2 | 0 | 1 |
| 108 | 11.2100 | 1 | | | 1 | 3 | 3 | 2 | 3 | | | 0 | 4 | 4 | 2 | 2 |
| 109 | 11.2100 | 2 | | | 3 | 3 | 4 | 3 | 3 | | | 1 | 4 | N | 3 | 0 |
| 110 | 11.2100 | 0 | | | 0 | 3 | 3 | 2 | 3 | | | 1 | 4 | 4 | 1 | 0 |
| 111 | 11.2100 | 1 | | | 3 | 4 | 4 | 4 | 4 | | | 4 | 4 | N | 4 | 3 |
| 112 | 11.2100 | 1 | | | 3 | 3 | 3 | 2 | 3 | | | 1 | 4 | 4 | 2 | 0 |
| 113 | 11.2100 | 0 | | | 3 | 3 | 4 | 2 | 4 | | | 2 | 4 | 3 | 2 | 0 |
| 114 | 11.2100 | 0 | | | 2 | 3 | 4 | 3 | 4 | | | 4 | — | 4 | 3 | 0 |
| 115 | 11.2100 | 2 | | | 1 | 3 | 4 | 4 | 4 | | | 3 | 4 | 1 | 1 | 1 |
| 116 | 11.2100 | 2 | | | 0 | 3 | 4 | 4 | 4 | | | 1 | 4 | 3 | 1 | 0 |
| 117 | 11.2100 | 3 | | | 0 | 4 | 4 | 4 | 4 | | | 3 | 4 | 2 | 1 | 2 |
| 118 | 11.2100 | 0 | | | 0 | 3 | 4 | 3 | 3 | | | 2 | 4 | 0 | 1 | 0 |
| 119 | 11.2100 | 1 | | | 0 | 4 | 4 | 4 | 4 | | | 3 | 4 | 1 | 0 | 0 |
| 120 | 11.2100 | 1 | | | 0 | 3 | 4 | 3 | 3 | | | 2 | 3 | 0 | 0 | 0 |
| 121 | 11.2100 | 0 | | | 0 | 3 | 3 | 4 | 3 | | | 4 | 4 | 4 | 0 | 0 |
| 122 | 11.2100 | 3 | | | 0 | 4 | 4 | 4 | 4 | | | 4 | 4 | 3 | 1 | 0 |
| 123 | 11.2100 | 4 | | | 3 | 4 | 4 | 4 | 4 | | | 4 | 4 | 4 | 3 | 4 |
| 124 | 11.2100 | 0 | | | 1 | 4 | 4 | 4 | 4 | | | 3 | — | 4 | 1 | 1 |
| 125 | 11.2100 | 0 | | | 1 | 2 | 4 | 3 | 4 | | | 1 | 2 | 1 | 0 | 1 |
| 126 | 11.2100 | 0 | | | 0 | 3 | 4 | 4 | 4 | | | 0 | 4 | 2 | 1 | 0 |
| 127 | 11.2100 | 2 | | | 2 | 4 | 4 | 4 | 3 | | | 3 | 4 | 3 | 2 | 2 |
| 128 | 11.2100 | 1 | | | 0 | 4 | 4 | 4 | 4 | | | 3 | 4 | N | 0 | 1 |
| 129 | 11.2100 | 2 | | | 0 | 3 | 4 | 4 | 4 | | | 4 | 4 | N | 1 | 2 |
| 130 | 11.2100 | 3 | | | 0 | 4 | 4 | 4 | 4 | | | 3 | N | 4 | 2 | 1 |
| 131 | 11.2100 | 2 | | | 0 | 4 | 4 | 4 | 4 | | | 4 | 4 | 3 | 1 | 4 |
| 132 | 11.2100 | 1 | | | 2 | 0 | 3 | 1 | 3 | | | 0 | 4 | 0 | 0 | 0 |
| 133 | 11.2100 | 3 | | | 1 | 4 | 4 | 4 | 4 | | | 4 | 4 | 4 | 2 | 3 |
| 134 | 11.2100 | 1 | | | 1 | 3 | 4 | 4 | 4 | | | 4 | 4 | 4 | 1 | 1 |
| 135 | 11.2100 | 1 | | | 0 | 3 | 4 | 4 | 4 | | | 4 | 4 | 3 | 0 | 1 |
| 136 | 11.2100 | 0 | | | 0 | 1 | 3 | 3 | 3 | | | 1 | 3 | N | 0 | 0 |
| 137 | 11.2100 | 2 | | | 0 | 4 | 4 | 4 | 4 | | | 4 | 4 | 3 | 1 | 1 |
| 138 | 11.2100 | 1 | | | 0 | 3 | 4 | 4 | 4 | | | 4 | 4 | 4 | 1 | 2 |
| 139 | 11.2100 | 0 | | | 0 | 2 | 3 | 3 | 2 | | | 2 | 4 | 2 | 0 | 2 |
| 140 | 11.2100 | 0 | | | 0 | 4 | 4 | 4 | 4 | | | 4 | 4 | 4 | 1 | 1 |
| 141 | 11.2100 | 2 | | | 2 | 4 | 4 | 4 | 4 | | | 4 | 4 | 2 | 3 | 0 |
| 142 | 11.2100 | 2 | | | 0 | 3 | 4 | 4 | 4 | | | 3 | 4 | 1 | 1 | 1 |
| 143 | 11.2100 | 2 | | | 0 | 3 | 4 | 4 | 4 | | | 3 | 4 | 2 | 1 | 0 |
| 144 | 11.2100 | 1 | | | 1 | 4 | 4 | 4 | 4 | | | 4 | — | 4 | 2 | 0 |
| 145 | 11.2100 | 3 | | | 1 | 3 | 4 | 4 | 4 | | | 4 | 4 | 4 | 2 | 2 |
| 146 | 11.2100 | 1 | | | 4 | 3 | 4 | 4 | 4 | | | 1 | 4 | 4 | 1 | 1 |
| 147 | 11.2100 | 0 | | | 0 | 1 | 1 | 0 | 1 | | | 1 | 4 | 0 | 0 | 0 |
| 148 | 11.2100 | 2 | | | 0 | 1 | 4 | 2 | 2 | | | 0 | 4 | 3 | 0 | 0 |
| 149 | 11.2100 | 3 | | | 2 | 3 | 4 | 3 | 4 | | | 1 | 4 | 4 | 2 | 2 |
| 150 | 11.2100 | 2 | | | 0 | 3 | 4 | 4 | 4 | | | 3 | 4 | 3 | 0 | 2 |

TABLE B-continued

Herbicide Primary Post, spectrums 25 and 90

| Ex. No. | Rate kg/ha | | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|---|
| 151 | 11.2100 | | 1 | | | 1 | 3 | 3 | 3 | 4 | | | 2 | 4 | 4 | 0 | 0 |
| 152 | 11.2100 | | 0 | | | 2 | 3 | 4 | 4 | 4 | | | 1 | 4 | 4 | 1 | 3 |
| 153 | 11.2100 | | 0 | | | 1 | 3 | 3 | 1 | 3 | | | 1 | 4 | 3 | 1 | 0 |
| 154 | 11.2100 | | 0 | | | 2 | 3 | 4 | 3 | 4 | | | 1 | 4 | 4 | 2 | 3 |
| 155 | 11.2100 | | 1 | | | 3 | 4 | 4 | 3 | 4 | | | 2 | 4 | 4 | 1 | 0 |
| 156 | 11.2100 | | 2 | | | 1 | 4 | 4 | 4 | 4 | | | 4 | 4 | 4 | 2 | 2 |
| 157 | 11.2100 | | 0 | | | 1 | 3 | 3 | 4 | 4 | | | 1 | 4 | 4 | 1 | 2 |
| 158 | 11.2100 | | 2 | | | 0 | 4 | 4 | 4 | 4 | | | 4 | 4 | 4 | 1 | 1 |
| 159 | 11.2100 | | 1 | | | 0 | 1 | 3 | 0 | 2 | | | 0 | N | 1 | 0 | 0 |
| 160 | 11.2100 | | 1 | | | 4 | 4 | 4 | 2 | 4 | | | 1 | 4 | 4 | 3 | 1 |
| 161 | 11.2100 | | 3 | | | 4 | 4 | 4 | 4 | 4 | | | 0 | 4 | 4 | 4 | 4 |
| 162 | 11.2100 | | 3 | | | 2 | 4 | 4 | 3 | 4 | | | 4 | 4 | 4 | 3 | 3 |
| 163 | 11.2100 | | 1 | | | 2 | 3 | 4 | 3 | 4 | | | 1 | 4 | 4 | 2 | 2 |
| 164 | 11.2100 | | 3 | | | 3 | 4 | 4 | 4 | 4 | | | 4 | 4 | 4 | 3 | N |
| 165 | 11.2100 | | 0 | | | 0 | 3 | 3 | 4 | 4 | | | 3 | 4 | 4 | 1 | N |
| 166 | 11.2100 | | 2 | | | 3 | 4 | 4 | 3 | 4 | | | 3 | 4 | 4 | 1 | N |
| 167 | 11.2100 | | 3 | | | 2 | 4 | 4 | 4 | 4 | | | — | 4 | 4 | 3 | 2 |
| 168 | 11.2100 | | 0 | | | 0 | 3 | 4 | 4 | 4 | | | 3 | 4 | 3 | 1 | 0 |
| 169 | 11.2100 | | 1 | | | 1 | 3 | 2 | 0 | 3 | | | 1 | — | 3 | 1 | 0 |
| 170 | 11.2100 | | 2 | | | 0 | 3 | 3 | 3 | 4 | | | 3 | — | 1 | 0 | 0 |
| 171 | 11.2100 | | 1 | | | 0 | 3 | 1 | 1 | 3 | | | 3 | — | 3 | 0 | N |
| 172 | 11.2100 | | 0 | | | 0 | 0 | 0 | 0 | 0 | | | 0 | 1 | 2 | 0 | 0 |
| 173 | 11.2100 | | 0 | | | 0 | 0 | 0 | 0 | 1 | | | 0 | 0 | 0 | 0 | 0 |
| 174 | 11.2100 | | 0 | | | 0 | 0 | 1 | 1 | 0 | | | 0 | 1 | 3 | 0 | 0 |
| 175 | 11.2100 | | 0 | | | 0 | 0 | 3 | 2 | 3 | | | 0 | 4 | 0 | 0 | 2 |
| 176 | 11.2100 | | 1 | | | 0 | 2 | 4 | 3 | 4 | | | 4 | 4 | 3 | 0 | 0 |
| 177 | 11.2100 | | 2 | | | 0 | 3 | 3 | 3 | 3 | | | 0 | 4 | N | 2 | 1 |
| 178 | 11.2100 | | 0 | | | 0 | 2 | 3 | 0 | 3 | | | 0 | 3 | 1 | 0 | 0 |
| 179 | 11.2100 | | 1 | | | 1 | 3 | 3 | 3 | 3 | | | 1 | 4 | N | 1 | 0 |
| 180 | 11.2100 | | 1 | | | 2 | 3 | 3 | 3 | 4 | | | 3 | — | 3 | 1 | 3 |
| 181 | 11.2100 | | 3 | | | 1 | 3 | 3 | 3 | 3 | | | 1 | — | 3 | 1 | 0 |
| 182 | 11.2100 | | 1 | | | 1 | 3 | 3 | 2 | 4 | | | 1 | 4 | 4 | 1 | N |
| 183 | 11.2100 | | 2 | | | 1 | 4 | 4 | 3 | 4 | | | — | 4 | 4 | 1 | N |
| 184 | 11.2100 | | 0 | | | 1 | 3 | 3 | 3 | 3 | | | 0 | 4 | 3 | 1 | — |
| 185 | 11.2100 | | 2 | | | 3 | 4 | 4 | 4 | 4 | | | 1 | 4 | — | 3 | 2 |
| 186 | 11.2100 | | 1 | | | 1 | 4 | 3 | 3 | 4 | | | 2 | 4 | 2 | 1 | 0 |
| 187 | 11.2100 | | 0 | | | 2 | 3 | 3 | 3 | 4 | | | 2 | 4 | N | 1 | 0 |
| 188 | 11.2100 | | 0 | | | 1 | 3 | 4 | 3 | 4 | | | 2 | 4 | N | 1 | 0 |
| 189 | 11.2100 | | 0 | | | 1 | 3 | 3 | 1 | 3 | | | 0 | 4 | N | 1 | 1 |
| 190 | 11.2100 | | 2 | | | 3 | 4 | 3 | 2 | 4 | | | 1 | 4 | 4 | 2 | 3 |
| 191 | 11.2100 | | 0 | | | 2 | 3 | 4 | 1 | 4 | | | 0 | 4 | N | 1 | 1 |
| 192 | 11.2100 | | 0 | | | 3 | 4 | 3 | 3 | 4 | | | 3 | — | 4 | 0 | 0 |
| 193 | 11.2100 | | 1 | | | 1 | 3 | 4 | 3 | 3 | | | 1 | 3 | 3 | 1 | 1 |
| 194 | 11.2100 | | 1 | | | 3 | 4 | 4 | 3 | 4 | | | 2 | 4 | 4 | 3 | 2 |
| 195 | 11.2100 | | 1 | | | 3 | 4 | 3 | 4 | 4 | | | 1 | 4 | 4 | 2 | 2 |
| 196 | + 11.2100 | | 0 | | | 1 | 3 | 3 | 2 | 4 | | | 2 | 4 | 3 | 1 | 1 |
| 197 | 11.2100 | | 2 | | | 3 | 3 | 3 | 3 | 3 | | | 2 | 4 | 3 | 1 | 3 |
| 198 | 11.2100 | | 0 | | | 1 | 3 | 4 | 3 | 4 | | | 1 | 4 | 4 | 2 | 1 |
| 199 | 11.2100 | | 0 | | | 1 | 3 | 4 | 2 | 4 | | | 0 | 4 | N | 1 | 1 |
| 200 | 11.2100 | | 0 | | | 0 | 3 | 2 | 1 | 3 | | | — | 4 | 3 | 0 | N |
| 201 | 11.2100 | | 1 | | | 1 | 3 | 4 | 3 | 4 | | | 2 | 4 | 3 | 1 | 2 |
| 202 | 11.2100 | | 0 | | | 1 | 3 | 3 | 1 | 4 | | | 1 | 4 | 1 | 1 | N |
| 203 | = 11.2100 | | 0 | | | 0 | 1 | 1 | 0 | 0 | | | 0 | 4 | 1 | 0 | 0 |
| 204 | 11.2100 | | 0 | | | 0 | 1 | 3 | 2 | 1 | | | 0 | 2 | 2 | 0 | 0 |
| 205 | 11.2100 | | 2 | | | 1 | 3 | 4 | 4 | 4 | | | 3 | 4 | 4 | 0 | 2 |
| 206 | < 11.2100 | | 2 | 4 | 2 | 4 | 4 | 3 | 3 | 2 | 3 | 4 | | | | | |
| 207 | 11.2100 | | 1 | | | 1 | 1 | 1 | 2 | 3 | | | 1 | 1 | 0 | 0 | 0 |
| 208 | 11.2100 | | 0 | | | 0 | 1 | 0 | 2 | 2 | | | 0 | 2 | 1 | 0 | 0 |
| 209 | 11.2100 | | 0 | | | 0 | 1 | 1 | 2 | 3 | | | 1 | 2 | 0 | 0 | 0 |
| | 11.2100 | | 0 | | | 0 | 2 | 1 | 2 | 3 | | | 1 | 2 | 0 | 0 | 0 |
| 210 | 11.2100 | | 1 | | | 0 | 0 | 1 | 1 | 0 | | | 0 | 1 | 0 | 0 | 1 |
| 211 | 11.2100 | | 1 | | | 1 | 1 | 1 | 1 | 3 | | | 1 | 3 | 1 | 0 | 1 |
| 212 | 11.2100 | | 0 | | | 0 | 0 | 0 | 0 | 0 | | | N | 0 | 0 | 0 | 0 |
| 213 | 11.2100 | | 0 | | | 0 | 0 | 0 | 0 | 0 | | | 0 | 0 | 0 | 0 | N |
| 214 | 11.2100 | | 0 | | | 0 | 0 | 0 | 0 | 0 | | | 0 | 0 | 0 | 0 | N |
| 215 | 11.2100 | | 0 | | | — | 0 | 3 | 1 | 2 | | | 0 | N | 1 | 0 | 0 |
| 216 | 11.2100 | | 0 | | | — | 0 | 0 | 0 | 0 | | | 0 | 0 | 0 | 0 | 0 |
| 217 | 11.2100 | | 1 | | | 0 | 3 | 1 | 2 | 3 | | | 0 | 4 | 2 | 0 | 0 |
| 218 | 11.2100 | | 1 | | | 0 | 3 | 3 | 1 | 3 | | | 0 | 4 | 1 | 1 | 1 |
| 219 | 11.2100 | | 0 | | | 0 | 2 | 3 | 0 | 3 | | | 0 | 2 | 0 | 0 | 0 |
| 220 | 11.2100 | | 0 | | | 0 | 3 | 3 | 2 | 3 | | | 0 | 4 | 1 | 0 | 0 |
| 221 | 11.2100 | | 0 | | | 0 | 0 | 0 | 0 | 0 | | | 0 | N | 0 | 0 | 0 |
| 222 | 11.2100 | | 0 | | | 0 | 0 | 1 | 1 | 0 | | | 0 | 0 | 0 | 0 | 0 |
| 223 | 11.2100 | | 1 | | | 1 | 1 | 2 | 1 | 2 | | | 1 | 4 | 3 | 1 | 0 |
| 224 | 11.2100 | | 0 | | | 0 | 0 | 0 | 1 | 0 | | | 1 | 3 | 1 | 0 | 0 |
| 225 | 11.2100 | | 0 | | | 0 | 1 | 2 | 1 | 2 | | | 0 | 2 | 2 | 0 | 0 |
| 226 | 11.2100 | | 0 | | | 0 | 3 | 3 | 0 | 4 | | | 0 | 4 | 1 | 0 | 0 |

TABLE B-continued

| | | Herbicide Primary Post, spectrums 25 and 90 | | | | | | | | | | | | | |
|---|---|---|---|---|---|---|---|---|---|---|---|---|---|---|---|
| Ex. No. | Rate kg/ha | Yens | Abg | Sejg | Dobr | Bygr | Mogl | Cobu | Vele | Inmu | Wibw | Cath | Colq | Pesw | Rhqg | Rhjg |
| 227 | 11.2100 | 1 | | | — | 3 | 2 | 1 | 2 | | | 0 | 3 | 2 | 0 | 0 |
| 228 | 11.2100 | 0 | | | — | 1 | 1 | 0 | 1 | | | 0 | 2 | 1 | 0 | 0 |
| 229 | 11.2100 | 0 | | | — | 2 | 1 | 0 | 1 | | | 0 | 1 | 2 | 0 | 0 |
| 230 | 11.2100 | 0 | | | 0 | 0 | 1 | 0 | 1 | | | 0 | 2 | 1 | 0 | 0 |
| 231 | 11.2100 | 0 | | | 0 | 1 | 3 | 0 | 2 | | | 0 | 2 | 3 | 0 | 0 |
| 232 | 11.2100 | 1 | | | 1 | 2 | 3 | 1 | 3 | | | — | 4 | 4 | 1 | 0 |
| 233 | 11.2100 | 0 | | | 1 | 0 | 2 | 1 | 3 | | | 0 | 3 | 1 | 0 | 0 |
| 234 | 11.2100 | 0 | | | 1 | 0 | 3 | 1 | 3 | | | 2 | 4 | 3 | 0 | 0 |
| 235 | 11.2100 | 0 | | | 0 | 2 | 3 | 1 | 3 | | | 0 | 4 | 3 | 1 | 0 |
| 236 | 11.2100 | 0 | | | 0 | 0 | 1 | 1 | 1 | | | 0 | N | 4 | 1 | 0 |
| 237 | 11.2100 | 0 | | | 2 | 1 | 1 | 0 | 3 | | | 0 | N | 4 | 2 | 0 |
| 238 | 11.2100 | 0 | | | 1 | 0 | 2 | 1 | 0 | | | 2 | 4 | 4 | 0 | 1 |
| 239 | 11.2100 | 1 | | | 0 | 3 | 3 | 1 | 3 | | | 0 | 4 | 3 | 1 | 0 |
| 240 | 11.2100 | 1 | | | 0 | 1 | 3 | 1 | 1 | | | 1 | N | 4 | 0 | 0 |
| 241 | 11.2100 | 0 | | | 0 | 0 | 1 | 0 | 0 | | | 0 | 3 | 2 | 0 | 0 |
| 242 | 11.2100 | 0 | | | 0 | 0 | 1 | 0 | 0 | | | 0 | 0 | 2 | 0 | 0 |
| 243 | 11.2100 | 0 | | | 0 | 0 | 3 | 1 | 3 | | | 0 | 1 | 2 | 0 | 0 |
| 244 | 11.2100 | 0 | | | 0 | 0 | 1 | 0 | 0 | | | 0 | 3 | 0 | 0 | 0 |
| 245 | 11.2100 | 0 | | | 0 | 2 | 3 | 2 | 2 | | | 1 | 4 | 0 | 0 | 0 |
| 246 | 11.2100 | 0 | | | 1 | 3 | 3 | 3 | 3 | | | 0 | 4 | 3 | 0 | 0 |
| 247 | 11.2100 | 0 | | | 0 | 1 | 3 | 0 | 3 | | | 0 | 3 | 0 | 0 | 0 |
| 248 | 11.2100 | 0 | | | 3 | 1 | 3 | 1 | 3 | | | 1 | 4 | 3 | 1 | 2 |
| 249 | 11.2100 | 0 | | | 0 | 0 | 0 | 0 | 0 | | | 0 | 0 | 0 | 0 | 0 |
| 250 | 11.2100 | 1 | | | 1 | 3 | 3 | 2 | 4 | | | 1 | 4 | 3 | 2 | 0 |
| 251 | 11.2100 | 0 | | | 1 | 2 | 3 | 2 | 2 | | | 0 | 4 | 4 | 2 | 1 |
| 252 | 11.2100 | 0 | | | 0 | 0 | 2 | 0 | 2 | | | 0 | 2 | 1 | 0 | 0 |
| 253 | 11.2100 | 0 | | | 1 | 0 | 2 | 0 | 4 | | | 0 | 2 | 0 | 0 | 0 |
| 254 | 11.2100 | 0 | | | 0 | 2 | 3 | 2 | 3 | | | 0 | 1 | 1 | 0 | 0 |
| 255 | 11.2100 | 0 | | | 0 | 0 | 1 | 0 | 0 | | | 0 | 2 | 0 | 0 | 0 |
| 256 | 11.2100 | 0 | | | 0 | 0 | 0 | 1 | 0 | | | 0 | 1 | 0 | 0 | 0 |
| 257 | 11.2100 | 0 | | | 0 | 0 | 1 | 0 | 0 | | | 0 | 3 | 0 | 0 | 0 |
| 258 | 11.2100 | 0 | | | 0 | 0 | 0 | 0 | 1 | | | 0 | 3 | 0 | 0 | 0 |
| 259 | 11.2100 | 0 | | | 0 | 0 | 1 | 0 | 0 | | | 0 | 1 | 0 | 0 | 0 |
| 260 | 11.2100 | 1 | | | 1 | 1 | 1 | 0 | 2 | | | 0 | 3 | 3 | 0 | 0 |
| 261 | 11.2100 | 0 | | | 0 | 1 | 4 | 2 | 4 | | | 0 | 4 | 4 | 0 | 0 |
| 262 | 11.2100 | 0 | | | 0 | 3 | 4 | 3 | 4 | | | 1 | 4 | 4 | 0 | 0 |
| 263 | 11.2100 | 0 | | | 1 | 3 | 4 | 2 | 3 | | | 1 | 4 | 4 | 0 | 0 |
| 264 | 11.2100 | 0 | | | 0 | 1 | 3 | 2 | 4 | | | 0 | 4 | 4 | 0 | 0 |
| 265 | 11.2100 | 0 | | | 0 | 3 | 3 | 2 | 4 | | | 0 | 4 | 3 | 0 | 1 |
| 266 | 11.2100 | 0 | | | 0 | 0 | 2 | 1 | 3 | | | 0 | — | 3 | 0 | 0 |
| 267 | 11.2100 | 0 | | | 4 | 4 | 4 | 4 | 4 | | | 4 | — | 4 | 2 | 0 |
| 268 | 11.2100 | 0 | | | 1 | 3 | 4 | 3 | 4 | | | 2 | — | 3 | 1 | 2 |
| 269 | 11.2100 | 1 | | | 0 | 2 | 3 | 3 | 3 | | | — | 4 | 3 | 0 | 1 |
| 270 | 11.2100 | 3 | | | 1 | 4 | 4 | 4 | 4 | | | 4 | 4 | 4 | 2 | 0 |
| 271 | 11.2100 | 0 | | | 0 | 3 | 4 | 2 | 3 | | | 0 | 4 | 2 | 1 | 0 |
| 272 | 11.2100 | 2 | | | 1 | 3 | 4 | 4 | 4 | | | 2 | — | 4 | 0 | 0 |
| 273 | 11.2100 | 0 | | | 0 | 1 | 1 | 0 | 2 | | | 0 | — | 3 | 0 | 0 |
| 274 | 11.2100 | 1 | | | 3 | 4 | 4 | 3 | 4 | | | 4 | 4 | 4 | 1 | 1 |
| 275 | 11.2100 | 0 | | | 3 | 4 | 4 | 4 | 4 | | | 4 | — | 4 | 0 | 3 |
| 276 | 11.2100 | 2 | | | 0 | 3 | 3 | 3 | 3 | | | 1 | 4 | 3 | 0 | 1 |
| 277 | 11.2100 | 0 | | | 0 | 2 | 1 | 0 | 3 | | | 3 | — | 1 | 0 | N |
| 278 | 11.2100 | 0 | | | 0 | 1 | 2 | 1 | 3 | | | 2 | — | 3 | 0 | 0 |
| 279 | 11.2100 | 0 | | | 0 | 3 | 2 | 1 | 2 | | | 0 | 4 | 3 | 1 | N |
| 280 | 11.2100 | 2 | | | 0 | 3 | 4 | 1 | 3 | | | 2 | 4 | 4 | 0 | 0 |
| 281 | 11.2100 | 0 | | | 0 | 0 | 0 | 0 | 0 | | | 0 | 0 | 0 | 0 | N |
| 282 | 11.2100 | 1 | | | 1 | 3 | 3 | 3 | 4 | | | 0 | 4 | 3 | 1 | 0 |
| 283 | 11.2100 | 1 | | | 1 | 3 | 3 | 3 | 4 | | | 0 | 4 | 4 | 0 | 0 |
| 284 | 11.2100 | 1 | 2 | 2 | 2 | 4 | 4 | 2 | 4 | 3 | 4 | | | | | |
| 285 | 11.2100 | 0 | | | 0 | 3 | 2 | 1 | 4 | | | 1 | 4 | 3 | 0 | 1 |
| 286 | 11.2100 | 0 | | | 0 | 0 | 3 | 0 | 1 | | | 1 | 1 | 0 | 0 | 0 |
| 287 | 11.2100 | 0 | | | 0 | 1 | 3 | 2 | 3 | | | 1 | 4 | 4 | 0 | 1 |
| 288 | 11.2100 | 1 | | | 1 | 3 | 4 | 3 | 4 | | | 2 | 4 | 4 | 1 | 0 |
| 289 = | 11.2100 | 0 | | | 0 | 1 | 3 | 3 | 4 | | | 1 | 4 | 4 | 0 | 1 |
| 290 | 11.2100 | 0 | | | 0 | 0 | 2 | 1 | 1 | | | 0 | 4 | 3 | 0 | 0 |
| 291 + | 11.2100 | 0 | | | 0 | 1 | 2 | 3 | 4 | | | 2 | 4 | N | 0 | 1 |
| 292 + | 11.2100 | 0 | | | 0 | 0 | 1 | 2 | 2 | | | 1 | 3 | N | 0 | 0 |
| 293 | 11.2100 | 2 | | | 0 | 4 | 4 | 4 | 4 | | | 4 | 4 | N | 0 | 0 |
| 294 | 11.2100 | 0 | | | 0 | 1 | 3 | 1 | 3 | | | 0 | 3 | N | 0 | 0 |
| 295 = | 11.2100 | 1 | | | 0 | 3 | 4 | 3 | 4 | | | 4 | 4 | 4 | 0 | 1 |
| 296 = | 11.2100 | 0 | | | 0 | 1 | 4 | 4 | 4 | | | 4 | 4 | 4 | 0 | 1 |
| 297 = | 11.2100 | 0 | | | 0 | 2 | 4 | 3 | 4 | | | 4 | 4 | 3 | 0 | 1 |
| 298 = | 11.2100 | 0 | | | 0 | 0 | 2 | 1 | 3 | | | 1 | 3 | 3 | 0 | 0 |
| 299 ( | 11.2100 | 2 | | | 0 | 2 | 4 | 4 | 3 | | | 1 | 4 | N | 0 | 1 |
| 300 = | 11.2100 | 0 | | | 0 | 0 | 1 | 1 | 1 | | | 0 | 3 | 1 | 0 | 2 |
| 301 = | 11.2100 | 0 | | | 0 | 1 | 4 | 3 | 4 | | | 3 | 4 | 2 | 0 | 0 |
| 302 = | 11.2100 | 3 | | | 0 | 1 | 4 | 3 | 3 | | | 2 | 4 | 0 | 0 | 0 |
| 303 = | 11.2100 | 1 | | | 0 | 3 | 4 | 4 | 4 | | | 2 | 4 | 0 | 0 | 1 |

TABLE B-continued

Herbicide Primary Post, spectrums 25 and 90

| Ex. No. | | Rate kg/ha | Yens | Abg | Sej g | Dobr | Bygr | Mogl | Cou u | Vle e | Imu u | Wbi w | Cat h | Col q | Pes w | Rhq g | Rhj g |
|---|---|---|---|---|---|---|---|---|---|---|---|---|---|---|---|---|---|
| 304 | = | 11.2100 | 3 | | | 0 | 3 | 4 | 4 | 4 | | | 3 | 4 | 1 | 0 | 1 |
| 305 | = | 11.2100 | 2 | | | 0 | 2 | 3 | 3 | 4 | | | 4 | 4 | 4 | 0 | 0 |
| 306 | = | 11.2100 | 2 | | | 0 | 2 | 4 | 3 | 2 | | | 1 | 3 | N | 0 | 1 |
| 307 | ( | 11.2100 | 1 | | | 0 | 1 | 3 | 4 | 3 | | | 3 | 4 | N | 0 | 1 |
| 308 | ( | 11.2100 | 3 | | | 0 | 3 | 4 | 3 | 4 | | | 4 | 4 | N | 0 | 3 |
| 309 | ( | 11.2100 | 0 | | | 0 | 3 | 4 | 4 | 4 | | | 0 | 4 | 0 | 0 | 0 |
| 310 | ( | 11.2100 | 1 | | | 0 | 2 | 4 | 4 | 3 | | | 4 | 4 | N | 0 | 0 |
| 311 | ( | 11.2100 | 0 | | | 0 | 2 | 4 | 4 | 4 | | | 3 | 4 | 1 | 0 | 0 |
| 312 | ( | 11.2100 | 0 | | | 0 | 2 | 4 | 4 | 4 | | | 2 | 4 | N | 0 | 1 |
| 313 | | 11.2100 | 2 | 0 | 3 | 0 | 2 | 4 | 4 | 4 | 2 | 4 | | | | | |
| 314 | | 11.2100 | 3 | 0 | 2 | 0 | 2 | 4 | 3 | 4 | 4 | 4 | | | | | |
| 315 | | 11.2100 | 0 | 0 | 2 | 0 | 2 | 4 | 3 | 4 | 2 | 4 | | | | | |
| 316 | | 11.2100 | 0 | 0 | 0 | 0 | 0 | 4 | 2 | 4 | 2 | 4 | | | | | |
| 317 | | 11.2100 | 0 | 0 | 0 | 0 | 0 | 2 | 2 | 1 | 1 | 1 | | | | | |
| 318 | | 11.2100 | 0 | 0 | 0 | 0 | 0 | 0 | 0 | 1 | 1 | 1 | | | | | |
| 319 | | 11.2100 | 0 | 0 | 0 | 0 | 0 | 2 | 1 | 2 | 2 | 3 | | | | | |
| 320 | | 11.2100 | 0 | 0 | 0 | 0 | 0 | 4 | 3 | 3 | 2 | 2 | | | | | |
| 321 | | 11.2100 | 0 | 0 | 0 | 0 | 0 | 0 | 0 | 1 | 0 | 1 | | | | | |
| 322 | | 11.2100 | 0 | 0 | 1 | 0 | 0 | 2 | 0 | 2 | 2 | 3 | | | | | |
| 323 | | 11.2100 | 0 | 2 | 2 | 0 | 2 | 2 | 0 | 2 | 2 | 3 | | | | | |
| 324 | | 11.2100 | 0 | 3 | 2 | 1 | 3 | 3 | 1 | 3 | 2 | 4 | | | | | |
| 325 | | 11.2100 | 0 | 0 | 1 | 0 | 2 | 3 | 2 | 3 | 2 | 4 | | | | | |
| 326 | | 11.2100 | 2 | 0 | 2 | 0 | 3 | 4 | 4 | 4 | 0 | 4 | | | | | |
| 327 | | 11.2100 | 2 | 0 | 2 | 0 | 3 | 4 | 4 | 4 | 4 | 4 | | | | | |
| 328 | | 11.2100 | 2 | 1 | 3 | 0 | 2 | 2 | 2 | 3 | 1 | 2 | | | | | |
| 329 | | 11.2100 | 0 | 0 | 0 | 0 | 0 | 2 | 2 | 3 | 2 | 2 | | | | | |
| 330 | | 11.2100 | 1 | 0 | 2 | 0 | 2 | 2 | 2 | 4 | 2 | 4 | | | | | |
| 331 | | 11.2100 | 2 | 1 | 3 | 0 | 3 | 3 | 3 | 4 | 3 | 4 | | | | | |
| 332 | | 11.2100 | 0 | 0 | 1 | 0 | 1 | 4 | 3 | 3 | 3 | 4 | | | | | |
| 333 | | 11.2100 | 0 | 0 | 2 | 0 | 2 | 4 | 3 | 4 | 4 | 4 | | | | | |
| 334 | | 11.2100 | 0 | 0 | 0 | 0 | 1 | 3 | 2 | 3 | 4 | 3 | | | | | |
| 335 | | 11.2100 | 3 | 2 | 4 | 1 | 4 | 4 | 3 | 4 | 3 | 4 | | | | | |
| 336 | | 11.2100 | 0 | 0 | 0 | 0 | 0 | 2 | 0 | 4 | 0 | 4 | | | | | |
| 337 | | 11.2100 | 2 | | | 0 | 4 | 4 | 4 | 4 | | | 4 | 4 | 3 | 1 | 1 |
| 338 | = | 11.2100 | 0 | | | 0 | 2 | 1 | 0 | 1 | | | 0 | 4 | 3 | 0 | 0 |
| 339 | = | 11.2100 | 0 | | | 2 | 3 | 1 | 0 | 1 | | | 0 | 4 | 2 | 0 | 2 |
| 340 | | 11.2100 | 2 | | | 1 | 3 | 3 | 3 | 4 | | | 2 | 4 | N | 2 | N |
| 341 | | 11.2100 | 0 | | | 0 | 0 | 0 | 0 | 0 | | | 0 | 0 | 0 | 0 | 0 |
| 342 | | 11.2100 | 0 | | | 0 | 0 | 0 | 0 | 0 | | | 0 | 2 | 0 | 0 | 0 |
| 343 | | 11.2100, | 0 | 3 | 4 | 3 | 4 | 3 | 3 | 4 | 3 | 4 | | | | | |
| 344 | = | 11.2100 | 0 | | | 0 | 2 | 3 | 1 | 3 | | | 0 | 4 | 3 | 1 | 1 |
| 345 | + | 11.2100 | 0 | | | 0 | 0 | 1 | 0 | 0 | | | 0 | 1 | N | 0 | 0 |
| 346 | + | 11.2100 | 0 | | | 0 | 0 | 0 | 0 | 0 | | | 0 | 4 | N | 0 | 0 |
| 347 | + | 11.2100 | 0 | | | 0 | 0 | 0 | 0 | 0 | | | 0 | 1 | N | 0 | 0 |
| 348 | + | 11.2100 | 0 | | | 0 | 1 | 1 | 1 | 0 | | | 0 | 4 | N | 0 | 0 |
| 349 | + | 11.2100 | 0 | | | 0 | 0 | 1 | 0 | 0 | | | 1 | 3 | N | 0 | 0 |
| 350 | + | 11.2100 | 0 | | | 0 | 0 | 1 | 0 | 1 | | | 0 | 2 | N | 0 | 0 |
| 351 | | 11.2100 | 0 | | | 0 | 0 | 1 | 0 | 0 | | | 0 | 0 | N | 0 | 0 |
| 352 | | 11.2100 | 0 | | | 0 | 1 | 3 | 3 | 4 | | | 1 | 4 | N | 0 | 0 |
| 353 | | 11.2100 | 0 | | | 0 | 0 | 0 | 0 | 0 | | | 0 | 2 | N | 0 | 0 |
| 354 | | 11.2100 | 0 | | | 0 | 0 | 0 | 0 | 0 | | | 0 | 0 | N | 0 | 0 |
| 355 | | 11.2100 | 0 | | | 0 | 0 | 2 | 1 | 3 | | | 0 | 2 | N | 0 | 0 |
| 356 | | 11.2100 | 0 | | | 0 | 2 | 3 | 3 | 3 | | | 2 | 4 | N | 0 | 0 |
| 357 | + | 11.2100 | 0 | | | 0 | 1 | 1 | 0 | 0 | | | 0 | 3 | N | 0 | 0 |
| 358 | + | 11.2100 | 0 | | | 0 | 0 | 1 | 1 | 0 | | | 0 | 1 | N | 0 | 0 |
| 359 | + | 11.2100 | 0 | | | 0 | 0 | 0 | 0 | 0 | | | 0 | 0 | N | 0 | 0 |
| 360 | + | 11.2100 | 0 | | | 0 | 0 | 2 | 2 | 1 | | | 0 | 1 | N | 0 | 0 |
| 361 | + | 11.2100 | 0 | | | 0 | 0 | 0 | 0 | 0 | | | 0 | 1 | N | 0 | 0 |
| 362 | + | 11.2100 | 0 | | | 0 | 0 | 0 | 0 | 0 | | | 0 | 1 | N | 0 | 0 |
| 363 | + | 11.2100 | 0 | | | 0 | 0 | 1 | 0 | 0 | | | 0 | 1 | N | 0 | 0 |
| 364 | = | 11.2100 | 0 | | | 0 | 0 | 1 | 1 | 0 | | | 1 | 0 | 0 | 0 | 0 |
| 365 | = | 11.2100 | 0 | | | 0 | 0 | 1 | 1 | 1 | | | 1 | 3 | 1 | 0 | 0 |
| 366 | = | 11.2100 | 0 | | | 0 | 0 | 1 | 1 | 1 | | | 1 | 3 | 2 | 0 | 0 |
| 367 | = | 11.2100 | 0 | | | 0 | 0 | 0 | 1 | 0 | | | 0 | 2 | 2 | 0 | 0 |
| 368 | = | 11.2100 | 0 | | | 0 | 0 | 1 | 1 | 0 | | | 1 | 1 | 1 | 0 | 0 |
| 369 | = | 11.2100 | 0 | | | 0 | 0 | 0 | 0 | 0 | | | 0 | 0 | 0 | 0 | 0 |
| 370 | = | 11.2100 | 0 | | | 0 | 0 | 1 | 0 | 1 | | | 0 | 4 | 3 | 0 | 0 |
| 371 | = | 11.2100 | 0 | | | 0 | 0 | 0 | 0 | 0 | | | 0 | 1 | 0 | 0 | 0 |
| 372 | = | 11.2100 | 1 | | | 0 | 1 | 2 | 1 | 3 | | | 0 | 4 | 3 | 0 | 0 |
| 373 | = | 11.2100 | 0 | | | 0 | 0 | 0 | 0 | 0 | | | 0 | 1 | N | 0 | 0 |
| 374 | = | 11.2100 | 1 | | | 0 | 1 | 0 | 0 | 2 | | | N | 4 | N | 0 | 0 |
| 375 | = | 11.2100 | 0 | | | 0 | 0 | 0 | 0 | 0 | | | 0 | 1 | N | 0 | 1 |
| 376 | = | 11.2100 | 0 | | | 0 | 0 | 0 | 0 | 0 | | | 0 | 0 | N | 0 | 1 |
| 377 | = | 11.2100 | 0 | | | 0 | 0 | 0 | 0 | 0 | | | 0 | 1 | N | 0 | 0 |
| 378 | = | 11.2100 | 0 | | | 0 | 0 | 0 | 1 | 0 | | | 0 | 3 | N | 0 | 0 |
| 379 | = | 11.2100 | 0 | | | 0 | 1 | 0 | 0 | 0 | | | 1 | 0 | N | 0 | 1 |
| 380 | = | 11.2100 | 0 | | | 0 | 0 | 0 | 0 | 0 | | | 0 | 0 | N | 0 | 0 |

TABLE B-continued

| | | Herbicide Primary Post, spectrums 25 and 90 | | | | | | | | | | | | | |
|---|---|---|---|---|---|---|---|---|---|---|---|---|---|---|---|
| Ex. No. | Rate kg/ha | Yens | Anbg | Sejg | Dobr | Bygr | Mogl | Cobu | Velu | Inmu | Wibw | Cath | Colq | Pesw | Rhqg | Rhjg |
| 381 | = 11.2100 | 1 | | | 0 | 3 | 3 | 3 | 3 | | | 1 | 4 | N | 0 | 0 |
| 382 | = 11.2100 | 2 | | | 0 | 2 | 4 | 4 | 3 | | | 3 | 4 | N | 0 | 0 |
| 383 | = 11.2100 | 0 | | | 0 | 2 | 0 | 2 | 1 | | | 0 | 4 | N | 0 | 2 |
| 384 | = 11.2100 | 0 | | | 0 | 1 | 2 | 3 | 3 | | | 0 | 4 | N | 0 | 0 |
| 385 | = 11.2100 | 2 | | | 0 | 1 | 1 | 3 | 3 | | | 3 | 4 | N | 0 | 0 |
| 386 | ( 11.2100 | 0 | | | 0 | 0 | 3 | 3 | 3 | | | 1 | 3 | N | 0 | 0 |
| 387 | ( 11.2100 | 0 | | | 0 | 2 | 4 | 3 | 4 | | | 1 | 4 | N | 0 | 0 |
| 388 | ( 11.2100 | 0 | | | 0 | 0 | 4 | 3 | 4 | | | 0 | 4 | 1 | 0 | 0 |
| 389 | ( 11.2100 | 0 | | | 0 | 0 | 0 | 0 | 0 | | | 0 | 2 | 0 | 0 | 0 |
| 390 | ( 11.2100 | 1 | | | 0 | 1 | 2 | 2 | 3 | | | 2 | 4 | N | 0 | 0 |
| 391 | ( 11.2100 | 0 | | | 0 | 0 | 0 | 0 | 0 | | | 0 | 3 | N | 0 | 0 |
| 392 | 11.2100 | 0 | 0 | 0 | 0 | 3 | 0 | 0 | 1 | 3 | 3 | | | | | |
| 393 | 11.2100 | 0 | 0 | 0 | 0 | 3 | 3 | 2 | 3 | 2 | 4 | | | | | |
| 394 | 11.2100 | 0 | 0 | 0 | 0 | 2 | 2 | 1 | 2 | 2 | 4 | | | | | |
| 395 | 11.2100 | 0 | 0 | 0 | 0 | 0 | 0 | 3 | 2 | 2 | 1 | | | | | |
| 396 | 11.2100 | 0 | 0 | 0 | 0 | 0 | 0 | 0 | 0 | 2 | 1 | | | | | |
| 397 | 11.2100 | 0 | 0 | 0 | 0 | 0 | 0 | 0 | 0 | 0 | 0 | | | | | |
| 398 | 11.2100 | 0 | 0 | 0 | 0 | 2 | 0 | 0 | 2 | 1 | 4 | | | | | |
| 399 | = 11.2100 | 2 | | | 0 | 3 | 4 | 3 | 4 | | | 3 | 4 | N | 1 | 2 |
| 400 | = 11.2100 | 1 | | | 0 | 3 | 4 | 3 | 4 | | | 0 | 4 | N | 1 | 3 |
| 401 | = 11.2100 | 0 | | | 0 | 3 | 2 | 0 | 1 | | | 0 | 4 | N | 0 | 2 |
| 402 | ( 11.2100 | 0 | | | 0 | 3 | 3 | 2 | 3 | | | 1 | 4 | N | 0 | 3 |
| 403 | 11.2100 | 0 | 0 | 3 | 0 | 3 | 3 | 2 | 3 | 3 | 4 | | | | | |
| 404 | 11.2100 | 2 | 0 | 3 | 0 | 3 | 3 | 2 | 4 | 3 | 4 | | | | | |
| 405 | 11.2100 | 0 | 2 | 2 | 3 | 2 | 2 | 1 | 3 | 2 | 4 | | | | | |
| 406 | 11.2100 | 2 | 2 | 3 | 2 | 3 | 3 | 2 | 3 | 2 | 4 | | | | | |
| 407 | = 11.2100 | 0 | | | 0 | 2 | 3 | 0 | 3 | | | 0 | 4 | N | 0 | 0 |
| 408 | ( 11.2100 | 0 | | | 0 | 3 | 3 | 2 | 4 | | | 1 | 4 | N | 0 | 0 |
| 409 | 11.2100 | 1 | 1 | 2 | 0 | 3 | 3 | 1 | 3 | 2 | 4 | | | | | |
| 410 | 11.2100 | 1 | 0 | 1 | 0 | 2 | 2 | 1 | 3 | 3 | 4 | | | | | |
| 411 | 11.2100 | 0 | 2 | 1 | 0 | 2 | 2 | 1 | 3 | 3 | 4 | | | | | |
| 412 | 11.2100 | 2 | 2 | 3 | 0 | 3 | 3 | 2 | 3 | 3 | 4 | | | | | |
| 413 | 11.2100 | 0 | 0 | 1 | 0 | 1 | 1 | 2 | 3 | 2 | 4 | | | | | |
| 414 | 11.2100 | 2 | 2 | 2 | 0 | 2 | 2 | 2 | 4 | 3 | 4 | | | | | |
| 415 | 11.2100 | 0 | 0 | 2 | 0 | 3 | 2 | 1 | 3 | 2 | 4 | | | | | |
| 417 | 11.2100 | 0 | 0 | 1 | 0 | 2 | 2 | 2 | 2 | 2 | 3 | | | | | |
| 418 | 11.2100 | 0 | 0 | 1 | 0 | 0 | 2 | 2 | 2 | 2 | 4 | | | | | |
| 419 | 11.2100 | 0 | 0 | 1 | 0 | 0 | 4 | 3 | 4 | 2 | 2 | | | | | |
| 420 | ( 11.2100 | 0 | | | 0 | 0 | 1 | 0 | 1 | | | 0 | 3 | N | 0 | 0 |
| 421 | 11.2100 | 1 | | | 0 | 0 | 1 | 0 | 1 | | | 0 | 3 | N | 0 | 0 |
| 422 | 11.2100 | 1 | 0 | 0 | 0 | 0 | 2 | 2 | 2 | 2 | 3 | | | | | |
| 423 | 11.2100 | 0 | 0 | 1 | 0 | 1 | 2 | 3 | 2 | 2 | 3 | | | | | |
| 424 | 11.2100 | 0 | 0 | 0 | 0 | 0 | 2 | 2 | 2 | 2 | 2 | | | | | |
| 425 | 11.2100 | 0 | 0 | 0 | 1 | 0 | 2 | 1 | 2 | 2 | 2 | | | | | |
| 426 | 11.2100 | 0 | 0 | 0 | 0 | 0 | 2 | 3 | 3 | 2 | 4 | | | | | |
| 427 | 11.2100 | 1 | 0 | 0 | 0 | 0 | 2 | 3 | 2 | 2 | 4 | | | | | |
| 428 | 11.2100 | 1 | 0 | 1 | 0 | 3 | 2 | 3 | 2 | 2 | 4 | | | | | |
| 429 | 11.2100 | 1 | 0 | 0 | 0 | 0 | 1 | 2 | 3 | 3 | 4 | | | | | |
| 430 | 11.2100 | 0 | 0 | 0 | 0 | 0 | 0 | 1 | 1 | 2 | 3 | | | | | |
| 431 | 11.2100 | 0 | 0 | 1 | 0 | 1 | 0 | 3 | 1 | 1 | 3 | | | | | |
| 432 | 11.2100 | 1 | 0 | 1 | 0 | 1 | 2 | 2 | 4 | 3 | 4 | | | | | |
| 433 | 11.2100 | 1 | 0 | 0 | 0 | 0 | 1 | 2 | 2 | 1 | 2 | | | | | |
| 434 | 11.2100 | 0 | 0 | 0 | 0 | 0 | 0 | 1 | 1 | 2 | 3 | | | | | |
| 435 | 11.2100 | 2 | 0 | 0 | 0 | 2 | 2 | 2 | 2 | 3 | 4 | | | | | |
| 436 | 11.2100 | 0 | 0 | 0 | 0 | 2 | 2 | 2 | 2 | 1 | 2 | | | | | |
| 437 | 11.2100 | 0 | 0 | 0 | 0 | 0 | 0 | 0 | 0 | 2 | 0 | | | | | |
| 438 | 11.2100 | 1 | 0 | 0 | 0 | 0 | 2 | 2 | 3 | 2 | 4 | | | | | |
| 439 | 11.2100 | 0 | 0 | 0 | 0 | 0 | 0 | 0 | 0 | 4 | 3 | | | | | |
| 440 | 11.2100 | 0 | 0 | 0 | 0 | 0 | 3 | 2 | 2 | 2 | 4 | | | | | |
| 441 | 11.2100 | 0 | 0 | 0 | 0 | 0 | 2 | 2 | 1 | 1 | 3 | | | | | |
| 442 | 11.2100 | 0 | 0 | 0 | 0 | 0 | 1 | 1 | 4 | 2 | 3 | | | | | |
| 443 | 11.2100 | 0 | 0 | 0 | 0 | 0 | 2 | 2 | 0 | 2 | 3 | | | | | |
| 444 | 11.2100 | 1 | 1 | 0 | 2 | 2 | 2 | 2 | 1 | 2 | 4 | | | | | |
| 445 | 11.2100 | 0 | 0 | 0 | 0 | 0 | 1 | 1 | 1 | 2 | 4 | | | | | |
| 446 | 11.2100 | 1 | 3 | 3 | 2 | 4 | 4 | 2 | 4 | 4 | 4 | | | | | |
| 447 | 11.2100 | 2 | 0 | 2 | 0 | 2 | 3 | 3 | 4 | 2 | 4 | | | | | |
| 448 | 11.2100 | 0 | 0 | 0 | 0 | 1 | 2 | 2 | 2 | 2 | 4 | | | | | |
| 449 | 11.2100 | 0 | 0 | 0 | 0 | 2 | 2 | 2 | 2 | 0 | 2 | | | | | |
| 450 | 11.2100 | 0 | 0 | 2 | 0 | 2 | 4 | 2 | 3 | 3 | 4 | | | | | |
| 451 | 11.2100 | 0 | 0 | 1 | 0 | 1 | 0 | 0 | 1 | 1 | 2 | | | | | |
| 452 | 11.2100 | 0 | 0 | 1 | 0 | 1 | 0 | 1 | 0 | 2 | 0 | | | | | |
| 453 | 11.2100 | 0 | 0 | 0 | 0 | 2 | 2 | 2 | 2 | 0 | 3 | | | | | |
| 454 | 11.2100 | 0 | 0 | 0 | 0 | 2 | 0 | 1 | 0 | 1 | 2 | | | | | |
| 455 | 11.2100 | 1 | 0 | 0 | 0 | 2 | 3 | 2 | 2 | 2 | 4 | | | | | |
| 456 | 11.2100 | 0 | 0 | 0 | 0 | 0 | 2 | 1 | 2 | 2 | 2 | | | | | |
| 457 | 11.2100 | 2 | 3 | 3 | 1 | 3 | 4 | 3 | 3 | 0 | 4 | | | | | |
| 458 | 11.2100 | 1 | 0 | 1 | 0 | 2 | 2 | 2 | 0 | 2 | 4 | | | | | |

TABLE B-continued

Herbicide Primary Post, spectrums 25 and 90

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 459 | 11.2100 | 0 | 0 | 0 | 0 | 0 | 2 | 3 | 3 | 2 | 3 | | | | | |
| 460 | 11.2100 | 3 | 0 | 3 | 1 | 3 | 0 | 4 | 4 | 4 | 3 | | | | | |
| 461 | 11.2100 | 2 | 0 | 0 | 0 | 1 | 2 | 2 | 3 | 1 | 2 | | | | | |
| 462 | 11.2100 | 0 | 0 | 0 | 0 | 0 | 0 | 0 | 2 | 2 | 2 | | | | | |
| 463 | 11.2100 | 2 | 0 | 1 | 0 | 1 | 2 | 0 | 1 | 0 | 3 | | | | | |
| 464 | 11.2100 | 0 | 2 | 3 | 0 | 3 | 3 | 2 | 4 | 3 | 4 | | | | | |
| 465 | 11.2100 | 0 | 1 | 3 | 0 | 3 | 4 | 2 | 4 | 2 | 4 | | | | | |
| 466 | 11.2100 | 2 | 0 | 3 | 0 | 3 | 3 | 2 | 3 | 2 | 4 | | | | | |
| 467 | 11.2100 | 0 | 0 | 2 | 0 | 3 | 3 | 2 | 4 | 2 | 4 | | | | | |
| 468 | 11.2100 | 2 | 0 | 2 | 0 | 3 | 4 | 2 | 4 | 2 | 4 | | | | | |
| 469 | 11.2100 | 0 | 2 | 3 | 1 | 3 | 4 | 2 | 4 | 3 | 4 | | | | | |
| 470 | 11.2100 | 1 | 2 | 3 | 0 | 3 | 4 | 3 | 4 | 3 | 4 | | | | | |
| 471 | 11.2100 | 0 | 2 | 2 | 0 | 2 | 2 | 1 | 3 | 4 | 4 | | | | | |
| 472 | 11.2100 | 0 | 2 | 3 | 0 | 3 | 3 | 2 | 4 | 3 | 4 | | | | | |
| 473 | 11.2100 | 0 | 0 | 2 | 1 | 3 | 3 | 3 | 4 | 2 | 4 | | | | | |
| 474 | 11.2100 | 0 | 0 | 2 | 0 | 3 | 3 | 2 | 4 | 2 | 4 | | | | | |
| 475 | 11.2100 | 0 | 0 | 0 | 0 | 2 | 3 | 2 | 4 | 1 | 1 | | | | | |
| 476 | 11.2100 | 0 | 4 | 2 | 4 | 3 | 3 | 2 | 4 | 2 | 3 | | | | | |
| 477 | 11.2100 | 1 | 0 | 2 | 0 | 2 | 3 | 2 | 4 | 2 | 3 | | | | | |
| 478 | 11.2100 | 0 | 0 | 0 | 0 | 1 | 2 | 0 | 4 | 2 | 4 | | | | | |
| 479 | 11.2100 | 0 | 0 | 2 | 0 | 3 | 2 | 0 | 4 | 2 | 4 | | | | | |
| 480 | 11.2100 | 0 | 4 | 4 | 4 | 4 | 3 | 4 | 3 | 4 | | | | | | |
| 481 | 11.2100 | 0 | 2 | 3 | 2 | 4 | 4 | 1 | 4 | 3 | 4 | | | | | |
| 482 | 11.2100 | 0 | 2 | 3 | 2 | 3 | 4 | 2 | 4 | 3 | 4 | | | | | |
| 483 | 11.2100 | 0 | 2 | 3 | 2 | 3 | 3 | 2 | 4 | 2 | 4 | | | | | |
| 484 | 11.2100 | 0 | 3 | 3 | 4 | 4 | 4 | 2 | 4 | 3 | 4 | | | | | |
| 485 | 11.2100 | 0 | 2 | 3 | 1 | 3 | 4 | 2 | 4 | 3 | 2 | | | | | |
| 486 | 11.2100 | 0 | 3 | 4 | 2 | 4 | 3 | 2 | 4 | 3 | 4 | | | | | |
| 487 | 11.2100 | 0 | 0 | 0 | 0 | 0 | 2 | 2 | 3 | 2 | 2 | | | | | |
| 488 | 11.2100 | 0 | 0 | 0 | 0 | 3 | 3 | 2 | 3 | 2 | 4 | | | | | |
| 489 | 11.2100 | 0 | 0 | 2 | 0 | 3 | 3 | 2 | 2 | 2 | 2 | | | | | |
| 490 | 11.2100 | 0 | 0 | 2 | 0 | 3 | 2 | 2 | 2 | 1 | 2 | | | | | |
| 491 | 11.2100 | 0 | 0 | 0 | 0 | 2 | 2 | 0 | 1 | 2 | 2 | | | | | |
| 492 | 11.2100 | 0 | 0 | 0 | 0 | 2 | 0 | 0 | 3 | 0 | 0 | | | | | |
| 493 | 11.2100 | 0 | 0 | 2 | 0 | 2 | 3 | 3 | 4 | 2 | 4 | | | | | |
| 494 | 11.2100 | 0 | 2 | 0 | 2 | 2 | 4 | 2 | 4 | 3 | 4 | | | | | |
| 495 | 11.2100 | 0 | 0 | 0 | 0 | 2 | 3 | 2 | 2 | 0 | 2 | | | | | |
| 496 | 11.2100 | 0 | 0 | 0 | 2 | 2 | 2 | 1 | 2 | 0 | 4 | | | | | |
| 497 | 11.2100 | 0 | 2 | 0 | 0 | 2 | 3 | 2 | 4 | 3 | 4 | | | | | |
| 498 | 11.2100 | 0 | 0 | 2 | 0 | 3 | 3 | 2 | 3 | 2 | 4 | | | | | |
| 499 | 11.2100 | 0 | 0 | 2 | 0 | 3 | 4 | 3 | 3 | 2 | 4 | | | | | |
| 500 | 11.2100 | 0 | 2 | 0 | 0 | 0 | 3 | 3 | 4 | 1 | 2 | | | | | |
| 501 | 11.2100 | 2 | 0 | 0 | 0 | 2 | 3 | 3 | 4 | 2 | 4 | | | | | |
| 502 | 11.2100 | 1 | 2 | 2 | 2 | 4 | 3 | 2 | 4 | 2 | 3 | | | | | |
| 503 | 11.2100 | 2 | 0 | 2 | 2 | 3 | 3 | 2 | 3 | 3 | 4 | | | | | |
| 504 | 11.2100 | 0 | 0 | 3 | 0 | 0 | 3 | 2 | 4 | 2 | 3 | | | | | |
| 505 | 11.2100 | 0 | 2 | 3 | 2 | 3 | 3 | 1 | 3 | 2 | 3 | | | | | |
| 506 | 11.2100 | 0 | 0 | 3 | 1 | 2 | 2 | 0 | 3 | 3 | 4 | | | | | |
| 507 | 11.2100 | 0 | 0 | 3 | 2 | 3 | 2 | 0 | 4 | 4 | 4 | | | | | |
| 508 | 11.2100 | 0 | 0 | 0 | 0 | 0 | 2 | 0 | 2 | 2 | 2 | | | | | |
| 509 | 11.2100 | 2 | 0 | 3 | 0 | 0 | 3 | 0 | 4 | 3 | 4 | | | | | |
| 510 | 11.2100 | 2 | 1 | 3 | 0 | 4 | 4 | 1 | 4 | 1 | 3 | | | | | |
| 511 | 11.2100 | 0 | 0 | 1 | 0 | 2 | 3 | 0 | 4 | 3 | 3 | | | | | |
| 512 | 11.2100 | 0 | 0 | 0 | 1 | 2 | 3 | 1 | 4 | 2 | 3 | | | | | |
| 513 | 11.2100 | 0 | 2 | 2 | 2 | 3 | 2 | 4 | 4 | 3 | 4 | | | | | |
| 514 | 11.2100 | 0 | 2 | 3 | 3 | 3 | 3 | 3 | 3 | 3 | 4 | | | | | |
| 515 | 11.2100 | 2 | 0 | 3 | 0 | 2 | 3 | 2 | 4 | 3 | 4 | | | | | |
| 516 | 11.2100 | 0 | 0 | 3 | 0 | 2 | 4 | 2 | 4 | 1 | 4 | | | | | |
| 517 | 11.2100 | 0 | 4 | 4 | 4 | 4 | 4 | 3 | 4 | 4 | 4 | | | | | |
| 518 | 11.2100 | 0 | 3 | 3 | 2 | 4 | 3 | 2 | 4 | 4 | 4 | | | | | |
| 519 | 11.2100 | 0 | 0 | 2 | 0 | 2 | 2 | 0 | 2 | 0 | N | | | | | |
| 520 | 11.2100 | 0 | 1 | 2 | 0 | 2 | 2 | 1 | 1 | 0 | 1 | | | | | |
| 521 | 11.2100 | 0 | 2 | 3 | 2 | 2 | 2 | 2 | 4 | 1 | 4 | | | | | |
| 522 | 11.2100 | 0 | 2 | 2 | 3 | 2 | 2 | 2 | 4 | 1 | 4 | | | | | |
| 523 | 11.2100 | 0 | 3 | 4 | 3 | 3 | 3 | 0 | 4 | 3 | 4 | | | | | |
| 524 | 11.2100 | 0 | 2 | 4 | 2 | 4 | 4 | 2 | 4 | 4 | 4 | | | | | |
| 525 | 11.2100 | 0 | 4 | 4 | 4 | 4 | 4 | 2 | 3 | 3 | 4 | | | | | |
| 526 | 11.2100 | 0 | 4 | 4 | 0 | 4 | 4 | 2 | 4 | 4 | 4 | | | | | |
| 527 | 11.2100 | 0 | 3 | 4 | 3 | 4 | 3 | 2 | 4 | 3 | 4 | | | | | |
| 528 | 11.2100 | 0 | 4 | 4 | 4 | 4 | 4 | 1 | 4 | 4 | 4 | | | | | |
| 529 | 11.2100 | 0 | 4 | 4 | 4 | 4 | 4 | 0 | 4 | 3 | 4 | | | | | |
| 530 | 11.2100 | 0 | 3 | 3 | 0 | 3 | 3 | 0 | 3 | 3 | 4 | | | | | |
| 531 | 11.2100 | 0 | 1 | 3 | 2 | 3 | 3 | 3 | 4 | 2 | 4 | | | | | |
| 532 | 11.2100 | 0 | 4 | 4 | 4 | 4 | 3 | 2 | 4 | 3 | 4 | | | | | |
| 533 | 11.2100 | 0 | 3 | 4 | 3 | 3 | 3 | 1 | 4 | 1 | 3 | | | | | |
| 534 | 11.2100 | 0 | 3 | 4 | 3 | 4 | 3 | 2 | 4 | 3 | 4 | | | | | |
| 535 | 11.2100 | 0 | 3 | 4 | 3 | 4 | 4 | 3 | 4 | 2 | 4 | | | | | |

TABLE B-continued

| | | Herbicide Primary Post, spectrums 25 and 90 | | | | | | | | | | | | | |
|---|---|---|---|---|---|---|---|---|---|---|---|---|---|---|---|
| Ex. No. | Rate kg/ha | Yens | Anbg | Sejg | Dobyr | Bogr | Mogl | Cobu | Vele | Inmu | Wbw | Ctlh | Colq | Pesw | Rhqg | Rhjg |
| 536 | 11.2100 | 0 | 0 | 0 | 0 | 0 | 3 | 1 | 3 | 2 | 3 | | | | | |
| 537 | 11.2100 | 0 | 0 | 0 | 0 | 0 | 0 | 0 | 0 | 1 | 2 | | | | | |
| 538 | 11.2100 | 0 | 2 | 4 | 1 | 3 | 3 | 1 | 4 | 2 | 3 | | | | | |
| 539 | 11.2100 | 0 | 2 | 4 | 3 | 4 | 4 | 3 | 4 | 3 | 4 | | | | | |
| 540 | 11.2100 | 0 | 3 | 4 | 2 | 4 | 4 | 2 | 4 | 3 | 4 | | | | | |
| 541 | 11.2100 | 2 | 2 | 4 | 1 | 3 | 4 | 2 | 4 | 3 | 4 | | | | | |
| 542 | 11.2100 | 2 | 0 | 3 | 1 | 4 | 4 | 2 | 4 | 2 | 3 | | | | | |
| 543 | 11.2100 | 2 | 0 | 3 | 2 | 4 | 3 | 1 | 4 | 2 | 4 | | | | | |
| 544 | 11.2100 | 0 | 3 | 4 | 3 | 4 | 4 | 3 | 4 | 3 | 4 | | | | | |
| 545 | 11.2100 | 2 | 2 | 3 | 2 | 4 | 3 | 3 | 4 | 2 | 3 | | | | | |
| 546 | 11.2100 | 2 | 3 | 4 | 3 | 4 | 4 | 3 | 4 | 3 | 2 | | | | | |
| 547 | 11.2100 | 0 | 2 | 3 | 2 | 3 | 4 | 3 | 4 | 2 | 2 | | | | | |
| 548 | 11.2100 | 0 | 2 | 4 | 2 | 4 | 4 | 4 | 4 | 4 | 4 | | | | | |
| 549 | 11.2100 | 1 | 4 | 4 | 4 | 4 | 2 | 3 | 4 | 4 | 4 | | | | | |
| 550 | 11.2100 | 0 | 0 | 4 | 1 | 3 | 4 | 4 | 4 | 2 | 3 | | | | | |
| 551 | 11.2100 | 0 | 4 | 4 | 4 | 4 | 3 | 3 | 4 | 4 | 4 | | | | | |
| 552 | 11.2100 | 1 | 3 | 4 | 3 | 4 | 3 | 3 | 4 | 4 | 4 | | | | | |
| 554 | 11.2100 | 0 | 2 | 2 | 2 | 1 | 1 | 0 | 3 | 0 | 3 | | | | | |
| 555 | 11.2100 | 0 | 2 | 2 | 2 | 4 | 4 | 4 | 4 | 2 | 4 | | | | | |
| 556 | 11.2100 | 1 | 0 | 2 | 0 | 2 | 4 | 4 | 4 | 3 | 4 | | | | | |
| 557 | 11.2100 | 0 | 2 | 4 | 2 | 4 | 4 | 2 | 4 | 3 | 3 | | | | | |
| 558 | 11.2100 | 2 | 3 | 4 | 1 | 3 | 3 | 1 | 4 | 3 | 3 | | | | | |
| 559 | 11.2100 | 0 | 0 | 2 | 0 | 2 | 2 | 0 | 0 | 2 | 2 | | | | | |
| 560 | 11.2100 | 2 | 2 | 4 | 2 | 4 | 4 | 2 | 4 | 3 | 4 | | | | | |
| 561 | 11.2100 | 0 | 1 | 3 | 0 | 2 | 3 | 1 | 4 | 2 | 3 | | | | | |
| 562 | 11.2100 | 2 | 3 | 3 | 3 | 4 | 3 | 2 | 4 | 3 | 4 | | | | | |
| 563 | 11.2100 | 1 | 1 | 3 | 1 | 3 | 3 | 4 | 4 | 3 | 4 | | | | | |
| 564 | 11.2100 | 0 | 2 | 3 | 0 | 3 | 4 | 3 | 4 | 2 | 3 | | | | | |
| 565 | 11.2100 | 0 | 4 | 4 | 2 | 4 | 3 | 4 | 4 | 3 | 4 | | | | | |
| 566 | ! 11.2100 | 0 | 4 | 4 | 3 | 4 | 4 | 4 | 4 | 3 | 4 | | | | | |
| 567 | 11.2100 | 0 | 3 | 3 | 0 | 4 | 4 | 4 | 4 | 2 | 3 | | | | | |
| 568 | 11.2100 | 2 | 3 | 4 | 4 | 4 | 3 | 3 | 4 | 4 | 4 | | | | | |
| 569 | ! 11.2100 | 0 | 0 | 3 | 0 | 3 | 3 | 2 | 3 | 2 | 4 | | | | | |
| 570 | ! 11.2100 | 3 | 4 | 4 | 3 | 4 | 4 | 3 | 4 | 3 | 4 | | | | | |
| 571 | % 11.2100 | 2 | 3 | 4 | 4 | 4 | 4 | 4 | 4 | 3 | 3 | | | | | |
| 572 | % 11.2100 | 2 | 1 | 3 | 0 | 3 | 4 | 2 | 4 | 3 | 4 | | | | | |
| 573 | % 11.2100 | 0 | 0 | 2 | 0 | 0 | 2 | 3 | 4 | 2 | 2 | | | | | |
| 574 | % 11.2100 | 2 | 1 | 2 | 0 | 1 | 4 | 4 | 4 | 3 | 2 | | | | | |
| 575 | % 11.2100 | 0 | 0 | 2 | 0 | 0 | 4 | 4 | 4 | 3 | 3 | | | | | |
| 576 | % 11.2100 | 0 | 0 | 3 | 0 | 3 | 3 | 3 | 4 | 1 | 2 | | | | | |
| 577 | % 11.2100 | 2 | 2 | 4 | 0 | 3 | 4 | 4 | 4 | 2 | 3 | | | | | |
| 578 | % 11.2100 | 0 | 0 | 3 | 0 | 3 | 4 | 4 | 4 | 1 | 2 | | | | | |
| 579 | % 11.2100 | 0 | 0 | 3 | 2 | 4 | 4 | 3 | 4 | 2 | 3 | | | | | |
| 580 | % 11.2100 | 2 | 0 | 4 | 2 | 4 | 3 | 4 | 4 | 0 | 3 | | | | | |
| 581 | % 11.2100 | 0 | 1 | 3 | 0 | 0 | 2 | 3 | 3 | 2 | 3 | | | | | |
| 582 | \| 11.2100 | 0 | 3 | 3 | 3 | 3 | 2 | 4 | 4 | 4 | 4 | | | | | |
| 583 | ~ 11.2100 | 0 | 0 | 0 | 0 | 0 | 0 | 0 | 0 | N | 0 | | | | | |
| 584 | ~ 11.2100 | 2 | 2 | 4 | 3 | 4 | 4 | 4 | 4 | 3 | 3 | | | | | |
| 585 | ~ 11.2100 | 2 | 4 | 4 | 3 | 4 | 3 | 3 | 4 | 3 | 3 | | | | | |
| 586 | ~ 11.2100 | 2 | 3 | 3 | 4 | 3 | 3 | 4 | 4 | 3 | 3 | | | | | |
| 587 | \| 11.2100 | 0 | 0 | 2 | 0 | 2 | 2 | 0 | 3 | 2 | 3 | | | | | |
| 588 | \| 11.2100 | 2 | 3 | 3 | 3 | 4 | 3 | 2 | 4 | 3 | 4 | | | | | |
| 589 | \| 11.2100 | 1 | 4 | 4 | 4 | 4 | 3 | 4 | 4 | 4 | 4 | | | | | |
| 590 | \| 11.2100 | 1 | 2 | 3 | 0 | 2 | 4 | 4 | 4 | 4 | 3 | | | | | |
| 591 | < 11.2100 | 0 | 4 | 4 | 4 | 4 | 3 | 3 | 4 | 3 | 3 | | | | | |
| 592 | < 11.2100 | 1 | 1 | 3 | 1 | 2 | 2 | 3 | 4 | 3 | 3 | | | | | |
| 593 | < 11.2100 | 0 | 4 | 3 | 4 | 3 | 3 | 3 | 4 | 4 | 4 | | | | | |
| 594 | < 11.2100 | 2 | 2 | 4 | 2 | 3 | 3 | 4 | 4 | 3 | 4 | | | | | |
| 595 | 11.2100 | 2 | 2 | 3 | 3 | 3 | 3 | 3 | 4 | 3 | 2 | | | | | |
| 596 | 11.2100 | 1 | 3 | 4 | 4 | 4 | 4 | 4 | 4 | 3 | 4 | | | | | |
| 597 | 11.2100 | 1 | 4 | 4 | 4 | 4 | 4 | 4 | 4 | 2 | 4 | | | | | |
| 598 | 11.2100 | 0 | 4 | 4 | 4 | 4 | 3 | 4 | 4 | 4 | 4 | | | | | |
| 599 | 11.2100 | 2 | 3 | 4 | 4 | 4 | 4 | 3 | 4 | 3 | 4 | | | | | |
| 600 | 11.2100 | 2 | 3 | 3 | 2 | 3 | 4 | 4 | 4 | 3 | 2 | | | | | |
| 601 | 11.2100 | 1 | 0 | 4 | 1 | 4 | 4 | 3 | 4 | 3 | 3 | | | | | |
| 602 | 11.2100 | 0 | 0 | 3 | 1 | 3 | 2 | 3 | 4 | 2 | 2 | | | | | |
| 603 | 11.2100 | 0 | 0 | 3 | 4 | 3 | 4 | 1 | 4 | 3 | 4 | | | | | |
| 604 | { 11.2100 | 0 | 4 | 4 | 4 | 4 | 3 | 4 | 3 | 3 | 4 | | | | | |
| 605 | { 11.2100 | 1 | 4 | 4 | 3 | 4 | 3 | 4 | 4 | 3 | 3 | | | | | |
| 606 | { 11.2100 | 0 | 0 | 2 | 0 | 2 | 2 | 2 | 2 | 0 | 0 | | | | | |
| 607 | { 11.2100 | 1 | 3 | 3 | 3 | 4 | 3 | 4 | 4 | 3 | 4 | | | | | |
| 608 | { 11.2100 | 1 | 4 | 4 | 4 | 4 | 4 | 2 | 4 | 4 | 4 | | | | | |
| 609 | 11.2100 | 0 | 0 | 1 | 0 | 1 | 4 | 3 | 3 | 2 | 3 | | | | | |
| 610 | 11.2100 | 1 | 0 | 3 | 0 | 1 | 4 | 3 | 4 | 2 | 3 | | | | | |
| 611 | 11.2100 | 0 | 0 | 0 | 0 | 0 | 2 | 0 | 2 | 1 | 1 | | | | | |
| 612 | 11.2100 | 0 | 0 | 0 | 0 | 0 | 2 | 0 | 3 | 1 | 3 | | | | | |
| 613 | 11.2100 | 0 | 0 | 2 | 0 | 1 | 2 | 0 | 2 | 0 | 2 | | | | | |

TABLE B-continued

| | | Herbicide Primary Post, spectrums 25 and 90 | | | | | | | | | | | | | |
|---|---|---|---|---|---|---|---|---|---|---|---|---|---|---|---|
| Ex. No. | Rate kg/ha | Yens | Anbg | Sejg | Dobr | Bygr | Mogl | Cobu | Velu | Inmu | Wibw | Cath | Colq | Pesw | Rhqg | Rhjg |
| 614 | 11.2100 | 0 | 3 | 2 | 3 | 3 | 2 | 2 | 3 | 0 | 4 | | | | | |
| 615 | 11.2100 | 0 | 0 | 3 | 0 | 2 | 3 | 4 | 4 | 2 | 4 | | | | | |
| 616 | 11.2100 | 0 | 0 | 2 | 0 | 2 | 3 | 3 | 3 | 0 | 4 | | | | | |
| 617 | 11.2100 | 0 | 0 | 0 | 0 | 1 | 2 | 0 | 1 | 1 | 2 | | | | | |
| 618 | 11.2100 | 0 | 2 | 2 | 0 | 3 | 3 | 1 | 3 | 2 | 4 | | | | | |
| 619 | 11.2100 | 0 | 0 | 2 | 0 | 2 | 2 | 1 | 0 | 1 | 2 | | | | | |
| 620 | 11.2100 | 0 | 3 | 3 | 3 | 3 | 3 | 1 | 3 | 2 | 4 | | | | | |
| 621 | 11.2100 | 0 | 2 | 2 | 1 | 3 | 3 | 1 | 3 | 1 | 4 | | | | | |
| 622 | 11.2100 | 0 | 0 | 4 | 1 | 3 | 3 | 3 | 4 | 1 | 3 | | | | | |
| 623 | 11.2100 | 0 | 0 | 1 | 0 | 1 | 0 | 2 | 1 | 0 | 2 | | | | | |
| 624 | 11.2100 | 1 | 3 | 4 | 3 | 4 | 4 | 4 | 4 | 3 | 4 | | | | | |
| 625 | 11.2100 | 0 | 2 | 3 | 3 | 3 | 4 | 4 | 4 | 3 | 4 | | | | | |
| 626 | 11.2100 | 0 | 2 | 4 | 3 | 3 | 3 | 4 | 4 | 3 | 4 | | | | | |
| 627 | 11.2100 | 0 | 2 | 3 | 4 | 4 | 3 | 0 | 4 | 3 | 4 | | | | | |
| 629 | 11.2100 | 3 | 2 | 4 | 1 | 4 | 3 | 2 | 4 | 3 | 4 | | | | | |
| 630 | 11.2100 | 0 | 2 | 3 | 1 | 4 | 4 | 0 | 4 | 3 | 4 | | | | | |
| 631 | 11.2100 | 0 | 0 | 3 | 2 | 3 | 4 | 0 | 4 | 3 | 4 | | | | | |
| 632 | 11.2100 | 0 | 2 | 4 | 2 | 3 | 4 | 0 | 4 | 3 | 4 | | | | | |
| 633 | 11.2100 | 2 | 0 | 0 | 1 | 3 | 4 | 0 | 4 | 3 | 4 | | | | | |
| 634 | 11.2100 | 2 | 1 | 3 | 2 | 4 | 4 | 0 | 4 | 3 | 4 | | | | | |
| 635 | 11.2100 | 1 | 2 | 3 | 2 | 4 | 3 | 2 | 4 | 4 | 4 | | | | | |
| 636 | 11.2100 | 0 | 4 | 4 | 3 | 4 | 3 | 0 | 4 | 4 | 4 | | | | | |
| 637 | 11.2100 | 2 | 4 | 4 | 3 | 4 | 4 | 2 | 4 | 4 | 4 | | | | | |
| 638 | 11.2100 | 0 | 0 | 3 | 1 | 3 | 3 | 0 | 4 | 3 | 3 | | | | | |
| 639 | 11.2100 | 0 | 2 | 2 | 2 | 0 | 3 | 0 | 4 | 2 | 4 | | | | | |
| 640 | 11.2100 | 0 | 4 | 4 | 3 | 4 | 3 | 0 | 4 | 3 | 4 | | | | | |
| 641 | 11.2100 | 1 | 4 | 4 | 4 | 4 | 3 | 2 | 4 | 4 | 4 | | | | | |
| 642 | 11.2100 | 1 | 2 | 4 | 2 | 4 | 3 | 2 | 4 | 3 | 4 | | | | | |
| 643 | 11.2100 | 1 | 3 | 4 | 4 | 4 | 4 | 2 | 4 | 4 | 4 | | | | | |
| 644 | 11.2100 | 2 | 4 | 4 | 4 | 4 | 4 | 2 | 4 | 4 | 4 | | | | | |
| 645 | 11.2100 | 0 | 0 | 2 | 0 | 2 | 4 | 1 | 4 | 3 | 4 | | | | | |
| 646 | 11.2100 | 2 | 4 | 4 | 3 | 4 | 3 | 3 | 4 | 3 | 4 | | | | | |
| 647 | 11.2100 | 1 | 2 | 2 | 0 | 2 | 2 | 0 | 4 | 2 | 4 | | | | | |
| 648 | 11.2100 | 0 | 1 | 4 | 3 | 2 | 2 | 0 | 4 | 3 | 4 | | | | | |
| 649 | 11.2100 | 2 | 0 | 4 | 0 | 2 | 4 | 1 | 4 | 1 | 4 | | | | | |
| 650 | 11.2100 | 0 | 4 | 4 | 4 | 4 | 3 | 1 | 4 | 3 | 4 | | | | | |
| 651 | 11.2100 | 0 | 2 | 2 | 2 | 1 | 4 | 1 | 3 | 3 | 3 | | | | | |
| 652 | 11.2100 | 0 | 3 | 4 | 3 | 4 | 3 | 1 | 4 | 3 | 4 | | | | | |
| 653 | 11.2100 | 2 | 2 | 4 | 2 | 4 | 4 | 1 | 4 | 3 | 4 | | | | | |
| 654 | 11.2100 | 3 | 0 | 3 | 2 | 3 | 4 | 3 | 4 | 3 | 4 | | | | | |
| 655 | 11.2100 | 2 | 4 | 4 | 4 | 4 | 3 | 3 | 4 | 4 | 4 | | | | | |
| 656 | 11.2100 | 0 | 0 | 2 | 2 | 2 | 3 | 3 | 3 | 3 | 3 | | | | | |
| 657 | 11.2100 | 1 | 3 | 3 | 2 | 3 | 3 | 3 | 4 | 3 | 4 | | | | | |
| 658 | 11.2100 | 2 | 2 | 3 | 1 | 2 | 4 | 4 | 4 | 3 | 4 | | | | | |
| 659 | 11.2100 | 1 | 0 | 2 | 0 | 2 | 3 | 3 | 4 | 3 | 4 | | | | | |
| 660 | 11.2100 | 0 | 0 | 2 | 0 | 3 | 3 | 4 | 3 | 2 | 4 | | | | | |
| 661 | 11.2100 | 2 | 3 | 3 | 3 | 4 | 3 | 2 | 4 | 2 | 4 | | | | | |
| 662 | 11.2100 | 2 | 4 | 4 | 4 | 4 | 3 | 4 | 4 | 3 | 4 | | | | | |
| 663 | ! 11.2100 | 0 | 0 | 2 | 0 | 1 | 2 | 2 | 4 | 2 | 2 | | | | | |
| 664 | ! 11.2100 | 0 | 0 | 2 | 0 | 1 | 2 | 3 | 3 | 2 | 2 | | | | | |
| 665 | ! 11.2100 | 0 | 3 | 3 | 3 | 3 | 3 | 2 | 4 | 3 | 4 | | | | | |
| 666 | ~ 11.2100 | 1 | 4 | 4 | 4 | 4 | 3 | 4 | 4 | 3 | 4 | | | | | |
| 667 | ~ 11.2100 | 0 | 2 | 4 | 3 | 4 | 3 | 2 | 4 | 3 | 4 | | | | | |
| 668 | ! 11.2100 | 0 | 3 | 4 | 2 | 3 | 3 | 2 | 4 | 2 | 2 | | | | | |
| 669 | ! 11.2100 | 0 | 0 | 3 | 0 | 3 | 2 | 2 | 4 | 3 | 4 | | | | | |
| 670 | ! 11.2100 | 0 | 3 | 4 | 3 | 4 | 4 | 2 | 4 | 3 | 4 | | | | | |
| 671 | ! 11.2100 | 0 | 1 | 3 | 0 | 4 | 4 | 2 | 4 | 2 | 4 | | | | | |
| 672 | ! 11.2100 | 0 | 0 | 3 | 0 | 2 | 2 | 2 | 4 | 3 | 4 | | | | | |
| 673 | ! 11.2100 | 0 | 0 | 3 | 0 | 3 | 2 | 2 | 4 | 2 | 3 | | | | | |
| 674 | ~ 11.2100 | 1 | 4 | 4 | 4 | 4 | 3 | 4 | 4 | 3 | 3 | | | | | |
| 675 | ~ 11.2100 | 1 | 4 | 4 | 4 | 4 | 3 | 3 | 4 | 3 | 4 | | | | | |
| 676 | % 11.2100 | 2 | 0 | 2 | 0 | 2 | 4 | 4 | 4 | 3 | 4 | | | | | |
| 677 | % 11.2100 | 0 | 1 | 4 | 1 | 3 | 3 | 4 | 4 | 2 | 3 | | | | | |
| 678 | % 11.2100 | 2 | 4 | 4 | 4 | 4 | 3 | 4 | 3 | 4 | | | | | | |
| 679 | % 11.2100 | 2 | 3 | 3 | 2 | 3 | 3 | 2 | 4 | 1 | 4 | | | | | |
| 680 | \| 11.2100 | 0 | 1 | 3 | 0 | 3 | 2 | 2 | 3 | N | N | | | | | |
| 681 | % 11.2100 | 0 | 0 | 2 | 0 | 0 | 0 | 0 | 2 | 0 | 2 | | | | | |
| 682 | 11.2100 | 0 | 3 | 3 | 3 | 4 | 3 | 3 | 4 | 3 | 4 | | | | | |
| 683 | 11.2100 | 1 | 3 | 3 | 2 | 3 | 4 | 3 | 4 | 3 | 4 | | | | | |
| 684 | 11.2100 | 0 | 0 | 0 | 0 | 1 | 1 | 0 | 3 | 2 | 2 | | | | | |
| 685 | 11.2100 | 0 | 3 | 4 | 3 | 3 | 3 | 2 | 4 | 3 | 4 | | | | | |
| 686 | 11.2100 | 0 | 3 | 4 | 2 | 3 | 4 | 1 | 3 | 1 | 4 | | | | | |
| 687 | 11.2100 | 0 | 4 | 4 | 4 | 4 | 3 | 2 | 4 | 2 | 4 | | | | | |
| 688 | 11.2100 | 0 | 0 | 2 | 0 | 2 | 3 | 3 | 4 | 2 | 4 | | | | | |
| 689 | 11.2100 | 1 | 4 | 4 | 4 | 4 | 4 | 2 | 4 | 4 | 4 | | | | | |
| 690 | 11.2100 | 1 | 4 | 4 | 4 | 4 | 3 | 2 | 4 | 4 | 4 | | | | | |
| 691 | ! 11.2100 | 0 | 1 | 2 | 0 | 2 | 2 | 0 | 3 | 1 | 2 | | | | | |

TABLE B-continued

| | | Herbicide Primary Post, spectrums 25 and 90 | | | | | | | | | | | | |
|---|---|---|---|---|---|---|---|---|---|---|---|---|---|---|
| Ex. No. | Rate kg/ha | Yens | Anbg | Sejg | Dobr | Bygr | Mogl | Cobu | Vene | Inmu | Wibw | Cath | Colq | Pehsw | Rhqg | Rhjg |
| 692 | ! 11.2100 | 0 | 0 | 2 | 0 | 2 | 2 | 2 | 4 | 1 | 2 | | | | |
| 693 | 11.2100 | 0 | 4 | 4 | 4 | 4 | 4 | 4 | 4 | 4 | 4 | | | | |
| 694 | 11.2100 | 0 | 2 | 3 | 2 | 4 | 4 | 2 | 4 | 2 | 3 | | | | |
| 695 | 11.2100 | 0 | 4 | 3 | 2 | 3 | 3 | 3 | 4 | 3 | 3 | | | | |
| 696 | 11.2100 | 0 | 2 | 3 | 2 | 3 | 4 | 2 | 4 | 3 | 4 | | | | |
| 697 | 11.2100 | 0 | 4 | 4 | 4 | 4 | 4 | 4 | 4 | 3 | 4 | | | | |
| 698 | 11.2100 | 0 | 3 | 4 | 4 | 4 | 4 | 3 | 4 | 4 | 4 | | | | |
| 699 | < 11.2100 | 2 | 1 | 2 | 3 | 2 | 4 | 4 | 4 | 4 | 4 | | | | |
| 700 | < 11.2100 | 0 | 2 | 4 | 3 | 4 | 2 | 2 | 4 | 3 | 4 | | | | |
| 701 | < 11.2100 | 0 | 0 | 2 | 1 | 2 | 3 | 4 | 4 | 3 | 3 | | | | |
| 702 | < 11.2100 | 2 | 1 | 3 | 2 | 4 | 3 | 3 | 4 | 3 | 4 | | | | |
| 703 | 11.2100 | 0 | 0 | 2 | 0 | 2 | 2 | 2 | 3 | 2 | 2 | | | | |
| 704 | 11.2100 | 2 | 0 | 2 | 2 | 3 | 4 | 2 | 4 | 2 | 2 | | | | |
| 705 | 11.2100 | 2 | 1 | 3 | 2 | 3 | 3 | 3 | 4 | 3 | 4 | | | | |
| 706 | 11.2100 | 2 | 4 | 4 | 4 | 4 | 3 | 4 | 3 | 3 | 3 | | | | |
| 707 | 11.2100 | 0 | 1 | 2 | 0 | 1 | 3 | 3 | 4 | 2 | 4 | | | | |
| 708 | 11.2100 | 1 | 2 | 3 | 0 | 3 | 3 | 4 | 4 | 2 | 3 | | | | |
| 709 | 11.2100 | 0 | 1 | 1 | 0 | 2 | 3 | 1 | 3 | 1 | 3 | | | | |
| 710 | 11.2100 | 0 | 2 | 3 | 2 | 2 | 4 | 3 | 4 | 2 | 4 | | | | |
| 711 | 11.2100 | 0 | 2 | 3 | 2 | 4 | 2 | 2 | 3 | 2 | 4 | | | | |
| 712 | 11.2100 | 2 | 0 | 3 | 1 | 3 | 4 | 3 | 4 | 2 | 4 | | | | |
| 713 | < 11.2100 | 2 | 4 | 2 | 3 | 4 | 2 | 3 | 4 | 1 | 4 | | | | |
| 714 | 11.2100 | 2 | 4 | 4 | 4 | 4 | 4 | 3 | 4 | 3 | 4 | | | | |
| 715 | < 11.2100 | 2 | 0 | 3 | 2 | 2 | 4 | 3 | 4 | 4 | 4 | | | | |
| 716 | < 11.2100 | 2 | 3 | 4 | 3 | 4 | 3 | 4 | 4 | 2 | 4 | | | | |
| 717 | 11.2100 | 0 | 0 | 2 | 0 | 1 | 2 | 0 | 2 | 2 | 4 | | | | |
| 718 | 11.2100 | 0 | 0 | 2 | 0 | 2 | 4 | 2 | 4 | 3 | 4 | | | | |
| 719 | \| 11.2100 | 0 | 3 | 4 | 3 | 3 | 3 | 2 | 4 | 4 | 3 | | | | |
| 720 | < 11.2100 | 2 | 4 | 3 | 3 | 3 | 3 | 2 | 4 | 3 | 4 | | | | |
| 721 | 11.2100 | 0 | 0 | 0 | 0 | 0 | 0 | 0 | 1 | 1 | 0 | | | | |
| 722 | 11.2100 | 0 | 0 | 2 | 0 | 1 | 3 | 1 | 1 | 1 | 3 | | | | |
| 723 | 11.2100 | 0 | 0 | 3 | 1 | 2 | 4 | 3 | 4 | 3 | 4 | | | | |
| 724 | 11.2100 | 0 | 0 | 1 | 0 | 0 | 3 | 1 | 1 | 1 | 3 | | | | |
| 725 | ~ 11.2100 | 2 | 4 | 4 | 4 | 4 | 3 | 3 | 4 | 4 | 4 | | | | |
| 726 | % 11.2100 | 0 | 4 | 4 | 4 | 4 | 3 | 2 | 3 | 2 | 4 | | | | |
| 727 | \| 11.2100 | 0 | 3 | 3 | 3 | 3 | 2 | 2 | 4 | 2 | 3 | | | | |
| 728 | \| 11.2100 | 0 | 0 | 3 | 0 | 2 | 3 | 4 | 4 | 3 | 4 | | | | |
| 729 | ~ 11.2100 | 2 | 4 | 4 | 4 | 4 | 3 | 3 | 4 | 4 | 4 | | | | |
| 730 | 11.2100 | 2 | 3 | 4 | 3 | 4 | 4 | 4 | 4 | 3 | 4 | | | | |
| 731 | \| 11.2100 | 2 | 0 | 3 | 2 | 3 | 3 | 2 | 4 | 2 | 4 | | | | |
| 732 | 11.2100 | 0 | 0 | 2 | 2 | 2 | 3 | 2 | 4 | 1 | 4 | | | | |
| 733 | < 11.2100 | 0 | 0 | 2 | 1 | 2 | 2 | 2 | 4 | 3 | 4 | | | | |
| 734 | < 11.2100 | 0 | 0 | 2 | 0 | 1 | 2 | 3 | 4 | 2 | 2 | | | | |
| 735 | < 11.2100 | 2 | 0 | 3 | 3 | 3 | 3 | 2 | 4 | 2 | 4 | | | | |
| 736 | 11.2100 | 2 | 1 | 3 | 1 | 3 | 3 | 3 | 4 | 3 | 4 | | | | |
| 737 | < 11.2100 | 2 | 0 | 2 | 0 | 2 | 3 | 3 | 4 | 2 | 2 | | | | |
| 738 | < 11.2100 | 2 | 0 | 4 | 2 | 2 | 4 | 2 | 4 | 3 | 4 | | | | |
| 739 | < 11.2100 | 0 | 0 | 2 | 0 | 2 | 2 | 2 | 4 | 3 | 4 | | | | |
| 740 | 11.2100 | 2 | 3 | 3 | 3 | 4 | 4 | 4 | 4 | 3 | 4 | | | | |
| 741 | 11.2100 | 2 | 0 | 4 | 0 | 4 | 4 | 2 | 4 | 3 | 4 | | | | |
| 742 | 11.2100 | 0 | 3 | 4 | 4 | 4 | 4 | 3 | 4 | 4 | 4 | | | | |
| 743 | 11.2100 | 1 | 0 | 3 | 0 | 2 | 4 | 4 | 4 | 0 | 2 | | | | |
| 744 | 11.2100 | 1 | 0 | 2 | 0 | 3 | 3 | 2 | 4 | 3 | 4 | | | | |
| 745 | 11.2100 | 0 | 0 | 4 | 0 | 2 | 3 | 3 | 4 | 3 | 4 | | | | |
| 746 | 11.2100 | 0 | 0 | 3 | 3 | 4 | 2 | 3 | 4 | 3 | 4 | | | | |
| 747 | 11.2100 | 1 | 0 | 2 | 0 | 2 | 4 | 4 | 4 | 1 | 3 | | | | |
| 748 | 11.2100 | 1 | 0 | 2 | 0 | 2 | 4 | 4 | 4 | 2 | 4 | | | | |
| 749 | 11.2100 | 0 | 0 | 4 | 1 | 4 | 4 | 4 | 4 | 3 | 4 | | | | |
| 750 | 11.2100 | 2 | 0 | 2 | 0 | 2 | 3 | 4 | 4 | 3 | 4 | | | | |
| 751 | 11.2100 | 2 | 0 | 2 | 0 | 2 | 4 | 4 | 4 | 1 | 4 | | | | |
| 752 | 11.2100 | 2 | 0 | 2 | 0 | 2 | 3 | 3 | 4 | 0 | 4 | | | | |
| 753 | 11.2100 | 0 | 0 | 3 | 0 | 2 | 4 | 4 | 4 | 2 | 2 | | | | |
| 754 | 11.2100 | 1 | 0 | 2 | 0 | 3 | 4 | 4 | 4 | 3 | 4 | | | | |
| 755 | { 11.2100 | 1 | 4 | 4 | 4 | 4 | 3 | 2 | 4 | 3 | 4 | | | | |
| 756 | { 11.2100 | 1 | 0 | 2 | 0 | 3 | 4 | 4 | 3 | 4 | 4 | | | | |
| 757 | 11.2100 | 2 | 0 | 2 | 0 | 2 | 4 | 4 | 4 | 2 | 4 | | | | |
| 758 | { 11.2100 | 0 | 0 | 2 | 0 | 2 | 1 | 0 | 2 | 2 | 2 | | | | |
| 759 | { 11.2100 | 2 | 0 | 2 | 0 | 3 | 4 | 4 | 4 | 3 | 3 | | | | |
| 760 | 11.2100 | 1 | 0 | 1 | 0 | 1 | 3 | 3 | 4 | 2 | 3 | | | | |
| 761 | 11.2100 | 2 | 0 | 2 | 0 | 2 | 4 | 3 | 4 | 0 | 4 | | | | |
| 762 | 11.2100 | 1 | 0 | 2 | 0 | 2 | 2 | 2 | 0 | 2 | 4 | | | | |
| 763 | 11.2100 | 0 | 0 | 3 | 1 | 3 | 3 | 2 | 4 | 2 | 4 | | | | |
| 764 | 11.2100 | 0 | 0 | 1 | 0 | 2 | 2 | 1 | 3 | 0 | 3 | | | | |
| 765 | 11.2100 | 0 | 3 | 3 | 3 | 3 | 3 | 3 | 4 | 0 | 3 | | | | |
| 766 | 11.2100 | 0 | 2 | 3 | 1 | 2 | 2 | 2 | 3 | 0 | 3 | | | | |
| 767 | 11.2100 | 0 | 3 | 3 | 3 | 2 | 2 | 2 | 4 | 0 | 4 | | | | |
| 768 | 11.2100 | 2 | 4 | 3 | 3 | 2 | 4 | 3 | 4 | 1 | 3 | | | | |

TABLE B-continued

| | | Herbicide Primary Post, spectrums 25 and 90 | | | | | | | | | | | | |
|---|---|---|---|---|---|---|---|---|---|---|---|---|---|---|
| Ex. No. | Rate kg/ha | Yens | Anbg | Sebjg | Dobr | Bygr | Mogl | Cobu | Vele | Inmu | Wibw | Cath | Colq | Pesw | Rhqg | Rhjg |
| 769 | 11.2100 | 0 | 0 | 2 | 0 | 2 | 2 | 2 | 0 | 0 | 0 | | | | |
| 770 | 11.2100 | 2 | 3 | 4 | 3 | 4 | 3 | 2 | 4 | 0 | 4 | | | | |
| 771 | 11.2100 | 1 | 3 | 3 | 3 | 3 | 3 | 2 | 4 | 2 | 4 | | | | |
| 772 | 11.2100 | 1 | 3 | 4 | 3 | 4 | 3 | 3 | 4 | 2 | 4 | | | | |
| 773 | 11.2100 | 1 | 2 | 3 | 2 | 2 | 3 | 2 | 4 | 1 | 4 | | | | |
| 774 | 11.2100 | 1 | 3 | 3 | 3 | 2 | 3 | 2 | 4 | 1 | 4 | | | | |
| 775 | 11.2100 | 0 | 3 | 2 | 3 | 2 | 3 | 2 | 4 | 1 | 4 | | | | |
| 776 | 11.2100 | 0 | 0 | 2 | 2 | 3 | 3 | 2 | 3 | 1 | 3 | | | | |
| 777 | 11.2100 | 1 | 4 | 4 | 3 | 3 | 3 | 2 | 4 | 1 | 3 | | | | |
| 778 | 11.2100 | 2 | 1 | 1 | 1 | 2 | 3 | 3 | 4 | 0 | 4 | | | | |
| 779 | 11.2100 | 0 | 0 | 1 | 0 | 1 | 2 | 2 | 3 | 2 | 4 | | | | |
| 780 | 11.2100 | 0 | 0 | 1 | 0 | 0 | 0 | 0 | 0 | 0 | 1 | | | | |
| 781 { | 11.2100 | 0 | 4 | 4 | 4 | 4 | 4 | 2 | 4 | 3 | 4 | | | | |
| 782 { | 11.2100 | 2 | 0 | 2 | 0 | 2 | 4 | 3 | 4 | 2 | 2 | | | | |
| 783 | 11.2100 | 0 | 0 | 1 | 1 | 1 | 4 | 4 | 4 | 3 | 3 | | | | |
| 784 | 11.2100 | 0 | 0 | 1 | 0 | 1 | 4 | 3 | 4 | 2 | 3 | | | | |
| 785 | 11.2100 | 0 | 0 | 1 | 0 | 0 | 3 | 3 | 4 | 2 | 3 | | | | |
| 786 | 11.2100 | 0 | 0 | 1 | 0 | 0 | 3 | 1 | 4 | 1 | 3 | | | | |
| 787 | 11.2100 | 2 | 0 | 1 | 0 | 0 | 4 | 3 | 3 | 2 | 4 | | | | |
| 788 | 11.2100 | 0 | 0 | 2 | 0 | 2 | 4 | 3 | 4 | 2 | 3 | | | | |
| 789 | 11.2100 | 2 | 0 | 2 | 0 | 2 | 4 | 4 | 4 | 1 | 4 | | | | |
| 790 | 11.2100 | 0 | 0 | 1 | 0 | 1 | 2 | 1 | 1 | 0 | 1 | | | | |
| 791 | 11.2100 | 1 | 0 | 2 | 0 | 2 | 4 | 4 | 4 | 2 | 4 | | | | |
| 792 | 11.2100 | 2 | 3 | 3 | 3 | 3 | 4 | 3 | 4 | 4 | 4 | | | | |
| 793 | 11.2100 | 0 | 0 | 2 | 0 | 2 | 4 | 3 | 2 | 0 | 2 | | | | |
| 794 | 11.2100 | 0 | 0 | 0 | 0 | 2 | 1 | 0 | 3 | 1 | 1 | | | | |
| 795 | 11.2100 | 1 | 2 | 4 | 3 | 4 | 4 | 2 | 4 | 2 | 4 | | | | |
| 796 | 11.2100 | 0 | 1 | 4 | 2 | 3 | 2 | 1 | 2 | 0 | 2 | | | | |
| 797 | 11.2100 | 0 | 0 | 2 | 0 | 2 | 0 | 0 | 2 | 0 | 2 | | | | |
| 798 | 11.2100 | 2 | 2 | 3 | 3 | 3 | 3 | 3 | 4 | 1 | 4 | | | | |
| 799 | 11.2100 | 1 | 0 | 1 | 0 | 3 | 3 | 4 | 4 | 2 | 2 | | | | |
| 800 | 11.2100 | 1 | 0 | 2 | 0 | 2 | 4 | 3 | 4 | 2 | 3 | | | | |
| 801 | 11.2100 | 2 | 3 | 3 | 3 | 2 | 3 | 2 | 4 | 2 | 4 | | | | |
| 802 | 11.2100 | 2 | 1 | 3 | 0 | 2 | 2 | 3 | 3 | 1 | 3 | | | | |
| 803 | 11.2100 | 0 | 0 | 0 | 0 | 1 | 1 | 0 | 2 | 1 | 2 | | | | |
| 804 | 11.2100 | 0 | 0 | 2 | 0 | 2 | 2 | 2 | 2 | 1 | 1 | | | | |
| 805 | 11.2100 | 2 | 0 | 2 | 0 | 2 | 4 | 4 | 4 | 2 | 3 | | | | |
| 806 | 11.2100 | 2 | 0 | 2 | 0 | 2 | 4 | 4 | 4 | 0 | 4 | | | | |
| 807 | 11.2100 | 0 | 0 | 3 | 0 | 2 | 0 | 0 | 2 | 1 | 2 | | | | |
| 808 | 11.2100 | 2 | 0 | 3 | 0 | 2 | 3 | 4 | 4 | 1 | 4 | | | | |
| 809 | 11.2100 | 0 | 0 | 3 | 0 | 3 | 3 | 3 | 4 | 1 | 4 | | | | |
| 810 | 11.2100 | 2 | 0 | 3 | 2 | 4 | 3 | 2 | 3 | 0 | 4 | | | | |
| 811 | 11.2100 | 2 | 0 | 2 | 0 | 2 | 4 | 3 | 4 | 2 | 4 | | | | |
| 812 | 11.2100 | 2 | 0 | 2 | 0 | 2 | 3 | 3 | 4 | 2 | 3 | | | | |
| 813 | 11.2100 | 2 | 0 | 2 | 0 | 2 | 4 | 4 | 4 | 2 | 3 | | | | |
| 814 | 11.2100 | 2 | 0 | 2 | 0 | 2 | 3 | 3 | 2 | 1 | 4 | | | | |
| 815 | 11.2100 | 2 | 0 | 2 | 1 | 3 | 3 | 3 | 3 | 0 | 4 | | | | |
| 816 | 11.2100 | 3 | 0 | 2 | 0 | 2 | 4 | 3 | 4 | 2 | 4 | | | | |
| 817 | 11.2100 | 1 | 2 | 2 | 2 | 2 | 2 | 4 | 3 | 2 | 3 | | | | |
| 818 | 11.2100 | 2 | 4 | 3 | 3 | 2 | 3 | 3 | 4 | 2 | 4 | | | | |
| 819 | 11.2100 | 0 | 1 | 3 | 1 | 3 | 3 | 1 | 4 | 1 | 3 | | | | |
| 820 | 11.2100 | 0 | 0 | 1 | 0 | 0 | 0 | 0 | 0 | 1 | 0 | | | | |
| 821 | 11.2100 | 0 | 0 | 0 | 0 | 2 | 2 | 1 | 1 | 0 | 2 | | | | |
| 822 | 11.2100 | 2 | 3 | 2 | 1 | 2 | 2 | 2 | 2 | 0 | 3 | | | | |
| 823 | 11.2100 | 1 | 1 | 0 | 0 | 2 | 3 | 2 | 1 | 2 | 3 | | | | |
| 824 | 11.2100 | 0 | 0 | 1 | 0 | 0 | 3 | 3 | 4 | 2 | 3 | | | | |
| 825 | 11.2100 | 1 | 2 | 2 | 2 | 0 | 2 | 2 | 3 | 1 | 3 | | | | |
| 826 | 11.2100 | 0 | 0 | 2 | 0 | 0 | 1 | 0 | 0 | 1 | 0 | | | | |
| 827 | 11.2100 | 0 | 0 | 0 | 0 | 0 | 1 | 0 | 0 | 1 | 2 | | | | |
| 828 | 11.2100 | 2 | 3 | 3 | 2 | 4 | 3 | 3 | 4 | 3 | 4 | | | | |
| 829 | 11.2100 | 0 | 2 | 0 | 0 | 2 | 3 | 2 | 4 | 2 | 4 | | | | |
| 830 | 11.2100 | 0 | 1 | 0 | 0 | 2 | 1 | 2 | 4 | 2 | 3 | | | | |
| 831 | 11.2100 | 1 | 3 | 1 | 2 | 3 | 3 | 3 | 4 | 2 | 3 | | | | |
| 835 | 11.2100 | 0 | 0 | 0 | 0 | 0 | 0 | 1 | 1 | 1 | 0 | | | | |
| 836 | 11.2100 | 2 | 3 | 3 | 3 | 3 | 4 | 4 | 4 | 3 | 3 | | | | |
| 837 | 11.2100 | 0 | 0 | 2 | 0 | 2 | 3 | 2 | 1 | 1 | 2 | | | | |
| 838 | 11.2100 | 1 | 0 | 4 | 4 | 4 | 3 | 3 | 4 | 3 | 4 | | | | |
| 839 | 11.2100 | 0 | 0 | 3 | 1 | 2 | 4 | 4 | 4 | 2 | 3 | | | | |
| 840 | 11.2100 | 2 | 0 | 3 | 0 | 3 | 4 | 4 | 4 | 2 | 4 | | | | |
| 841 | 11.2100 | 2 | 0 | 3 | 0 | 2 | 3 | 4 | 4 | 2 | 4 | | | | |
| 842 | 14.2100 | 2 | 0 | 3 | 0 | 3 | 4 | 4 | 4 | 3 | 3 | | | | |
| 843 | 11.2100 | 0 | 0 | 2 | 0 | 2 | 4 | 4 | 4 | 2 | 4 | | | | |
| 844 | 11.2100 | 2 | 4 | 3 | 2 | 2 | 2 | 4 | 4 | 2 | 4 | | | | |
| 845 | 11.2100 | 2 | 0 | 3 | 0 | 4 | 4 | 4 | 4 | 2 | 4 | | | | |
| 846 | 11.2100 | 1 | 0 | 0 | 0 | 0 | 2 | 3 | 3 | 0 | 0 | | | | |
| 847 | 11.2100 | 1 | 2 | 2 | 1 | 3 | 3 | 4 | 4 | 1 | 2 | | | | |
| 848 | 11.2100 | 2 | 3 | 2 | 2 | 2 | 3 | 3 | 4 | 1 | 4 | | | | |

TABLE B-continued

Herbicide Primary Post, spectrums 25 and 90

| Ex. No. | Rate kg/ha | Yens | Abg | Sejg | Dobr | Byggr | Mogl | Cobu | Vlle | Imuw | Wibw | Cath | Calqw | Peshqw | Rhqg | Rhjg |
|---|---|---|---|---|---|---|---|---|---|---|---|---|---|---|---|---|
| 849 | 11.2100 | 0 | 0 | 1 | 0 | 2 | 4 | 4 | 4 | 1 | 4 | | | | | |
| 850 | 11.2100 | 2 | 0 | 3 | 1 | 2 | 4 | 4 | 4 | 1 | 3 | | | | | |
| 851 | 11.2100 | 0 | 0 | 2 | 0 | 0 | 3 | 2 | 2 | 0 | 2 | | | | | |
| 852 | 11.2100 | 2 | 0 | 2 | 0 | 1 | 3 | 2 | 3 | 0 | 3 | | | | | |
| 853 | 11.2100 | 0 | 0 | 0 | 0 | 0 | 1 | 1 | 0 | 0 | 2 | | | | | |
| 854 | 11.2100 | 0 | 3 | 2 | 2 | 3 | 4 | 3 | 4 | 3 | 4 | | | | | |
| 855 | 11.2100 | 0 | 0 | 0 | 0 | 0 | 1 | 0 | 0 | 1 | 1 | | | | | |
| 856 | 11.2100 | 0 | 0 | 0 | 0 | 0 | 2 | 0 | 0 | 1 | 0 | | | | | |
| 857 | 11.2100 | 1 | 1 | 3 | 2 | 4 | 2 | 1 | 4 | 1 | 4 | | | | | |
| 858 | 11.2100 | 1 | 0 | 0 | 0 | 1 | 2 | 1 | 1 | 1 | 2 | | | | | |
| 859 | 11.2100 | 0 | 2 | 3 | 2 | 3 | 3 | 2 | 4 | 1 | 4 | | | | | |
| 860 | 11.2100 | 0 | 0 | 0 | 0 | 1 | 3 | 2 | 3 | 2 | 3 | | | | | |
| 862 | 11.2100 | 3 | 0 | 2 | 0 | 2 | 4 | 4 | 4 | 2 | 4 | | | | | |
| 863 | 11.2100 | 3 | 0 | 1 | 0 | 2 | 4 | 4 | 4 | 3 | 4 | | | | | |
| 864 | 11.2100 | 2 | 0 | 2 | 0 | 2 | 4 | 4 | 4 | 2 | 3 | | | | | |
| 865 | 11.2100 | 2 | 0 | 2 | 0 | 2 | 4 | 4 | 4 | 2 | 4 | | | | | |
| 866 | 11.2100 | 2 | 0 | 0 | 0 | 2 | 3 | 3 | 4 | 3 | 4 | | | | | |
| 867 | 11.2100 | 0 | 0 | 0 | 0 | 2 | 4 | 3 | 4 | 2 | 3 | | | | | |
| 868 | 11.2100 | 1 | 2 | 3 | 2 | 3 | 2 | 2 | 4 | 0 | 4 | | | | | |
| 869 | 11.2100 | 2 | 0 | 0 | 0 | 2 | 4 | 3 | 4 | 2 | 3 | | | | | |
| 870 | 11.2100 | 2 | 0 | 0 | 0 | 2 | 4 | 4 | 4 | 2 | 3 | | | | | |
| 871 | 11.2100 | 2 | 0 | 1 | 0 | 2 | 3 | 3 | 3 | 2 | 3 | | | | | |
| 872 | 11.2100 | 2 | 2 | 3 | 2 | 2 | 2 | 2 | 4 | 0 | 4 | | | | | |
| 873 | 11.2100 | 2 | 3 | 3 | 3 | 3 | 3 | 2 | 4 | 0 | 4 | | | | | |
| 874 | 11.2100 | 1 | 0 | 2 | 1 | 2 | 4 | 3 | 4 | 0 | 4 | | | | | |
| 875 | 11.2100 | 2 | 0 | 1 | 0 | 2 | 4 | 3 | 2 | 2 | 3 | | | | | |
| 876 | 11.2100 | 1 | 0 | 0 | 0 | 2 | 4 | 2 | 3 | 2 | 4 | | | | | |
| 877 | 11.2100 | 0 | 0 | 1 | 0 | 1 | 2 | 0 | 0 | 1 | 3 | | | | | |
| 878 | 11.2100 | 2 | 0 | 2 | 0 | 2 | 4 | 4 | 4 | 2 | 4 | | | | | |
| 879 | 11.2100 | 2 | 1 | 2 | 2 | 2 | 2 | 2 | 4 | 0 | 3 | | | | | |
| 880 | 11.2100 | 2 | 0 | 2 | 0 | 2 | 3 | 3 | 3 | 0 | 3 | | | | | |
| 881 | 11.2100 | 0 | 0 | 1 | 0 | 2 | 3 | 3 | 2 | 1 | 2 | | | | | |
| 882 | 11.2100 | 3 | 0 | 0 | 1 | 2 | 4 | 4 | 3 | 1 | 4 | | | | | |
| 883 | 11.2100 | 0 | 0 | 2 | 0 | 0 | 2 | 2 | 2 | 0 | 2 | | | | | |
| 884 | 11.2100 | 2 | 0 | 0 | 0 | 2 | 3 | 4 | 3 | 2 | 4 | | | | | |
| 885 | 11.2100 | 1 | 2 | 2 | 0 | 2 | 3 | 2 | 4 | 1 | 4 | | | | | |
| 886 | 11.2100 | 0 | 0 | 2 | 0 | 1 | 1 | 2 | 1 | 0 | 2 | | | | | |
| 887 | 11.2100 | 0 | 0 | 0 | 0 | 1 | 2 | 2 | 2 | 1 | 1 | | | | | |
| 888 | 11.2100 | 0 | 0 | 1 | 0 | 0 | 3 | 1 | 0 | 0 | 2 | | | | | |
| 889 | 11.2100 | 0 | 0 | 0 | 0 | 0 | 2 | 2 | 1 | 2 | 2 | | | | | |
| 890 | 11.2100 | 1 | 0 | 0 | 1 | 2 | 3 | 2 | 1 | 0 | 2 | | | | | |
| 891 | 11.2100 | 0 | 0 | 2 | 0 | 2 | 4 | 4 | 3 | 2 | 4 | | | | | |
| 892 | 11.2100 | 0 | 0 | 2 | 2 | 3 | 2 | 2 | 4 | 1 | 4 | | | | | |
| 893 | 11.2100 | 2 | 0 | 0 | 0 | 2 | 4 | 4 | 4 | 1 | 4 | | | | | |
| 896 | 11.2100 | 0 | 0 | 0 | 0 | 0 | 2 | 0 | 2 | 0 | 2 | | | | | |
| 897 | 11.2100 | 1 | 0 | 0 | 0 | 2 | 2 | 1 | 2 | 0 | 2 | | | | | |
| 898 | 11.2100 | 2 | 0 | 3 | 1 | 2 | 4 | 4 | 4 | 2 | 4 | | | | | |
| 899 | 11.2100 | 0 | 0 | 0 | 0 | 0 | 1 | 0 | 0 | 0 | 1 | | | | | |
| 900 | 11.2100 | 1 | 0 | 2 | 0 | 1 | 3 | 3 | 4 | 1 | 3 | | | | | |
| 901 | 11.2100 | 0 | 0 | 1 | 0 | 0 | 4 | 3 | 4 | 1 | 3 | | | | | |
| 902 | 11.2100 | 2 | 2 | 3 | 2 | 3 | 2 | 2 | 3 | 2 | 4 | | | | | |
| 903 | 11.2100 | 0 | 0 | 1 | 0 | 2 | 3 | 2 | 3 | 1 | 3 | | | | | |

+ NO SMARTWEED GERMINATION
= POOR SMARTWEED GERMINATION
( POOR GERMINATION-SW
! DAMPING OFF - IM, WB
% DAMPING OFF - IM, WB
~ DAMPING OFF - IM, WB POOR GERMINATION-CB
| DAMPING OFF - IM, WB POOR GERMINATION-CB
< DAMPING OFF - IM, WB
{ DAMPING OFF - IM, WB
E CUPPING-MG.

PRE-EMERGENCE ACTIVITY ON WEEDS AND CROPS

In another set of tests, the pre-emergence activity of compounds of this invention was tested on weeds in the presence of crop plants. In these tests the following procedure was used:

Topsoil is sieved to pass through a ½ inch (1.27 cm) screen. Fertilizer is added to the topsoil in some of the tests, while in testing other compounds the fertilizer is omitted. The mixture is then sterilized.

The topsoil mixture is placed in an aluminum pan compacted to a depth of about 1.27 cm. from the top of the pan. On the top of the soil is placed a predetermined number of seeds of each of several monocotyledonous and dicotyledonous plant species and where noted vegetative propagules of various perennial plant species. The soil required to level fill a pan after seeding or adding vegetative propagules is weighed into another pan. A known amount of the active ingredient is dissolved or suspended in acetone or a suitable organic solvent as a 1% solution or suspension and applied to the cover soil using a sprayer at the desired rate. The spray is thoroughly mixed with this cover soil, and the herbicide/soil mixture is used as a cover layer for the previously prepared pan. Untreated soil is used as a cover layer for control pans. Alternatively, the pans may be covered with the soil layer and the spray solution uniformly applied to the soil surface. When this latter method is used, the statement "surface application" accompanies the test data. In Table C below the amount of active ingredient applied is a kg/ha shown in the Table. After treatment, the pans are moved to a greenhouse bench. Moisture is supplied to each pan as needed for germination and growth. Growth of each species is observed and corrective measures (greenhouse fumigation, insecticide treatment, and the like) are applied as needed.

Approximately 10–14 days (usually 11 days) after seeding and treating, the pans are observed and the results recorded. In some instances, a second observation is made (usually 24–28 days after seeding and treating, although this time interval is at the discretion of the observer), and these observations are indicated in the following tables by a "pound" sign (#) immediately following the Example number.

The pre-emergence data for weeds in the presence of crop plants is shown in the following Table C. In these tests, the plants are identified according to the following column headings:

| | | | |
|---|---|---|---|
| SOBE | Soybean | VELE | Velvetleaf |
| SUBE | Sugarbeet | DOBR | Downy Brome |
| WHEZ | Wheat | PRMI | Proso Millet |
| RICE | Rice | BYGR | Barnyardgrass |
| GRSO | Grain Sorghum | LACG | Large Crabgrass |
| COBU | Cocklebur | GRFT | Green Foxtail |
| WIBW | Wild Buckwheat | CORN | Corn |
| NOGL | Morningglory | COTZ | Cotton |
| HESE | Hemp Sesbania | RAPE | Oilseed Rape |
| COLQ | Common Lambsquarters | JIWE | Jimsonweed |
| PESW | Pennsylvania Smartweed | | |

TABLE C

Herbicide Secondary Pre, spectrums 26, 88, 91, and 93

| Ex. No. | CP | Rate kg/ha | Sbe | Cotn | Rape | Cbu | Wbw | Mgl | Hese | Jiwe | Vile | Whez | Rice | Grso | Corn | Dobr | Pimi | Bygr | Lacg | Grft | Sube | Cblq | Pesw | Cocw |
|---|---|---|---|---|---|---|---|---|---|---|---|---|---|---|---|---|---|---|---|---|---|---|---|---|
| 7 | | 5.6050 | 100 | 90 | | 100 | 100 | 95 | 100 | | 100 | 45 | 98 | 95 | 100 | 100 | 100 | 100 | 100 | 100 | 100 | 100 | 100 | |
| | | 5.6050 | 95 | 95 | | 100 | 100 | 100 | 95 | | 100 | 80 | 95 | 90 | 100 | 98 | 98 | 100 | 100 | 100 | 100 | 100 | 100 | |
| | | 1.1210 | 55 | 80 | | 40 | 40 | 95 | 90 | | 100 | 10 | 90 | 20 | 95 | 25 | 98 | 98 | 100 | 95 | 100 | 100 | 100 | |
| | | 1.1210 | 20 | 30 | | 98 | 98 | 90 | 100 | | 100 | 10 | 95 | 25 | 80 | 10 | 80 | 85 | 100 | 85 | 100 | 100 | 100 | |
| | | 0.5605 | 10 | 0 | | 100 | 100 | 40 | 95 | | 100 | 0 | 85 | 25 | 50 | 20 | 100 | 60 | 100 | 95 | 100 | 100 | 100 | |
| | | 0.5605 | 90 | 25 | | N | 25 | 60 | 100 | | 100 | 10 | 90 | 25 | 65 | 20 | 95 | 60 | 100 | 100 | 90 | 85 | 100 | |
| | | 0.2803 | 0 | N | | 100 | 100 | N | 90 | | 80 | 0 | 45 | 0 | 30 | 20 | 70 | 80 | 100 | 80 | 85 | 100 | 100 | |
| | | 0.2803 | N | 0 | | 25 | 25 | 60 | 98 | | 95 | 0 | 85 | 25 | 15 | 30 | 85 | 95 | 45 | 95 | 60 | 85 | 100 | |
| | | 0.1401 | 25 | 0 | | 0 | 0 | 20 | 55 | | 70 | 0 | 50 | 0 | 20 | N | 75 | 80 | 45 | 100 | 95 | 95 | 100 | |
| | | 0.1401 | 0 | 0 | | 0 | 0 | 85 | 95 | | 95 | 0 | 10 | 25 | 30 | 30 | 25 | 40 | 100 | 100 | 60 | 90 | 100 | |
| | | 0.0701 | N | 0 | | 50 | 95 | 30 | 55 | | 90 | 0 | 0 | 0 | 10 | 0 | 10 | 0 | 85 | 100 | 95 | 95 | 90 | |
| | | 0.0701 | 15 | 0 | | 40 | 85 | 50 | 85 | | 60 | 0 | 20 | 25 | 0 | 40 | 15 | 40 | 20 | 70 | 40 | 90 | 85 | |
| | | 0.0350 | 0 | N | | N | 0 | N | 0 | | 0 | 0 | 30 | 0 | 0 | 0 | 0 | 0 | 0 | N | 90 | 100 | 100 | |
| | | 0.0350 | 0 | 0 | | N | N | 0 | 90 | | 90 | 0 | 10 | 0 | 10 | 40 | 0 | 0 | 0 | N | 70 | 100 | 90 | |
| | | 0.0175 | 0 | 0 | | 95 | N | 0 | 30 | | 60 | 0 | 30 | 0 | 0 | 0 | N | 0 | 0 | 35 | 35 | 90 | 85 | |
| | | 0.0175 | N | N | | 0 | 0 | 0 | N | | N | 0 | N | 0 | 0 | 0 | 0 | 0 | 0 | 0 | 45 | 100 | 100 | |
| | | 0.0087 | 0 | 0 | | 0 | 95 | 0 | 40 | | 35 | 0 | 0 | 0 | 0 | 0 | 0 | 0 | 0 | N | 60 | 100 | 80 | |
| | | 0.0087 | 5 | 0 | | 0 | 0 | 0 | 0 | | 40 | 0 | 30 | 0 | 0 | 0 | 0 | 0 | 0 | 0 | 65 | 0 | 100 | |
| | | 0.0044 | N | 0 | | 0 | 0 | 0 | 0 | | 0 | 0 | 0 | 0 | 0 | 0 | 0 | 0 | 0 | 0 | 60 | N | 80 | |
| | | 0.0044 | N | 0 | | 0 | 0 | 0 | 0 | | N | 0 | 0 | 0 | 0 | 0 | 0 | 0 | 0 | 0 | 0 | 95 | 30 | |
| 13 | | 5.6050 | 98 | 90 | 100 | | | | | 100 | | | | | | | | | | | | | | |
| | | 1.1210 | 100 | 60 | 80 | | | | | 100 | | | | | | | | | | | | | | |
| | | 0.2803 | 60 | 35 | 80 | | | | | 100 | | | | | | | | | | | | | | |
| | | 0.0701 | 20 | 25 | 60 | | | | | 95 | | | | | | | | | | | | | | |
| | | 0.0175 | 40 | 30 | 0 | | | | | 90 | | | | | | | | | | | | | | |
| | | 0.0044 | 0 | | | | | | | | | | | | | | | | | | | | | |
| 105 | | 1.1210 | 98 | 98 | | 100 | 100 | 95 | 100 | | 100 | 90 | 85 | 95 | 95 | 95 | 100 | 100 | 100 | 100 | 100 | 100 | 100 | |
| | | 0.2803 | 100 | 50 | | 100 | 100 | 90 | 90 | | 95 | 35 | 30 | 85 | 85 | 90 | 95 | 95 | 100 | 80 | 100 | 100 | 100 | |
| | | 0.0701 | 60 | 70 | | 100 | 100 | 85 | 95 | | 85 | 0 | 80 | 0 | 75 | 35 | 55 | 45 | 100 | 0 | 95 | 80 | 100 | |
| | | 0.0175 | 20 | 50 | | 100 | 95 | 85 | 100 | | 80 | 0 | 0 | 0 | 60 | 0 | 0 | 0 | 80 | 0 | 75 | 100 | 100 | |
| | | 0.0044 | 40 | 70 | | 85 | 85 | 30 | 100 | | 30 | 0 | 20 | 0 | 45 | 0 | 15 | 0 | 40 | 0 | 40 | 80 | 75 | |
| | | 0.0087 | 0 | 35 | | 15 | 25 | 0 | 90 | | 50 | 0 | 30 | 0 | 25 | 0 | 0 | 0 | 20 | 0 | 0 | 100 | 100 | |
| 151 | | 5.6050 | 95 | 15 | | 100 | 100 | 95 | 100 | | 100 | 45 | 95 | 60 | 100 | 100 | 100 | 100 | 100 | 100 | 100 | 100 | 100 | |
| | | 1.1210 | 95 | 20 | | 100 | 100 | 60 | 99 | | 95 | 20 | 50 | 25 | 95 | 65 | 65 | 100 | 100 | 95 | 98 | 100 | 100 | |
| | | 0.5605 | 40 | 10 | | 100 | 100 | 60 | 95 | | 70 | 15 | 30 | 5 | 95 | 70 | 70 | 90 | 60 | 95 | 95 | 100 | 95 | |
| | | 0.2803 | 10 | 30 | | 100 | 100 | 60 | 95 | | 55 | 0 | 20 | 0 | 75 | 45 | 35 | 60 | 25 | 20 | 80 | 100 | 100 | |
| | | 0.1401 | 15 | 25 | | 65 | 85 | 30 | 35 | | 35 | 0 | 10 | 0 | 45 | 50 | 25 | 35 | 0 | 0 | 60 | 100 | 75 | |
| | | 0.0701 | 0 | 10 | | 100 | 15 | 0 | 80 | | 20 | 0 | 15 | 0 | 40 | 40 | 20 | 0 | 0 | 0 | 40 | 100 | 100 | |
| | | 0.0350 | 15 | 5 | | 100 | 25 | 20 | 99 | | 15 | 10 | 5 | 0 | 25 | 25 | 20 | 30 | 0 | 0 | 40 | 100 | 100 | |
| | | 0.0175 | 0 | 0 | | 100 | 100 | 20 | 75 | | 15 | 0 | 15 | 0 | 10 | 10 | 15 | 15 | 25 | 0 | 0 | 98 | 95 | |
| 153 | | 5.6050 | 90 | 30 | | 100 | 100 | 50 | 100 | | 100 | 30 | 10 | 65 | 100 | 100 | 50 | 100 | 100 | 0 | 100 | 100 | 100 | |
| | | 1.1210 | 40 | 0 | | 100 | 95 | 20 | 60 | | 95 | 0 | 40 | 20 | 60 | 60 | 30 | 70 | 100 | 80 | 100 | 100 | 100 | |
| | | 0.5605 | 40 | 0 | | 100 | 100 | 10 | 30 | | 70 | 0 | 20 | 20 | 0 | N | 0 | 0 | 100 | 80 | 70 | 100 | 100 | |
| | | 0.2803 | 0 | 0 | | 100 | 100 | N | 0 | | 20 | 0 | 0 | 0 | 0 | 0 | 0 | 0 | 0 | N | 0 | 100 | 90 | |
| | | 0.1401 | 0 | 0 | | 95 | 100 | 0 | 0 | | 0 | 0 | 0 | 0 | 0 | 0 | 0 | 0 | 0 | 0 | 0 | 100 | 100 | |
| | | 0.0701 | N | N | | 0 | 0 | N | 0 | | 0 | 0 | 0 | 0 | 0 | 0 | 0 | 0 | 0 | 0 | 0 | 80 | 80 | |

TABLE C-continued

Herbicide Secondary Pre, spectrums 26, 88, 91, and 93

| Ex. No. | CP | Rate kg/ha | Sobe | Cotn | Rape | Cbua | Wbw | Mogl | Hese | Jiwe | Vele | Whez | Rice | Grso | Corn | Dobr | Prmi | Bygr | Lacg | Grfl | Sube | Colq | Pesw | Cocw |
|---|---|---|---|---|---|---|---|---|---|---|---|---|---|---|---|---|---|---|---|---|---|---|---|
| 156 | * | 5.6050 | 95 | | | 75 | 100 | 95 | 100 | | 100 | 60 | 95 | 95 | 100 | 95 | 100 | 100 | 100 | 100 | 100 | 100 | N | |
|  | * | 5.6050 | 90 | | | 85 | 100 | 95 | 95 | | 100 | 35 | 95 | 95 | 100 | 85 | 90 | 100 | 100 | 100 | 100 | 100 | N | |
|  | * | 1.1210 | 40 | | | 50 | 95 | 70 | 95 | | 95 | 10 | 75 | 45 | 35 | 55 | 75 | 95 | 100 | 95 | 100 | 100 | N | |
|  | * | 1.1210 | 40 | | | 0 | 80 | 95 | 90 | | 90 | 0 | 60 | 35 | 60 | 35 | 0 | 90 | 100 | 95 | 100 | 100 | N | |
|  | * | 0.5605 | 60 | | | 35 | 100 | 95 | 100 | | 95 | 0 | 85 | 30 | 35 | 30 | 100 | 95 | 90 | 95 | 90 | 100 | N | |
|  | * | 0.2803 | 55 | | | 35 | 85 | 35 | 0 | | 30 | 25 | 0 | 90 | 80 | 30 | 0 | 95 | 35 | 85 | 100 | 100 | N | |
|  | * | 0.2803 | 10 | | | 0 | 45 | 25 | N | | 20 | 0 | 35 | 10 | 35 | 0 | 0 | 0 | 100 | 95 | 100 | 100 | N | |
|  | * | 0.1401 | 40 | | | 0 | 100 | 95 | 90 | | 95 | 0 | 20 | 65 | 80 | 80 | 85 | 85 | 100 | 90 | 100 | 100 | N | |
|  | * | 0.1401 | 0 | | | 0 | 100 | 95 | 95 | | 0 | 0 | 10 | 0 | 0 | 0 | 0 | 30 | N | 0 | 100 | 80 | N | |
|  | * | 0.0701 | 0 | | | 0 | 20 | 0 | 0 | | 0 | 0 | 0 | 0 | 0 | 0 | 20 | 80 | 0 | 0 | 95 | 0 | N | |
|  | * | 0.0701 | 30 | | | 0 | 0 | 60 | 70 | | 25 | 0 | 10 | 45 | 15 | 30 | 50 | 30 | 50 | 70 | 60 | 100 | N | |
|  | * | 0.0350 | 0 | | | 0 | 95 | 25 | 40 | | 45 | 0 | 0 | 0 | 5 | 0 | 0 | 0 | 40 | 25 | 100 | 0 | N | |
| 157 | * | 5.6050 | 40 | | | 10 | 100 | 100 | 100 | | 100 | 35 | 90 | 95 | 95 | 98 | 100 | 100 | 100 | 100 | 100 | 100 | N | |
|  | * | 1.1210 | 80 | | | 0 | 100 | 95 | 100 | | 100 | 30 | 30 | 85 | 40 | 90 | 100 | 100 | 50 | 100 | 95 | 100 | N | |
|  | * | 0.5605 | 15 | | | 35 | 100 | 100 | 100 | | 90 | 0 | 40 | 80 | 65 | 90 | 95 | 95 | 100 | 100 | 100 | 100 | N | |
|  | * | 0.2803 | 35 | | | 40 | 98 | 90 | 95 | | 85 | 0 | 35 | 30 | 25 | 30 | 80 | 90 | 100 | 95 | 100 | 100 | N | |
|  | * | 0.1401 | 20 | | | 0 | 95 | 80 | 90 | | 70 | 0 | 25 | 25 | 10 | 30 | 20 | 45 | 80 | 95 | 100 | 100 | N | |
|  | * | 0.0701 | 0 | | | 0 | 90 | 80 | 85 | | 100 | 0 | 95 | 90 | 0 | 10 | 100 | 100 | 100 | 100 | 100 | 100 | N | |
| 199 | * | 5.6050 | 90 | | | 10 | 100 | 100 | 100 | | 90 | 55 | 80 | 60 | 90 | 80 | 100 Z | 100 | 100 | 100 | 100 | 100 | N | |
|  | * | 1.1210 | 40 | | | 90 | 100 | 95 | 90 | | 85 | 35 | 85 | 25 | 85 | Z 80 | 100 | 95 | 95 | 95 | 100 | 100 | N | |
|  | * | 1.1210 | 25 | | | 30 | 100 | 98 | 90 | | 95 | 0 | 80 | 55 | 35 | 85 | 90 | 95 | 100 | 100 | 100 | 100 | N | |
|  | * | 0.5605 | 60 | | | 10 | 95 | 95 | 95 | | 80 | 20 | 85 | 30 | 25 | 75 | 80 | 90 | 100 | 95 | 100 | 100 | N | |
|  | * | 0.5605 | 20 | | | 45 | 100 | 98 | 95 | | 75 | 15 | 60 | 50 | 45 | 75 | 20 | 95 | 80 | 100 | 100 | 100 | N | |
|  | * | 0.2803 | 60 | | | 35 | 100 | 95 | 90 | | 70 | 0 | 40 | 40 | 10 | 75 | 10 | 45 | 100 | 100 | 95 | 100 | N | |
|  | * | 0.2803 | 20 | | | 20 | 95 | 95 | 90 | | 40 | 0 | 30 | 0 | 0 | 10 | 50 | 100 | 100 | 100 | 100 | 100 | N | |
|  | * | 0.1401 | 40 | | | 0 | 35 | 50 | 35 | | 0 | 0 | 0 | 0 | 0 | 0 | 10 | 60 | 90 | 30 | 30 | 80 | N | |
|  | * | 0.1401 | 20 | | | 0 | 0 | 40 | 85 | | 35 | 0 | 25 | 0 | 30 | 25 | 30 | 0 | 0 | 0 | 0 | 100 | N | |
|  | * | 0.0701 | 0 | | | 0 | 90 | 90 | 70 | | 0 | 0 | 0 | 10 | 0 | 0 | 0 | 80 | 100 | 95 | 100 | 100 | N | |
|  | * | 0.0350 | 0 | | | 0 | 95 Z | 70 Z | 25 | | 0 | 0 | 0 | 0 | 15 | 0 | 0 | 0 | 0 | 30 | 10 | 70 | N | |
|  | * | 0.0350 | 0 | | | 0 | 0 | 0 | 0 | | 0 | 0 | 0 | 0 | 0 | 0 | 0 | 0 | 0 | 0 | 0 | 40 | N | |
|  | * | 0.0175 | 0 | | | 0 | 95 | 30 | 85 | 100 | 20 | 20 | 20 | 0 | 0 | 0 | 30 | 0 | 0 | 60 | 0 | 100 | N | |
|  | * | 0.0175 | 0 | | 100 | 70 | 80 | 60 | 50 | 20 | 0 | 40 | 0 | 0 | 0 | 0 | 0 | 0 | 0 | 0 | 0 | 0 | N | |
| 296 | * | 5.6050 | 0 | | 50 | 50 | 0 | 0 | 0 | 0 | 0 | 0 | 0 | 0 | 0 | 0 | 0 | 0 | 0 | 0 | 0 | 0 | N | |
|  | * | 1.1210 | 0 | | 40 | 0 | 0 | 0 | 0 | 0 | 0 | 0 | 0 | 0 | 0 | 0 | 0 | 0 | 0 | 0 | 0 | 0 | N | |
|  | * | 0.5605 | 0 | | 0 | 0 | 0 | 0 | 0 | 0 | 0 | 0 | 0 | 0 | 0 | 0 | 0 | 0 | 0 | 0 | 0 | 0 | N | |
|  | * | 0.1401 | 0 | | 0 | 0 | 0 | 0 | 0 | 0 | 0 | 0 | 0 | 0 | 0 | 0 | 0 | 0 | 0 | 0 | 0 | 70 Z | N | |
|  | * | 0.0701 | 0 | 90 | 0 | 0 | 0 | 0 | 0 | 100 | 0 | 40 | 0 | 0 | 0 | 0 | 0 | 90 Z | 0 | 0 | 0 | 0 | N | |
|  | * | 0.0351 | 0 | 60 | 0 | 0 | 0 | 0 | 0 | 95 | 0 | 0 | 0 | 0 | 0 | 0 | 0 | 0 | 20 | 30 | 0 | 0 | N | |
| 299 | * | 5.6050 | 75 | 0 | 100 | 100 | 100 | 100 | 100 | 100 | 100 | 40 | 100 | 95 | 85 | 90 | 80 | 0 | 0 | 90 | 90 | 100 | N | |
|  | * | 1.1210 | 70 | 15 | 95 | 99 | 45 | 100 | 95 | 98 | 90 | 0 | 55 | 55 | 50 | 0 | 0 | 0 | 0 | 30 | 0 | 0 | N | |
|  | * | 0.5605 | 20 | 0 | 80 | 85 | 75 | 95 | 85 | 85 | 99 | 0 | 45 | 35 | 20 | 0 | 0 | 25 | 0 | 30 | 30 | 40 | N | |
|  | * | 0.2803 | 0 | 0 | 60 | 40 | 25 | 95 | 90 | | 90 | 0 | 40 | 0 | 0 | 0 | 0 | 0 | 0 | 0 | 0 | 100 | N | |
|  | * | 0.1401 | 0 | 0 | 45 | 0 | 10 | 0 | 0 | | 0 | 0 | 25 | 0 | 0 | 0 | 0 | 0 | 0 | 0 | 0 | 0 | N | |

TABLE C-continued

Herbicide Secondary Pre, spectrums 26, 88, 91, and 93

| Ex. No. | CP | Rate kg/ha | Soyb | Cotn | Rape | Cbun | Wbw | Mogl | Hese | Jiwe | Vele | Whez | Rice | Grso | Corn | Dobr | Prmi | Bygr | Lacg | Grft | Sube | Colq | Pesw | Cocw |
|---|---|---|---|---|---|---|---|---|---|---|---|---|---|---|---|---|---|---|---|---|---|---|---|---|
| 305 | | 0.0701 | 10 | 0 | 45 | 0 | 0 | 90 | 55 | 0 | 25 | 0 | 0 | 0 | 10 | 0 | 0 | 0 | 0 | 0 | | | | |
|  | | 0.0351 | 20 | 0 | 25 | 35 | N | 90 | 0 | 0 | 0 | 0 | 0 | 0 | 0 | 25 | 0 | 0 | 0 | 0 | | | | |
|  | @ | 5.6050 | 25 | 90 | 100 | 100 | 100 | 100 | 100 | 100 | 100 | 35 | 95 | 55 | 70 | 90 | 85 | 95 | 100 | 100 | | | | |
|  | @ | 1.1210 | 60 | 85 | 90 | 100 | 98 | 100 | 95 | 100 | 90 | 55 | 85 | 85 | 70 | 85 | 90 | 0 | 90 | 40 | | | | |
|  | @ | 0.5605 | 20 | 95 | 60 | 90 | 90 | 100 | 95 | 100 | 100 | 25 | 35 | 15 | 10 | 40 | 0 | 0 | 25 | 0 | | | | |
|  | @ | 0.2803 | 25 | 0 | 75 | 0 | 85 | 100 | 50 | 95 | 65 | 0 | 60 | 10 | 5 | 0 | 0 | 0 | 0 | 0 | | | | |
|  | @ | 0.1401 | 20 | 0 | 70 | 0 | 0 | 80 | 90 | 90 | 35 | 20 | 0 | 30 | 20 | 40 | 0 | 0 | 0 | 20 | | | | |
|  | @ | 0.0701 | 20 | 40 | 30 | 35 | 0 | 90 | 30 | 70 | 35 | 0 | 50 | N | N | 95 | 65 | 85 | 0 | 0 | | | | |
|  | @ | 0.0351 | N | 0 | 25 | 0 | N | 0 | 100 | 100 | N | 20 | 40 | N | 50 | 40 | 0 | 25 | 0 | 0 | | | | |
| 314 | | 5.6050 | 50 | 70 | 100 | 95 | 100 | 100 | 100 | 100 | 100 | 80 | 100 | 65 | 50 | 95 | 65 | 85 | 100 | 100 | | | | |
|  | | 1.1210 | 70 | 0 | 95 | 90 | 100 | 100 | 100 | 100 | 95 | 60 | 45 | 85 | 65 | 0 | 0 | 25 | 90 | 40 | | | | |
|  | | 0.5605 | 10 | 30 | 95 | 40 | 75 | 65 | 80 | 100 | 80 | 0 | 45 | 0 | 15 | 0 | 30 | 0 | 25 | 0 | | | | |
|  | | 0.2803 | 10 | 0 | 85 | 0 | 80 | 70 | 95 | 40 | 30 | 0 | 0 | 0 | 0 | 0 | 0 | 0 | 0 | 0 | | | | |
|  | | 0.1401 | 25 | 0 | 85 | 0 | 30 | 0 | 60 | 30 | 30 | 0 | 25 | 0 | 0 | 35 | 0 | 0 | 0 | 0 | | | | |
|  | | 0.0701 | 0 | 0 | 0 | 0 | 35 | 0 | 65 | 0 | 50 | 0 | 0 | 0 | 20 | 40 | 45 | 0 | 0 | 0 | | | | |
|  | | 0.0351 | N | 0 | 0 | N | 0 | 0 | 60 | N | 0 | 0 | 0 | 0 | 0 | 0 | 0 | 0 | 0 | 0 | | | | |
|  | | 0.0175 | 0 | 0 | 0 | 0 | 35 | 0 | 0 | 0 | 50 | 0 | 0 | 0 | 0 | 0 | 0 | 0 | 0 | 100 | | | | |
|  | | 0.0087 | 5 | 95 | 100 | 100 | 100 | 100 | 100 | 100 | 100 | 90 | 95 | 100 | 95 | 100 | 100 | 100 | 100 | 100 | | | | |
| 327 | | 5.6050 | 55 | 100 | 100 | 100 | 100 | 100 | 100 | 100 | 100 | 85 | 90 | 98 | 90 | 100 | 98 | 100 | 100 | 100 | | | | |
|  | | 1.1210 | 30 | 95 | 100 | 90 | 100 | 95 | 100 | 100 | 100 | 55 | 90 | 95 | 50 | 100 | 45 | 95 | 95 | 95 | | | | |
|  | | 0.2803 | 10 | 95 | 100 | 100 | 60 | 60 | 100 | 95 | 100 | 35 | 30 | 60 | 45 | 85 | 95 | 75 | 100 | 99 | | | | |
|  | | 0.0701 | 10 | 85 | 95 | 85 | 90 | 85 | 90 | 90 | 100 | 20 | 20 | 35 | 15 | 40 | 30 | 70 | 50 | 45 | | | | |
|  | | 0.0175 | 20 | 80 | 85 | 55 | 90 | 85 | 100 | 95 | 100 | 0 | 45 | 35 | 25 | 0 | 0 | 30 | 50 | 35 | | | | |
|  | | 0.0175 | 20 | 35 | 45 | 10 | N | 100 | 45 | 50 | 100 | 0 | 35 | 0 | 15 | 0 | 0 | 0 | 40 | 0 | | | | |
|  | | 0.0087 | 25 | 30 | 30 | 60 | 0 | 55 | 50 | 55 | 100 | 0 | 40 | 10 | 20 | 35 | 0 | 0 | 100 | 0 | | | | |
|  | | 0.0087 | 15 | N | 45 | N | N | 0 | 90 | 50 | 100 | 0 | 25 | 20 | 5 | 0 | 45 | 0 | 0 | 0 | | | | |
| 329 | | 5.6050 | 100 | 10 | 40 | 0 | 35 | 80 | 95 | 90 | 95 | 0 | N | 0 | 20 | 45 | 0 | 0 | 0 | 0 | | | | |
|  | | 1.1210 | 60 | 20 | 95 | N | 100 | 90 | 100 | 100 | 100 | 20 | 90 | 50 | 50 | 99 | 100 | 98 | N | 100 | | | | |
|  | | 0.2803 | 80 | 90 | 90 | 0 | 100 | 95 | 100 | 100 | 100 | 0 | 50 | 50 | 80 | 90 | 95 | 95 | Z | 100 | | | | |
|  | | 0.0701 | 80 | 15 | 60 | Z | 100 | 60 | 90 | 100 | 100 | 20 | 60 | 0 | 30 | 90 | 95 | 85 | Z | 99 | | | | |
|  | | 0.0175 | 0 | 0 | 20 | 0 | 80 | 20 | 90 | 100 | 30 | 0 | 30 | 0 | 20 | 50 | 30 | 80 | Z | 20 | | | | |
|  | | 0.0087 | 0 | 0 | 0 | Z | 0 | 0 | 0 | 0 | 0 | 0 | 0 | 0 | 0 | 0 | 0 | 0 | Z | 100 | | | | |
| 331 | | 5.6050 | 99 | 75 | 100 | 0 | 100 | 100 | 100 | 100 | 100 | 60 | 80 | 99 | 99 | 50 | 100 | 98 | Z | 100 | | | | |
|  | | 1.1210 | 100 | 30 | 95 | 0 | 100 | 80 | 100 | 100 | 100 | 70 | 40 | 70 | 85 | 75 | 99 | 85 | Z | 100 | | | | |
|  | | 0.2803 | 60 | 0 | 50 | 0 | 70 | 50 | 50 | 80 | 30 | 30 | 0 | 40 | 20 | 60 | 100 | 50 | Z | 75 | | | | |
|  | | 0.0701 | 20 | 0 | 40 | N | 90 | 65 | 0 | 0 | 0 | 0 | Z | 0 | 40 | 0 | 0 | 0 | Z | 50 | | | | |
|  | | 0.0175 | Z | Z | 0 | Z | 0 | 0 | Z | 0 | 0 | 0 | 0 | 0 | 10 | Z | Z | 0 | Z | 0 | | | | |
|  | | 0.0087 | 0 | 0 | 0 | 0 | 0 | 0 | 0 | 0 | 0 | 0 | 0 | 0 | 0 | 0 | 0 | 0 | Z | 15 | | | | |
| 332 | | 5.6050 | 30 | 35 | 95 | 0 | 100 | 95 | 100 | 100 | 100 | 90 | 50 | 50 | 0 | 95 | 35 | 20 | 90 | 35 | | | | |
|  | | 1.1210 | 0 | 35 | 80 | 90 | 100 | 85 | 100 | 100 | 100 | 0 | 45 | 0 | 0 | 0 | 55 | 40 | 0 | 20 | | | | |
|  | | 0.2803 | 0 | 15 | 30 | 45 | 90 | 35 | 90 | 80 | 95 | 0 | 0 | 0 | 0 | 0 | N | 0 | N | 0 | | | | |
|  | | 0.0701 | 0 | 0 | 30 | 0 | 50 | 30 | 30 | 35 | 60 | 0 | 0 | 0 | 0 | Z | 0 | 0 | 25 | 15 | | | | |
|  | | 0.0351 | 0 | 0 | 60 | N | 50 | 0 | 0 | 0 | 0 | 0 | 0 | 0 | 0 | 0 | 0 | 0 | 0 | 20 | | | | |
| 402 | | 5.6050 | 100 | 65 | 75 | 85 | 100 | 90 | 100 | 100 | 100 | 90 | 45 | 80 | 75 | 100 | 95 | 98 | 100 | 100 | | | | |

TABLE C-continued

Herbicide Secondary Pre, spectrums 26, 88, 91, and 93

| Ex. No. | CP | Rate kg/ha | Sobe | Cotn | Rape | Cabu | Wibw | Mogl | Hese | Jiwe | Vele | Whez | Rice | Grso | Corn | Dobr | Prmi | Bygr | Lacg | Grft | Sube | Colq | Pesw | Cocw |
|---|---|---|---|---|---|---|---|---|---|---|---|---|---|---|---|---|---|---|---|---|---|---|---|
| 446 |  | 1.1210 | 75 | 45 | 45 | 0 | 100 | 95 | 100 | 95 | 95 | 30 | 25 | 85 | 65 | 98 | 90 | 95 | 100 | 100 | | | | |
|  |  | 0.5605 | 25 | 45 | 0 | 0 | 100 | 80 | 85 | 25 | 50 | 25 | 35 | 55 | 60 | 95 | 80 | 95 | 100 | 95 | | | | |
|  |  | 0.2803 | N | 0 | 35 | 15 | 100 | 35 | 90 | N | 30 | 25 | N | 65 | 20 | 75 | 35 | 90 | 100 | 90 | | | | |
|  |  | 0.1401 | 30 | 0 | 0 | 0 | 90 | 25 | 90 | 45 | 35 | 0 | 40 | 15 | 25 | 0 | 20 | 80 | 0 | 90 | | | | |
|  |  | 0.0701 | 40 | 0 | 0 | 0 | 45 | 0 | 60 | 55 | 0 | 0 | 0 | 25 | 5 | 0 | 20 | 35 | 0 | 75 | | | | |
|  |  | 0.0351 | 50 | 0 | 0 | 0 | 0 | 0 | 40 | 60 | 0 | 0 | 35 | 25 | 0 | 0 | 20 | 0 | 0 | 20 | | | | |
|  |  | 0.0175 | 50 | 95 | 0 | 0 | 0 | 0 | 0 | 20 | 0 | 0 | 0 | 0 | 0 | 0 | 0 | 0 | 0 | 0 | | | | |
|  |  | 5.6050 | 100 | 95 | 100 | 90 | 100 | 100 | 100 | 100 | 100 | 90 | 95 | 90 | 95 | 100 | 100 | 100 | 100 | 100 | | | | |
|  | = | 1.1210 | 100 | 80 | 100 | 90 | 100 | 100 | 100 | 100 | 100 | 0 | 95 | 50 | 100 | 100 | 100 | 100 | 100 | 100 | | | | |
|  | = | 0.2803 | 100 | 50 | 80 | 60 | 100 | 65 | 80 | 100 | 100 | 0 | 55 | 30 | 98 | 90 | 30 | 95 | 70 | 95 | | | | |
|  | = | 0.0701 | 80 | 0 | 0 | 100 | 90 | 30 | 80 | 100 | 40 | 30 | 45 | 20 | 25 | 85 | 35 | 80 | 50 | 20 | | | | |
|  | = | 0.0175 | 35 | 25 | 0 | 30 | 0 | 25 | 50 | 0 | 75 | N | 60 | 0 | 20 | 40 | 10 | 0 | 20 | 0 | | | | |
| 464 | = | 0.0087 | N | 0 | 0 | N | 45 | 0 | 0 | 0 | 0 | 80 | 0 | 25 | 15 | 0 | 20 | 0 | 0 | 0 | | | | |
|  |  | 5.6050 | 100 | 100 | 100 | 95 | 100 | 100 | 100 | 100 | 100 | 80 | 95 | 95 | 100 | 100 | 100 | 100 | 100 | 100 | | | | |
|  |  | 1.1210 | 95 | 100 | 100 | 30 | 100 | 90 | 95 | 100 | 100 | 10 | 95 | 90 | 95 | 95 | 100 | 95 | 100 | 90 | | | | |
|  |  | 0.2803 | 90 | 15 | 70 | 20 | 100 | 100 | 90 | 100 | 100 | 0 | 80 | 40 | 20 | 30 | 100 | 35 | 80 | 45 | | | | |
|  |  | 0.0701 | 0 | 0 | 0 | 0 | 100 | 0 | 80 | 100 | 90 | 0 | 0 | 0 | 0 | 0 | 40 | 0 | 30 | 0 | | | | |
|  |  | 0.0175 | 30 | 10 | 0 | 10 | 95 | 10 | 0 | 25 | 20 | 30 | 60 | 25 | 15 | 0 Z | 25 | 0 | 0 | 45 | | | | |
| 586 |  | 0.0087 | 15 | 0 | 0 | 0 | 0 | 0 | 100 | 25 | 100 | N | 0 | 0 | 0 | N | 90 | 95 | 100 | 0 | | | | |
|  |  | 5.6050 | 100 | 100 | 100 | 100 | 100 | 100 | 100 | 100 | 100 | 80 | 90 | 90 | 90 | 100 | 85 | 95 | 100 | 100 | | | | |
|  |  | 1.1210 | 100 | 95 | 95 | 85 | 100 | 90 | 95 | 100 | 100 | 40 | 70 | 85 | 90 | 65 | 40 | 90 | 100 | 100 | | | | |
|  |  | 0.2803 | 60 | 70 | 75 | 65 | 100 | 80 | 75 | 50 | 85 | 0 | 50 | 20 | 70 | 35 | 45 | 45 | 75 | 50 | | | | |
|  |  | 0.0701 | 20 | 45 | 60 | 55 | 75 | 0 | 70 | 40 | 0 | 0 | 30 | 30 | 25 | 20 | 0 | 20 | 30 | 35 | | | | |
|  |  | 0.0175 | N | 0 | 0 | 0 | 45 | 0 | 70 | 65 | 0 | 65 | 0 | 0 | 40 | 0 | 0 | 10 | 45 | 15 | | | | |
| 639 |  | 0.0087 | 0 | 0 | 30 | 10 | 0 | 0 | 100 | 95 | 100 | 30 | 35 | 15 | 0 | 0 | 30 | 0 | 25 | 0 | | | | |
|  |  | 5.6050 | 70 | 60 | 100 | 0 | 100 | 90 | 100 | 85 | 100 | 0 | 25 | 30 | 10 | 90 | 0 | 90 | 100 | 100 | | | | |
|  |  | 1.1210 | 75 | 40 | 95 | 20 | 100 | 75 | 35 | 40 | 100 | 0 | 45 | 30 | 25 | 85 | 30 | 55 | 95 | 40 | | | | |
|  |  | 0.2803 | 35 | 10 | 75 | 20 | 100 | 60 | 0 | 95 | 95 | 0 | 40 | 0 | 0 | 0 | 0 | 0 | 0 | 40 | | | | |
|  |  | 0.0701 | 10 | 0 | 0 | 0 | 95 | 0 | 20 | 0 | 0 | 0 | 20 | 0 | 0 | 0 | 0 | 0 | 0 | 0 | | | | |
|  |  | 0.0175 | 0 | 35 | 0 | N | 0 | 0 | 100 | 0 | 100 | 0 | 0 | 95 | 0 | 25 | 0 | 0 | 0 | 0 | | | | |
| 642 |  | 0.0087 | 0 | 50 | 100 | N | 100 | 90 | 100 | 100 | 95 | 95 | 30 | 95 | 20 | 95 | 100 | 100 | 100 | 100 | | | | |
|  | — | 5.6050 | 100 | 30 | 95 | Z | 100 | 100 | 95 | 100 | 0 | 35 | 30 | 25 | 65 | 55 | 85 | 85 | 100 | 95 | | | | |
|  | — | 1.1210 | 90 | 0 | 80 | Z | 100 | 90 | 90 | 100 | 95 | 0 | 30 | 0 | 10 | 0 | 45 | 30 | 75 | 55 | | | | |
|  | — | 0.2803 | 35 | Z | 0 | Z | 100 | 80 | 70 | 75 | 30 | 0 | 30 | N | 20 | 0 | 0 | 0 | 0 | 0 | | | | |
|  | — | 0.0701 | 0 | 0 | 0 | Z | 25 | 0 | 0 | 0 | 0 | 0 | 30 | 30 | 0 | 0 | 0 | 0 | 30 | 0 | | | | |
|  | — | 0.0175 | 0 | 30 | 0 | Z | 0 | 25 | 20 | 0 | 30 | 0 | 80 | Z | 0 | 0 | 0 | 0 | 30 | 0 | | | | |
| 644 | — | 0.0087 | 0 | 0 | 30 | Z | 100 | 95 | 100 | 100 | 100 | 0 | 95 | 95 | 95 | 100 | 100 | 100 | 100 | 100 | | | | |
|  |  | 5.6050 | 0 | 75 | 100 | 80 | 100 | 90 | 100 | 100 | 100 | 0 | 80 | 80 | 60 | 95 | 90 | 90 | 100 | 95 | | | | |
|  |  | 1.1210 | 75 | 85 | 90 | 80 | 100 | 80 | 98 | 100 | 90 | 20 | 25 | 55 | 50 | 95 | 95 | 85 | 100 | 85 | | | | |
|  |  | 0.2803 | 0 | 20 | 40 | 90 | 100 | 0 | 85 | 90 | 30 | 30 | 45 | 35 | 20 | 30 | 80 | 20 | 60 | 15 | | | | |
|  |  | 0.0701 | 30 | 15 | 20 | 50 | 80 | 0 | 0 | 55 | 60 | 15 | 40 | 0 | 30 | 35 | 0 | 0 | 30 N | 0 | | | | |
|  | V | 0.0175 | 35 | 15 Z | 0 | N | 50 | 0 | 25 | 10 | 0 | 0 | 35 | 0 | 0 | 35 | 35 | 15 | 50 | 50 | | | | |
| 701 | V | 0.0087 | N N | N | 0 | 0 | 0 | 0 | 0 | 0 | 0 | 0 | 0 Z | 0 | 0 | 0 | 0 | 0 | 45 | 65 | | | | |
|  | V |  |  |  |  |  |  |  |  |  |  |  |  |  |  |  |  |  | 30 | 15 | | | | |
|  | V |  |  |  |  |  |  |  |  |  |  |  |  |  |  |  |  |  | 0 | 0 | | | | |
|  | V |  |  |  |  |  |  |  |  |  |  |  |  |  |  |  |  |  | 0 | 0 | | | | |
|  | V |  |  |  |  |  |  |  |  |  |  |  |  |  |  |  |  |  | 0 | 0 | | | | |

TABLE C-continued

Herbicide Secondary Pre, spectrums 26, 88, 91, and 93

| Ex. No. CP | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Subе | Colq | Pesw | Cocw |
|---|---|---|---|---|---|---|---|---|---|---|---|---|---|---|---|---|---|---|---|---|---|---|---|
| 705 | 5.6050 | 90 | 85 | 100 | 100 | 100 | 100 | 100 | 100 | 100 | 50 | 45 | 55 | 55 | 80 | 35 | 90 | 95 | 100 | | | | |
| | 1.1210 | 5 | 60 | 100 | 75 | 100 | 100 | 100 | 100 | 100 | 0 | 35 | 5 | 5 | 30 | 5 | 40 | 90 | 50 | | | | |
| | 0.2803 | 0 | 25 | 60 | 40 | 100 | 50 | 100 | 100 | 100 | 0 | 40 | 20 | 0 | 0 | 0 | 0 | 0 | 0 | | | | |
| | 0.0701 | 0 | 0 | 40 | 60 | 100 | 20 | 100 | 100 | 100 | 0 | 20 | 0 | 0 | 0 | 0 | 0 | 0 | 0 | | | | |
| | 0.0175 | 10 | 0 | 0 | 0 | 95 | 0 | 90 | 100 | 0 | 0 | 0 | 0 | 0 | 0 | 0 | 0 | 0 | 0 | | | | |
| | 0.0087 | 0 | 0 | 0 | 0 | 75 | 0 | 0 | 40 | 0 | 25 | 0 | 0 | 0 | 0 | 0 | 0 | 0 | 0 | | | | |
| 786 | 5.6050 | 95 | 80 | 100 | 65 | 100 | 100 | 100 | 100 | 100 | 0 | 90 | 90 | 95 | 50 | 100 | 100 | 100 | 100 | | | | |
| | 1.1210 | 50 | 15 | 85 | 0 | 95 | 90 | 95 | 80 | 100 | 0 | 45 | 20 | 70 | 0 | 100 | 90 | 95 | 90 | | | | |
| | 0.2803 | 0 | 15 | 60 | 0 | 45 | 25 | 45 | 30 | 100 | 0 | 35 | 10 | 35 | 0 | 85 | 50 | 80 | 40 | | | | |
| | 0.0701 | N | N | 0 | 0 | 85 | 0 | 25 | 20 | 30 | 0 | 0 | 0 | 0 | 0 | 55 | 0 | 65 | 0 | | | | |
| | 0.0175 | N | 0 | 0 | 0 | 40 | 0 | 0 | 0 | 0 | 0 | 0 | 0 | 0 | 0 | 0 | 0 | 0 | 0 | | | | |

*POOR PESW EMERGENCE @ PANS DRY ON 4/13/87 = RICE VARIABLE THROUGHOUT TEST ( NO DATA FOR LACG AND COBU DUE TO POOR EMERGENCE - COBU EMERGENCE AND RICE GROWTH VARIABLE NO DATA FOR COBU DUE TO POOR EMERGENCE  Greenhouse temp. flucuations Oct. 10,11,17,18 < POOR SOBE PLANTS THROUGHOUT TEST

POST-EMERGENCE ACTIVITY ON WEEDS AND CROPS

Compounds of this invention were tested for herbicidal activity on weed plants in the presence of crop plants according to the following procedure.

Topsoil is sieved through a screen having 1.27 cm openings. In some of the tests the soil was mixed with fertilizer, while in other tests the fertilizer was omitted. This mixture is sterilized and then placed in pans having holes in the bottom. The soil mixture is compacted to a depth of 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered and the pans are then placed on a greenhouse bench and watered as needed. After the plants reach the desired stage, 10 to 14 days, 1 to 3 true leaf stage, each pan (except the control pans) is removed to a spraying chamber and sprayed by means of an atomizer, operating at a spray pressure of 170.3 kPa (10 psig) at the application rates noted in Table D. In the spray solution is an amount of an emulsifying agent mixture to give a spray solution or suspension which contains about 0.4% by volume of the emulsifier. The spray solution or suspension contains a sufficient amount of the candidate chemical in order to give application rates of the active ingredient corresponding to those shown in Table D below while applying a total amount of solution or suspension equivalent to 1870 L/Ha (200 gallons/acre). The pans are returned to the greenhouse and watered as below and the injury to the plants as compared to the control pans is observed at approximately 10–14 days (usually 11 days) and in some instances observed again at 24–28 days (usually 25 days) after spraying. These latter observations are designated by a "pound" sign (#) following the column of example numbers in the Table.

In the following Table D the legends used to identify the plant species are the same as those used in the proceeding Table C.

TABLE D

| Ex. No. | Rate kg/ha | Sobe | Cotn | Rape | Cobu | Wbw | Mogl | Hese | Jiwe | Vele | Whez | Rice | Grso | Corn | Dobr | Ptmi | Bygr | Lacg | Grft | Sube | Colq | Pesw | Cocw |
|---|---|---|---|---|---|---|---|---|---|---|---|---|---|---|---|---|---|---|---|---|---|---|---|
| 7 | 5.6050 | 70 | | | 75 | 80 | 100 | 95 | | 99 | 50 | 30 | 60 | 90 | 25 | 60 | 90 | 95 | 90 | 100 | 50 | 100 | |
|  | 1.1210 | 90 | | | 100 | 90 | 90 | 90 | | 95 | 35 | 30 | 50 | 90 | 10 | 20 | 50 | 100 | 95 | 90 | 50 | 99 | |
|  | 0.5605 | 80 | | | N | 100 | 100 | 90 | | 100 | 25 | 30 | 40 | 95 | 10 | 15 | 50 | 95 | 99 | 95 | 60 | 95 | |
|  | 0.2803 | 60 | | | 100 | 90 | 95 | 100 | | 80 | 20 | 5 | 25 | 70 | 0 | 25 | 50 | 100 | 80 | 95 | 35 | 100 | |
|  | 0.1401 | 65 | | | 75 | 100 | 95 | 99 | | 75 | 10 | N | 15 | 95 | 5 | 10 | 35 | 50 | 70 | 65 | 50 | 95 | |
|  | 0.0701 | 50 | | | 100 | 95 | 80 | 100 | | 70 | 20 | 0 | 25 | 70 | 10 | 30 | 60 | 60 | 75 | 65 | 30 | 90 | |
|  | 0.0350 | 50 | | | N | 95 | 95 | 85 | | 30 | 5 | N | 30 | 75 | 0 | 5 | 5 | 50 | 50 | 65 | 25 | 95 | |
|  | 0.0175 | 25 | | | 50 | 100 | 80 | 50 | | 0 | 10 | 0 | 15 | 40 | 0 | 30 | 5 | 50 | 20 | 20 | 30 | 50 | |
|  | 0.0087 | 30 | | | 35 | 80 | 35 | 50 | | 0 | 20 | 0 | 15 | 45 | 0 | 0 | 0 | 0 | 20 | 0 | 25 | 0 | |
| 13 | 5.6050 | 95 | 99 | | 95 | 100 | 100 | 100 | 100 | 100 | 20 | 25 | 80 | 50 | 30 | 80 | 90 | 100 | 100 | | 100 | | |
|  | 1.1210 | 95 | 99 | 100 | 100 | 100 | 100 | 100 | 100 | 100 | 20 | 10 | 65 | 80 | 20 | 50 | 75 | 65 | 100 | 100 | 100 | 100 | |
|  | 0.2803 | 90 | 90 | 100 | 100 | 100 | 95 | 90 | 99 | 60 | 10 | 10 | 50 | 65 | 10 | 30 | 40 | 60 | 95 | 100 | N | 95 | |
|  | 0.0701 | 65 | 85 | 80 | 80 | 100 | 90 | 70 | 100 | 40 | 5 | 10 | 30 | 50 | 10 | 20 | 20 | 40 | 75 | 95 | 50 | 100 | |
|  | 0.0175 | 40 | 50 | 70 | 40 | 75 | 50 | 65 | 90 | 30 | 0 | N | 10 | 35 | 0 | N | 10 | 60 | 20 | 65 | 30 | 50 | |
|  | 0.0044 | 20 | | 30 | 10 | 100 | 30 | 100 | | 95 | | 0 | 5 | | 0 | 0 | 0 | 100 | | 20 | 25 | 0 | |
| 105 | 5.6050 | 99 | | | 80 | 100 | 100 | 100 | 100 | 100 | 100 | 60 | 100 | 100 | 95 | 95 | 100 | 100 | 100 | 100 | 100 | 100 | |
|  | 5.6050 | 95 | | | 100 | 100 | 100 | 100 | 100 | 100 | 100 | 95 | 100 | 100 | 100 | 100 | 100 | 100 | 100 | 100 | 100 | 100 | |
|  | 1.1210 | 90 | | | 100 | 100 | 100 | 100 | 100 | 100 | 70 | 80 | 100 | 100 | 65 | 85 | 100 | 100 | 100 | 100 | 100 | 100 | |
|  | 1.1210 | 85 | | | 100 | 100 | 100 | 100 | | 100 | 25 | 90 | 95 | 100 | 85 | 95 | 100 | 100 | 100 | 100 | 100 | 100 | |
|  | 1.1210 | 80 | | | 100 | 100 | 100 | 100 | 100 | 95 | 75 | 60 | 100 | 95 | 85 | 40 | 100 | 100 | 100 | 99 | 100 | 100 | |
|  | 1.1210 | 85 | | | 80 | 100 | 100 | 95 | | 95 | 95 | 50 | 100 | 100 | 90 | 95 | 100 | 100 | 100 | 100 | 100 | 100 | |
|  | 1.1210 | 100 | 100 | | 100 | 100 | 100 | 100 | | 100 | 100 | 45 | 100 | 100 | 70 | 40 | 100 | 100 | 100 | 90 | 100 | 100 | |
|  | 0.5605 | 75 | | | 99 | 100 | 100 | 95 | | 95 | 25 | 25 | 80 | 80 | 50 | 95 | 100 | 60 | 95 | 95 | 100 | 100 | |
|  | 0.5605 | 70 | | | 95 | 100 | 100 | 100 | 95 | 95 | 65 | 85 | 90 | 95 | 70 | 100 | 100 | 95 | 100 | 90 | 95 | 100 | |
|  | 0.5605 | 85 | | | 95 | 100 | 100 | N | | 100 | 25 | 90 | 100 | 95 | 100 | 75 | 100 | 100 | 100 | 90 | 100 | 95 | |
|  | 0.2803 | 85 | | | 80 | N | 100 | 90 | | 100 | 65 | 60 | 85 | 80 | 10 | 75 | 100 | 80 | 100 | 95 | N | 100 | |
|  | 0.2803 | 75 | | | 100 | 100 | 100 | 80 | | 100 | 25 | 25 | 60 | 100 | 25 | 75 | 75 | 95 | 100 | 100 | 95 | 100 | |
|  | 0.2803 | 75 | | | 100 | 95 | 100 | 100 | | 100 | 45 | 45 | 60 | 60 | 50 | 100 | 25 | 50 | 100 | N | 95 | 95 | |
|  | 0.0175 | 20 | | | 60 | 100 | 100 | 75 | | 50 | 20 | 15 | 20 | 50 | 10 | 10 | 65 | 10 | 40 | 80 | N | N | |
|  | 0.0087 | 30 | | | 60 | 90 | 60 | 70 | | 60 | 10 | 20 | 10 | 50 | 25 | 5 | 50 | 45 | 60 | 75 | 100 | 95 | |
| 151 | 5.6050 | 80 | 80 | | N | 90 | 100 | 95 | | 100 | 5 | 5 | 15 | 50 | 0 | 10 | 30 | 100 | 45 | 100 | 100 | 100 | |
|  | 5.6050 | 95 | | 35 | 100 | 100 | 100 | 100 | 95 | 100 | 65 | 10 | 95 | 45 | 5 | 50 | 95 | 45 | 100 | 95 | 100 | 100 | |
|  | 1.1210 | 90 | | | 100 | 100 | 100 | 95 | | 100 | 40 | 95 | 75 | 50 | 70 | 100 | 75 | 100 | 100 | 95 | 100 | 95 | |
|  | 1.1210 | 85 | | | 100 | 100 | 100 | 100 | | 100 | 35 | 25 | 55 | 65 | 50 | 75 | 25 | 50 | 100 | 100 | 100 | 100 | |
|  | 0.5605 | 90 | | | 100 | 95 | 100 | 100 | | 100 | 30 | 60 | 40 | 50 | 80 | 85 | 10 | 85 | 100 | 100 | 100 | 100 | |
|  | 0.5605 | 85 | | | 100 | 100 | 100 | 100 | | 100 | 25 | 25 | 30 | 70 | 25 | 60 | 65 | 60 | 100 | 100 | 100 | 95 | |
|  | 0.2803 | 70 | | | 100 | 100 | 80 | 80 | | 100 | 70 | 45 | 75 | 25 | 50 | 95 | 50 | 60 | 80 | 85 | 100 | 100 | |
|  | 0.2803 | 75 | | | 90 | 100 | 80 | 100 | | 95 | 45 | 25 | 30 | 25 | 25 | 30 | 10 | 80 | 95 | 60 | 100 | 95 | |
|  | 0.1401 | 70 | | | 80 | 90 | 80 | 80 | | 50 | 25 | 20 | 20 | 55 | 25 | 20 | 65 | 80 | 75 | 80 | 100 | 90 | |
|  | 0.0701 | 70 | | | 95 | 100 | 95 | 100 | | 95 | 70 | 0 | 60 | 35 | 25 | 75 | 50 | 60 | 75 | 75 | 100 | 95 | |
|  | 0.0701 | 65 | | | 70 | 100 | 75 | 75 | | 70 | 45 | 0 | 35 | 25 | 10 | 30 | 5 | 10 | 25 | 50 | 100 | 50 | |
|  | 0.0350 | 70 | | | 90 | 100 | 75 | 95 | | 80 | 25 | 20 | 20 | 35 | 0 | 20 | 45 | 60 | 95 | 35 | 100 | 70 | |
|  | 0.0350 | 25 | | | 90 | 100 | 20 | 55 | | 60 | 10 | 10 | 30 | 25 | 0 | 75 | 0 | 10 | 20 | 35 | 25 | 35 | |
|  | 0.0175 | 60 | | | 70 | 100 | 75 | 95 | | 80 | 35 | 30 | 10 | 25 | 0 | 60 | 25 | 90 | 50 | N | 70 | 50 | |
|  | 0.0175 | 25 | | | 60 | N | 20 | 65 | | 0 | 0 | 35 | 15 | 40 | 0 | 156 | 0 | 25 | 40 | 0 | N | 70 | |
| 153 | 5.6050 | 40 | | | 70 | 95 | 90 | 95 | | 90 | 25 | 20 | 65 | 65 | 30 | 5 | 20 | 25 | 85 | 75 | 35 | 80 | |

TABLE D-continued

Herbicide Secondary Post, spectrums 26, 88, 91, and 93

| Ex. No. | Rate kg/ha | Sobe | Cotn | Rape | Cobu | Wbw | Mogl | Hese | Jwe | Vele | Whez | Rice | Grso | Cotn | Dobr | Prmi | Bygr | Lacg | Grft | Sube | Colq | Pesw | Cocw |
|---|---|---|---|---|---|---|---|---|---|---|---|---|---|---|---|---|---|---|---|---|---|---|---|
| | 1.1210 | 45 | | | 65 | 100 | 85 | 95 | | 100 | 15 | 15 | 25 | 55 | 50 | 35 | 50 | 70 | 95 | 70 | 95 | 95 | |
| | 0.5605 | 20 | | | 65 | 100 | 80 | 85 | | 85 | 10 | 10 | 25 | 25 | 25 | 0 | N | 75 | 95 | 50 | 90 | 80 | |
| | 0.2803 | 30 | | | 40 | 95 | 60 | 50 | | 70 | 0 | 20 | 0 | 35 | 20 | 20 | 0 | 40 | 75 | 35 | 95 | 50 | |
| | 0.1401 | 10 | | | 70 | 95 | 50 | 80 | | 90 | 0 | 5 | 10 | 10 | 0 | 5 | 25 | 15 | 60 | 20 | 80 | 30 | |
| | 0.0701 | 15 | | | 40 | 60 | 35 | 50 | | 55 | 15 | 0 | 0 | 20 | 0 | 0 | 0 | 15 | 75 | 40 | 70 | 0 | |
| | 0.0350 | 10 | | | 55 | 70 | 15 | 45 | | 50 | 0 | 0 | 15 | 30 | 30 | 0 | 0 | 25 | 10 | 100 | 75 | 0 | |
| 157 | 5.6050 | 99 | | | 100 | 100 | 100 | 100 | | 100 | 60 | 45 | 75 | 85 | 90 | 70 | 99 | 99 | 100 | 100 | 100 | 100 | |
| * | 1.1210 | 90 | | | 75 | 85 | 100 | 100 | | 100 | 30 | 30 | 45 | 60 | 20 | 50 | 85 | 90 | 100 | 100 | 95 | 100 | |
| * | 0.5605 | 75 | | | 80 | 100 | 100 | 95 | | 100 | 15 | 35 | 65 | 95 | 10 | 25 | 75 | 80 | 95 | 99 | 90 | 100 | |
| * | 0.2803 | 45 | | | 65 | 75 | 75 | 80 | | 100 | 15 | 20 | 60 | 60 | 10 | 20 | 65 | 50 | 70 | 95 | 90 | 99 | |
| * | 0.1401 | 50 | | | 70 | 65 | 65 | 80 | | 80 | 10 | 10 | 30 | 30 | 10 | 20 | 40 | 40 | 30 | 70 | 70 | 70 | |
| * | 0.0701 | 35 | | | 40 | 65 | 50 | 80 | | 90 | 15 | 5 | 20 | 60 | 10 | 25 | 40 | 40 | 10 | 65 | 90 | 75 | |
| * | 0.0350 | 30 | | | 30 | 50 | 50 | 40 | | 60 | 15 | 0 | 15 | 60 | 0 | 10 | 20 | 20 | 30 | 50 | 35 | 10 | |
| * | 0.0175 | 20 | | | 10 | 25 | 25 | 70 | | 25 | 0 | 10 | 25 | 20 | 0 | 10 | 10 | 0 | 0 | 50 | 70 | 25 | |
| * | 0.0087 | 0 | | | 0 | 0 | 0 | 0 | | 5 | 0 | N | 0 | 0 | 0 | 0 | 0 | 5 | 0 | 0 | N | 0 | |
| 199 | 5.6050 | 99 | 100 | 100 | 100 | 95 | 100 | 100 | 100 | 100 | 70 | 40 | 65 | 95 | 90 | 50 | 95 | 100 | 100 | 100 | 100 | 100 | 0 |
|  | 1.1210 | 95 | 100 | 90 | 95 | 100 | 100 | 100 | 100 | 80 | 50 | 25 | 35 | 60 | 40 | 20 | 50 | 70 | 99 | 100 | 100 | 100 | 0 |
|  | 0.5605 | 65 | 100 | 85 | 70 | 95 | 95 | 100 | 100 | 100 | 50 | 40 | 20 | 99 | 15 | 40 | 20 | 95 | 95 | 99 | 100 | 100 | 0 |
|  | 0.2803 | 95 | 99 | 55 | 25 | 98 | 50 | 95 | 100 | 90 | 50 | 25 | 35 | 80 | 20 | 50 | 10 | N | 80 | 95 | 100 | 99 | 0 |
|  | 0.1401 | 90 | 75 | 70 | 50 | 98 | 60 | 100 | 100 | 100 | 20 | 40 | 20 | 70 | 10 | 20 | 10 | 70 | 60 | 80 | 100 | 100 | 0 |
|  | 0.0701 | 70 | 80 | 20 | 50 | 65 | 55 | 80 | 95 | 35 | 20 | 20 | 20 | 40 | 5 | 20 | 25 | 100 | 30 | 30 | 0 | 0 | 0 |
|  | 0.0350 | 50 | 45 | 15 | 10 | N | 60 | N | 80 | 40 | N | N | 5 | 35 | 0 | 5 | 10 | 75 | 75 | 60 | N | 35 | 0 |
| 296 | 5.6050 | 35 | 25 | 35 | 50 | 40 | 60 | 100 | 100 | 100 | 10 | 0 | 5 | 35 | 5 | 20 | 10 | 10 | 100 | 100 | 100 | N | |
|  | 1.1210 | 20 | 20 | 25 | 100 | 99 | 100 | 100 | 100 | 100 | 60 | 25 | 25 | 95 | 70 | 20 | 0 | 75 | 100 | 75 | 100 | N | |
|  | 0.5605 | 95 | 100 | 99 | 100 | 100 | 95 | 100 | 95 | 100 | 50 | 30 | 70 | 70 | 30 | 75 | 95 | 100 | 100 | 100 | 100 | N | |
|  | 0.2803 | 95 | 100 | 99 | 99 | 98 | 100 | 100 | 80 | 100 | 20 | 30 | 60 | 30 | 40 | 40 | 80 | 98 | 100 | 99 | 100 | N | |
|  | 0.1401 | 90 | 99 | 60 | 98 | 98 | 100 | 100 | 95 | 90 | 5 | 20 | 20 | 50 | 10 | 20 | 80 | 98 | 98 | 95 | 100 | N | |
|  | 0.0701 | 70 | 95 | 40 | 75 | 65 | 100 | 100 | 85 | 75 | 10 | 20 | 20 | 40 | 10 | 10 | 20 | 50 | 70 | 65 | 99 | N | |
|  | 0.0351 | 50 | 85 | 35 | 70 | 75 | 100 | 100 | 95 | 45 | 5 | 5 | 10 | 25 | 0 | 0 | 20 | 50 | 70 | 65 | 99 | N | |
|  | 0.0175 | N | 50 | 25 | 50 | 35 | 95 | 75 | 85 | 45 | 0 | 5 | 10 | 25 | 0 | 0 | 20 | 60 | Z | 50 | 100 | N | |
|  | 0.0087 | 30 | 25 | 10 | 30 | 25 | 60 | 65 | 95 | 45 | 5 | 5 | 10 | 50 | 15 | 5 | 20 | 10 | 50 | 30 | 100 | N | |
| 299 | 5.6050 | 90 | 100 | 99 | 100 | 100 | 100 | 100 | 100 | 100 | 85 | 75 | 95 | 99 | 65 | 70 | 100 | 100 | 100 | 100 | 100 | 100 | |
|  | 1.1210 | 75 | 100 | 99 | 85 | 85 | 100 | 100 | 100 | 100 | 60 | 65 | 80 | 70 | 10 | 75 | 95 | 85 | 95 | 85 | 100 | 99 | |
|  | 0.5605 | 80 | 100 | 60 | 95 | 95 | 100 | 100 | 80 | 95 | 40 | 50 | 65 | 80 | 20 | 20 | 75 | 70 | 75 | 65 | 100 | 70 | |
|  | 0.2803 | 35 | 35 | 40 | 70 | 70 | 100 | 100 | 100 | 95 | 20 | 25 | 60 | 40 | 10 | 10 | 50 | 75 | 70 | 50 | 90 | 75 | |
|  | 0.1401 | 40 | 40 | 35 | 95 | 75 | 100 | 100 | 95 | 80 | 15 | 25 | 55 | 45 | 0 | 15 | 40 | 60 | 70 | 75 | 90 | 10 | |
|  | 0.0701 | 20 | 20 | 25 | 70 | 75 | 95 | 100 | 85 | 75 | 20 | 25 | 60 | 45 | 10 | 5 | 40 | 55 | 40 | 30 | 65 | 25 | |
|  | 0.0351 | 20 | 45 | 15 | 60 | 55 | 55 | 80 | 95 | 45 | 15 | 40 | 55 | 5 | 0 | 15 | 20 | 25 | 50 | 60 | 35 | N | |
|  | 0.0175 | 15 | 25 | 10 | 65 | 35 | 80 | 30 | 95 | 50 | 10 | 10 | 15 | 10 | 0 | 5 | 10 | 5 | 30 | 40 | 70 | Z | |
| 305+ | 5.6050 | 95 | 100 | 95 | 100 | 80 | 100 | 70 | 100 | 60 | 45 | 30 | 30 | 80 | 50 | 0 | 50 | 70 | 25 | Z | 100 | Z | |
| + | 1.1210 | 30 | 95 | 75 | 100 | 80 | 100 | 100 | 100 | 99 | 20 | 10 | 25 | 50 | 10 | 5 | 25 | 60 | 70 | 20 | 30 | N | |

TABLE D-continued

Herbicide Secondary Post, spectrums 26, 88, 91, and 93

| Ex. No. | Rate kg/ha | Sob e | Cot n | Rap e | Cbu | Wib w | Mog l | Hes e | Jiw e | Vel e | Whe n | Ric e | Grs o | Cor n | Dbr r | Prm i | Byg r | Lac g | Grft | Sub e | Colq | Psw | Cow |
|---|---|---|---|---|---|---|---|---|---|---|---|---|---|---|---|---|---|---|---|---|---|---|---|
| +  | 0.5605 | 45 | 100 | 75 | 100 | 75 | 100 | 100 | 100 | 100 | 20 | 10 | 20 | 20 | 10 | 10 | 25 | 25 | 40 | | | | |
| +  | 0.2803 | 20 | 90 | 60 | 100 | 50 | 100 | 100 | 75 | 95 | 10 | 5 | 30 | 50 | 10 | 5 | 5 | 60 | 35 | | | | |
| +  | 0.1401 | 10 | 75 | 60 | 90 | 60 | 100 | 60 | 95 | 75 | 10 | 0 | 10 | 40 | 10 | 5 | 10 | 20 | 45 | | | | |
| +  | 0.0701 | 15 | 70 | 35 | 99 | 10 | 95 | 75 | 95 | 75 | 5 | 0 | 15 | 20 | 0 | 0 | 5 | 10 | 10 | | | | |
| +  | 0.0351 | 10 | 45 | 20 | 75 | N | 20 | 75 | 100 | 70 | 5 | 15 | 0 | 20 | 0 | 0 | 0 | 10 | 10 | | | | |
| 314 | 5.6050 | 60 | 100 | 95 | 100 | 75 | 100 | 100 | 100 | 100 | 50 | 20 | 30 | 95 | 10 | 40 | 95 | 40 | 75 | | | | |
|  | 1.1210 | 65 | 99 | 90 | 75 | 50 | 100 | 100 | 80 | 95 | 20 | 15 | 10 | 60 | 0 | 25 | 65 | 20 | 60 | | | | |
|  | 0.5605 | 30 | 100 | 85 | 100 | 30 | 100 | 100 | 90 | 100 | 15 | 5 | 20 | 40 | 0 | 20 | 40 | 0 | 10 | | | | |
|  | 0.2803 | 50 | 85 | 70 | 70 | 20 | 100 | 100 | 80 | 75 | 10 | 10 | 10 | 60 | 0 | 25 | 20 | 0 | 60 | | | | |
|  | 0.1401 | 50 | 95 | 65 | 60 | 10 | 90 | 100 | 95 | 95 | 15 | 5 | 5 | 35 | 0 | 15 | 0 | 0 | 10 | | | | |
|  | 0.0701 | 10 | 90 | 50 | 60 | 25 | 80 | 75 | 80 | 55 | 10 | 5 | 10 | 15 | 0 | 5 | 0 | 0 | 25 | | | | |
|  | 0.0351 | 20 | 10 | 10 | 60 | 0 | 50 | 70 | 75 | 45 | 10 | 0 | 5 | 10 | 0 | 5 | 0 | 0 | 0 | | | | |
|  | 0.0175 | 15 | 15 | 10 | 45 | 0 | 65 | 95 | 80 | 25 | 0 | 0 | 0 | 0 | 0 | 0 | 0 | 0 | 0 | | | | |
|  | 0.0087 | 5 | 5 | 10 | 5 | 0 | 25 | 70 | 75 | 25 | 0 | 0 | 5 | 15 | 0 | 0 | 0 | 0 | 0 | | | | |
| 327 ) | 5.6050 | 75 | 100 | 100 | 100 | 100 | 100 | 100 | 100 | 100 | 70 | 75 | 75 | 100 | 80 | 75 | 100 | 100 | 100 | | | | |
| ) | 1.1210 | 90 | 100 | 100 | 100 | 100 | 100 | 100 | 100 | 100 | 100 | 85 | 85 | 80 | 70 | 70 | 100 | 100 | 100 | | | | |
| ) | 0.2803 | 35 | 100 | 100 | 100 | 100 | 100 | 100 | 100 | 100 | 75 | 65 | 60 | 50 | 55 | 35 | 100 | 100 | 100 | | | | |
| ) | 0.2803 | 90 | 100 | 100 | 95 | 100 | 100 | 100 | 100 | 100 | 65 | 40 | 60 | 70 | 60 | 50 | 90 | 90 | 90 | | | | |
| ) | 0.0701 | 25 | 100 | 95 | 100 | 80 | 100 | 95 | 100 | 100 | 35 | 10 | 40 | 75 | 20 | 15 | 80 | 100 | 80 | | | | |
|  | 0.0701 | 50 | 100 | 100 | 100 | 100 | 100 | 75 | 100 | 100 | 30 | 25 | 20 | 45 | 20 | 50 | 80 | 45 | 80 | | | | |
|  | 0.0175 | 20 | 100 | 100 | 80 | 95 | 100 | 98 | 100 | 100 | 10 | N | 20 | 65 | 5 | 15 | 40 | 50 | 60 | | | | |
|  | 0.0175 | 35 | 65 | 70 | 45 | 85 | 70 | 35 | 95 | 95 | 5 | 5 | 5 | 5 | 10 | 20 | 70 | 65 | 65 | | | | |
|  | 0.0087 | 10 | 99 | 25 | 65 | 60 | 80 | 20 | 95 | 75 | 0 | 15 | 10 | 40 | 5 | 0 | 0 | 40 | 40 | | | | |
| 329 ) | 0.0044 | 15 | 35 | 5 | 25 | 45 | 25 | 85 | 80 | 50 | 5 | 0 | 0 | 25 | 40 | 35 | 50 | 25 | 55 | | | | |
| ) | 5.6050 | 0 | 95 | 85 | 40 | 30 | 30 | 75 | 90 | 75 | 25 | 35 | 25 | 20 | 25 | 35 | 10 | 50 | 25 | | | | |
|  | 1.1210 | 50 | 95 | 80 | 50 | 60 | 35 | 20 | 95 | 99 | 20 | 40 | 10 | 30 | 25 | 35 | 0 | 95 | 99 | | | | |
|  | 0.2803 | 50 | 60 | 85 | 95 | 75 | 50 | 85 | 99 | 100 | 5 | 25 | 0 | 35 | 0 | 25 | 0 | 60 | 85 | | | | |
|  | 0.0701 | 25 | 100 | 70 | 60 | 40 | 30 | 75 | 100 | 60 | 25 | 10 | 35 | 60 | 10 | 35 | 10 | 40 | 80 | | | | |
| 331 | 5.6050 | 99 | 100 | 100 | 100 | 65 | 95 | 95 | 100 | 100 | 45 | 15 | 60 | 100 | 30 | 35 | 0 | 75 | 100 | 95 | 100 | N | |
|  | 0.2803 | 95 | 100 | 80 | 99 | 100 | 99 | 100 | 99 | 75 | 10 | 45 | 0 | 25 | 100 | 55 | 60 | 35 | 95 | 95 | 100 | 100 | |
|  | 0.1401 | 65 | 60 | 30 | 60 | 100 | 100 | 80 | 100 | 95 | 55 | 0 | 50 | 60 | 55 | 10 | 35 | 50 | 95 | 95 | 100 | 95 | |
|  | 0.1401 | 60 | 100 | 80 | 70 | 100 | 100 | 85 | 100 | 100 | 10 | 75 | 25 | 95 | 10 | 0 | 45 | 90 | 95 | | | | |
|  | 0.0701 | 75 | 100 | 30 | 100 | 100 | 80 | 95 | 100 | 95 | 55 | 85 | 80 | 90 | 5 | 45 | 55 | 55 | 90 | | | | |
|  | 0.0701 | 95 | 100 | | 65 | 80 | 100 | 80 | 100 | | 30 | 20 | 50 | 65 | 5 | 95 | 85 | 55 | 80 | 95 | 95 | 90 | |
|  | 0.0701 | 75 | 100 | | 100 | 100 | 90 | 90 | 100 | 90 | 25 | 85 | 25 | 85 | 0 | 15 | 90 | 80 | 75 | 65 | 90 | 85 | |
|  | 0.0701 | 40 | 80 | | 80 | 100 | 80 | 100 | | 85 | 5 | 25 | 40 | 45 | 10 | 55 | 65 | 85 | 80 | 100 | 100 | 99 | |
|  | 0.0350 | 45 | 100 | | 100 | 70 | 100 | 70 | | 70 | 10 | 60 | 25 | 55 | 5 | 20 | 40 | 80 | 75 | 90 | 100 | 85 | |
|  | 0.0350 | 35 | 99 | | 60 | 70 | 80 | 80 | | 80 | 10 | 65 | 40 | 75 | 0 | 30 | 60 | 90 | 60 | 70 | N | 75 | |
|  | 0.0350 | 55 | 50 | | 30 | N | 70 | 75 | | 65 | 20 | 70 | 60 | 70 | 10 | 5 | 40 | 95 | 55 | 80 | 100 | 95 | |
|  | 0.0175 | 35 | 75 | 20 | 75 | 100 | 80 | 75 | | 80 | 15 | 10 | 15 | 80 | 5 | 10 | 75 | 50 | 60 | 70 | 95 | 85 | |
|  | 0.0175 | 90 | 100 | | 55 | 80 | 70 | 85 | | 50 | 5 | 25 | 35 | 65 | 0 | 40 | 70 | 50 | 55 | 70 | 85 | 75 | |
|  | 0.0175 | 20 | 100 | | 95 | 90 | 60 | 100 | 99 | 70 | 35 | 50 | 30 | 75 | 0 | 10 | 55 | 55 | 60 | | | | |
|  | 1.1210 | 85 | 80 | 95 | 30 | 100 | 75 | 85 | 100 | 95 | 40 | 15 | 10 | 80 | 40 | 40 | 60 | 60 | 80 | 35 | 95 | 60 | |
|  | 0.2803 | 75 | 99 | 70 | 95 | 99 | 75 | 75 | 99 | 95 | 10 | 5 | 35 | 65 | 20 | 40 | 50 | 40 | 100 | | | | |
|  | 0.0701 | 70 | 99 | 80 | 75 | 80 | 75 | 75 | 95 | 95 | 40 | 20 | 10 | 80 | 30 | 30 | 60 | 80 | 100 | | | | |
|  | 0.0175 | 60 | 50 | 50 | 60 | 50 | 20 | 65 | 70 | 25 | 10 | 20 | 10 | 0 | 0 | 25 | 0 | 20 | 80 | | | | |

TABLE D-continued

Herbicide Secondary Post, spectrums 26, 88, 91, and 93

| Ex. No. | Rate kg/ha | Sobe | Cotn | Rape | Cob u | Wbw | Mogl | Hese | Jiwe | Vel | Whez | Rice | Grso | Corn | Dobr | Prmi | Bygr | Lacg | Grft | Subc | Colq | Pesw | Cocw |
|---|---|---|---|---|---|---|---|---|---|---|---|---|---|---|---|---|---|---|---|---|---|---|---|
| 332 | 0.0087 | 35 | 30 | 25 | 20 | 20 | 25 | 70 | 50 | 65 | 0 | 5 | 0 | 35 | 0 | 0 | 0 | 20 | 40 | | | | |
|  | 5.6050 | 95 | 100 | 100 | 100 | 100 | 100 | 100 | 100 | 100 | 60 | 50 | 80 | 90 | 30 | 40 | 99 | 75 | 100 | | | | |
|  | 1.1210 | 75 | 100 | 100 | 100 | 100 | 100 | 100 | 100 | 100 | 20 | 75 | 70 | 65 | 25 | 70 | 70 | 70 | 90 | | | | |
|  | 0.2803 | 65 | 100 | 99 | 50 | N | 100 | 100 | 100 | 100 | 10 | 30 | 50 | 60 | 30 | 50 | 65 | 50 | 70 | | | | |
|  | 0.0701 | 65 | 85 | 75 | 65 | 85 | 70 | 80 | 95 | 95 | 0 | 60 | 40 | 40 | 0 | 30 | 40 | 40 | 75 | | | | |
|  | 0.0175 | 50 | 100 | 40 | 90 | 100 | 100 | 99 | 100 | 30 | 70 | 20 | 10 | 65 | 70 | 20 | 0 | 30 | 60 | | | | |
| 402 | 5.6050 | 95 | 100 | 45 | 70 | 99 | 100 | 99 | 100 | 100 | 40 | 45 | 75 | 65 | 60 | 75 | 99 | 99 | 100 | | | | |
|  | 1.1210 | 90 | 95 | 35 | 90 | 95 | 95 | 95 | 99 | 95 | 35 | 20 | 75 | 50 | 35 | 35 | 99 | 99 | 100 | | | | |
|  | 0.5605 | 65 | 95 | 10 | 70 | 95 | 90 | 85 | 95 | 95 | 10 | 15 | 55 | 60 | 50 | 10 | 85 | 80 | 100 | | | | |
|  | 0.2803 | 55 | 90 | 20 | 75 | 95 | 85 | 75 | 95 | 95 | 20 | 10 | 30 | 85 | 25 | 30 | 65 | 95 | 100 | | | | |
|  | 0.1401 | 65 | 95 | 20 | 70 | 95 | 90 | 75 | 80 | 95 | 15 | 10 | 35 | 25 | 0 | 25 | 75 | 60 | 85 | | | | |
|  | 0.0701 | 40 | 100 | 20 | 70 | 100 | 75 | 75 | 100 | 100 | 90 | 10 | 30 | 40 | 80 | 15 | 25 | 80 | 80 | | | | |
| 446 | 5.6050 | 99 | 100 | 100 | 100 | 100 | 100 | 100 | 100 | 100 | 45 | 85 | 95 | 95 | 75 | 100 | 100 | 99 | 100 | | | | |
|  | 1.1210 | 99 | 100 | 99 | 70 | 100 | 90 | 100 | 100 | 100 | 20 | 95 | 98 | 40 | 100 | 70 | 100 | 75 | 100 | | | | |
|  | 0.2803 | 100 | 100 | 80 | 60 | 100 | 100 | 90 | 100 | 100 | 75 | 30 | 75 | 75 | 35 | 25 | 100 | 100 | 100 | | | | |
|  | 0.0701 | 99 | 100 | 95 | 95 | 100 | 100 | 95 | 100 | 100 | 25 | 65 | 90 | 100 | 75 | 60 | 99 | 75 | 95 | | | | |
|  | 0.2803 | 100 | 100 | 70 | 95 | 100 | 60 | 99 | 100 | 80 | 10 | 45 | 75 | 80 | 60 | 65 | 100 | 100 | 100 | | | | |
|  | 0.0701 | 95 | 100 | 70 | 40 | 90 | 100 | 100 | 100 | 100 | 10 | 10 | 10 | 50 | 20 | 20 | 65 | 90 | 100 | | | | |
|  | 0.0175 | 50 | 100 | 55 | Z | 60 | 60 | 75 | 100 | 95 | 15 | 20 | 55 | 10 | 20 | 5 | 85 | 20 | 85 | | | | |
|  | 0.0701 | 90 | 100 | 10 | 10 | 100 | 100 | 100 | 100 | 100 | 10 | 10 | 10 | 10 | 10 | 30 | 10 | 20 | 10 | | | | |
|  | 0.0175 | 30 | 80 | 25 | 60 | 75 | 60 | 65 | 95 | 80 | 15 | 20 | 55 | 60 | 20 | 10 | 60 | 90 | 70 | | | | |
| 464 | 5.6050 | 70 | 100 | 100 | 100 | 100 | 100 | 100 | 100 | 100 | 20 | 10 | 99 | 100 | 99 | 100 | 100 | 99 | 100 | | | | |
|  | 1.1210 | 95 | 100 | 100 | 70 | 99 | 100 | 100 | 100 | 100 | 75 | 99 | 80 | 85 | 80 | 75 | 95 | 80 | 100 | | | | |
|  | 0.2803 | 90 | 95 | 99 | Z | 100 | 95 | 99 | 100 | 100 | 30 | 75 | 70 | 95 | 10 | 60 | 80 | 40 | 100 | | | | |
|  | 0.0701 | 95 | 95 | 20 | Z | 99 | 80 | 75 | 60 | 100 | 20 | 50 | 40 | 60 | 10 | 25 | 60 | 75 | 85 | | | | |
|  | 0.0175 | 60 | 60 | 0 | 40 | 75 | 30 | 70 | 95 | 95 | 10 | 50 | 30 | 30 | 0 | 10 | 30 | 30 | 65 | | | | |
| 586 | 5.6050 | 40 | 85 | 100 | Z | 85 | 30 | 100 | 60 | 95 | 0 | 30 | 40 | 70 | 0 | 50 | 98 | 100 | 40 | | | | |
|  | 1.1210 | 75 | 100 | 99 | 100 | 100 | 100 | 100 | 95 | 100 | 20 | 35 | 65 | 100 | 35 | 10 | 75 | 65 | 99 | | | | |
|  | 0.2803 | 70 | 99 | 98 | Z | 99 | 100 | 100 | 100 | 100 | 10 | 75 | 40 | 20 | 30 | 20 | 75 | 99 | 95 | | | | |
|  | 0.0701 | 75 | 80 | 80 | 100 | 75 | 98 | 100 | 60 | 100 | 15 | 35 | 60 | 100 | 40 | 75 | 75 | 100 | 75 | | | | |
|  | 0.0175 | 50 | 99 | 50 | Z | 85 | 80 | 75 | 99 | 95 | 10 | 5 | 40 | 98 | 30 | 40 | 40 | 75 | 75 | | | | |
|  | 0.0044 | 65 | 80 | 0 | 100 | 30 | 20 | 75 | 60 | 50 | 10 | N | 60 | 99 | 20 | 20 | 20 | 65 | 65 | | | | |
| 639 | 5.6050 | 30 | 50 | 85 | 25 | 100 | 75 | 70 | 60 | 10 | 5 | 0 | 25 | 40 | 10 | 10 | 10 | 40 | 40 | | | | |
|  | 1.1210 | 60 | 70 | 95 | 30 | 99 | 60 | 75 | 100 | 65 | 0 | 10 | 20 | 20 | 20 | 5 | 0 | 65 | 35 | | | | |
|  | 0.2803 | 50 | 65 | 99 | 30 | 100 | 95 | 75 | 75 | 40 | 5 | 5 | 40 | 10 | 0 | 10 | 0 | 65 | 50 | | | | |
|  | 0.0701 | 80 | 99 | 95 | 50 | 100 | 65 | 75 | 95 | 80 | 0 | 0 | 20 | 210 | 0 | 20 | 0 | 80 | 50 | | | | |
|  | 0.0175 | 65 | 80 | 80 | 30 | 100 | 65 | 70 | 75 | 50 | 5 | 10 | 30 | 20 | 10 | 60 | 0 | 25 | 0 | | | | |
| 642 | 5.6050 | 50 | 60 | 40 | 0 | 75 | 40 | 40 | 100 | 10 | 65 | 0 | 20 | 10 | 10 | 10 | 0 | 0 | 100 | | | | |
|  | 1.1210 | 99 | 99 | N | 20 | 100 | 50 | Z | 95 | 100 | 20 | 10 | 40 | 100 | 10 | 20 | 0 | 100 | 95 | | | | |
|  | 0.2803 | 99 | 99 | 75 | 100 | 100 | 99 | 100 | 100 | 100 | 0 | 5 | 85 | 90 | 70 | 60 | 99 | 75 | 100 | | | | |
|  | 0.0701 | 75 | 99 | 75 | N | 95 | 35 | 95 | 100 | 80 | 70 | 0 | 95 | 65 | 60 | 100 | 35 | 100 | 65 | | | | |
| 644 | 5.6050 | 40 | 99 | 5 | Z | 95 | 35 | 95 | 100 | 99 | 15 | 65 | 40 | 25 | 35 | 85 | 30 | 65 | 75 | | | | |
|  | 1.1210 | 25 | 90 | 0 | Z | 80 | 40 | 75 | 100 | 35 | 5 | 20 | 65 | 65 | 10 | 65 | 0 | 75 | 60 | | | | |

TABLE D-continued

Herbicide Secondary Post, spectrums 26, 88, 91, and 93

| Ex. No. | Rate kg/ha | Sobe | Cotn | Rape | Cbu | Wibw | Mogl | Hese | Jiwe | Vele | Whez | Rice | Grso | Cotn | Dobr | Prmi | Bygr | Lacg | Grft | Sube | Colq | Pesw | Cocw |
|---|---|---|---|---|---|---|---|---|---|---|---|---|---|---|---|---|---|---|---|---|---|---|---|
| 701 | 0.0044 | 30 | 60 | 0 | 50 | 75 | 70 | 65 | 85 | 10 | 5 | 5 | 50 | 65 | 0 | 50 | 50 | 80 | 65 | | | | |
| >) | 5.6050 | 70 | 100 | 100 | 100 | 98 | 95 | 100 | 100 | 98 | 20 | 60 | 40 | 100 | 25 | 10 | 40 | 20 | 60 | | | | |
| >) | 1.1210 | 75 | 100 | 95 | 100 | 100 | 80 | 100 | 100 | 100 | 10 | 40 | 40 | 99 | 10 | 0 | 35 | 0 | 40 | | | | |
| >) | 0.2803 | 40 | 95 | 75 | 90 | 60 | 65 | 90 | 100 | 60 | 0 | 0 | 35 | 60 | 0 | 0 | 20 | 0 | 30 | | | | |
| >) | 0.0701 | 35 | 75 | 20 | 35 | N | 35 | N | 90 | 75 | 0 | 0 | 20 | 65 | 0 | 0 | 0 | 0 | 0 | | | | |
| >) | 0.0175 | 5 | 65 | 0 | 60 | 25 | 20 | 99 | 65 | 60 | 0 | N | 5 | 25 | 0 | 0 | 0 | 0 | 0 | | | | |
| 705 | 5.6050 | 70 | 100 | 100 | 100 | 95 | 100 | 100 | 100 | 100 | 10 | 95 | 30 | 70 | 30 | 35 | 60 | 95 | 90 | | | | |
| >) | 1.1210 | 60 | 100 | 100 | 100 | 80 | 75 | 100 | 100 | 95 | 5 | 20 | 30 | 99 | 10 | 10 | 35 | 75 | 80 | | | | |
| >) | 0.2803 | 35 | 100 | 90 | 80 | 95 | 95 | 100 | 100 | 40 | 0 | 40 | 25 | 65 | 10 | 10 | 20 | 75 | 65 | | | | |
| >) | 0.0701 | 20 | 90 | 50 | 40 | 85 | 75 | N | 100 | 35 | 0 | 0 | 25 | 75 | 0 | 0 | 20 | 20 | 35 | | | | |
| >) | 0.0175 | 20 | 90 | 50 | 20 | 40 | 75 | N | 100 | 35 | 0 | 0 | 25 | 30 | 0 | 0 | 0 | 20 | 40 | | | | |
| >) | 5.6050 | 70 | 95 | 75 | 35 | 100 | 50 | 90 | 100 | 50 | 10 | 10 | 35 | 95 | 10 | 25 | 0 | 20 | 50 | | | | |
| 786 | 1.1210 | 75 | 99 | 60 | 40 | 100 | 100 | 100 | 100 | 95 | 5 | 20 | 20 | 60 | 0 | 50 | 0 | 10 | 25 | | | | |
| >) | 0.2803 | 60 | 75 | 20 | 25 | 100 | 35 | 95 | 100 | 75 | 0 | 10 | 25 | 60 | 10 | 25 | 0 | 25 | 65 | | | | |
| >) | 0.0701 | 35 | 85 | 0 | 10 | 75 | 25 | N | 80 | 50 | 5 | 0 | 25 | 25 | 5 | 10 | 0 | 10 | 10 | | | | |
| >) | 0.0175 | 5 | 40 | 0 | 0 | 70 | 0 | N | 75 | 65 | 0 | 0 | 5 | 10 | 0 | N | 0 | 20 | 0 | | | | |

*POOR PESW EMERGENCE NO SMARTWEED EMERGENCE, VERY POOR WHEAT STANDS. + Poor soybean stands throughout the test.) Coded comments recorded only at the highest rate observed. > Coded comments recorded only at the highest rate observed; dampingoff l Damping off Hese and Vele.

As can be seen from the data above, the compounds appear to be safe on certain crops and can thus be used for selective control of weeds in these crops.

The herbicidal compositions of this invention, including concentrates suitable for transportation which require dilution prior to application, and dilute composition suitable for application generally in accordance with concentrations set forth below. Compositions may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid ester of hexitol anhydrides (e.g., sorbitan). Preferred dispersants are methyl, cellulose, polyvinyl alcohol, sodium lignin sulfonates, polymeric alkyl naphthalene sulfonates, sodium naphthalene sulfonate, polymethylene bisnaphthalene sulfonate and polyethyleneoxide-polypropyleneoxide copolymers.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably from 5-20 parts) of active ingredient, from about 0.25 to 25 parts (preferably 1-15 parts) of wetting agent, from about 0.25 to 25 parts (preferably 1.0-15 parts) of dispersant and from 5 to about 95 parts (preferably 5-50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0 1 to 60% by weight of the active ingredient on a suitable extender; these dusts may be diluted for application at concentrations within the range of from about 0.1-10% by weight.

Aqueous suspensions or emulsions may be prepared by stirring a nonaqueous solution of a water-insoluble active ingredient and an emulsification agent with water until uniform and then homogenizing to give stable emulsion of very finely-divided particles. The resulting concentrated aqueous suspension is characterized by its extremely small particle size, so that when diluted and sprayed, coverage is very uniform. Suitable concentrations of these formulations contain from about 0.1-60% preferably 5-50% by weight of active ingredient, the upper limit being determined by the solubility limit of active ingredient in the solvent.

Concentrates which are suitable for transportation are usually solutions of active ingredient in water-immiscible or partially water-immiscible solvents together with a surface active agent. Suitable solvents for the active ingredient of this invention include dimethylformamide, dimethylsulfoxide, N-methylpyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5-60 parts) active ingredient, about 0.25 to 50 parts (preferably 1-25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate extender, a surface active agent such as those listed hereinbefore can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compounds of the present invention appear to show the greatest activity when applied as a postemergence herbicide. Further, when applied as a preplant incorporated, the activity appears to decrease with increasing organic matter in the soil.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, carbamates, acetamides, acetanilides, dinitroanilines uracils, acetic acid or phenol derivatives, thiolcarbamates, triazoles, benzoic acids, nitriles, biphenyl ethers and the like such as:

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-α:2',1'-c)-pyrazidiinium salt
5-Bromo-3-isopropyl-6-methyluracil 1,1'-Dimethyl-4,4'-bipyridinium
2-(4-isopropyl-4-methyl-5-oxo-2-imidazolin-2-yl)-3-quinolinecarboxylic acid Isopropylamine salt of 2-(4-isopropyl-4-methyl-5-oxo-2-imidazolin-2-yl)nicotinic acid Methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate

Ureas

N-(4-chlorophenoxy) phenyl-N,N-dimethylurea
N,N-dimethyl-N'-(3-chloro-4-methylphenyl) urea
3-(3,4-dichlorophenyl)-1,1-dimethylurea
1,3-Dimethyl-3-(2-benzothiazolyl) urea
3-(p-Chlorophenyl)-1,1-dimethylurea
1-Butyl-3-(3,4-dichlorophenyl)-1-methylurea
2-Chloro-N[(4-methoxy-6-methyl-1,3,5-triazin-2-yl) aminocarbonyl]-benzenesulfonamide
Methyl 2-(((((4,6-dimethyl-2-pyrimidinyl)amino)carbonyl)amino)sulfonyl) benzoate
Ethyl 2-[methyl 2-(((((4,6-dimethyl-2-pyrimidinyl)amino)carbonyl)amino)sulfonyl)]benzoate
Methyl-2((4,6-dimethoxy pyrimidin-2-yl)aminocarbonyl)amino sulfonyl methyl) benzoate
Methyl 2-(((((4-methoxy-6-methyl-1,3,5-triazin-2yl)amino)carbonyl)amino)sulfonyl) benzoate classic

Carbamates/Thiolcarbamates

2-Chloroallyl diethyldithiocarbamate
S-(4-chlorobenzyl)N,N-diethylthiolcarbamate
Isopropyl N-(3-chlorophenyl) carbamate
S-2,3-dichloroallyl N,N-diisopropylthiolcarbamate
S-ethyl-N,N-dipropylthiolcarbamate
S-propyl N,N-dipropylthiolcarbamate
S-2,3,3-trichloroallyl N,N-diisopropylthiolcarbamate
S-ethyl-N,N-diisobutylthiolcarbamate

Acetamides/Acetanilides/Anilines/Amides

2-Chloro-N,N-diallylacetamide
N,N-dimethyl-2,2-diphenylacetamide
N-(2,4-dimethyl-5-[[(trifluoromethyl)sulfonyl]amino]-phenyl]acetamide N-Isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide
α,α,α-Trifluoro-2,6-dinitro-N,N-dipropyl-p-toluidine
N-(1,1-dimethylpropynyl)-3,5-dichlorobenzamide

Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dini tro-o-sec-butylphenol
Butyl 2-[4-[(5-(trifluoromethyl)-2-pyridinyl)oxy]-phenoxy]-propanoate glyphosate

Ethers 2,4-Dichlorophenyl-4-nitrophenyl ether
2-Chloro-α,α,α-trifluoro-p-tolyl-3-ethoxy-4-nitrodiphenyl ether
5-(2-chloro-4-trifluoromethylphenoxy)-N-methylsulfonyl 2-nitrobenzamide
1'-(Carboethoxy) ethyl 5-[2-chloro-4-(trifluoromethyl)-phenoxy]-2-nitrobenzoate Acifluorfen
Bifenox
Chloroxuron
Diclofop-methyl
Fluazifop-butyl

Miscellaneous 2,6-Dichlorobenzonitrile
Monosodium acid methanearsonate
Disodium methanearsonate
2-(2-chlorophenyl)methyl-4,4-dimethyl-3-isoxazolidinone
7-oxabicyclo (2.2.1) heptane, 1-methyl-4-(1-methyl ethyl)-2-(2-methylphenylmethoxy)-,exo- Sethoxydin
imazethapyr
imazaquin
imazapyr Fertilizers useful in combination with the active ingredients include, for example ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

I. Emulsifiable Concentrates

| 1. Emulsifiable Concentrates | | |
|---|---|---|
| | | Weight Percent |
| A. | Compound of Example No. 5 | 11.0 |
| | Free acid of complex organic phosphate or aromatic or aliphatic hydrophobe base (e.g., GAFAC RE-610, registered trademark of GAF Corp.) | 5.59 |
| | Polyoxyethylene/polyoxypropylene block copolymer with butanol (e.g., Tergitol XH, registered trademark of Union Carbide Corp.) | 1.11 |
| | Phenol | 5.34 |
| | Monochlorobenzene | 76.96 |
| | | 100.00 |
| B. | Compound of Example No. 6 | 25.00 |
| | Free acid of complex organic phosphate of aromatic or aliphatic hydrophobe base (e.g., GAFAC RE-610) | 5.00 |
| | Polyoxyethylene/polyoxypropylene block copolymer with butanol (e.g., Tergitol XH) | 1.60 |
| | Phenol | 4.75 |
| | Monochlorobenzene | 63.65 |
| | | 100.00 |

II. Flowables

| II. Flowables | | |
|---|---|---|
| | | Weight Percent |
| A. | Compound of Example No. 5 | 25.00 |
| | Methyl cellulose | 0.3 |
| | Silica Aerogel | 1.5 |
| | Sodium lignosulfonate | 3.5 |
| | Sodium N-methyl-N-oleyl taurate | 2.0 |
| | Water | 67.7 |
| | | 100.00 |
| B. | Compound of Example No. 5 | 45.0 |
| | Methyl cellulose | .3 |
| | Silica aerogel | 1.5 |
| | Sodium lignosulfonate | 3.5 |

-continued

| II. Flowables | |
|---|---|
| | Weight Percent |
| Sodium N-methyl-N-oleyl taurate | 2.0 |
| Water | 47.7 |
| | 100.00 |

III. Wettable Powders

| III. Wettable Powders | |
|---|---|
| | Weight Percent |
| A. Compound of Example No. 5 | 25.0 |
| Sodium lignosulfonate | 3.0 |
| Sodium N-methyl-N-oleyl-taurate | 1.0 |
| Amorphous silica (synthetic) | 71.0 |
| | 100.00 |
| B. Compound of Example 5 | 80.00 |
| Sodium dioctyl sulfosuccinate | 1.25 |
| Calcium lignosulfonate | 2.75 |
| Amorphous silica (synthetic) | 16.00 |
| | 100.00 |
| C. Compound of Example No. 5 | 10.0 |
| Sodium lignosulfonate | 3.0 |
| Sodium N-methyl-N-oleyl-taurate | 1.0 |
| Kaolinite clay | 86.0 |
| | 100.00 |

IV. Dusts

| IV. Dusts | |
|---|---|
| | Weight Percent |
| A. Compound of Example No. 5 | 2.0 |
| Attapulgite | 98.0 |
| | 100.00 |
| B. Compound of Example No. 5 | 30.0 |
| Ethylene glycol | 1.0 |
| Bentonite | 69.0 |
| | 100.00 |

V. Granules

| V. Granules | |
|---|---|
| | Weight Percent |
| A. Compound of Example No. 5 | 15.0 |
| Granular attapulgite (20/40 mesh) | 85.0 |
| | 100.00 |
| B. Compound of Example No. 6 | 30.0 |
| Diatomaceous earth (20/40) | 70.0 |
| | 100.00 |
| C. Compound of Example No. 11 | 1.0 |
| Ethylene glycol | 5.0 |
| Methylene blue | 0.1 |
| Pyrophyllite | 93.9 |
| | 100.00 |

When operating in accordance with the present invention, effective amounts of the compounds of this invention are applied to the soil containing the seeds, or vegetative propagules or may be incorporated into the soil media in any convenient fashion. The application of liquid and particulate solid compositions to the soil can be carried out by conventional methods, e.g., power-dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective preemergence application or to the soil, a dosage of from about 0.02 to about 11.2 kg/ha, preferably from about 0.1 to about 5.60 kg/ha, is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in *Webster's New International Dictionary*, Second Edition, Unabridged (1961). Thus, the term refers to any substance or medium in which vegetation may take root and grow, and includes not only earth but also compost, manure, muck, humus, loam, silt, mire, clay, sand, and the like, adapted to support plant growth.

Although the invention is described with respect to specific modifications, the details thereof are not to be construed as limitations, for it will be apparent that various embodiments, changes and modifications may be resorted to without departing from the spirit and scope thereof and it is understood that such equivalent embodiments are intended to be included within the scope of this invention.

We claim:

1. A 3-phenoxypyrazole or agronomically acceptable salt thereof wherein:
the phenyl ring has a para nitro substituent; and the pyrazole ring has a methyl, ethyl, halomethyl or haloethyl substituent in the 1-position; a hydrido, halo or nitro substituent in the 4-position; and a chloro, cyano, halomethyl, haloethyl, methylthio, ethylthio, methylsulfinyl, ethylsulfinyl, methylsulfonyl, ethylsulfonyl or methoxymethyl substituent in the 5-position; and optionally a meta substituent.

2. The 3-phenoxypyrazole or salt of claim 1 wherein the pyrazole ring has a methyl substituent in the 1-position.

3. The 3-phenoxypyrazole or salt of claim 2 wherein the pyrazole ring has a halo substituent in the 4-position.

4. The 3-phenoxypyrazole or salt of claim 3 wherein the pyrazole ring has a chloro or bromo substituent in the 4-position.

5. The 3-phenoxypyrazole or salt of claim 3 wherein the pyrazole ring has a halomethyl or methyl sulfonyl substituent in the 5-position.

6. The 3-phenoxypyrazole or salt of claim 5 wherein the pyrazole ring has a trifluoromethyl, a difluoromethyl or a methylsulfonyl substituent in the 5-position.

7. The 3-phenoxypyrazole or salt of claim 1 wherein the phenyl ring has a meta substituent having a molecular weight of less than about 300 and selected from alkoxy, haloalkoxy, di(alkoxy), alkoxycarbonyl, alkoxycarbonylalkoxy, aminocarbonylalkoxy, alkylsulfonylaminocarbonylalkoxy, alkylamino, hydroxyalkylamino, alkoxyamino, alkoxyalkylamino, hydroxycarbonylalkylamino, and alkoxycarbonylalkyloximino.

8. The 3-phenoxypyrazole or salt of claim 7 wherein said meta substituent has about 10 or less carbon atoms.

9. The 3-phenoxypyrazole or salt of claim 8 wherein the pyrazole ring has a halo substituent in the 4-position.

10. The 3-phenoxypyrazole or salt of claim 9 wherein the pyrazole ring has a chloro or bromo substituent in the 4-position.

11. The 3-phenoxypyrazole or salt of claim 10 wherein the pyrazole ring has a halomethyl or methylsulfonyl substituent in the 5-position.

12. The 3-phenoxypyrazole or salt of claim 11 wherein the pyrazole ring has a difluoromethyl, trifluoromethyl or methylsulfonyl substituent in the 5-position.

13. A herbicidal composition comprising an effective amount of a 3-phenoxypyrazole or agronomically acceptable salt thereof wherein:

the phenyl ring has a para nitro substituent; and the pyrazole ring has a methyl, ethyl, halomethyl or haloethyl substituent in the 1-position; a hydrido, halo or nitro substituent in the 4-position; and a chloro, cyano, halomethyl, haloethyl, methylthio, ethylthio, methylsulfinyl, ethylsulfinyl, methylsulfonyl, ethylsulfonyl or methoxymethyl substituent in the 5-position; and optionally a meta substituent.

14. The composition of claim 13 wherein the pyrazole ring has a methyl substituent in the 1-position.

15. The composition of claim 14 wherein the pyrazole ring has a halo substituent in the 4-position.

16. The composition of claim 15 wherein the pyrazole ring has a chloro or bromo substituent in the 4-position.

17. The composition of claim 15 wherein the pyrazole ring has a halomethyl or methylsulfonyl substituent in the 5-position.

18. The composition of claim 17 wherein the pyrazole ring has a trifluoromethyl, a difluoromethyl or a methylsulfonyl substituent in the 5-position.

19. The composition of claim 13 wherein the phenyl ring has a meta substituent having a molecular weight of less than about 300 and selected from alkoxy, haloalkoxy, di(alkoxy), alkoxycarbonyl, alkoxycarbonylalkoxy, aminocarbonylalkoxy, alkylsulfonylaminocarbonylalkoxy, alkylamino, hydroxyalkylamino, alkoxyamino, alkoxyalkylamino, hydroxycarbonylalkylamino, and alkoxycarbonylalkyloximino.

20. The composition of claim 19 wherein said meta substituent has about 10 or less carbon atoms.

21. The composition of claim 20 wherein the pyrazole ring has a halo substituent in the 4-position.

22. The composition of claim 21 wherein the pyrazole ring has a chloro or bromo substituent in the 4-position.

23. The composition of claim 22 wherein the pyrazole ring has a halomethyl or methylsulfonyl substituent in the 5-position.

24. The composition of claim 23 wherein the pyrazole ring has a difluoromethyl, trifluoromethyl or methylsulfonyl substituent in the 5-position.

25. The composition of claim 13 wherein said composition is a concentrate

26. The composition of claim 13 wherein said composition is a dilute composition.

27. A method of controlling the growth of undesirable vegetation comprising apply to the plant locus an effective amount of a 3-phenoxypyrazole or agronomically acceptable salt thereof wherein:

the phenyl ring has a para nitro substituent; and the pyrazole ring has a methyl, ethyl, halomethyl or haloethyl substituent in the 1-position; a hydrido, halo or nitro substituent in the 4-position; and a chloro, cyano, halomethyl, haloethyl, methylthio, ethylthio, methylsulfinyl, ethylsulfinyl, methylsulfonyl, ethylsulfonyl or methoxymethyl substituent in the 5-position; and optionally a meta substituted.

28. The method of claim 27 wherein the pyrazole ring has a methyl substituent in the 1-position.

29. The method of claim 28 wherein the pyrazole ring has a halo substituent in the 4-position.

30. The method of claim 29 wherein the pyrazole ring has a chloro or bromo substituent in the 4-position.

31. The method of claim 29 wherein the pyrazole ring has a halomethyl or methylsulfonyl substituent in the 5-position.

32. The method of claim 31 wherein the pyrazole ring has a trifluoromethyl, a difluoromethyl or a methylsulfonyl substituent in the 5-position.

33. The method of claim 27 wherein the phenyl ring has a meta substituent having a molecular weight of less than about 300 and selected from alkoxy, haloalkoxy, di(alkoxy), alkoxycarbonyl, alkoxycarbonylalkoxy, aminocarbonylalkoxy, alkylsulfonylaminocarbonylalkoxy, alkylamino, hydroxyalkylamino, alkoxyamino, alkoxyalkylamino, hydroxycarbonylalkylamino, and alkoxycarbonylalkoxyimino.

34. The method of claim 33 wherein said meta substituent has about 10 or less carbon atoms.

35. The method of claim 34 wherein the pyrazole ring has a halo substituent in the 4-position.

36. The method of claim 35 wherein the pyrazole ring has a chloro or bromo substituent in the 4-position.

37. The method of claim 36 wherein the pyrazole ring has a halomethyl or methylsulfonyl substituent in the 5-position.

38. The method of claim 37 wherein the pyrazole ring has a difluoromethyl, trifluoromethyl or methylsulfonyl substituent in the 5-position.

* * * * *

UNITED STATES PATENT OFFICE
CERTIFICATE OF CORRECTION

PATENT NO. : 4,964,895

DATED : Oct. 23, 1990

INVENTOR(S) : Kurt Moedritzer and Michael D. Rogers

Page 1 of 16

It is certified that error appears in the above-identified patent and that said Letters Patent is hereby corrected as shown below:

On the Cover Page, in the Title Section [54], after "SUBSTITUTED", delete "4-(4-" and substitute -- 3-(4- --.

On the Cover Page, in the Related U.S. Application Data Section [63], line 3, delete "Jun. 8, 1981" and substitute -- Jun. 8, 1987 --.

Col. 1, line 1, in title after "Substituted", delete "4-(4-" and substitute -- 3-(4- --.

Col. 3, line 66, delete "alkoxycarbonylalkylcarbonyloxy-bis" and substitute -- alkoxycarbonylalkylcarbonyloxybis --.

Col. 4, line 38, delete "4,5dihydro" and substitute -- 4,5-dihydro --.

Col. 8, line 23, delete "3 TM hydroxy" and substitute -- 3-hydroxy --.

Col. 8, line 25, delete "5-Trifluoromethyl TM 4" and substitute -- 5-Trifluoromethyl-4 --.

Col. 10, line 24, delete "with with" and substitute -- with --.

Col. 15, line 61, delete "t-butylnitrite and alkenyl" and substitute -- t-butylnitrite and (ii) with methyl acrylate and $CuCl_2$. Compounds having alkenyl --.

Col. 22, line 30, delete "trifluoromethyl-4- chloro-3-" and substitute -- trifluoromethyl-4-chloro-3- --. On line 66 delete "trifluoromethyl-4- chloro-3-" and substitute -- trifluoromethyl-4-chloro-3- --.

UNITED STATES PATENT OFFICE
CERTIFICATE OF CORRECTION

PATENT NO. : 4,964,895
DATED : Oct. 23, 1990
INVENTOR(S) : Kurt Moedritzer and Michael D. Rogers It is certified that error appears in the above-identified patent and that said Letters Patent is hereby corrected as shown below:

Col. 23, line 60, delete "recrystallied" and substitute -- recrystallized --.

Col. 26, line 13, delete "y]amino4'-nitrophenoxy" and substitute -- y]amino-4'-nitrophenoxy --.

Col. 26, line 21, delete "qive" and substitute -- give --.

Col. 27, line 31, delete "recystallized" and substitute -- recrystallized --. On line 40 delete "recystallized" and substitute -- recrystallized --.

Col. 30, Ex CP # 18, delete the chemical structure and substitute the following structure:

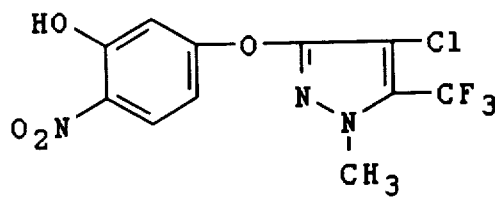

Col. 31, Ex CP # 21, delete the chemical structure and substitute the following structure:

UNITED STATES PATENT OFFICE
CERTIFICATE OF CORRECTION

PATENT NO. : 4,964,895  
DATED : Oct. 23, 1990  
INVENTOR(S) : Kurt Moedritzer and Michael D. Rogers Page 3 of 16

It is certified that error appears in the above-identified patent and that said Letters Patent is hereby corrected as shown below:

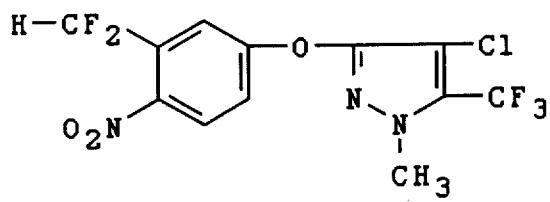

Col. 34, Ex CP # 28, delete the chemical structure and substitute the following structure:

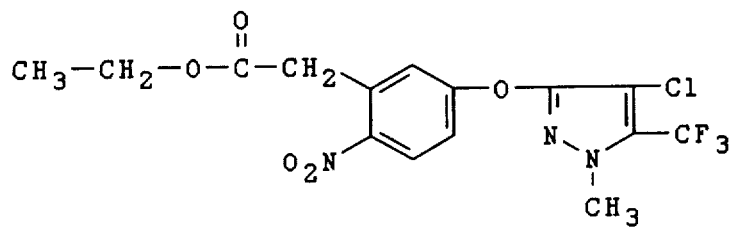

Col. 47 Ex CP # 59, delete the chemical structure and substitute the following structure:

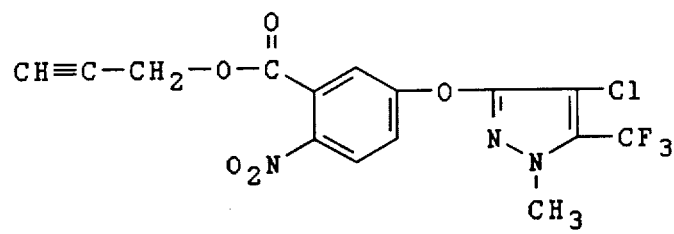

UNITED STATES PATENT AND TRADEMARK OFFICE
CERTIFICATE OF CORRECTION

PATENT NO. : 4,964,895
DATED : Oct. 23, 1990
INVENTOR(S) : Kurt Moedritzer and Michael D. Rogers It is certified that error appears in the above-identified patent and that said Letters Patent is hereby corrected as shown below:

Col. 49, Ex CP # 65, delete the chemical structure and substitute the following structure:

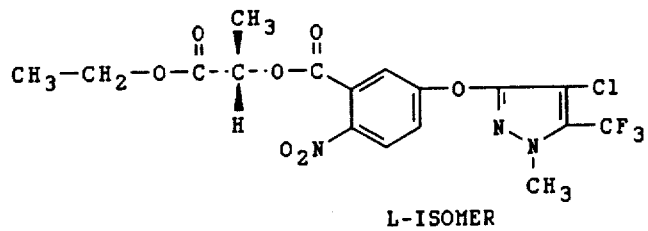

L-ISOMER

Cols. 67-68, Ex CP # 110, delete "nD: 1.5257" and substitute -- nD: 1.5357 --.

Col. 68, Ex CP # 111, delete the chemical structure and substitute the following structure:

UNITED STATES PATENT AND TRADEMARK OFFICE
CERTIFICATE OF CORRECTION

PATENT NO. : 4,964,895
DATED : Oct. 23, 1990
INVENTOR(S) : Kurt Moedritzer and Michael D. Rogers It is certified that error appears in the above-identified patent and that said Letters Patent is hereby corrected as shown below:

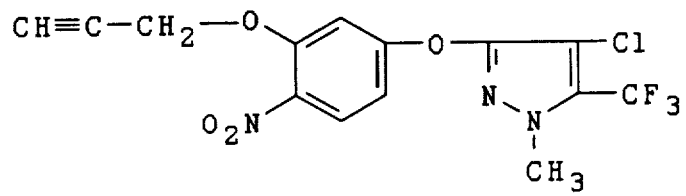

Col. 72, Ex CP # 122, delete the chemical structure and insert the following structure:

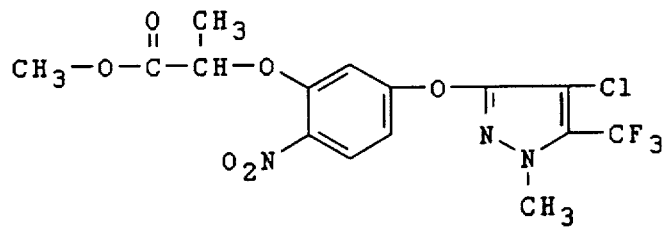

Col. 83, Ex CP # 147, delete the chemical structure and substitute the following structure:

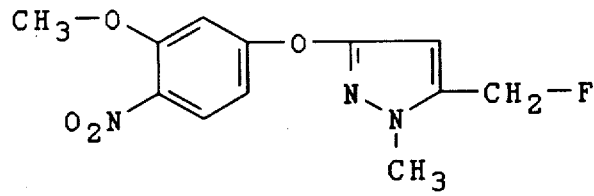

Col. 89 Ex CP # 162, in the Name column, line 5, delete "(3-

UNITED STATES PATENT AND TRADEMARK OFFICE
CERTIFICATE OF CORRECTION

PATENT NO. : 4,964,895

DATED : Oct. 23, 1990

INVENTOR(S) : Kurt Moedritzer and Michael D. Rogers

It is certified that error appears in the above-identified patent and that said Letters Patent is hereby corrected as shown below:

methoxy-4" and substitute -- (3-methoxy-4- --.

Cols. 115-116, Ex CP # 227, delete the chemical structure and substitute the following structure:

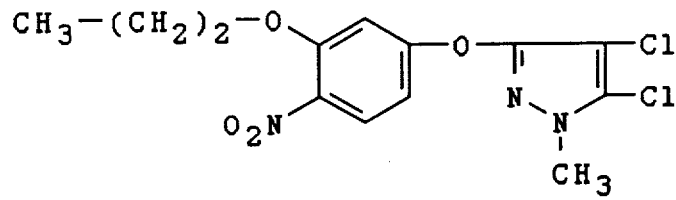

Cols. 119-120, Ex CP # 237, in the Name column, line 4, delete "nD:" and substitute -- nD: 1.5767 --.

Col. 132, Ex CP # 269, in the Name column, line 1, delete "3-[3-(bromoethyl)" and substitute -- 3-[3-(bromomethyl) --.

Col. 161, Ex CP # 337, in the Name column, line 2, delete "2-[5-[[fluoro-1-methyl-5" and substitute -- 2-[5-[[4-fluoro-1-methyl-5 --.

Col. 164, Ex CP # 346, in the Name column, line 1, delete "4-[[4-chloro" and substitute -- 4-[[5-[4-chloro --.

Col. 176, Ex CP # 374, in the Name column, line 1, delete "-5-]]4-chloro-1" and substitute -- -5-[[4-chloro-1 --.

Col. 201, Ex CP # 437, delete the chemical structure and substitute the following structure:

UNITED STATES PATENT AND TRADEMARK OFFICE
CERTIFICATE OF CORRECTION

PATENT NO. : 4,964,895
DATED : Oct. 23, 1990
INVENTOR(S) : Kurt Moedritzer and Michael D. Rogers It is certified that error appears in the above-identified patent and that said Letters Patent is hereby corrected as shown below:

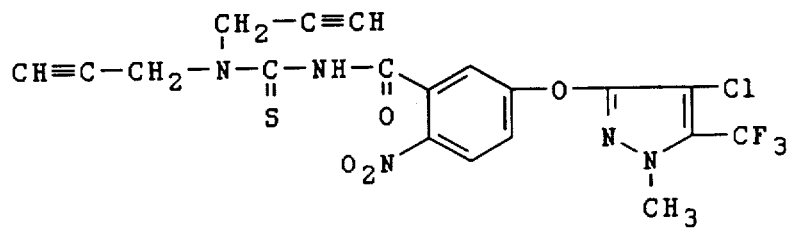

Col. 202, Ex CP # 439, delete the chemical structure and substitute the following structure:

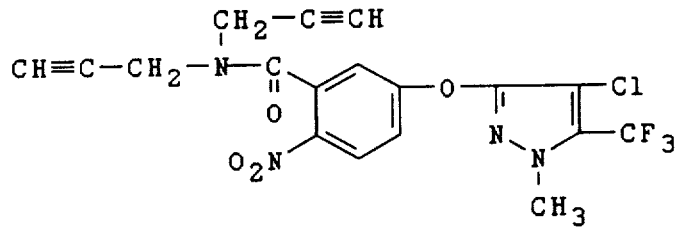

Col. 203, Ex CP # 442, delete the chemical structure and substitute the following structure:

UNITED STATES PATENT AND TRADEMARK OFFICE
CERTIFICATE OF CORRECTION

PATENT NO. : 4,964,895

DATED : Oct. 23, 1990

INVENTOR(S) : Kurt Moedritzer and Michael D. Rogers

It is certified that error appears in the above-identified patent and that said Letters Patent is hereby corrected as shown below:

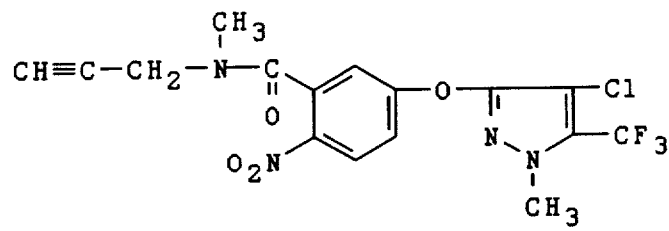

Cols. 221-222, Ex CP # 488, delete the chemical structure and substitute the following structure:

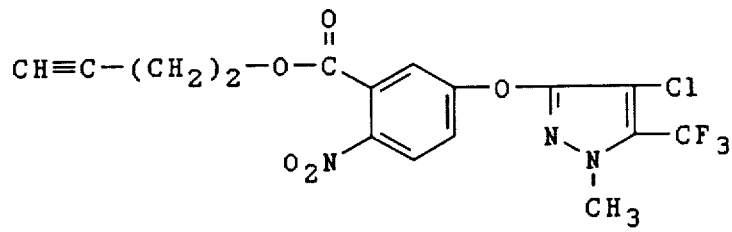

Col. 222, Ex CP # 489, delete the chemical structure and substitute the following structure:

UNITED STATES PATENT AND TRADEMARK OFFICE
CERTIFICATE OF CORRECTION

PATENT NO. : 4,964,895
DATED : Oct. 23, 1990
INVENTOR(S) : Kurt Moedritzer and Michael D. Rogers It is certified that error appears in the above-identified patent and that said Letters Patent is hereby corrected as shown below:

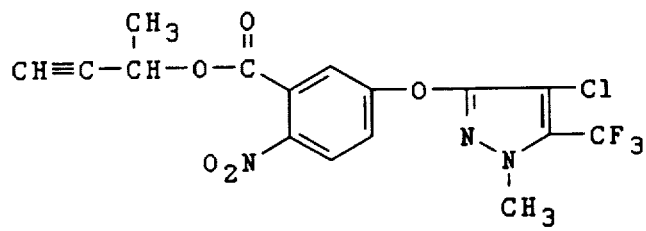

Col. 222, Ex CP # 490, delete the chemical structure and substitute the following structure:

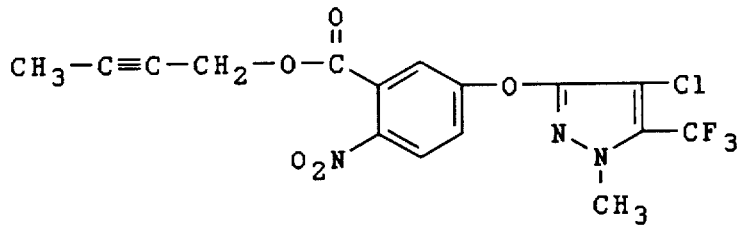

Col. 245, Ex CP # 546, delete the chemical structure and substitute the following structure:

UNITED STATES PATENT AND TRADEMARK OFFICE
CERTIFICATE OF CORRECTION

PATENT NO. : 4,964,895
DATED : Oct. 23, 1990
INVENTOR(S) : Kurt Moedritzer and Michael D. Rogers It is certified that error appears in the above-identified patent and that said Letters Patent is hereby corrected as shown below:

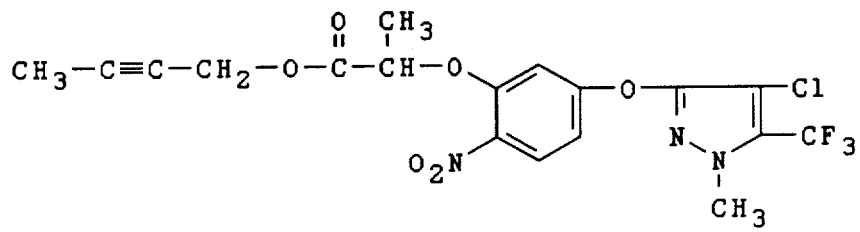

Col. 279, Ex CP # 622, in the Name column, line 1, delete "[[[1-5-[[4-chloro" and substitute -- [[[1-[5-[[4-chloro --.

Col. 287, Ex CP # 638, in the Name column, line 2, delete "3-yl]oxy]-2-" and substitute -- 3-yl]oxy]-2-nitro- --.

Col. 290, Ex CP # 646, delete the chemical structure and substitute the following structure:

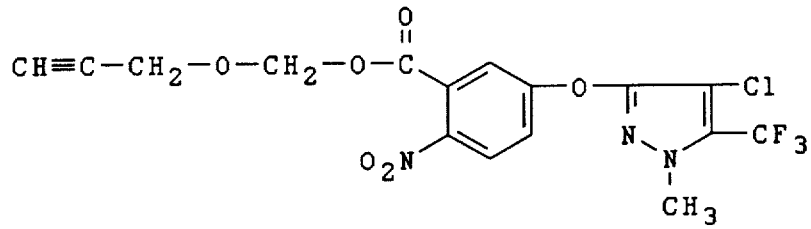

Col. 300, Ex CP # 669, in the Name column, line 1, delete "5-[[4-chloro" and substitute -- [5-[[4-chloro --.

UNITED STATES PATENT AND TRADEMARK OFFICE
CERTIFICATE OF CORRECTION

PATENT NO. : 4,964,895

DATED : Oct. 23, 1990

INVENTOR(S) : Kurt Moedritzer and Michael D. Rogers

It is certified that error appears in the above-identified patent and that said Letters Patent is hereby corrected as shown below:

Col. 301, Ex CP # 672, in the Name column, line 1, delete "5-[[4-chloro" and substitute -- [5-[[4-chloro --.

Col. 302, Ex CP # 675, delete the chemical structure and substitute the following structure:

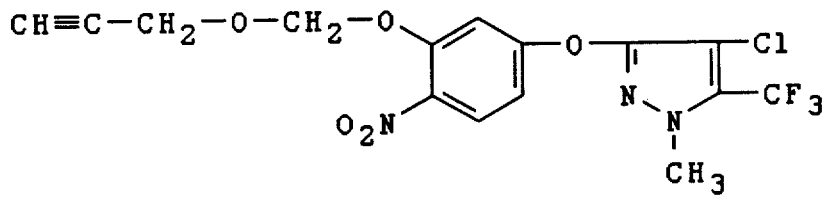

Col. 325, Ex CP # 729, in the Name column, lines 1 and 2, delete "pyrazole, 4-hloro-" and substitute -- pyrazole, 4-chloro- --.

Cols. 343-344, Ex CP # 778, delete the chemical structure and substitute the following structure:

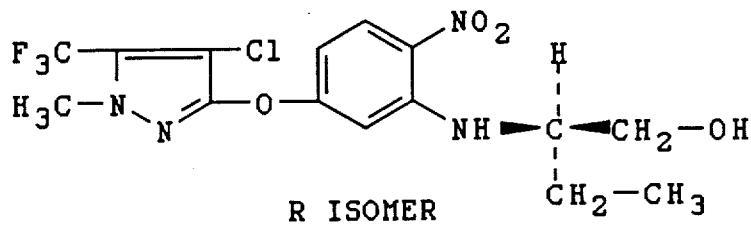

Col. 344, Ex CP # 779, delete the chemcial structure and substitute the following structure:

UNITED STATES PATENT AND TRADEMARK OFFICE
CERTIFICATE OF CORRECTION

PATENT NO. : 4,964,895
DATED : Oct. 23, 1990
INVENTOR(S) : Kurt Moedritzer and Michael D. Rogers It is certified that error appears in the above-identified patent and that said Letters Patent is hereby corrected as shown below:

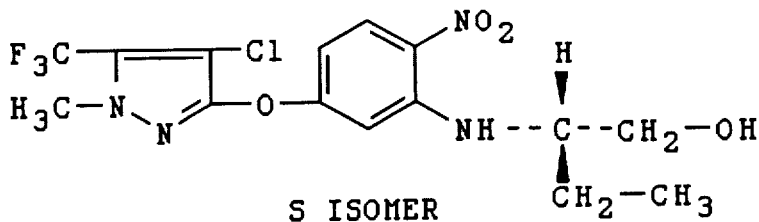

Cols. 347-348, Ex CP # 787, in the Name column, line 4, delete "MP: 115.0-115.0" and substitute -- MP: 115.0-116.0 --.

Col. 365, Ex CP # 833, in the Name column, line 3, delete "oxy]-N-methyl-N-methyl" and substitute -- oxy]-N-methoxy-N-methyl" --.

Col. 376, Ex CP # 861, delete the chemical structure and substitute the following structure:

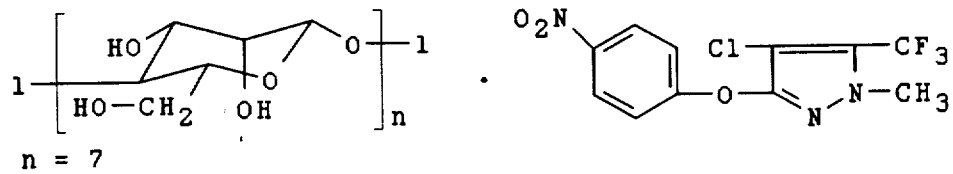

n = 7

1 = CYCLIC POLYMER

Col. 379, Ex CP # 869, delete the chemical structure and substitute the following structure:

UNITED STATES PATENT AND TRADEMARK OFFICE
CERTIFICATE OF CORRECTION

PATENT NO. : 4,964,895
DATED : Oct. 23, 1990
INVENTOR(S) : Kurt Moedritzer and Michael D. Rogers It is certified that error appears in the above-identified patent and that said Letters Patent is hereby corrected as shown below:

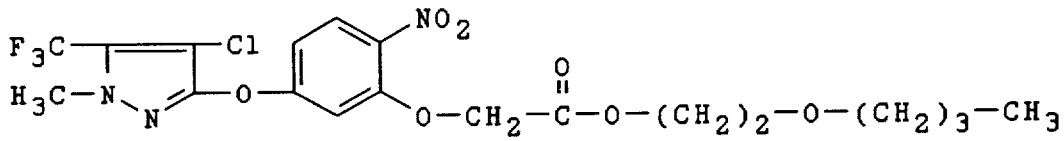

Col. 389, Ex CP # 900, in the Name column, line 2, delete "methy-5-" and substitute -- methyl-5- --.

Col. 390, Ex CP # 903, in the Name column, line 2, delete "1H-pyrasol-3" and substitute -- 1H-pyrazol-3 --.

Cols. 395-396, Table A, Ex. No. 94, line 10 of data for compound 94, Rate column, delete "11.2100" and substitute -- \ 11.2100 --.

Cols. 395-396, Table A, Ex. No. 102, Rate column, delete "11.2100" and substitute -- C 11.2100 --.

Cols. 397-398, Table A, Ex. No. 184, Rate column, delete "11.2100" and substitute -- * 11.2100 --.

Cols. 397-398, Table A, Ex. No. 206, Rate column, delete "11.2100" and substitute -- > 11.2100 --.

Cols. 399-400, Table A, Ex. No. 213, Col. Vele, insert -- 0 --; Col. Wibw delete "0"; Col. Cath, delete "1" and substitute -- 0 --; Col. Colq, delete "2" and substitute -- 1 --; Col. Pesw, delete "0" and substitute -- 2 --; Col. Rhjg, insert -- 0 --.

Cols. 407-408, Table A, Ex. No. 517, Rate column, delete "11.2100" and substitute -- \ 11.2100 --.

UNITED STATES PATENT AND TRADEMARK OFFICE
CERTIFICATE OF CORRECTION

PATENT NO. : 4,964,895
DATED : Oct. 23, 1990
INVENTOR(S) : Kurt Moedritzer and Michael D. Rogers It is certified that error appears in the above-identified patent and that said Letters Patent is hereby corrected as shown below:

Cols. 407-408, Table A, Ex. No. 518, Rate column, delete "11.2100" and substitute -- \ 11.2100 --.

Cols. 407-408, Table A, Ex. 557-558-559-560-561-562-563, Rate column, delete "11.2100" and substitute -- \ 11.2100 --.

Cols. 409-410, Table A, Ex. 645, Rate column, delete "11.2100" and substitute -- \ 11.2100 --.

Cols. 409-410, Table A, Ex. 652, 653, 654, 655, 656, 657, 658, 659, 660, 661 and 662, Rate column, delete "11.2100" and substitute -- \ 11.2100 --.

Cols. 411-412, Table A, Ex. 687-688-689, Rate column, delete "11.2100" and substitute -- \ 11.2100 --.

Cols. 415-416, Table A, Ex. 848, Yens column, delete "0" and substitute -- 1 --; Anbg column, delete "0" and substitute -- 3 --; Sejg column, delete "0" and substitute -- 3 --; Dobr column, delete "0" and substitute -- 3 --; Bygr column, delete "2" and substitute -- 3 --.

Cols. 413-414, Table A, Ex. 819, Rate column, delete "11.2100" and substitute -- > 11.2100 --.

Cols. 417-418, Table A, line 9, insert -- } -- in front of "NO TO POOR SMARTWEED GERMINATION."

Cols. 417-418, Table A, line 15, insert -- \ -- in front of "DAMPING OFF-IM,WB."

Cols. 417-418, Table A, line 16, insert -- \ -- in front of "FREQUENT DAMPING OFF-IM,WB.

UNITED STATES PATENT AND TRADEMARK OFFICE
CERTIFICATE OF CORRECTION

PATENT NO. : 4,964,895
DATED : Oct. 23, 1990
INVENTOR(S) : Kurt Moedritzer and Michael D. Rogers It is certified that error appears in the above-identified patent and that said Letters Patent is hereby corrected as shown below:

"FREQUENT DAMPING OFF-IM,WB.

Cols. 427-428, Table B, Ex. No. 306, Rhjg column, delete "1" and substitute -- 0 --.

Cols. 451-452, Table C, Ex. No. 464, Rate column 0.0087, Bygr column, insert -- 0 --.

Cols. 451-452, Table C, Ex. No. 586, Rate column, delete "/ 5.6050" and substitute -- \ 5.6050 --. Insert -- \ -- in front of Rate columns 1.1210, 0.2803, 0.0701, 0.0175, and 0.0087.

Cols. 451-452, Table C, Ex. No. 644, insert -- \ -- in front of Rate columns 5.6050, 1.1210, 0.2803, 0.0701, 0.0175, and 0.0087.

Col. 453, Table C, footnote at end of table, insert -- \ -- after "GROWTH VARIABLE" and after "NO DATA FOR COBU DUE TO POOR EMERGENCE".

Cols. 457-458, Table D, Ex. No. 151, Rate column 0.0175, Prmi column, delete "156" and substitute -- 10 --.

Cols. 459-460, Table D, Ex. No. 156, insert -- 156 -- before Rate column 5.6050 on Line 7.

Cols. 463-464, Table D, Ex. No. 639, Rate column 2.803, Corn column, delete "210" and substitute -- 20 --.

Cols. 465-466, Table D, footnote at end of table, last line, delete "rate observed; dampingoff !" and substitute -- rate observed; HS damping off ! --.

Col. 467, line 55, delete "prising from 0 1 to 60% by weight" and

UNITED STATES PATENT AND TRADEMARK OFFICE
CERTIFICATE OF CORRECTION

PATENT NO.   : 4,964,895
DATED        : Oct. 23, 1990
INVENTOR(S)  : Kurt Moedritzer and Michael D. Rogers It is certified that error appears in the above-identified patent and that said Letters Patent is hereby corrected as shown below:

substitute    -- prising from 0.1 to 60% by weight --.

Col. 469, line 22, delete "triazin-2yl-" and substitute
-- triazin-2-yl --.

Col. 473, line 22, delete "in the 5-position; and optionally a meta substituent." and substitute -- in the 5-position. --.

Col. 474, line 19, delete "in the 5-position; and optionally a meta substituted." and substitute -- in the 5-position. --.

Signed and Sealed this

Seventeenth Day of November, 1992

Attest:

DOUGLAS B. COMER

*Attesting Officer*      Acting Commissioner of Patents and Trademarks